United States Patent
Guckian et al.

(10) Patent No.: US 9,550,798 B2
(45) Date of Patent: Jan. 24, 2017

(54) COMPOUNDS THAT ARE S1P MODULATING AGENTS AND/OR ATX MODULATING AGENTS

(71) Applicant: BIOGEN MA INC., Cambridge, MA (US)

(72) Inventors: Kevin Guckian, Northborough, MA (US); Gnanasambandam Kumaravel, Lexington, MA (US); Bin Ma, Arlington, MA (US); Sha Mi, Belmont, MA (US); Hairuo Peng, Needham, MA (US); Zhaohui Shao, Brookline, MA (US); Lihong Sun, Lexington, MA (US); Arthur Taveras, Boston, MA (US); Zhili Xin, Lexington, MA (US); Lei Zhang, Westford, MA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

(21) Appl. No.: 14/417,293

(22) PCT Filed: Jul. 26, 2013

(86) PCT No.: PCT/US2013/052329
§ 371 (c)(1),
(2) Date: Jan. 26, 2015

(87) PCT Pub. No.: WO2014/018891
PCT Pub. Date: Jan. 30, 2014

(65) Prior Publication Data
US 2015/0203515 A1    Jul. 23, 2015

Related U.S. Application Data

(60) Provisional application No. 61/676,692, filed on Jul. 27, 2012.

(51) Int. Cl.
| | |
|---|---|
| C07C 229/48 | (2006.01) |
| C07D 223/06 | (2006.01) |
| C07D 221/22 | (2006.01) |
| C07D 209/52 | (2006.01) |
| C07D 211/62 | (2006.01) |
| C07D 295/096 | (2006.01) |
| A61K 31/5375 | (2006.01) |
| A61K 31/439 | (2006.01) |
| A61K 31/46 | (2006.01) |
| A61K 31/445 | (2006.01) |
| A61K 31/196 | (2006.01) |
| A61K 31/136 | (2006.01) |

(Continued)

(52) U.S. Cl.
CPC ........... *C07F 7/0809* (2013.01); *A61K 31/195* (2013.01); *A61K 31/196* (2013.01); *A61K 31/397* (2013.01); *A61K 31/41* (2013.01); *A61K 31/439* (2013.01); *A61K 31/4545* (2013.01); *A61K 31/47* (2013.01); *A61K 31/4709* (2013.01); *A61K 31/4725* (2013.01); *A61K 31/495* (2013.01); *A61K 31/496* (2013.01); *A61K 31/506* (2013.01); *A61K 31/551* (2013.01); *A61K 31/5513* (2013.01); *A61K 31/695* (2013.01); *A61K 45/06* (2013.01); *C07C 211/38* (2013.01); *C07C 217/58* (2013.01); *C07C 229/46* (2013.01); *C07C 233/61* (2013.01); *C07C 235/66* (2013.01); *C07D 205/04* (2013.01); *C07D 213/74* (2013.01); *C07D 215/20* (2013.01); *C07D 215/38* (2013.01); *C07D 217/22* (2013.01); *C07D 401/04* (2013.01); *C07D 401/06* (2013.01); *C07D 471/08* (2013.01); *C07F 7/0818* (2013.01); *C07C 2101/14* (2013.01); *C07C 2102/08* (2013.01); *C07C 2102/10* (2013.01); *C07C 2102/42* (2013.01); *C07C 2102/44* (2013.01); *C07C 2102/46* (2013.01); *C07C 2102/50* (2013.01); *C07C 2103/62* (2013.01); *C07C 2103/74* (2013.01)

(58) Field of Classification Search
None
See application file for complete search history.

(56) References Cited

U.S. PATENT DOCUMENTS

| 7,825,109 B2 | 11/2010 | Nakade et al. |
| 2008/0207584 A1 | 8/2008 | Habashita et al. |

(Continued)

FOREIGN PATENT DOCUMENTS

| EP | 1661881 A2 | 5/2006 |
| EP | 1760071 A1 | 3/2007 |

(Continued)

OTHER PUBLICATIONS

Tomishima et al.; "Novel echinocandin antifungals. Part 1: Novel side-chain analogs of the natural product FR901379"; Bioorganic & Medicinal Chemistry Letters; 18(4):1474-1477 (2008).

*Primary Examiner* — Zinna Northington Davis
(74) *Attorney, Agent, or Firm* — McCarter & English, LLP; Steven G. Davis; Xin Zhang

(57) ABSTRACT

Compounds of formula (I) can modulate the activity of one or more S1P receptors and/or the activity of autotaxin (ATX).

(I)

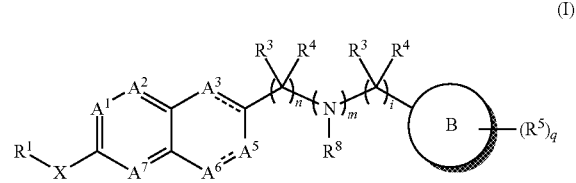

25 Claims, No Drawings

(51) Int. Cl.
*C07F 7/08* (2006.01)
*A61K 45/06* (2006.01)
*A61K 31/195* (2006.01)
*A61K 31/41* (2006.01)
*A61K 31/4709* (2006.01)
*A61K 31/4725* (2006.01)
*A61K 31/5513* (2006.01)
*C07D 215/38* (2006.01)
*C07D 217/22* (2006.01)
*C07D 401/04* (2006.01)
*C07D 471/08* (2006.01)
*C07C 217/58* (2006.01)
*C07C 229/46* (2006.01)
*C07C 233/61* (2006.01)
*C07C 235/66* (2006.01)
*A61K 31/397* (2006.01)
*A61K 31/4545* (2006.01)
*A61K 31/47* (2006.01)
*A61K 31/495* (2006.01)
*A61K 31/496* (2006.01)
*A61K 31/506* (2006.01)
*A61K 31/551* (2006.01)
*A61K 31/695* (2006.01)
*C07C 211/38* (2006.01)
*C07D 205/04* (2006.01)
*C07D 213/74* (2006.01)
*C07D 215/20* (2006.01)
*C07D 401/06* (2006.01)

(56) References Cited

U.S. PATENT DOCUMENTS

2011/0318388 A1 12/2011 Gill et al.
2015/0183741 A1 7/2015 Guckian et al.
2015/0203493 A1 7/2015 Guckian et al.
2015/0210647 A1 7/2015 Guckian et al.
2015/0246063 A1 9/2015 Guckian et al.
2015/0361029 A1 12/2015 Guckian et al.

FOREIGN PATENT DOCUMENTS

WO   WO 2005/117865 A1 * 12/2005
WO   WO-2011/017561 A1   2/2011
WO   WO-2012/109108 A1   8/2012

* cited by examiner

COMPOUNDS THAT ARE S1P MODULATING AGENTS AND/OR ATX MODULATING AGENTS

RELATED APPLICATIONS

This application is a 35 U.S.C. §371 national stage filing of International Application No. PCT/US2013/052329, filed on Jul. 26, 2013, which claims the benefit of the filing date of U.S. Provisional Application No. 61/676,692, filed on Jul. 27, 2012, the entire contents of which are incorporated herein by reference.

TECHNICAL FIELD

This invention relates to compounds that are S1P modulating agents and/or ATX modulating agents, and methods of making and using such compounds.

BACKGROUND

Sphingosine 1-phosphate (S1P) is a lysophospholipid mediator that evokes a variety of cellular responses by stimulation of five members of the endothelial cell differentiation gene (EDG) receptor family. The EDG receptors are G-protein coupled receptors (GPCRs) and on stimulation propagate second messenger signals via activation of heterotrimeric G-protein alpha (G$\alpha$) subunits and beta-gamma (G$\beta\gamma$) dimers. Ultimately, this S1P-driven signaling results in cell survival, increased cell migration and, often, mitogenesis. The recent development of agonists targeting S1P receptors has provided insight regarding the role of this signaling system in physiologic homeostasis. For example, the immunomodulating agent, FTY720 (2-amino-2-[2-(4-octylphenyl)ethyl]propane 1,3-diol), that following phosphorylation, is an agonist at 4 of 5 S1P receptors, revealed that affecting S1P receptor activity influences lymphocyte trafficking. Further, S1P type 1 receptor (S1P$_1$) antagonists cause leakage of the lung capillary endothelium, which suggests that S1P may be involved in maintaining the integrity of the endothelial barrier in some tissue beds. S1P type 4 receptors (S1P$_4$) are expressed mainly in leukocytes, and specifically S1P$_4$ mediates immunosuppressive effects of S1P by inhibiting proliferation and secretion of effector cytokines, while enhancing secretion of the suppressive cytokine IL-10. See, for example, Wang, W. et. al., (2005) *FASEB J.* 19(12): 1731-3, which is incorporated by reference in its entirety. S1P type 5 receptors (S1P$_5$) are exclusively expressed in oligodendrocytes and oligodendrocyte precursor cells (OPCs) and are vital for cell migration. Stimulation of S1P$_5$ inhibits OPC migration, which normally migrate considerable distances during brain development. See, for example, Novgorodov, A. et al., (2007) *FASEB J,* 21: 1503-1514, which is incorporated by reference in its entirety.

S1P has been demonstrated to induce many cellular processes, including those that result in platelet aggregation, cell proliferation, cell morphology, tumor-cell invasion, endothelial cell chemotaxis and angiogenesis. For these reasons, S1P receptors are good targets for therapeutic applications such as wound healing, tumor growth inhibition, and autoimmune diseases.

Sphingosine-1-phosphate signals cells in part via a set of G protein-coupled receptors named S1P$_1$, S1P$_2$, S1P$_3$, S1P$_4$, and S1P$_5$ (formerly EDG1, EDG5, EDG3, EDG6 and EDG8). The EDG receptors are G-protein coupled receptors (GPCRs) and on stimulation propagate second messenger signals via activation of heterotrimeric G-protein alpha (G$\alpha$) subunits and beta-gamma (G$\beta\gamma$) dimers. These receptors share 50-55% amino acid sequence identity and cluster with three other receptors (LPA$_1$, LPA$_2$, and LPA$_3$ (formerly EDG2, EDG4 and EDG7) for the structurally related lysophosphatidic acid (LPA)).

A conformational shift is induced in the G-Protein Coupled Receptor (GPCR) when the ligand binds to that receptor, causing GDP to be replaced by GTP on the $\alpha$-subunit of the associated G-proteins and subsequent release of the G-proteins into the cytoplasm. The $\alpha$-subunit then dissociates from the $\beta\gamma$-subunit and each subunit can then associate with effector proteins, which activate second messengers leading to a cellular response. Eventually the GTP on the G-proteins is hydrolyzed to GDP and the subunits of the G-proteins reassociate with each other and then with the receptor. Amplification plays a major role in the general GPCR pathway. The binding of one ligand to one receptor leads to the activation of many G-proteins, each capable of associating with many effector proteins leading to an amplified cellular response.

S1P receptors make good drug targets because individual receptors are both tissue and response specific. Tissue specificity of the S1P receptors is desirable because development of an agonist or antagonist selective for one receptor localizes the cellular response to tissues containing that receptor, limiting unwanted side effects. Response specificity of the S1P receptors is also of importance because it allows for the development of agonists or antagonists that initiate or suppress certain cellular responses without affecting other responses. For example, the response specificity of the S1P receptors could allow for an S1P mimetic that initiates platelet aggregation without affecting cell morphology.

Sphingosine-1-phosphate is formed as a metabolite of sphingosine in its reaction with sphingosine kinase and is stored in abundance in the aggregates of platelets where high levels of sphingosine kinase exist and sphingosine lyase is lacking. S1P is released during platelet aggregation, accumulates in serum, and is also found in malignant ascites. Reversible biodegradation of S1P most likely proceeds via hydrolysis by ectophosphohydrolases, specifically the sphingosine-1-phosphate phosphohydrolases. Irreversible degradation of S1P is catalyzed by S1P lyase yielding ethanolamine phosphate and hexadecanal.

Autotaxin (ATX, ENPP2) is a secreted glycoprotein widely present in biological fluids, including blood, cancer ascites, synovial, pleural and cerebrospinal fluids, originally isolated from the supernatant of melanoma cells as an autocrine motility stimulation factor (Stracke, M. L., et al. Identification, purification, and partial sequence analysis of autotaxin, a novel motility-stimulating protein. J Biol Chem 267, 2524-2529 (1992), which is incorporated by reference in its entirety). ATX is encoded by a single gene on human chromosome 8 (mouse chromosome 15) whose transcription, regulated by diverse transcription factors (Hoxal3, NFAT-1 and v-jun), results in four alternatively spliced isoforms ($\alpha$, $\beta$, $\gamma$, and $\delta$). See, for example, Giganti, A., et al Murine and Human Autotaxin alpha, beta, and gamma Isoforms: Gene organization, tissue distribution and biochemical characterization. J Biol Chem 283, 7776-7789 (2008); and van Meeteren, L. A. & Moolenaar, W. H. Regulation and biological activities of the autotaxin-LPA axis. Prog Lipid Res 46, 145-160 (2007); Hashimoto, et al, "Identification and Biochemical Charaterization of a Novel Autotaxin Isoform, ATX$\delta$," J. of Biochemistry Advance Access (Oct. 11, 2011); each of which is incorporated by reference in its entirety.

ATX is synthesized as a prepro-enzyme, secreted into the extracellular space after the proteolytic removal of its N-terminal signal peptide (Jansen, S., el al Proteolytic maturation and activatio of autotaxin (NPP2), a secreted metastasis-enhancing lysophospho lipase D. J Cell Sci 118, 3081-3089 (2005), which is incorporated by reference in its entirety). ATX is a member of the ectonucleotide pyrophosphatase/phosphodiesterase family of ectoenzymes (E-NPP) that hydrolyze phosphodiesterase (PDE) bonds of various nucleotides and derivatives (Stefan, C, Jansen, S. & Bollen, M. NPP-type ectophosphodiesterases: unity in diversity. Trends Biochem Sci 30, 542-550 (2005), which is incorporated by reference in its entirety). The enzymatic activity of ATX was enigmatic, until it was shown to be identical to lysophospholipase D (lysoPLD) (Umezu-Goto, M., et al. Autotaxin has lysophospholipase D activity leading to tumor cell growth and motility by lysophosphatidic acid production. J Cell Biol 158, 227-233 (2002), which is incorporated by reference in its entirety), which is widely present in biological fluids. Since ATX is a constitutively active enzyme, the biological outcome of ATX action will largely depend on its expression levels and the local availability of its substrates. The major lysophospholipid substrate for ATX, lysophosphatidylcholine (LPC), is secreted by the liver and is abundantly present in plasma (at about 100 µM) as a predominantly albumin bound form (Croset, M., Brossard, N., Polette, A. & Lagarde, M. Characterization of plasma unsaturated lysophosphatidylcholines in human and rat Biochem J 345 Pt 1, 61-67 (2000), which is incorporated by reference in its entirety). LPC is also detected in tumor-cell conditioned media (Umezu-Goto, M., et al.), presumably as a constituent of shed microvesicles. ATX, through its lysoPLD activity converts LPC to lysophosphatidic acid (LPA).

LPC is an important inflammatory mediator with recognized effects in multiple cell types and pathophysiological processes. It is a major component of oxidized low density lipoprotein (oxLDL) and it can exist in several other forms including free, micellar, bound to hydrophobic proteins such as albumin and incorporated in plasma membranes. It is produced by the hydrolysis of phosphatidylcholine (PC) by PLA2 with concurrent release of arachidonic acid and in turn of other pro-inflammatory mediators (prostaglandins and leukotrienes). Moreover, LPC externalization constitutes a chemotactic signal to phagocytic cells, while interaction with its receptors can also stimulate lymphocytic responses. LPC has been shown to have therapeutic effects in experimental sepsis, possibly by suppressing endotoxin-induced HMGB1 release from macrophages/monocytes.

LPA, the product of ATX action on LPC, is a bioactive phospholipid with diverse functions in almost every mammalian cell line (Moolenaar, W. H., van Meeteren, L. A. & Giepmans, B. N. The ins and outs of lysophosphatidic acid signaling. Bioessays 28, 870-881 (2004), which is incorporated by reference in its entirety). LPA is a major constituent of serum bound tightly to albumin, gelsolin and possibly other as yet unidentified proteins. See, e.g., Goetzl, E. J., et al Gelsolin binding and. cellular presentation of lysophosphatidic acid. J Biol Chem 275, 14573-14578 (2000); and Tigyi, G. & Miledi, R, Lysophosphatidates bound to serum albumin activate membrane currents in *Xenopus oocytes* and neurite retraction in PC12 pheochromocytoma cells. J Biol Chem 267, 21360-21367 (1992); each of which is incoporated by reference in its entirety.

LPA is also found in other biofluids, such as saliva and follicular fluid, and has been implicated in a wide array of functions, such as wound heeling, tumor invasion and metastasis, neurogenesis, myelination, astrocytes outgrowth and neurite retraction. The long list of LPA functions was also explained with the discovery that it signals through G-protein coupled receptors (GPCRs), via classical second messenger pathways. Five mammalian cell-surface LPA receptors have been identified so far. The best known are LPA1-3 (namely Edg-2, Edg-4 and Edg7) which are all members of the so-called 'endothelial differentiation gene' (EDG) family of GPCRs (Contos, J. J., Ishii, I. & Chun, J. Lysophosphatidic acid receptors. Mol Pharmacol 58, 1188-1196 (2000), which is incorporated by reference in its entirety). LPA receptors can couple to at least three distinct G proteins ($G_q$, $G_i$ and $G_{12/13}$), which, in turn, feed into multiple effector systems. LPA activates $G_q$ and thereby stimulates phospholipase C (PLC), with subsequent phosphatidylinositol-bisphosphate hydrolysis and generation of multiple second messengers leading to protein kinase C activation and changes in cytosolic calcium. LPA also activates $G_i$, which leads to at least three distinct signaling routes: inhibition of adenylyl cyclase with inhibition of cyclic AMP accumulation; stimulation of the mitogenic RAS-MAPK (mitogen-activated protein kinase) cascade; and activation of phosphatidylinositol 3-kinase (PI3K), leading to activation of the guanosine diphosphate/guanosine triphosphate (GDP/GTP) exchange factor TIAM1 and the downstream RAC GTPase, as well as to activation of the AKT/PKB antiapoptotic pathway. Finally, LPA activates $G_{12/13}$, leading to activation of the small GTPase RhoA, which drives cytoskeletal contraction and cell rounding. So, LPA not only signals via classic second messengers such as calcium, diacylglycerol and cAMP, but it also activates RAS- and RHO-family GTPases, the master switches that control cell proliferation, migration and morphogenesis.

LPA signaling through the RhoA-Rho kinase pathway mediates neurite retraction and inhibition of axon growth. Interfering with LPA signaling has been shown to promote axonal regeneration and functional recovery after CNS injury or cerebral ischemia. (See Broggini, et al., *Molecular Biology of the Cell* (2010), 21:521-537.) It has been reported that addition of LPA to dorsal root fibers in ex vivo culture causes demyelination, whereas LPC fails to cause significant demyelination of nerve fibers in ex vivo cultures without further addition of recombinant ATX to the culture which when added caused significant demyelination at equivalent levels to LPA presumable due to conversion of LPC to LPA through the enzymatic activity of ATX. Moreover, injury induced demyelination was attenuated by about 50% in $atx^{+/-}$ mice (Nagai, et al., *Molecular Pain* (2010), 6:78).

A number of diseases or disorders involve demyelination of the central or peripheral nervous system which can occur for a number of reasons such as immune dysfunction as in multiple sclerosis, encephalomyelitis, Guillain-Barre Syndrome, chronic inflammatory demyelinating polyneuropathy (CIDP), transverse myelitis, and optic neuritis; demyelination due to injury such as spinal cord injury, traumatic brain injury, stroke, acute ischemic optic neuropathy, or other ischemia, cerebral palsy, neuropathy (e.g. neuropathy due to diabetes, chronic renal failure, hypothyroidism, liver failure, or compression of the nerve (e.g. in Bell's palsy)), post radiation injury, and central pontine myelolysis (CPM); inherited conditions such as Charcot-Marie-Tooth disease (CMT), Sjogren-Larsson syndrome, Refsum disease, Krabbe disease, Canavan disease, Alexander disease, Friedreich's ataxia, Pelizaeus-Merzbacher disease, Bassen-Kornzweig syndrome, metachromatic leukodystrophy (MLD), adrenoleukodystrophy, and nerve damage due to pernicious anemia; viral infection such as progressive multifocal leukoencephalopathy (PML), Lyme disease, or tabes dorsalis due to untreated syphilis; toxic exposure due to chronic alcoholism (which is a possible cause of Marchiafava-Bignami disease), chemotherapy, or exposure to chemicals such as organophosphates; or dietary deficiencies such as vitamin B12 deficiency, vitamin E deficiency and copper deficiency. Other demyelination disorders may have unknown causes or multiple causes such as trigeminal neuralgia, Marchiafava-Bignami disease and Bell's palsy. One particularly successful approach to treating demyelination disorders which are caused by autoimmune dysfunction has been to attempt to limit the extent of demyelination by treating the patient with immunoregulatory drugs. However, typically this approach has merely postponed but not avoided the onset of disability in these patients. Patients with demyelination due to other causes have even fewer treatment options. Therefore, the need exists to develop new treatments for patients with demyelination diseases or disorders.

SUMMARY

A compound of formula (I), or a pharmaceutically acceptable salt thereof, can be an S1P modulating agent and/or an ATX modulating agent, e.g., an S1P4 antagonist or ATX inhibitor.

In one aspect, a compound is represented by formula (I):

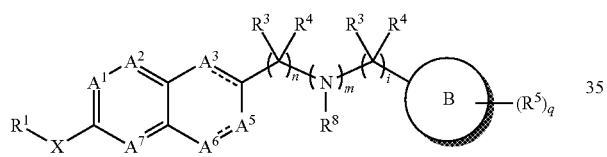

(I)

or a pharmaceutically acceptable salt thereof.

In formula (I), X can be O, $S(O)_r$, $NR^{12}$, C(O) or $CH_2$, in which r is 0, 1, or 2.

$A^1$, $A^2$, and $A^7$ can each independently be $CR^2$ or N.

$A^3$, $A^5$, and $A^6$ can each independently be $CR^2$, $C(R^2)_2$, N, or $NR^{19}$, wherein at least three of $A^1$, $A^2$, $A^3$, $A^5$, $A^6$, and $A^7$ are $CR^2$ or $C(R^2)_2$.

"------" indicates a double or a single bond.

$R^1$ can be a $C_{6-20}$alkyl, a $C_{3-14}$carbocyclyl, a 3- to 15-membered heterocyclyl, a $C_{6-10}$aryl, or a five- to 14-membered heteroaryl, wherein $R^1$ may be optionally substituted with from one to six independently selected $R^6$.

$R^2$, for each occurrence, can be independently selected from the group consisting of hydrogen, halo, hydroxyl, nitro, cyano, carboxy, $C_{1-6}$alkyl, $C_{1-6}$haloalkyl, $C_{3-8}$cycloalkyl, $C_{3-8}$halocycloalkyl, $C_{1-6}$alkoxy, $C_{1-6}$haloalkoxy, $C_{3-8}$cycloalkoxy, $C_{3-8}$halocycloalkoxy, $C_{1-6}$alkanoyl, amino, N—($C_{1-6}$alkyl)amino, N,N-di-($C_{1-6}$alkyl)amino, $C_{1-6}$alkoxycarbonyl, $C_{1-6}$alkanoyloxy, carbamoyl, N—($C_{1-6}$alkyl)carbamoyl, N,N-di-($C_{1-6}$alkyl)carbamoyl, $C_{1-6}$alkylamido, mercapto, $C_{1-6}$alkylthio, $C_{1-6}$alkylsulfonyl, sulfamoyl, N—($C_{1-6}$alkyl)sulfamoyl, N,N-di-($C_{1-6}$alkyl)sulfamoyl, and $C_{1-6}$alkylsulfonamido.

each $R^3$ and each $R^4$ can each independently be hydrogen, a carboxy, $C_{1-6}$alkyl, or a $C_{2-6}$alkenyl; or $R^3$ and $R^4$ together with the carbon to which they are attached are —C(=O)—, a $C_{3-8}$spirocycloalkyl, or a 3- to 8-membered spiroheterocycloalkyl.

B can be a fused ring system, a bridged ring system, a spiro ring system, or a combination thereof; or B is a bicyclic ring system represented by the following formula:

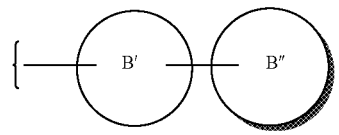

wherein B' and B" are each independently selected from the group consisting of monocyclic $C_{3-8}$carbocyclyl, a monocyclic 3- to 8-membered heterocyclyl, phenyl, or a 5- to 6-membered heteroaryl, wherein the heterocyclyl and the heteroaryl comprises 1 to 3 heteroatoms independently selected from N, S, or O; provided that when B is a fused ring system it is not 1H-benzo[d][1,2,3]triazole.

$R^5$, for each occurrence, can be independently hydroxyl, halo, $C_{1-6}$alkyl, or —$(CR^{17}R^{18})_p$—$R^7$; or two $R^5$ on the same carbon atom may be =O.

$R^6$, for each occurrence, can be independently selected from the group consisting of halo, $C_{1-6}$alkyl, $C_{1-6}$alkoxy, $C_{1-6}$haloalkyl, $C_{3-8}$cycloalkyl, $C_{6-10}$aryl, $C_{1-6}$alkoxy-$C_{1-6}$alkyl, and tri-($C_{1-6}$alkyl)silyl; or two $R^6$ that are attached to the same carbon atom may form $C_{3-8}$spirocycloalkyl or 3- to 8-membered spiroheterocycloalkyl.

$R^7$ can be —OH, —C(O)$OR^{15}$, —C(O)$N(R^{16})_2$, —C(O)$N(R^{15})$—S(O)$_2R^{15}$, —S(O)$_2OR^{15}$—C(O)NHC(O)$R^5$, —Si(O)OH, —B(OH)$_2$, —N($R^{15}$)S(O)$_2R^{15}$, —S(O)$_2$N($R^{15}$)$_2$, —O—P(O)(O$R^{15}$)$_2$, —P(O)(O$R^{15}$)$_2$, —CN, —S(O)$_2$NHC(O)$R^{15}$, —C(O)NHS(O)$_2R^{15}$, —C(O)NHOH, —C(O)NHCN, or a heteroaryl or a heterocyclyl selected from the group consisting of formulae (a)-(i'):

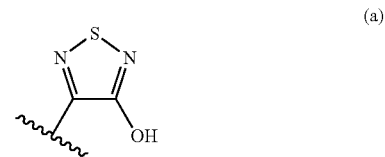

(a)

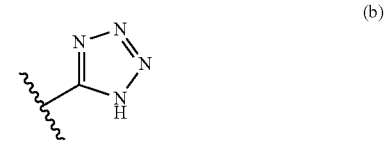

(b)

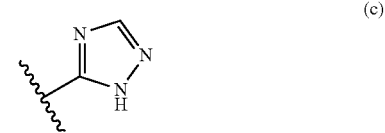

(c)

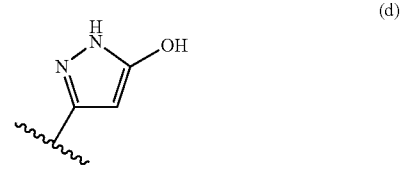

(d)

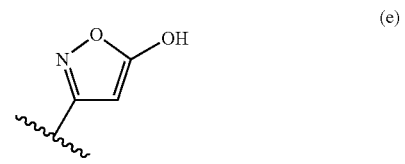

(e)

-continued
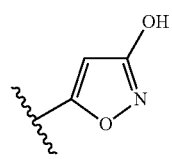 (f)
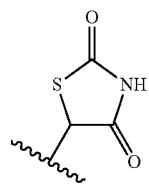 (g)
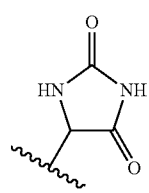 (h)
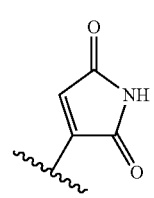 (i)
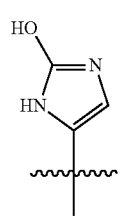 (j)
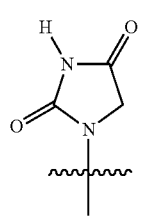 (k)
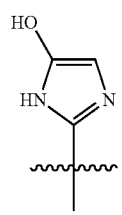 (l)
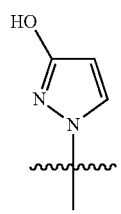 (m)
-continued
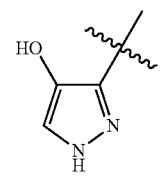 (n)
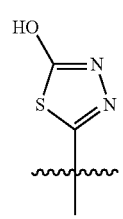 (o)
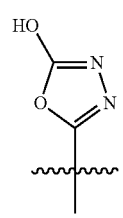 (p)
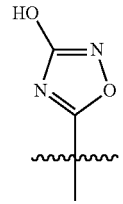 (q)
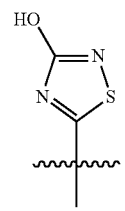 (r)
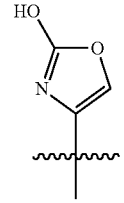 (s)
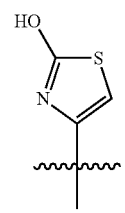 (t)

-continued
(u) 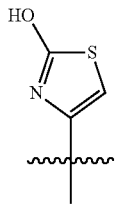
(v) 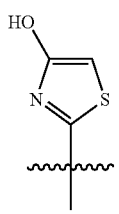
(w) 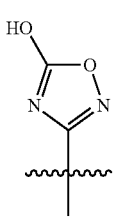
(x) 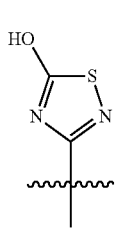
(y) 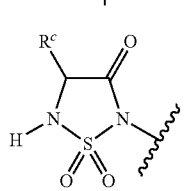
(z) 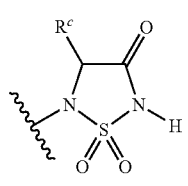
(a') 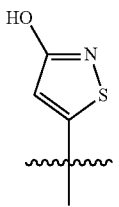
(b') 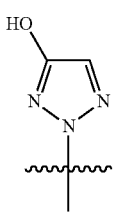
-continued
(c') 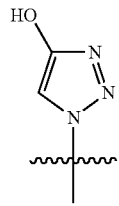
(d') 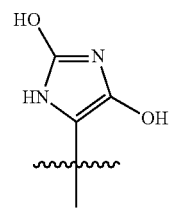
(e') 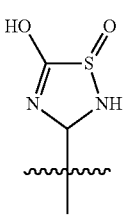
(f') 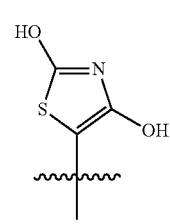
(g') 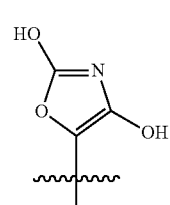
(h') 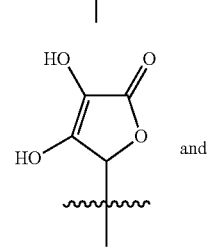
and
(i') 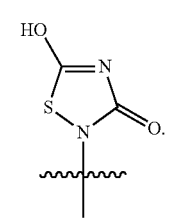
$R^8$, $R^{12}$, and $R^{19}$ can each independently be hydrogen or a $C_{1-6}$alkyl.
$R^{15}$ for each occurrence can be independently selected from the group consisting of hydrogen, $C_{1-6}$alkyl, $C_{2-6}$alkenyl, $C_{2-6}$alkynyl, $C_{3-8}$cycloalkyl, $C_{3-8}$cycloalkenyl, $C_{6-10}$aryl, a 5 to 14 membered heteroaryl, and a 3 to 15 membered heterocyclyl; wherein the heteroaryl or heterocyclyl comprises from 1 to 10 heteroatoms independently selected from O, N, or S; and wherein $R^{15}$ may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—($C_{1-4}$alkyl)sulfamoyl, and N,N—($C_{1-4}$dialkyl)-sulfamoyl.

$R^{16}$ can be $R^{15}$; or two $R^{16}$ together with the nitrogen atom to which they are attached can form a 5 to 14 membered heteroaryl or a 3 to 15 membered heterocyclyl, wherein the heteroaryl or heterocyclyl comprises from 1 to 10 heteroatoms independently selected from O, N, or S; and wherein the heteroaryl or heterocyclyl may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—$C_{1-4}$alkylsulfamoyl, and N,N—($C_{1-4}$dialkyl)-sulfamoyl.

$R^{17}$ and $R^{18}$, for each occurrence, can each independently be hydrogen, a halo, or a $C_{1-4}$haloalkyl.

$R^c$ is hydrogen or a $C_{1-4}$alkyl.

i can be an integer from 0 to 6.

n can be an integer from 1 to 6.

m can be 0 or 1, provided that when m is 0, B comprises at least one nitrogen.

p can be 0 or an integer from 1 to 6.

q can be 0, 1, 2, 3, or 4.

The compound is not 2-((6-(trans-4-tert-butylcyclohexyloxy)naphthalen-2-yl)methyl)octahydrocyclopenta[c]pyrrole-3a-carboxylic acid or 6-phenoxy-2-(2-(4-phenylpiperidin-1-yl)ethyl)-1,2,3,4-tetrahydronaphthalen-1-ol.

In some embodiments, q is 1 and $R^6$ is t-butyl.

In some embodiments, q is 1 and $R^6$ is methyl, ethyl or isopropyl.

In some embodiments, $R^6$ is trifluoromethyl, difluoromethyl or monofluoromethyl.

In some embodiments, B can be selected from the group consisting of 9-azabicyclo[3.3.1]nonanyl, 8-azabicyclo[3.2.1]octanyl, decahydroisoquinolinyl, 2-azaspiro[3.3]heptanyl, bicyclo[3.2.1]octanyl, 5-azaspiro[2.3]hexanyl, 3-cyclohexylazetidinyl, bicyclo[2.2.1]heptanyl, adamantyl, 6-oxa-9-azaspiro[4.5]decanyl, 3-azabicyclo[3.3.1]nonanyl, 6-oxa-2-azaspiro[3.4]octanyl, 4-(1H-imidazol-4-yl)piperidinyl, octahydro-1H-pyrido[1,2-a]pyrazinyl, 2,3-dihydro-1H-indenyl, (1R,5S)-bicyclo[3.1.0]hexanyl, 3-azabicyclo[3.1.1]heptanyl, 1-(pyridin-4-yl)piperazinyl, 1-(pyridin-2-yl)piperazinyl, 1-(pyridin-3-yl)piperazinyl, 2-oxa-6-azaspiro[3.3]heptanyl, 4-(pyrimidin-2-yl)piperazin-1-yl, 3-azabicyclo[3.3.1]nonanyl, 4-(pyridin-2-yl)piperidin-1-yl, 4-phenylpiperazin-1-yl, 4-phenylpiperidin-1-yl, 4-(pyrazin-2-yl)piperazin-1-yl, 4-(pyridin-2-yl)-1,4-diazepan-1-yl, 4-(pyrimidin-2-yl)-1,4-diazepan-1-yl, 4-(pyrimidin-4-yl)piperazin-1-yl, 2,7-diazaspiro[3.5]nonanyl, 3-phenylazetidinyl, 2-oxa-7-azaspiro[3.5]nonanyl, 3-azabicyclo[3.1.0]hexanyl, 2,8-diazaspiro[4.5]decanyl, 3-oxa-9-azabicyclo[3.3.1]nonanyl, 7-azabicyclo[2.2.1]heptanyl, spiro[3.5]nonanyl, and tricyclo[2.2.1.02,6]heptanyl.

In some embodiments, B can be a bridged ring system.

In some embodiments, m can be 1, B can be a ring system represented by the following formula:

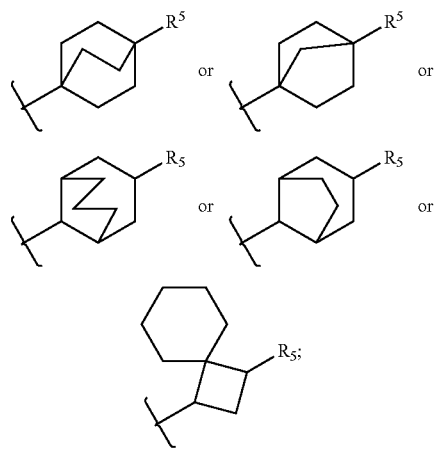

and $R^5$ can be $CO_2H$.

In some embodiments, B can be a bridged ring system represented by the following formula:

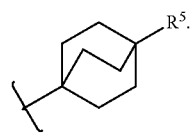

In some embodiments, m can be 0, B can be a ring system represented by the following formula:

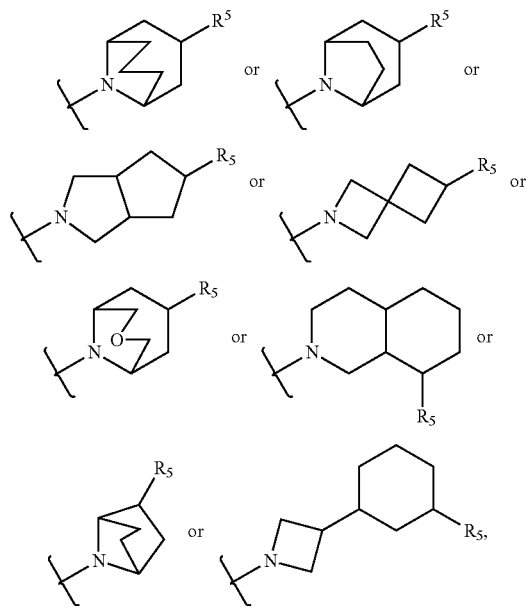

wherein B is optionally further substituted by oxo, hydroxy, —$NH_2$, —$CONH_2$, or —$CO_2H$; and $R^5$ can be $CO_2H$.

In some embodiments, the compound can be represented by formula (II):

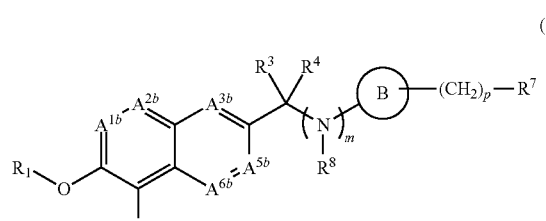

(II)

or a pharmaceutically acceptable salt thereof. In formula (II):

$A^{1b}$, $A^{2b}$, $A^{3b}$, $A^{5b}$, and $A^{6b}$ can be $CR^{2b}$ or N, wherein at least two of $A^{1b}$, $A^{2b}$, $A^{3b}$, $A^{5b}$, and $A^{6b}$ are $CR^{2b}$, $R^{2a}$ can be a halo, $C_{1-6}$haloalkyl or cyano, and $R^{2b}$, for each occurrence, can be independently selected from the group consisting of hydrogen, halo, hydroxyl, nitro, cyano, carboxy, $C_{1-6}$alkyl, $C_{1-6}$haloalkyl, $C_{3-8}$cycloalkyl, $C_{3-8}$halocycloalkyl, $C_{1-6}$alkoxy, $C_{1-6}$haloalkoxy, $C_{3-8}$cycloalkoxy, $C_{3-8}$halocycloalkoxy, $C_{1-6}$alkanoyl, amino, N—($C_{1-6}$alkyl)amino, N,N-di-($C_{1-6}$alkyl)amino, $C_{1-6}$alkoxycarbonyl, carbamoyl, N—($C_{i-6}$alkyl)carbamoyl, N,N-di-($C_{1-6}$alkyl)carbamoyl, $C_{1-6}$alkylamido, mercapto, $C_{1-6}$alkylthio, $C_{1-6}$alkylsulfonyl, sulfamoyl, N—($C_{1-6}$alkyl)sulfamoyl, N,N-di-($C_{1-6}$alkyl)sulfamoyl, and $C_{1-6}$alkylsulfonamido.

In some embodiments, $R^{2b}$, for each occurrence, can be independently hydrogen or a halo.

In some embodiments, compound can be represented by formula (IIa):

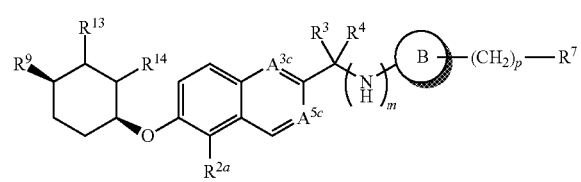

or a pharmaceutically acceptable salt thereof. In formula (IIa):

$A^{3c}$ and $A^{5c}$ can be N or CH, provided that only one of $A^{3c}$ or $A^{5c}$ is N, $R^9$ can be a halo, an $C_{1-6}$alkyl, or a $C_{1-6}$haloalkyl, and $R^{13}$ and $R^{14}$ can each independently be hydrogen or a $C_{1-6}$alkyl.

In some embodiments, the compound can be represented by formula (IIb):

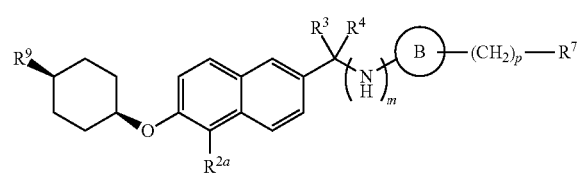

or a pharmaceutically acceptable salt thereof.

In some embodiments, m can be 0, B can be a ring system represented by the following formula:

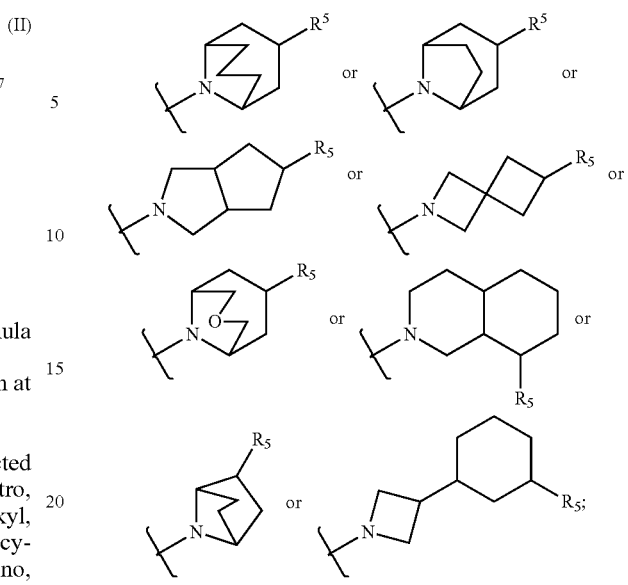

wherein B is optionally further substituted by oxo, hydroxy, —$NH_2$, —$CONH_2$, or —$CO_2H$; and $R^5$ can be $CO_2H$.

In some embodiments, $R^{2a}$ can be —Cl, —$CF_3$ or —$CHF_2$.

In some embodiments, $R^9$ can be methyl, ethyl, —$CF_3$ or tert-butyl.

In some embodiments, the compound can be represented by formula (III):

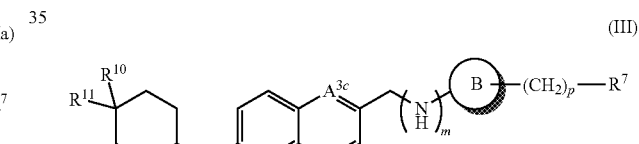

or a pharmaceutically acceptable salt thereof. In formula (III):

$A^{3c}$ can be N or CH, and $R^{10}$ and $R^{11}$ can each independently be hydrogen, $C_{1-6}$alkyl, $C_{1-6}$haloalkyl, tri-$C_{1-6}$alkylsilyl, or phenyl, wherein at least one of $R^{10}$ or $R^{11}$ is not hydrogen; or $R^{10}$ and $R^{11}$ together with the carbon to which they are attached form a $C_{3-8}$spirocycloalkyl or 3- to 8-membered spiroheterocycloalkyl.

In some embodiments, m can be 1, B can be a bridged ring system represented by the following formula:

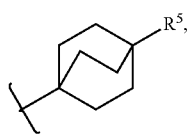

and $R^5$ can be $CO_2H$.

In some embodiments, X can be NH.

In some embodiments, the compound, or a pharmaceutically acceptable salt thereof, is selected from the group consisting of:

4-(((6-(cyclohexyloxy)naphthalen-2-yl)methyl)amino) bicyclo[2.2.2]octane-1-carboxylic acid;

4-(((6-((trans-4-methylcyclohexyl)oxy)naphthalen-2-yl)methyl)amino)bicyclo[2.2.2]octane-1-carboxylic acid;
4-(((6-((trans-4-ethylcyclohexyl)oxy)naphthalen-2-yl)methyl)amino)bicyclo[2.2.2]octane-1-carboxylic acid;
4-(((6-((trans-4-isopropylcyclohexyl)oxy)naphthalen-2-yl)methyl)amino)bicyclo[2.2.2]octane-1-carboxylic acid;
4-(((6-((trans-4-(tert-pentyl)cyclohexyl)oxy)naphthalen-2-yl)methyl)amino)bicyclo[2.2.2]octane-1-carboxylic acid;
4-(((6-((trans-4-phenylcyclohexyl)oxy)naphthalen-2-yl)methyl)amino)bicyclo[2.2.2]octane-1-carboxylic acid;
4-(((6-((4,4-dimethylcyclohexyl)oxy)naphthalen-2-yl)methyl)amino)bicyclo[2.2.2]octane-1-carboxylic acid;
4-(((6-(spiro[2.5]octan-6-yloxy)naphthalen-2-yl)methyl)amino)bicyclo[2.2.2]octane-1-carboxylic acid;
4-(((6-(spiro[3.5]nonan-7-yloxy)naphthalen-2-yl)methyl)amino)bicyclo[2.2.2]octane-1-carboxylic acid;
4-(((6-(spiro[4.5]decan-8-yloxy)naphthalen-2-yl)methyl)amino)bicyclo[2.2.2]octane-1-carboxylic acid;
4-(((6-(spiro[5.5]undecan-3-yloxy)naphthalen-2-yl)methyl)amino)bicyclo[2.2.2]octane-1-carboxylic acid;
4-(((6-(heptyloxy)naphthalen-2-yl)methyl)amino)bicyclo[2.2.2]octane-1-carboxylic acid;
4-(((6-((cis-4-methylcyclohexyl)oxy)naphthalen-2-yl)methyl)amino)bicyclo[2.2.2]octane-1-carboxylic acid;
4-(((6-((cis-4-ethylcyclohexyl)oxy)naphthalen-2-yl)methyl)amino)bicyclo[2.2.2]octane-1-carboxylic acid;
4-(((6-((cis-4-isopropylcyclohexyl)oxy)naphthalen-2-yl)methyl)amino)bicyclo[2.2.2]octane-1-carboxylic acid;
4-(((6-((cis-4-(trifluoromethyl)cyclohexyl)oxy)naphthalen-2-yl)methyl)amino)bicyclo[2.2.2]octane-1-carboxylic acid;
4-(((6-((cis-4-phenylcyclohexyl)oxy)naphthalen-2-yl)methyl)amino)bicyclo[2.2.2]octane-1-carboxylic acid;
4-(((6-((trans-4-(trifluoromethyl)cyclohexyl)oxy)naphthalen-2-yl)methyl)amino)bicyclo[2.2.2]octane-1-carboxylic acid;
4-(((6-((cis-4-(tert-butyl)cyclohexyl)oxy)naphthalen-2-yl)methyl)amino)bicyclo[2.2.2]octane-1-carboxylic acid;
4-(((6-(cyclohexyloxy)quinolin-2-yl)methyl)amino)bicyclo[2.2.2]octane-1-carboxylic acid;
4-(((6-((trans-4-methylcyclohexyl)oxy)quinolin-2-yl)methyl)amino)bicyclo[2.2.2]octane-1-carboxylic acid;
4-(((6-((trans-4-ethylcyclohexyl)oxy)quinolin-2-yl)methyl)amino)bicyclo[2.2.2]octane-1-carboxylic acid;
4-(((6-((trans-4-isopropylcyclohexyl)oxy)quinolin-2-yl)methyl)amino)bicyclo[2.2.2]octane-1-carboxylic acid;
4-(((6-((trans-4-(tert-pentyl)cyclohexyl)oxy)quinolin-2-yl)methyl)amino)bicyclo[2.2.2]octane-1-carboxylic acid;
4-(((6-((trans-4-phenylcyclohexyl)oxy)quinolin-2-yl)methyl)amino)bicyclo[2.2.2]octane-1-carboxylic acid;
4-(((6-((4,4-dimethylcyclohexyl)oxy)quinolin-2-yl)methyl)amino)bicyclo[2.2.2]octane-1-carboxylic acid;
4-(((6-(spiro[2.5]octan-6-yloxy)quinolin-2-yl)methyl)amino)bicyclo[2.2.2]octane-1-carboxylic acid;
4-(((6-(spiro[3.5]nonan-7-yloxy)quinolin-2-yl)methyl)amino)bicyclo[2.2.2]octane-1-carboxylic acid;
4-(((6-(spiro[4.5]decan-8-yloxy)quinolin-2-yl)methyl)amino)bicyclo[2.2.2]octane-1-carboxylic acid;
4-(((6-(spiro[5.5]undecan-3-yloxy)quinolin-2-yl)methyl)amino)bicyclo[2.2.2]octane-1-carboxylic acid;
4-(((6-(heptyloxy)naphthalen-2-yl)methyl)amino)bicyclo[2.2.2]octane-1-carboxylate;
4-(((6-((cis-4-methylcyclohexyl)oxy)quinolin-2-yl)methyl)amino)bicyclo[2.2.2]octane-1-carboxylic acid;
4-(((6-((cis-4-ethylcyclohexyl)oxy)quinolin-2-yl)methyl)amino)bicyclo[2.2.2]octane-1-carboxylic acid;
4-(((6-((cis-4-isopropylcyclohexyl)oxy)quinolin-2-yl)methyl)amino)bicyclo[2.2.2]octane-1-carboxylic acid;
4-(((6-((cis-4-(trifluoromethyl)cyclohexyl)oxy)quinolin-2-yl)methyl)amino)bicyclo[2.2.2]octane-1-carboxylic acid;
4-(((6-((cis-4-phenylcyclohexyl)oxy)quinolin-2-yl)methyl)amino)bicyclo[2.2.2]octane-1-carboxylic acid;
4-(((6-((trans-4-(tert-butyl)cyclohexyl)oxy)-5-(trifluoromethyl)naphthalen-2-yl)methyl)amino)bicyclo[2.2.2]octane-1-carboxylic acid;
4-(((6-((trans-4-(tert-butyl)cyclohexyl)oxy)-5-(trifluoromethyl)quinolin-2-yl)meth yl)amino)bicyclo[2.2.2]octane-1-carboxylic acid;
2-(1-((6-((trans-4-(tert-butyl)cyclohexyl)oxy)naphthalen-2-yl)methyl)piperidin-4-yl)pyridine;
2-(1-((6-((trans-4-(tert-butyl)cyclohexyl)oxy)naphthalen-2-yl)methyl)piperidin-4-yl)pyrimidine; 1-((6-((trans-4-(tert-butyl)cyclohexyl)oxy)naphthalen-2-yl)methyl)-4-phenylpiperazine;
1-((6-((trans-4-(tert-butyl)cyclohexyl)oxy)naphthalen-2-yl)methyl)-4-(pyridin-3-yl)piperazine;
1-((6-((trans-4-(tert-butyl)cyclohexyl)oxy)naphthalen-2-yl)methyl)-4-(pyridin-2-yl)-1,4-diazepane;
2-(4-((6-((trans-4-(tert-butyl)cyclohexyl)oxy)naphthalen-2-yl)methyl)piperazin-1-yl)pyrimidine;
2-(4-((6-((trans-4-(tert-butyl)cyclohexyl)oxy)naphthalen-2-yl)methyl)piperazin-1-yl)pyrazine;
1-((6-((trans-4-(tert-butyl)cyclohexyl)oxy)naphthalen-2-yl)methyl)-4-(pyridin-4-yl)piperazine;
1-((6-((trans-4-(tert-butyl)cyclohexyl)oxy)naphthalen-2-yl)methyl)-4-(pyrimidin-2-yl)-1,4-diazepane;
4-(4-((6-((trans-4-(tert-butyl)cyclohexyl)oxy)naphthalen-2-yl)methyl)piperazin-1-yl)pyrimidine;
4-(4-((6-((trans-4-(tert-butyl)cyclohexyl)oxy)naphthalen-2-yl)methyl)piperazin-1-yl)-2-methylpyrimidine;
1-((6-((trans-4-(tert-butyl)cyclohexyl)oxy)naphthalen-2-yl)methyl)-4-phenylpiperidine;
1-((6-((trans-4-(tert-butyl)cyclohexyl)oxy)naphthalen-2-yl)methyl)-4-(pyridin-2-yl)piperazine;
1-((6-((cis-4-isopropylcyclohexyl)oxy)naphthalen-2-yl)methyl)-4-(pyridin-2-yl)piperazine;
1-((6-((cis-4-ethylcyclohexyl)oxy)naphthalen-2-yl)methyl)-4-(pyridin-2-yl)piperazine;
1-(pyridin-2-yl)-4-((6-(spiro[4.5]decan-8-yloxy)naphthalen-2-yl)methyl)piperazine;
1-((6-(heptyloxy)naphthalen-2-yl)methyl)-4-(pyridin-2-yl)piperazine;
6-((cis-4-isopropylcyclohexyl)oxy)-2-((4-(pyridin-2-yl)piperazin-1-yl)methyl)quinoline;
3-(1-((6-((cis-4-isopropylcyclohexyl)oxy)naphthalen-2-yl)methyl)azetidin-3-yl)cyclohexanecarboxylic acid;
3-(1-((6-((trans-4-(tert-butyl)cyclohexyl)oxy)naphthalen-2-yl)methyl)azetidin-3-yl)cyclohexanecarboxylic acid;
3-(1-((6-((4,4-dimethylcyclohexyl)oxy)quinolin-2-yl)methyl)azetidin-3-yl)cyclohexanecarboxylic acid;
3-(1-((6-(heptyloxy)naphthalen-2-yl)methyl)azetidin-3-yl)cyclohexanecarboxylic acid;
3-(1-((6-((cis-4-ethylcyclohexyl)oxy)naphthalen-2-yl)methyl)azetidin-3-yl)cyclohexanecarboxylic acid;
3-(1-((6-((4,4-dimethylcyclohexyl)oxy)naphthalen-2-yl)methyl)azetidin-3-yl)cyclohexanecarboxylic acid;
3-(1-((6-(spiro[4.5]decan-8-yloxy)naphthalen-2-yl)methyl)azetidin-3-yl)cyclohex anecarboxylic acid;
3-(1-((6-((cis-4-ethylcyclohexyl)oxy)quinolin-2-yl)methyl)azetidin-3-yl)cyclohex anecarboxylic acid;
3-(1-((6-((cis-4-isopropylcyclohexyl)oxy)quinolin-2-yl)methyl)azetidin-3-yl)cyclohexanecarboxylic acid;

4-(1-((6-((trans-4-(tert-butyl)cyclohexyl)oxy)naphthalen-2-yl)methyl)azetidin-3-yl)cyclohexanecarboxylic acid;
6-((6-((trans-4-(tert-butyl)cyclohexyl)oxy)naphthalen-2-yl)methyl)-2-oxa-6-azaspiro [3.3]heptane;
3-((6-((trans-4-(tert-butyl)cyclohexyl)oxy)naphthalen-2-yl)methyl)-3-azabicyclo[3.1.0]hexane-6-carboxylic acid;
4-(((6-((trans-4-(tert-butyl)cyclohexyl)oxy)quinolin-2-yl)methyl)amino)bicyclo[2.2.2]octane-1-carboxylic acid;
4-(((6-((trans-4-(tert-butyl)cyclohexyl)oxy)naphthalen-2-yl)methyl)(methyl)amino)bicyclo[2.2.2]octane-1-carboxylic acid;
8-((6-((trans-4-(tert-butyl)cyclohexyl)oxy)naphthalen-2-yl)methyl)-8-azabicyclo[3.2.1]octane-3-carboxylic acid;
9-((6-((trans-4-(tert-butyl)cyclohexyl)oxy)naphthalen-2-yl)methyl)-9-azabicyclo[3.3.1]nonane-3-carboxylic acid;
3-((6-((trans-4-(tert-butyl)cyclohexyl)oxy)naphthalen-2-yl)methyl)-3-azabicyclo[3.3.1]nonane-9-carboxylic acid;
3-((6-((trans-4-(tert-butyl)cyclohexyl)oxy)naphthalen-2-yl)methyl)-3-azabicyclo [3.1.1]heptane-6-carboxylic acid;
4-(((6-((trans-4-(tert-butyl)cyclohexyl)oxy)naphthalen-2-yl)methyl)amino)bicyclo[2.2.1]heptane-1-carboxylic acid;
4-(((6-((trans-4-(tert-butyl)cyclohexyl)oxy)-5-(trifluoromethyl)naphthalen-2-yl)methyl)amino)bicyclo [2.2.1]heptane-1-carboxylic acid;
4-((6-(trans-4-(Trimethylsilyl)cyclohexyloxy)naphthalen-2-yl)methylamino)bicyclo [2.2.2]octane-1-carboxylic acid;
4-(((6-((cis-4-(Trimethylsilyl)cyclohexyl)oxy)naphthalen-2-yl)methyl)amino)bicyclo [2.2.2]octane-1-carboxylic acid;
4-((6-(trans-4-tert-Butylcyclohexyloxy)naphthalen-2-yl)methylamino)-2-hydroxybicyclo[2.2.2]octane-1-carboxylic acid;
4-((6-(trans-4-tert-Butylcyclohexyloxy)naphthalen-2-yl)methylamino)-1-(hydroxymethyl)bicyclo[2.2.2]octan-2-ol; and
4-(((6-((trans-4-(tert-butyl)cyclohexyl)oxy)naphthalen-2-yl)methyl)amino)bicyclo[2.2.2]octane-1-carboxylic acid;
or a pharmaceutically acceptable salt thereof.

In some embodiments, a compound can be selected from the group consisting of:
9-((6-((cis-4-ethylcyclohexyl)oxy)naphthalen-2-yl)methyl)-9-azabicyclo[3.3.1]nonane-3-carboxylic acid;
9-((5-(trifluoromethyl)-6-((cis-4-(trifluoromethyl)cyclohexyl)oxy)naphthalen-2-yl)methyl)-9-azabicyclo[3.3.1]nonane-3-carboxylic acid;
3-(((5-(trifluoromethyl)-6-((cis-4-(trifluoromethyl)cyclohexyl)oxy)naphthalene-2-yl)methyl)amino)spiro[3.5]nonane-1-carboxylic acid;
3-(4-{[5-trifluoromethyl-6-(4-trifluoromethyl-cyclohexyloxy)-naphthalen-2-ylmethyl]-amino}-bicyclo[2.2.2]oct-1-yl)-propionic acid;
3-(4-(methyl((5-(trifluoromethyl)-6-((cis-4-(trifluoromethyl)cyclohexyl)oxy)naphthalene-2-yl)methyl)amino)bicyclo[2.2.2]octan-1-yl)propanoic acid;
9-1-(5-(trifluoromethyl)-6-((cis-4-(trifluoromethyl)cyclohexyl)oxy)naphthalen-2-yl)ethyl)-9-azabicyclo[3.3.1]nonane-3-carboxylic acid;
9-((R)-1-(5-(trifluoromethyl)-6-((cis-4-(trifluoromethyl)cyclohexyl)oxy)naphthalen-2-yl)ethyl)-9-azabicyclo[3.3.1]nonane-3-carboxylic acid;
9-((S)-1-(5-(trifluoromethyl)-6-((cis-4-(trifluoromethyl)cyclohexyl)oxy)naphthalen-2-yl)ethyl)-9-azabicyclo[3.3.1]nonane-3-carboxylic acid;
9-(1-(6-(((cis-4-ethylcyclohexyl)oxy)-5-(trifluoromethyl)naphthalene-2-yl)ethyl)-9-azabicyclo[3.3.1]-nonane-3-carboxylic acid;
9-(1-(6-((cis-4-ethylcyclohexyl)oxy)-5-(trifluoromethyl)naphthalene-2-yl)propyl)-9-azabicyclo[3.3.1]nonane-3-carboxylic acid;
9-(1-(6-((cis-4-Methylcyclohexyl)oxy)-5-(trifluoromethyl)naphthalen-2-yl)ethyl)-9-azabicyclo[3.3.1]nonane-3-carboxylic acid;
9-(1-(6-((cis-4-Methylcyclohexyl)oxy)-5-(trifluoromethyl)naphthalen-2-yl)ethyl)-9-azabicyclo[3.3.1]nonane-3-carboxylic acid, enantiomer 1;
9-(1-(6-((cis-4-Methylcyclohexyl)oxy)-5-(trifluoromethyl)naphthalen-2-yl)ethyl)-9-azabicyclo[3.3.1]nonane-3-carboxylic acid, enantiomer 2;
8-((6-((cis-4-Methylcyclohexyl)oxy)-5-(trifluoromethyl)naphthalen-2-yl)methyl)-8-azabicyclo[3.2.1]octane-3-carboxylic acid;
9-((6-((cis-4-Methylcyclohexyl)oxy)-5-(trifluoromethyl)naphthalen-2-yl)methyl)-9-azabicyclo[3.3.1]nonane-3-carboxylic acid;
9-((6-((4,4-difluorocyclohexyl)oxy)-5-(trifluoromethyl)naphthalene-2-yl)methyl)-9-azabicyclo[3.3.1]nonane-3-carboxylic acid;
8-(1-(5-(difluoromethyl)-6-((cis-4-methylcyclohexyl)oxy)naphthalen-2-yl)propyl)-8-azabicyclo[3.2.1]octane-3-carboxylic acid;
9-((5-(difluoromethyl)-6-((cis-4-(trifluoromethyl)cyclohexyl)oxy)naphthalene-2-yl)methyl)-9-azabicyclo[3.3.1]nonane-3-carboxylic acid;
9-((5-(trifluoromethyl)-6-((cis-4-(trifluoromethyl)cyclohexyl)oxy)quinolin-2-yl)methyl)-9-azabicyclo[3.3.1]nonane-3-carboxylic acid;
8-(1-(5-(trifluoromethyl)-6-((cis-4-(trifluoromethyl)cyclohexyl)oxy)quinolin-2-yl)ethyl)-8-azabicyclo[3.2.1]octane-3-carboxylic acid;
9-((6-(((trans,trans)-3,5-dimethylcyclohexyl)oxy)-5-(trifluoromethyl) naphthalene-2-yl)methyl)-9-azabicyclo[3.3.1]nonane-3-carboxylic acid;
8-(6-((cis-4-Methylcyclohexyl)oxy)-5-(trifluoromethyl)-2-naphthoyl)-8-azabicyclo[3.2.1]octane-3-carboxylic acid;
9-(5-(trifluoromethyl)-6-((cis-4-(trifluoromethyl)cyclohexyl)oxy)-2-naphthoyl)-9-azabicyclo[3.3.1]nonane-3-carboxylic acid;
9-(2-(5-(trifluoromethyl)-6-((cis-4-(trifluoromethyl)cyclohexyl)oxy)naphthalene-2-yl)acetyl)-9-azabicyclo[3.3.1]nonane-3-carboxylic acid;
9-(2-(5-(trifluoromethyl)-6-((cis-4-(trifluoromethyl)cyclohexyl)oxy)naphthalene-2-yl)ethyl)-9-azabicyclo[3.3.1]nonane-3-carboxylic acid;
9-((6-((cis-4-methylcyclohexyl)amino)-5-(trifluoromethyl)naphthalen-2-yl)methyl)-9-azabicyclo[3.3.1]nonane-3-carboxylic acid;
2-(9-Azabicyclo[3.3.1]nonan-9-yl)-2-(6-((cis-4-methylcyclohexyl)oxy)-5-(trifluoromethyl)naphthalen-2-yl)acetic acid;
9-((5-Chloro-6-((cis-4-ethylcyclohexyl)oxy)naphthalen-2-yl)methyl)-9-azabicyclo[3.3.1]nonane-3-carboxylic acid;
9-((5-Chloro-6-((cis-4-(trifluoromethyl)cyclohexyl)oxy)naphthalen-2-yl)methyl)-9-azabicyclo[3.3.1]nonane-3-carboxylic acid;
4-(((5-(trifluoromethyl)-6-((cis-4-(trifluoromethyl)cyclohexyl)oxy)naphthalen-2-yl)methyl)carbamoyl)bicyclo[2.2.2]octane-1-carboxylic acid;
N-(6-((cis-4-trifluoromethylcyclohexyl)oxy)-5-(trifluoromethyl)naphthalene-2-ylcarbonyl)-1-aminoindane-6-carboxylic acid;
N-(6-((cis-4-trifluoromethylcyclohexyl)oxy)-5-(trifluoromethyl)naphthalene-2-ylcarbonyl)-6-aminoindole-3-carboxylic acid;

N-(6-((cis-4-trifluoromethylcyclohexyl)oxy)-5-(trifluoromethyl)naphthalene-2-ylcarbonyl)-2-azabicyclo[1.2.3]octane-7-carboxylic acid;
N-(6-((cis-4-trifluoromethylcyclohexyl)oxy)-5-(trifluoromethyl)naphthalene-2-ylcarbonyl)-decahydroisoquinoline-5-carboxylic acid;
2-(2-(5-(trifluoromethyl)-6-((cis-4-(trifluoromethyl)cyclohexyl)oxy)naphthalene-2-yl)acetyl)-2-azabicyclo[1.2.3]octane-7-carboxylic acid;
2-(2-(5-(difluoromethyl)-6-((cis-4-(trifluoromethyl)cyclohexyl)oxy)naphthalene-2-yl)acetyl)-2-azabicyclo[1.2.3]octane-7-carboxylic acid;
4-(((5-(trifluoromethyl)-6-((cis-4-(trifluoromethyl)cyclohexyl)oxy)naphthalen-2-yl)methyl)aminomethyl)bicyclo[2.2.2]octane-1-carboxylic acid;
4-(((5-(trifluoromethyl)-6-((cis-4-(trifluoromethyl)cyclohexyl)oxy)naphthalen-2-yl)methyl)amino)-2-hydroxybicyclo[2.2.2]octane-1-carboxylic acid;
7-(((5-(trifluoromethyl)-6-((cis-4-(trifluoromethyl)cyclohexyl)oxy)naphthalen-2-yl)methyl)amino)-tricyclo[3.1.1.0]heptane-5-carboxylic acid;
8-(1-(5-(trifluoromethyl)-6-((cis-4-(trifluoromethyl)cyclohexyl)oxy)-naphthalene-2-yl)ethyl)-8-azabicyclo[3.2.1]octane-3-carboxylic acid;
3-(((5-(trifluoromethyl)-6-((cis-4-(trifluoromethyl)cyclohexyl)oxy)naphthalen-2-yl)methyl)amino)-7,7-dimethylbicyclo[2.2.1]heptane-4-carboxylic acid;
8-(1-(6-((cis-4-Methylcyclohexyl)oxy)-5-(trifluoromethyl)naphthalen-2-yl)ethyl)-8-azabicyclo[3.2.1]octane-3-carboxylic acid;
9-(6-((cis-4-Methylcyclohexyl)oxy)-5-(trifluoromethyl)-2-naphthoyl)-9-azabicyclo[3.3.1]nonane-3-carboxylic acid;
9-((6-((cis-4-Methylcyclohexyl)oxy)-5-(trifluoromethyl)naphthalen-2-yl)methyl)-9-aza-7-oxa-bicyclo[3.3.1]nonane-3-carboxylic acid;
8-(1-(6-((cis-4-Methylcyclohexyl)oxy)-5-(trifluoromethyl)naphthalen-2-yl)propyl)-8-azabicyclo[3.2.1]octane-3-carboxylic acid;
9-(1-(6-((cis-4-Methylcyclohexyl)oxy)-5-(trifluoromethyl)naphthalen-2-yl)propyl)-9-azabicyclo[3.3.1]nonane-3-carboxylic acid;
9-(6-((cis-4-Methylcyclohexyl)oxy)-5-(trifluoromethyl)naphthalen-2-yl)methyl)-7-hydroxy-9-aza-bicyclo[3.3.1]nonane-3-carboxylic acid;
8-(1-(6-((cis-4-Methylcyclohexyl)oxy)-5-(trifluoromethyl)naphthalen-2-yl)ethyl)-8-azabicyclo[3.2.1]octane-3-carboxylic acid, enantiomer 1;
8-(1-(6-((cis-4-Methylcyclohexyl)oxy)-5-(trifluoromethyl)naphthalen-2-yl)ethyl)-8-azabicyclo[3.2.1]octane-3-carboxylic acid, enantiomer 2;
9-(1-(5-(difluoromethyl)-6-((cis-4-methylcyclohexyl)oxy)naphthalen-2-yl)ethyl)-9-azabicyclo[3.3.1]nonane-3-carboxylic acid;
8-(1-(5-(difluoromethyl)-6-((cis-4-methylcyclohexyl)oxy)naphthalen-2-yl)ethyl)-8-azabicyclo[3.2.1]octane-3-carboxylic acid;
8-(1-(5-(difluoromethyl)-6-((cis-4-methylcyclohexyl)oxy)naphthalen-2-yl)methyl)-8-azabicyclo[3.2.1]octane-3-carboxylic acid;
9-(1-(5-(difluoromethyl)-6-((cis-4-methylcyclohexyl)oxy)naphthalen-2-yl)propyl)-9-azabicyclo[3.3.1]nonane-3-carboxylic acid;
8-(1-(5-(difluoromethyl)-6-((cis-4-methyl)-8-azabicyclo[3.2.1]octane-3-carboxylic acid, enantiomer 1;
8-(1-(5-(difluoromethyl)-6-((cis-4-methyl)-8-azabicyclo[3.2.1]octane-3-carboxylic acid, enantiomer 1;
9-(1-(5-(difluoromethyl)-6-((cis-4-methylcyclohexyl)oxy)naphthalen-2-yl)ethyl)-9-azabicyclo[3.3.1]nonane-3-carboxylic acid, enantiomer 1;
9-(1-(5-(difluoromethyl)-6-((cis-4-methylcyclohexyl)oxy)naphthalen-2-yl)ethyl)-9-azabicyclo[3.3.1]nonane-3-carboxylic acid, enantiomer 2;
8-(1-(5-(difluoromethyl)-6-((cis-4-methylcyclohexyl)oxy)naphthalen-2-yl)propyl)-8-azabicyclo[3.2.1]octane-3-carboxylic acid, enantiomer 1;
8-(1-(5-(difluoromethyl)-6-((cis-4-methylcyclohexyl)oxy)naphthalen-2-yl)propyl)-8-azabicyclo[3.2.1]octane-3-carboxylic acid, enantiomer 2;
9-((6-((cis-4-trifluoromethylcyclohexyl)oxy)naphthalen-2-yl)methyl)-9-azabicyclo[3.3.1]nonane-3-carboxylic acid;
methyl 2-((5-(trifluoromethyl)-6-((cis-4-(trifluoromethyl)cyclohexyl)oxy)naphthalen-2-yl)methyl)-(7R,9aR)-octahydro-1H-pyrido[1,2-a]pyrazine-7-carboxylic acid;
3-(4-{[5-trifluoromethyl-6-(4-trifluoromethyl-cyclohexyloxy)-naphthalen-2-ylmethyl]-amino}-bicyclo[2.2.2]oct-1-yl)-carboxylic acid;
2-((5-(trifluoromethyl)-6-((cis-4-(trifluoromethyl)cyclohexyl)oxy)naphthalen-2-yl)methyl)-(7R,9aR)-octahydro-1H-pyrido[1,2-a]pyrazine-7-carboxylic acid;
2-((5-(trifluoromethyl)-6-((cis-4-(trifluoromethyl)cyclohexyl)oxy)naphthalen-2-yl)methyl)-2-azaspiro[3.3]heptane-6-carboxylic acid;
N-((5-(trifluoromethyl)-6-((cis-4-(trifluoromethyl)cyclohexyl)oxy)naphthalen-2-yl)methyl)-3-amino-indane-5-carboxylic acid;
3-((5-(trifluoromethyl)-6-((cis-4-(trifluoromethyl)cyclohexyl)oxy)naphthalen-2-yl)methyl)-3-azabicyclo[3.1.0]hexane-6-carboxylic acid;
2-((5-(trifluoromethyl)-6-((cis-4-(trifluoromethyl)cyclohexyl)oxy)naphthalen-2-yl)methyl)-2-azaspiro[3.2]hexane-5-carboxylic acid;
N-((5-(trifluoromethyl)-6-((cis-4-(trifluoromethyl)cyclohexyl)oxy)naphthalen-2-yl)methyl)-decahydroisoquinoline-8-carboxylic acid;
3-((6-((cis-4-trifluoromethylcyclohexyl)oxy)naphthalen-2-yl)methyl)-3-azabicyclo[3.3.1]nonane-9-carboxylic acid;
N-(5-trifluoromethyl-6-(4-trifluoromethyl-cyclohexyloxy)-naphthalen-2-ylmethyl)-4-aminobicyclo[2.2.1]heptane-1-carboxylic acid;
N-(5-trifluoromethyl-6-(4-trifluoromethyl-cyclohexyloxy)-naphthalen-2-ylmethyl)-1-aminoadamantane-3-carboxylic acid;
3-(5-trifluoromethyl-6-(4-trifluoromethyl-cyclohexyloxy)-naphthalen-2-ylmethyl)-3-azabicyclo[3.3.0]octane-7-carboxylic acid;
2-((5-(trifluoromethyl)-6-((cis-4-(trifluoromethyl)cyclohexyl)oxy)naphthalen-2-yl)methyl)-((9S,9aR)-octahydro-1H-pyrido[1,2-a]pyrazin-9-yl)methanol;
8-((6-((4,4-difluorocyclohexyl)oxy)-5-(trifluoromethyl)naphthalene-2-yl)methyl)-8-azabicyclo[3.2.1]octane-3-carboxylic acid;
2-(5-trifluoromethyl-6-(4-trifluoromethyl-cyclohexyloxy)-naphthalen-2-ylmethyl)-2-aza-6-oxaspiro[3.4]octane-7-carboxylic acid;
(1R,5S,7r)-3-((2-(4-(trifluoromethyl)cyclohexyloxy)-1-(trifluoromethyl)naphthalen-6-yl)methyl)-3-aza-bicyclo[3.3.1]nonane-7-carboxylic acid;
N-(5-trifluoromethyl-6-(cis-4-trifluoromethyl-cyclohexyloxy)-naphthalen-2-ylmethyl)-3-(azetidine-3-yl)-cyclohexane-1-carboxylic acid;
8-((5-(trifluoromethyl)-6-((cis-4-(trifluoromethyl)cyclohexyl)oxy)quinolin-2-yl)methyl)-8-azabicyclo[3.2.1]octane-3-carboxylic acid;

2-(5-trifluoromethyl-6-(cis-4-trifluoromethyl-cyclohexyloxy)-naphthalen-2-ylmethyl)-2-aza-5-oxaspiro[5.4]decane-8-carboxylic acid;
N-(5-trifluoromethyl-6-(cis-4-trifluoromethyl-cyclohexyloxy)-naphthalen-2-ylmethyl)-8-aminobicyclo[3.2.1]octane-3-carboxylic acid, enantiomer 1;
N-(5-trifluoromethyl-6-(cis-4-trifluoromethyl-cyclohexyloxy)-naphthalen-2-ylmethyl)-8-aminobicyclo[3.2.1]octane-3-carboxylic acid, enantiomer 2;
N-(5-trifluoromethyl-6-(cis-4-trifluoromethyl-cyclohexyloxy)-naphthalen-2-ylmethyl)-1-amino-3,5-dimethyladamantane;
7-(5-trifluoromethyl-6-(cis-4-trifluoromethyl-cyclohexyloxy)-naphthalen-2-ylmethyl)-7-azabicyclo[2.2.1]heptane-2-carboxylic acid;
N-(5-trifluoromethyl-6-(cis-4-trifluoromethyl-cyclohexyloxy)-naphthalen-2-ylmethyl)-9-aminobicyclo[3.3.1]nonane-3-carboxylic acid;
9-(5-trifluoromethyl-6-(cis-4-trifluoromethyl-cyclohexyloxy)-naphthalen-2-ylmethyl)-9-aza-7-oxabicyclo[3.3.1]nonane-3-carboxylic acid;
9-(5-trifluoromethyl-6-(cis-4-trifluoromethyl-cyclohexyloxy)-naphthalen-2-ylmethyl)-9-azabicyclo[3.3.1]nonane;
9-(5-trifluoromethyl-6-(cis-4-trifluoromethyl-cyclohexyloxy)-naphthalen-2-ylmethyl)-7-hydroxy-9-azabicyclo[3.3.1]nonane-3-carboxylic acid;
9-(5-trifluoromethyl-6-(cis-4-trifluoromethyl-cyclohexyloxy)-naphthalen-2-ylmethyl)-7-oxo-9-azabicyclo[3.3.1]nonane-3-carboxylic acid;
9-((6-((cis-4-ethylcyclohexyl)oxy)-5-(trifluoromethyl)naphthalen-2-yl)methyl)-9-azabicyclo[3.3.1]nonane-3-carboxylic acid;
8-((6-((cis-4-ethylcyclohexyl)oxy)-5-(trifluoromethyl)naphthalen-2-yl)methyl)-8-azabicyclo[3.2.1]octane-3-carboxylic acid;
8-(1-(5-(trifluoromethyl)-6-((cis-4-(trifluoromethyl)cyclohexyl)oxy)naphthalen-2-yl)ethyl)-8-azabicyclo[3.2.1]octane-3-carboxylic acid, enantiomer 1;
8-(1-(5-(trifluoromethyl)-6-((cis-4-(trifluoromethyl)cyclohexyl)oxy)naphthalen-2-yl)ethyl)-8-azabicyclo[3.2.1]octane-3-carboxylic acid, enantiomer 2;
9-(1-(6-((cis-4-ethylcyclohexyl)oxy)-5-(trifluoromethyl)naphthalen-2-yl)ethyl)-9-azabicyclo[3.3.1]nonane-3-carboxylic acid;
8-(1-(6-((cis-4-ethylcyclohexyl)oxy)-5-(trifluoromethyl)naphthalen-2-yl)ethyl)-8-azabicyclo[3.2.1]octane-3-carboxylic acid;
9-(1-(6-((cis-4-trifluoromethylcyclohexyl)oxy)-5-(trifluoromethyl)naphthalen-2-yl) propyl)-9-azabicyclo[3.3.1]nonane-3-carboxylic acid;
8-(1-(6-((cis-4-trifluoromethylcyclohexyl)oxy)-5-(trifluoromethyl)naphthalen-2-yl) propyl)-8-azabicyclo[3.2.1]octane-3-carboxylic acid;
9-(1-(6-((cis-4-ethylcyclohexyl)oxy)-5-(trifluoromethyl)naphthalen-2-yl)propyl)-9-azabicyclo[3.3.1]nonane-3-carboxylic acid;
8-(1-(6-((cis-4-ethylcyclohexyl)oxy)-5-(trifluoromethyl)naphthalen-2-yl)propyl)-8-azabicyclo[3.2.1]octane-3-carboxylic acid;
8-((5-(trifluoromethyl)-6-((cis-4-(trifluoromethyl)cyclohexyl)oxy)naphthalen-2-yl)methyl)-8-azabicyclo[3.2.1]octane-3-carboxylic acid;
9-(1-(6-((cis-4-ethylcyclohexyl)oxy)-5-chloronaphthalen-2-yl)ethyl)-9-azabicyclo[3.3.1]nonane-3-carboxylic acid;
9-((5-Chloro-6-((cis-4-methylcyclohexyl)oxy)naphthalen-2-yl)methyl)-9-azabicyclo[3.3.1]nonane-3-carboxylic acid;
8-(1-(5-Chloro-6-((cis-4-ethylcyclohexyl)oxy)naphthalen-2-yl)ethyl)-8-azabicyclo[3.2.1]octane-3-carboxylic acid; and
8-((5-Chloro-6-((cis-4-ethylcyclohexyl)oxy)naphthalen-2-yl)methyl)-8-azabicyclo[3.2.1]octane-3-carboxylic acid;
or a pharmaceutically acceptable salt thereof.

In another aspect, a pharmaceutical composition can include a pharmaceutically acceptable carrier or excipient and a compound, or a pharmaceutically acceptable salt thereof, according to any one of formulae (I), (IIa), (IIb) or (III).

In another aspect, a method of preventing, treating, or reducing symptoms of a condition mediated by S1P activity or ATX activity in a mammal can include administering to said mammal an effective amount of a compound according to any one of formulae (I), (IIa), (IIb) or (III), or a pharmaceutically acceptable salt thereof.

In some embodiments, the condition can be selected from the group consisting of multiple sclerosis, an autoimmune disease, a chronic inflammatory disorder, asthma, an inflammatory neuropathy, arthritis, transplantation rejection, Crohn's disease, ulcerative colitis, lupus erythematosis, psoriasis, an ischemia-reperfusion injury, a solid tumor, a tumor metastasis, a disease associated with angiogenesis, a vascular disease, a pain condition, an acute viral disease, an inflammatory bowel condition, insulin-dependent diabetes, non-insulin dependent diabetes, a fibrosis of the lung, or a malignancy of the lung in a mammal.

In some embodiments, the condition can be multiple sclerosis.

In some embodiments, the condition can be rheumatoid arthritis.

In some embodiments, the method can include administering to the mammal an effective amount of one or more drugs selected from the group consisting of: a corticosteroid, a bronchodilator, an antiasthmatic, an antiinflammatory, an antirheumatic, an immunosuppressant, an antimetabolite, an immunomodulating agent, an antipsoriatic, and an antidiabetic.

In another aspect, a method of preventing, treating, or reducing chronic pain in a mammal can include comprising administering to said mammal an effective amount of a compound according to any one of any one of formulae (I), (IIa), (IIb) or (III), or a pharmaceutically acceptable salt thereof.

In some embodiments, the chronic pain can be inflammatory pain.

In some embodiments, the chronic pain can be neuropathic pain.

Other features or advantages will be apparent from the following detailed description of several embodiments, and also from the appended claims.

DETAILED DESCRIPTION

The disclosed compounds can be S1P modulating agents and/or ATX modulating agents. In other words, the disclosed compounds can have activity as receptor agonists or receptor antagonists at one or more S1P receptors, or as an ATX modulating agent. In particular, the compounds can be S1P4 antagonists, or ATX inhibitors. A given compound can be an S1P modulating agent with little or substantially no ATX activity; or can be an ATX modulating agent with little or substantially no S1P activity; or, in some cases, can simultaneously be an S1P modulating agent and an ATX modulating agent. Preferably, a given compound is either an S1P modulating agent with little or substantially no ATX activity; or is an ATX modulating agent with little or substantially no S1P activity.

A compound, or a pharmaceutically acceptable salt thereof, can be represented by formula (I):

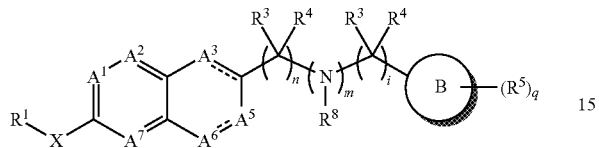

(I)

In formula (I), X can be O, $S(O)_r$, $NR^{12}$, $C(O)$ or $CH_2$, wherein r is 0, 1, or 2; $A^1$, $A^2$, and $A^7$ can each independently be $CR^2$ or N; $A^3$, $A^5$, and $A^6$ can each independently be $CR^2$, $C(R^2)_2$, N, or $NR^{19}$, wherein at least three of $A^1$, $A^2$, $A^3$, $A^5$, $A^6$, and $A^7$ are $CR^2$ or $C(R^2)_2$.

"------" can indicate a double or a single bond.

$R^1$ can be a $C_{6-20}$alkyl, a $C_{3-14}$carbocyclyl, a 3- to 15-membered heterocyclyl, a $C_{6-10}$aryl, or a five- to 14-membered heteroaryl, wherein $R^1$ may be optionally substituted with from one to six independently selected $R^6$.

$R^2$, for each occurrence, can be independently selected from the group consisting of hydrogen, halo, hydroxyl, nitro, cyano, carboxy, $C_{1-6}$alkyl, $C_{1-6}$haloalkyl, $C_{3-8}$cycloalkyl, $C_{3-8}$halocycloalkyl, $C_{1-6}$alkoxy, $C_{1-6}$haloalkoxy, $C_{3-8}$cycloalkoxy, $C_{3-8}$halocycloalkoxy, $C_{1-6}$alkanoyl, amino, N—($C_{1-6}$alkyl)amino, N,N-di-($C_{1-6}$alkyl)amino, $C_{1-6}$alkoxycarbonyl, $C_{1-6}$alkanoyloxy, carbamoyl, N—($C_{1-6}$alkyl)carbamoyl, N,N-di-($C_{1-6}$alkyl)carbamoyl, $C_{1-6}$alkylamido, mercapto, $C_{1-6}$alkylthio, $C_{1-6}$alkylsulfonyl, sulfamoyl, N—($C_{1-6}$alkyl)sulfamoyl, N,N-di-($C_{1-6}$alkyl)sulfamoyl, and $C_{1-6}$alkylsulfonamido.

Each $R^3$ and each $R^4$ can each independently be hydrogen, a carboxy, $C_{1-6}$alkyl, or a $C_{2-6}$alkenyl; or $R^3$ and $R^4$ together with the carbon to which they are attached can be —C(=O)—, a $C_{3-8}$spirocycloalkyl, or a 3- to 8-membered spiroheterocycloalkyl.

B can be a fused ring system, a bridged ring system, a spiro ring system, or a combination thereof; or B can be a bicyclic ring system represented by the following formula:

$$\{-(B')-(B'')\}$$

wherein B' and B" can each independently be selected from the group consisting of monocyclic $C_{3-8}$carbocyclyl, a monocyclic 3- to 8-membered heterocyclyl, phenyl, or a 5- to 6-membered heteroaryl, wherein the heterocyclyl and the heteroaryl comprises 1 to 3 heteroatoms independently selected from N, S, or O; provided that when B is a fused ring system it is not 1H-benzo[d][1,2,3]triazole.

$R^5$, for each occurrence, can independently be hydroxyl, halo, $C_{1-6}$alkyl, or —$(CR^{17}R^{18})_p$—$R^7$; or two $R^5$ on the same carbon atom may be =O.

$R^6$, for each occurrence, can be independently selected from the group consisting of halo, $C_{1-6}$alkyl, $C_{1-6}$alkoxy, $C_{1-6}$haloalkyl, $C_{3-8}$cycloalkyl, $C_{6-10}$aryl, $C_{1-6}$alkoxy-$C_{1-6}$alkyl, and tri-($C_{1-6}$alkyl)silyl; or two $R^6$ that are attached to the same carbon atom may form $C_{3-8}$spirocycloalkyl or 3- to 8-membered spiroheterocycloalkyl.

$R^7$ can be —OH, —C(O)O$R^{15}$, —C(O)N($R^{16}$)$_2$, —C(O)N($R^{15}$)—S(O)$_2$$R^{15}$, —S(O)$_2$O$R^{15}$, —C(O)NHC(O)$R^{15}$, —Si(O)OH, —B(OH)$_2$, —N($R^{15}$)S(O)$_2$$R^{15}$, —S(O)$_2$N($R^{15}$)$_2$, —O—P(O)(O$R^{15}$)$_2$, —P(O)(O$R^{15}$)$_2$, —CN, —S(O)$_2$NHC(O)$R^{15}$, —C(O)NHS(O)$_2$$R^{15}$, —C(O)NHOH, —C(O)NHCN, —N($R^{20}$)$_2$, or a heteroaryl or a heterocyclyl selected from the group consisting of formulae (a)-(i'):

(a)

![structure a: thiadiazole with OH]

(b)

![structure b: tetrazole]

(c)

![structure c: triazole]

(d)

![structure d: pyrazole with OH]

(e)

![structure e: isoxazole with OH]

(f)

![structure f: isoxazole with OH]

(g)

![structure g: thiazolidinedione]

(h)

![structure h: hydantoin]

-continued
(i) 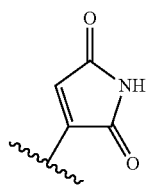
(j) 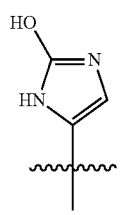
(k) 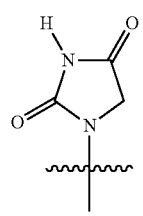
(l) 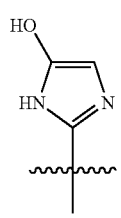
(m) 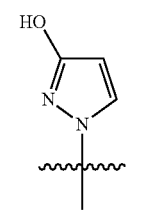
(n) 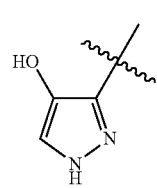
(o) 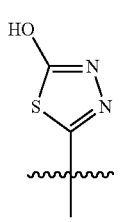
-continued
(p) 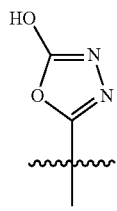
(q) 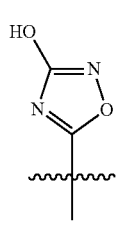
(r) 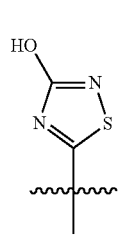
(s) 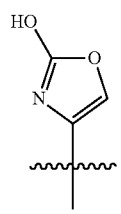
(t) 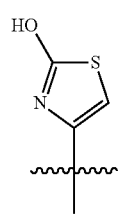
(u) 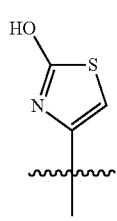
(v) 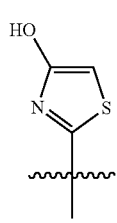

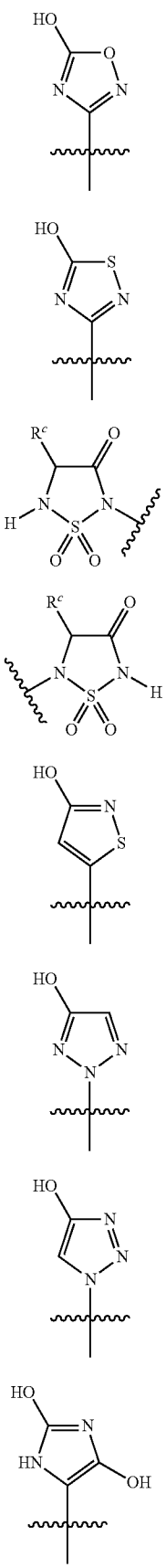
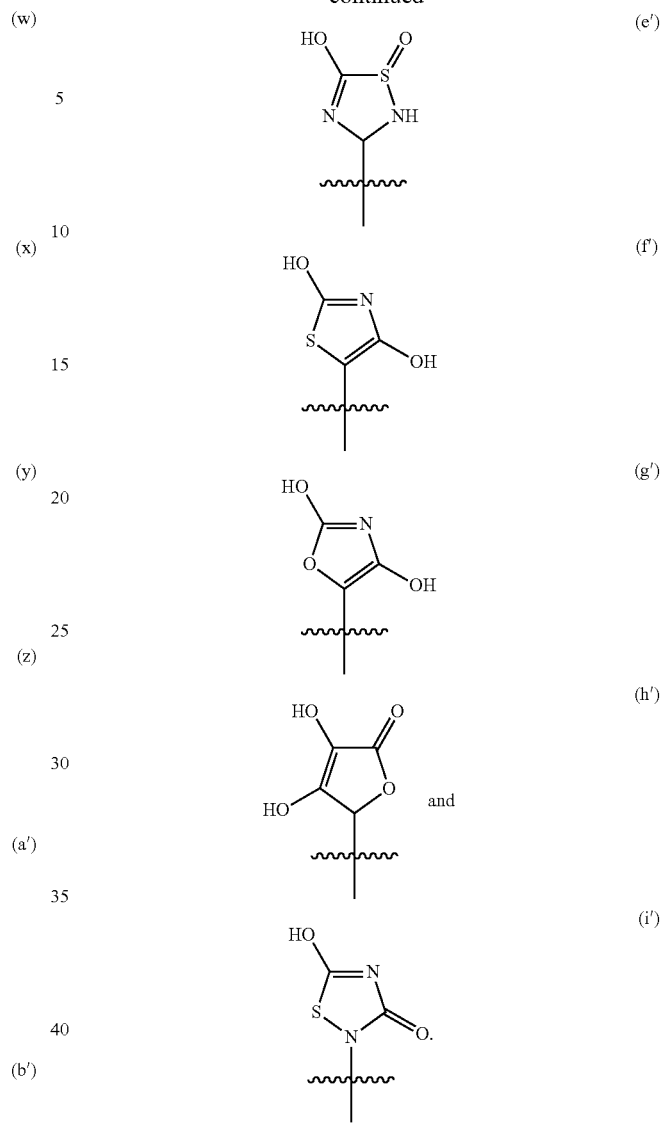

$R^8$, $R^{12}$, $R^{19}$, and $R^{20}$ can each independently be hydrogen or a $C_{1-6}$alkyl.

$R^{15}$ for each occurrence can be independently selected from the group consisting of hydrogen, $C_{1-6}$alkyl, $C_{2-6}$alkenyl, $C_{2-6}$alkynyl, $C_{3-8}$cycloalkyl, $C_{3-8}$cycloalkenyl, $C_{6-10}$aryl, a 5 to 14 membered heteroaryl, and a 3 to 15 membered heterocyclyl; wherein the heteroaryl or heterocyclyl can comprise from 1 to 10 heteroatoms independently selected from O, N, or S; and wherein $R^{15}$ may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—($C_{1-4}$alkyl)sulfamoyl, and N,N—($C_{1-4}$dialkyl)-sulfamoyl.

$R^{16}$ can be $R^{15}$; or two $R^{16}$ together with the nitrogen atom to which they are attached can form a 5 to 14 membered heteroaryl or a 3 to 15 membered heterocyclyl, wherein the heteroaryl or heterocyclyl can comprise from 1 to 10 heteroatoms independently selected from O, N, or S; and wherein the heteroaryl or heterocyclyl may be optionally substituted with from 1 to 3 substituents independently selected from the group consisting of halo, $C_{1-4}$alkoxy, $C_{1-4}$alkyl, cyano, nitro, hydroxyl, amino, N—($C_{1-4}$alkyl)amino, N,N-di-($C_{1-4}$alkyl)amino, carbamoyl, N—($C_{1-4}$alkyl)carbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—$C_{1-4}$alkylsulfamoyl, and N,N—($C_{1-4}$dialkyl)-sulfamoyl.

$R^{17}$ and $R^{18}$, for each occurrence, can each independently be hydrogen, a halo, or a $C_{1-4}$haloalkyl.

$R^c$ is hydrogen or a $C_{1-4}$alkyl.

i can be an integer from 0 to 6.

n can be 0 or an integer from 1 to 6, provided that when n is 0, then m is 1, q is 0 and $R^1$ is a $C_{3-14}$carbocyclyl which is optionally substituted with from one to six $R^6$.

m can be 0 or 1, provided that when m is 0, B comprises at least one nitrogen.

p can be 0 or an integer from 1 to 6.

q can be 0, 1, 2, 3, or 4.

The compound of formula is not 2-((6-(trans-4-tert-butylcyclohexyloxy)-naphthalen-2-yl)methyl)octahydrocyclopenta[c]pyrrole-3a-carboxylic acid or 6-phenoxy-2-(2-(4-phenylpiperidin-1-yl)ethyl)-1,2,3,4-tetrahydronaphthalen-1-ol.

In some embodiments, B can be selected from the group consisting of 9-azabicyclo[3.3.1]nonanyl, 8-azabicyclo[3.2.1]octanyl, decahydroisoquinolinyl, 2-azaspiro[3.3]heptanyl, bicyclo[3.2.1]octanyl, 5-azaspiro[2.3]hexanyl, 3-cyclohexylazetidinyl, bicyclo[2.2.1]heptanyl, adamantyl, 6-oxa-9-azaspiro[4.5]decanyl, 3-azabicyclo[3.3.1]nonanyl, 6-oxa-2-azaspiro[3.4]octanyl, 4-(1H-imidazol-4-yl)piperidinyl, octahydro-1H-pyrido[1,2-a]pyrazinyl, 2,3-dihydro-1H-indenyl, (1R,5S)-bicyclo[3.1.0]hexanyl, 3-azabicyclo[3.1.1]heptanyl, 1-(pyridin-4-yl)piperazinyl, 1-(pyridin-2-yl)piperazinyl, 1-(pyridin-3-yl)piperazinyl, 2-oxa-6-azaspiro[3.3]heptanyl, 4-(pyrimidin-2-yl)piperazin-1-yl, 3-azabicyclo[3.3.1]nonanyl, 4-(pyridin-2-yl)piperidin-1-yl, 4-phenylpiperazin-1-yl, 4-phenylpiperidin-1-yl, 4-(pyrazin-2-yl)piperazin-1-yl, 4-(pyridin-2-yl)-1,4-diazepan-1-yl, 4-(pyrimidin-2-yl)-1,4-diazepan-1-yl, 4-(pyrimidin-4-yl)piperazin-1-yl, 2,7-diazaspiro[3.5]nonanyl, 3-phenylazetidinyl, 2-oxa-7-azaspiro[3.5]nonanyl, 3-azabicyclo[3.1.0]hexanyl, 2,8-diazaspiro[4.5]decanyl, 3-oxa-9-azabicyclo[3.3.1]nonanyl, 7-azabicyclo[2.2.1]heptanyl, spiro[3.5]nonanyl, and tricyclo[2.2.1.02,6]heptanyl.

B can be a bridged ring system.

In some embodiments, m can be 1; B can be a ring system represented by the following formula:

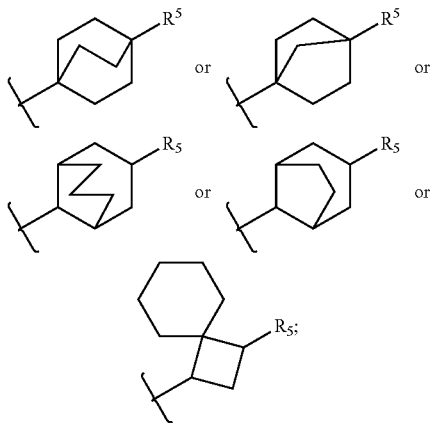

and $R^5$ can be $CO_2H$.

B can be a bridged ring system represented by the following formula:

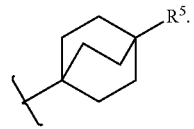

In some embodiments, m can be 0; B can be a ring system represented by the following formula:

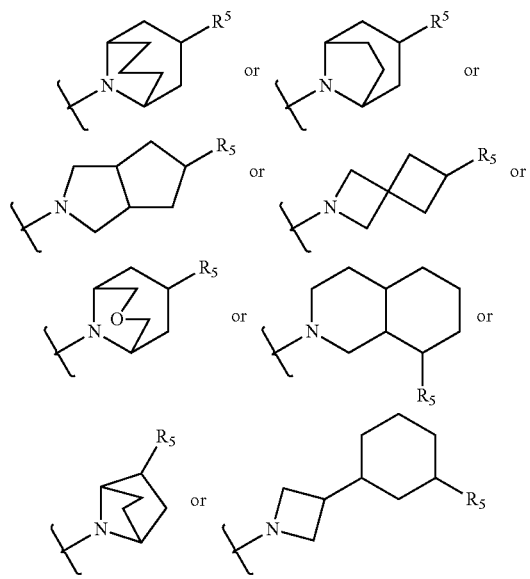

wherein B is optionally further substituted by oxo, hydroxy, —$NH_2$, —$CONH_2$, or —$CO_2H$; and $R^5$ can be $CO_2H$.

B can be a bridged ring system selected from 9-azabicyclo[3.3.1]nonane substituted with $R^5$ at the 3-position; and 8-aza-bicyclo[3.2.1]octane substituted with $R^5$ at the 3-position.

In some embodiments, the compound of formula (I), or a pharmaceutically acceptable salt thereof, can be represented by formula (II):

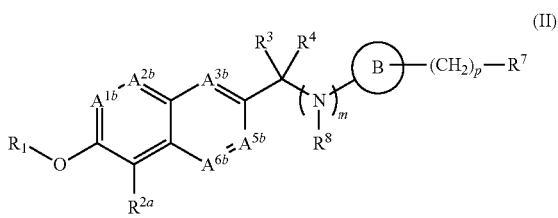

In formula (II), $A^{1b}$, $A^{2b}$, $A^{3b}$, $A^{5b}$, and $A^{6b}$ can be $CR^{2b}$ or N, wherein at least two of $A^{1b}$, $A^{2b}$, $A^{3b}$, $A^{5b}$, and $A^{6b}$ can be $CR^{2b}$.

$R^{2a}$ can be a halo, $C_{1-6}$haloalkyl or cyano.

$R^{2b}$, for each occurrence, can be independently selected from the group consisting of hydrogen, halo, hydroxyl, nitro, cyano, carboxy, $C_{1-6}$alkyl, $C_{1-6}$haloalkyl, $C_{3-8}$cycloalkyl, $C_{3-8}$halocycloalkyl, $C_{1-6}$alkoxy, $C_{1-6}$haloalkoxy, $C_{3-8}$cycloalkoxy, $C_{3-8}$halocycloalkoxy, $C_{1-6}$alkanoyl, amino, N—($C_{1-6}$alkyl)amino, N,N-di-($C_{1-6}$alkyl)amino, $C_{1-6}$alkoxycarbonyl, carbamoyl, N—($C_{1-6}$alkyl)carbamoyl, N,N-di-($C_{1-6}$alkyl)carbamoyl, $C_{1-6}$alkylamido, mercapto, $C_{1-6}$alkylthio, $C_{1-6}$alkylsulfonyl, sulfamoyl, N—($C_{1-6}$alkyl)sulfamoyl, N,N-di-($C_{1-6}$alkyl)sulfamoyl, and $C_{1-6}$alkylsulfonamido.

In some embodiments of formula (II), $R^{2b}$, for each occurrence, can independently be hydrogen or a halo.

In some embodiments, the compound of formula (I), or a pharmaceutically acceptable salt thereof, can be represented by formula (IIa):

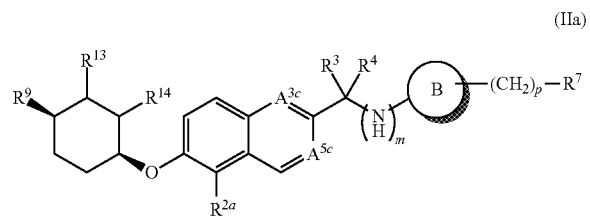

(IIa)

In formula (IIa), $A^{3c}$ and $A^{5c}$ can be N or CH, provided that only one of $A^{3c}$ or $A^{5c}$ is N.

$R^9$ can be a halo, an $C_{1-6}$alkyl, or a $C_{1-6}$haloalkyl.

$R^{13}$ and $R^{14}$ can each independently be hydrogen or a $C_{1-6}$alkyl.

In some embodiments, the compound of formula (I), or a pharmaceutically acceptable salt thereof, can be represented by formula (IIb):

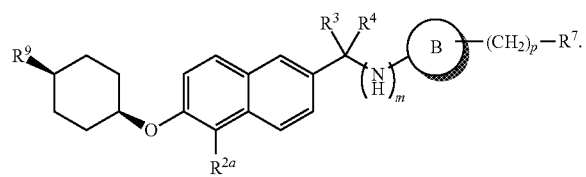

(IIb)

In some embodiments, for a compound of formula (II), (IIa), or (IIb), or a pharmaceutically acceptable salt thereof, m can be 0; B can be a ring system represented by the following formula:

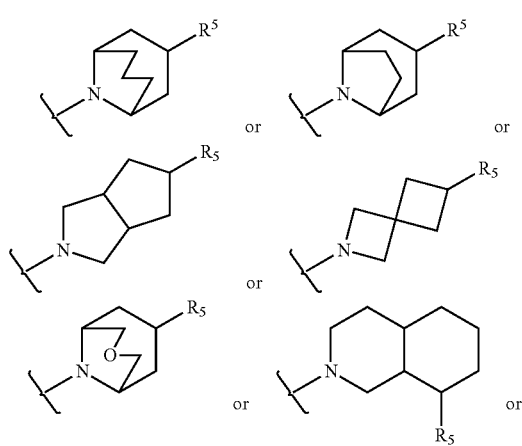

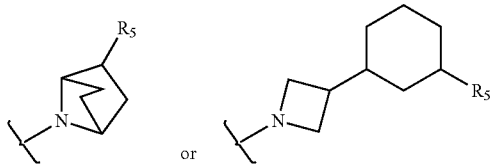

wherein B is optionally further substituted by oxo, hydroxy, —$NH_2$, —$CONH_2$, or —$CO_2H$; and $R^5$ can be $CO_2H$.

In some embodiments, for a compound of formula (II), (IIa), or (IIb), or a pharmaceutically acceptable salt thereof, B can be a bridged ring system selected from 9-aza-bicyclo[3.3.1]nonane substituted with $R^5$ at the 3-position; and 8-aza-bicyclo[3.2.1]octane substituted with $R^5$ at the 3-position.

In some embodiments, for a compound of formula (II), (IIa), or (IIb), or a pharmaceutically acceptable salt thereof, $R^{2a}$ can be —Cl, —$CF_3$ or —$CHF_2$.

In some embodiments, for a compound of formula (IIb), or a pharmaceutically acceptable salt thereof, $R^9$ can be methyl, ethyl, —$CF_3$ or tert-butyl.

In some embodiments, the compound of formula (I), or a pharmaceutically acceptable salt thereof, can be represented by formula (III):

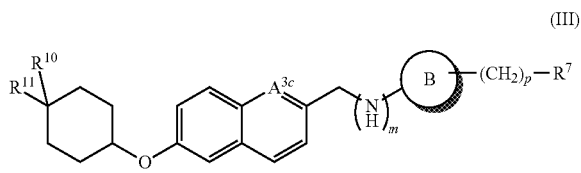

(III)

In formula (III), $A^{3c}$ can be N or CH.

$R^{10}$ and $R^{11}$ can each independently be hydrogen, $C_{1-6}$alkyl, $C_{1-6}$haloalkyl, tri-$C_{1-6}$alkylsilyl, or phenyl, wherein at least one of $R^{10}$ or $R^{11}$ is not hydrogen; or $R^{10}$ and $R^{11}$ together with the carbon to which they are attached can form a $C_{3-8}$spirocycloalkyl or 3- to 8-membered spiroheterocycloalkyl.

In some embodiments, for a compound of formula (III), or a pharmaceutically acceptable salt thereof, m can be 1; B can be a bridged ring system represented by the following formula:

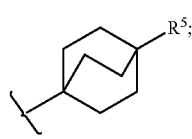

and $R^5$ can be $CO_2H$.

A compound can be selected from the group consisting of:
4-(((6-(cyclohexyloxy)naphthalen-2-yl)methyl)amino)bicyclo[2.2.2]octane-1-carboxylic acid;
4-(((6-((trans-4-methylcyclohexyl)oxy)naphthalen-2-yl)methyl)amino)bicyclo[2.2.2]octane-1-carboxylic acid;
4-(((6-((trans-4-ethylcyclohexyl)oxy)naphthalen-2-yl)methyl)amino)bicyclo[2.2.2]octane-1-carboxylic acid;
4-(((6-((trans-4-isopropylcyclohexyl)oxy)naphthalen-2-yl)methyl)amino)bicyclo[2.2.2]octane-1-carboxylic acid;
4-(((6-((trans-4-(tert-pentyl)cyclohexyl)oxy)naphthalen-2-yl)methyl)amino)bicyclo[2.2.2]octane-1-carboxylic acid;

4-(((6-((trans-4-phenylcyclohexyl)oxy)naphthalen-2-yl) methyl)amino)bicyclo[2.2.2]octane-1-carboxylic acid;
4-(((6-((4,4-dimethylcyclohexyl)oxy)naphthalen-2-yl) methyl)amino)bicyclo[2.2.2]octane-1-carboxylic acid;
4-(((6-(spiro[2.5]octan-6-yloxy)naphthalen-2-yl)methyl) amino)bicyclo[2.2.2]octane-1-carboxylic acid;
4-(((6-(spiro[3.5]nonan-7-yloxy)naphthalen-2-yl)methyl) amino)bicyclo[2.2.2]octane-1-carboxylic acid;
4-(((6-(spiro[4.5]decan-8-yloxy)naphthalen-2-yl)methyl) amino)bicyclo[2.2.2]octane-1-carboxylic acid;
4-(((6-(spiro[5.5]undecan-3-yloxy)naphthalen-2-yl)methyl) amino)bicyclo[2.2.2]octane-1-carboxylic acid;
4-(((6-(heptyloxy)naphthalen-2-yl)methyl)amino)bicyclo [2.2.2]octane-1-carboxylic acid;
4-(((6-((cis-4-methylcyclohexyl)oxy)naphthalen-2-yl) methyl)amino)bicyclo[2.2.2]octane-1-carboxylic acid;
4-(((6-((cis-4-ethylcyclohexyl)oxy)naphthalen-2-yl)methyl) amino)bicyclo[2.2.2]octane-1-carboxylic acid;
4-(((6-((cis-4-isopropylcyclohexyl)oxy)naphthalen-2-yl) methyl)amino)bicyclo[2.2.2]octane-1-carboxylic acid;
4-(((6-((cis-4-(trifluoromethyl)cyclohexyl)oxy)naphthalen-2-yl)methyl)amino)bicyclo[2.2.2]octane-1-carboxylic acid;
4-(((6-((cis-4-phenylcyclohexyl)oxy)naphthalen-2-yl) methyl)amino)bicyclo[2.2.2]octane-1-carboxylic acid;
4-(((6-((trans-4-(trifluoromethyl)cyclohexyl)oxy)naphthalen-2-yl)methyl)amino)bicyclo[2.2.2]octane-1-carboxylic acid;
4-(((6-((cis-4-(tert-butyl)cyclohexyl)oxy)naphthalen-2-yl) methyl)amino)bicyclo[2.2.2]octane-1-carboxylic acid;
4-(((6-(cyclohexyloxy)quinolin-2-yl)methyl)amino)bicyclo [2.2.2]octane-1-carboxylic acid;
4-(((6-((trans-4-methylcyclohexyl)oxy)quinolin-2-yl) methyl)amino)bicyclo[2.2.2]octane-1-carboxylic acid;
4-(((6-((trans-4-ethylcyclohexyl)oxy)quinolin-2-yl)methyl) amino)bicyclo[2.2.2]octane-1-carboxylic acid;
4-(((6-((trans-4-isopropylcyclohexyl)oxy)quinolin-2-yl) methyl)amino)bicyclo[2.2.2]octane-1-carboxylic acid;
4-(((6-((trans-4-(tert-pentyl)cyclohexyl)oxy)quinolin-2-yl) methyl)amino)bicyclo[2.2.2]octane-1-carboxylic acid;
4-(((6-((trans-4-phenylcyclohexyl)oxy)quinolin-2-yl) methyl)amino)bicyclo[2.2.2]octane-1-carboxylic acid;
4-(((6-((4,4-dimethylcyclohexyl)oxy)quinolin-2-yl)methyl) amino)bicyclo[2.2.2]octane-1-carboxylic acid;
4-(((6-(spiro[2.5]octan-6-yloxy)quinolin-2-yl)methyl) amino)bicyclo[2.2.2]octane-1-carboxylic acid;
4-(((6-(spiro[3.5]nonan-7-yloxy)quinolin-2-yl)methyl) amino)bicyclo[2.2.2]octane-1-carboxylic acid;
4-(((6-(spiro[4.5]decan-8-yloxy)quinolin-2-yl)methyl) amino)bicyclo[2.2.2]octane-1-carboxylic acid;
4-(((6-(spiro[5.5]undecan-3-yloxy)quinolin-2-yl)methyl) amino)bicyclo[2.2.2]octane-1-carboxylic acid;
4-(((6-(heptyloxy)naphthalen-2-yl)methyl)amino)bicyclo [2.2.2]octane-1-carboxylate;
4-(((6-((cis-4-methylcyclohexyl)oxy)quinolin-2-yl)methyl) amino)bicyclo[2.2.2]octane-1-carboxylic acid;
4-(((6-((cis-4-ethylcyclohexyl)oxy)quinolin-2-yl)methyl) amino)bicyclo[2.2.2]octane-1-carboxylic acid;
4-(((6-((cis-4-isopropylcyclohexyl)oxy)quinolin-2-yl) methyl)amino)bicyclo[2.2.2]octane-1-carboxylic acid;
4-(((6-((cis-4-(trifluoromethyl)cyclohexyl)oxy)quinolin-2-yl)methyl)amino)bicyclo[2.2.2]octane-1-carboxylic acid;
4-(((6-((cis-4-phenylcyclohexyl)oxy)quinolin-2-yl)methyl) amino)bicyclo[2.2.2]octane-1-carboxylic acid;
4-(((6-((trans-4-(tert-butyl)cyclohexyl)oxy)-5-(trifluoromethyl)naphthalen-2-yl)methyl)amino)bicyclo[2.2.2]octane-1-carboxylic acid;
4-(((6-((trans-4-(tert-butyl)cyclohexyl)oxy)-5-(trifluoromethyl)quinolin-2-yl)methyl)amino)bicyclo[2.2.2]octane-1-carboxylic acid;
2-(1-((6-((trans-4-(tert-butyl)cyclohexyl)oxy)naphthalen-2-yl)methyl)piperidin-4-yl)pyridine;
2-(1-((6-((trans-4-(tert-butyl)cyclohexyl)oxy)naphthalen-2-yl)methyl)piperidin-4-yl)pyrimidine;
1-((6-((trans-4-(tert-butyl)cyclohexyl)oxy)naphthalen-2-yl) methyl)-4-phenylpiperazine;
1-((6-((trans-4-(tert-butyl)cyclohexyl)oxy)naphthalen-2-yl) methyl)-4-(pyridin-3-yl)piperazine;
1-((6-((trans-4-(tert-butyl)cyclohexyl)oxy)naphthalen-2-yl) methyl)-4-(pyridin-2-yl)-1,4-diazepane;
2-(4-((6-((trans-4-(tert-butyl)cyclohexyl)oxy)naphthalen-2-yl)methyl)piperazin-1-yl)pyrimidine;
2-(4-((6-((trans-4-(tert-butyl)cyclohexyl)oxy)naphthalen-2-yl)methyl)piperazin-1-yl)pyrazine;
1-((6-((trans-4-(tert-butyl)cyclohexyl)oxy)naphthalen-2-yl) methyl)-4-(pyridin-4-yl)piperazine;
1-((6-((trans-4-(tert-butyl)cyclohexyl)oxy)naphthalen-2-yl) methyl)-4-(pyrimidin-2-yl)-1,4-diazepane;
4-(4-((6-((trans-4-(tert-butyl)cyclohexyl)oxy)naphthalen-2-yl)methyl)piperazin-1-yl)pyrimidine;
4-(4-((6-((trans-4-(tert-butyl)cyclohexyl)oxy)naphthalen-2-yl)methyl)piperazin-1-yl)-2-methylpyrimidine;
1-((6-((trans-4-(tert-butyl)cyclohexyl)oxy)naphthalen-2-yl) methyl)-4-phenylpiperi dine;
1-((6-((trans-4-(tert-butyl)cyclohexyl)oxy)naphthalen-2-yl) methyl)-4-(pyridin-2-yl)piperazine;
1-((6-((cis-4-isopropylcyclohexyl)oxy)naphthalen-2-yl) methyl)-4-(pyridin-2-yl)piperazine;
1-((6-((cis-4-ethylcyclohexyl)oxy)naphthalen-2-yl)methyl)-4-(pyridin-2-yl)piperazine;
1-(pyridin-2-yl)-4-((6-(spiro[4.5]decan-8-yloxy)naphthalen-2-yl)methyl)piperazine;
1-((6-(heptyloxy)naphthalen-2-yl)methyl)-4-(pyridin-2-yl) piperazine;
6-((cis-4-isopropylcyclohexyl)oxy)-2-((4-(pyridin-2-yl)piperazin-1-yl)methyl)quinoline;
3-(1-((6-((cis-4-isopropylcyclohexyl)oxy)naphthalen-2-yl) methyl)azetidin-3-yl)cyclohexanecarboxylic acid;
3-(1-((6-((trans-4-(tert-butyl)cyclohexyl)oxy)naphthalen-2-yl)methyl)azetidin-3-yl)cyclohexanecarboxylic acid;
3-(1-((6-((4,4-dimethylcyclohexyl)oxy)quinolin-2-yl) methyl)azetidin-3-yl)cyclohexanecarboxylic acid;
3-(1-((6-(heptyloxy)naphthalen-2-yl)methyl)azetidin-3-yl) cyclohexanecarboxylic acid;
3-(1-((6-((cis-4-ethylcyclohexyl)oxy)naphthalen-2-yl) methyl)azetidin-3-yl)cyclohexanecarboxylic acid;
3-(1-((6-((4,4-dimethylcyclohexyl)oxy)naphthalen-2-yl) methyl)azetidin-3-yl)cyclohexanecarboxylic acid;
3-(1-((6-(spiro[4.5]decan-8-yloxy)naphthalen-2-yl)methyl) azetidin-3-yl)cyclohexanecarboxylic acid;
3-(1-((6-((cis-4-ethylcyclohexyl)oxy)quinolin-2-yl)methyl) azetidin-3-yl)cyclohexanecarboxylic acid;
3-(1-((6-((cis-4-isopropylcyclohexyl)oxy)quinolin-2-yl) methyl)azetidin-3-yl)cyclohexanecarboxylic acid;
4-(1-((6-((trans-4-(tert-butyl)cyclohexyl)oxy)naphthalen-2-yl)methyl)azetidin-3-yl)cyclohexanecarboxylic acid;
6-((6-((trans-4-(tert-butyl)cyclohexyl)oxy)naphthalen-2-yl) methyl)-2-oxa-6-azaspiro[3.3]heptane;
3-((6-((trans-4-(tert-butyl)cyclohexyl)oxy)naphthalen-2-yl) methyl)-3-azabicyclo[3.1.0]hexane-6-carboxylic acid;
4-(((6-((trans-4-(tert-butyl)cyclohexyl)oxy)quinolin-2-yl) methyl)amino)bicyclo[2.2.2]octane-1-carboxylic acid;

4-(((6-((trans-4-(tert-butyl)cyclohexyl)oxy)naphthalen-2-yl)methyl)(methyl)amino)bicyclo[2.2.2]octane-1-carboxylic acid;
8-((6-((trans-4-(tert-butyl)cyclohexyl)oxy)naphthalen-2-yl)methyl)-8-azabicyclo[3.2.1]octane-3-carboxylic acid;
9-((6-((trans-4-(tert-butyl)cyclohexyl)oxy)naphthalen-2-yl)methyl)-9-azabicyclo[3.3.1]nonane-3-carboxylic acid;
3-((6-((trans-4-(tert-butyl)cyclohexyl)oxy)naphthalen-2-yl)methyl)-3-azabicyclo[3.3.1]nonane-9-carboxylic acid;
3-((6-((trans-4-(tert-butyl)cyclohexyl)oxy)naphthalen-2-yl)methyl)-3-azabicyclo[3.1.1]heptane-6-carboxylic acid;
4-(((6-((trans-4-(tert-butyl)cyclohexyl)oxy)naphthalen-2-yl)methyl)amino)bicyclo[2.2.1]heptane-1-carboxylic acid;
4-(((6-((trans-4-(tert-butyl)cyclohexyl)oxy)-5-(trifluoromethyl)naphthalen-2-yl)methyl)amino)bicyclo[2.2.1]heptane-1-carboxylic acid;
4-((6-(trans-4-(Trimethylsilyl)cyclohexyloxy)naphthalen-2-yl)methylamino)bicyclo[2.2.2]octane-1-carboxylic acid;
4-(((6-((cis-4-(Trimethylsilyl)cyclohexyl)oxy)naphthalen-2-yl)methyl)amino)bicyclo[2.2.2]octane-1-carboxylic acid;
4-((6-(trans-4-tert-Butylcyclohexyloxy)naphthalen-2-yl)methylamino)-2-hydroxy bicyclo[2.2.2]octane-1-carboxylic acid;
4-((6-(trans-4-tert-Butylcyclohexyloxy)naphthalen-2-yl)methylamino)-1-(hydroxy methyl)bicyclo[2.2.2]octan-2-ol; and
4-(((6-((trans-4-(tert-butyl)cyclohexyl)oxy)naphthalen-2-yl)methyl)amino)bicyclo[2.2.2]octane-1-carboxylic acid; or a pharmaceutically acceptable salt thereof.

A compound can be selected from the group consisting of:
9-((6-((cis-4-ethylcyclohexyl)oxy)naphthalen-2-yl)methyl)-9-azabicyclo[3.3.1]nonane-3-carboxylic acid;
9-((5-(trifluoromethyl)-6-((cis-4-(trifluoromethyl)cyclohexyl)oxy)naphthalen-2-yl)methyl)-9-azabicyclo[3.3.1]nonane-3-carboxylic acid;
3-(((5-(trifluoromethyl)-6-((cis-4-(trifluoromethyl)cyclohexyl)oxy)naphthalene-2-yl)methyl)amino)spiro[3.5]nonane-1-carboxylic acid;
3-(4-{[5-trifluoromethyl-6-(4-trifluoromethyl-cyclohexyloxy)-naphthalen-2-ylmethyl]-amino}-bicyclo[2.2.2]oct-1-yl)-propionic acid;
3-(4-(methyl((5-(trifluoromethyl)-6-((cis-4-(trifluoromethyl)cyclohexyl)oxy)naphthalene-2-yl)methyl)amino)bicyclo[2.2.2]octan-1-yl)propanoic acid;
9-1-(5-(trifluoromethyl)-6-((cis-4-(trifluoromethyl)cyclohexyl)oxy)naphthalen-2-yl)ethyl)-9-azabicyclo[3.3.1]nonane-3-carboxylic acid;
9-((R)-1-(5-(trifluoromethyl)-6-((cis-4-(trifluoromethyl)cyclohexyl)oxy)naphthalen-2-yl)ethyl)-9-azabicyclo[3.3.1]nonane-3-carboxylic acid;
9-((S)-1-(5-(trifluoromethyl)-6-((cis-4-(trifluoromethyl)cyclohexyl)oxy)naphthalen-2-yl)ethyl)-9-azabicyclo[3.3.1]nonane-3-carboxylic acid;
9-(1-(6-((cis-4-ethylcyclohexyl)oxy)-5-(trifluoromethyl)naphthalene-2-yl)ethyl)-9-azabicyclo[3.3.1]-nonane-3-carboxylic acid;
9-(1-(6-((cis-4-ethylcyclohexyl)oxy)-5-(trifluoromethyl)naphthalene-2-yl)propyl)-9-azabicyclo[3.3.1]nonane-3-carboxylic acid;
9-(1-(6-((cis-4-Methylcyclohexyl)oxy)-5-(trifluoromethyl)naphthalene-2-yl)ethyl)-9-azabicyclo[3.3.1]nonane-3-carboxylic acid;
9-(1-(6-((cis-4-Methylcyclohexyl)oxy)-5-(trifluoromethyl)naphthalen-2-yl)ethyl)-9-azabicyclo[3.3.1]nonane-3-carboxylic acid, enantiomer 1;
9-(1-(6-((cis-4-Methylcyclohexyl)oxy)-5-(trifluoromethyl)naphthalen-2-yl)ethyl)-9-azabicyclo[3.3.1]nonane-3-carboxylic acid, enantiomer 2;
8-((6-((cis-4-Methylcyclohexyl)oxy)-5-(trifluoromethyl)naphthalen-2-yl)methyl)-8-azabicyclo[3.2.1]octane-3-carboxylic acid;
9-((6-((cis-4-Methylcyclohexyl)oxy)-5-(trifluoromethyl)naphthalen-2-yl)methyl)-9-azabicyclo[3.3.1]nonane-3-carboxylic acid;
9-((6-((4,4-difluorocyclohexyl)oxy)-5-(trifluoromethyl)naphthalene-2-yl)methyl)-9-azabicyclo[3.3.1]nonane-3-carboxylic acid;
8-(1-(5-(difluoromethyl)-6-((cis-4-methylcyclohexyl)oxy)naphthalen-2-yl)propyl)-8-azabicyclo[3.2.1]octane-3-carboxylic acid;
9-((5-(difluoromethyl)-6-((cis-4-(trifluoromethyl)cyclohexyl)oxy)naphthalene-2-yl)methyl)-9-azabicyclo[3.3.1]nonane-3-carboxylic acid;
9-((5-(trifluoromethyl)-6-((cis-4-(trifluoromethyl)cyclohexyl)oxy)quinolin-2-yl)methyl)-9-azabicyclo[3.3.1]nonane-3-carboxylic acid;
8-(1-(5-(trifluoromethyl)-6-((cis-4-(trifluoromethyl)cyclohexyl)oxy)quinolin-2-yl)ethyl)-8-azabicyclo[3.2.1]octane-3-carboxylic acid;
9-((6-((((trans,trans)-3,5-dimethylcyclohexyl)oxy)-5-(trifluoromethyl) naphthalene-2-yl)methyl)-9-azabicyclo[3.3.1]nonane-3-carboxylic acid;
8-(6-((cis-4-Methylcyclohexyl)oxy)-5-(trifluoromethyl)-2-naphthoyl)-8-azabicyclo[3.2.1]octane-3-carboxylic acid;
9-(5-(trifluoromethyl)-6-((cis-4-(trifluoromethyl)cyclohexyl)oxy)-2-naphthoyl)-9-azabicyclo[3.3.1]nonane-3-carboxylic acid;
9-(2-(5-(trifluoromethyl)-6-((cis-4-(trifluoromethyl)cyclohexyl)oxy)naphthalene-2-yl)acetyl)-9-azabicyclo[3.3.1]nonane-3-carboxylic acid;
9-(2-(5-(trifluoromethyl)-6-((cis-4-(trifluoromethyl)cyclohexyl)oxy)naphthalene-2-yl)ethyl)-9-azabicyclo[3.3.1]nonane-3-carboxylic acid;
9-((6-((cis-4-methylcyclohexyl)amino)-5-(trifluoromethyl)naphthalen-2-yl)methyl)-9-azabicyclo[3.3.1]nonane-3-carboxylic acid;
2-(9-Azabicyclo[3.3.1]nonan-9-yl)-2-(6-((cis-4-methylcyclohexyl)oxy)-5-(trifluoromethyl)naphthalen-2-yl)acetic acid;
9-((5-Chloro-6-((cis-4-ethylcyclohexyl)oxy)naphthalen-2-yl)methyl)-9-azabicyclo[3.3.1]nonane-3-carboxylic acid;
9-((5-Chloro-6-((cis-4-(trifluoromethyl)cyclohexyl)oxy)naphthalen-2-yl)methyl)-9-azabicyclo[3.3.1]nonane-3-carboxylic acid;
4-(((5-(trifluoromethyl)-6-((cis-4-(trifluoromethyl)cyclohexyl)oxy)naphthalen-2-yl)methyl)carbamoyl)bicyclo[2.2.2]octane-1-carboxylic acid;
N-(6-((cis-4-trifluoromethylcyclohexyl)oxy)-5-(trifluoromethyl)naphthalene-2-ylcarbonyl)-1-aminoindane-6-carboxylic acid;
N-(6-((cis-4-trifluoromethylcyclohexyl)oxy)-5-(trifluoromethyl)naphthalene-2-ylcarbonyl)-6-aminoindole-3-carboxylic acid;
N-(6-((cis-4-trifluoromethylcyclohexyl)oxy)-5-(trifluoromethyl)naphthalene-2-ylcarbonyl)-2-azabicyclo[1.2.3]octane-7-carboxylic acid;
N-(6-((cis-4-trifluoromethylcyclohexyl)oxy)-5-(trifluoromethyl)naphthalene-2-ylcarbonyl)-decahydroisoquinoline-5-carboxylic acid;
2-(2-(5-(trifluoromethyl)-6-((cis-4-(trifluoromethyl)cyclohexyl)oxy)naphthalene-2-yl)acetyl)-2-azabicyclo[1.2.3]octane-7-carboxylic acid;

2-(2-(5-(difluoromethyl)-6-((cis-4-(trifluoromethyl)cyclohexyl)oxy)naphthalene-2-yl)acetyl)-2-azabicyclo[1.2.3]octane-7-carboxylic acid;

4-(((5-(trifluoromethyl)-6-((cis-4-(trifluoromethyl)cyclohexyl)oxy)naphthalen-2-yl)methyl)aminomethyl)bicyclo[2.2.2]octane-1-carboxylic acid;

4-(((5-(trifluoromethyl)-6-((cis-4-(trifluoromethyl)cyclohexyl)oxy)naphthalen-2-yl)methyl)amino)-2-hydroxybicyclo[2.2.2]octane-1-carboxylic acid;

7-(((5-(trifluoromethyl)-6-((cis-4-(trifluoromethyl)cyclohexyl)oxy)naphthalen-2-yl)methyl)amino)-tricyclo[3.1.1.0]heptane-5-carboxylic acid;

8-(1-(5-(trifluoromethyl)-6-((cis-4-(trifluoromethyl)cyclohexyl)oxy)-naphthalene-2-yl)ethyl)-8-azabicyclo[3.2.1]octane-3-carboxylic acid;

3-(((5-(trifluoromethyl)-6-((cis-4-(trifluoromethyl)cyclohexyl)oxy)naphthalen-2-yl)methyl)amino)-7,7-dimethylbicyclo[2.2.1]heptane-4-carboxylic acid;

8-(1-(6-((cis-4-Methylcyclohexyl)oxy)-5-(trifluoromethyl)naphthalen-2-yl)ethyl)-8-azabicyclo[3.2.1]octane-3-carboxylic acid;

9-(6-((cis-4-Methylcyclohexyl)oxy)-5-(trifluoromethyl)-2-naphthoyl)-9-azabicyclo[3.3.1]nonane-3-carboxylic acid;

9-((6-((cis-4-Methylcyclohexyl)oxy)-5-(trifluoromethyl)naphthalen-2-yl)methyl)-9-aza-7-oxa-bicyclo[3.3.1]nonane-3-carboxylic acid;

8-(1-(6-((cis-4-Methylcyclohexyl)oxy)-5-(trifluoromethyl)naphthalen-2-yl)propyl)-8-azabicyclo[3.2.1]octane-3-carboxylic acid;

9-(1-(6-((cis-4-Methylcyclohexyl)oxy)-5-(trifluoromethyl)naphthalen-2-yl)propyl)-9-azabicyclo[3.3.1]nonane-3-carboxylic acid;

9-((6-((cis-4-Methylcyclohexyl)oxy)-5-(trifluoromethyl)naphthalen-2-yl)methyl)-7-hydroxy-9-aza-bicyclo[3.3.1]nonane-3-carboxylic acid;

8-(1-(6-((cis-4-Methylcyclohexyl)oxy)-5-(trifluoromethyl)naphthalen-2-yl)ethyl)-8-azabicyclo[3.2.1]octane-3-carboxylic acid, enantiomer 1;

8-(1-(6-((cis-4-Methylcyclohexyl)oxy)-5-(trifluoromethyl)naphthalen-2-yl)ethyl)-8-azabicyclo[3.2.1]octane-3-carboxylic acid, enantiomer 2;

9-(1-(5-(difluoromethyl)-6-((cis-4-methylcyclohexyl)oxy)naphthalen-2-yl)ethyl)-9-azabicyclo[3.3.1]nonane-3-carboxylic acid;

8-(1-(5-(difluoromethyl)-6-((cis-4-methyl)-8-azabicyclo[3.2.1]octane-3-carboxylic acid;

8-(1-(5-(difluoromethyl)-6-((cis-4-methylcyclohexyl)oxy)naphthalen-2-yl)methyl)-8-azabicyclo[3.2.1]octane-3-carboxylic acid;

9-(1-(5-(difluoromethyl)-6-((cis-4-methylcyclohexyl)oxy)naphthalen-2-yl)propyl)-9-azabicyclo[3.3.1]nonane-3-carboxylic acid;

8-(1-(5-(difluoromethyl)-6-((cis-4-methylcyclohexyl)oxy)naphthalen-2-yl)ethyl)-8-azabicyclo[3.2.1]octane-3-carboxylic acid, enantiomer 1;

8-(1-(5-(difluoromethyl)-6-((cis-4-methyl)-8-azabicyclo[3.2.1]octane-3-carboxylic acid, enantiomer 1;

9-(1-(5-(difluoromethyl)-6-((cis-4-methylcyclohexyl)oxy)naphthalen-2-yl)ethyl)-9-azabicyclo[3.3.1]nonane-3-carboxylic acid, enantiomer 1;

9-(1-(5-(difluoromethyl)-6-((cis-4-methylcyclohexyl)oxy)naphthalen-2-yl)ethyl)-9-azabicyclo[3.3.1]nonane-3-carboxylic acid, enantiomer 2;

8-(1-(5-(difluoromethyl)-6-((cis-4-methylcyclohexyl)oxy)naphthalen-2-yl)propyl)-8-azabicyclo[3.2.1]octane-3-carboxylic acid, enantiomer 1;

8-(1-(5-(difluoromethyl)-6-((cis-4-methylcyclohexyl)oxy)naphthalen-2-yl)propyl)-8-azabicyclo[3.2.1]octane-3-carboxylic acid, enantiomer 2;

9-((6-((cis-4-trifluoromethylcyclohexyl)oxy)naphthalen-2-yl)methyl)-9-azabicyclo[3.3.1]nonane-3-carboxylic acid;

methyl 2-((5-(trifluoromethyl)-6-((cis-4-(trifluoromethyl)cyclohexyl)oxy)naphthalen-2-yl)methyl)-(7R,9aR)-octahydro-1H-pyrido[1,2-a]pyrazine-7-carboxylic acid;

3-(4-{[5-trifluoromethyl-6-(4-trifluoromethyl-cyclohexyloxy)-naphthalen-2-ylmethyl]-amino}-bicyclo[2.2.2]oct-1-yl)-carboxylic acid;

2-((5-(trifluoromethyl)-6-((cis-4-(trifluoromethyl)cyclohexyl)oxy)naphthalen-2-yl)methyl)-(7R,9aR)-octahydro-1H-pyrido[1,2-a]pyrazine-7-carboxylic acid;

2-((5-(trifluoromethyl)-6-((cis-4-(trifluoromethyl)cyclohexyl)oxy)naphthalen-2-yl)methyl)-2-azaspiro[3.3]heptane-6-carboxylic acid;

N-((5-(trifluoromethyl)-6-((cis-4-(trifluoromethyl)cyclohexyl)oxy)naphthalen-2-yl)methyl)-3-amino-indane-5-carboxylic acid;

3-((5-(trifluoromethyl)-6-((cis-4-(trifluoromethyl)cyclohexyl)oxy)naphthalen-2-yl)methyl)-3-azabicyclo[3.1.0]hexane-6-carboxylic acid;

2-((5-(trifluoromethyl)-6-((cis-4-(trifluoromethyl)cyclohexyl)oxy)naphthalen-2-yl)methyl)-2-azaspiro[3.2]hexane-5-carboxylic acid;

N-((5-(trifluoromethyl)-6-((cis-4-(trifluoromethyl)cyclohexyl)oxy)naphthalen-2-yl)methyl)-decahydroisoquinoline-8-carboxylic acid;

3-((6-((cis-4-trifluoromethylcyclohexyl)oxy)naphthalen-2-yl)methyl)-3-azabicyclo[3.3.1]nonane-9-carboxylic acid;

N-(5-trifluoromethyl-6-(4-trifluoromethyl-cyclohexyloxy)-naphthalen-2-ylmethyl)-4-aminobicyclo[2.2.1]heptane-1-carboxylic acid;

N-(5-trifluoromethyl-6-(4-trifluoromethyl-cyclohexyloxy)-naphthalen-2-ylmethyl)-1-aminoadamantane-3-carboxylic acid;

3-(5-trifluoromethyl-6-(4-trifluoromethyl-cyclohexyloxy)-naphthalen-2-ylmethyl)-3-azabicyclo[3.3.0]octane-7-carboxylic acid;

2-((5-(trifluoromethyl)-6-((cis-4-(trifluoromethyl)cyclohexyl)oxy)naphthalen-2-yl)methyl)-((9S,9aR)-octahydro-1H-pyrido[1,2-a]pyrazin-9-yl)methanol;

8-((6-((4,4-difluorocyclohexyl)oxy)-5-(trifluoromethyl)naphthalene-2-yl)methyl)-8-azabicyclo[3.2.1]octane-3-carboxylic acid;

2-(5-trifluoromethyl-6-(4-trifluoromethyl-cyclohexyloxy)-naphthalen-2-ylmethyl)-2-aza-6-oxaspiro[3.4]octane-7-carboxylic acid;

(1R,5S,7r)-3-((2-(4-(trifluoromethyl)cyclohexyloxy)-1-(trifluoromethyl)naphthalen-6-yl)methyl)-3-aza-bicyclo[3.3.1]nonane-7-carboxylic acid;

N-(5-trifluoromethyl-6-(cis-4-trifluoromethyl-cyclohexyloxy)-naphthalen-2-ylmethyl)-3-(azetidine-3-yl)-cyclohexane-1-carboxylic acid;

8-((5-(trifluoromethyl)-6-((cis-4-(trifluoromethyl)cyclohexyl)oxy)quinolin-2-yl)methyl)-8-azabicyclo[3.2.1]octane-3-carboxylic acid;

2-(5-trifluoromethyl-6-(cis-4-trifluoromethyl-cyclohexyloxy)-naphthalen-2-ylmethyl)-2-aza-5-oxaspiro[5.4]decane-8-carboxylic acid;

N-(5-trifluoromethyl-6-(cis-4-trifluoromethyl-cyclohexyloxy)-naphthalen-2-ylmethyl)-8-aminobicyclo[3.2.1]octane-3-carboxylic acid, enantiomer 1;

N-(5-trifluoromethyl-6-(cis-4-trifluoromethyl-cyclohexyloxy)-naphthalen-2-ylmethyl)-8-aminobicyclo[3.2.1]octane-3-carboxylic acid, enantiomer 2;

N-(5-trifluoromethyl-6-(cis-4-trifluoromethyl-cyclohexyloxy)-naphthalen-2-ylmethyl)-1-amino-3,5-dimethyladamantane;
7-(5-trifluoromethyl-6-(cis-4-trifluoromethyl-cyclohexyloxy)-naphthalen-2-ylmethyl)-7-azabicyclo[2.2.1]heptane-2-carboxylic acid;
N-(5-trifluoromethyl-6-(cis-4-trifluoromethyl-cyclohexyloxy)-naphthalen-2-ylmethyl)-9-aminobicyclo[3.3.1]nonane-3-carboxylic acid;
9-(5-trifluoromethyl-6-(cis-4-trifluoromethyl-cyclohexyloxy)-naphthalen-2-ylmethyl)-9-aza-7-oxabicyclo[3.3.1]nonane-3-carboxylic acid;
9-(5-trifluoromethyl-6-(cis-4-trifluoromethyl-cyclohexyloxy)-naphthalen-2-ylmethyl)-9-azabicyclo[3.3.1]nonane;
9-(5-trifluoromethyl-6-(cis-4-trifluoromethyl-cyclohexyloxy)-naphthalen-2-ylmethyl)-7-hydroxy-9-azabicyclo[3.3.1]nonane-3-carboxylic acid;
9-(5-trifluoromethyl-6-(cis-4-trifluoromethyl-cyclohexyloxy)-naphthalen-2-ylmethyl)-7-oxo-9-azabicyclo[3.3.1]nonane-3-carboxylic acid;
9-((6-((cis-4-ethylcyclohexyl)oxy)-5-(trifluoromethyl)naphthalen-2-yl)methyl)-9-azabicyclo[3.3.1]nonane-3-carboxylic acid;
8-((6-((cis-4-ethylcyclohexyl)oxy)-5-(trifluoromethyl)naphthalen-2-yl)methyl)-8-azabicyclo[3.2.1]octane-3-carboxylic acid;
8-(1-(5-(trifluoromethyl)-6-((cis-4-(trifluoromethyl)cyclohexyl)oxy)naphthalen-2-yl)ethyl)-8-azabicyclo[3.2.1]octane-3-carboxylic acid, enantiomer 1;
8-(1-(5-(trifluoromethyl)-6-((cis-4-(trifluoromethyl)cyclohexyl)oxy)naphthalen-2-yl)ethyl)-8-azabicyclo[3.2.1]octane-3-carboxylic acid, enantiomer 2;
9-(1-(6-((cis-4-ethylcyclohexyl)oxy)-5-(trifluoromethyl)naphthalen-2-yl)ethyl)-9-azabicyclo[3.3.1]nonane-3-carboxylic acid;
8-(1-(6-((cis-4-ethylcyclohexyl)oxy)-5-(trifluoromethyl)naphthalen-2-yl)ethyl)-8-azabicyclo[3.2.1]octane-3-carboxylic acid;
9-(1-(6-((cis-4-trifluoromethylcyclohexyl)oxy)-5-(trifluoromethyl)naphthalen-2-yl) propyl)-9-azabicyclo[3.3.1]nonane-3-carboxylic acid;
8-(1-(6-((cis-4-trifluoromethylcyclohexyl)oxy)-5-(trifluoromethyl)naphthalen-2-yl) propyl)-8-azabicyclo[3.2.1]octane-3-carboxylic acid;
9-(1-(6-((cis-4-ethylcyclohexyl)oxy)-5-(trifluoromethyl)naphthalen-2-yl)propyl)-9-azabicyclo[3.3.1]nonane-3-carboxylic acid;
8-(1-(6-((cis-4-ethylcyclohexyl)oxy)-5-(trifluoromethyl)naphthalen-2-yl)propyl)-8-azabicyclo[3.2.1]octane-3-carboxylic acid;
8-((5-(trifluoromethyl)-6-((cis-4-(trifluoromethyl)cyclohexyl)oxy)naphthalen-2-yl)methyl)-8-azabicyclo[3.2.1]octane-3-carboxylic acid;
9-(1-(6-((cis-4-ethylcyclohexyl)oxy)-5-chloronaphthalen-2-yl)ethyl)-9-azabicyclo[3.3.1]nonane-3-carboxylic acid;
9-((5-Chloro-6-((cis-4-methylcyclohexyl)oxy)naphthalen-2-yl)methyl)-9-azabicyclo[3.3.1]nonane-3-carboxylic acid;
8-(1-(5-Chloro-6-((cis-4-ethylcyclohexyl)oxy)naphthalen-2-yl)ethyl)-8-azabicyclo[3.2.1]octane-3-carboxylic acid; and
8-((5-Chloro-6-((cis-4-ethylcyclohexyl)oxy)naphthalen-2-yl)methyl)-8-azabicyclo[3.2.1]octane-3-carboxylic acid;
or a pharmaceutically acceptable salt thereof.

The term "fused ring system," as used herein, is a ring system that has two or three rings (preferably two rings) independently selected from carbocyclyl, heterocyclyl, aryl or heteroaryl rings that share one side. A fused ring system may have from 4-15 ring members, preferably from 5-10 ring members. Examples of fused ring systems include octahydroisoquinolin-2(1H)-yl, 2,3-dihydro-1H-indenyl, octahydro-1H-pyrido[1,2-a]pyrazinyl, and decahydroisoquinolinyl).

The term "bridged ring system," as used herein, is a ring system that has a carbocyclyl or heterocyclyl ring wherein two non-adjacent atoms of the ring are connected (bridged) by one or more (preferably from one to three) atoms selected from C, N, O, or S. A bridged ring system can have more than one bridge within the ring system (e.g., adamantyl). A bridged ring system may have from 6-10 ring members, preferably from 7-10 ring members. Examples of bridged ring systems include adamantyl, 9-azabicyclo[3.3.1]nonan-9-yl, 8-azabicyclo[3.2.1]octanyl, bicyclo[2.2.2]octanyl, 3-azabicyclo[3.1.1]heptanyl, bicyclo[2.2.1]heptanyl, (1R,5S)-bicyclo[3.2.1]octanyl, 3-azabicyclo[3.3.1]nonanyl, and bicyclo[2.2.1]heptanyl. More preferably, the bridged ring system is selected from the group consisting of 9-azabicyclo[3.3.1]nonan-9-yl, 8-azabicyclo[3.2.1]octanyl, and bicyclo[2.2.2]octanyl.

The term "spiro ring system," as used herein, is a ring system that has two rings each of which are independently selected from a carbocyclyl or a heterocyclyl, wherein the two ring structures having one atom in common. Spiro ring systems have from 5 to 14 ring members. Example of spiro ring systems include 2-azaspiro[3.3]heptanyl, spiropentanyl, 2-oxa-6-azaspiro[3.3]heptanyl, 2,7-diazaspiro[3.5]nonanyl, 2-oxa-7-azaspiro[3.5]nonanyl, 6-oxa-9-azaspiro[4.5]decanyl, 6-oxa-2-azaspiro[3.4]octanyl, 5-azaspiro[2.3]hexanyl and 2,8-diazaspiro[4.5]decanyl.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 6 carbon atoms, or 1 to 4 carbon atoms. In some embodiments, an alkyl comprises from 6 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, or n-decyl.

"Alkylene" refers to a divalent alkyl group. Examples of alkylene groups include methylene, ethylene, propylene, n-butylene, and the like. The alkylene is attached to the rest of the molecule through a single bond and to the radical group through a single bond. The points of attachment of the alkylene to the rest of the molecule and to the radical group can be through one carbon or any two carbons within the carbon chain.

As used herein, the term "haloalkyl" refers to an alkyl, as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro substituent. Dihaloalkyl and polyhaloalkyl groups can be substituted with two or more of the same halo atoms or a combination of different halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms. Preferred haloalkyl groups are trifluoromethyl and difluoromethyl.

"Halogen" or "halo" may be fluoro, chloro, bromo or iodo.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-6 carbon atoms, more preferably about 1-4 carbon atoms.

As used herein, the term "haloalkoxy" refers to haloalkyl-O—, wherein haloalkyl is defined herein above. Representative example of haloalkoxy groups are trifluoromethoxy, difluoromethoxy, and 1,2-dichloroethoxy. Preferably, haloalkoxy groups have about 1-6 carbon atoms, more preferably about 1-4 carbon atoms.

As used herein, the term "alkylthio" refers to alkyl-S—, wherein alkyl is defined herein above.

As used herein, the term "carbocyclyl" refers to saturated or partially unsaturated (but not aromatic) monocyclic, bicyclic or tricyclic hydrocarbon groups of 3-14 carbon atoms, preferably 3-9, or more preferably 3-8 carbon atoms. Carbocyclyls include fused or bridged ring systems. The term "carbocyclyl" encompasses cycloalkyl groups. The term "cycloalkyl" refers to completely saturated monocyclic, bicyclic or tricyclic hydrocarbon groups of 3-12 carbon atoms, preferably 3-9, or more preferably 3-8 carbon atoms. Exemplary monocyclic carbocyclyl groups include, but are not limited to, cyclopropyl, cyclobutyl, cyclopentyl, cyclopentenyl, cyclohexyl or cyclohexenyl. Exemplary bicyclic carbocyclyl groups include bornyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, or bicyclo[2.2.2]octyl. Exemplary tricyclic carbocyclyl groups include adamantyl.

As used herein, the term "halocycloalkyl" refers to a cycloalkyl, as defined herein, that is substituted by one or more halo groups as defined herein. Preferably the halocycloalkyl can be monohalocycloalkyl, dihalocycloalkyl or polyhalocycloalkyl including perhalocycloalkyl. A monohalocycloalkyl can have one iodo, bromo, chloro or fluoro substituent. Dihalocycloalkyl and polyhalocycloalkyl groups can be substituted with two or more of the same halo atoms or a combination of different halo groups.

As used herein, the term "cycloalkoxy" refers to cycloalkyl-O—, wherein cycloalkyl is defined herein above.

As used herein, the term "halocycloalkoxy" refers to halocycloalkyl-O—, wherein halocycloalkyl is defined herein above.

The term "spirocycloalkyl" as used herein, is a cycloalkyl that has one ring atom in common with the group to which it is attached. Spirocycloalkyl groups may have from 3 to 14 ring members. In a preferred embodiment, the spirocycloalkyl has from 3 to 8 ring carbon atoms and is monocyclic.

The term "aryl" refers to monocyclic, bicyclic or tricyclic aromatic hydrocarbon groups having from 6 to 14 carbon atoms in the ring portion. In one embodiment, the term aryl refers to monocyclic and bicyclic aromatic hydrocarbon groups having from 6 to 10 carbon atoms. Representative examples of aryl groups include phenyl, naphthyl, fluorenyl, and anthracenyl.

The term "aryl" also refers to a bicyclic or tricyclic group in which at least one ring is aromatic and is fused to one or two non-aromatic hydrocarbon ring(s). Nonlimiting examples include tetrahydronaphthalene, dihydronaphthalenyl and indanyl.

As used herein, the term "heterocyclyl" refers to a saturated or unsaturated, non-aromatic monocyclic, bicyclic or tricyclic ring system which has from 3- to 15-ring members at least one of which is a heteroatom, and up to 10 of which may be heteroatoms, wherein the heteroatoms are independently selected from O, S and N, and wherein N and S can be optionally oxidized to various oxidation states. In one embodiment, a heterocyclyl is a 3-8-membered monocyclic. In another embodiment, a heterocyclyl is a 6-12-membered bicyclic. In yet another embodiment, a heterocyclycyl is a 10-15-membered tricyclic ring system. The heterocyclyl group can be attached at a heteroatom or a carbon atom. Heterocyclyls include fused or bridged ring systems. The term "heterocyclyl" encompasses heterocycloalkyl groups. The term "heterocycloalkyl" refers to completely saturated monocyclic, bicyclic or tricyclic heterocyclyl comprising 3-15 ring members, at least one of which is a heteroatom, and up to 10 of which may be heteroatoms, wherein the heteroatoms are independently selected from O, S and N, and wherein N and S can be optionally oxidized to various oxidation states. Examples of heterocyclyls include dihydrofuranyl, [1,3]dioxolane, 1,4-dioxane, 1,4-dithiane, piperazinyl, 1,3-dioxolane, imidazolidinyl, imidazolinyl, pyrrolidine, dihydropyran, oxathiolane, dithiolane, 1,3-dioxane, 1,3-dithianyl, oxathianyl, thiomorpholinyl, oxiranyl, aziridinyl, oxetanyl, azetidinyl, tetrahydrofuranyl, pyrrolidinyl, tetrahydropyranyl, piperidinyl, morpholinyl, piperazinyl, azepinyl, oxapinyl, oxazepinyl and diazepinyl.

The term "spiroheterocycloalkyl" as used herein, is a heterocycloalkyl that has one ring atom in common with the group to which it is attached. Spiroheterocycloalkyl groups may have from 3 to 15 ring members. In a preferred embodiment, the spiroheterocycloalkyl has from 3 to 8 ring atoms selected from carbon, nitrogen, sulfur and oxygen and is monocyclic.

As used herein, the term "heteroaryl" refers to a 5-14 membered monocyclic-, bicyclic-, or tricyclic-ring system, having 1 to 10 heteroatoms independently selected from N, O or S, wherein N and S can be optionally oxidized to various oxidation states, and wherein at least one ring in the ring system is aromatic. In one embodiment, the heteroaryl is monocyclic and has 5 or 6 ring members. Examples of monocyclic heteroaryl groups include pyridyl, thienyl, furanyl, pyrrolyl, pyrazolyl, imidazoyl, oxazolyl, isoxazolyl, thiazolyl, isothiazolyl, triazolyl, oxadiazolyl, thiadiazolyl and tetrazolyl. In another embodiment, the heteroaryl is bicyclic and has from 8 to 10 ring members. Examples of bicyclic heteroaryl groups include indolyl, benzofuranyl, quinolyl, isoquinolyl indazolyl, indolinyl, isoindolyl, indolizinyl, benzamidazolyl, quinolinyl, 5,6,7,8-tetrahydroquinoline and 6,7-dihydro-5H-pyrrolo[3,2-d]pyrimidine.

An amino is a group having the formula $NH_2$—. The term N-alkylamino is an amino group in which one of the hydrogen atoms is replaced with an alkyl group. The term N,N-dialkylamino is an amino group in which each hydrogen atoms is replaced with an alkyl group which may be the same or different.

The term "alkanoyl" refers to alkyl-C(O)— wherein the alkyl is defined as above.

The term "alkoxycarbonyl" refers to alkoxy-C(O)—, wherein the alkoxy group is defined as above.

The term "alkanoyloxy" refers to alkyl-C(O)O—, wherein the alkyl is defined as above.

A carbamoyl is a group having the formula NH$_2$C(O)—. The term N-alkylcarbamoyl is a carbamoyl group in which one of the hydrogen atoms is replaced with an alkyl group. The term N,N-dialkylcarbamoyl is a carbamoyl group in which each hydrogen atoms is replaced with an alkyl group which may be the same or different.

The term "alkylamido" refers to a group having the formula alkyl-C(O)—NH—. As used herein, the term "alkylsulfonyl" refers to a group having the formula alkyl-SO$_2$—.

A sulfamoyl is a group having the formula NH$_2$S(O)$_2$—. The term N-alkylsulfamoyl is a sulfamoyl group in which one of the hydrogen atoms is replaced with an alkyl group. The term N,N-dialkylsulfamoyl is a sulfamoyl group in which each hydrogen atoms is replaced with an alkyl group which may be the same or different.

The term "alkylsulfonamido" refers to a group having the formula alkyl-S(O)$_2$—NH—.

The term "trialkylsilyl" refers to (alkyl)$_3$-Si—, wherein each of the alkyl groups may be the same or different.

The number of carbon atoms in a group is specified herein by the prefix "C$_{x-xx}$", wherein x and xx are integers. For example, "C$_{1-4}$alkyl" is an alkyl group which has from 1 to 4 carbon atoms; C$_{1-6}$alkoxy is an alkoxy group having from 1 to 6 carbon atoms; C$_{6-10}$aryl is an aryl group which has from 6 to 10 carbon atoms; C$_{1-4}$haloalkyl is a haloalkyl group which has from 1 to 4 carbon atoms; and N,N-di-C$_{1-6}$ alkylamino is a N,N-dialkylamino group in which the nitrogen is substituted with two alkyl groups each of which is independently from 1 to 6 carbon atoms.

The phrase "compound of the invention," as used herein, refers to compounds represented by formulae (I), (II), (IIa), (IIb), and (III), and any of the specific examples disclosed herein.

The disclosed compounds can contain one or more asymmetric centers in the molecule. In accordance with the present disclosure any structure that does not designate the stereochemistry is to be understood as embracing all the various optical isomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase). The compounds can be isotopically-labeled compounds, for example, compounds including various isotopes of hydrogen, carbon, nitrogen, oxygen, phosphorous, fluorine, iodine, or chlorine. The disclosed compounds may exist in tautomeric forms and mixtures and separate individual tautomers are contemplated. In addition, some compounds may exhibit polymorphism.

By way of clarity, compounds of the invention included all isotopes of the atoms present in formulae (I), (II), (IIa), (IIb), and (III) and any of the examples or embodiments disclosed herein. For example, H (or hydrogen) represents any isotopic form of hydrogen including $^1$H, $^2$H (D), and $^3$H (T); C represents any isotopic form of carbon including $^{12}$C, $^{13}$C, and $^{14}$C; O represents any isotopic form of oxygen including $^{16}$O, $^{17}$O and $^{18}$O; N represents any isotopic form of nitrogen including $^3$N, $^{14}$N and $^{15}$N; P represents any isotopic form of phosphorous including $^{31}$P and $^{32}$P; S represents any isotopic form of sulfur including $^{32}$S and $^{35}$S; F represents any isotopic form of fluorine including $^{19}$F and $^{18}$F; Cl represents any isotopic form of chlorine including $^{35}$Cl, $^{37}$Cl and $^{36}$Cl; and the like. In a preferred embodiment, compounds represented by formulae (I)-(III) and any of the examples or embodiments disclosed herein comprises isotopes of the atoms therein in their naturally occurring abundance. However, in certain instances, it is desirable to enrich one or more atom in a particular isotope which would normally be present in less abundance. For example, $^1$H would normally be present in greater than 99.98% abundance; however, a compound of the invention can be enriched in $^2$H or $^3$H at one or more positions where H is present. In particular embodiments of the compounds of formulae (I)-(III), when, for example, hydrogen is enriched in the deuterium isotope, the symbol "D" may be used to represent the enrichment in deuterium. In one embodiment, when a compound of the invention is enriched in a radioactive isotope, for example $^3$H and $^{14}$C, they may be useful in drug and/or substrate tissue distribution assays. It is to be understood that the invention encompasses all such isotopic forms which modulate S1P and/or ATX activity.

Exemplary compounds represented by formula (I) which may be useful as S1P modulating agents and/or ATX modulating agents include:

4-(((6-(trans-4-tert-butylcyclohexyloxy)naphthalen-2-yl)methyl)amino)bicyclo[2.2.2]octane-1-carboxylic acid;

4-(((6-(cis-4-ethylcyclohexyloxy)naphthalen-2-yl)methyl)amino)bicyclo[2.2.2]octane-1-carboxylic acid;

4-(((6-(trans-4-tert-butylcyclohexyloxy)quinolin-2-yl)methyl)amino)bicyclo[2.2.2]octane-1-carboxylic acid;

4-(((6-(spiro[3.5]nonan-7-yl-oxy)naphthalen-2-yl)methyl)amino)bicyclo[2.2.2]octane-1-carboxylic acid;

4-(((6-(trans-4-tert-butylcyclohexyloxy)naphthalen-2-yl)methyl)methylamino)bicyclo[2.2.2]octane-1-carboxylic acid;

2-((2-(trans-4-tert-butylcyclohexyloxy)naphthalen-6-yl)methyl)-octahydro-1H-pyrido[1,2-a]pyrazine-7-carboxylic acid;

4-(((5-trifluoromethyl-6-(trans-4-tert-butylcyclohexexyloxy)quinolin-2-yl)methyl)amino)bicyclo[2.2.2]octane-1-carboxylic acid;

4-(((5-trifluoromethyl-6-(trans-4-tert-butylcyclohexyloxy)naphthalen-2-yl)methyl)amino) bicyclo[2.2.2]octane-1-carboxylic acid;

4-(((6-(cis-4-methylcyclohexyloxy)naphthalen-2-yl)methyl)amino)bicyclo[2.2.2]octane-1-carboxylic acid;

4-(((6-(cis-4-trifluoromethylcyclohexyloxy)naphthalen-2-yl)methyl)amino)bicyclo[2.2.2]octane-1-carboxylic acid;

4-(((6-(heptyloxy)naphthalen-2-yl)methyl)amino)bicyclo[2.2.2]octane-1-carboxylic acid;

4-(((6-(cyclohexyl)naphthalen-2-yl)methyl)amino)bicyclo[2.2.2]octane-1-carboxylic acid;

4-(((6-(spiro[5.5]undecan-3-yl-oxy)naphthalen-2-yl)methyl)amino)bicyclo[2.2.2]octane-1-carboxylic acid;

4-(((6-(cyclohexyloxy)quinolin-2-yl)methyl)amino)bicyclo[2.2.2]octane-1-carboxylic acid;

4-(((6-(trans-4-methylcyclohexyloxy)naphthalen-2-yl)methyl)amino)bicyclo[2.2.2]octane-1-carboxylic acid;

4-(((6-(trans-4-isopropylcyclohexyloxy)naphthalen-2-yl)methyl)amino)bicyclo[2.2.2]octane-1-carboxylic acid;

4-(((6-(trans-4-methylcyclohexyloxy)quinolin-2-yl)methyl)amino)bicyclo[2.2.2]octane-1-carboxylic acid;

4-(((6-(heptyloxy)quinolin-2-yl)methyl)amino)bicyclo[2.2.2]octane-1-carboxylic acid;

4-(((6-(trans-4-tert-butylcyclohexyloxy)naphthalen-2-yl)methyl)amino)-2-hydroxybicyclo[2.2.2]octane-1-carboxylic acid;

4-(((6-(cis-4-phenylcyclohexyloxy)naphthalen-2-yl)methyl)amino)bicyclo[2.2.2]octane-1-carboxylic acid;

4-(((6-(trans-4-ethylcyclohexyloxy)quinolin-2-yl)methyl)amino)bicyclo[2.2.2]octane-1-carboxylic acid;

4-(((6-(trans-4-isopropylcyclohexyloxy)quinolin-2-yl)methyl)amino)bicyclo[2.2.2]octane-1-carboxylic acid;

4-(((6-(4,4-dimethylcyclohexyloxy)quinolin-2-yl)methyl)amino)bicyclo[2.2.2]octane-carboxylic acid;

4-(((6-(trans-4-ethylcyclohexyloxy)naphthalen-2-yl)methyl)amino)bicyclo[2.2.2]octane-1-carboxylic acid;

4-(((6-(cis-4-isopropylcyclohexyloxy)quinolin-2-yl)methyl)amino)bicyclo[2.2.2]octane-1-carboxylic acid;

4-(((6-(trans-4-tert-butylcyclohexyloxy)naphthalen-2-yl)methyl)amino)-2-hydroxybicyclo[2.2.2]octane-1-acetic acid;

4-(((6-(4,4-dimethylcyclohexyloxy)napthalen-2-yl)methyl)amino)bicyclo[2.2.2]octane-1-carboxylic acid;

4-(((6-(trans-4-(1,1-dimethylpropyl)cyclohexyloxy)quinolin-2-yl)methyl)amino)bicyclo[2.2.2]octane-1-carboxylic acid;

4-(((6-(spiro[3.5]nonan-7-yl-oxy)quinolin-2-yl)methyl)amino)bicyclo[2.2.2]octane-1-carboxylic acid;

4-(((6-(spiro[5.5]undecan-3-yl-oxy)quinolin-2-yl)methyl)amino)bicyclo[2.2.2]octane-1-carboxylic acid;

4-(((6-(cis-4-isopropylcyclohexyloxy)naphthalen-2-yl)methyl)amino)bicyclo[2.2.2]octane-1-carboxylic acid;

4-(((6-(trans-4-(1,1-dimethylpropyl)cyclohexyloxy)naphthalen-2-yl)methyl)amino)bicyclo[2.2.2]octane-1-carboxylic acid;

4-(((6-(cis-4-trifluoromethylcyclohexyloxy)quinolin-2-yl)methyl)amino)bicyclo[2.2.2]octane-1-carboxylic acid;

4-(((6-(cis-4-ethylcyclohexyloxy)quinolin-2-yl)methyl)amino)bicyclo[2.2.2]octane-1-carboxylic acid;

4-(((6-(spiro[4.5]decan-8-yl-oxy)naphthalen-2-yl)methyl)amino)bicyclo[2.2.2]octane-1-carboxylic acid;

4-(((6-(cis-4-phenylcyclohexyloxy)quinolin-2-yl)methyl)amino)bicyclo[2.2.2]octane-1-carboxylic acid;

4-(((6-(trans-4-phenylcyclohexyloxy)naphthalen-2-yl)methyl)amino)bicyclo[2.2.2]octane-1-carboxylic acid;

4-(((6-(cis-4-tert-butylcyclohexyloxy)naphthalen-2-yl)methyl)amino)bicyclo[2.2.2]octane-1-carboxylic acid;

4-(((6-(trans-4-phenylcyclohexyloxy)quinolin-2-yl)methyl)amino)bicyclo[2.2.2]octane-1-carboxylic acid;

4-(((6-(cis-4-methylcyclohexyloxy)quinolin-2-yl)methyl)amino)bicyclo[2.2.2]octane-1-carboxylic acid;

4-(((6-(trans-4-(trimethylsilyl)cyclohexyloxy)naphthalen-2-yl)methyl)amino)bicyclo[2.2.2]octane-1-carboxylic acid;

4-(((6-(cis-4-(trimethylsilyl)cyclohexyloxy)naphthalen-2-yl)methyl)amino)bicyclo[2.2.2]octane-1-carboxylic acid;

4-(((6-(trans-4-trifluoromethylcyclohexyloxy)naphthalen-2-yl)methyl)amino)bicyclo[2.2.2]octane-1-carboxylic acid;

4-(((6-(spiro[3.5]nonan-7-yl-oxy)quinolin-2-yl)methyl)amino)bicyclo[2.2.2]octane-1-carboxylic acid;

4-(((6-(spiro[2.5]octan-6-yl-oxy)napthalen-2-yl)methyl)amino)bicyclo[2.2.2]octane-1-carboxylic acid;

4-(((6-(spiro[2.5]octan-6-yl-oxy)quinolin-2-yl)methyl)amino)bicyclo[2.2.2]octane-1-carboxylic acid;

4-((6-(trans-4-tert-butylcyclohexyloxy)naphthalen-2-yl)methyl)-1-(pyridine-2-yl)piperazine;

4-((6-(trans-4-tert-butylcyclohexyloxy)naphthalen-2-yl)methyl)-1-(pyridine-4-yl)piperazine;

4-((6-(trans-4-tert-butylcyclohexyloxy)naphthalen-2-yl)methyl)-1-phenylpiperazine;

4-((6-(trans-4-tert-butylcyclohexyloxy)naphthalen-2-yl)methyl)-1-(pyrimidine-2-yl)piperazine;

1-((6-(trans-4-tert-butylcyclohexyloxy)naphthalen-2-yl)methyl)-4-phenylpiperidine;

4-((6-(trans-4-tert-butylcyclohexyloxy)naphthalen-2-yl)methyl)-1-(pyrimidine-2-yl)piperazine;

4-((6-(trans-4-tert-butylcyclohexyloxy)naphthalen-2-yl)methyl)-1-(pyrazine-2-yl)piperazine;

4-((6-(cis-4-ethylcyclohexyloxy)naphthalen-2-yl)methyl-1-(pyridine-2-yl)piperazine;

4-((6-(spiro[4.5]decan-8-yl-oxy)naphthalen-2-yl)methyl)-1-(pyridine-2-yl)piperazine;

4-((6-(heptyloxy)naphthalen-2-yl)methyl)-1-(pyridine-2-yl)piperazine;

4-((6-(cis-4-isopropylcyclohexyloxy)quinolin-2-yl)methyl)-1-(pyridine-2-yl)piperazine;

4-((6-(trans-4-tert-butylcyclohexyloxy)naphthalen-2-yl)methyl)-1-(pyridine-2-yl)-1,4-diazepane;

1-((6-(trans-4-tert-butylcyclohexyloxy)naphthalen-2-yl)methyl)-4-(pyrimidine-2-yl)piperidine;

4-((6-(trans-4-tert-butylcyclohexyloxy)naphthalen-2-yl)methyl)-1-(pyrimidine-2-yl)-1,4-diazepane;

4-((6-(trans-4-tert-butylcyclohexyloxy)naphthalen-2-yl)methyl)-1-(pyrimidine-4-yl)piperazine;

4-((6-(cis-4-isopropylcyclohexyloxy)naphthalen-2-yl)methyl)-1-(pyridine-2-yl)piperazine 1-((6-(trans-4-tert-butylcyclohexyloxy)naphthalen-2-yl)methyl)-4-(pyridine-2-yl)piperidine;

4-((6-(trans-4-tert-butylcyclohexyloxy)naphthalen-2-yl)methyl)-1-(pyridine-3-yl)piperazine;

4-((6-(trans-4-tert-butylcyclohexyloxy)naphthalen-2-yl)methyl)-1-(2-methylpyrimidine-4-yl)piperazine;

3-(1-((6-(trans-4-tert-butylcyclohexyloxy)naphthalen-2-yl)methyl)azetidin-3-yl)cyclohex anecarboxylic acid;

3-(1-((6-(4,4-dimethylcyclohexyloxy)quinolin-2-yl)methyl)azetidin-3-yl)cyclohexanecarboxylic acid;

3-(1-((6-(heptyloxy)naphthalen-2-yl)methyl)azetidin-3-yl)cyclohexanecarboxylic acid;

4-(1-((6-(trans-4-tert-butylcyclohexyloxy)naphthalen-2-yl)methyl)azetidin-3-yl)cyclohexanecarboxylic acid;

3-(1-((6-(cis-2-ethylcyclohexyloxy)naphthalen-2-yl)methyl)azetidin-3-yl)cyclohexanecarboxylic acid;

3-(1-((6-(cis-2-isopropylcyclohexyloxy)quinolin-2-yl)methyl)azetidin-3-yl)cyclohexanecarboxylic acid;

3-(1-((6-(cis-2-ethylcyclohexyloxy)quinolin-2-yl)methyl)azetidin-3-yl)cyclohexanecarboxylic acid;

3-(1-((6-(cis-2-isopropylcyclohexyloxy)naphthalen-2-yl)methyl)azetidin-3-yl)cyclohexanecarboxylic acid;

3-(1-((6-(4,4-dimethylcyclohexyloxy)napthalen-2-yl)methyl)azetidin-3-yl)cyclohexanecarboxylic acid;

3-(1-((6-(spiro[4.5]decan-8-yloxy)naphthalen-2-yl)methyl)azetidin-3-yl)cyclohexanecarboxylic acid;

2-((6-(trans-4-tert-butylcyclohexyloxy)naphthalen-2-yl)methyl)-2-aza-6-oxaspiro[3.3]heptane;

7-((6-(trans-4-tert-butylcyclohexyloxy)naphthalen-2-yl)methyl)-2,7-diazaspiro[3.5]nonane;

2-((6-(trans-4-tert-butylcyclohexyloxy)naphthalen-2-yl)methyl)-6-hydroxy-2-azaspiro[3.3]heptane;

1-((6-(trans-4-tert-butylcyclohexyloxy)naphthalen-2-yl)methyl)-3-phenylazetidine;

2-((6-(trans-4-tert-butylcyclohexyloxy)naphthalen-2-yl)methyl)-2,7-diazaspiro[3.5]nonane;

1-((6-(trans-4-tert-butylcyclohexyloxy)naphthalen-2-yl)methyl)-3,3-di(hydroxymethyl)azetidine;

7-((6-(trans-4-tert-butylcyclohexyloxy)naphthalen-2-yl)methyl)-2-oxa-7-azaspiro[3.5]nonane;

8-((6-(trans-4-tert-butylcyclohexyloxy)naphthalen-2-yl)methyl)-3-oxo-2-aza-8-azaspiro[4.5]decane;

4-(((6-(trans-4-tert-butylcyclohexyloxy)naphthalen-2-yl)methyl)amino)bicyclo[2.2.1]heptane-1-carboxylic acid;

4-(((5-trifluoromethyl-6-(trans-4-tert-butylcyclohexyloxy)naphthalen-2-yl)methyl)amino) bicyclo[2.2.1]heptane-1-carboxylic acid;

3-((6-(trans-4-tert-butylcyclohexyloxy)naphthalen-2-yl)
methyl)-3-azabicyclo[3.1.1]heptane-6-carboxylic acid;
3-((6-(trans-4-tert-butylcyclohexyloxy)naphthalen-2-yl)
methyl)-3-azabicyclo[3.3.1]nonane-9-carboxylic acid;
3-((6-(trans-4-tert-butylcyclohexyloxy)naphthalen-2-yl)
methyl)-3-azabicyclo[3.1.0]hexane-6-carboxylic acid;
8-((6-(trans-4-tert-butylcyclohexyloxy)naphthalen-2-yl)
methyl)-8-azabicyclo[3.2.1]octane-3-carboxylic acid; or
9-((6-(trans-4-tert-butylcyclohexyloxy)naphthalen-2-yl)
methyl)-9-azabicyclo[3.3.1]nonane-3-carboxylic acid.

Additional exemplary compounds represented by formula (I) which may be useful as ATX modulating agents and/or S1P modulating agents include:

8-((5-difluoromethyl-6-(cis-4-trifluoromethycyclohexyloxy)naphthalen-2-yl)methyl)-8-azabicyclo[3.2.1]octane-3-carboxylic acid;
8-(2-(5-trifluoromethyl-6-(cis-4-trifluoromethylcyclohexyloxy)naphthalen-2-yl)acetyl)-8-azabicyclo[3.2.1]octane-3-carboxylic acid;
9-(2-(5-trifluoromethyl-6-(cis-4-trifluoromethylcyclohexyloxy)naphthalen-2-yl)acetyl)-9-azabicyclo[3.3.1]nonane-3-carboxylic acid;
2-(5-trifluoromethyl-6-(cis-4-trifluoromethylcyclohexyloxy)naphthalen-2-oyl)decahydroisoquinolin-8-carboxylic acid;
9-(5-trifluoromethyl-6-(cis-4-trifluoromethylcyclohexyloxy)naphthalen-2-oyl)-9-azabicyclo[3.3.1]nonane-3-carboxylic acid;
8-(5-trifluoromethyl-6-(cis-4-methcyclohexyloxy)naphthalen-2-oylcyclo[3.2.1]octane-3-carboxylic acid;
9-(2-(5-trifluoromethyl-6-(trans-(cis-3,5-dimethyl)cyclohexyloxy)naphthalen-2-yl)acetyl)-9-azabicyclo[3.3.1]nonane-3-carboxylic acid;
8-(5-trifluoromethyl-6-(cis-4-trifluoromethylcyclohexyloxy)naphthalen-2-oyl)-8-azabicyclo[3.2.1]octane-3-carboxylic acid;
8-(((5-trifluoromethyl-6-(cis-4-trifluoromethylcyclohexyloxy)naphthalene-2-yl)methyl)amino)bicyclo[3.2.1]octane-3-carboxylic acid;
8-(1-(5-trifluoromethyl-6-(cis-4-methylcyclohexyloxy)naphthalen-2-yl)ethyl)-8-azabicyclo[3.2.1]octane-3-carboxylic acid;
9-(1-(5-trifluoromethyl-6-(cis-4-methylcyclohexyloxy)naphthalen-2-yl)ethyl)-9-azabicyclo[3.3.1]nonane-3-carboxylic acid;
1-((5-trifluoromethyl-6-(cis-4-trifluoromethylcyclohexyloxy)naphthalene-2-yl)methyl)4-imidazol-4-yl-piperidine;
8-((5-trifluoromethyl-6-(cis-4-methylcyclohexyloxy)naphthalene-2-yl)methyl)-8-azabicyclo[3.2.1]octane-3-carboxylic acid;
9-((5-trifluoromethyl-6-(cis-4-methylcyclohexyloxy)naphthalene-2-yl)methyl)-8-azabicyclo[3.3.1]nonane-3-carboxylic acid;
7-((5-trifluoromethyl-6-(cis-4-methylcyclohexyloxy)naphthalen-2-yl)methyl)-7-aza-10-oxaspiro[4.5]decane-3-carboxylic acid;
9-((5-trifluoromethyl-6-(cis-4-trifluoromethylcyclohexyloxy)quinolin-2-yl)methyl)-9-aza bicyclo[3.3.1]nonane-3-carboxylic acid;
8-((5-trifluoromethyl-6-(cis-4-trifluoromethylcyclohexyloxy)quinolin-2-yl)methyl)-8-aza bicyclo[3.2.1]octane-3-carboxylic acid;
3-(1-((5-trifluoromethyl-6-(cis-4-trifluoromethylcyclohexyloxy)naphthalen-2-yl)methyl)azetidine-3-yl)cyclohexane-1-carboxylic acid;
3-((5-trifluoromethyl-6-(cis-4-trifluoromethylcyclohexyloxy)naphthalen-2-yl)methyl)-3-azabicyclo[3.3.1]nonane-7-carboxylic acid;
2-((5-trifluoromethyl-6-(cis-4-trifluoromethylcyclohexyloxy)naphthalen-2-yl)methyl)-2-aza-6-oxaspiro[3.4]octane-7-carboxylic acid;
8-((5-trifluoromethyl-6-(4,4-difluorocyclohexyloxyl)naphthalen-2-yl)methyl)-8-azabicyclo[3.2.1]octane-3-carboxylic acid;
9-((5-trifluoromethyl-6-(4,4-difluorocyclohexyloxyl)naphthalen-2-yl)methyl)-9-azabicyclo[3.3.1]nonane-3-carboxylic acid;
3-((5-trifluoromethyl-6-(cis-4-trifluoromethylcyclohexyloxy)naphthalen-2-yl)methyl)-3-azabicyclo[3.3.0]octane-7-carboxylic acid;
3-(1-(((5-trifluoromethyl-6-(cis-4-trifluoromethylcyclohexyloxy)naphthalene-2-yl)methyl)methylamino)bicyclo[2.2.2]octan-4-yl)propionic acid;
3-(((5-trifluoromethyl-6-(cis-4-trifluoromethylcyclohexyloxy)naphthalene-2-yl)methyl)amino)adamantyl-1-carboxylic acid;
1-(((5-trifluoromethyl-6-(cis-4-trifluoromethylcyclohexyloxy)naphthalene-2-yl)methyl)amino)bicyclo[2.2.1]heptane-4-carboxylic acid;
3-((5-trifluoromethyl-6-(cis-4-trifluoromethylcyclohexyloxy)naphthalen-2-yl)methyl)-3-azabicyclo[3.3.1]nonane-9-carboxylic acid;
2-((5-trifluoromethyl-6-(cis-4-trifluoromethylcyclohexyloxy)naphthalen-2-yl)methyl)decahydroisoquinolin-8-carboxylic acid;
5-((5-trifluoromethyl-6-(cis-4-trifluoromethylcyclohexyloxy)naphthalen-2-yl)methyl)-5-azaspiro[2.3]hexane-1-carboxylic acid;
9-((5-trifluoromethyl-6-(cis-4-trifluoromethylcyclohexyloxy)naphthalen-2-yl)methyl)-9-azabicyclo[3.3.1]nonane-3-carboxylic acid;
8-((5-trifluoromethyl-6-(cis-4-trifluoromethycyclohexyloxy)naphthalen-2-yl)methyl)-8-azabicyclo[3.2.1]octane-2-carboxylic acid;
3-((5-trifluoromethyl-6-(cis-4-trifluoromethylcyclohexyloxy)naphthalen-2-yl)methyl)-3-azabicyclo[3.1.0]hexane-6-carboxylic acid;
1-(5-trifluoromethyl-6-(cis-4-trifluoromethylcyclohexyloxy)naphthalen-2-oyl)amino-2,3-dihydroindene-6-carboxylic acid;
3-(1-(((5-trifluoromethyl-6-(cis-4-trifluoromethylcyclohexyloxy)naphthalen-2-yl)methyl)amino)bicyclo[2.2.2]octan-4-yl)propionic acid;
2-((5-trifluoromethyl-6-(cis-4-trifluoromethylcyclohexyloxy)naphthalen-2-yl)methyl)-2-azaspiro[3.3]heptane-6-carboxylic acid;
(7R,9aR)-2-((2-(trans-4-(trifluoromethyl)cyclohexyloxy)-1-(trifluoromethyl)naphthalen-6-yl)methyl)-octahydro-1H-pyrido[1,2-a]pyrazine-7-carboxylic acid;
1-(((5-trifluoromethyl-6-(cis-4-trifluoromethylcyclohexyloxy)naphthalene-2-yl)methyl)amino)bicyclo[2.2.2]octane-4-carboxylic acid; methyl
(7R,9aR)-2-((2-(trans-4-(trifluoromethyl)cyclohexyloxy)-1-(trifluoromethyl)naphthalen-6-yl)methyl)-octahydro-1H-pyrido[1,2-a]pyrazine-7-carboxylate;
8-(5-chloro-6-((cis-4-(trifluoromethyl)cyclohexyl)oxy)-2-naphthoyl)-8-azabicyclo[3.2.1]octane-3-carboxylic acid;
8-(1-(5-cyano-6-((cis-4-methylcyclohexyl)oxy) naphthalen-2-yl)ethyl)-8-azabicyclo[3.2.1]octane-3-carboxylic acid;
8-((5-cyano-6-((cis-4-methylcyclohexyl)oxy)naphthalen-2-yl)methyl)-8-azabicyclo[3.2.1]octane-3-carboxylic acid;

8-(1-(5-cyano-6-((cis-4-methylcyclohexyl)oxy) naphthalen-2-yl)ethyl)-8-azabicyclo[13.2.1]octane-3-carboxylic acid;

8-(5-(trifluoromethyl)-6-((cis-4-(trifluoromethyl)cyclohexyl)amino)-2-naphthoyl)-8-azabicyclo[13.2.1]octane-3-carboxylic acid;

2-((trans-4-(tert-butyl)cyclohexyl)amino)quinazoline-6-carboxylic acid;

9-(2-((trans-4-(tert-butyl)cyclohexyl)amino) quinazoline-6-carbonyl)-9-azabicyclo[3.3.1]nonane-3-carboxylic acid;

9-((3-((cis-4-methylcyclohexyl)amino)isoquinolin-7-yl) methyl)-9-azabicyclo[3.3.1]nonane-3-carboxylic acid;

8-((4-chloro-3-((cis-4-methylcyclohexyl)amino)isoquinolin-7-yl)methyl)-8-azabicyclo[13.2.1]octane-3-carboxylic acid;

8-(3-((trans-4-(tert-butyl)cyclohexyl)amino)isoquinoline-7-carbonyl)-8-azabicyclo[3.2.1]octane-3-carboxylic acid;

9-((8-chloro-7-((cis-4-ethylcyclohexyl)oxy) isoquinolin-3-yl)methyl)-9-azabicyclo[3.3.1]nonane-3-carboxylic acid;

9-((8-bromo-7-((cis-4-ethylcyclohexyl)oxy) isoquinolin-3-yl)methyl)-9-azabicyclo[3.3.1]nonane-3-carboxylic acid;

9-((8-(trifluoromethyl)-7-((cis-4-(trifluoromethyl) cyclohexyl)oxy)isoquinolin-3-yl)methyl)-9-azabicyclo[3.3.1] nonane-3-carboxylic acid;

9-((6-((cis-4-ethylcyclohexyl)oxy)-5-(trifluoromethyl)quinolin-2-yl)amino)bicyclo[3.3.1]nonane-3-carboxylic acid;

9-((5-cyano-6-((cis-4-ethylcyclohexyl)oxy)naphthalen-2-yl)methyl)-9-azabicyclo[3.3.1]nonane-3-carboxylic acid;

8-((5-cyano-6-((cis-4-ethylcyclohexyl)oxy)naphthalen-2-yl)methyl)-8-azabicyclo[3.2.1]octane-3-carboxylic acid;

9-(5-chloro-6-((cis-4-(trifluoromethyl)cyclohexyl)oxy)-2-naphthoyl)-9-azabicyclo[3.3.1]nonane-3-carboxylic acid;

8-(1-(5-chloro-6-((cis-4-(trifluoromethyl)cyclohexyl) oxy)naphthalen-2-yl)propyl)-8-azabicyclo[3.2.1]octane-3-carboxylic acid;

8-(5-chloro-6-((cis-4-methylcyclohexyl)oxy)-2-naphthoyl)-8-azabicyclo[3.2.1]octane-3-carboxylic acid;

8-(1-(6-((cis-4-(1,1-difluoroethyl)cyclohexyl)oxy)-5-(trifluoromethyl)naphthalen-2-yl)propyl)-8-azabicyclo[3.2.1] octane-3-carboxylic acid;

8-(1-(5-chloro-6-((cis-4-methylcyclohexyl)oxy)naphthalen-2-yl)ethyl)-8-azabicyclo[3.2.1]octane-3-carboxylic acid;

9-(5-cyano-6-((cis-4-(trifluoromethyl)cyclohexyl)oxy)-2-naphthoyl)-9-azabicyclo[3.3.1]nonane-3-carboxylic acid;

9-((5-cyano-6-((cis-4-methylcyclohexyl)oxy)naphthalen-2-yl)methyl)-9-azabicyclo[3.3.1]nonane-3-carboxylic acid;

9-(5-chloro-6-((cis-4-methylcyclohexyl)oxy)-2-naphthoyl)-9-azabicyclo[3.3.1]nonane-3-carboxylic acid;

9-((6-((cis-4-(1,1-difluoroethyl)cyclohexyl)oxy)-5-(trifluoro-methyl)naphthalen-2-yl)methyl)-9-azabicyclo [3.3.1]nonane-3-carboxylic acid;

8-(1-(5-chloro-6-((cis-4-methylcyclohexyl)oxy)naphthalen-2-yl)propyl)-8-azabicyclo[3.2.1]octane-3-carboxylic acid;

9-(1-(5-chloro-6-((cis-4-methylcyclohexyl)oxy)naphthalen-2-yl)propyl)-9-azabicyclo[3.3.1]nonane-3-carboxylic acid;

8-(1-(5-cyano-6-((cis-4-ethylcyclohexyl)oxy)naphthalen-2-yl)ethyl)-8-azabicyclo[3.2.1]octane-3-carboxylic acid;

9-(1-(5-cyano-6-((cis-4-ethylcyclohexyl)oxy)naphthalen-2-yl)ethyl)-9-azabicyclo[3.3.1]nonane-3-carboxylic acid;

9-(1-(5-chloro-6-((cis-4-methylcyclohexyl)oxy)naphthalen-2-yl)ethyl)-9-azabicyclo[3.3.1]nonane-3-carboxylic acid;

8-(5-chloro-6-((cis-4-ethylcyclohexyl)oxy)-2-naphthoyl)-8-azabicyclo[3.2.1]octane-3-carboxylic acid;

8-(1-(6-((cis-4-(1,1-difluoroethyl)cyclohexyl)oxy)-5-(trifluoromethyl)naphthalen-2-yl)ethyl)-8-azabicyclo[3.2.1] octane-3-carboxylic acid;

9-(1-(6-((cis-4-(1,1-difluoroethyl)cyclohexyl)oxy)-5-(trifluoromethyl)naphthalen-2-yl)ethyl)-9-azabicyclo[3.3.1] nonane-3-carboxylic acid;

9-(5-cyano-6-((cis-4-methylcyclohexyl)oxy)-2-naphthoyl)-9-azabicyclo[3.3.1]nonane-3-carboxylic acid;

8-(5-cyano-6-((cis-4-methylcyclohexyl)oxy)-2-naphthoyl)-8-azabicyclo[3.2.1]octane-3-carboxylic acid;

8-(1-(5-cyano-6-((cis-4-ethylcyclohexyl)oxy)naphthalen-2-yl)propyl)-8-azabicyclo[3.2.1]octane-3-carboxylic acid;

9-(5-cyano-6-((cis-4-ethylcyclohexyl)oxy)-2-naphthoyl)-9-azabicyclo[3.3.1]nonane-3-carboxylic acid;

8-(6-((cis-4-ethylcyclohexyl)oxy)-5-(trifluoromethyl)-2-naphthoyl)-8-azabicyclo[3.2.1]octane-3-carboxylic acid;

8-(5-cyano-6-((cis-4-ethylcyclohexyl)oxy)-2-naphthoyl)-8-azabicyclo[3.2.1]octane-3-carboxylic acid;

9-(6-((cis-4-ethylcyclohexyl)oxy)-5-(trifluoromethyl)-2-naphthoyl)-9-azabicyclo[3.3.1]nonane-3-carboxylic acid;

9-(1-(5-cyano-6-((cis-4-methylcyclohexyl)oxy)naphthalen-2-yl)ethyl)-9-azabicyclo[3.3.1]nonane-3-carboxylic acid;

8-(1-(5-cyano-6-((cis-4-methylcyclohexyl)oxy)naphthalen-2-yl)propyl)-8-azabicyclo[3.2.1]octane-3-carboxylic acid;

9-(5-chloro-6-((cis-4-ethylcyclohexyl)oxy)-2-naphthoyl)-9-azabicyclo[3.3.1]nonane-3-carboxylic acid;

9-(1-(5-cyano-6-(((1s,4s)-4-(trifluoromethyl)cyclohexyl) oxy)naphthalen-2-yl)ethyl)-9-azabicyclo[3.3.1]nonane-3-carboxylic acid;

9-((5-cyano-6-((cis-4-(trifluoromethyl)cyclohexyl)oxy) naphthalen-2-yl)methyl)-9-azabicyclo[3.3.1]nonane-3-carboxylic acid;

9-((5-(trifluoromethyl)-6-((cis-4-(trifluoromethyl)cyclohexyl)amino)naphthalen-2-yl)methyl)-9-azabicyclo [3.3.1]nonane-3-carboxylic acid; methyl 8-(5-(trifluoromethyl)-6-((cis-4-(trifluoromethyl)cyclohexyl)amino)-2-naphthoyl)-8-azabicyclo[3.2.1]octane-3-carboxylate;

8-((r)-1-(6-((cis-4-methylcyclohexyl)oxy)-5-(trifluoromethyl) naphthalen-2-yl)propyl)-8-azabicyclo[3.2.1]octane-3-carboxylic acid;

8-((s)-1-(6-((cis-4-methylcyclohexyl)oxy)-5-(trifluoromethyl) naphthalen-2-yl)propyl)-8-azabicyclo[3.2.1]octane-3-carboxylic acid;

8-(1-(5-chloro-6-((cis-4-(trifluoromethyl)cyclohexyl)oxy) naphthalen-2-yl)ethyl)-8-azabicyclo[3.2.1]octane-3-carboxylic acid;

9-(1-(5-chloro-6-((cis-4-(trifluoromethyl)cyclohexyl)oxy) naphthalen-2-yl)ethyl)-9-azabicyclo[3.3.1]nonane-3-carboxylic acid;

8-(1-(5-chloro-6-((cis-4-ethylcyclohexyl)oxy)naphthalen-2-yl)propyl)-8-azabicyclo[3.2.1]octane-3-carboxylic acid;

9-(1-(5-chloro-6-((cis-4-ethylcyclohexyl)oxy)naphthalen-2-yl)propyl)-9-azabicyclo[3.3.1]nonane-3-carboxylic acid;

9-((R)-1-(5-chloro-6-((cis-4-ethylcyclohexyl)oxy)naphthalen-2-yl)ethyl)-9-azabicyclo[3.3.1]nonane-3-carboxylic acid;

9-((S)-1-(5-chloro-6-((cis-4-ethylcyclohexyl)oxy)naphthalen-2-yl)ethyl)-9-azabicyclo[3.3.1]nonane-3-carboxylic acid; 9-((R)-1-(5-chloro-6-((cis-4-(trifluoromethyl)cyclohexyl)oxy)naphthalen-2-yl)ethyl)-9-azabicyclo[3.3.1] nonane-3-carboxylic acid;

9-((S)-1-(5-chloro-6-((cis-4-(trifluoromethyl)cyclohexyl) oxy)naphthalen-2-yl)ethyl)-9-azabicyclo[3.3.1]nonane-3-carboxylic acid;

8-((R)-1-(5-chloro-6-((cis-4-(trifluoromethyl)cyclohexyl)oxy)naphthalen-2-yl)ethyl)-8-azabicyclo[3.2.1]octane-3-carboxylic acid;
8-((S)-1-(5-chloro-6-((cis-4-(trifluoromethyl)cyclohexyl)oxy)naphthalen-2-yl)ethyl)-8-azabicyclo[3.2.1]octane-3-carboxylic acid; methyl
9-(5-(trifluoromethyl)-6-((cis-4-(trifluoromethyl)cyclohexyl)amino)-2-naphthoyl)-9-azabicyclo[3.3.1]nonane-3-carboxylate; methyl
9-(5-(trifluoromethyl)-6-((cis-4-(trifluoromethyl)cyclohexyl)amino)-2-naphthoyl)-9-azabicyclo[3.3.1]nonane-3-carboxylate;
8-((R)-1-(5-chloro-6-((cis-4-ethylcyclohexyl)oxy)naphthalen-2-yl)propyl)-8-azabicyclo[3.2.1]octane-3-carboxylic acid;
8-((S)-1-(5-chloro-6-((cis-4-ethylcyclohexyl)oxy)naphthalen-2-yl)propyl)-8-azabicyclo[3.2.1]octane-3-carboxylic acid;
9-((R)-1-(5-chloro-6-((cis-4-ethylcyclohexyl)oxy)naphthalen-2-yl)propyl)-9-azabicyclo[3.3.1]nonane-3-carboxylic acid;
9-((S)-1-(5-chloro-6-((cis-4-ethylcyclohexyl)oxy)naphthalen-2-yl)propyl)-9-azabicyclo[3.3.1]nonane-3-carboxylic acid;
8-((R)-1-(5-chloro-6-((cis-4-ethylcyclohexyl)oxy)naphthalen-2-yl)ethyl)-8-azabicyclo[3.2.1]octane-3-carboxylic acid;
8-((S)-1-(5-chloro-6-((cis-4-ethylcyclohexyl)oxy)naphthalen-2-yl)ethyl)-8-azabicyclo[3.2.1]octane-3-carboxylic acid; methyl 8-(5-(trifluoromethyl)-6-((cis-4-(trifluoromethyl)cyclohexyl)amino)-2-naphthoyl)-8-azabicyclo[3.2.1]octane-3-carboxylate;
8-(5-(trifluoromethyl)-6-((cis-4-(trifluoromethyl)cyclohexyl)amino)-2-naphthoyl)-8-azabicyclo[3.2.1]octane-3-carboxylic acid;
9-(2-((cis-4-(tert-butyl)cyclohexyl)amino) quinazoline-6-carbonyl)-9-azabicyclo[3.3.1]nonane-3-carboxylic acid;
8-((3-((trans-4-methylcyclohexyl)amino) isoquinolin-7-yl)methyl)-8-azabicyclo[3.2.1]octane-3-carboxylic acid;
8-(2-((cis-4-(tert-butyl)cyclohexyl)amino) quinazoline-6-carbonyl)-8-azabicyclo[3.2.1]octane-3-carboxylic acid;
8-(2-((trans-4-methylcyclohexyl)amino) quinazoline-6-carbonyl)-8-azabicyclo[3.2.1]octane-3-carboxylic acid;
9-((3-((trans-4-methylcyclohexyl)amino)isoquinolin-7-yl)methyl)-9-azabicyclo[3.3.1]nonane-3-carboxylic acid;
8-((4-chloro-3-((trans-4-methylcyclohexyl)amino)isoquinolin-7-yl)methyl)-8-azabicyclo[3.2.1]octane-3-carboxylic acid;
9-(3-(((1s,4s)-4-methylcyclohexyl)amino) isoquinoline-7-carbonyl)-9-azabicyclo[3.3.1]nonane-3-carboxylic acid;
8-(3-((cis-4-methylcyclohexyl)amino) isoquinoline-7-carbonyl)-8-azabicyclo[3.2.1]octane-3-carboxylic acid;
8-(2-((trans-4-(tert-butyl)cyclohexyl)amino) quinazoline-6-carbonyl)-8-azabicyclo[3.2.1]octane-3-carboxylic acid;
9-(3-((trans-4-methylcyclohexyl)amino)isoquinoline-7-carbonyl)-9-azabicyclo[3.3.1]nonane-3-carboxylic acid;
8-(3-((trans-4-methylcyclohexyl)amino)isoquinoline-7-carbonyl)-8-azabicyclo[3.2.1]octane-3-carboxylic acid;
9-(2-((trans-4-methylcyclohexyl)amino) quinazoline-6-carbonyl)-9-azabicyclo[3.3.1]nonane-3-carboxylic acid;
9-(2-((cis-4-methylcyclohexyl)amino) quinazoline-6-carbonyl)-9-azabicyclo[3.3.1]nonane-3-carboxylic acid;
9-((4-chloro-3-((trans-4-methylcyclohexyl) amino)isoquinolin-7-yl)methyl)-9-azabicyclo[3.3.1]nonane-3-carboxylic acid;
8-(3-((cis-4-(tert-butyl)cyclohexyl)amino)isoquinoline-7-carbonyl)-8-azabicyclo[3.2.1]octane-3-carboxylic acid;
8-(2-((cis-4-methylcyclohexyl)amino)quinazoline-6-carbonyl)-8-azabicyclo[3.2.1]octane-3-carboxylic acid;
8-((3-((cis-4-methylcyclohexyl)amino)isoquinolin-7-yl)methyl)-8-azabicyclo[3.2.1]octane-3-carboxylic acid;
9-((4-chloro-3-((cis-4-methylcyclohexyl)amino)isoquinolin-7-yl)methyl)-9-azabicyclo[3.3.1]nonane-3-carboxylic acid;
8-(3-((cis-4-(tert-butyl)cyclohexyl)amino)-4-chloroisoquinoline-7-carbonyl)-8-azabicyclo[3.2.1]octane-3-carboxylic acid;
8-(3-((trans-4-(tert-butyl)cyclohexyl)amino)-4-chloroisoquinoline-7-carbonyl)-8-azabicyclo[3.2.1]octane-3-carboxylic acid;
9-((8-bromo-7-((cis-4-(trifluoromethyl)cyclohexyl)oxy)isoquinolin-3-yl)methyl)-9-azabicyclo[3.3.1]nonane-3-carboxylic acid;
8-((8-bromo-7-((cis-4-(trifluoromethyl)cyclohexyl)oxy)isoquinolin-3-yl)methyl)-8-azabicyclo[3.2.1]octane-3-carboxylic acid;
8-((8-bromo-7-((cis-4-ethylcyclohexyl)oxy)isoquinolin-3-yl)methyl)-8-azabicyclo[3.2.1]octane-3-carboxylic acid;
8-((8-chloro-7-((cis-4-ethylcyclohexyl)oxy)isoquinolin-3-yl)methyl)-8-azabicyclo[3.2.1]octane-3-carboxylic acid;
8-((6-((cis 4-ethylcyclohexyl)oxy)quinolin-2-yl)amino)bicyclo[3.2.1]octane-3-carboxylic acid;
9-((8-bromo-7-((cis-4-methylcyclohexyl)oxy) isoquinolin-3-yl)methyl)-9-azabicyclo[3.3.1]nonane-3-carboxylic acid;
8-((6-((cis-4-ethylcyclohexyl)oxy)-5-(trifluoromethyl)quinolin-2-yl)amino)bicyclo[3.2.1]octane-3-carboxylic acid;
9-((5-chloro-6-((cis-4-ethylcyclohexyl)oxy)quinolin-2-yl)amino)bicyclo[3.3.1]nonane-3-carboxylic acid;
(1R,3 S,5S)-9-((5-(trifluoromethyl)-6-((cis-4-(trifluoromethyl)cyclohexyl)oxy)naphthalen-2-yl)methyl)-9-azabicyclo[3.3.1]nonane-3,7-dicarboxylic acid;
9-(1R,3S,5S,7s)-2-((5-(trifluoromethyl)-6-((cis-4-(trifluoromethyl)cyclohexyl)oxy)naphthalen-2-yl)methyl)-2-azaadamantane-5-carboxylic acid;
9-(1R,3R,5S)-7-amino-9-((5-(trifluoromethyl)-6-((cis-4-(trifluoromethyl)cyclohexyl)oxy) naphthalen-2-yl)methyl)-9-azabicyclo[3.3.1]nonane-3-carboxylic acid;
9-((6-(bicyclo[3.1.0]hexan-3-yloxy)-5-(trifluoromethyl)naphthalen-2-yl)methyl)-9-azabicyclo[3.3.1]nonane-3-carboxylic acid;
8-((6-(bicyclo[3.1.0]hexan-3-yloxy)-5-(trifluoromethyl)naphthalen-2-yl)methyl)-8-azabicyclo[3.2.1]octane-3-carboxylic acid;
8-((R)-1-(5-(trifluoromethyl)-6-((cis-4-(trifluoromethyl)cyclohexyl)oxy)naphthalen-2-yl)propyl)-8-azabicyclo[3.2.1]octane-3-carboxylic acid;
8-((S)-1-(5-(trifluoromethyl)-6-((cis-4-(trifluoromethyl)cyclohexyl)oxy)naphthalen-2-yl)propyl)-8-azabicyclo[3.2.1]octane-3-carboxylic acid;
8-((R)-1-(6-((cis-4-ethylcyclohexyl)oxy)-5-(trifluoromethyl)naphthalen-2-yl)ethyl)-8-azabicyclo[3.2.1]octane-3-carboxylic acid;
8-((S)-1-(6-((cis-4-ethylcyclohexyl)oxy)-5-(trifluoromethyl)naphthalen-2-yl)ethyl)-8-azabicyclo[3.2.1]octane-3-carboxylic acid;
9-((R)-1-(6-((cis-4-ethylcyclohexyl)oxy)-5-(trifluoromethyl)naphthalen-2-yl)ethyl)-9-azabicyclo[3.3.1]nonane-3-carboxylic acid;
9-((S)-1-(6-((cis-4-ethylcyclohexyl)oxy)-5-(trifluoromethyl)naphthalen-2-yl)ethyl)-9-azabicyclo[3.3.1]nonane-3-carboxylic acid;

8-((R)-1-(6-((cis-4-ethylcyclohexyl)oxy)-5-(trifluoromethyl) naphthalen-2-yl)propyl)-8-azabicyclo[3.2.1]octane-3-carboxylic acid;

8-((S)-1-(6-((cis-4-ethylcyclohexyl)oxy)-5-(trifluoromethyl) naphthalen-2-yl)propyl)-8-azabicyclo[3.2.1]octane-3-carboxylic acid;

9-((R)-1-(5-(trifluoromethyl)-6-((cis-4-(trifluoromethyl)cyclohexyl)oxy)naphthalen-2-yl)propyl)-9-azabicyclo[3.3.1]nonane-3-carboxylic acid;

9-((S)-1-(5-(trifluoromethyl)-6-((cis-4-(trifluoromethyl)cyclohexyl)oxy)naphthalen-2-yl)propyl)-9-azabicyclo[3.3.1]nonane-3-carboxylic acid;

9-((R)-1-(6-(((1s,4S)-4-ethylcyclohexyl)oxy)-5-(trifluoromethyl) naphthalen-2-yl)propyl)-9-azabicyclo[3.3.1]nonane-3-carboxylic acid;

9-((S)-1-(6-(((1s,4R)-4-ethylcyclohexyl)oxy)-5-(trifluoromethyl) naphthalen-2-yl)propyl)-9-azabicyclo[3.3.1]nonane-3-carboxylic acid;

4-(2-(1-(5-(trifluoromethyl)-6-((cis-4-(trifluoromethyl)cyclohexyl)oxy)naphthalen-2-yl)propyl)-2H-tetrazol-5-yl) piperidine;

9-(1-(5-(trifluoromethyl)-6-((cis-4-(trifluoromethyl)cyclohexyl)oxy)naphthalen-2-yl)ethyl)-9-azabicyclo[3.3.1]nonane-3-carbonitrile; or 8-(1-(5-(trifluoromethyl)-6-((cis-4-(trifluoromethyl)cyclohexyl)oxy)naphthalen-2-yl)ethyl)-8-azabicyclo[3.2.1]octane-3-carbonitrile.

Compounds of the invention can modulate the activity of S1P receptors. A compound of the invention can have S1P receptor agonist or antagonist activity. The compound can be selective for the S1P4 receptor. The compound can be a selective S1P4 antagonist. Being selective can mean that the compound binds to the receptor (or relatively small group of related molecules or proteins) in a complex mixture, or in other words, when exposed to a variety of closely related receptor types, the compound can bind preferentially to just one of the receptor types.

The compound can have a greater affinity for the S1P4 receptor, by at by at least 100-fold, by at least 50-fold, by at least 10-fold, by at least 5-fold or by at least 2-fold, than for a S1P1 receptor, S1P2 receptor, S1P3 receptor, or S1P5 receptor.

An inhibitor of S1P4 mediated activity can block S1P interaction with an S1P4 receptor. For example, the inhibitor can be an antagonist of an S1P4 receptor. An antagonist can be a molecule that has affinity for the receptor but does not induce activity or a specific activity from the receptor. The antagonist can bind with an S1P4 receptor with an $IC_{50}$ value of less than 1 µM, less than 750 nM, less than 500 nM, less than 250 nM or less than 100 nM. The antagonist can bind with an S1P4 receptor with an $IC_{50}$ value in a range between 1 nM and 1 µM, between 1 nM and 500 nM, between 10 nM and 250 nM, between 25 nm and 100 nM, or between 50 nM and 100 nM.

The compounds can also promote oligodendrocyte progenitor cell differentiation. The compounds can promote myelination or remyelination.

An "S1P modulating agent" refers a compound or composition that is capable of inducing a detectable change in S1P receptor activity in vivo or in vitro (e.g., at least 10% increase or decrease in S1P activity as measured by a given assay such as the assays described in the examples and known in the art. "S1P receptor," refers to all of the S1P receptor subtypes (for example, the S1P receptors S1P1, S1P2, S1P3, S1P4, or S1P5), unless the specific subtype is indicated. It is well known in the art how to determine S1P agonist or antagonist activity using the standard tests described herein, or using other similar tests which are well known in the art. In some cases, depending on the cell type and conditions used, an S1P modulating agent can have agonist or antagonist activity, even at the same receptor subtype.

The biological effects of an S1P modulating agent vary depending on whether the compound has S1P receptor agonist or antagonist activity. Potential uses of an S1P modulating agent include, but are not limited to, prevention or treatment of a pathological condition or symptom in a mammal. For example, the condition can include asthma, an inflammatory neuropathies, arthritis, lupus erythematosis, psoriasis, an ischemia reperfusion injury, a solid tumor, a tumor metastasis, a disease associated with angiogenesis, a vascular disease, a pain condition, an acute viral disease, or insulin-dependent diabetes, and non-insulin dependent diabetes. The condition can alter lymphocyte trafficking as a method of treatment for neuropathic pain, inflammation-induced pain (e.g., where prostaglandins are involved) or treatment of autoimmune pathologies such as uveitis, type I diabetes, rheumatoid arthritis, chronic inflammatory disorders, inflammatory bowel diseases (e.g., Crohn's disease and ulcerative colitis), multiple sclerosis, and in drug-eluting stents. Additional uses can include treatment of brain degenerative diseases, heart diseases, cancers, or hepatitis C. See, for example, WO 2005/085295, WO 2004/010987, WO 03/097028, and WO 2006/072562, each of which is incorporated by reference in its entirety. A class of S1P receptor agonists are described in provisional U.S. Application No. 60/956,111, filed Aug. 15, 2007, and PCT/US2008/073378, filed Aug. 15, 2008, each of which is incorporated by reference in its entirety. See also provisional U.S. Application No. 61/231,539, filed Aug. 5, 2009, and PCT/US2010/44607, filed Aug. 5, 2010, each of which is incorporated by reference in its entirety. See also provisional U.S. Application No. 61/440,254, filed Feb. 7, 2011, and PCT/US2012/23799 filed Feb. 6, 2012, each of which is incorporated by reference in its entirety.

Additional potential uses of an S1P modulating agent include, but are not limited to, prevention or treatment of a pathological condition or symptom in a mammal. For example, the condition can include inhibited cell migration of oligodendrocyte precursor cells (OPCs).

Potential uses of an S1P receptor antagonist, and S1P4 receptor type selective antagonists particularly, include, but are not limited to, prevention or treatment of a pathological condition or symptom in a mammal.

LPA has been shown to be involved in lymphocyte trafficking and helps promote entry of lymphocytes into secondary lymphoid organs (see Kanda, et al., Nat. Immunology (2008), 9:415-423). Therefore, the disclosed compounds are expected to be useful for altering lymphocyte trafficking as a method for prolonging allograft survival, for example transplantation including solid organ transplants, treatment of graft vs. host disease, bone marrow transplantation, and the like.

An "ATX modulating agent" refers a compound or composition that is capable of inducing a detectable change in ATX activity in vivo or in vitro (e.g., at least 10% increase or decrease in ATX activity as measured by a given assay such as the assays described in the examples and known in the art. A compound of the invention be an ATX modulating agent, i.e., it can modulate the activity of ATX. For example, a compound of the invention can be an ATX inhibitor. The compound can be a selective ATX modulating agent. Being selective can mean that the compound binds to ATX preferentially when exposed to a variety of potential binding partners. The compound can have a greater affinity for the ATX, by at by at least 100-fold, by at least 50-fold, by at least 10-fold, by at least 5-fold or by at least 2-fold, than for other binding partners. Affinity can be measured, for example, as a dissociation constant ($K_d$), as an inhibition constant (such as $IC_{50}$), or another measure; provided that affinity is measured in a consistent fashion between ATX and the other binding partners it is compared to.

An inhibitor of ATX mediated activity can block interaction of ATX with its native substrate(s), such as LPC. For example, the inhibitor can show an $IC_{50}$ value of less than 1 µM, less than 750 nM, less than 500 nM, less than 250 nM, less than 100 nM, less than 50 nM, less than 25 nM, or less than 10 nM, when measured in a FRET-based assay using FS-3 substrate (see, e.g., Ferguson, C. G., et al., Org Lett. 2006 May 11; 8(10): 2023-2026, which is incorporated by reference in its entirety).

Some substrates and inhibitors of ATX are described in WO 2011/151461, which is incorporated by reference in its entirety.

Potential uses of an ATX modulating agent include, but are not limited to, prevention or treatment of a pathological condition or symptom in a mammal. The pathological disorder can be an inflammatory disorder, an autoimmune disorder, a fibrosis of the lung, or a malignancy of the lung. Prevention or treatment of the pathological condition or symptom can include administering to the mammal an effective amount of an ATX modulating agent, e.g., an ATX inhibitor, to prevent, treat or reduce symptoms of the inflammatory disorder, autoimmune disorder, the fibrosis of the lung, or the malignancy of the lung. In one embodiment, the inflammatory disorder is rheumatoid arthritis (RA). In another embodiment, the autoimmune disorder is multiple sclerosis (MS). A particular example of lung fibrosis is an interstitial lung disease, for instance, pulmonary fibrosis. See, for example, WO 2011/151461, which is incorporated by reference in its entirety.

In some embodiments, an ATX inhibitor of the present invention can be used to treat or prevent a demyelinating disease or disorder. Demyelinating diseases or disorders include multiple sclerosis, Guillain-Barre Syndrome, chronic inflammatory demyelinating polyneuropathy (CIDP), transverse myelitis, and optic neuritis, spinal cord injury, stroke or other ischemia, cerebral palsy, Charcot-Marie-Tooth disease (CMT), Sjogren-Larsson syndrome, Refsum disease, Krabbe disease, Canavan disease, Alexander disease, nerve damage due to pernicious anemia, progressive multifocal leukoencephalopathy (PML), Lyme disease, tabes dorsalis due to untreated syphilis, demyelination due to exposure to an organophosphates, demyelination due to vitamin B12 deficiency or copper deficiency.

In addition, disclosed compounds can be useful as antagonists of the cannabinoid $CB_1$ receptor. $CB_1$ antagonism is associated with a decrease in body weight and an improvement in blood lipid profiles. The $CB_1$ antagonism could be in concert with S1P receptor activity, or be independent of activity at any S1P receptor.

In addition, disclosed compounds can be useful for inhibition of group IVA cytosolic $PLA_2$ ($cPLA_2$). $cPLA_2$ catalyzes the release of eicosanoic acids (e.g., arachidonic acid). The eicosanoic acids are transformed to pro-inflammatory eicosanoids such as prostaglandins and leukotrienes. Thus, disclosed compounds may be useful as anti-inflammatory agents. This inhibition could be in concert with S1P receptor activity, or be independent of activity at any S1P receptor.

In addition, disclosed compounds may be useful for inhibition of the multiple substrate lipid kinase (MuLK). MuLK is highly expressed in many human tumor cells and thus its inhibition might slow the growth or spread of tumors.

Neurological Disorders

MS can begin with a relapsing-remitting pattern of neurologic involvement, which then can progress to a chronic phase with increasing neurological damage. MS can be associated with the destruction of myelin, oligodendrocytes or axons localized to chronic lesions. The demyelination observed in MS may not always permanent and remyelination has been documented in early stages of the disease. Remyelination of neurons can require oligodendrocytes.

The distal tip of an extending axon or neurite can include a specialized region, known as the growth cone. Growth cones can sense the local environment and can guide axonal growth toward a neuron's target cell. Growth cones can respond to environmental cues, for example, surface adhesiveness, growth factors, neurotransmitters and electric fields. The growth cones can advance at a rate of one to two millimeters per day. The growth cone can explore the area ahead of it and on either side, by means of elongations classified as lamellipodia and filopodia. When an elongation contacts an unfavorable surface, it can withdraw. When an elongation contacts a favorable growth surface, it can continue to extend and guides the growth cone in that direction. When the growth cone reaches an appropriate target cell a synaptic connection can be created.

Nerve cell function can be influenced by contact between neurons and other cells in their immediate environment (Rutishauser, et al., 1988, *Physiol. Rev.* 68:819, which is incorporated by reference in its entirety). These cells can include specialized glial cells, oligodendrocytes in the central nervous system (CNS), and Schwann cells in the peripheral nervous system (PNS), which can sheathe the neuronal axon with myelin (Lemke, 1992, in *An Introduction to Molecular Neurobiology*, Z. Hall, Ed., p. 281, Sinauer, each of which is incorporated by reference in its entirety). LPA causes the collapse of the neuron growth cone and tends to inhibit or reverse the morphological differentiation of many neuronal cell lines (see Gendaszewska-Darmach, Acta Biochimica Polonica (2008), 55(2):227-240). Since ATX activity is involved in the generation of LPA, inhibitors of ATX should increase the ability of the nervous system to make synaptic connections. Thus, ATX inhibitors may be useful in treating neurodegenerative disorders such as Alzheimer's disease, Huntington's disease, Parkinson's disease (including Parkinson's dementia), Lewy Body Dementia, amylotrophic lateral sclerosis (ALS), Friedreich's ataxia, spinal muscular atrophy.

CNS neurons can have the inherent potential to regenerate after injury, but they can be inhibited from doing so by inhibitory proteins present in myelin (Brittis et al., 2001, *Neuron* 30:11-14; Jones et al., 2002, *J. Neurosci.* 22:2792-2803; Grimpe et al., 2002, *J.* Neurosci.: 22:3144-3160, each of which is incorporated by reference in its entirety).

Several myelin inhibitory proteins found on oligodendrocytes have been characterized. Known examples of myelin inhibitory proteins can include NogoA (Chen et al., Nature, 2000, 403, 434-439; Grandpre et al., *Nature* 2000, 403, 439-444, each of which is incorporated by reference in its entirety), myelin associated glycoprotein (MAG) (McKerracher et al., 1994, *Neuron* 13:805-811; Mukhopadhyay et al., 1994, *Neuron* 13:757-767, each of which is incorporated by reference in its entirety) or oligodendrocyte glycoprotein (OM-gp), Mikol et al., 1988, *J. Cell. Biol.* 106:1273-1279, each of which is incorporated by reference in its entirety). Each of these proteins can be a ligand for the neuronal Nogo receptor-1(NgR1 (Wang et al., *Nature* 2002, 417, 941-944; Grandpre et al., *Nature* 2000, 403, 439-444; Chen et al., *Nature*, 2000, 403, 434-439; Domeniconi et al., *Neuron* 2002, published online Jun. 28, 2002, each of which is incorporated by reference in its entirety).

Nogo receptor-1(NgR1) is a GPI-anchored membrane protein that contains 8 leucine rich repeats (Fournier et al., 2001, *Nature* 409:341-346, which is incorporated by reference in its entirety). Upon interaction with inhibitory proteins (e.g., NogoA, MAG and OM-gp), the NgR1 complex can transduce signals that lead to growth cone collapse and inhibition of neurite outgrowth.

There is a need for molecules and methods for inhibiting NgR1-mediated growth cone collapse and the resulting inhibition of neurite outgrowth. Additionally, there is a need for molecules which increase neuronal survival and axon regeneration, particularly for the treatment of disease, disorders or injuries that involve axonal injury, neuronal or oligodendrocyte cell death, demyelination or dymyelination or generally relate to the nervous system.

Such diseases, disorders or injuries can include, but are not limited to, multiple sclerosis (MS), progressive multifocal leukoencephalopathy (PML), encephalomyelitis (EPL), central pontine myelolysis (CPM), adrenoleukodystrophy, Alexander's disease, Pelizaeus Merzbacher disease (PMZ), Globoid cell Leucodystrophy (Krabbe's disease) and Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, or Bell's palsy. Among these diseases, MS may the most widespread, affecting approximately 2.5 million people worldwide.

Various disease-modifying treatments may be available for MS, including the use of corticosteroids and immunomodulating agents such as interferon beta or Tysabri®. In addition, because of the central role of oligodendrocytes and myelination in MS, there have been efforts to develop therapies to increase oligodendrocyte numbers or enhance myelination. See, e.g., Cohen et al., U.S. Pat. No. 5,574,009; Chang et al., *N. Engl. J. Med.* 346: 165-73 (2002), each of which is incorporated by reference in its entirety. However, there remains an urgent need to devise additional therapies for MS and other demyelination and dismyelination disorders.

A compound of the invention, or a pharmaceutically acceptable salt thereof, can promote myelination or remyelination. A method can include administering a compound of the invention, or a pharmaceutically acceptable salt thereof, to cells. A method of promoting oligodendrocyte progenitor cell differentiation can include administering a compound of the invention, or a pharmaceutically acceptable salt thereof, to cells. A method of treating multiple sclerosis can include administering a compound of the invention, or a pharmaceutically acceptable salt thereof, to a subject.

A number of studies have shown that ATX is expressed in non-pathological conditions, throughout development, with high expression levels in the CNS among other tissues. ATX mRNA was identified as highly upregulated during oligodendrocyte differentiation and ATX protein expression is also apparent in maturing ODCs, temporally correlated with the process of myelination. Finally, in the adult brain ATX is expressed in secretory epithelial cells, such as the choroid plexus, ciliary, iris pigment, and retinal pigment epithelial cells, whereas there is evidence for ATX expression in leptomenigneal cells and cells of the CNS vasculature. See, for example, Fuss, B., et al., J Neurosci 17, 9095-9103 (1997); Kawagoe, H., et al. Genomics 30, 380-384 (1995); Lee, H. Y., et al. J Biol Chem 271, 24408-24412 (1996); Narita, M., et al., J Biol Chem 269, 28235-28242 (1994); Bachner, D., et al., Mechanisms of Development 84, 121-125 (1999); Awatramani, R., et al., Nat Genet 35, 70-75 (2003); Li, Y., et al., J Neurol Sci 193, 137-146 (2002); Dugas, J. C., et al., J Neurosci 26, 10967-10983 (2006); Fox, M. A., et al., Molecular and Cellular Neuroscience 27, 140-150 (2004); Hoelzinger, D. B., et al., Neoplasia 7, 7-16 (2005); and Sato, K., et al., J Neurochem 92, 904-914 (2005); each of which is incorporated by reference in its entirety.

Although neurons and astrocytes do not seem to express ATX under physiological conditions, ATX is highly upregulated in astrocytes following brain lesion. Two hallmarks of reactive astrogliosis can be induced by LPA itself: hypertrophy of astrocytes and stress fiber formation. This may indicate an autoregulation loop of astrocytic activation, in which astrocytes upregulate the LPA-generating enzyme ATX and become activated by its metabolite LPA, while increased amounts of the metabolite inhibit the catalytic activity of ATX. See, e.g., Savaskan, N. E., et al., Cell Mol Life Sci 64, 230-243 (2007); Ramakers, G. J, & Moolenaar, W. H., Exp Cell Res 245, 252-262 (1998); and van Meeteren, L. A., et al., J Biol Chem 280, 21155-21161 (2005); each of which is incorporated by reference in its entirety.

ATX expression levels were shown to be elevated in glioblastoma multiform samples, and ATX was shown to augment invasiveness of cells transformed with ras, a key signaling molecule that promotes gliomagenesis. ATX expression was also detected in primary tumor tissues from neuroblastoma patients and retinoic acid induced expression of ATX in N-myc-amplified neuroblastoma cells.

There is significant evidence for ATX signaling in demyelination processes and in other neurodegenerative conditions. As noted above, it has been reported that addition of LPA to dorsal root fibers in ex vivo culture causes demyelination, whereas LPC fails to cause significant demyelination of nerve fibers in ex vivo cultures without further addition of recombinant ATX to the culture. Addition of recombinant ATX caused significant demyelination at equivalent levels to LPA presumable due to conversion of LPC to LPA through the enzymatic activity of ATX. In addition, injury induced demyelination was attenuated by about 50% in atx$^{+/-}$ mice over their wild type counterparts (Nagai, et al., *Molecular Pain* (2010), 6:78).

ATX protein levels were found deregulated in an animal model of MS (experimental autoimmune encephalitis; EAE) at the onset of clinical symptoms. See, e.g., Hoelzinger, D. B., et al. Neoplasia 7, 7-16 (2005); Nam, S. W., et al., Oncogene 19, 241-247 (2000); Kawagoe, H., et al., Cancer Res 57, 2516-2521 (1997); Dufner-Beattie, J., et al., Mol Carcinog 30, 181-189 (2001); Umemura, K., et al., Neuroscience Letters 400, 97-100 (2006); and Fuss, B., et al., J Neurosci 17, 9095-9103 (1997); each of which is incorporated by reference in its entirety. Moreover, significant ATX expression was been detected in the cerebrospinal fluid of patients suffering with multiple sclerosis (MS), while completely lacking from the control samples, suggesting a role for ATX in maintenance of cerebrospinal fluid homeostasis during pathological/demyelinating conditions. Hammack, B. N., et al. Proteomic analysis of multiple sclerosis cerebrospinal fluid. Mult Scler 10, 245-260 (2004); and Dennis, J., et al., J Neurosci Res 82, 737-742 (2005); each of which is incorporated by reference in its entirety.

Interestingly, ATX mRNA expression was found to be elevated in the frontal cortex of Alzheimer-type dementia patients indicating a potential involvement for ATX signaling in neurodegenerative diseases. LPA receptors are enriched in the CNS and their expression patterns suggest their potential involvement in developmental process including neurogenesis, neuronal migration, axon extension and myelination. Noteworthy, only two receptors have the same spatiotemporal expression as ATX in the CNS (Contos, J. J., et al., Mol Cell Biol 22, 6921-6929 (2002); Jaillard, C, ei al, Edg8/S1P5: an oligodendroglial receptor with dual function on process retraction and cell survival. J Neurosci 25, 1459-1469 (2005); and Saba, J. D. Journal of cellular biochemistry 92, 967-992 (2004); each of which is incorporated by reference in its entirety). LPAi and SIPS are specific for ODCs, and their expression highly correlates with the process of myelination. LPA1 is expressed in restricted fashion within the neuroblasts of the neuroproliferatve Ventricular Zone (VZ) of the developing cortex, in the dorsal olfactory bulb, along the pial cells of neural crest origin, and in developing facial bone tissue. Expression is observed during E11-E18, corresponding to a time period during which neurogenesis occurs. LPA1 expression is undetectable in the VZ after this point, to reappear during the first postnatal week within ODCs. Notably, Schwann cells (the myelinating cells of the Peripheral Nervous System; PNS) express high levels of LPA1 early in development and persistently throughout life, suggesting an influence of LPA on myelinating processes (Weiner. J. A. & Chun, J., Proc Natl Acad Sci USA 96, 5233-5238 (1999), which is incorporated by reference in its entirety).

The above data strongly support a critical role for ATX and LPA signaling in neuronal development, oligodendrocyte differentiation and myelination, as well as possibly in the autoregulation of astrocyte activation. Moreover, the regulation of ATX and thus LPA production at local sites of CNS injury, inflammatory or autoimmune, could contribute to tissue homeostasis through the numerous effects of LPA. As demyelination and deregulated cerebrospinal fluid homeostasis are the hallmarks of multiple sclerosis, a role of ATX and LPA signaling in the pathophysiology of multiple sclerosis seems very likely.

The S1P modulating agents and/or ATX modulating agents of the invention can be used to various forms of MS including relapsing-remitting, secondary-progressive, primary-progressive, and progressive-relapsing forms. In addition, S1P modulating agents and/or ATX modulating agents of the invention can be used alone or in conjunction with other agents to treat or prevent MS. In a preferred embodiment, the compounds of the invention can be used to treat or prevent MS in combination with an immunomodulating therapy such as corticosteroids, beta interferon-1a (such as Avonex® or Rebif®), beta interferon-1b (Betaseron®), natalizumab (Tysabri®), glatiramer, and mitoxantrone.

Pain Mediation

Pain experienced by mammals can be divided into two main categories: acute pain (or nociceptive) and chronic pain which can be subdivided into chronic inflammatory pain and chronic neuropathic pain. Acute pain is a response to stimulus that causes tissue injury and is a signal to move away from the stimulus to minimize tissue damage. Chronic pain, on the other hand, serves no biological function and develops as a result of inflammation caused by tissue damage (inflammatory pain) or by damage to the nervous system such as demyelination (neuropathic pain). Chronic pain is generally characterized by stimulus-independent, persistent pain or by abnormal pain perception triggered by innocuous stimuli.

LPA has been found to be a mediator of both inflammatory pain and neuropathic pain. The transient receptor potential channel TRPV1 is known to be the originator of inflammatory pain. LPA has been shown to directly activate TRPV1 thereby creating pain stimulus by binding to its intracellular C-terminus (Tigyi, Nature Chemical Biology (January 2012), 8:22-23). Thus, compounds which inhibit the formation of LPA by inhibiting the action of ATX would be useful in treating inflammatory pain.

LPA has also been shown to play a role in neuropathic pain. For example, sciatic nerve injury has been shown to induce demyelination, down-regulation of myelin-associated glycoprotein (MAG) and damage to Schwann cell partitioning of C-fiber-containing Remak bundles in the sciatic nerve and dorsal root. However, demyelination, MAG down-regulation and Remak bundle damage in the dorsal root were abolished in $LPA_1$ receptor-deficient ($Lpar1^{-/-}$ mice (Nagai, et al., *Molecular Pain* (2010), 6:78). These results indicate that compounds that inhibit the formation of LPA by inhibiting the action of ATX would decrease dorsal root demyelination following nerve injury and decrease or eliminate neuropathic pain.

Thus the compounds of the invention are useful in treating or preventing chronic pain such as inflammatory pain and neuropathic pain in mammals.

Rheumatoid Arthritis (RA)

Studies in human and animal models of RA suggest that ATX plays a role in the development and progress of the disease. For example, increased ATX mRNA expression was detected in synovial fibroblasts (SFs) from animal models of RA during differential expression profiling, and human RA SFs were shown to express mRNA for both ATX and LPARs (Aidinis, V., et al., PLoS genetics 1, e48 (2005); Zhao, C, et al., Molecular pharmacology 73, 587-600 (2008); each of which is incorporated by reference in its entirety). ATX is overexpressed from activated SFs in arthritic joints, both in animal models and human patients (see WO 2011/151461). ATX expression was shown to be induced from TNF, the major pro-inflammatory factor driving RA.

Disease development was assessed in well-established animal models of RA. When ATX expression was conditionally ablated specifically in SFs, the lack of ATX expression in the joints resulted in marked decreased inflammation and synovial hyperplasia. This suggested an active involvement of the ATX-LPA axis in the pathogenesis of the disease. Similar results were also obtained with pharmacologic inhibition of ATX enzymatic activity and LPA signaling. A series of ex vivo experiments on primary SFs revealed that ATX, through LPA production, stimulates rearrangements of the actin cytoskeleton, proliferation and migration to the extracellular matrix (ECM), as well as the secretion of proinflammatory cytokines and matrix metalloproteinases (MMPs). Moreover, the LPA effect was shown to be synergistic with TNF and dependent on the activation of MAPK cellular signaling pathways. See, e.g., Armaka, M., et al., The Journal of experimental medicine 205, 331-337 (2008); which is incorporated by reference in its entirety.

In one embodiment a method for treating an individual with RA or the individual at risk of suffering thereof comprises administering to said individual an S1P modulating agent and/or ATX modulating agent of the invention in conjunction with an anti-TNF antibody for use in the treatment of RA. Examples of suitable anti-TNF antibodies are adalimumab, etanercept, golimumab, and infliximab (Taylor P C, Feldmann M. Anti-TNF biologic agents: still the therapy of choice for rheumatoid arthritis. Nat Rev Rheumatol. 2009 October; 5(10):578-82).

Pulmonary Fibrosis

Evidence also suggests a role for ATX in pulmonary fibrosis. Mice lacking lysophosphatidic acid (LPA) receptor 1(LPAR1) were protected from Bleomycin (BLM)-induced pulmonary fibrosis and mortality, suggesting a major role for LPA in disease pathophysiology. The majority of circulating LPA is produced by the phospholipase D activity of Autotaxin (ATX) and the hydrolysis of lysophosphatidylcholine (LPC). Increased ATX expression has been previously reported in the hyperplastic epithelium of fibrotic lungs of human patients and animal models.

Therefore, we hypothesized that genetic or pharmacologic inhibition of ATX activity would reduce local or circulating LPA levels and hence attenuate disease pathogenesis.

Lung Cancer

Increased ATX expression has been detected in a large number of malignancies, including mammary, thyroid, hepatocellular and renal cell carcinomas, glioblastoma and neuroblastoma, as well as NSCLC. Strikingly, transgenic overexpression of ATX was shown to induce spontaneous mammary carcinogenesis. In accordance, in vitro ATX overexpression in various cell types promotes proliferation and metastasis while inhibiting apoptosis. LPA's actions are concordant with many of the "hallmarks of cancer", indicating a role for LPA in the initiation or progression of malignant disease. Indeed LPA levels are significantly increased in malignant effusions, and its receptors are aberrantly expressed in several human cancers. See, for example: Euer, N., et al., Anticancer Res 22, 733-740 (2002); Liu, S., et al., Cancer Cell 15, 539-550 (2009); Zhang, G., et al., Chin Med J (Engl) 112, 330-332 (1999); Stassar, M. J., et al., Br J Cancer 85. 1372-1382 (2001); Kishi, Y., et al., J Biol Chem 281, 17492-17500 (2006); Kawagoe, H., et al., Cancer Res 57, 2516-2521 (1997); Yang, Y., et al., Am J Respir Cell Mol Biol 21, 216-222 (1999); and Toews, M. L., et al. Biochim Biophys Acta 1582, 240-250 (2002); each of which is incorporated by reference in its entirety.

In cases where a compound of the invention can be sufficiently basic or acidic to form stable nontoxic acid or base salts, preparation and administration of the compounds as pharmaceutically acceptable salts may be appropriate. Examples of pharmaceutically acceptable salts can be organic acid addition salts formed with acids which form a physiological acceptable anion, for example, tosylate, methanesulfonate, acetate, citrate, malonate, tartarate, succinate, benzoate, ascorbate, α-ketoglutarate, or α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, can include but are not limited to, sodium, potassium, lithium, ammonium, calcium or magnesium salts. Salts derived from organic bases can include, but are not limited to, salts of primary, secondary or tertiary amines, such as alkyl amines, dialkyl amines, trialkyl amines, substituted alkyl amines, di(substituted alkyl)amines, tri(substituted alkyl)amines, alkenyl amines, dialkenyl amines, trialkenyl amines, substituted alkenyl amines, di(substituted alkenyl)amines, tri(substituted alkenyl)amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, or mixed di- and tri-amines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, or heterocyclic and the like. Also included can be amines where the two or three substituents, together with the amino nitrogen, form a heterocyclic or heteroaryl group. Non-limiting examples of amines can include, isopropylamine, trimethyl amine, diethyl amine, tri(iso-propyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, or N-ethylpiperidine, and the like. Other carboxylic acid derivatives can be useful, for example, carboxylic acid amides, including carboxamides, lower alkyl carboxamides, or dialkyl carboxamides, and the like.

Pharmaceutical compositions can include a compound of the invention, or a pharmaceutically acceptable salt thereof. More particularly, such compounds can be formulated as pharmaceutical compositions using standard pharmaceutically acceptable carriers, fillers, solubilizing agents and stabilizers known to those skilled in the art. For example, a pharmaceutical composition including a compound of the invention, or a salt, analog, derivative, or modification thereof, as described herein, is used to administer the appropriate compound to a subject.

The compounds of the invention, or a pharmaceutically acceptable salt thereof, are useful for treating a disease or disorder associated with S1P receptor activity, and/or ATX activity. In one embodiment, a therapeutically effective amount of a compound of the invention, or a pharmaceutically acceptable salt thereof, is administered to a subject in need thereof. In another embodiment, a pharmaceutical composition comprising a therapeutically effective amount of a compound of the invention, or a pharmaceutically acceptable salt thereof, and a pharmaceutically-acceptable carrier is administered to a subject in need thereof.

The compounds of the invention can be used in combination with at least one further active ingredient, such as a medicament used in the treatment of multiple sclerosis such as Tysabri®, dimethyl fumarate, an interferon (such as pegylated or non-pegylated interferons, preferably interferon β-1a or pegylated interferon β-1a), glatiramer acetate, a compound improving vascular function, an immunomodulating agent (such as Fingolimod, cyclosporins, rapamycins or ascomycins, or their immunosuppressive analogs, e.g. cyclosporine A, cyclosporine G, FK-506, ABT-281, ASM981, rapamycin, 40-O-(2-hydroxyl)ethyl-rapamycin etc.); corticosteroids; cyclophosphamide; azathioprine; mitoxanthrone, methotrexate; leflunomide; mizoribine; mycophenolic add; mycophenolate mofetil; 15-deoxyspergualine; diflucortolone valerate; difluprednate; Alclometasone dipropionate; amcinonide; amsacrine; asparaginase;

azathioprine; basiliximab; beclometasone dipropionate; betamethasone; betamethasone dipropionate; betamethasone phosphate sodique; betamethasone valerate; budesonide; captopril; chlormethine chlorhydrate; clobetasol propionate; cortisone acetate; cortivazol; cyclophosphamide; cytarabine; daclizumab; dactinomycine; desonide; desoximetasone; dexamethasone; dexamethasone acetate; dexamethasone isonicotinate; dexamethasone metasulfobenzoate sodique; dexamethasonephosphate; dexamethasone tebutate; dichlorisone acetate; doxorubicinee chlorhydrate; epirubicine chlorhydrate; fluclorolone acetonide; fludrocortisone acetate; fludroxycortide; flumetasone pivalate; flunisolide; fluocinolone acetonide; fluocinonide; fluocortolone; fluocortolone hexanoate; fluocortolone pivalate; fluorometholone; fluprednidene acetate; fluticasone propionate; gemcitabine chlorhydrate; halcinonide; hydrocortisone; hydrocortisone acetate; hydrocortisone butyrate; hydrocortisone hemisuccinate; melphalan; meprednisone; mercaptopurine; methylprednisolone; methylprednisolone acetate; methylprednisolone hemisuccinate; misoprostol; muromonab-cd3; mycophenolate mofetil; paramethansone acetate; prednazoline, prednisolone; prednisolone acetate; prednisolone caproate; prednisolone metasulfobenzoate sodique; prednisolone phosphate sodique; prednisone; prednylidene; rifampicine; rifampicine sodique; tacrolimus; teriflunomide; thalidomide; thiotepa; tixocortol pivalate; triamcinolone; triamcinolone acetonide hemisuccinate; triamcinolone benetonide; triamcinolone diacetate; triamcinolone hexacetonide; immunosuppressive monoclonal antibodies, e.g., monoclonal antibodies to leukocyte receptors, e.g., MHC, CD2, CD3, CD4,CD7, CD20 (e.g., rituximab and ocrelizumab), CD25, CD28, B7, CD40, CD45, CD56 (e.g., daclizumab), or CD58 or their ligands; or other immunomodulating agenty compounds, e.g. CTLA41 g, or other adhesion molecule inhibitors, e.g. mAbs or low molecular weight inhibitors including Selectin antagonists and VLA-4 antagonists (such as Tysabri®); remyelinating agents such as BIIB033. Compounds of the invention can also be used in combination with agents which treat the symptoms of multiple sclerosis such as fampridine.

The dose of a compound of the invention, or a pharmaceutically acceptable salt thereof, administered to a subject can be less than 10 µg, less than 25 µg, less than 50 µg, less than 75 µg, less than 0.10 mg, less than 0.25 mg, less than 0.5 mg, less than 1 mg, less than 2.5 mg, less than 5 mg, less than 10 mg, less than 15 mg, less than 20 mg, less than 50 mg, less than 75 mg, less than 100 mg, or less than 500 mg.

Administering can include administering by topical, enteral, parenteral, transdermal, transmucosal, inhalational, intracisternal, epidural, intravaginal, intravenous, intramuscular, subcutaneous, intradermal or intravitreal administration. In addition, the term "administer" or "administering" encompasses delivering a compound of the invention as a prodrug which is converted or metabolized in the body of the mammal into a compound of the invention. In one embodiment, a compound of the invention is administered in a non-prodrug form. In another embodiment, the compound is administered as a prodrug which is metabolized to a compound of the invention in the body of a mammal.

The duration of administering can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours or for more than 24 hours.

Administering the inhibitor or compound can include multiple administrations. The duration between administrations can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours or for more than 24 hours.

The duration between successive administrations can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours, between 24 hours and 48 hours, between 48 hours and 72 hours, between 72 hours and 1 week or between 1 week and 2 weeks.

Administering an inhibitor or compound to cells can include cells of an in vitro or in vivo system or model. The cells can be part of a cell line. The cell line can be a primary or secondary cell line. The cell line can be an immortal cell line. The cells can be ruptured and be in the form of a cell lysate. The cells can be part of a living organism, i.e., a subject, for example, a mammal. A mammal can include a rat, a mouse, a gerbil, a hamster, a rabbit or a human. The human can be a subject or a patient.

A method can further include monitoring a property of a sample or a subject. A sample can be removed from a subject. For instance, a sample can include a sample of cells or a tissue from a subject. A sample can include blood, plasma, or neuronal tissue including neurons or glial cells. A sample can also remain in the subject. For example, a sample can be a tissue or cells that are observed within the patient.

A method can further include providing untreated control cells, sample or subject and measuring a property of a sample of the untreated control cells, sample or subject.

A property can include the presence or absence of a molecule, the concentration of a molecule, for example myelin basic protein, myelin associated glycoprotein or myelin oligodendrocyte glycoprotein. In some embodiments, determining the presence of a molecule can include determining the concentration of the molecule, determining the purity of the molecule or determining the quantity of the molecule.

A property can be the conductivity of a tissue or cell. A property can be an emission, for example, electromagnetic radiation.

Monitoring a property can include observing the property of the sample or subject alone. Monitoring a property can include monitoring the property before the sample or subject has been administered a compound of the invention. Monitoring a property can include monitoring the property after the sample or subject has been administered a compound. Monitoring a property can include monitoring a property after the sample or subject has been administered a known concentration of a compound.

Monitoring a property of a sample or subject can include observing the property through a microscope. Monitoring a property of the composition can include measuring the property using a microscope. Monitoring a property of the composition can include monitoring the property using still photography or movies. The photography or movies can be on film media or digital form. Monitoring a property can include taking a scan, for example, an MRI or CT scan.

Promoting myelination, remyelination or oligodendrocyte progenitor cell differentiation can prevent or can treat a pathological condition or symptom in a mammal. A number of diseases or disorders involve demyelination of the central or peripheral nervous system which can occur for a number of reasons such as immune dysfunction as in multiple sclerosis, encephalomyelitis, Guillain-Barre Syndrome, chronic inflammatory demyelinating polyneuropathy (CIDP), transverse myelitis, and optic neuritis; demyelination due to injury such as spinal cord injury, traumatic brain injury, stroke, acute ischemic optic neuropathy, or other ischemia, cerebral palsy, neuropathy (e.g. neuropathy due to diabetes, chronic renal failure, hypothyroidism, liver failure, or compression of the nerve), post radiation injury, and central pontine myelolysis (CPM); inherited conditions such as Charcot-Marie-Tooth disease (CMT), Sjogren-Larsson syndrome, Refsum disease, Krabbe disease, Canavan disease, Alexander disease, Friedreich's ataxia, Pelizaeus-Merzbacher disease, Bassen-Kornzweig syndrome, metachromatic leukodystrophy (MLD), adrenoleukodystrophy, and nerve damage due to pernicious anemia; viral infection such as progressive multifocal leukoencephalopathy (PML), Lyme disease, or tabes dorsalis due to untreated syphilis; toxic exposure due to chronic alcoholism (which is a possible cause of Marchiafava-Bignami disease), chemotherapy, or exposure to chemicals such as organophosphates; or dietary deficiencies such as vitamin B12 deficiency, vitamin E deficiency, and copper deficiency. Some demyelination disorders can have unknown or multiple causes such as trigeminal neuralgia, Marchiafava-Bignami disease and Bell's palsy. In addition, demyelination can contribute to neuropathic pain. Compounds of the invention are expected to be useful in treating demyelination disorders.

Since LPA is a proinflammatory factor reducing the amount of LPA producted by inhibiting ATX is useful for treating inflammatory disorders such as asthma, allergies, arthritis, inflammatory neuropathies, transplantation rejection, Crohn's disease, ulcerative colitis, lupus erythematosis, psoriasis, an inflammatory bowel condition, and diabetes.

LPA has been shown to be involved in wound healing and stimulates the proliferation and migration of endothelial cells promoting processes such as angiogenesis. However, these same processes when deregulated can promote tumor growth and metastasis, and LPA is thought to contribute to the development, progression, and metastasis of several types of cancer including ovarian, prostate, melanoma, breast, head and neck cancers (see Gendaszewska-Darmach, Acta Biochimica Polonica (2008), 55(2):227-240). In addition, since ATX is located outside the cell in circulation, ATX inhibitors are expected to be of most benefit outside the cell. Therefore, ATX inhibitors are expected to be useful in treating cancer, particularly multidrug resistant (MDR) cancers where drug efflux mechanisms are the largest contributor to the drug resistance.

A compound of the invention, or a pharmaceutically acceptable salt thereof, formulated as a pharmaceutical composition and administered to a mammalian host, such as a human patient in a variety of forms adapted to the chosen route of administration, e.g., orally or parenterally, as eyedrops, by intravenous, intramuscular, topical or subcutaneous routes.

Thus, compound of the invention, or a pharmaceutically acceptable salt thereof, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, or wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that an effective dosage level will be obtained.

The tablets, troches, pills, capsules, and the like can include the following: binders such as gum tragacanth, acacia, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl or propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, or nontoxic glyceryl esters, and mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, or thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate or gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

For topical administration, a compound of the invention may be applied in pure form, e.g., when they are liquids. However, it can be generally be desirable to administer them to the skin as compositions or formulations, in combination with a dermatologically acceptable carrier, which may be a solid or a liquid.

Exemplary solid carriers can include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts or esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), each of which is incorporated by reference in its entirety.

Useful dosages of the compounds of the invention can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

Generally, the concentration of the compound(s) of the invention in a liquid composition, such as a lotion, can be from about 0.1 to about 25 weight percent, preferably from about 0.5-10 weight percent. The concentration in a semi-solid or solid composition such as a gel or a powder can be about 0.1-5 wt-%, preferably about 0.5-2.5 weight percent based on the total weight of the composition.

The amount of the compound, or an active salt or derivative thereof, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The compound can be conveniently administered in unit dosage form; for example, containing 0.01 to 10 mg, or 0.05 to 1 mg, of active ingredient per unit dosage form. In some embodiments, a dose of 5 mg/kg or less can be suitable.

The active ingredient can be administered so as to achieve a desired peak plasma concentration of the active compound. The desired peak plasma concentration can be from about 0.5 μM to about 75 μM, preferably, about 1 μM to 50 μM, or about 2 μM to about 30 μM. This may be achieved, for example, by the intravenous injection of a 0.05 to 5% solution of the active ingredient, optionally in saline, or orally administered as a bolus containing between about 1 mg to about 100 mg of the active ingredient.

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple inhalations from an insufflator or by application of a plurality of drops into the eye.

The disclosed method can include a kit comprising a compound of the invention and instructional material which can describe administering the compound or a composition comprising the compound to a cell or a subject. This should be construed to include other embodiments of kits that are known to those skilled in the art, such as a kit comprising a (preferably sterile) solvent for dissolving or suspending the compound or composition prior to administering the compound or composition to a cell or a subject. Preferably, the subject can be a human.

In accordance with the disclosed methods, as described above or as discussed in the Examples below, there can be employed conventional chemical, cellular, histochemical, biochemical, molecular biology, microbiology, and in vivo techniques which are known to those of skill in the art. Such techniques are explained fully in the literature.

EXAMPLES

In one embodiment, certain compounds of the invention, and pharmaceutically acceptable salts thereof, may be prepared according to general scheme 1:

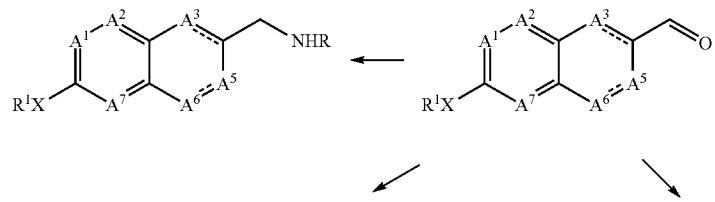

Scheme 1

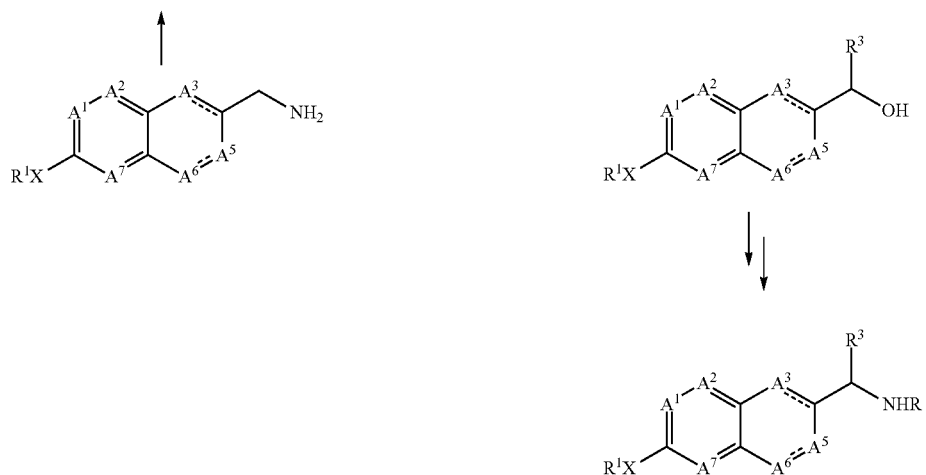
In one embodiment, certain compounds of the invention, and pharmaceutically acceptable salts thereof, may be prepared according to general scheme 2:
Scheme 2
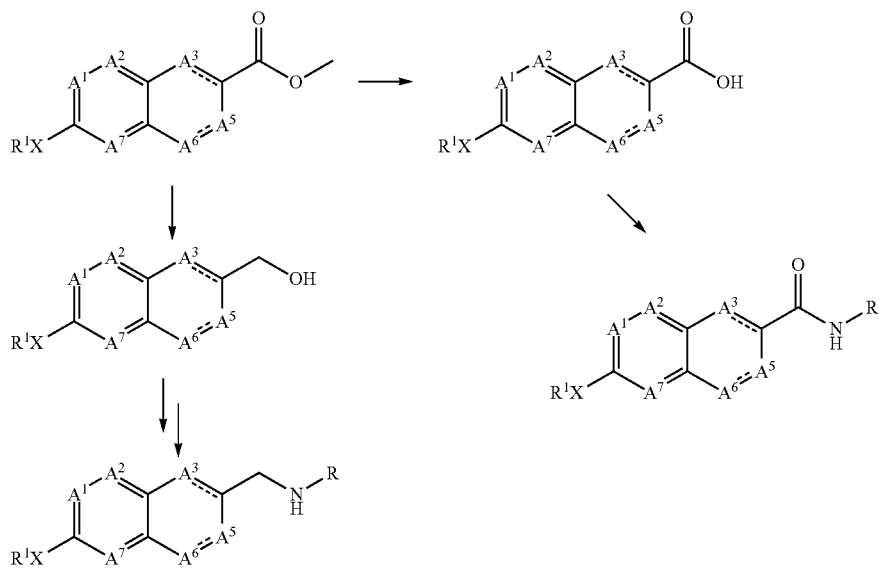
In one embodiment, certain compounds of the invention, and pharmaceutically acceptable salts thereof, may be prepared according to general scheme 3:
Scheme 3
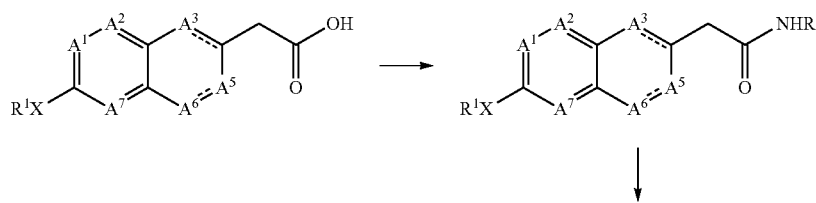

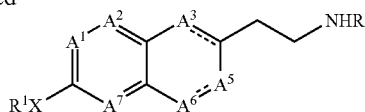

Example 1

4-(((6-(cyclohexyloxy)naphthalen-2-yl)methyl)amino) bicyclo[2.2.2]octane-1-carboxylic acid

Step 1: 4-(((6-hydroxynaphthalen-2-yl)methyl)amino)bicyclo[2.2.2]octane-1-carboxylate

Step 2: 4-(((6-(cyclohexyloxy)naphthalen-2-yl)methyl)amino)bicyclo[2.2.2]octane-1-carboxylic acid

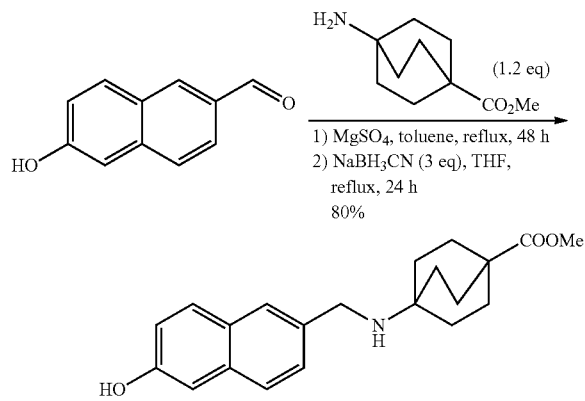

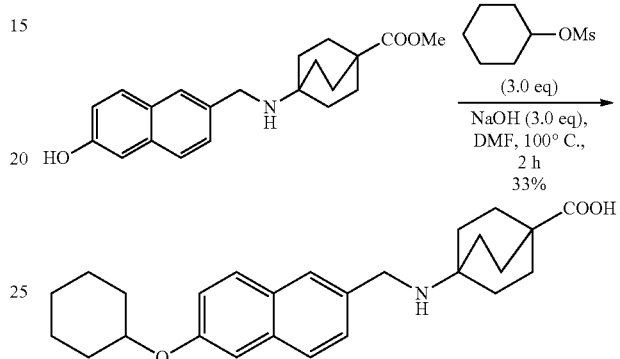

6-hydroxy-2-naphthaldehyde (520 mg, 3.02 mmol, 1.0 eq) and methyl 4-aminobicyclo[2.2.2]octane-1-carboxylate (663 mg, 3.62 mmol, 1.2 eq) were dissolved in toluene (100 mL). Magnesium sulfate (72 mg, 0.60 mmol, 0.2 eq) was added to the solution and refluxed for 48 h. The solvent was removed in vacuo. The residue was dissolved in THF (150 mL) and sodium cyanoborohydride (571 mg, 9.06 mmol, 3.0 eq) was added. The mixture was refluxed for 24 h. The solvent was removed in vacuo. Water (50 mL) was added to the residue and extracted with EtOAc (2×150 mL). The combined organic phase was washed with brine and dried over $Na_2SO_4$. The organic phase was concentrated to give methyl 4-(((6-hydroxynaphthalen-2-yl)methyl)amino)bicyclo[2.2.2]octane-1-carboxylate as yellow solid (819 mg, Y: 80%). ESI-MS (M+H)$^+$: 340.2. $^1$H NMR (400 MHz, DMSO-$d_6$) δ: 9.98 (s, 1H), 8.91 (br, 1H), 7.89 (s, 1H), 7.77 (d, J=9.2 Hz, 1H), 7.75 (d, J=8.4 Hz, 1H), 7.47 (dd, J=8.4, 1.6 Hz, 1H), 7.15 (s, 1H), 7.14 (dd, J=8.0, 2.4 Hz, 1H), 4.17 (s, 2H), 3.60 (s, 3H), 1.91-1.87 (m, 12H).

Methyl 4-(((6-hydroxynaphthalen-2-yl)methyl)amino)bicyclo[2.2.2]octane-1-carboxylate (100 mg, 0.295 mmol, 1.0 eq), cyclohexyl methanesulfonate (100 mg, 0.885 mmol, 3.0 eq) and sodium hydroxide (35 mg, 0.875 mmol, 3.0 eq) were dissolved in DMF (2 mL). The mixture was stirred at 100° C. for 2 h. After cooling to rt, 1 N HCl was added to adjust pH=6-7 and extracted with DCM (2×40 mL). The organic phase was washed with brine and dried over $Na_2SO_4$. After filtration and concentration, the residue was purified by prep-HPLC (65% MeOH/$H_2O$) to give 4-(((6-(cyclohexyloxy)naphthalen-2-yl)methyl)amino)bicyclo[2.2.2]octane-1-carboxylic acid as a white solid (40 mg, yield: 33% in two steps). ESI-MS (M+H)$^+$: 408.2. $^1$H NMR (400 MHz, CD$_3$OD) δ: 7.89 (s, 1H), 7.84 (d, J=8.4 Hz, 1H), 7.81 (d, J=8.8 Hz, 1H), 7.49 (dd, J=8.8, 2.0 Hz, 1H), 7.28 (d, J=2.0 Hz, 1H), 7.20 (dd, J=8.8, 2.4 Hz, 1H), 4.52-4.48 (m, 1H), 4.24 (s, 2H), 2.04-1.99 (m, 14H), 1.86-1.83 (m, 2H), 1.63-1.47 (m, 6H).

Example 2

4-(((6-((trans-4-methylcyclohexyl)oxy)naphthalen-2-yl)methyl)amino)bicyclo[2.2.2]octane-1-carboxylic acid

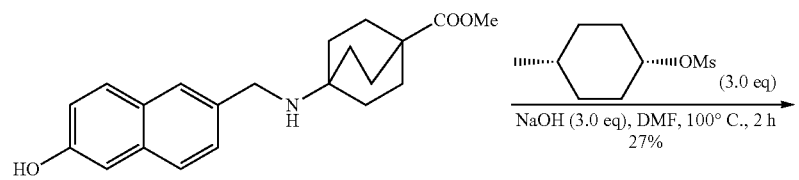

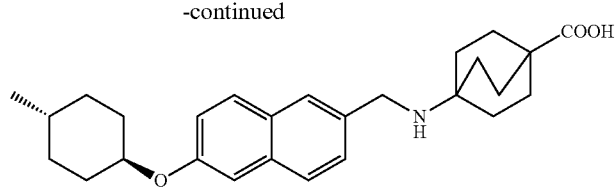

The preparation of 4-(((6-((trans-4-methylcyclohexyl)oxy)naphthalen-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 34 mg, white solid, yield: 27% in two steps. ESI-MS (M+H)+: 422.3. $^1$H NMR (400 MHz, CD$_3$OD) δ: 7.78 (s, 1H), 7.74 (d, J=8.8 Hz, 1H), 7.69 (d, J=9.2 Hz, 1H), 7.37 (dd, J=8.4, 2.0 Hz, 1H), 7.17 (d, J=2.0 Hz, 1H), 7.07 (dd, J=9.2, 2.4 Hz, 1H), 4.32-4.25 (m, 1H), 4.14 (s, 2H), 2.11-2.07 (m, 2H), 1.94-1.88 (m, 12H), 1.74-1.71 (m, 2H), 1.41-1.39 (m, 3H), 1.09-1.06 (m, 2H), 0.86 (d, J=6.8 Hz, 3H).

Example 3

4-(((6-((trans-4-ethylcyclohexyl)oxy)naphthalen-2-yl)methyl)amino)bicyclo[2.2.2]octane-1-carboxylic acid ESI-MS (M+H)+: 436.2. $^1$H NMR (400 MHz, CD$_3$OD) δ: 7.89 (s, 1H), 7.85 (d, J=8.4 Hz, 1H), 7.80 (d, J=9.2 Hz, 1H), 7.48 (dd, J=8.8, 2.0 Hz, 1H), 7.28 (d, J=2.8 Hz, 1H), 7.18 (dd, J=8.8, 2.4 Hz, 1H), 4.43-4.39 (m, 1H), 4.26 (s, 2H), 2.25-2.21 (m, 2H), 2.05-1.99 (m, 12H), 1.92-1.89 (m, 2H), 1.48-1.45 (m, 2H), 1.33-1.28 (m, 3H), 1.19-1.13 (m, 2H), 0.95 (t, J=7.2 Hz, 3H).

Example 4

4-(((6-((trans-4-isopropylcyclohexyl)oxy)naphthalen-2-yl)methyl)amino)bicyclo[2.2.2]octane-1-carboxylic acid

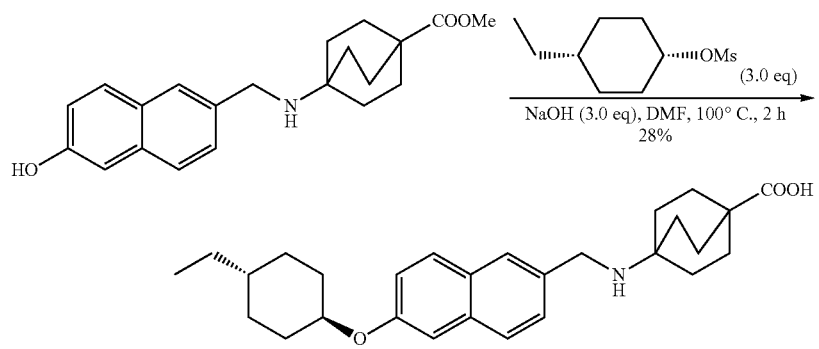

The preparation of 4-(((6-((trans-4-ethylcyclohexyl)oxy)naphthalen-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 36 mg, white solid, yield: 28% in two steps.

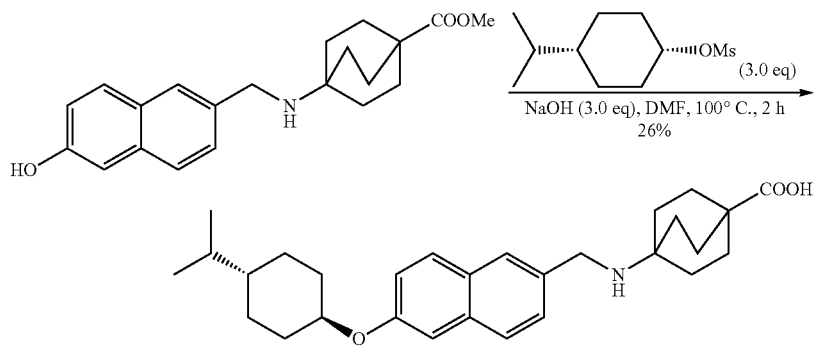

The preparation of 4-(((6-((trans-4-isopropylcyclohexyl)oxy)naphthalen-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 34 mg, white solid, yield: 26% in two steps. ESI-MS (M+H)⁺: 450.3. ¹H NMR (400 MHz, CD₃OD) δ: 7.78 (s, 1H), 7.74 (d, J=8.4 Hz, 1H), 7.69 (d, J=9.2 Hz, 1H), 7.37 (dd, J=8.4, 1.6 Hz, 1H), 7.18 (d, J=2.4 Hz, 1H), 7.07 (dd, J=8.8, 2.0 Hz, 1H), 4.30-4.25 (m, 1H), 4.14 (s, 2H), 2.16-2.13 (m, 2H), 1.94-1.88 (m, 12H), 1.78-1.75 (m, 2H), 1.41-1.32 (m, 3H), 1.19-1.09 (m, 3H), 0.83 (d, J=6.8 Hz, 6H).

Example 5

4-(((6-((trans-4-(tert-pentyl)cyclohexyl)oxy)naphthalen-2-yl)methyl)amino)bicyclo[2.2.2]octane-1-carboxylic acid

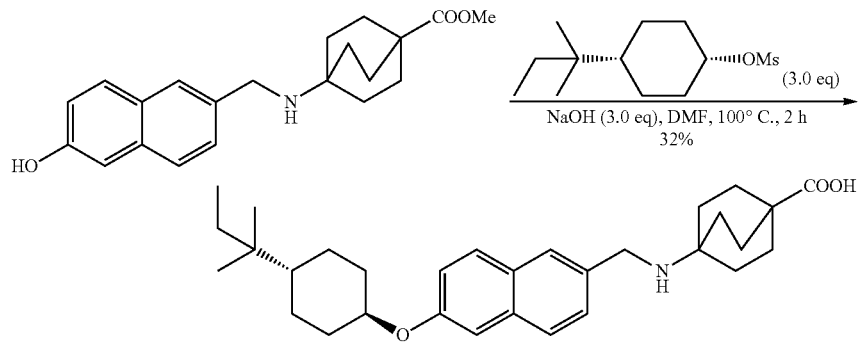

The preparation of 4-(((6-((trans-4-(tert-pentyl)cyclohexyl)oxy)naphthalen-2-yl)methyl)amino)bicyclo[2.2.2]octane-1-carboxylic acid was the same as that of 4-(((6-(cyclohexyloxy)naphthalen-2-yl)methyl)amino) bicyclo[2.2.2]octane-1-carboxylic acid. 45 mg, white solid, yield: 32% in two steps. ESI-MS (M+H)⁺: 478.2. ¹H NMR (400 MHz, CD₃OD) δ: 7.78 (s, 1H), 7.74 (d, J=8.4 Hz, 1H), 7.69 (d, J=9.2 Hz, 1H), 7.38 (dd, J=8.8, 1.6 Hz, 1H), 7.17 (d, J=2.0 Hz, 1H), 7.06 (dd, J=8.8, 2.4 Hz, 1H), 4.30-4.21 (m, 1H), 4.12 (s, 2H), 2.18-2.15 (m, 2H), 1.93-1.90 (m, 12H), 1.76-1.73 (m, 2H), 1.32-1.14 (m, 8H), 0.76-0.72 (m, 8H).

Example 6

4-(((6-((trans-4-phenylcyclohexyl)oxy)naphthalen-2-yl)methyl)amino)bicyclo[2.2.2]octane-1-carboxylic acid

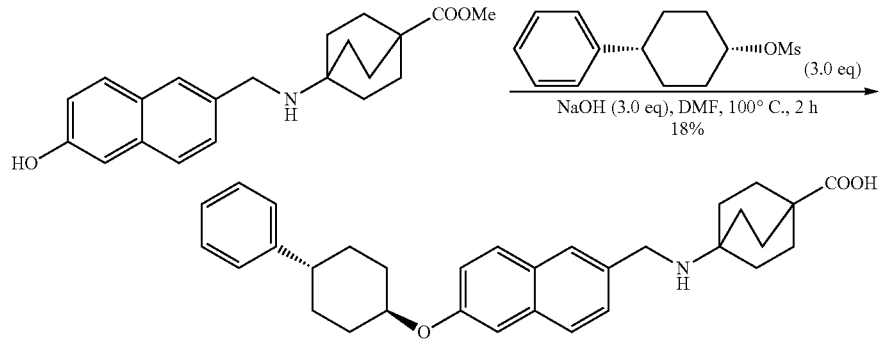

The preparation of 4-(((6-((trans-4-phenylcyclohexyl)oxy)naphthalen-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 26 mg, white solid, yield: 18% in two steps. ESI-MS (M+H)⁺: 483.3. ¹H NMR (400 MHz, CD₃OD) δ: 7.90 (s, 1H), 7.88 (d, J=8.4 Hz, 1H), 7.83 (d, J=8.8 Hz, 1H), 7.50 (dd, J=8.8, 1.6 Hz, 1H), 7.35 (d, J=2.4 Hz, 1H), 7.29-7.26 (m, 4H), 7.22 (dd, J=9.2, 2.4 Hz, 1H), 7.20-7.17 (m, 1H), 4.59-4.52 (m, 1H), 4.25 (s, 2H), 2.67-2.61 (m, 1H), 2.37-2.34 (m, 2H), 2.05-1.98 (m, 14H), 1.78-1.71 (m, 2H), 1.69-1.63 (m, 2H).

Example 7

4-(((6-((4,4-dimethylcyclohexyl)oxy)naphthalen-2-yl)methyl)amino)bicyclo[2.2.2]octane-1-carboxylic acid

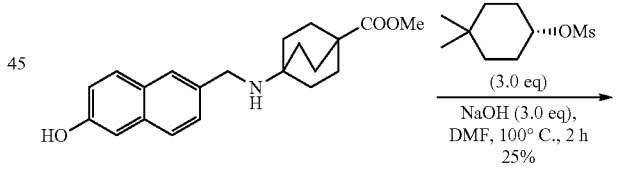

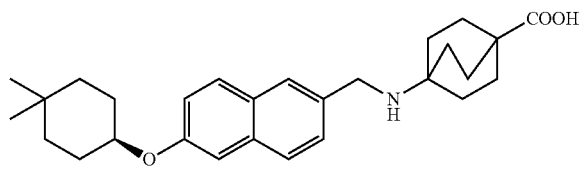

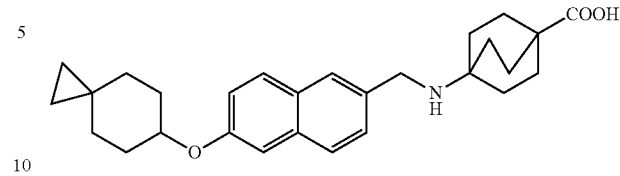

The preparation of 4-(((6-((4,4-dimethylcyclohexyl)oxy)naphthalen-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 32 mg, white solid, yield: 25% in two steps. ESI-MS (M+H)+: 436.2. 1H NMR (400 MHz, CD3OD) δ: 7.89 (s, 1H), 7.85 (d, J=8.8 Hz, 1H), 7.81 (d, J=9.2 Hz, 1H), 7.48 (dd, J=8.4, 2.0 Hz, 1H), 7.28 (d, J=2.4 Hz, 1H), 7.21 (dd, J=8.8, 2.4 Hz, 1H), 4.51-4.49 (m, 1H), 4.26 (s, 2H), 2.05-1.94 (m, 14H), 1.79-1.74 (m, 2H), 1.59-1.56 (m, 2H), 1.40-1.35 (m, 2H), 1.01 (s, 3H), 1.00 (s, 3H).

The preparation of 4-(((6-(spiro[2.5]octan-6-yloxy)naphthalen-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 12 mg, white solid, yield: 25% in two steps. ESI-MS (M+H)+: 434.2. 1H NMR (400 MHz, CD3OD) δ: 7.90 (s, 1H), 7.86 (d, J=8.4 Hz, 1H), 7.82 (d, J=9.2 Hz, 1H), 7.49 (dd, J=8.8, 2.0 Hz, 1H), 7.31 (d, J=2.0 Hz, 1H), 7.22 (dd, J=8.4, 2.0 Hz, 1H), 4.64-4.60 (m, 1H), 4.26 (s, 2H), 2.04-1.99 (m, 14H), 1.83-1.74 (m, 2H), 1.60-1.54 (m, 2H), 1.43-1.39 (m, 2H), 0.38-0.29 (m, 4H).

Example 9

4-(((6-(spiro[3.5]nonan-7-yloxy)naphthalen-2-yl)methyl)amino)bicyclo[2.2.2]octane-1-carboxylic acid

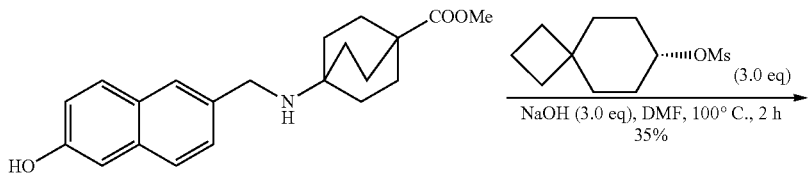

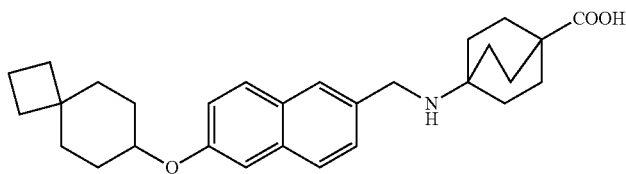

Example 8

4-(((6-(spiro[2.5]octan-6-yloxy)naphthalen-2-yl)methyl)amino)bicyclo[2.2.2]octane-1-carboxylic acid

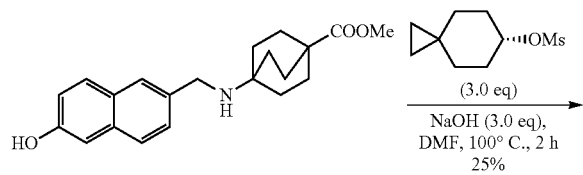

The preparation of 4-(((6-(spiro[3.5]nonan-7-yloxy)naphthalen-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 46 mg, white solid, yield: 35% in two steps. ESI-MS (M+H)+: 448.3. 1H NMR (400 MHz, CD3OD) δ: 7.89 (s, 1H), 7.85 (d, J=8.4 Hz, 1H), 7.81 (d, J=9.2 Hz, 1H), 7.48 (dd, J=8.8, 2.0 Hz, 1H), 7.28 (d, J=2.4 Hz, 1H), 7.19 (dd, J=8.8, 2.4 Hz, 1H), 4.51-4.43 (m, 1H), 4.26 (s, 2H), 2.05-1.99 (m, 12H), 1.94-1.81 (m, 10H), 1.55-1.52 (m, 4H).

Example 10

4-(((6-(spiro[4.5]decan-8-yloxy)naphthalen-2-yl)methyl)amino)bicyclo[2.2.2]octane-1-carboxylic acid

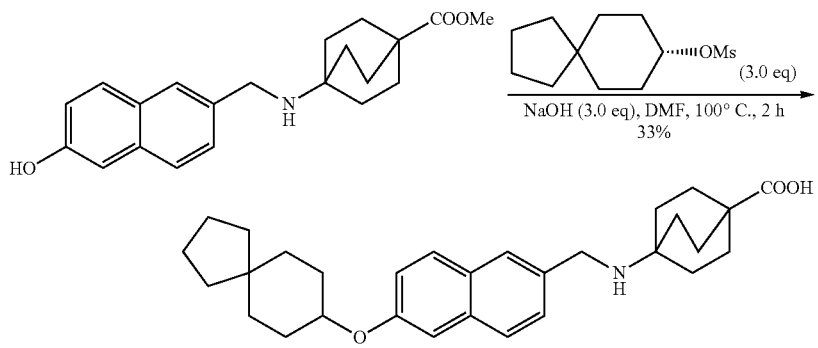

The preparation of 4-(((6-(spiro[4.5]decan-8-yloxy)naphthalen-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 45 mg, white solid, yield: 33% in two steps. ESI-MS (M+H)$^+$: 462.3. $^1$H NMR (400 MHz, CD$_3$OD) δ: 7.89 (s, 1H), 7.85 (d, J=8.8 Hz, 1H), 7.81 (d, J=8.8 Hz, 1H), 7.48 (dd, J=8.4, 1.6 Hz, 1H), 7.29 (d, J=2.0 Hz, 1H), 7.20 (dd, J=8.8, 2.4 Hz, 1H), 4.53-4.51 (m, 1H), 4.25 (s, 2H), 2.05-1.99 (m, 14H), 1.73-1.65 (m, 8H), 1.54-1.42 (m, 6H).

Example 11

4-(((6-(spiro[5.5]undecan-3-yloxy)naphthalen-2-yl)methyl)amino)bicyclo[2.2.2]octane-1-carboxylic acid

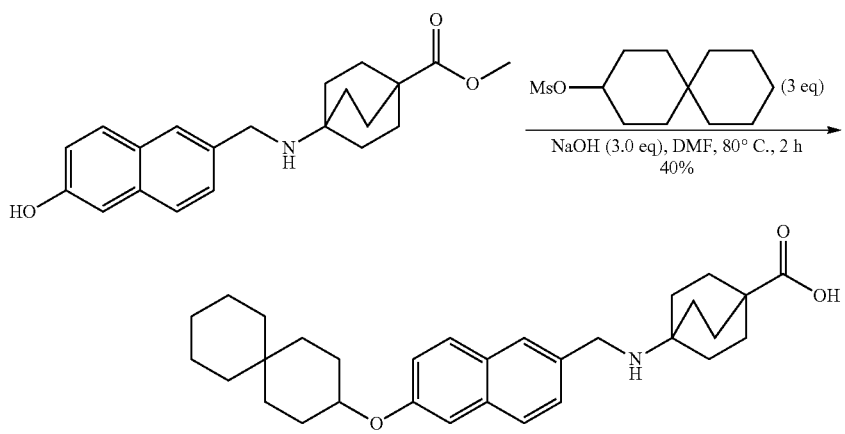

The preparation of 4-(((6-(spiro[5.5]undecan-3-yloxy)naphthalen-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 50 mg, white solid, yield: 40% in two steps. ESI-MS (M+H)$^+$: 476.3. $^1$H NMR (400 MHz, CD$_3$OD) δ: 7.89 (s, 1H), 7.86-7.79 (m, 2H), 7.48 (dd, J=8.4, 1.2 Hz, 1H), 7.28 (d, J=1.2 Hz, 1H), 7.20 (dd, J=8.8, 1.2 Hz, 1H), 4.52-4.48 (m, 1H), 4.26 (s, 2H), 2.05-1.92 (m, 14H), 1.75-1.66 (m, 4H), 1.47 (br, 8H), 1.37-1.30 (m, 4H).

Example 12

4-(((6-(heptyloxy)naphthalen-2-yl)methyl)amino)bicyclo[2.2.2]octane-1-carboxylic acid Step 1: methyl 4-(((6-(heptyloxy)naphthalen-2-yl)methyl)amino)bicyclo[2.2.2]octane-1-carboxylate

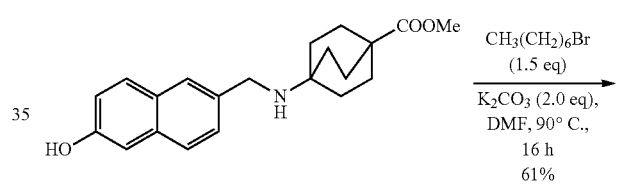

-continued

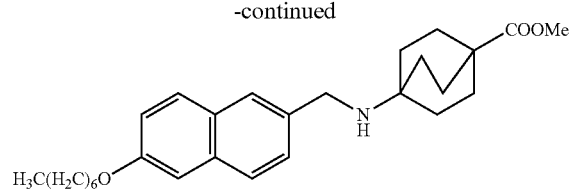

To a solution of methyl 4-(((6-hydroxynaphthalen-2-yl)methyl)amino)bicyclo[2.2.2]octane-1-carboxylate (153 mg, 0.45 mmol, 1.0 eq) in DMF (3 mL) was added 1-bromoheptane (119 mg, 0.68 mmol, 1.5 eq) and $K_2CO_3$ (124 mg, 0.9 mmol, 2.0 eq). The mixture was stirred at 90° C. for 16 h. After cooling down to room temperature, the mixture was diluted with brine (50 mL) and extracted with EtOAc (60 mL×3). The combined organic phase was dried over $Na_2SO_4$ and concentrated under reduced pressure. The residue was purified by pre-HPLC to give methyl 4-(((6-(heptyloxy)naphthalen-2-yl)methyl)amino)bicyclo[2.2.2]octane-1-carboxylate as a white solid (120 mg, yield: 61%). ESI-MS (M+H)$^+$: 321.1. ESI-MS (M+H)$^+$: 438.3. $^1$H NMR (400 MHz, $CDCl_3$) δ: 7.73 (s, 1H), 7.66 (d, J=9.2 Hz, 1H), 7.62 (d, J=8.4 Hz, 1H), 7.34 (dd, J=8.4, 2.0 Hz, 1H), 7.13 (dd, J=8.8, 2.4 Hz, 1H), 7.02 (d, J=2.4 Hz, 1H), 3.98 (t, J=6.8 Hz, 2H), 3.85 (d, J=2.4 Hz, 2H), 3.60 (s, 3H), 1.83-1.80 (m, 2H), 1.50-1.30 (m, 20H), 0.90 (t, J=7.2 Hz, 3H).

Step 2: 4-((16-(heptyloxy)naphthalen-2-yl)methyl)amino)bicyclo[2.2.2]octane-1-carboxylic acid

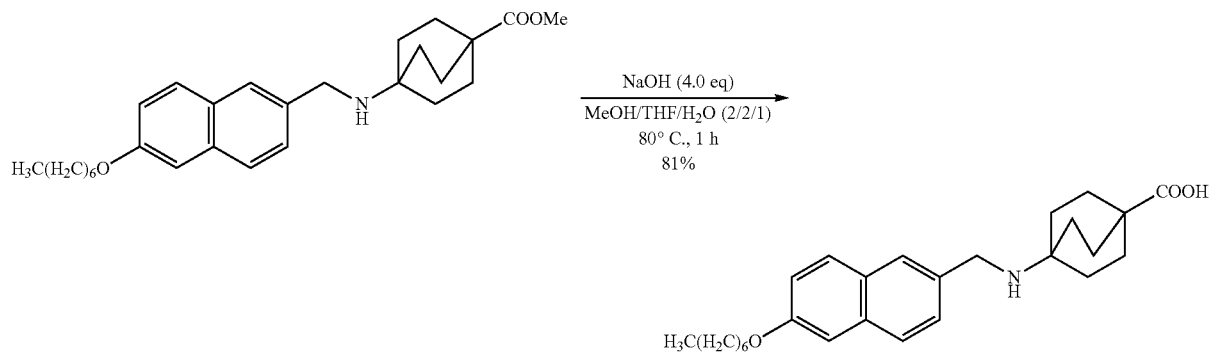

To a solution of methyl 4-(((6-(heptyloxy)naphthalen-2-yl)methyl)amino) bicyclo[2.2.2]octane-1-carboxylate (120 mg, 0.27 mmol, 1.0 eq) in MeOH/THF/$H_2O$ (2:2:1, 10 mL) was added NaOH (43 mg, 1.08 mmol, 4.0 eq). The mixture was stirred at reflux for 1 h. After cooling down to room temperature, the mixture was adjusted to pH=6 with 1 N HCl and extracted with DCM (30 mL×2). The combined organic phase was dried over $Na_2SO_4$ and concentrated under reduced pressure. The residue was purified by pre-HPLC to give 4-(((6-(heptyloxy)naphthalen-2-yl)methyl)amino)bicyclo[2.2.2]octane-1-carboxylic acid as a white solid (94 mg, yield: 81%). ESI-MS (M+H)$^+$: 424.2. $^1$H NMR (400 MHz, $CD_3OD$) δ: 7.90 (s, 1H), 7.87 (d, J=8.8 Hz, 1H), 7.81 (d, J=8.8 Hz, 1H), 7.49 (dd, J=8.4, 1.6 Hz, 1H), 7.27 (d, J=2.4 Hz, 1H), 7.21 (dd, J=8.8, 2.4 Hz, 1H), 4.25 (s, 2H), 4.11 (t, J=6.4 Hz, 2H), 2.05-2.01 (m, 12H), 1.87-1.83 (m, 2H), 1.55-1.50 (m, 2H), 1.42-1.33 (m, 6H), 0.93 (t, J=7.2 Hz, 3H).

Example 13

4-(((6-((cis-4-methylcyclohexyl)oxy)naphthalen-2-yl)methyl)amino)bicyclo[2.2.2]octane-1-carboxylic acid

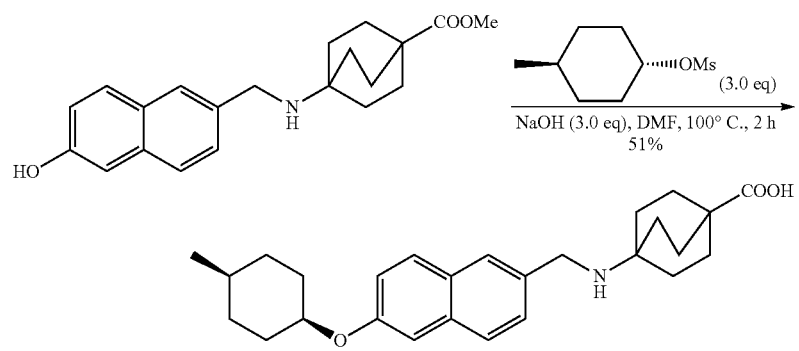

The preparation of 4-(((6-((cis-4-methylcyclohexyl)oxy)naphthalen-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 64 mg, white solid, yield: 51% in two steps. ESI-MS (M+H)$^+$: 422.3. $^1$H NMR (500 MHz, $CD_3OD$) δ: 7.91 (s, 1H), 7.85 (d, J=8.5 Hz, 1H), 7.83 (d, J=9.5 Hz, 1H), 7.49 (dd, J=8.5, 2.0 Hz, 1H), 7.29 (d, J=2.0 Hz, 1H), 7.24 (dd, J=9.0, 2.5 Hz, 1H), 4.76-4.74 (m, 1H), 4.26 (s, 2H), 2.09-2.00 (m, 14H), 1.72-1.68 (m, 2H), 1.57-1.54 (m, 3H), 1.46-1.43 (m, 2H), 0.98 (d, J=6.5 Hz, 3H).

Example 14

4-(((6-((cis-4-ethylcyclohexyl)oxy)naphthalen-2-yl)methyl)amino)bicyclo[2.2.2]octane-1-carboxylic acid The preparation of 4-(((6-((cis-4-isopropylcyclohexyl)oxy)naphthalen-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 30 mg, white solid, yield: 23% in two steps. ESI-MS (M+H)+: 450.3. $^1$H NMR (400 MHz, CD$_3$OD) δ: 7.78 (s, 1H), 7.72 (d, J=8.4 Hz, 1H), 7.71 (d, J=9.2 Hz, 1H), 7.37 (dd, J=8.4, 1.6 Hz, 1H), 7.16 (d, J=2.0 Hz, 1H), 7.11 (dd, J=8.8, 2.4 Hz, 1H), 4.64-4.63 (m, 1H), 4.12 (s, 2H), 2.03-2.00 (m, 2H), 1.93-1.87 (m, 12H), 1.52-1.38 (m, 7H), 1.12-1.05 (m, 1H), 0.82 (d, J=6.8 Hz, 6H).

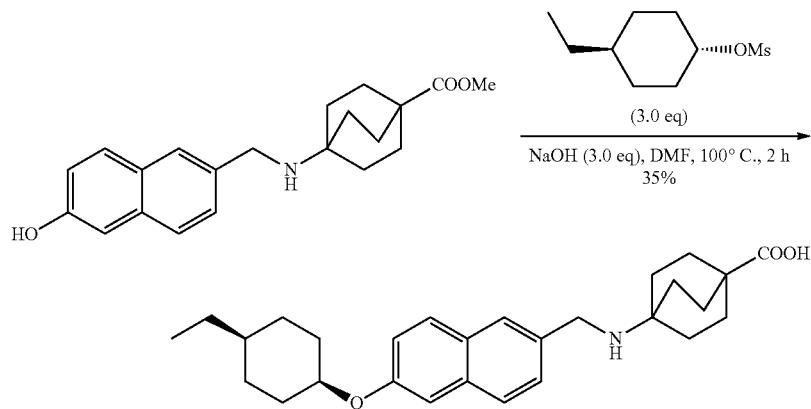

The preparation of 4-(((6-((cis-4-ethylcyclohexyl)oxy)naphthalen-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 45 mg, white solid, yield: 35% in two steps. ESI-MS (M+H)+: 436.2. $^1$H NMR (400 MHz, CD$_3$OD) δ: 7.89 (s, 1H), 7.84 (d, J=8.4 Hz, 1H), 7.82 (d, J=9.2 Hz, 1H), 7.48 (dd, J=8.4, 1.6 Hz, 1H), 7.28 (d, J=1.6 Hz, 1H), 7.23 (dd, J=8.8, 2.0 Hz, 1H), 4.77-4.73 (m, 1H), 4.25 (s, 2H), 2.10-1.99 (m, 14H), 1.67-1.59 (m, 4H), 1.44-1.30 (m, 5H), 0.94 (t, J=7.2 Hz, 3H).

Example 15

4-(((6-((cis-4-isopropylcyclohexyl)oxy)naphthalen-2-yl)methyl)amino)bicyclo[2.2.2]octane-carboxylic Acid

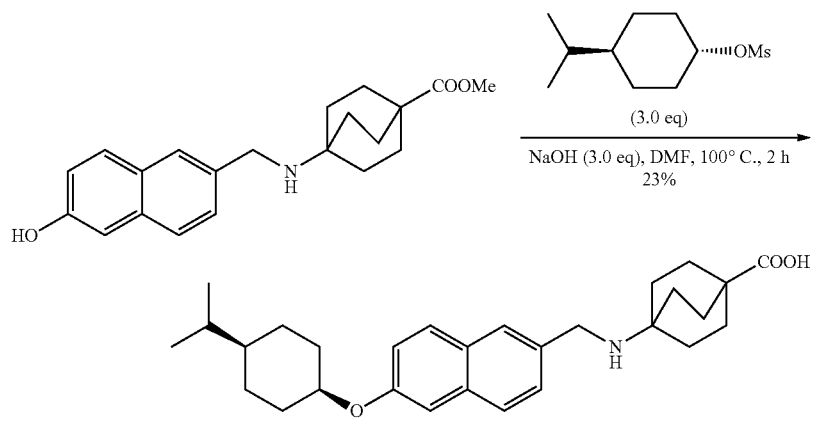

Example 16

4-(((6-((cis-4-(trifluoromethyl)cyclohexyl)oxy)naphthalen-2-yl)methyl)amino)bicyclo[2.2.2]octane-1-carboxylic acid

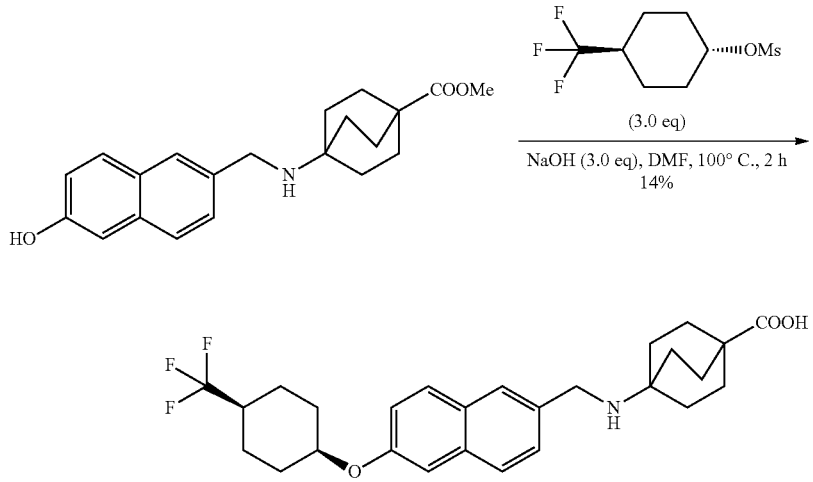

The preparation of 4-(((6-((cis-4-(trifluoromethyl)cyclohexyl)oxy)naphthalen-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 20 mg, white solid, yield: 14% in two steps. ESI-MS (M+H)$^+$: 476.3. $^1$H NMR (400 MHz, CD$_3$OD) δ: 7.80 (s, 1H), 7.74 (d, J=8.4 Hz, 1H), 7.73 (d, J=9.2 Hz, 1H), 7.39 (dd, J=8.4, 2.4 Hz, 1H), 7.20 (d, J=2.4 Hz, 1H), 7.14 (dd, J=8.8, 2.4 Hz, 1H), 4.72-4.70 (m, 1H), 4.13 (s, 2H), 2.13-2.08 (m, 3H), 1.93-1.88 (m, 12H), 1.67-1.65 (m, 6H).

Example 17

4-(((6-((cis-4-phenylcyclohexyl)oxy)naphthalen-2-yl)methyl)amino)bicyclo[2.2.2]octane-1-carboxylic acid

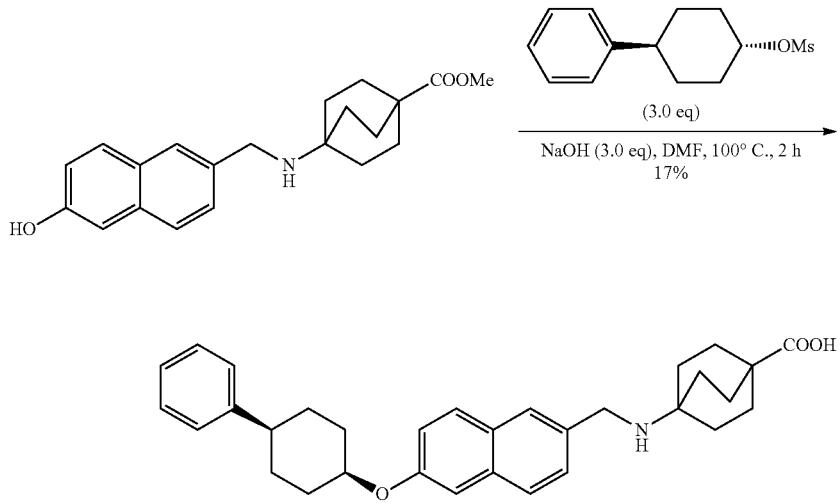 [SMILES: COC(=O)C12CCC(NCc3ccc4cc(O)ccc4c3)(CC1)CC2 ; CS(=O)(=O)O[C@H]1CC[C@H](c2ccccc2)CC1 ; O=C(O)C12CCC(NCc3ccc4cc(O[C@H]5CC[C@@H](c6ccccc6)CC5)ccc4c3)(CC1)CC2]

The preparation of 4-(((6-((cis-4-phenylcyclohexyl)oxy)naphthalen-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 24 mg, white solid, yield: 17% in two steps. ESI-MS (M+H)$^+$: 484.3. $^1$H NMR (400 MHz, CD$_3$OD) δ: 7.91 (s, 1H), 7.85 (d, J=8.0 Hz, 1H), 7.84 (d, J=9.2 Hz, 1H), 7.50 (dd, J=8.4, 1.2 Hz, 1H), 7.34-7.17 (m, 6H), 7.16-7.14 (m, 1H), 4.86-4.84 (m, 1H), 4.23 (s, 2H), 2.79-2.51 (m, 1H), 2.25-2.22 (m, 2H), 2.01-1.93 (m, 14H), 1.84-1.69 (m, 4H).

Example 18

4-(((6-((trans-4-(trifluoromethyl)cyclohexyl)oxy)naphthalen-2-yl)methyl)amino)bicyclo[2.2.2]octane-1-carboxylic acid

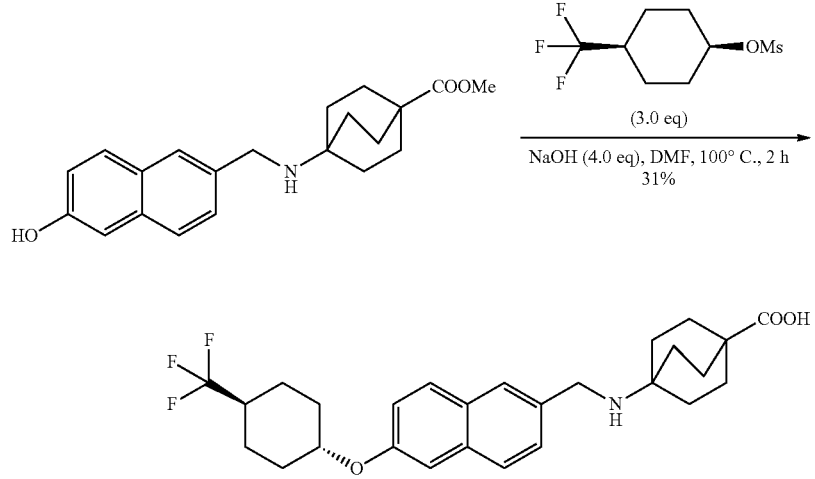

The preparation of 4-(((6-((trans-4-(trifluoromethyl)cyclohexyl)oxy)naphthalen-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 42 mg, white solid, yield: 31% in two steps. ESI-MS (M+H)+: 476.3. 1H NMR (400 MHz, CD3OD) δ: 7.91 (s, 1H), 7.86 (d, J=8.0 Hz, 1H), 7.84 (d, J=8.8 Hz, 1H), 7.50 (dd, J=8.8, 1.6 Hz, 1H), 7.32 (d, J=2.4 Hz, 1H), 7.26 (dd, J=8.8, 2.4 Hz, 1H), 4.84-4.81 (m, 1H), 4.26 (s, 2H), 2.23-2.20 (m, 3H), 2.05-1.99 (m, 12H), 1.79-1.72 (m, 6H).

Example 19

4-(((6-((cis-4-(tert-butyl)cyclohexyl)oxy)naphthalen-2-yl)methyl)amino)bicyclo[2.2.2]octane-1-carboxylic acid

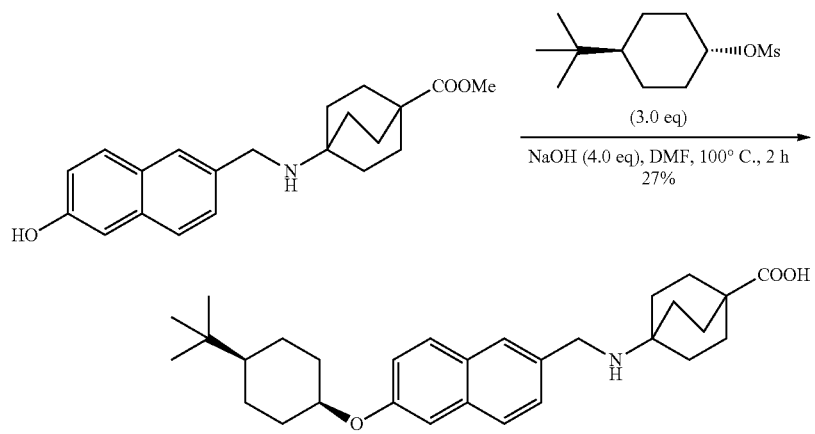

The preparation of 4-(((6-((cis-4-(tert-butyl)cyclohexyl)oxy)naphthalen-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 37 mg, white solid, yield: 27% in two steps. ESI-MS (M+H)+: 464.3. 1H NMR (400 MHz, CD3OD) δ: 7.90 (s, 1H), 7.83 (d, J=8.4 Hz, 1H), 7.82 (d, J=8.8 Hz, 1H), 7.49 (dd, J=8.4, 2.0 Hz, 1H), 7.27 (d, J=2.4 Hz, 1H), 7.23 (dd, J=8.8, 2.4 Hz, 1H), 4.76-4.74 (m, 1H), 4.22 (s, 2H), 2.19-2.16 (m, 2H), 2.04-1.98 (m, 12H), 1.63-1.50 (m, 6H), 1.18-1.13 (m, 1H), 0.92 (s, 9H).

Example 20

4-(((6-(cyclohexyloxy)quinolin-2-yl)methyl)amino)bicyclo[2.2.2]octane-1-carboxylic acid Step 1: Methyl 4-(((6-hydroxyquinolin-2-yl)methyl)amino)bicyclo[2.2.2]octane-1-carboxylate

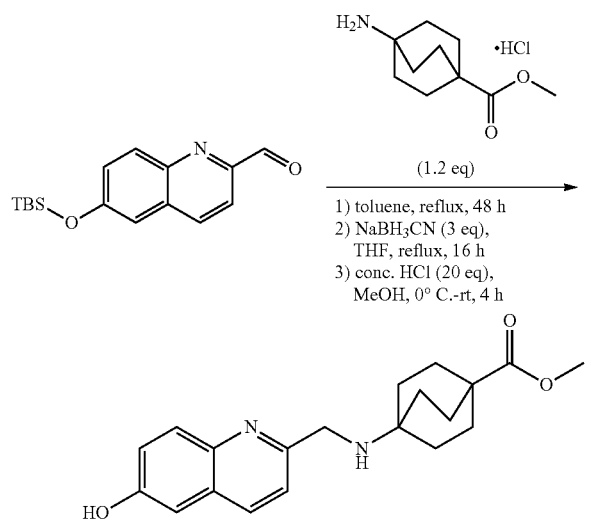

A mixture of 6-((tert-butyldimethylsilyl)oxy)quinoline-2-carbaldehyde (1 g, 3.48 mmol) and methyl 4-amino bicyclo[2.2.2]octane-1-carboxylate hydrochloride salt (766 mg, 4.18 mmol, 1.2 eq) in dry toluene (200 mL) was stirred at reflux for 48 h. Then the mixture was concentrated and the residue was dissolved in THF (150 mL), and NaBH$_3$CN (658 mg, 10.44 mmol, 3 eq) was added. The reaction mixture was stirred at reflux for 16 h. After concentration, EA (200 mL) was added and the mixture was washed with H$_2$O (100 mL×2). The organic phase was dried and concentrated to give methyl 4-(((6-((tert-butyldimethylsilyl)oxy)quinolin-2-yl)methyl)amino)bicyclo[2.2.2]octane-1-carboxylate as yellow solid (crude 1.5 g), which was used for the next step without further purification. ESI-MS (M+H)$^+$: 455.2.

To a solution of crude methyl 4-(((6-((tert-butyldimethylsilyl)oxy)quinolin-2-yl)methyl)amino)bicyclo[2.2.2]octane-1-carboxylate (1.5 g, 3.3 mmol) in MeOH (100 mL) was added conc. HCl (5.5 mL, 12 M, 20 eq) slowly at 0° C. Then the reaction mixture was stirred at room temperature for 4 h. The mixture was adjusted to pH=8 with sat. NaHCO$_3$ and concentrated. The residue was extracted with EA (200 mL) and washed with H$_2$O (200 mL×2). The organic phase was dried and concentrated to give methyl 4-(((6-hydroxyquinolin-2-yl)methyl)amino)bicyclo[2.2.2]octane-1-carboxylate as yellow solid (940 mg, yield: 80% in two steps). ESI-MS (M+H)$^+$: 341.2. $^1$H NMR (400 MHz, CDCl$_3$) δ: 7.65 (d, J=9.2 Hz, 1H), 7.30 (d, J=8.4 Hz, 1H), 7.07 (dd, J=8.8, 2.4 Hz, 1H), 7.02 (d, J=8.8 Hz, 1H), 6.37 (d, J=2.4 Hz, 1H), 3.93 (s, 2H), 3.66 (s, 3H), 1.96-1.92 (m, 6H), 1.83-1.79 (m, 6H).

Step 2: 4-(((6-(cyclohexyloxy)quinolin-2-yl)methyl)amino)bicyclo[2.2.2]octane-1-carboxylic acid

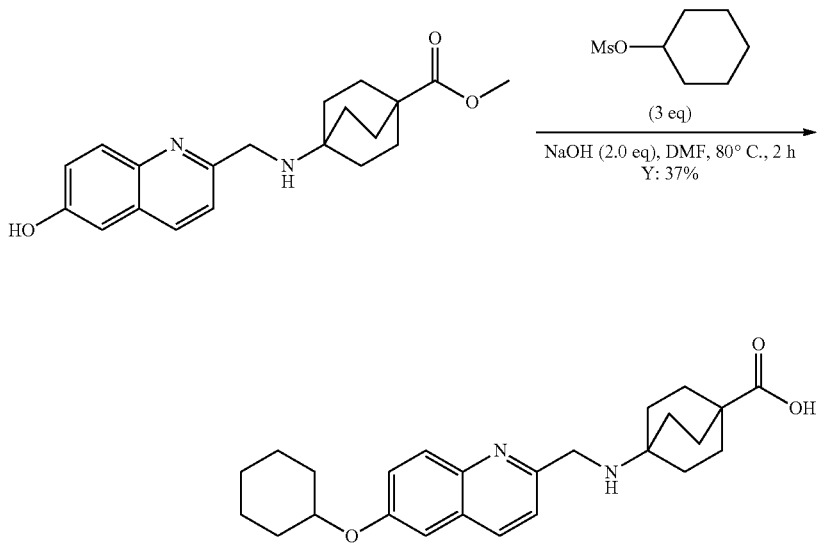

The preparation of 4-(((6-(cyclohexyloxy)quinolin-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 40 mg, a yellow solid, yield: 37%. ESI-MS (M+H)$^+$: 409.2, HPLC: 100%. $^1$H NMR (400 MHz, CD$_3$OD) δ: 8.26 (d, J=8.4 Hz, 1H), 8.00 (d, J=9.2 Hz, 1H), 7.46 (d, J=8.8 Hz, 1H), 7.43 (dd, J=9.2, 2.4 Hz, 1H), 7.31 (d, J=2.4 Hz, 1H), 4.54-4.52 (m, 1H), 4.47 (s, 2H), 2.09-2.03 (m, 14H), 1.86-1.83 (m, 2H), 1.65-1.46 (m, 6H).

Example 21

4-(((6-((trans-4-methylcyclohexyl)oxy)quinolin-2-yl)methyl)amino)bicyclo[2.2.2]octane-1-carboxylic acid

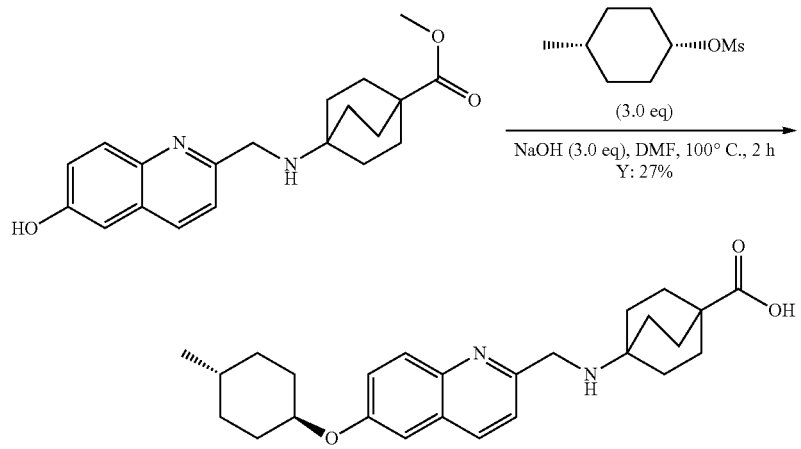

The preparation of 4-(((6-((trans-4-methylcyclohexyl)oxy)quinolin-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 34 mg, a white solid, yield: 27%. ESI-MS (M+H)$^+$: 423.3, HPLC: 100%. $^1$H NMR (400 MHz, CD$_3$OD) δ: 8.26 (d, J=8.4 Hz, 1H), 8.00 (d, J=9.2 Hz, 1H), 7.48 (d, J=8.4 Hz, 1H), 7.40 (dd, J=9.2, 2.8 Hz, 1H), 7.31 (d, J=2.4 Hz, 1H), 4.47 (s, 2H), 4.44-4.40 (m, 1H), 2.22-2.20 (m, 2H), 2.04-2.00 (m, 12H), 1.84-1.81 (m, 2H), 1.50-1.44 (m, 3H), 1.20-1.17 (m, 2H), 0.96 (d, J=6.4 Hz, 3H).

Example 22

4-(((6-((trans-4-ethylcyclohexyl)oxy)quinolin-2-yl)methyl)amino)bicyclo[2.2.2]octane-1-carboxylic acid The preparation of 4-(((6-((trans-4-ethylcyclohexyl)oxy)quinolin-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 50 mg, a yellow solid, yield: 36%. ESI-MS (M+H)$^+$: 437.2, HPLC: 98.93%. $^1$H NMR (400 MHz, CD$_3$OD) δ: 8.26 (d, J=8.4 Hz, 1H), 8.00 (d, J=9.2 Hz, 1H), 7.46 (d, J=8.8 Hz, 1H), 7.41 (dd, J=9.2, 2.4 Hz, 1H), 7.32 (d, J=2.4 Hz, 1H), 4.47 (s, 2H), 4.45-4.40 (m, 1H), 2.25-2.22 (m, 2H), 2.06-2.00 (m, 12H), 1.93-1.90 (m, 2H), 1.53-1.49 (m, 2H), 1.35-1.27 (m, 3H), 1.20-1.10 (m, 2H), 0.95 (t, J=7.2 Hz, 3H).

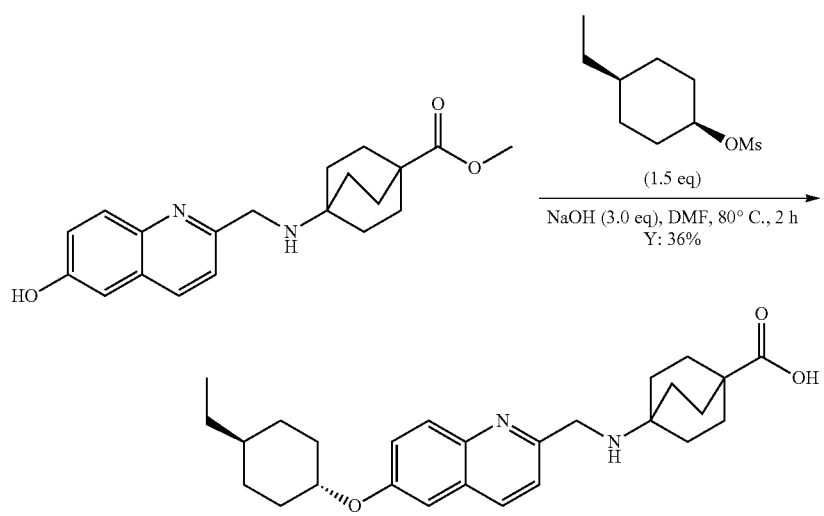

Example 23

4-(((6-((trans-4-isopropylcyclohexyl)oxy)quinolin-2-yl)methyl)amino)bicyclo[2.2.2]octane-1-carboxylic acid

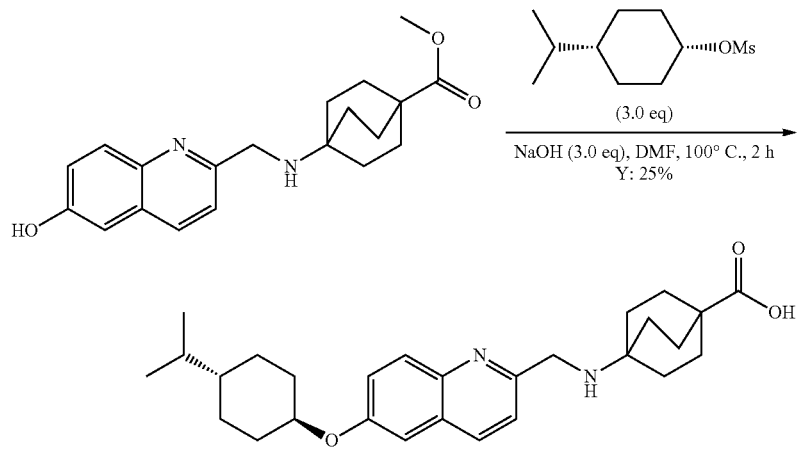

The preparation of 4-(((6-((trans-4-isopropylcyclohexyl)oxy)quinolin-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 34 mg, a white solid, yield: 25%. ESI-MS (M+H)+: 451.2, HPLC: 100%. 1H NMR (400 MHz, CD3OD) δ: 8.27 (d, J=8.8 Hz, 1H), 8.00 (d, J=8.8 Hz, 1H), 7.48 (d, J=8.8 Hz, 1H), 7.40 (dd, J=8.8, 2.8 Hz, 1H), 7.32 (d, J=2.8 Hz, 1H), 4.47 (s, 2H), 4.42-4.38 (m, 1H), 2.27-2.25 (m, 2H), 2.04-2.00 (m, 12H), 1.88-1.85 (m, 2H), 1.50-1.43 (m, 3H), 1.29-1.23 (m, 3H), 0.93 (d, J=6.4 Hz, 6H).

Example 24

4-(((6-((trans-4-(tert-pentyl)cyclohexyl)oxy)quinolin-2-yl)methyl)amino)bicyclo[2.2.2]octane-1-carboxylic acid The preparation of 4-(((6-((trans-4-(tert-pentyl)cyclohexyl)oxy)quinolin-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 24 mg, a yellow solid, yield: 16%. ESI-MS (M+H)+: 479.3, HPLC: 97.56%. 1H NMR (400 MHz, CD3OD) δ: 8.25 (d, J=8.4 Hz, 1H), 7.98 (d, J=8.8 Hz, 1H), 7.46 (d, J=8.8 Hz, 1H), 7.39 (dd, J=8.8, 2.4 Hz, 1H), 7.31 (d, J=2.8 Hz, 1H), 4.46 (s, 2H), 4.41-4.35 (m, 1H), 2.30-2.27 (m, 2H), 2.02-1.97 (m, 12H), 1.87-1.84 (m, 2H), 1.47-1.41 (m, 2H), 1.38-1.22 (m, 5H), 0.88-0.81 (m, 9H).

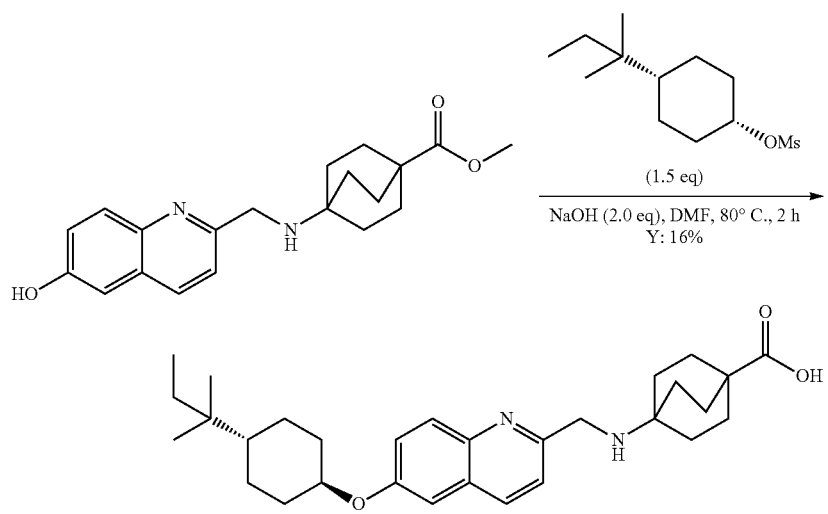

Example 25

4-(((6-((trans-4-phenylcyclohexyl)oxy)quinolin-2-yl)methyl)amino)bicyclo[2.2.2]octane-1-carboxylic acid

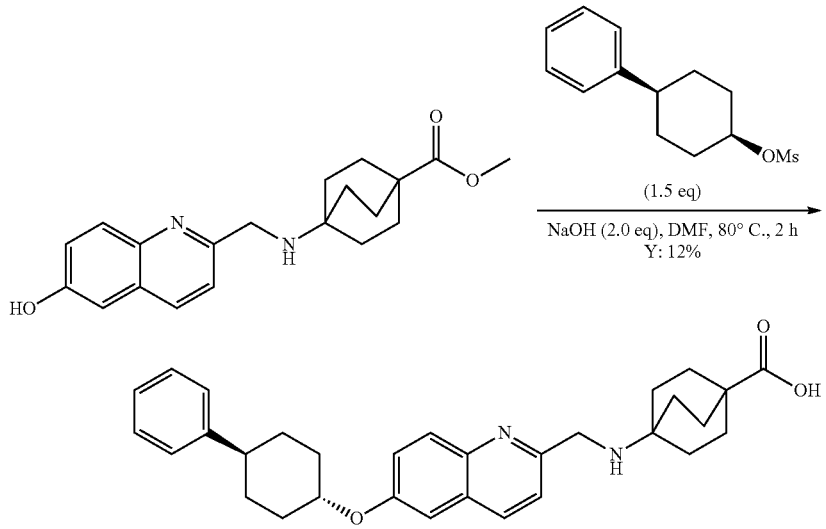

The preparation of 4-(((6-((trans-4-phenylcyclohexyl)oxy)quinolin-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 40 mg, a yellow solid, yield: 12%. ESI-MS (M+H)$^+$: 485.2, HPLC: 95.88%. $^1$H NMR (400 MHz, CD$_3$OD) δ: 8.26 (d, J=8.4 Hz, 1H), 8.01 (d, J=9.2 Hz, 1H), 7.49 (d, J=8.8 Hz, 1H), 7.43 (dd, J=8.8, 2.4 Hz, 1H), 7.37 (d, J=2.8 Hz, 1H), 7.30-7.24 (m, 4H), 7.19-7.14 (m, 1H), 4.58-4.51 (m, 1H), 4.38 (s, 2H), 2.63-2.56 (m, 1H), 2.35-2.32 (m, 2H), 1.98-1.93 (m, 14H), 1.78-1.57 (m, 4H).

The preparation of 4-(((6-((4,4-dimethylcyclohexyl)oxy)quinolin-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 50 mg, a yellow solid, yield: 42%. ESI-MS (M+H)$^+$: 437.3, HPLC: 100%. $^1$H NMR (400 MHz, CD$_3$OD) δ: 8.21 (d, J=8.4 Hz, 1H), 8.00 (d, J=8.8 Hz, 1H), 7.46 (d, J=8.8 Hz, 1H), 7.43 (dd, J=9.2, 2.8 Hz, 1H), 7.32 (d, J=2.4 Hz, 1H), 4.53-4.50 (m, 1H), 4.47 (s, 2H), 2.03-1.95 (m, 14H), 1.78-1.75 (m, 2H), 1.60-1.55 (m, 2H), 1.42-1.37 (m, 2H), 1.00 (s, 3H), 0.97 (s, 3H).

Example 26

4-(((6-((4,4-dimethylcyclohexyl)oxy)quinolin-2-yl)methyl)amino)bicyclo[2.2.2]octane-1-carboxylic acid

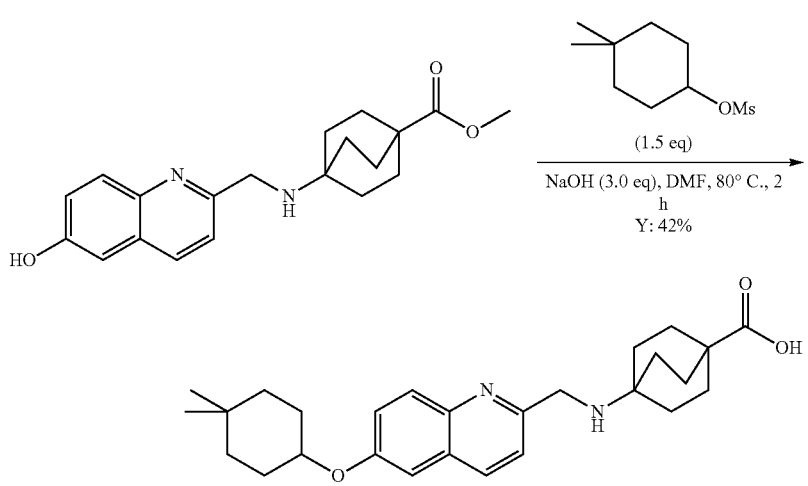

Example 27

4-(((6-(spiro[2.5]octan-6-yloxy)quinolin-2-yl)methyl)amino)bicyclo[2.2.2]octane-1-carboxylic acid

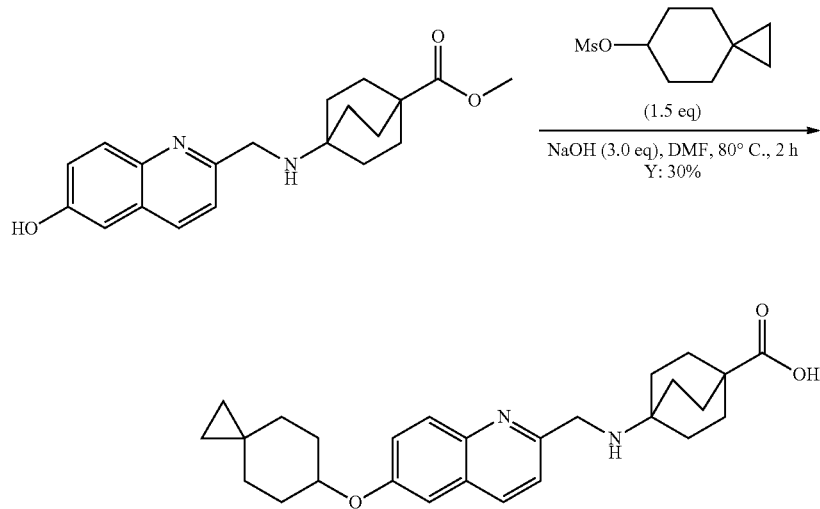 [SMILES: COC(=O)C12CCC(NCc3ccc4cc(O)ccc4n3)(CC1)CC2 ; CS(=O)(=O)OC1CCC2(CC1)CC2 ; O=C(O)C12CCC(NCc3ccc4cc(OC5CCC6(CC5)CC6)ccc4n3)(CC1)CC2]

The preparation of 4-(((6-(spiro[2.5]octan-6-yloxy)quinolin-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 20 mg, a white solid, yield: 30%. ESI-MS (M+H)$^+$: 435.0, HPLC: 100%. $^1$H NMR (400 MHz, CD$_3$OD) δ: 8.26 (d, J=8.8 Hz, 1H), 8.00 (d, J=9.6 Hz, 1H), 7.46 (d, J=8.8 Hz, 1H), 7.45 (dd, J=9.2, 2.0 Hz, 1H), 7.35 (d, J=2.0 Hz, 1H), 4.65-4.61 (m, 1H), 4.47 (s, 2H), 2.04-2.01 (m, 14H), 1.83-1.75 (m, 2H), 1.60-1.55 (m, 2H), 1.43-1.39 (m, 2H), 0.37-0.30 (m, 4H).

Example 28

4-(((6-(spiro[3.5]nonan-7-yloxy)quinolin-2-yl)methyl)amino)bicyclo[2.2.2]octane-1-carboxylic acid The preparation of 4-(((6-(spiro[3.5]nonan-7-yloxy)quinolin-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 80 mg, a yellow solid, yield: 43%. ESI-MS (M+H)$^+$: 449.2, HPLC: 99.68%. $^1$H NMR (400 MHz, CD$_3$OD) δ: 8.26 (d, J=8.8 Hz, 1H), 8.00 (d, J=8.8 Hz, 1H), 7.46 (d, J=8.4 Hz, 1H), 7.42 (dd, J=8.8, 2.8 Hz, 1H), 7.35 (d, J=2.8 Hz, 1H), 4.51-4.49 (m, 1H), 4.47 (s, 2H), 2.03-2.01 (m, 12H), 1.98-1.80 (m, 10H), 1.65-1.50 (m, 4H).

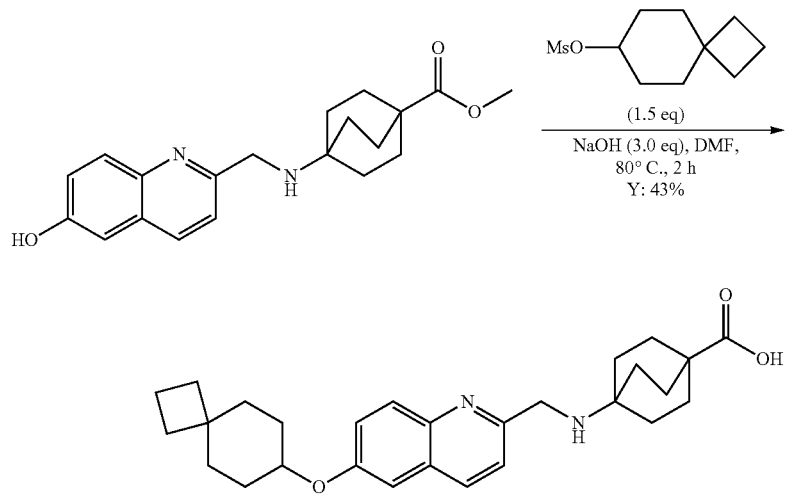

Example 29

4-(((6-(spiro[4.5]decan-8-yloxy)quinolin-2-yl)methyl)amino)bicyclo[2.2.2]octane-1-carboxylic acid

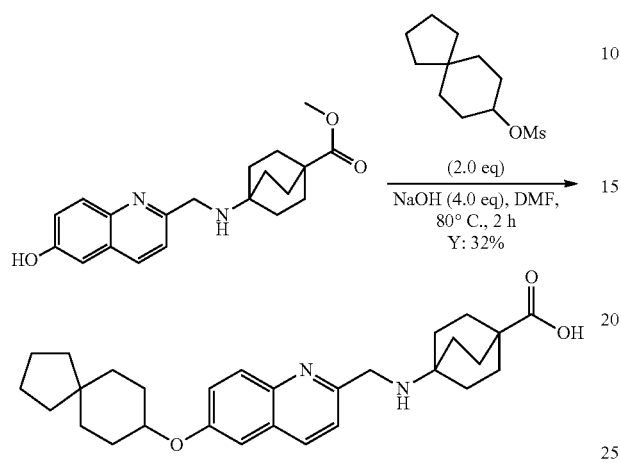

The preparation of 4-(((6-(spiro[4.5]decan-8-yloxy)quinolin-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 44 mg, a white solid, yield: 32%. ESI-MS (M+H)$^+$: 463.2, HPLC: 100.00%. $^1$H NMR (400 MHz, CD$_3$OD) δ: 8.26 (d, J=8.4 Hz, 1H), 8.00 (d, J=9.2 Hz, 1H), 7.46 (d, J=8.4 Hz, 1H), 7.43 (dd, J=8.8, 2.4 Hz, 1H), 7.32 (d, J=2.4 Hz, 1H), 4.57-4.51 (m, 1H), 4.47 (s, 2H), 2.04-2.02 (m, 14H), 1.65-1.72 (m, 8H), 1.46-1.54 (m, 6H).

Example 30

4-(((6-(spiro[5.5]undecan-3-yloxy)quinolin-2-yl)methyl)amino)bicyclo[2.2.2]octane-1-carboxylic acid

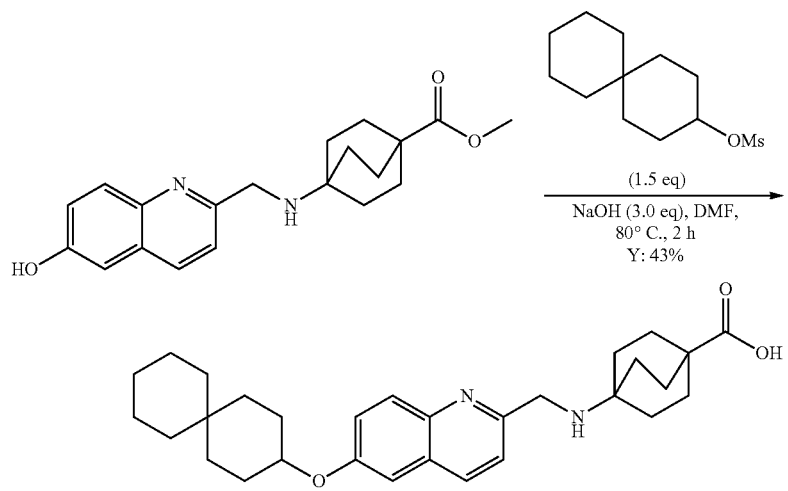

The preparation of 4-(((6-(spiro[5.5]undecan-3-yloxy)quinolin-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 60 mg, a yellow solid, yield: 43%. ESI-MS (M+H)$^+$: 477.3, HPLC: 100%. $^1$H NMR (400 MHz, CD$_3$OD) δ: 8.25 (d, J=8.4 Hz, 1H), 8.00 (d, J=9.2 Hz, 1H), 7.46 (d, J=8.4 Hz, 1H), 7.43 (dd, J=8.8, 2.4 Hz, 1H), 7.31 (d, J=2.8 Hz, 1H), 4.54-4.31 (m, 1H), 4.47 (s, 2H), 2.02-1.92 (m, 14H), 1.77-1.68 (m, 4H), 1.50-1.46 (m, 8H), 1.38-1.30 (m, 4H).

Example 31

4-(((6-(heptyloxy)naphthalen-2-yl)methyl)amino)bicyclo[2.2.2]octane-1-carboxylate

Step 1: methyl 4-(((6-(heptyloxy)quinolin-2-yl)methyl)amino)bicyclo[2.2.2]octane-1-carboxylate

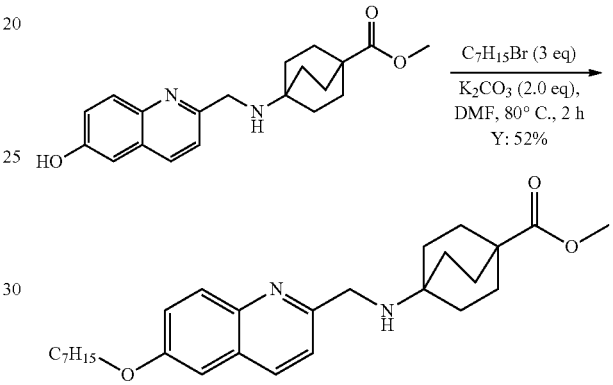

The preparation of methyl 4-(((6-(heptyloxy)quinolin-2-yl)methyl)amino)bicyclo[2.2.2]octane-1-carboxylate was the same as that of methyl 4-(((6-(heptyloxy)naphthalen-2-yl)methyl)amino)bicyclo[2.2.2]octane-1-carboxylate. 60 mg, a yellow solid, yield: 52%. ESI-MS (M+H)$^+$: 439.3. $^1$H NMR (400 MHz, CDCl$_3$) δ: 8.08 (d, J=8.4 Hz, 1H), 7.90 (d, J=9.6 Hz, 1H), 7.41 (dd, J=9.2, 2.4 Hz, 1H), 7.31 (d, J=8.4 Hz, 1H), 7.07 (d, J=2.4 Hz, 1H), 4.52 (s, 2H), 4.06 (t, J=6.8 Hz, 2H), 3.66 (s, 3H), 1.98-1.94 (m, 12H), 1.88-1.83 (m, 2H), 1.52-1.48 (m, 2H), 1.41-1.31 (m, 6H), 0.91 (t, J=6.8 Hz, 3H).

Step 2: 4-(((6-(heptyloxy)naphthalen-2-yl)methyl)amino)bicyclo[2.2.2]octane-1-carboxylate

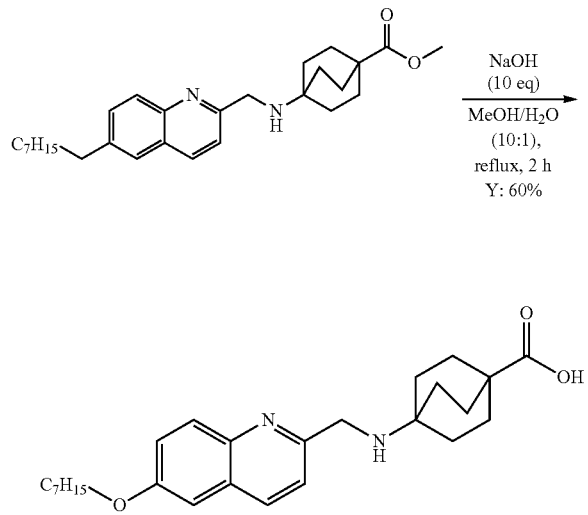

The preparation of 4-(((6-(heptyloxy)naphthalen-2-yl)methyl)amino)bicyclo[2.2.2]octane-1-carboxylate was the same as that of 4-(((6-(cyclohexyloxy)naphthalen-2-yl)methyl)amino)bicyclo[2.2.2]octane-1-carboxylic acid. 35 mg, a yellow solid, yield: 60%. ESI-MS (M+H)+: 425.3, HPLC: 95.53%. $^1$H NMR (400 MHz, CD$_3$OD) δ: 8.27 (d, J=8.4 Hz, 1H), 8.00 (d, J=9.2 Hz, 1H), 7.48 (d, J=8.8 Hz, 1H), 7.44 (dd, J=9.2, 2.8 Hz, 1H), 7.30 (d, J=2.8 Hz, 1H), 4.48 (s, 2H), 4.13 (t, J=6.4 Hz, 2H), 2.04-1.98 (m, 12H), 1.88-1.83 (m, 2H), 1.56-1.50 (m, 2H), 1.44-1.33 (m, 6H), 0.93 (t, J=6.8 Hz, 3H).

Example 32

4-(((6-((cis-4-methylcyclohexyl)oxy)quinolin-2-yl)methyl)amino)bicyclo[2.2.2]octane-1-carboxylic acid

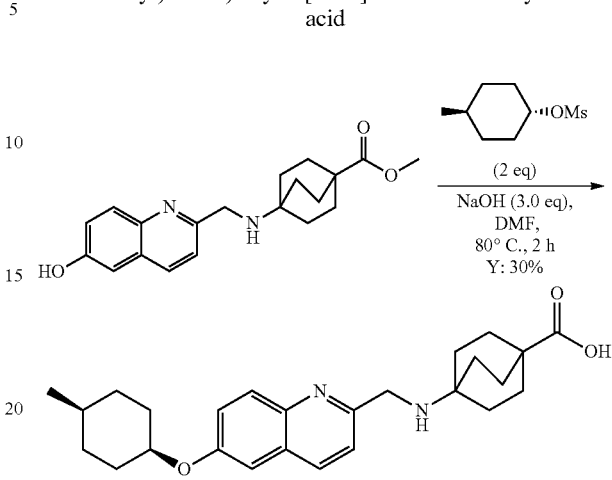

The preparation of 4-(((6-((cis-4-methylcyclohexyl)oxy)quinolin-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 50 mg, a yellow solid, yield: 30%. ESI-MS (M+H)+: 423.3, HPLC: 100%. $^1$H NMR (400 MHz, CD$_3$OD) δ: 8.23 (d, J=8.4 Hz, 1H), 8.00 (d, J=9.2 Hz, 1H), 7.47 (d, J=8.8 Hz, 1H), 7.45 (dd, J=9.6, 2.8 Hz, 1H), 7.31 (d, J=2.4 Hz, 1H), 4.77-4.73 (m, 1H), 4.42 (s, 2H), 2.09-1.97 (m, 14H), 1.69-1.64 (m, 2H), 1.57-1.53 (m, 3H), 1.45-1.41 (m, 2H), 0.96 (d, J=6.0 Hz, 3H).

Example 33

4-(((6-((cis-4-ethylcyclohexyl)oxy)quinolin-2-yl)methyl)amino)bicyclo[2.2.2]octane-1-carboxylic acid

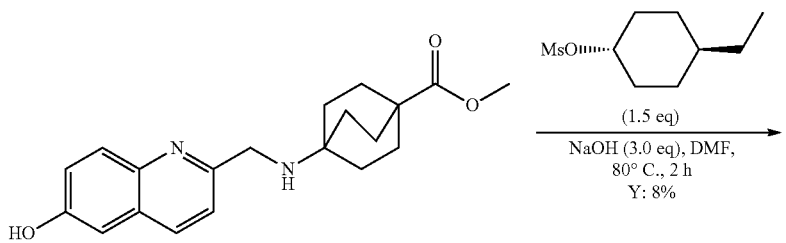

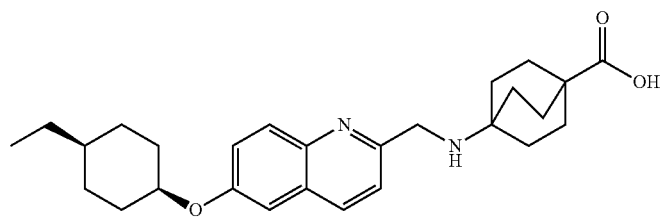

The preparation of 4-(((6-((cis-4-ethylcyclohexyl)oxy)quinolin-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 10 mg, a yellow solid, yield: 8%. ESI-MS (M+H)⁺: 436.9, HPLC: 100%. ¹H NMR (400 MHz, CD₃OD) δ: 8.24 (d, J=8.4 Hz, 1H), 8.01 (d, J=9.2 Hz, 1H), 7.46 (d, J=8.4 Hz, 1H), 7.45 (dd, J=9.2, 2.8 Hz, 1H), 7.31 (d, J=2.4 Hz, 1H), 4.77-4.75 (m, 1H), 4.40 (s, 2H), 2.11-2.06 (m, 2H), 2.01-1.99 (m, 12H), 1.72-1.60 (m, 4H), 1.47-1.39 (m, 2H), 1.34-1.30 (m, 3H), 0.95 (t, J=6.8 Hz, 3H).

Example 34

4-(((6-((cis-4-isopropylcyclohexyl)oxy)quinolin-2-yl)methyl)amino)bicyclo[2.2.2]octane-1-carboxylic acid

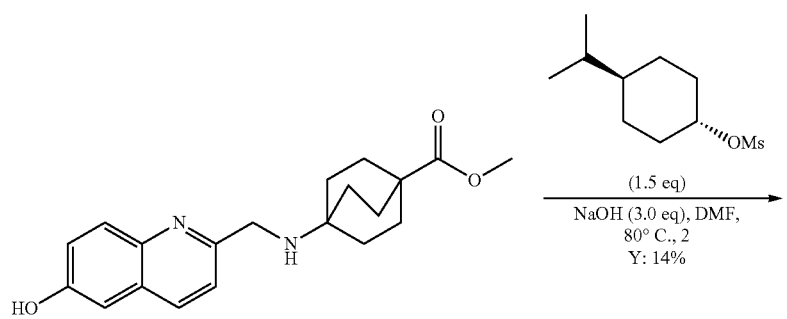

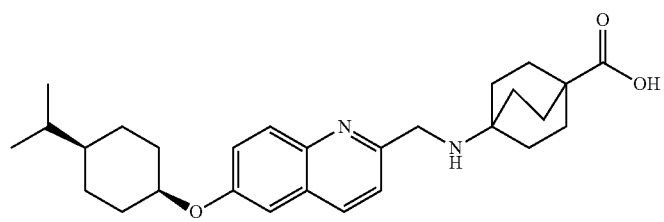

The preparation of 4-(((6-((cis-4-isopropylcyclohexyl)oxy)quinolin-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 35 mg, a yellow solid, yield: 60%. ESI-MS (M+H)⁺: 451.3, HPLC: 100%. ¹H NMR (400 MHz, CD₃OD) δ: 8.24 (d, J=8.8 Hz, 1H), 8.01 (d, J=9.2 Hz, 1H), 7.47-7.44 (m, 2H), 7.31 (d, J=2.8 Hz, 1H), 4.78-4.76 (m, 1H), 4.46 (s, 2H), 2.15-2.11 (m, 2H), 2.03-1.98 (m, 12H), 1.69-1.46 (m, 7H), 1.25-1.17 (m, 1H), 0.93 (d, J=6.8 Hz, 6H).

Example 35

4-(((6-((cis-4-(trifluoromethyl)cyclohexyl)oxy)quinolin-2-yl)methyl)amino)bicyclo[2.2.2]octane-1-carboxylic acid

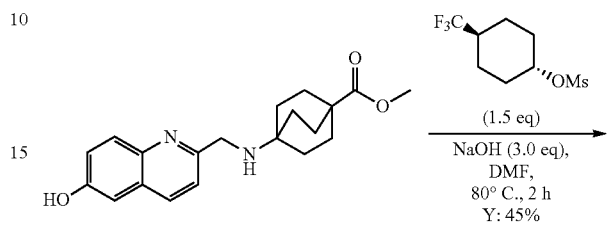

-continued

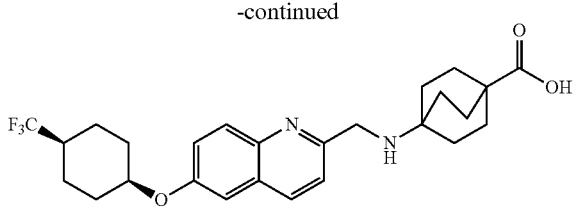

The preparation of 4-(((6-((cis-4-(trifluoromethyl)cyclohexyl)oxy)quinolin-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 70 mg, a yellow solid, yield: 60%. ESI-MS (M+H)⁺: 477.2, HPLC: 100%. ¹H NMR (400 MHz, CD₃OD) δ: 8.26 (d, J=8.8 Hz, 1H), 8.03

(d, J=9.2 Hz, 1H), 7.50-7.47 (m, 2H), 7.35 (d, J=2.8 Hz, 1H), 4.86-4.83 (m, 1H), 4.48 (s, 2H), 2.28-2.20 (m, 3H), 2.04-2.00 (m, 12H), 1.81-1.71 (m, 6H).

Example 36

4-(((6-((cis-4-phenylcyclohexyl)oxy)quinolin-2-yl)methyl)amino)bicyclo[2.2.2]octane-1-carboxylic acid

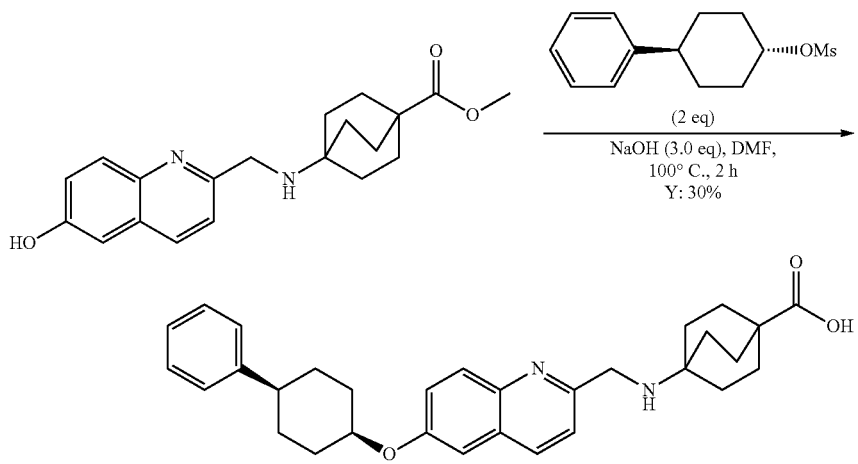

The preparation of 4-(((6-((cis-4-phenylcyclohexyl)oxy)quinolin-2-yl)methyl)amino)bicyclo[2.2.2]octane-1-carboxylic acid was the same as that of 4-(((6-(cyclohexyloxy)naphthalen-2-yl)methyl)amino)bicyclo[2.2.2]octane-1-carboxylic acid. 50 mg, a yellow solid, yield: 30%. ESI-MS (M+H)+: 485.2, HPLC: 97.27%. $^1$H NMR (400 MHz, CD$_3$OD) δ: 8.23 (d, J=8.8 Hz, 1H), 8.02 (d, J=9.2 Hz, 1H), 7.52 (dd, J=9.2, 2.8 Hz, 1H), 7.47 (d, J=8.4 Hz, 1H), 7.36 (d, J=2.4 Hz, 1H), 7.30-7.25 (m, 4H), 7.18-7.16 (m, 1H), 4.86-4.84 (m, 1H), 4.34 (s, 2H), 2.69-2.63 (m, 1H), 2.26-2.23 (m, 2H), 1.99-1.79 (m, 16H), 1.73-1.70 (m, 2H).

Example 37

4-(((6-((trans-4-(tert-butyl)cyclohexyl)oxy)-5-(trifluoromethyl)naphthalen-2-yl)methyl)amino)bicyclo[2.2.2]octane-1-carboxylic acid Step 1: cis-4-tert-Butylcyclohexyl methanesulfonate

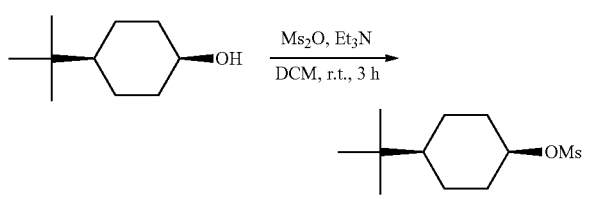

Cis-4-t-butylcyclohexanol (6.0 g, 38.5 mmol, 1.0 eq.) was dissolved in dichloromethane (10 mL). Then methanesulfonic anhydride (8.03 g, 46.2 mmol, 1.1 eq.) was added to the mixture slowly at 0° C. Then triethylamine (6.4 mL, 46.2 mmol, 1.5 eq.) was added to the mixture and the mixture stirred at room temperature for 3 h. The mixture was extracted with dichloromethane and the organic layer was concentrated to give product as a white power (8.0 g, yield: 90%). The product was used to next step without further purification. $^1$H NMR (400 MHz, CDCl$_3$) δ 4.99-4.98 (m, 1H), 3.02 (s, 3H), 2.14-2.12 (m, 2H), 1.65-1.28 (m, 7H), 0.84 (s, 9H).

Step 2: 2-Bromo-6-(trans-4-tert-butylcyclohexyloxy)naphthalene

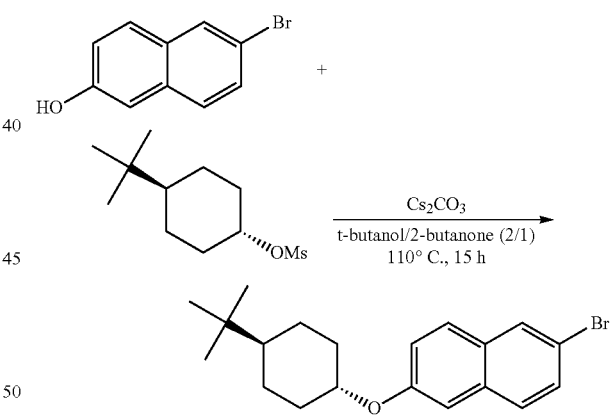

6-bromonaphthalen-2-ol (CAS no. 15231-91-1) (3.0 g, 14.8 mmol, 1.0 eq.) was dissolved in a mixture of t-butanol/2-butanone (4 mL/2 mL). Then cesium carbonate (12 g, 37.2 mmol, 2.5 eq.) was added to the mixture and the mixture was stirred at 110° C. for 10 min. Then trans-4-tert-butylcyclohexyl methanesulfonate (3.48 g, 16.2 mmol, 1.1 eq.) was added to the mixture. The suspension was stirred at 110° C. under a nitrogen atmosphere for 15 h. The reaction mixture was extracted with ethyl acetate and the organic layer was purified by silica gel column chromatography using petroleum ether as eluent to give 2-bromo-6-(trans-4-tert-butylcyclohexyloxy)naphthalene as a slight yellow solid (1.7 g, yield: 32%). ESI-MS: 361.0 (M+H)+. $^1$H NMR (400 MHz, CDCl$_3$) δ 7.89 (s, 1H), 7.63 (d, 1H), 7.56 (d, 1H), 7.47 (d, 1H), 7.15-7.11 (m, 2H), 4.26-4.24 (m, 1H), 2.27-2.25 (m, 2H), 1.89-1.87 (m, 2H), 1.45-1.09 (m, 5H), 0.89 (s, 9H).

Step 3: 6-(trans-4-tert-Butylcyclohexyloxy)-2-naphthaldehyde

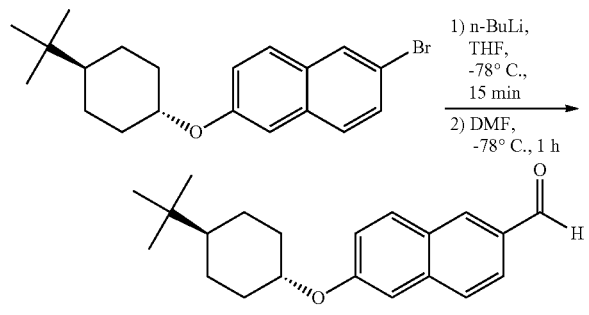

2-bromo-6-(trans-4-tert-butylcyclohexyloxy)naphthalene (2.249 g, 6.25 mmol, 1.0 eq.) was dissolved in THF (10 mL) under nitrogen atmosphere. Then the mixture was cooled down to −78° C. and a solution of n-BuLi in THF (2.5 M, 7.5 mL, 18.8 mmol, 3.0 eq.) was added to the mixture dropwise. The mixture was stirred at −78° C. for 15 min. Then DMF (2.4 mL, 31.2 mmol, 5.0 eq.) was added to the mixture and stirred at −78° C. for 1 h. When the reaction completed, 1 M HCl was added to adjust the pH to 6. The mixture was extracted with EtOAc and the organic layer was concentrated and purified by silica gel chromatography using petroleum ether/ethyl acetate (10/1) as eluent to give 6-(trans-4-tert-butylcyclohexyloxy)-2-naphthaldehyde as a white solid (1.16 g, 60%). EDI-MS: 311.1 (M+H)$^+$. $^1$H NMR (400 MHz, CDCl$_3$) δ 10.08 (s, 1H), 8.24 (s, 1H), 7.92-7.87 (m, 2H), 7.77 (d, 1H), 7.22-7.19 (m, 2H), 4.42-4.30 (m, 1H), 2.30-2.28 (m, 2H), 1.93-1.90 (m, 2H), 1.48-1.11 (m, 5H), 0.82 (s, 9H).

Step 4: 6-Bromo-2-(trans-4-tert-butylcyclohexyloxy)-1-iodonaphthalene

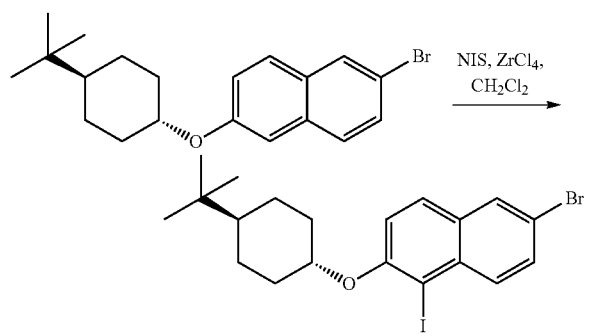

A solution of 2-bromo-6-(trans-4-tert-butylcyclohexyloxy)naphthalene
(160.0 g, 444.4 mmol) in methylene chloride (2.5 L) was purged under an atmosphere of argon. N-iodosuccinimide (202.1 g, 888.8 mmol) and zirconium tetrachloride (20.4 g, 88.9 mmol) was added and the reaction was stirred at room temperature under an atmosphere of argon. The reaction was monitored by $^1$H NMR and showed complete conversion to product after 30 minutes. The mixture was then concentrated under reduced pressure to give ~250 g crude as a brown solid. The crude material was purified by silica gel chromatography with hexanes to give 200 g of desired product as a brown solid (yield: 92.6%). EDI-MS: 487.1 (M+H)+.

Step 5: 6-Bromo-2-(trans-4-tert-butylcyclohexyloxy)-1-(trifluoromethyl)naphthalene

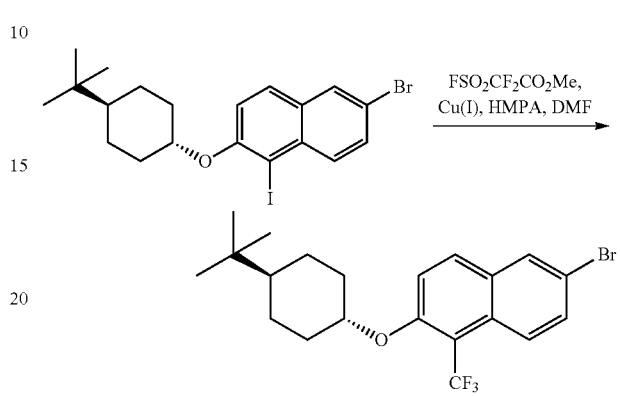

A solution of 6-bromo-2-(trans-4-tert-butylcyclohexyloxy)-1-iodonaphthalene
(210.0 g, 433 mmol), hexamethylphosphoramide (386.4 g, 2.16 mol; 5 eq) in N,N-dimethylformamide (2.0 L) was degassed by stirring under vacuum and replacing the vacuum with argon (4 times). To this mixture was added copper(I) iodide (140.0 g, 735 mmol; 1.7 eq) and methyl fluorosulphonyldifluoroacetate (415 g, 2.16 mol; 5 eq). The reaction mixture was warmed to 80° C. under an atmosphere of argon. After stirring for 6 hrs, thin layer chromatography showed complete conversion to product. Saturated NaHCO$_3$ solution was added to adjust the final pH to 9-10 followed by adding EtOAc (3.5 L). The mixture was extracted with EtOAc (2.5 L×3), and washed with brine (1.0 L×4), then dried over Na$_2$SO$_4$ (500 g). The solvent was removed under reduced pressure to give crude 195 g as a sticky off white solid with purity of >90%, which was purified by silica gel chromatography with 0-30% EtOAc in hexanes to give the final product (156 g, yield: 84.3%). EDI-MS: 430.0 (M+H)$^+$.

Step 6: 6-(trans-4-tert-Butylcyclohexyloxy)-5-(trifluoromethyl)-2-naphthaldehyde

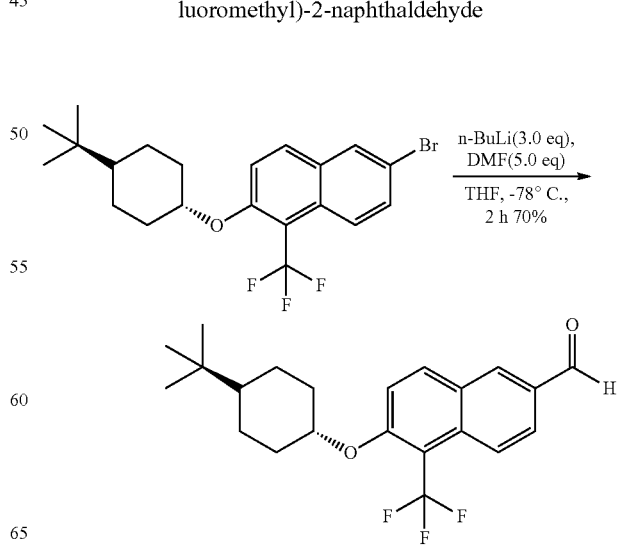

To a solution of 6-bromo-2-(trans-4-tert-butylcyclohexyloxy)-1-(trifluoromethyl)naphthalene (1 g, 2.3 mmol) in THF (30 mL) was added n-BuLi (2.8 mL, 2.5M in THF, 3.0 equiv) dropwise at −78° C. in 30 min, then DMF (840 mg, 11.5 mmol, 5.0 equiv) was added slowly at −78° C. The reaction mixture was stirred at −78° C. for 1.5 h. Then saturated NH₄Cl solution was added to the mixture to quench the reaction. The mixture was extracted with EtOAc and purified by silica gel chromatography (petroleum ether: ethyl acetate 10:1) to give product 6-(trans-4-tert-butylcyclohexyloxy)-5-(trifluoromethyl)-2-naphthaldehyde as a yellow solid (608 mg, yield: 70%). ESI-MS: 379.2 (M+H)⁺. ¹H NMR (400 MHz, CDCl₃) δ: 10.13 (s, 1H), 8.28 (d, 2H), 8.08 (d, 1H), 7.98-8.01 (dd, 1H), 7.41 (d, 1H), 4.39 (m, 1H), 2.21 (d, 2H), 1.90 (d, 2H), 1.49-1.58 (q, 2H), 1.10-1.17 (m, 3H), 0.86 (s, 9H)

Step 7: ethyl 4-(((6-((trans-4-(tert-butyl)cyclohexyl)oxy)-5-(trifluoromethyl)naphthalen-2-yl)methyl)amino)bicyclo[2.2.2]octane-1-carboxylate

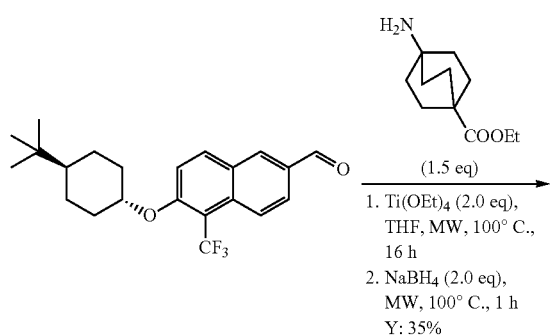

The preparation of ethyl 4-(((6-((trans-4-(tert-butyl)cyclohexyl)oxy)-5-(trifluoromethyl)naphthalen-2-yl)methyl)amino)bicyclo[2.2.2]octane-1-carboxylate was similar to that of methyl 4-(((6-hydroxynaphthalen-2-yl)methyl)amino) bicyclo[2.2.2]octane-1-carboxylate. yellow solid, 60 mg, Y: 35%. ESI-MS (M+H)⁺: 560.3. ¹H NMR (400 MHz, CDCl₃) δ: 8.12 (d, J=8.0 Hz, 1H), 7.88 (d, J=9.2 Hz, 1H), 7.83 (s, 1H), 7.54 (d, J=9.2 Hz, 1H), 7.24 (d, J=9.2 Hz, 1H), 4.28-4.20 (m, 1H), 4.07 (q, J=6.8 Hz, 2H), 3.84 (s, 2H), 2.14-2.12 (m, 2H), 1.86-1.84 (m, 2H), 1.75-1.70 (m, 12H), 1.24-1.02 (m, 8H), 0.87 (s, 9H).

Step 8: 4-(((6-((trans-4-(tert-butyl)cyclohexyl)oxy)-5-(trifluoromethyl)naphthalen-2-yl)methyl)amino)bicyclo[2.2.2]octane-1-carboxylic acid

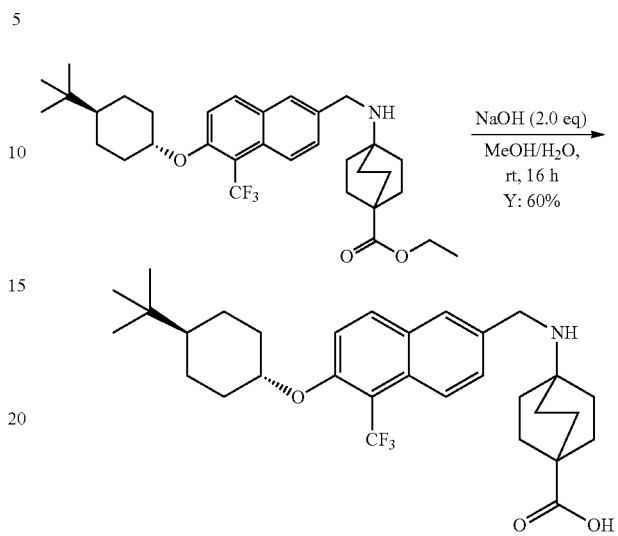

4-(((6-((trans-4-(tert-butyl)cyclohexyl)oxy)-5-(trifluoromethyl)naphthalen-2-yl)meth yl)amino)bicyclo[2.2.2]octane-1-carboxylic acid, as a white solid, 35 mg, Y: 60%. ESI-MS (M+H)⁺: 532.3. HPLC: 100.00%; ¹H NMR (400 MHz, CD₃OD) δ: 8.22 (d, J=8.0 Hz, 1H), 8.07 (d, J=9.2 Hz, 1H), 7.98 (s, 1H), 7.60 (d, J=9.2 Hz, 1H), 7.55-7.52 (m, 1H), 4.50-4.42 (m, 1H), 4.27 (s, 2H), 2.22-2.19 (m, 2H), 2.05-1.98 (m, 12H), 1.92-1.89 (m, 2H), 1.53-1.46 (m, 2H), 1.23-1.11 (m, 3H), 0.90 (s, 9H).

Example 38

4-(((6-((trans-4-(tert-butyl)cyclohexyl)oxy)-5-(trifluoromethyl)quinolin-2-yl)methyl)amino)bicyclo[2.2.2]octane-1-carboxylic acid Step 1: 6-((trans-4-(tert-butyl)cyclohexyl)oxy)-2-methylquinoline

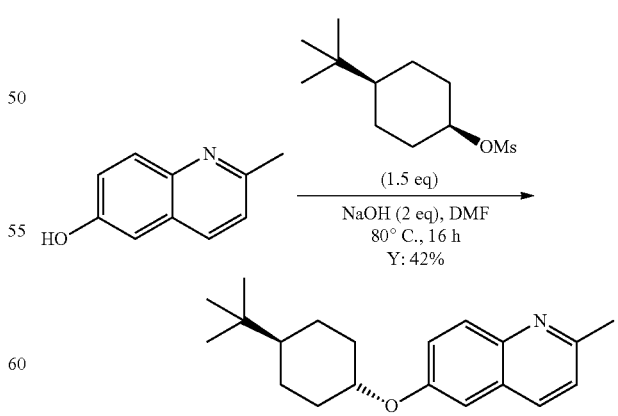

A mixture of 2-methylquinolin-6-ol (2 g, 12.6 mmol, 1 eq), cis-4-tert-butylcyclohexyl methanesulfonate (4.42 g, 18.9 mmol, 1.5 eq) and NaOH (1.06 g, 25.2 mmol, 2 eq) in DMF (6 mL) was stirred at 80° C. for 16 h. Then H₂O (15 mL) was added to the reaction mixture which was extracted with EA (30 mL×2). The collected organic layer was dried (Na₂SO₄) and concentrated. The crude product was purified by silica gel chromatography (PE:EA=20:1) to give 6-((trans-4-(tert-butyl)cyclohexyl)oxy)-2-methylquinoline as a yellow solid, 1.6 g, Y: 42%. ESI-MS (M+H)⁺: 298.3. ¹H NMR (400 MHz, CDCl₃) δ: 7.91 (d, J=8.4 Hz, 2H), 7.32 (dd, J=9.2, 2.8 Hz, 1H), 7.22 (d, J=8.4 Hz, 1H), 7.06 (d, J=2.8 Hz, 1H), 4.27-4.22 (m, 1H), 2.27 (s, 3H), 2.28-2.25 (m, 2H), 1.91-1.88 (m, 2H), 1.49-1.43 (m, 2H), 1.19-1.10 (m, 3H), 0.86 (s, 9H).

Step 2: 6-((trans-4-(tert-butyl)cyclohexyl)oxy)-5-iodo-2-methylquinoline

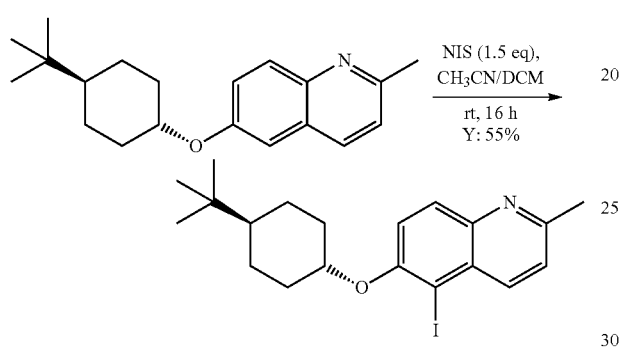

The preparation of 6-((trans-4-(tert-butyl)cyclohexyl)oxy)-5-iodo-2-methylquinoline was the same as that of 6-Bromo-2-(trans-4-tert-butylcyclohexyloxy)-1-iodonaphthalene, 1.35 g, as a yellow solid, Y: 55%. ESI-MS (M+H)⁺: 424.1. ¹H NMR (400 MHz, CDCl₃) δ: 8.30 (d, J=9.2 Hz, 1H), 7.95 (d, J=9.2 Hz, 1H), 7.38 (d, J=9.2 Hz, 1H), 7.27 (d, J=8.4 Hz, 1H), 4.32-4.25 (m, 1H), 2.73 (s, 3H), 2.25-2.22 (m, 2H), 1.88-1.85 (m, 2H), 1.64-1.58 (m, 2H), 1.11-1.09 (m, 3H), 0.86 (s, 9H).

Step 3: 6-((trans-4-(tert-butyl)cyclohexyl)oxy)-2-methyl-5-(trifluoromethyl)quinoline

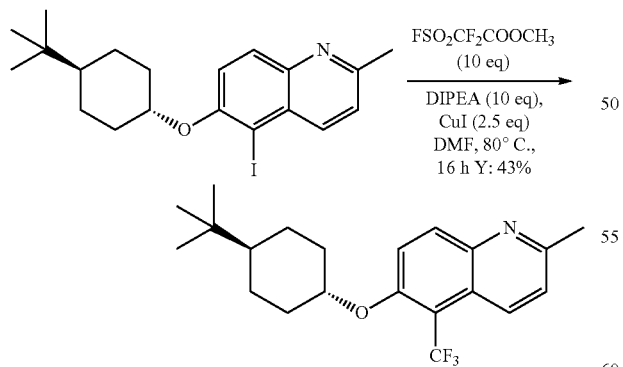

The preparation of 6-((trans-4-(tert-butyl)cyclohexyl)oxy)-2-methyl-5-(trifluoromethyl)quinolone was the same as that of 6-Bromo-2-(trans-4-tert-butylcyclohexyloxy)-1-(trifluoromethyl)naphthalene, 550 mg, as a yellow solid, Y: 43%. ESI-MS (M+H)⁺: 366.3. ¹H NMR (400 MHz, CDCl₃) δ: 8.43 (d, J=8.8 Hz, 1H), 8.14 (d, J=9.6 Hz, 1H), 7.51 (d, J=9.2 Hz, 1H), 7.33 (d, J=8.8 Hz, 1H), 4.35-4.30 (m, 1H), 2.72 (s, 3H), 2.21-1.98 (m, 2H), 1.89-1.87 (m, 2H), 1.58-1.49 (m, 2H), 1.15-1.11 (m, 3H), 0.88 (s, 9H).

Step 4: 6-((trans-4-(tert-butyl)cyclohexyl)oxy)-5-(trifluoromethyl)quinoline-2 carbaldehyde

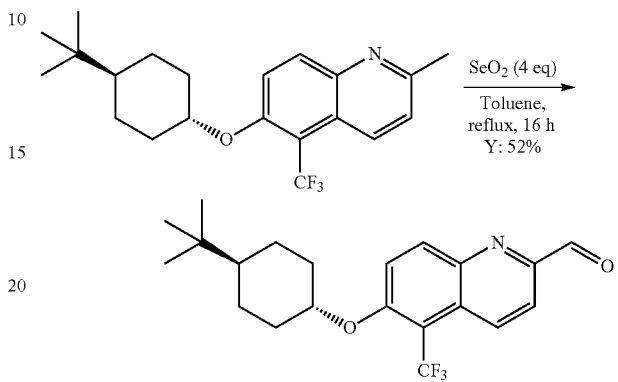

A mixture of 6-((trans-4-(tert-butyl)cyclohexyl)oxy)-2-methyl-5-(trifluoromethyl)quinoline (550 mg, 1.51 mmol, 1 eq) and SeO₂ (670 mg, 6.04 mmol, 4 eq) in toluene (8 mL) was refluxed for 16 h. After cooling down to room temperature, the mixture was filtered and the filtrate was concentrated. The crude product was purified by silica gel column to give 6-((trans-4-(tert-butyl)cyclohexyl)oxy)-5-(trifluoromethyl)quinoline-2-carbaldehyde (PE:EA=20:1) as a yellow solid, 320 mg, Y: 52%, ESI-MS (M+H)⁺: 380.2. ¹H NMR (400 MHz, CDCl₃) δ: 10.17 (s, 1H), 8.68 (d, J=8.8 Hz, 1H), 8.34 (d, J=9.2 Hz, 1H), 8.05 (d, J=9.2 Hz, 1H), 7.64 (d, J=9.6 Hz, 1H), 4.48-4.41 (m, 1H), 2.25-2.21 (m, 2H), 1.93-1.90 (m, 2H), 1.62-1.54 (m, 2H), 1.18-1.11 (m, 3H), 0.89 (s, 9H).

Step 5: methyl 4-(((6-((trans-4-(tert-butyl)cyclohexyl)oxy)-5-(trifluoromethyl)quinolin-2-yl)methyl)amino)bicyclo[2.2.2]octane-1-carboxylate

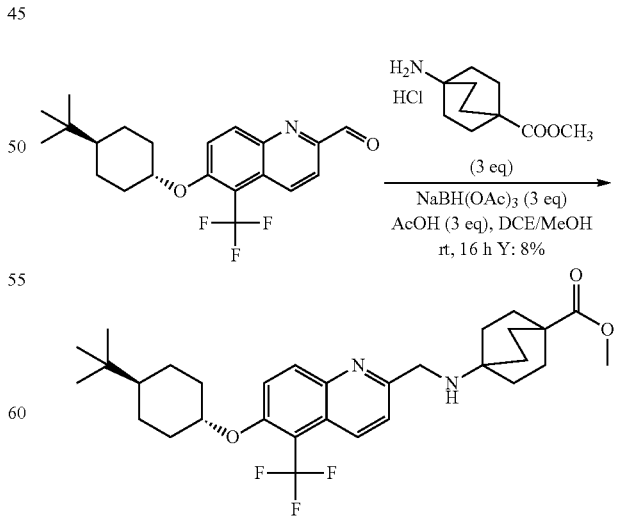

The preparation of methyl 4-(((6-((trans-4-(tert-butyl)cyclohexyl)oxy)-5-(trifluoromethyl)quinolin-2-yl)methyl)

amino)bicyclo[2.2.2]octane-1-carboxylate was the same as that of methyl 4-(((6-hydroxynaphthalen-2-yl)methyl) amino) bicyclo[2.2.2]octane-1-carboxylate, 20 mg, as a yellow solid, Y: 8%. ESI-MS (M+H)+: 547.3.

Step 6: 4-(((6-((trans-4-(tert-buty)cyclohexyl)oxy)-5-(trifluoromethyl)quinolin-2-yl)methyl)amino)bicyclo[2.2.2]octane-1-carboxylic acid

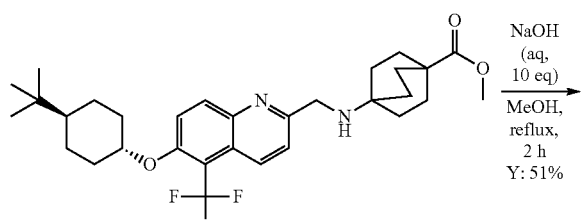

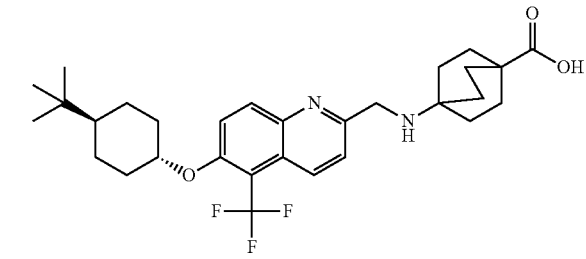

The preparation of 4-(((6-((trans-4-(tert-butyl)cyclohexyl)oxy)-5-(trifluoromethyl)quinolin-2-yl)methyl)amino) bicyclo[2.2.2]octane-1-carboxylic acid was the same as that of 4-(((6-((trans-4-(tert-butyl)cyclohexyl)oxy)-5-(trifluoromethyl)naphthalen-2-yl)methyl)amino)bicyclo[2.2.2]octane-1-carboxylic acid, 10 mg, as a yellow solid, Y: 51%. ESI-MS (M+H)+: 533.3, HPLC: 92.11%. ¹H NMR (400 MHz, CD₃OD) δ: 8.50 (d, J=8.4 Hz, 1H), 8.19 (d, J=9.6 Hz, 1H), 7.73 (d, J=9.6 Hz, 1H), 7.49 (d, J=9.6 Hz, 1H), 4.47-4.44 (m, 1H), 4.42 (s, 2H), 2.13-2.11 (m, 2H), 1.93 (br, 10H), 1.83-1.80 (m, 2H), 1.45-1.38 (m, 2H), 1.23-1.10 (m, 4H), 1.05-0.97 (m, 1H), 0.81 (s, 9H).

Example 39

2-(1-((6-((trans-4-(tert-butyl)cyclohexyl)oxy)naphthalen-2-yl)methyl)piperidin-4-yl)pyridine

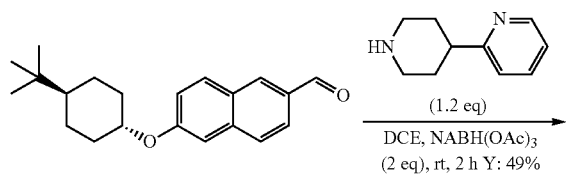

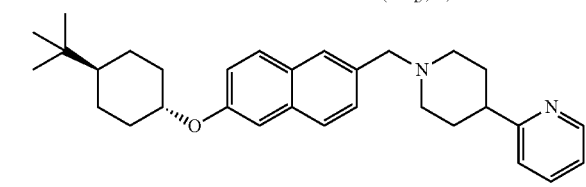

A mixture of 6-((trans-4-(tert-butyl)cyclohexyl)oxy)-2-naphthaldehyde (100 mg, 0.32 mmol, 1.0 eq), 2-(piperidin-4-yl)pyridine (62 mg, 0.38 mmol, 1.2 eq) and NaBH(OAc)₃ (136 mg, 0.64 mol, 2.0 eq) in DCE (20 mL) was stirred at room temperature for 2 h. Water (20 mL) was added to the mixture. The organic layer was washed with brine (20 mL), dried over Na₂SO₄ and concentrated to give 2-(1-((6-((trans-4-(tert-butyl)cyclohexyl)oxy)naphthalen-2-yl)methyl)piperidin-4-yl)pyridine as a white solid (72 mg, Y: 49%). ESI-MS (M+H)+: 457.0, HPLC: 100.00%. ¹H NMR (400 MHz, CD₃OD) δ: 8.58 (d, J=4.8 Hz, 1H), 8.01 (t, J=8.4 Hz, 1H), 7.96 (s, 1H), 7.88 (d, J=8.4 Hz, 1H), 7.83 (d, J=9.2 Hz, 1H), 7.56-7.46 (m, 3H), 7.31 (d, J=2.0 Hz, 1H), 7.19 (dd, J=8.8, 2.0 Hz, 1H), 4.49 (s, 2H), 4.41-4.35 (m, 1H), 3.69-3.66 (m, 2H), 3.26-3.17 (m, 3H), 2.29-2.10 (m, 6H), 1.92-1.89 (m, 2H), 1.44-1.41 (m, 2H), 1.31-1.25 (m, 2H), 1.15-1.11 (m, 1H), 0.92 (s, 9H).

Example 40

2-(1-((6-((trans-4-(tert-butyl)cyclohexyl)oxy)naphthalen-2-yl)methyl)piperidin-4-yl)pyrimidine

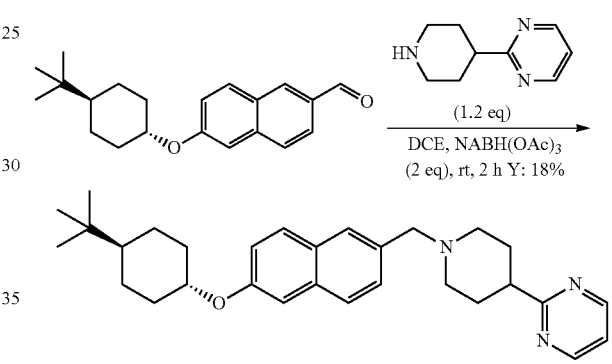

The preparation of 2-(1-((6-((trans-4-(tert-butyl)cyclohexyl)oxy)naphthalen-2-yl)methyl)piperidin-4-yl)pyrimidine was the same as that of 2-(1-((6-((trans-4-(tert-butyl)cyclohexyl)oxy)naphthalen-2-yl)methyl)piperidin-4-yl)pyridine. 8.8 mg, as yellow oil, Y: 18%. ESI-MS (M+H)+: 458.2, HPLC: 100.00%. ¹H NMR (400 MHz, CD₃OD) δ: 8.75 (d, J=8.4 Hz, 2H), 7.94 (s, 1H), 7.88 (d, J=8.8 Hz, 1H), 7.83 (d, J=9.2 Hz, 1H), 7.53 (d, J=8.4 Hz, 1H), 7.36 (t, J=4.8 Hz, 1H), 7.31 (s, 1H), 7.19 (dd, J=8.8, 2.0 Hz, 1H), 4.46 (s, 2H), 4.41-4.35 (m, 1H), 3.61-3.59 (m, 2H), 3.32-3.24 (m, 3H), 2.29-2.18 (m, 6H), 1.94-1.91 (m, 2H), 1.45-1.42 (m, 2H), 1.39-1.26 (m, 2H), 1.16-1.13 (m, 1H), 0.89 (s, 9H).

Example 41

1-((6-((trans-4-(tert-butyl)cyclohexyl)oxy)naphthalen-2-yl)methyl)-4-phenylpiperazine

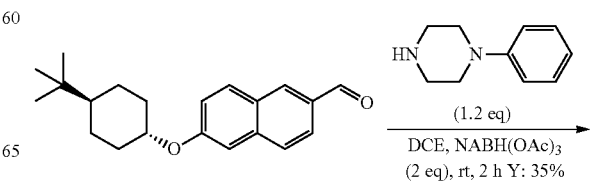

-continued

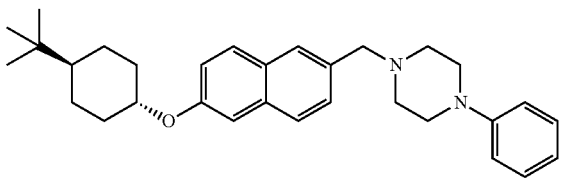

The preparation of 1-((6-(((trans-4-(tert-butyl)cyclohexyl)oxy)naphthalen-2-yl)methyl)-4-phenylpiperazine was the same as that of 2-(1-((6-(((trans-4-(tert-butyl)cyclohexyl)oxy)naphthalen-2-yl)methyl)piperidin-4-yl)pyridine. 64 mg, as a yellow solid, Y: 35%. ESI-MS (M+H)$^+$: 457.0, HPLC: 100.00%. $^1$H NMR (400 MHz, CD$_3$OD) δ: 7.77 (t, J=9.2 Hz, 2H), 7.71 (s, 1H), 7.44 (dd, J=8.8, 1.2 Hz, 1H), 7.34 (d, J=2.4 Hz, 1H), 7.20 (d, J=8.4 Hz, 1H), 7.18 (d, J=8.0 Hz, 1H), 7.11 (dd, J=8.8, 2.4 Hz, 1H), 6.91 (d, J=8.0 Hz, 2H), 6.76 (t, J=8.0 Hz, 1H), 4.40-4.35 (m, 1H), 3.63 (s, 2H), 3.14-3.12 (m, 4H), 2.55-2.53 (m, 4H), 2.22-2.19 (m, 2H), 2.01-1.83 (m, 2H), 1.33-1.02 (m, 5H), 0.88 (s, 9H).

Example 42

1-((6-(((trans-4-(tert-butyl)cyclohexyl)oxy)naphthalen-2-yl)methyl)-4-(pyridin-3-yl)piperazine

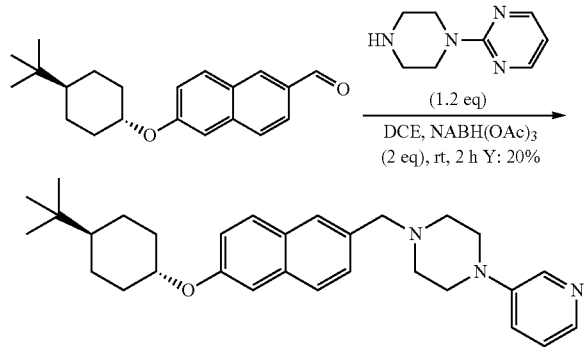

The preparation of 1-((6-(((trans-4-(tert-butyl)cyclohexyl)oxy)naphthalen-2-yl)methyl)-4-(pyridin-3-yl)piperazine was the same as that of 2-(1-((6-(((trans-4-(tert-butyl)cyclohexyl)oxy)naphthalen-2-yl)methyl)piperidin-4-yl)pyridine. 30 mg, as a yellow solid, Y: 41%. ESI-MS (M+H)$^+$: 458.0, HPLC: 100.00%. $^1$H NMR (400 MHz, CD$_3$OD) δ: 8.38 (d, J=2.8 Hz, 1H), 8.13 (d, J=5.2 Hz, 1H), 8.01 (dd, J=8.8, 2.4 Hz, 1H), 7.86 (s, 1H), 7.78 (d, J=8.4 Hz, 1H), 7.76 (dd, J=8.4, 2.4 Hz, 1H), 7.72 (d, J=8.8 Hz, 1H), 7.44 (dd, J=8.4, 2.0 Hz, 1H), 7.20 (d, J=2.0 Hz, 1H), 7.09 (dd, J=8.8, 2.0 Hz, 1H), 4.45 (s, 2H), 4.31-4.25 (m, 1H), 3.64-3.62 (m, 4H), 3.43-3.40 (m, 4H), 2.19-2.16 (m, 2H), 1.83-1.80 (m, 2H), 1.37-1.28 (m, 2H), 1.22-1.16 (m, 2H), 1.06-1.02 (m, 1H), 0.82 (s, 9H).

Example 43

1-((6-(((trans-4-(tert-butyl)cyclohexyl)oxy)naphthalen-2-yl)methyl)-4-(pyridin-2-yl)-1,4-diazepane

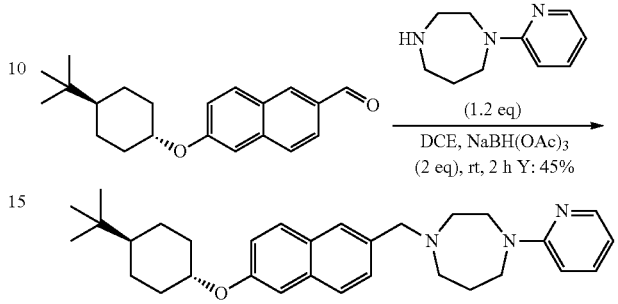

The preparation of 1-((6-(((trans-4-(tert-butyl)cyclohexyl)oxy)naphthalen-2-yl)methyl)-4-pyridin-2-yl)-1,4-diazepane was the same as that of 2-(1-6-(((trans-4-(tert-butyl)cyclohexyl)oxy)naphthalen-2-yl)methyl)piperidin-4-yl)pyridine. 93 mg, as a yellow solid, Y: 45%. ESI-MS (M+H)$^+$: 472.2, HPLC: 100.00%. $^1$H NMR (400 MHz, CD$_3$OD) δ: 8.05 (d, J=5.2 Hz, 1H), 7.98 (d, J=8.8 Hz, 1H), 7.94 (s, 1H), 7.88 (d, J=8.4 Hz, 1H), 7.81 (d, J=9.2 Hz, 1H), 7.53 (dd, J=8.4, 1.6 Hz, 1H), 7.31 (d, J=1.6 Hz, 1H), 7.23-7.19 (m, 2H), 6.99 (t, J=6.8 Hz, 1H), 4.54 (s, 2H), 4.40-4.38 (m, 1H), 4.10-4.08 (m, 2H), 3.76-3.73 (m, 2H), 3.57-3.54 (m, 3H), 2.43-2.40 (m, 2H), 2.30-2.27 (m, 2H), 1.94-1.91 (m, 2H), 1.48-1.39 (m, 2H), 1.33-1.23 (m, 3H), 1.17-1.13 (m, 1H), 0.93 (s, 9H).

Example 44

2-(4-((6-(((trans-4-(tert-butyl)cyclohexyl)oxy)naphthalen-2-yl)methyl)piperazin-1-yl) pyrimidine

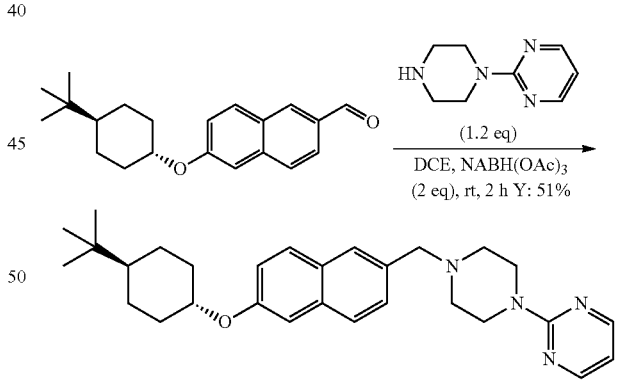

The preparation of 2-(4-((6-(((trans-4-(tert-butyl)cyclohexyl)oxy)naphthalen-2-yl)methyl)piperazin-1-yl)pyrimidine was the same as that of 2-(1-((6-(((trans-4-(tert-butyl)cyclohexyl)oxy)naphthalen-2-yl)methyl)piperidin-4-yl) pyridine. 85 mg, as a yellow solid, Y: 51%. ESI-MS (M+H)$^+$: 459.3, HPLC: 100.00%. $^1$H NMR (400 MHz, CD$_3$OD) δ: 8.30 (d, J=4.8 Hz, 2H), 7.77-7.70 (m, 3H), 7.42 (dd, J=8.8, 1.2 Hz, 1H), 7.17 (dd, J=8.8, 2.4 Hz, 1H), 7.14 (s, 1H), 6.57 (t, J=4.8 Hz, 1H), 4.85-4.65 (m, 2H), 4.31 (s, 2H), 4.31-4.28 (m, 1H), 3.80-2.80 (m, 6H), 2.28-2.25 (m, 2H), 1.90-1.88 (m, 2H), 1.45-1.42 (m, 2H), 1.20-1.18 (m, 3H), 0.90 (s, 9H).

Example 45

2-(4-((6-((trans-4-(tert-butyl)cyclohexyl)oxy)naphthalen-2-yl)methyl)piperazin-1-yl) pyrazine

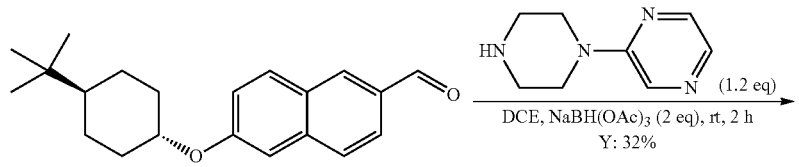

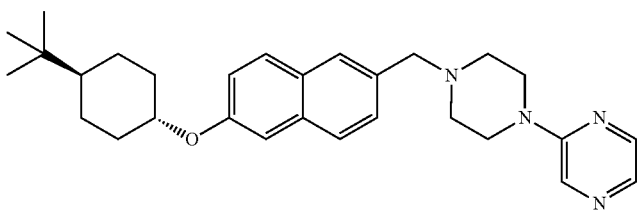

The preparation of 2-(4-((6-((trans-4-(tert-butyl)cyclohexyl)oxy)naphthalen-2-yl)methyl)piperazin-1-yl)pyrazine was the same as that of 2-(1-((6-((trans-4-(tert-butyl)cyclohexyl)oxy)naphthalen-2-yl)methyl)piperidin-4-yl)pyridine. 89 mg, as a yellow solid, Y: 51%. ESI-MS (M+H)+: 459.3, HPLC: 100.00%. $^1$H NMR (400 MHz, CD$_3$OD) δ: 8.32 (s, 1H), 8.18 (dd, J=2.4, 1.6 Hz, 1H), 7.96 (s, 1H), 7.93 (d, J=2.4 Hz, 1H), 7.90 (d, J=8.4 Hz, 1H), 7.83 (d, J=8.8 Hz, 1H), 7.54 (dd, J=8.4, 1.6 Hz, 1H), 7.32 (d, J=2.4 Hz, 1H), 7.20 (dd, J=8.4, 2.0 Hz, 1H), 4.91-4.90 (m, 4H), 4.53 (s, 2H), 4.42-4.37 (m, 1H), 3.50-3.48 (m, 4H), 2.30-2.27 (m, 2H), 1.94-1.91 (m, 2H), 1.45-1.39 (m, 2H), 1.33-1.14 (m, 3H), 0.93 (s, 9H).

The preparation of 1-((6-((trans-4-(tert-butyl)cyclohexyl)oxy)naphthalen-2-yl)methyl)-4-(pyridin-4-yl)piperazine was the same as that of 2-(1-((6-((trans-4-(tert-butyl)cyclohexyl)oxy)naphthalen-2-yl)methyl)piperidin-4-yl)pyridine. 44 mg, as a yellow solid, Y: 43%. ESI-MS (M+H)+: 458.0, HPLC: 100.00%. $^1$H NMR (400 MHz, DMSO-d$_6$) δ: 8.14 (s, 2H), 7.78 (d, J=8.4 Hz, 1H), 7.76 (d, J=8.0 Hz, 1H), 7.71 (s, 1H), 7.43 (d, J=8.4 Hz, 1H), 7.34 (d, J=2.0 Hz, 1H), 7.12 (dd, J=8.8, 2.0 Hz, 1H), 6.79 (d, J=5.2 Hz, 2H), 4.38-4.35 (m, 1H), 3.62 (s, 2H), 3.18-3.16 (m, 4H), 2.51-2.49 (m, 4H), 2.21-2.19 (m, 2H), 1.83-1.80 (m, 2H), 1.38-1.03 (m, 5H), 0.88 (s, 9H).

Example 46

1-((6-((trans-4-(tert-butyl)cyclohexyl)oxy)naphthalen-2-yl)methyl)-4-(pyridin-4-yl)piperazine

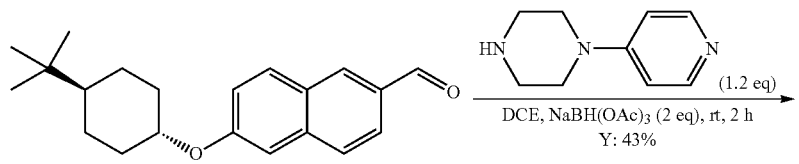

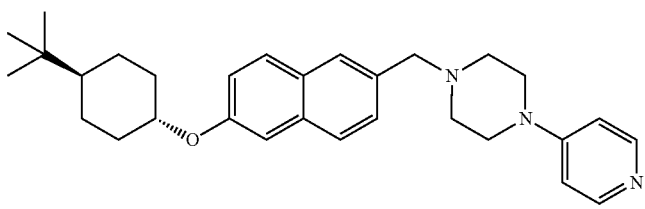

Example 47

1-((6-((trans-4-(tert-butyl)cyclohexyl)oxy)naphthalen-2-yl)methyl)-4-(pyrimidin-2-yl)-1,4-diazepane

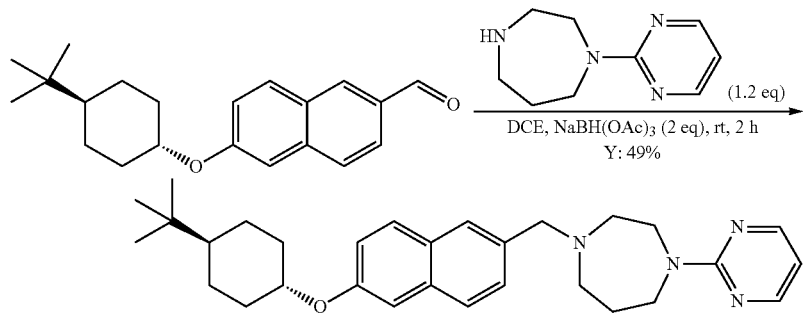

The preparation of 1-((6-((trans-4-(tert-butyl)cyclohexyl)oxy)naphthalen-2-yl)methyl)-4-(pyrimidin-2-yl)-1,4-diazepane was the same as that of 2-(1-((6-((trans-4-(tert-butyl)cyclohexyl)oxy)naphthalen-2-yl)methyl)piperidin-4-yl)pyridine. 90 mg, as a yellow solid, Y: 49%. ESI-MS (M+H)$^+$: 473.4, HPLC: 98.35%. $^1$H NMR (400 MHz, CD$_3$OD) δ: 8.05 (d, J=5.2 Hz, 2H), 7.89 (s, 1H), 7.82 (d, J=8.4 Hz, 1H), 7.77 (d, J=9.2 Hz, 1H), 7.49 (dd, J=8.4, 1.6 Hz, 1H), 7.25 (d, J=1.6 Hz, 1H), 7.15 (dd, J=8.8, 2.4 Hz, 1H), 6.69 (t, J=5.2 Hz, 1H), 4.44 (s, 2H), 4.40-4.31 (m, 1H), 4.00-3.58 (m, 5H), 3.32-3.20 (m, 3H), 2.25-2.22 (m, 4H), 1.87-1.83 (m, 2H), 1.39-1.36 (m, 2H), 1.22-1.19 (m, 2H), 1.09-1.06 (m, 1H), 0.88 (s, 9H).

Example 48

4-(4-((6-((trans-4-(tert-butyl)cyclohexyl)oxy)naphthalen-2-yl)methyl)piperazin-1-yl) pyrimidine

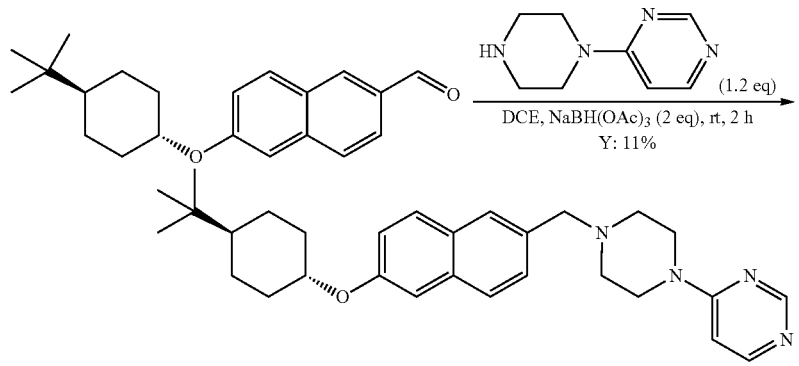

The preparation of 4-(4-((6-((trans-4-(tert-butyl)cyclohexyl)oxy)naphthalen-2-yl)methyl)piperazin-1-yl)pyrimidine was the same as that of 2-(1-((6-((trans-4-(tert-butyl)cyclohexyl)oxy)naphthalen-2-yl)methyl)piperidin-4-yl)pyridine. 9 mg, as yellow oil, Y: 11%. ESI-MS (M+H)$^+$: 459.2, HPLC: 93.96%. $^1$H NMR (400 MHz, CD$_3$OD) δ: 8.58 (s, 1H), 8.18-8.17 (m, 1H), 7.80 (s, 1H), 7.75 (d, J=8.4 Hz, 1H), 7.70 (d, J=9.2 Hz, 1H), 7.42 (d, J=8.4 Hz, 1H), 7.19 (d, J=2.0 Hz, 1H), 7.07 (dd, J=8.8, 2.4 Hz, 1H), 6.97 (d, J=6.8 Hz, 1H), 4.30-4.25 (m, 3H), 4.03-4.00 (m, 4H), 3.21-3.19 (m, 4H), 2.19-2.16 (m, 2H), 1.83-1.80 (m, 2H), 1.34-1.02 (m, 5H), 0.82 (s, 9H).

Example 49

4-(4-((6-((trans-4-(tert-butyl)cyclohexyl)oxy)naphthalen-2-yl)methyl)piperazin-1-yl)-2-methylpyrimidine

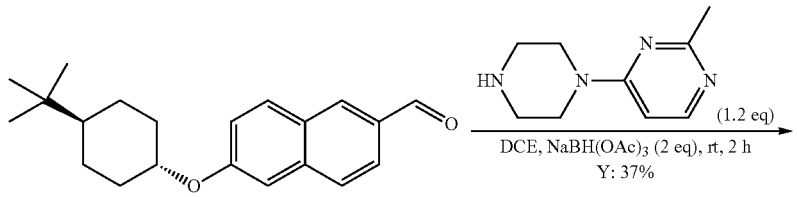

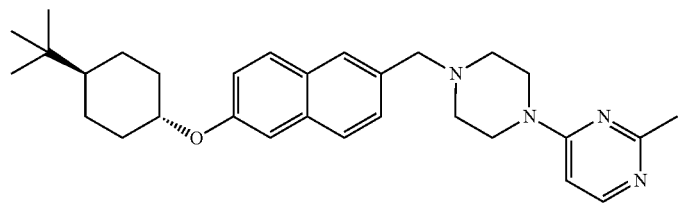

The preparation of 4-(4-((6-((trans-4-(tert-butyl)cyclohexyl)oxy)naphthalen-2-yl)methyl)piperazin-1-yl)-2-methylpyrimidine was the same as that of 2-(1-((6-((trans-4-(tert-butyl)cyclohexyl)oxy)naphthalen-2-yl)methyl)piperidin-4-yl)pyridine. 30 mg, as a yellow solid, Y: 37%. ESI-MS (M+H)$^+$: 473.0, HPLC: 98.76%. $^1$H NMR (400 MHz, CD$_3$OD) δ: 8.11 (d, J=7.2 Hz, 1H), 7.81 (s, 1H), 7.75 (d, J=8.4 Hz, 1H), 7.69 (d, J=9.2 Hz, 1H), 7.42 (dd, J=8.4, 1.6 Hz, 1H), 7.19 (d, J=2.4 Hz, 1H), 7.07 (dd, J=8.8, 2.4 Hz, 1H), 6.97 (d, J=7.6 Hz, 1H), 4.33 (s, 2H), 4.29-4.23 (m, 1H), 4.10-4.06 (m, 4H), 3.28-3.26 (m, 4H), 2.49 (s, 3H), 2.18-2.15 (m, 2H), 1.82-1.79 (m, 2H), 1.36-1.01 (m, 5H), 0.81 (s, 9H).

Example 50

1-((6-((trans-4-(tert-butyl)cyclohexyl)oxy)naphthalen-2-yl)methyl)-4-phenylpiperidine The preparation of 1-((6-((trans-4-(tert-butyl)cyclohexyl)oxy)naphthalen-2-yl)methyl)-4-phenylpiperidine was the same as that of 2-(1-((6-((trans-4-(tert-butyl)cyclohexyl)oxy)naphthalen-2-yl)methyl)piperidin-4-yl)pyridine. 34 mg, as a white solid, Y: 22%. ESI-MS (M+H)$^+$: 456.3, HPLC: 97.45%. $^1$H NMR (400 MHz, CD$_3$OD) δ: 7.96 (s, 1H), 7.89 (d, J=8.8 Hz, 1H), 7.84 (d, J=9.2 Hz, 1H), 7.55 (dd, J=8.4, 1.6 Hz, 1H), 7.33-7.30 (m, 3H), 7.26-7.19 (m, 4H), 4.48 (s, 2H), 4.42-4.36 (m, 1H), 3.66-3.62 (m, 2H), 3.24-3.17 (m, 2H), 2.93-2.86 (m, 1H), 2.30-2.26 (m, 2H), 2.12-2.07 (m, 2H), 2.03-1.91 (m, 4H), 1.47-1.40 (m, 2H), 1.33-1.23 (m, 2H), 1.17-1.10 (m, 1H), 0.93 (s, 9H).

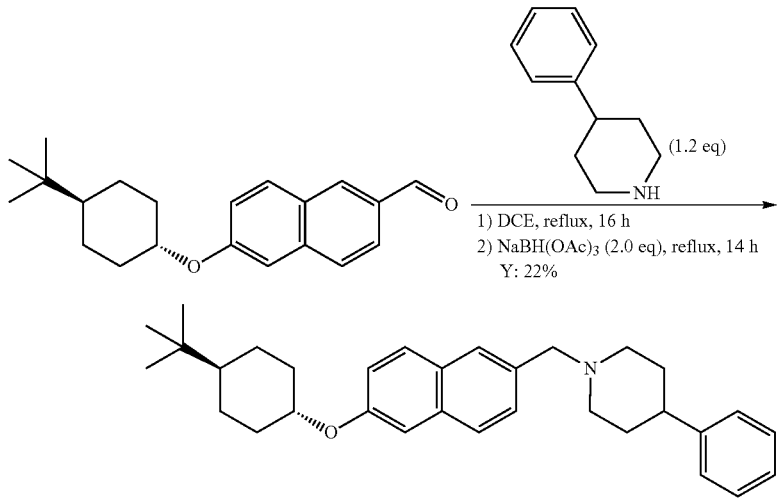

Example 51

1-((6-((trans-4-(tert-butyl)cyclohexyl)oxy)naphthalen-2-yl)methyl)-4-(pyridin-2-yl)piperazine

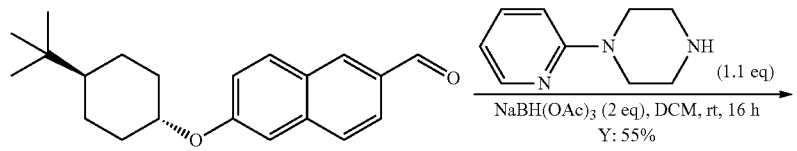

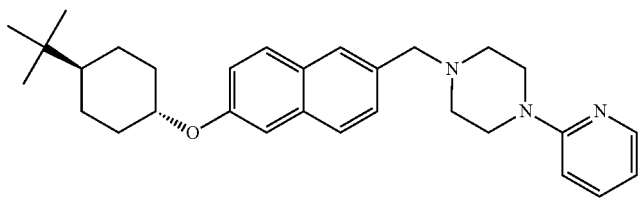

The preparation of 1-((6-((trans-4-(tert-butyl)cyclohexyl)oxy)naphthalen-2-yl)methyl)-4-(pyridin-2-yl)piperazine was the same as that of 2-(1-((6-((trans-4-(tert-butyl)cyclohexyl)oxy)naphthalen-2-yl)methyl)piperidin-4-yl)pyridine, 200 mg, as a white solid, Y: 55%. ESI-MS (M+H)$^+$: 458.2. HPLC: 97.89%. $^1$H NMR (400 MHz, CDCl$_3$) δ: 8.19 (dd, J=5.2, 1.2 Hz, 1H), 7.76 (t, J=8.4 Hz, 2H), 7.71 (s, 1H), 7.52-7.48 (m, 1H), 7.44 (dd, J=8.4, 1.2 Hz, 1H), 7.34 (d, J=2.8 Hz, 1H), 7.11 (dd, J=8.8, 2.0 Hz, 1H), 6.79 (d, J=8.8 Hz, 1H), 6.62 (dd, J=6.8, 4.8 Hz, 1H), 4.37-4.34 (m, 1H), 3.62 (s, 2H), 3.49-3.46 (m, 4H), 2.51-2.48 (m, 4H), 2.22-2.19 (m, 2H), 1.83-1.79 (m, 2H), 1.33-1.07 (m, 5H), 0.88 (s, 9H).

Example 52

1-((6-((cis-4-isopropylcyclohexyl)oxy)naphthalen-2-yl)methyl)-4-(pyridin-2-yl)piperazine Step 1: 2-bromo-6-((cis-4-isopropylcyclohexyl)oxy)naphthalene

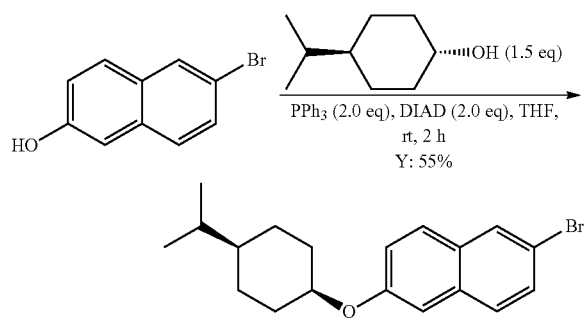

To a mixture of 6-bromonaphthalen-2-ol (1.39 g, 6.25 mmol, 1.0 eq), trans-4-isopropyl cyclohexanol (1.33 g, 9.38 mmol, 1.5 eq) and PPh$_3$ (3.28 g, 12.5 mmol, 2.0 eq) in dry THF (30 mL) was quickly added DIAD (2.53 g, 12.5 mmol, 2.0 eq) in one portion at 0° C. under N$_2$. Then the reaction mixture was stirred at room temperature for 2 h. The solvent was removed in vacuum and the residue was purified by silica gel column with PE as eluent to give 2-bromo-6-((cis-4-isopropylcyclohexyl)oxy)naphthalene as a white solid (1.18 g, Y: 55%). ESI-MS (M+H)$^+$: 347.1. $^1$H NMR (400 MHz, CDCl$_3$) δ: 7.83 (d, J=1.2 Hz, 1H), 7.57 (d, J=8.8 Hz, 1H), 7.49 (d, J=8.8 Hz, 1H), 7.40 (dd, J=8.8, 2.0 Hz, 1H), 7.11 (dd, J=8.8, 2.0 Hz, 1H), 7.04 (d, J=2.4 Hz, 1H), 4.60-4.58 (m, 1H), 2.06-2.03 (m, 2H), 1.54-1.36 (m, 7H), 1.10-1.04 (m, 1H), 0.83 (d, J=6.8 Hz, 6H).

Step 2: 6-((cis-4-isopropylcyclohexyl)oxy)-2-naphthaldehyde

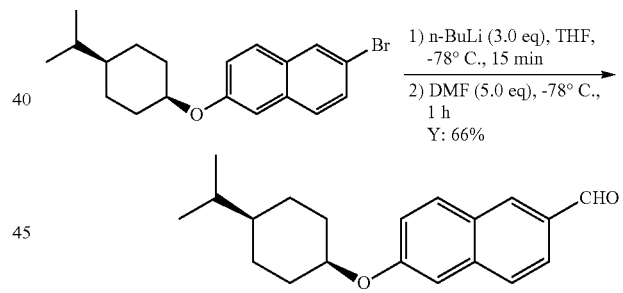

2-bromo-6-((cis-4-isopropylcyclohexyl)oxy)naphthalene (1.18 g, 3.4 mmol, 1.0 eq) was dissolved in dry THF (20 mL) and cooled to −78° C. under N$_2$. n-BuLi (6.4 mL, 1.6 M, 3.0 eq) was added to the solution. The mixture was stirred at −78° C. for 15 min and DMF (1.2 mL, 17.0 mmol, 5.0 eq) was added. The mixture was stirred at −78° C. for 1 h and then washed with water (20 mL) and extracted with EtOAc (20 mL×2). The combined organic phase was washed with brine (20 mL), dried over Na$_2$SO$_4$, filtered, and concentrated in vacuo. The residue was purified by silica gel column chromatography (PE/EA=40/1) to give 6-((cis-4-isopropylcyclohexyl)oxy)-2-naphthaldehyde as a yellow solid (657 mg, Y: 66%). ESI-MS (M+H)$^+$: 297.2. $^1$H NMR (400 MHz, CDCl$_3$) δ: 10.08 (s, 1H), 8.23 (s, 1H), 7.90-7.87 (m, 2H), 7.75 (d, J=8.4 Hz, 1H), 7.25 (dd, J=9.2, 2.8 Hz, 1H), 7.18 (d, J=2.4 Hz, 1H), 4.74-4.72 (m, 1H), 2.16-2.12 (m, 2H), 1.66-1.46 (m, 7H), 1.19-1.14 (m, 1H), 0.90 (d, J=6.8 Hz, 6H).

Step 3: 1-((6-((cis-4-isopropylcyclohexyl)oxy)naphthalen-2-yl)methyl)-4-(pyridin-2-yl)piperazine

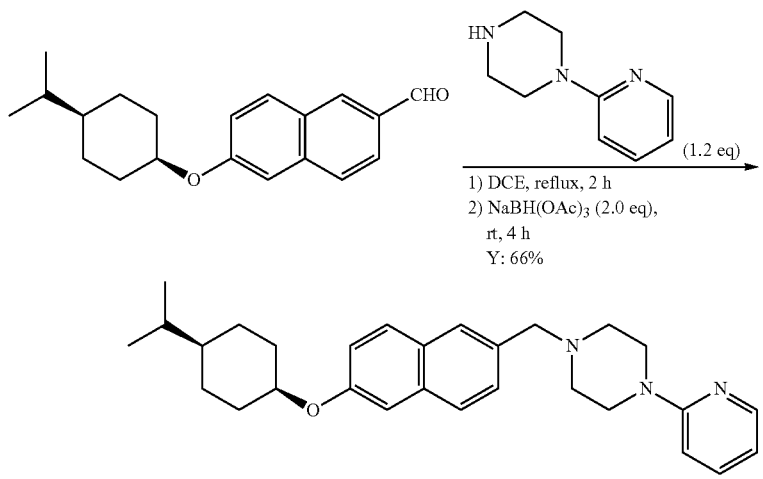

1) DCE, reflux, 2 h
2) NaBH(OAc)$_3$ (2.0 eq), rt, 4 h
Y: 66%

A mixture of 6-((cis-4-isopropylcyclohexyl)oxy)-2-naphthaldehyde (107 mg, 0.36 mmol, 1.0 eq) and 1-(pyridin-2-yl)piperazine (70 mg, 0.432 mmol, 1.2 eq) in DCE (15 mL) was stirred at reflux for 2 h. After cooling down to room temperature, NaBH(OAc)$_3$ (153 mg, 0.72 mmol, 2.0 eq) was added to the mixture and stirred at room temperature for 4 h. Water (15 mL) was added to the mixture and the mixture was extracted with DCM (20 mL×2). The combined organic phase was washed with water (15 mL) and brine (20 mL), dried over Na$_2$SO$_4$, filtered, and concentrated in vacuo. The residue was purified by pre-HPLC to give 1-((6-((cis-4-isopropylcyclohexyl)oxy)naphthalen-2-yl)methyl)-4-(pyridin-2-yl)piperazine. 77 mg, as white gum, Y: 66%. ESI-MS (M+H)$^+$: 444.3, HPLC: 100.00%. $^1$H NMR (400 MHz, CD$_3$OD) δ: 8.00 (dd, J=5.6, 0.8 Hz, 1H), 7.84 (s, 1H), 7.80-7.70 (m, 3H), 7.42 (dd, J=8.0, 1.2 Hz, 1H), 7.17 (s, 1H), 7.13-7.07 (m, 2H), 6.85 (t, J=6.8 Hz, 1H), 4.63-4.61 (m, 1H), 4.41 (s, 2H), 3.82-3.80 (m, 4H), 3.36-3.34 (m, 4H), 2.01-1.97 (m, 2H), 1.53-1.33 (m, 7H), 1.07-1.05 (m, 1H), 0.79 (d, J=6.8 Hz, 6H).

Example 53

1-((6-((cis-4-ethylcyclohexyl)oxy)naphthalen-2-yl)methyl)-4-(pyridin-2-yl)piperazine Step 1: 6-((cis-4-ethylcyclohexyl)oxy)-2-naphthaldehyde

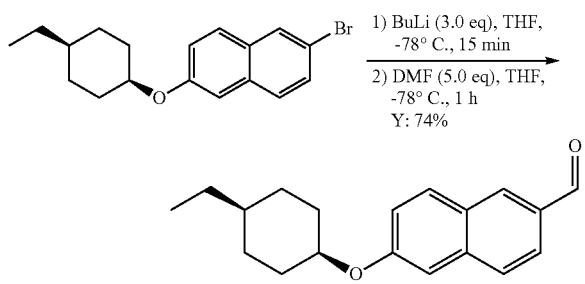

1) BuLi (3.0 eq), THF, -78° C., 15 min
2) DMF (5.0 eq), THF, -78° C., 1 h
Y: 74%

The preparation of 6-((cis-4-ethylcyclohexyl)oxy)-2-naphthaldehyde was the same as that of 6-((cis-4-isopropylcyclohexyl)oxy)-2-naphthaldehyde. 440 mg, as a yellow solid, Y: 74%. ESI-MS (M+H)$^+$: 283.2. $^1$H NMR (400 MHz, CDCl$_3$) δ: 10.08 (s, 1H), 8.24 (s, 1H), 7.91-7.88 (m, 2H), 7.76 (d, J=8.4 Hz, 1H), 7.25 (dd, J=8.4, 2.4 Hz, 1H), 7.19 (d, J=2.8 Hz, 1H), 4.73-4.70 (m, 1H), 2.11-2.07 (m, 2H), 1.67-1.57 (m, 4H), 1.47-1.37 (m, 2H), 1.33-1.26 (m, 3H), 0.91 (t, J=7.2 Hz, 3H).

Step 2: 1-((6-((cis-4-ethylcyclohexyl)oxy)naphthalen-2-yl)methyl)-4-(pyridin-2-yl)piperazine

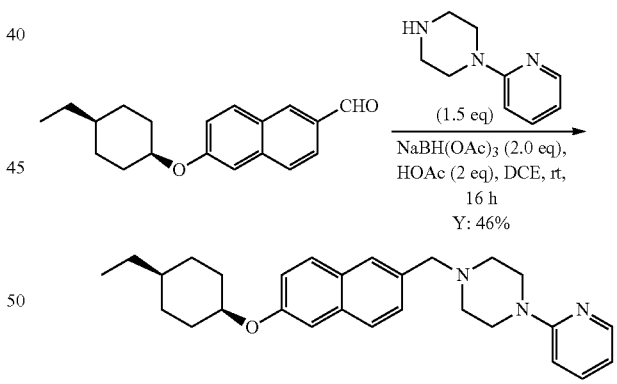

NaBH(OAc)$_3$ (2.0 eq), HOAc (2 eq), DCE, rt, 16 h
Y: 46%

The preparation of 1-((6-((cis-4-ethylcyclohexyl)oxy)naphthalen-2-yl)methyl)-4-(pyridin-2-yl)piperazine was the same as that of 1-((6-((cis-4-isopropylcyclohexyl)oxy)naphthalen-2-yl)methyl)-4-(pyridin-2-yl)piperazine. 90 mg, as a yellow solid, Y: 46%. ESI-MS (M+H)$^+$: 430.3, HPLC: 99.53%. $^1$H NMR (400 MHz, CD$_3$OD) δ: 8.16 (d, J=3.6 Hz, 1H), 7.95 (s, 1H), 7.89-7.83 (m, 2H), 7.63 (t, J=8.8 Hz, 1H), 7.53 (dd, J=8.4, 1.6 Hz, 1H), 7.31 (d, J=2.0 Hz, 1H), 7.25 (dd, J=8.8, 2.0 Hz, 1H), 6.93 (d, J=8.8 Hz, 1H), 6.80 (dd, J=6.8, 1.6 Hz, 1H), 4.92-4.90 (m, 4H), 4.78-4.76 (m, 1H), 4.48 (s, 2H), 3.40-3.36 (m, 4H), 2.10-2.06 (m, 2H), 1.71-1.60 (m, 4H), 1.47-1.30 (m, 5H), 0.94 (t, J=7.2 Hz, 3H).

Example 54

1-(pyridin-2-yl)-4-((6-(spiro[4.5]decan-8-yloxy)naphthalen-2-yl)methyl)piperazine

Step 1: 2-bromo-6-(spiro[4.5]decan-8-yloxy)naphthalene

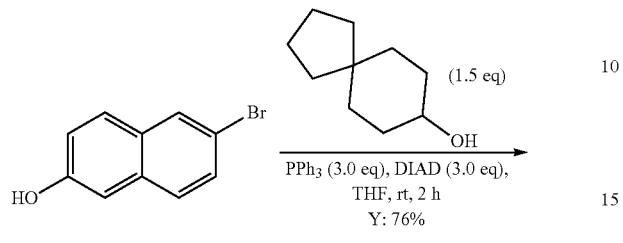

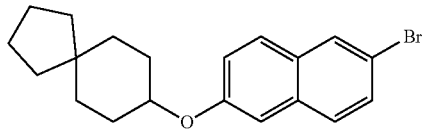

The preparation of 2-bromo-6-(spiro[4.5]decan-8-yloxy)naphthalene was the same as that of 2-bromo-6-((cis-4-isopropylcyclohexyl)oxy)naphthalene. 1.09 g, as a white solid, Y: 76%. ESI-MS (M+H)$^+$: 359.1.

Step 2: 6-(spiro[4.5]decan-8-yloxy)-2-naphthaldehyde

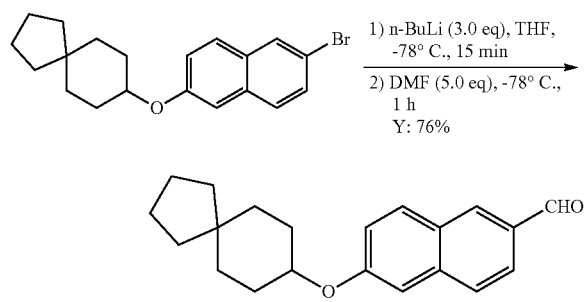

The preparation of 6-(spiro[4.5]decan-8-yloxy)-2-naphthaldehyde was the same as that of 6-((cis-4-isopropylcyclohexyl)oxy)-2-naphthaldehyde. 700 mg, as a yellow solid, Y: 76%. ESI-MS (M+H)$^+$: 309.2. $^1$H NMR (400 MHz, CDCl$_3$) δ: 10.08 (s, 1H), 8.24 (s, 1H), 7.91-7.88 (m, 2H), 7.77 (d, J=8.8 Hz, 1H), 7.22 (dd, J=8.8, 2.4 Hz, 1H), 7.19 (d, J=2.4 Hz, 1H), 4.50-4.44 (m, 1H), 2.02-1.97 (m, 2H), 1.73-1.58 (m, 8H), 1.51-1.38 (m, 6H).

Step 3: 1-(pyridin-2-yl)-4-((6-(spiro[4.5]decan-8-yloxy)naphthalen-2-yl)methyl)piperazine

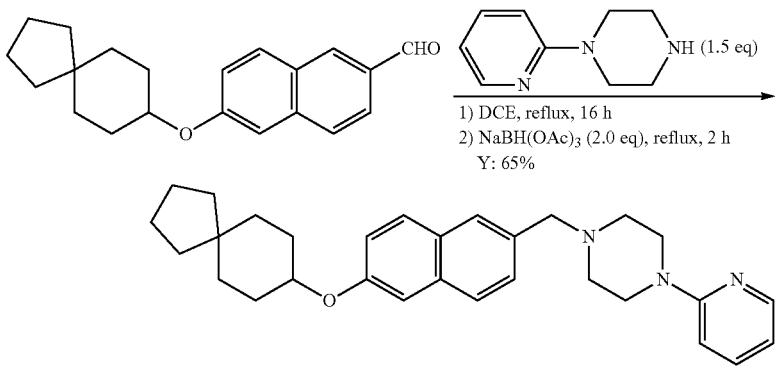

The preparation of 1-(pyridin-2-yl)-4-((6-(spiro[4.5]decan-8-yloxy)naphthalen-2-yl)methyl)piperazine was the same as that of 1-((6-((cis-4-isopropylcyclohexyl)oxy)naphthalen-2-yl)methyl)-4-(pyridin-2-yl)piperazine. 144 mg, as a white solid, Y: 65%. ESI-MS (M+H)$^+$: 456.3, HPLC: 100.00%. $^1$H NMR (400 MHz, CD$_3$OD) δ: 8.02 (d, J=4.4 Hz, 1H), 7.83 (s, 1H), 7.75 (d, J=8.4 Hz, 1H), 7.71 (d, J=8.8 Hz, 1H), 7.63 (t, J=8.4 Hz, 1H), 7.42 (dd, J=8.4, 1.2 Hz, 1H), 7.17 (s, 1H), 7.09 (dd, J=8.8, 2.4 Hz, 1H), 6.92 (d, J=8.8 Hz, 1H), 6.75 (t, J=6.8 Hz, 1H), 4.39-4.37 (m, 3H), 3.75-3.73 (m, 4H), 3.31-3.29 (m, 4H), 1.87-1.84 (m, 2H), 1.59-1.51 (m, 8H), 1.38-1.27 (m, 6H).

Example 55

1-((6-(heptyloxy)naphthalen-2-yl)methyl)-4-(pyridin-2-yl)piperazine

Step 1: 2-bromo-6-(heptyloxy)naphthalene

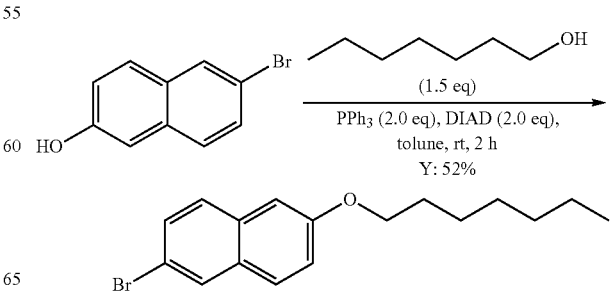

The preparation of 2-bromo-6-(heptyloxy)naphthalene was the same as that of 2-bromo-6-((cis-4-isopropylcyclohexyl)oxy)naphthalene. 1.2 g, as a yellow solid, Y: 52%. ESI-MS (M+H)⁺: 321.1. ¹H NMR (400 MHz, CDCl₃) δ: 7.88 (d, J=2.0 Hz, 1H), 7.60 (d, J=9.2 Hz, 1H), 7.55 (d, J=8.4 Hz, 1H), 7.46 (dd, J=8.8, 2.0 Hz, 1H), 7.14 (dd, J=8.8, 2.4 Hz, 1H), 7.05 (d, J=2.8 Hz, 1H), 4.02 (t, J=6.8 Hz, 2H), 1.85-1.79 (m, 2H), 1.51-1.44 (m, 2H), 1.40-1.24 (m, 6H), 0.90 (t, J=6.8 Hz, 3H).

Step 2: 6-(heptyloxy)-2-naphthaldehyde

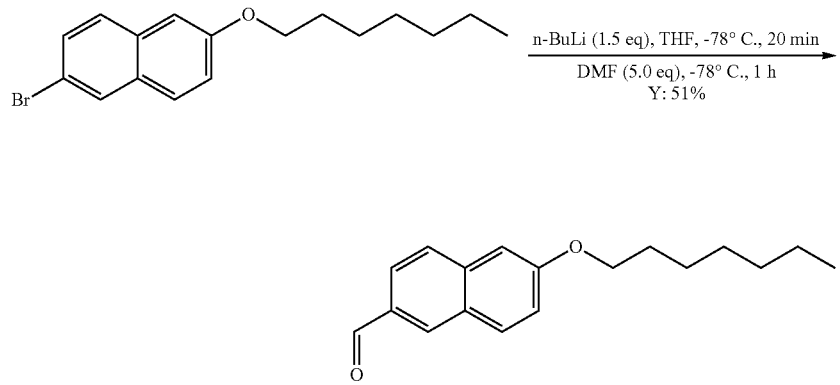

The preparation of 6-(heptyloxy)-2-naphthaldehyde was the same as that of 6-((cis-4-isopropylcyclohexyl)oxy)-2-naphthaldehyde. 516 mg, as a yellow solid, Y: 51%. ESI-MS (M+H)⁺: 270.1.

Step 3: 1-((6-(heptyloxy)naphthalen-2-yl)methyl)-4-(pyridin-2-yl)piperazine

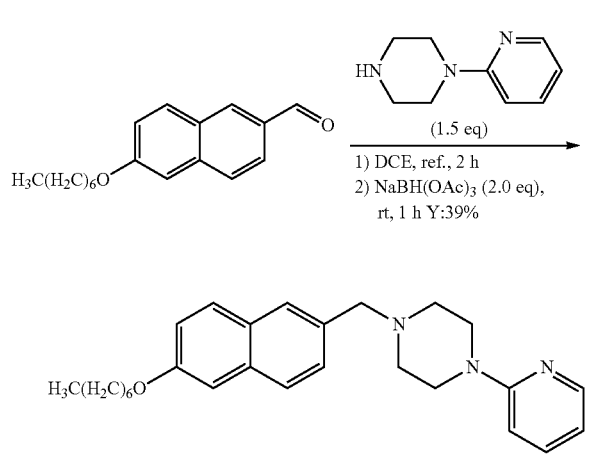

The preparation of 1-((6-(heptyloxy)naphthalen-2-yl)methyl)-4-(pyridin-2-yl)piperazine was the same as that of 1-((6-((cis-4-isopropylcyclohexyl)oxy)naphthalen-2-yl)methyl)-4-(pyridin-2-yl)piperazine. 29 mg, as a yellow solid, Y: 39%. ESI-MS (M+H)⁺: 418.2, HPLC: 100.00%. ¹H NMR (400 MHz, CD₃OD) δ: 8.12 (d, J=3.6 Hz, 1H), 7.91 (s, 1H), 7.84 (d, J=8.8 Hz, 1H), 7.79 (d, J=8.8 Hz, 1H), 7.60 (td, J=8.0, 2.0 Hz, 1H), 7.51 (d, J=8.0 Hz, 1H), 7.22 (s, 1H), 7.19 (dd, J=8.8, 2.0 Hz, 1H), 6.86 (d, J=8.4 Hz, 1H), 6.75 (dd, J=6.8, 5.2 Hz, 1H), 5.00-4.96 (m, 2H), 4.41 (s, 2H), 4.03 (t, J=6.4 Hz, 2H), 3.79-3.77 (m, 2H), 3.32-3.30 (m, 4H), 1.82-1.75 (m, 2H), 1.50-1.30 (m, 8H), 0.90 (t, J=6.8 Hz, 3H).

Example 56

6-((cis-4-isopropylcyclohexyl)oxy)-2-((4-(pyridin-2-yl)piperazin-1-yl)methyl)quinoline Step 1: 6-((cis-4-isopropylcyclohexyl)oxy)-2-methylquinoline

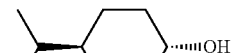
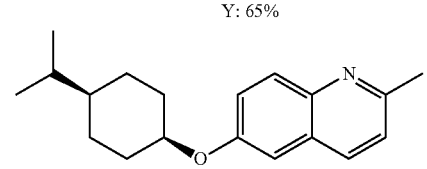

To a mixture of 2-methylquinolin-6-ol (2.0 g, 12.6 mmol, 1.0 eq), trans-4-isopropyl cyclohexanol (1.96 g, 13.8 mmol, 1.1 eq) and PPh₃ (3.96 g, 15.1 mmol, 1.2 eq) in dry toluene (60 mL) was quickly added DIAD (3.05 g, 15.1 mmol, 1.2 eq) in one portion at 0° C. under N₂. Then the reaction mixture was stirred at room temperature for 24 h. The solvent was removed in vacuum and the residue was purified by silica gel column (PE:EA=10:1) to give 6-((cis-4-isopropylcyclohexyl)oxy)-2-methylquinoline as yellow oil (2.43 g, Y: 65%). ESI-MS (M+H)⁺: 284.1. ¹H NMR (400 MHz, CDCl₃) δ: 7.91 (d, J=9.2 Hz, 1H), 7.90 (d, J=8.0 Hz, 1H), 7.35 (dd, J=9.2, 2.8 Hz, 1H), 7.21 (d, J=8.0 Hz, 1H), 7.07 (d, J=2.4 Hz, 1H), 4.66-4.64 (m, 1H), 2.70 (s, 3H), 2.14-2.10 (m, 2H), 1.57-1.47 (m, 7H), 1.26-1.23 (m, 1H), 0.91-085 (m, 6H).

Step 2: 6-((cis-4-isopropylcyclohexyl)oxy)quinoline-2-carbaldehyde

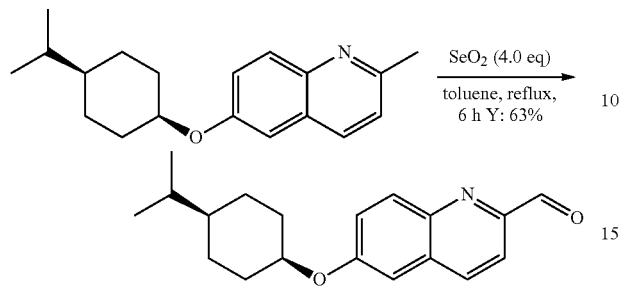

To a solution of 6-((cis-4-isopropylcyclohexyl)oxy)-2-methylquinoline (2.34 g, 8.27 mmol, 1.0 eq) in dry toluene (100 mL) was added SeO$_2$ (3.67 g, 33.1 mmol, 4.0 eq). The reaction mixture was heated to reflux with stirring for 6 h. After cooling to room temperature and filtration, the filtrate was concentrated in vacuo. The residue was purified by silica gel column (PE/EA=10:1) to give 6-((cis-4-isopropylcyclohexyl)oxy)quinoline-2-carbaldehyde as a pale yellow solid (1.5 g, Y: 63%). ESI-MS (M+H)$^+$: 298.1. $^1$H NMR (400 MHz, CDCl$_3$) δ: 10.19 (s, 1H), 8.15-8.13 (m, 2H), 7.98 (d, J=8.4 Hz, 1H), 7.50 (dd, J=9.2, 2.8 Hz, 1H), 7.13 (d, J=2.8 Hz, 1H), 4.75-4.73 (m, 1H), 2.17-2.13 (m, 2H), 1.66-1.47 (m, 7H), 1.18-1.16 (m, 1H), 0.91 (d, J=6.8 Hz, 6H).

Step 3

6-((cis-4-isopropylcyclohexyl)oxy)-2-((4-(pyridin-2-yl)piperazin-1-yl)methyl)quinoline

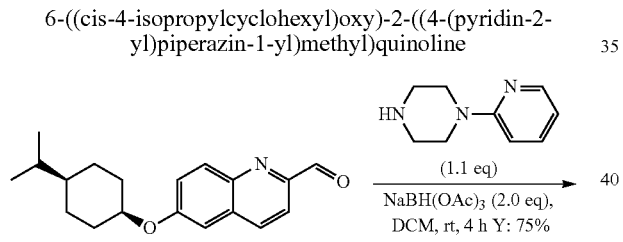

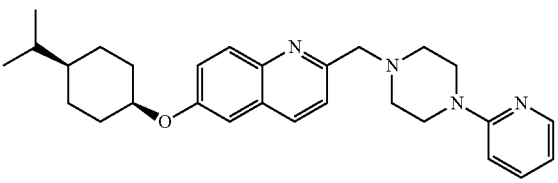

The preparation of 6-((cis-4-isopropylcyclohexyl)oxy)-2-((4-(pyridin-2-yl)piperazin-1-yl)methyl)quinoline was the same as that of 1-((6-((cis-4-isopropylcyclohexyl)oxy)naphthalen-2-yl)methyl)-4-(pyridin-2-yl)piperazine. 135 mg, as pale yellow gum, Y: 75%. ESI-MS (M+H)$^+$: 445.3, HPLC: 99.31%-99.36%. $^1$H NMR (400 MHz, CD$_3$OD) δ: 8.41 (d, J=8.4 Hz, 1H), 8.13 (dd, J=5.6, 1.6 Hz, 1H), 8.07 (d, J=9.2 Hz, 1H), 7.86-7.85 (m, 1H), 7.60 (d, J=8.4 Hz, 1H), 7.54 (dd, J=9.2, 2.4 Hz, 1H), 7.40 (d, J=2.4 Hz, 1H), 7.18 (d, J=9.2 Hz, 1H), 6.95-6.92 (m, 1H), 4.82-4.80 (m, 1H), 4.62 (s, 2H), 3.97-3.94 (m, 4H), 3.49-3.47 (m, 4H), 2.17-2.13 (m, 2H), 1.67-1.68 (m, 7H), 1.24-1.20 (m, 1H), 0.93 (d, J=6.8 Hz, 6H).

Example 57

3-(1-((6-((cis-4-isopropylcyclohexyl)oxy)naphthalen-2-yl)methyl)azetidin-3-yl)cyclohexanecarboxylic acid Step 1: methyl 3-(1-((6-((cis-4-isopropylcyclohexyl)oxy)naphthalen-2-yl)methyl)azet)meth)azetidin-3-yl)cyclohexanecarboxylate

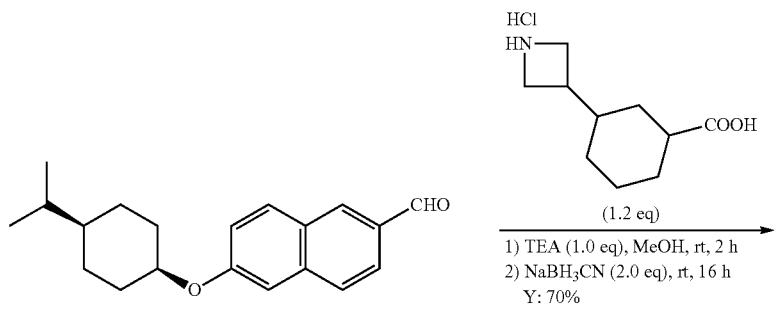

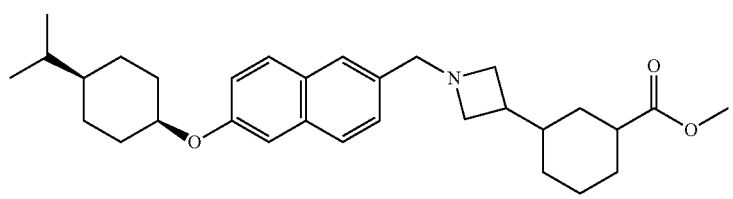

To a mixture of 6-((cis-4-isopropylcyclohexyl)oxy)-2-naphthaldehyde (160 mg, 0.54 mmol, 1.0 eq) and 3-(azetidin-3-yl)cyclohexanecarboxylic acid hydrochloride (142 mg, 0.648 mmol, 1.2 eq) in MeOH (10 mL) was added TEA (55 mg, 0.54 mmol, 1.0 eq). The mixture was stirred at room temperature for 2 h. Then NaBH$_3$CN (68 mg, 1.08 mmol, 2.0 eq) was added and stirred at room temperature for 16 h. After concentration, the residue was purified by pre-HPLC to give methyl 3-(1-((6-((cis-4-isopropylcyclohexyl)oxy)naphthalen-2-yl)methyl)azetidin-3-yl)cyclohexanecarboxylate as a white solid (180 mg, Y: 70%). ESI-MS (M+H)$^+$: 478.4.

Step 2: 3-(1-((6-((cis-4-isopropylcyclohexyl)oxy)naphthalen-2-yl)methyl)azetidin-3-yl)cyclohexanecarboxylic acid

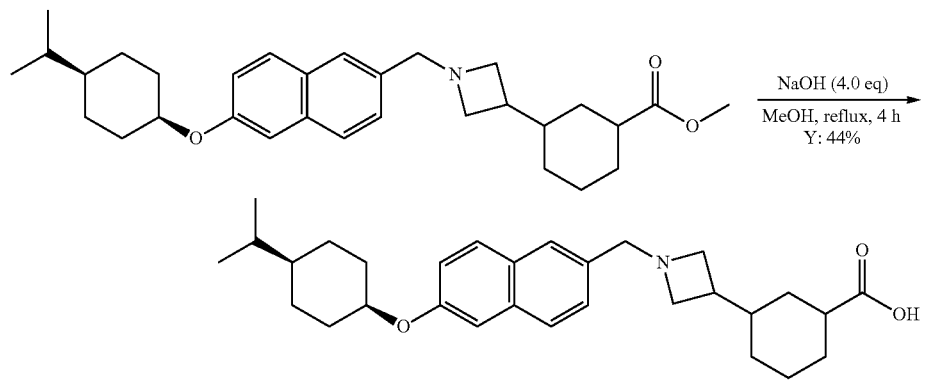

To a solution of methyl 3-(1-((6-((cis-4-isopropylcyclohexyl)oxy)naphthalen-2-yl)methyl)azetidin-3-yl)cyclohexanecarboxylate (180 mg, 0.38 mmol, 1.0 eq) in MeOH (10 mL) was added NaOH (61 mg, 1.52 mmol, 4.0 eq) in H$_2$O (1 mL). The reaction solution was heated to 65° C. for 4 h with stirring. After cooling down to rt, 1 N HCl was added to adjust pH=6. Then the solvent was evaporated in vacuo to give yellow solid, which was purified by pre-HPLC to give 3-(1-((6-((cis-4-isopropylcyclohexyl)oxy)naphthalen-2-yl)methyl)azetidin-3-yl)cyclohexa necarboxylic acid. 77 mg, as a white solid, Y: 44%. ESI-MS (M+H)$^+$: 464.3, HPLC: 100.00%. $^1$H NMR (400 MHz, CD$_3$OD) δ: 7.90 (s, 1H), 7.84 (d, J=8.8 Hz, 2H), 7.45 (d, J=8.4 Hz, 1H), 7.28 (d, J=2.0 Hz, 1H), 7.24 (dd, J=8.8, 2.4 Hz, 1H), 4.76-4.75 (m, 1H), 4.52-4.43 (m, 2H), 4.23-3.96 (m, 4H), 2.68-2.58 (m, 1H), 2.36-2.28 (m, 1H), 2.14-2.11 (m, 2H), 2.01-1.85 (m, 3H), 1.68-1.45 (m, 9H), 1.37-1.30 (m, 2H), 1.24-1.17 (m, 1H), 1.03-0.78 (m, 8H).

Example 58

3-(1-((6-((trans-4-(tert-butyl)cyclohexyl)oxy)naphthalen-2-yl)methyl)azetidin-3-yl)cyclohexanecarboxylic acid Step 1: methyl 3-(1-((6-((trans-4-(tert-butyl)cyclohexyl)oxy)naphthalen-2-yl)methyl)azetidin-3-yl)cyclohexanecarboxylate

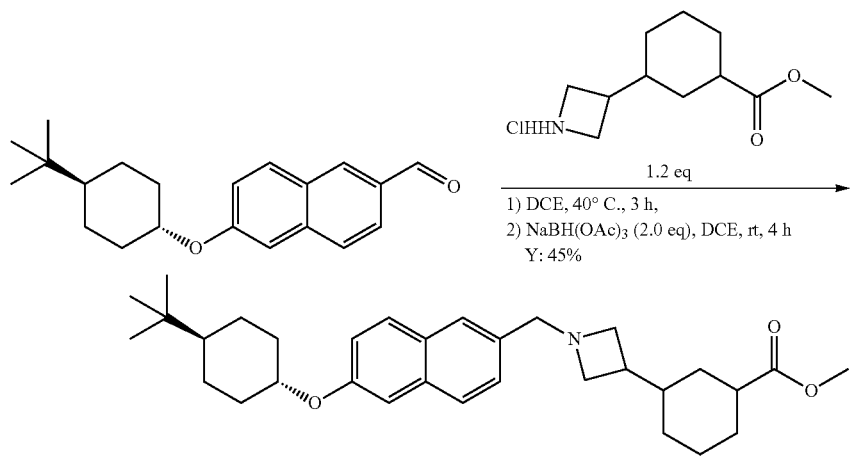

The preparation of methyl 3-(1-((6-((trans-4-(tert-butyl)cyclohexyl)oxy)naphthalen-2-yl)methyl)azetidin-3-yl)cyclohexanecarboxylate was the same as that of methyl 3-(1-

((6-((cis-4-isopropylcyclohexyl)oxy)naphthalen-2-yl)methyl)azetidin-3-yl)cyclohexanecarboxylate. 80 mg, as a yellow solid, Y: 45%. ESI-MS (M+H)+: 492.3.

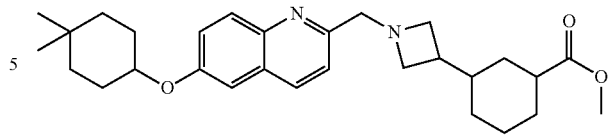

Step 2: 3-(1-((6-(((trans-4-(tert-butyl)cyclohexyl)oxy)naphthalen-2-yl)methyl)azetidin-3-yl)cyclohexanecarboxylic acid

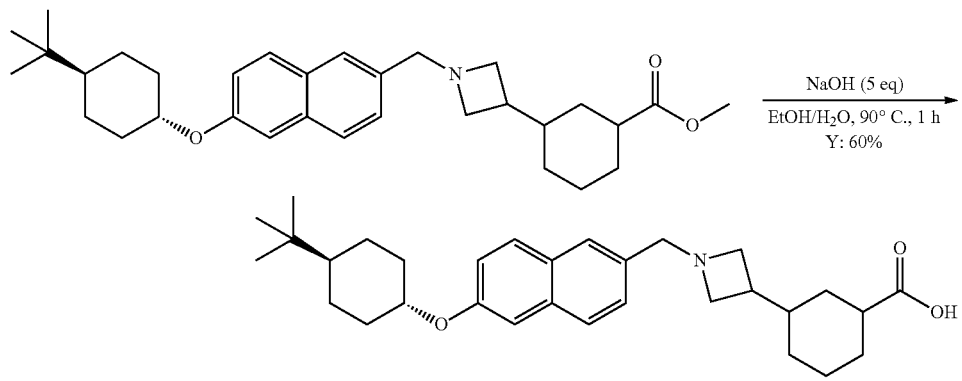

The preparation of 3-(1-((6-(((trans-4-(tert-butyl)cyclohexyl)oxy)naphthalen-2-yl)methyl)azetidin-3-yl)cyclohexanecarboxylic acid was the same as that of 3-(1-((6-((cis-4-isopropylcyclohexyl)oxy)naphthalen-2-yl)methyl)azetidin-3-yl)cyclohexa necarboxylic acid. 40 mg, as a white solid, Y: 60%. ESI-MS (M+H)+: 478.3, HPLC: 100.00%. $^1$H NMR (400 MHz, CDCl$_3$) δ: 7.75-7.67 (m, 3H), 7.47 (dd, J=8.4, 16 Hz, 1H), 7.16-7.12 (m, 2H), 4.30-4.23 (m, 1H), 4.17 (s, 2H), 3.97-3.88 (m, 4H), 3.61-3.48 (m, 2H), 2.56-2.52 (m, 1H), 2.27-2.20 (m, 3H), 2.03-1.75 (m, 4H), 1.52-1.37 (m, 5H), 1.28-1.05 (m, 5H), 0.89 (s, 9H).

Example 59

3-(1-((6-((4,4-dimethylcyclohexyl)oxy)quinolin-2-yl)methyl)azetidin-3-yl)cyclohexane carboxylic acid Step 1: methyl 3-(1-((6-((4,4-dimethylcyclohexyl)oxy)quinolin-2-yl)methyl)azetidin-3-yl)cyclohexanecarboxylate

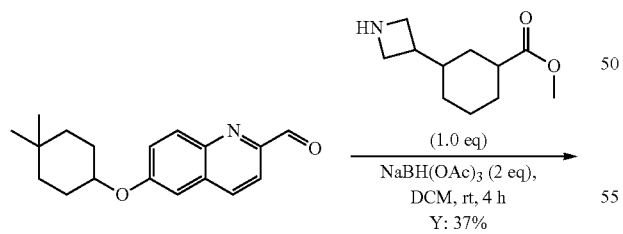

Step 2: 3-(1-((6-((4,4-dimethylcyclohexyl)oxy)quinolin-2-yl)methyl)azetidin-3-yl)cyclohexanecarboxylic acid

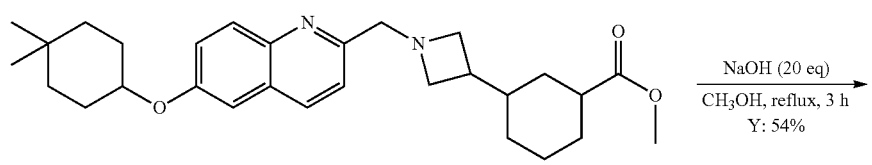

The preparation of methyl 3-(1-((6-((4,4-dimethylcyclohexyl)oxy)quinolin-2-yl)methyl)azetidin-3-yl)cyclohexanecarboxylate was the same as that of methyl 3-(1-((6-((cis-4-isopropylcyclohexyl)oxy)naphthalen-2-yl)methyl)azetidin-3-yl)cyclohexanecarboxylate. 78 mg, as yellow gum, Y: 37%. ESI-MS (M+H)+: 465.3. $^1$H NMR (400 MHz, CDCl$_3$) δ: 8.23 (d, J=8.4 Hz, 1H), 8.09 (d, J=9.2 Hz, 1H), 7.88 (d, J=8.4 Hz, 1H), 7.47 (dd, J=9.2, 2.8 Hz, 1H), 7.13 (d, J=2.4 Hz, 1H), 4.62 (s, 2H), 4.45-4.42 (m, 1H), 4.23-4.21 (m, 2H), 4.01-3.99 (m, 2H), 3.65 (s, 3H), 2.66-2.64 (m, 1H), 2.37-2.35 (m, 1H), 1.98-1.92 (m, 3H), 1.86-1.75 (m, 4H), 1.58-1.54 (m, 3H), 1.36-1.28 (m, 6H), 1.00 (s, 3H), 0.99 (s, 3H), 0.88-0.85 (m, 1H).

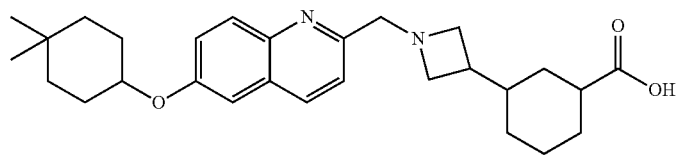

The preparation of 3-(1-((6-((4,4-dimethylcyclohexyl)oxy)quinolin-2-yl)methyl)azetidin-3-yl)cyclohexanecarboxylic acid was the same as that of 3-(1-((6-((cis-4-isopropylcyclohexyl)oxy)naphthalen-2-yl)methyl)azetidin-3-yl)cyclohexa necarboxylic acid. 36 mg, as yellow gum, Y: 54%. ESI-MS (M+H)$^+$: 451.2, HPLC: 96.10%-98.29%. $^1$H NMR (400 MHz, CD$_3$OD) δ: 8.24 (d, J=8.4 Hz, 1H), 7.98 (d, J=9.6 Hz, 1H), 7.43-7.39 (m, 2H), 7.30 (d, J=2.4 Hz, 1H), 4.72 (s, 2H), 4.54-4.49 (m, 1H), 4.39-4.38 (m, 2H), 4.10-4.08 (m, 2H), 2.78-2.70 (m, 1H), 2.35-2.32 (m, 1H), 1.98-1.94 (m, 5H), 1.78-1.72 (m, 7H), 1.41-1.36 (m, 4H), 1.01 (s, 3H), 1.00 (s, 3H), 0.88-0.86 (m, 1H).

Example 60

3-(1-((6-(heptyloxy)naphthalen-2-yl)methyl)azetidin-3-yl)cyclohexanecarboxylic acid Step 1: methyl 3-(1-((6-(heptyloxy)naphthalen-2-yl)methyl)azetidin-3-yl)cyclohexanecarboxylate

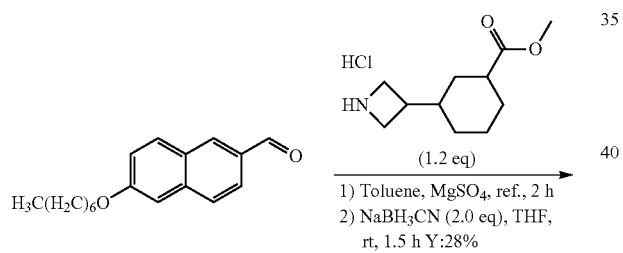

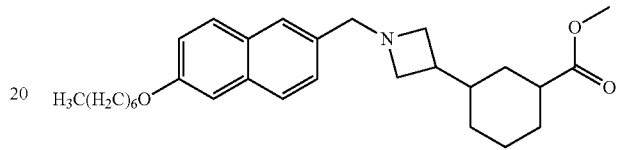

The preparation of methyl 3-(1-((6-(heptyloxy)naphthalen-2-yl)methyl)azetidin-3-yl)cyclohexanecarboxylate was the same as that of methyl 3-(1-((6-((cis-4-isopropylcyclohexyl)oxy)naphthalen-2-yl)methyl)azetidin-3-yl)cyclohexanecarboxylate. 1.2 g, as a yellow solid, Y: 28%. ESI-MS (M+H)$^+$: 452.3.

Step 2: 3-(1-((6-(heptyloxy)naphthalen-2-yl)methyl)azetidin-3-yl)cyclohexanecarboxylic acid

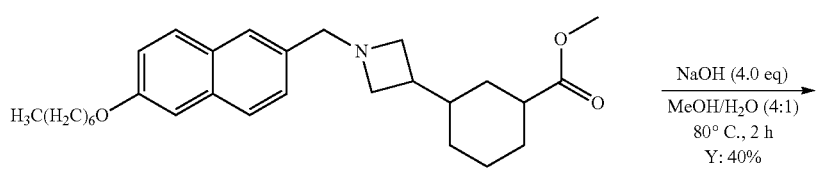

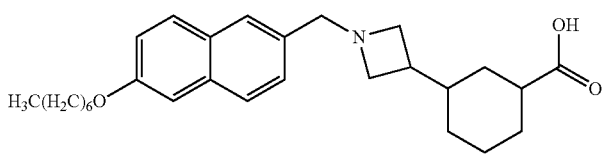

The preparation of 3-(1-((6-(heptyloxy)naphthalen-2-yl)methyl)azetidin-3-yl)cyclohexanecarboxylic acid was the same as that of 3-(1-((6-((cis-4-isopropylcyclohexyl)oxy)naphthalen-2-yl)methyl)azetidin-3-yl)cyclohexa necarboxylic acid. 22 mg, as a yellow solid, Y: 40%. ESI-MS (M+H)⁺: 438.0, HPLC: 100.00%. ¹H NMR (400 MHz, CD₃OD) δ: 7.91 (s, 1H), 7.85 (d, J=8.4 Hz, 1H), 7.82 (d, J=8.8 Hz, 1H), 7.47 (dd, J=8.4, 1.2 Hz, 1H), 7.25 (d, J=2.0 Hz, 1H), 7.20 (dd, J=8.8, 2.0 Hz, 1H), 4.93 (s, 2H), 4.16-4.08 (m, 4H), 4.00-3.96 (m, 2H), 2.64-2.59 (m, 1H), 2.26-2.24 (m, 1H), 2.00-1.84 (m, 5H), 1.65-1.52 (m, 4H), 1.50-1.28 (m, 8H), 1.01-0.90 (m, 5H).

Example 61

3-(1-((6-((cis-4-ethylcyclohexyl)oxy)naphthalen-2-yl)methyl)azetidin-3-yl)cyclohexanecarboxylic acid Step 1: methyl 3-(1-((6-((-4-ethylcyclohexyl)oxy)naphthalen-2-yl)methyl)azetidin-3-yl)cyclohexanecarboxylate

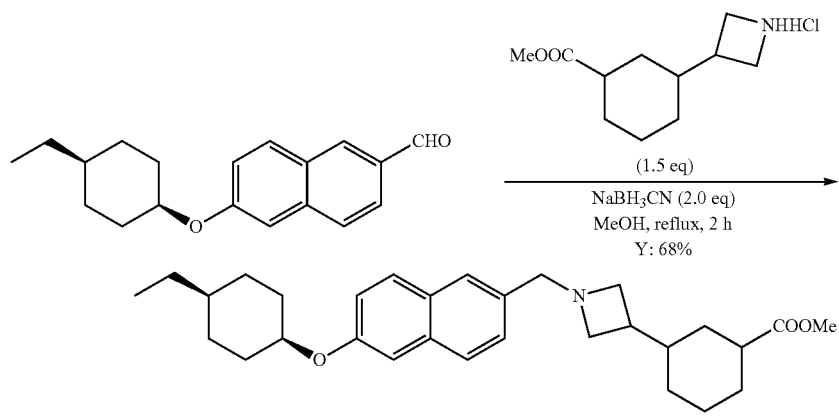

The preparation of methyl 3-(1-((6-((cis-4-ethylcyclohexyl)oxy)naphthalen-2-yl)methyl)azetidin-3-yl)cyclohexanecarboxylate was the same as that of methyl 3-(1-((6-((cis-4-isopropylcyclohexyl)oxy)naphthalen-2-yl)methyl)azetidin-3-yl)cyclohexanecarboxylate. 100 mg, as a white solid, Y: 68%. ESI-MS (M+H)⁺: 464.3.

Step 2: 3-(1-((6-((cis-4-ethylcyclohexyl)oxy)naphthalen-2-yl)methyl)azetidin-3-yl)cyclohexanecarboxylic acid

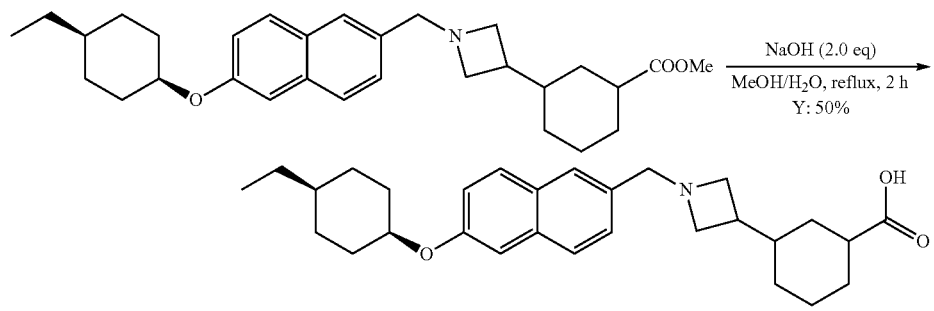

The preparation of 3-(1-((6-((cis-4-ethylcyclohexyl)oxy)naphthalen-2-yl)methyl)azetidin-3-yl)cyclohexanecarboxylic acid was the same as that of 3-(1-((6-((cis-4-isopropylcyclohexyl)oxy)naphthalen-2-yl)methyl)azetidin-3-yl)cyclohexa necarboxylic acid. 40 mg, as a white solid, Y: 50%. ESI-MS (M+H)⁺: 450.2, HPLC: 98.19%. ¹H NMR (400 MHz, CD₃OD) δ: 7.90 (s, 1H), 7.83 (d, J=8.8 Hz, 2H), 7.45 (dd, J=8.4, 1.6 Hz, 1H), 7.28 (s, 1H), 7.22 (d, J=9.2 Hz, 1H), 4.76-4.73 (m, 1H), 4.43 (br, 2H), 4.14-4.08 (m, 2H), 4.04-3.95 (m, 2H), 2.65-2.61 (m, 1H), 2.35-2.30 (m, 2H), 2.08-1.84 (m, 5H), 1.69-1.58 (m, 6H), 1.46-1.30 (m, 7H), 0.96-0.79 (m, 4H).

Example 62

3-(1-((6-((4,4-dimethylcyclohexyl)oxy)naphthalen-2-yl)methyl)azetidin-3-yl)cyclohexanecarboxylic acid

Step 1: methyl 3-(1-((6-((4,4-dimethylcyclohexyl)oxy)naphthalen-2-yl)methyl)azetidin-3-yl)cyclohexanecarboxylate

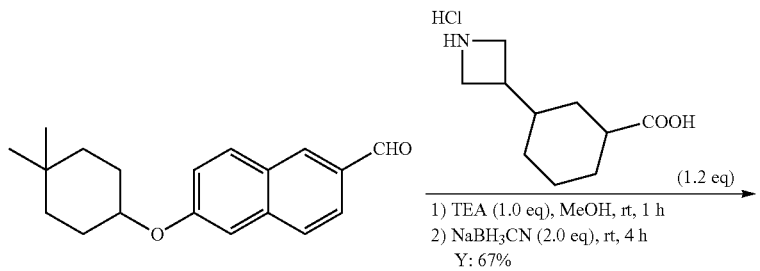

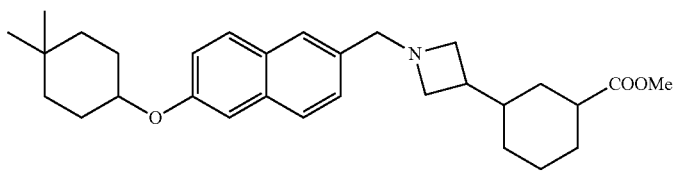

The preparation of methyl 3-(1-((6-((4,4-dimethylcyclohexyl)oxy)naphthalen-2-yl)methyl)azetidin-3-yl)cyclohexane carboxylate was the same as that of methyl 3-(1-((6-((cis-4-isopropylcyclohexyl)oxy)naphthalen-2-yl)methyl)azetidin-3-yl)cyclohexanecarboxylate. 110 mg, as a white solid, Y: 67%. ESI-MS (M+H)$^+$: 464.3.

Step 2: 3-(1-((6-((4,4-dimethylcyclohexyl)oxy)naphthalen-2-yl)methyl)azetidin-3-yl)cyclohexane carboxylic acid

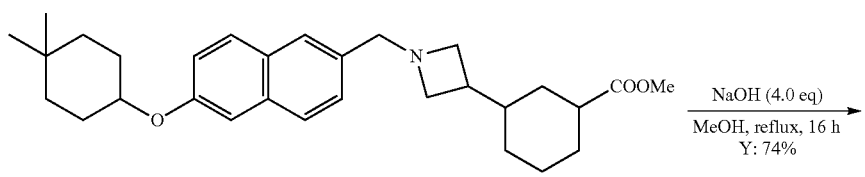

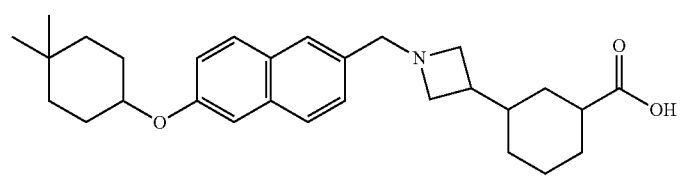

The preparation of 3-(1-((6-((4,4-dimethylcyclohexyl)oxy)naphthalen-2-yl)methyl)azetidin-3-yl)cyclohexane carboxylic acid was the same as that of 3-(1-((6-((cis-4-isopropylcyclohexyl)oxy)naphthalen-2-yl)methyl)azetidin-3-yl)cyclohexa necarboxylic acid. 78 mg, as a white solid, Y: 74%. ESI-MS (M+H)$^+$: 450.3, HPLC: 100.00%. $^1$H NMR (400 MHz, CD$_3$OD) δ: 7.78 (s, 1H), 7.72 (d, J=8.0 Hz, 1H), 7.70 (d, J=8.8 Hz, 1H), 7.34 (d, J=8.8 Hz, 1H), 7.15 (d, J=2.0 Hz, 1H), 7.09 (dd, J=8.8, 2.4 Hz, 1H), 4.39-4.29 (m, 3H), 4.08-3.97 (m, 2H), 3.90-3.84 (m, 2H), 2.55-2.46 (m, 1H), 2.21-2.15 (m, 1H), 1.88-1.71 (m, 5H), 1.66-1.41 (m, 6H), 1.27-1.16 (m, 4H), 0.88-0.66 (m, 8H).

Example 63

3-(1-((6-(spiro[4.5]decan-8-yloxy)naphthalen-2-yl)methyl)azetidin-3-yl)cyclohexanecarboxylic acid Step 1: methyl 3-(1-((6-(spiro[4.5]decan-8-yloxy)naphthalen-2-yl)methyl)azetidin-3-yl)cyclohexanecarboxylate

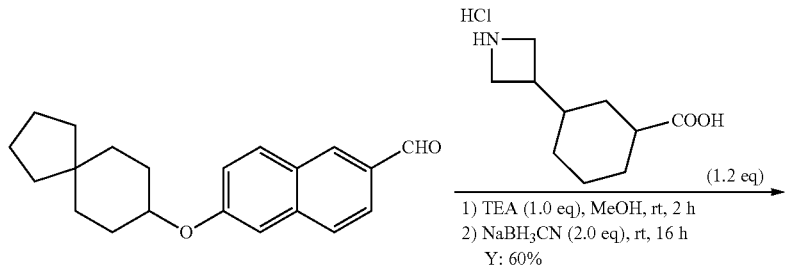

The preparation of methyl 3-(1-((6-(spiro[4.5]decan-8-yloxy)naphthalen-2-yl)methyl)azetidin-3-yl)cyclohexanecarboxylate was the same as that of methyl 3-(1-((6-((cis-4-isopropylcyclohexyl)oxy)naphthalen-2-yl)methyl)azetidin-3-yl)cyclohexanecarboxylate. 160 mg, as a white solid, Y: 60%. ESI-MS (M+H)$^+$: 490.3.

Step 2: 3-(1-((6-(spiro[4.5]decan-8-yloxy)naphthalen-2-yl)methyl)azetidin-3-yl)cyclohexanecarboxylic acid The preparation of 3-(1-((6-(spiro[4.5]decan-8-yloxy)naphthalen-2-yl)methyl)azetidin-3-yl)cyclohexanecarboxylic acid was the same as that of 3-(1-((6-((cis-4-isopropylcyclohexyl)oxy)naphthalen-2-yl)methyl)azetidin-3-yl)cyclohexa necarboxylic acid. 113 mg, as a white solid, Y: 60%. ESI-MS (M+H)$^+$: 446.2, HPLC: 100.00%. $^1$H NMR (400 MHz, CD$_3$OD) δ: 7.90 (s, 1H), 7.85 (d, J=8.8 Hz, 1H), 7.82 (d, J=8.8 Hz, 1H), 7.46 (d, J=8.4 Hz, 1H), 7.29 (d, J=2.0 Hz, 1H), 7.20 (dd, J=9.2, 2.4 Hz, 1H), 4.55-4.50 (m, 2H), 4.43-4.41 (m, 1H), 4.22-3.97 (m, 4H), 2.68-2.58 (m, 1H), 2.33-2.28 (m, 1H), 2.01-1.84 (m, 5H), 1.73-1.61 (m, 10H), 1.56-1.41 (m, 6H), 1.37-1.28 (m, 2H), 1.02-0.80 (m, 2H).

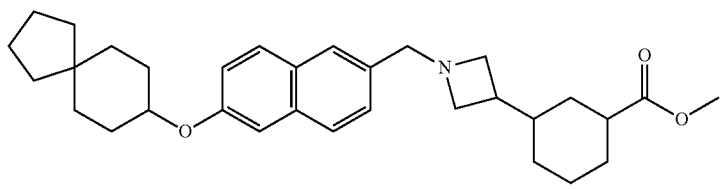

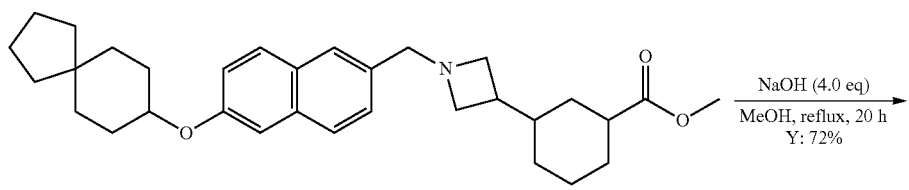

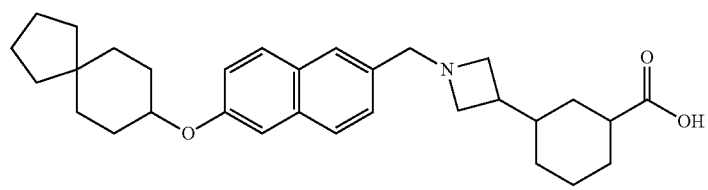

Example 64

3-(1-((6-((cis-4-ethylcyclohexyl)oxy)quinolin-2-yl)methyl)azetidin-3-yl)cyclohexanecarboxylic acid Step 1: methyl 3-(1-((6-((cis-4-ethylcyclohexyl)oxy)quinolin-2-yl)methyl)azetidin-3-yl)cyclohexanecarboxylate

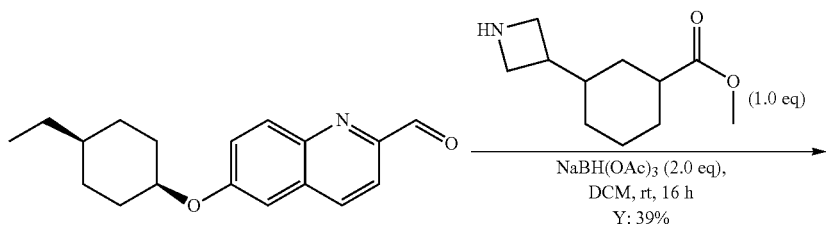

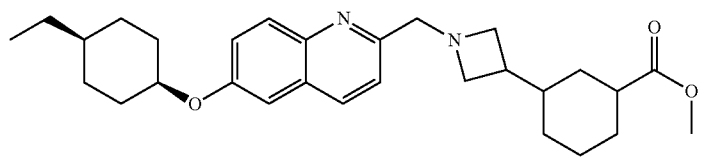

The preparation of methyl 3-(1-((6-((cis-4-ethylcyclohexyl)oxy)quinolin-2-yl)methyl)azetidin-3-yl)cyclohexanecarboxylate was the same as that of methyl 3-(1-((6-((cis-4-isopropylcyclohexyl)oxy)naphthalen-2-yl)methyl)azetidin-3-yl)cyclohexanecarboxylate. 150 mg, as pale yellow gum, Y: 39%. ESI-MS (M+H)$^+$: 465.2. $^1$H NMR (400 MHz, CDCl$_3$) δ: 7.97 (d, J=8.0 Hz, 1H), 7.95 (d, J=8.0 Hz, 1H), 7.42 (d, J=8.8 Hz, 1H), 7.36 (dd, J=9.2, 2.8 Hz, 1H), 7.07 (d, J=2.4 Hz, 1H), 4.66-4.64 (m, 1H), 3.88 (s, 2H), 3.65 (s, 3H), 3.68-3.52 (m, 2H), 2.98-2.96 (m, 2H), 2.15-2.11 (m, 2H), 2.09-2.05 (m, 2H), 1.90-1.79 (m, 3H), 1.64-1.55 (m, 5H), 1.44-1.41 (m, 3H), 1.32-1.25 (m, 7H), 0.90 (t, J=7.6 Hz, 3H).

Step 2: 3-(1-((6-((cis-4-ethylcyclohexyl)oxy)quinolin-2-yl)methyl)azetidin-3-yl)cyclohexanecarboxylic acid The preparation o 3-(1-((6-((cis-4-ethylcyclohexyl)oxy)quinolin-2-yl)methyl)azetidin-3-yl)cyclohexanecarboxylic acid was the same as that of 3-(1-((6-((cis-4-isopropylcyclohexyl)oxy)naphthalen-2-yl)methyl)azetidin-3-yl)cyclohexanecarboxylic acid. 35 mg, as pale yellow gum, Y: 30%. ESI-MS (M+H)$^+$: 451.2, HPLC: 94.16%-98.14%. $^1$H NMR (400 MHz, CD$_3$OD) δ: 8.24 (d, J=8.8 Hz, 1H), 7.99 (d, J=9.2 Hz, 1H), 7.44 (dd, J=8.8, 2.4 Hz, 1H), 7.41 (d, J=8.8 Hz, 1H), 7.30 (d, J=2.4 Hz, 1H), 4.76-4.72 (m, 3H), 4.39-4.37 (m, 2H), 4.12-4.10 (m, 2H), 2.76-2.73 (m, 1H), 2.42-4.40 (m, 1H), 2.10-1.86 (m, 5H), 1.71-1.63 (m, 6H), 1.43-1.29 (m, 7H), 1.03-0.95 (m, 1H), 0.92 (t, J=7.2 Hz, 3H), 0.87-0.83 (m, 1H).

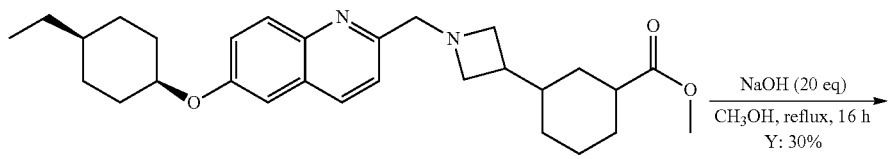

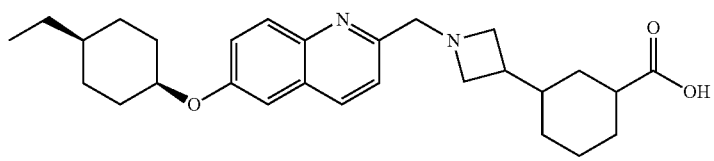

Example 65

3-(1-((6-((cis-4-isopropylcyclohexyl)oxy)quinolin-2-yl)methyl)azetidin-3-yl)cyclohexa necarboxylic acid

Step 1: methyl 3-(1-((6-((cis-4-isopropylcyclohexyl)oxy)quinolin-2-yl)methyl)azetidin-3-yl)cyclohexanecarboxylate

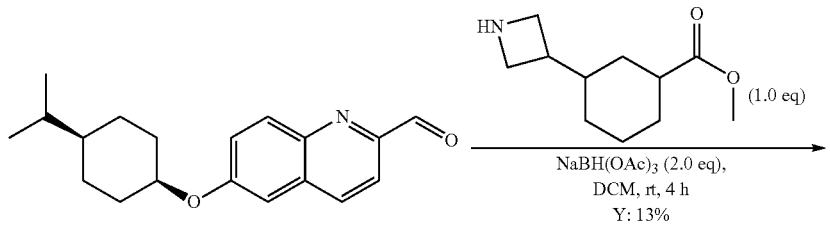

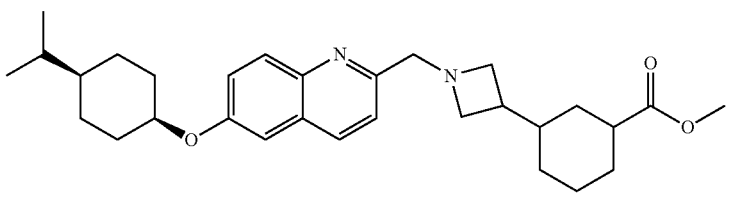

To a mixture of methyl 6-((cis-4-isopropylcyclohexyl)oxy)quinoline-2-carbaldehyde (200 mg, 0.673 mmol, 1.0 eq) and methyl 3-(azetidin-3-yl)cyclohexanecarboxylate (132 mg, 0.673 mmol, 1.0 eq) in DCM (40 mL) was added NaBH(OAc)$_3$ (285 mg, 1.346 mmol, 2.0 eq). The mixture was stirred for 4 h at room temperature. Then saturated aqueous NaHCO$_3$ was added to adjust pH=8 and extracted with EtOAc (50 mL×2). The combined organic phase was washed with water (15 mL) and brine (20 mL), dried over Na$_2$SO$_4$, filtered, and concentrated in vacuo. The residue was purified by silica gel column chromatography (EA) to give methyl 3-(1-((6-((cis-4-isopropylcyclohexyl)oxy)quinolin-2-yl)methyl)azetidin-3-yl)cyclohexane carboxylate as yellow gum (41 mg, Y: 13%). ESI-MS (M+H)$^+$: 479.3.

Step 2: 3-(1-((6-((cis-4-isopropylcyclohexyl)oxy)quinolin-2-yl)methyl)azetidin-3-yl)cyclohexanecarboxylic acid

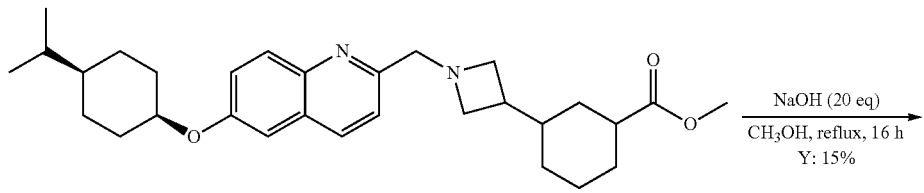

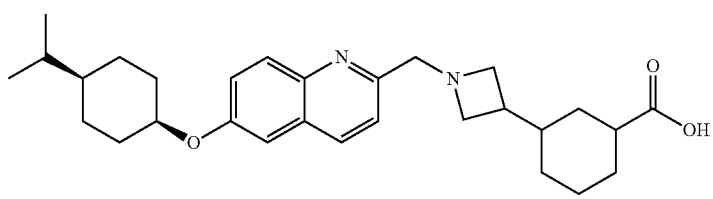

To the solution of methyl 3-(1-((6-((cis-4-isopropylcyclohexyl)oxy)quinolin-2-yl)methyl)azetidin-3-yl)cyclohexane carboxylate (35 mg, 0.073 mmol, 1.0 eq) in MeOH (20 mL) was added NaOH (58 mg, 1.46 mmol, 20.0 eq) in H$_2$O (4 ml). The reaction solution was heated to 80° C. for 16 h with stirring. After concentration, the residue was adjusted to pH=6 with 1N HCl, extracted with EtOAc (50 mL×2), washed with H$_2$O (15 mL) and brine (20 mL), dried over Na$_2$SO$_4$, filtered, and concentrated in vacuo. The residue was purified by pre-HPLC to give 3-(1-((6-((cis-4-isopropylcyclohexyl)oxy)quinolin-2-yl)methyl)azetidin-3-yl)cyclohexane carboxylic acid as colorless gum (5 mg, Y: 15%). ESI-MS (M+H)$^+$:465.2, HPLC: 95.96%-97.07%. $^1$H NMR (400 MHz, CD$_3$OD) δ: 8.11 (d, J=8.4 Hz, 1H), 7.86 (d, J=9.2 Hz, 1H), 7.37 (d, J=8.8 Hz, 1H), 7.34 (dd, J=9.2, 2.8 Hz, 1H), 7.19 (d, J=2.8 Hz, 1H), 4.68-4.67 (m, 1H), 4.06 (s, 2H), 3.75-3.71 (m, 2H), 3.34-3.30 (m, 2H), 2.06-2.02 (m, 3H), 1.82-1.72 (m, 3H), 1.56-1.41 (m, 9H), 1.25-1.20 (m, 6H), 0.84 (d, J=6.8 Hz, 6H).

Example 66

4-(1-((6-((trans-4-(tert-butyl)cyclohexyl)oxy)naphthalen-2-yl)methyl)azetidin-3-yl)cyclohexanecarboxylic acid

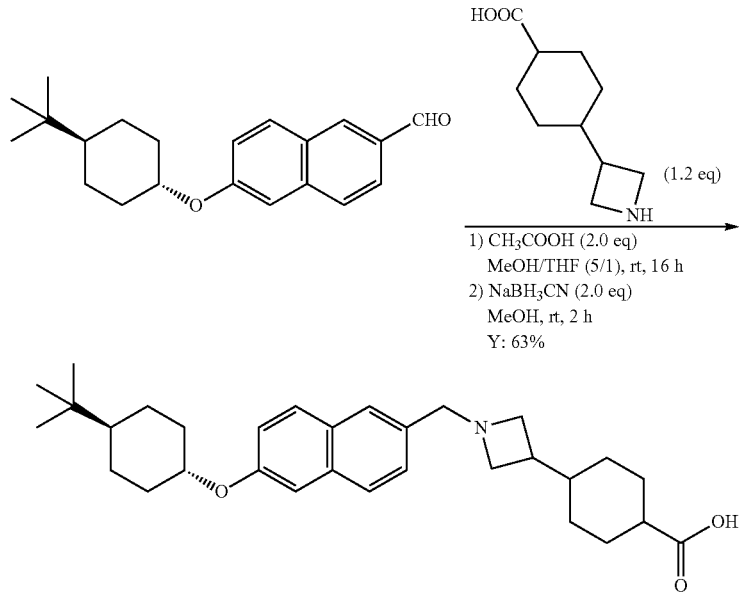

The preparation of 4-(1-((6-((trans-4-(tert-butyl)cyclohexyl)oxy)naphthalen-2-yl)methyl)azetidin-3-yl)cyclohexanecarboxylic acid was the same as that of 1-((6-(((cis-4-isopropylcyclohexyl)oxy)naphthalen-2-yl)methyl)-4-(pyridin-2-yl)piperazine. 85 mg, as a white solid, Y: 63%. ESI-MS (M+H)+: 478.3, HPLC: 100.00%. $^1$H NMR (400 MHz, CD$_3$OD) δ: 7.89 (s, 1H), 7.84 (d, J=8.0 Hz, 1H), 7.81 (d, J=9.2 Hz, 1H), 7.45 (d, J=8.8 Hz, 1H), 7.28 (d, J=1.6 Hz, 1H), 7.18 (dd, J=9.2, 2.0 Hz, 1H), 4.50-4.44 (m, 2H), 4.39-4.35 (m, 1H), 4.17-4.08 (m, 2H), 4.00-3.93 (m, 2H), 2.75-2.55 (m, 2H), 2.28-2.25 (m, 2H), 2.02-1.99 (m, 2H), 1.92-1.89 (m, 2H), 1.73-1.71 (m, 1H), 1.68-1.62 (m, 3H), 1.60-1.52 (m, 3H), 1.33-1.21 (m, 3H), 1.18-1.09 (m, 2H), 0.92 (s, 9H).

Example 67

6-((6-((trans-4-(tert-butyl)cyclohexyl)oxy)naphthalen-2-yl)methyl)-2-oxa-6-azaspiro[3.3]heptane

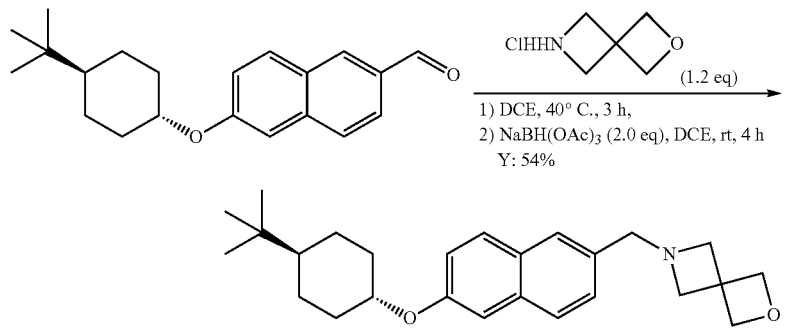

The preparation of 6-((6-((trans-4-(tert-butyl)cyclohexyl)oxy)naphthalen-2-yl)methyl)-2-oxa-6-azaspiro[3.3]heptane was the same as that of 2-(1-((6-((trans-4-(tert-butyl)cyclohexyl)oxy)naphthalen-2-yl)methyl)piperidin-4-yl)pyridine. 50 mg, as a yellow solid, Y: 54%. ESI-MS (M+H)+: 492.3, HPLC: 100.00%. $^1$H NMR (400 MHz, CD$_3$OD) δ: 7.72 (d, J=8.8 Hz, 1H), 7.71 (d, J=8.4 Hz, 1H), 7.64 (s, 1H), 7.33 (dd, J=8.4, 1.6 Hz, 1H), 7.21 (d, J=2.4 Hz, 1H), 7.09 (dd, J=8.8, 2.4 Hz, 1H), 4.73 (s, 4H), 4.35-4.30 (m, 1H), 3.72 (s, 2H), 3.51 (s, 4H), 2.28-2.25 (m, 2H), 1.92-1.87 (m, 2H), 1.45-1.36 (m, 2H), 1.30-1.20 (m, 2H), 1.15-1.08 (m, 1H), 0.91 (s, 9H).

Example 68

3-((6-((trans-4-(tert-butyl)cyclohexyl)oxy)naphthalen-2-yl)methyl)-3-azabicyclo[3.1.0]hexane-6-carboxylic acid Step 1: ethyl 3-((6-((trans-4-(tert-butyl)cyclohexyl)oxy)naphthalen-2-yl)methyl)-3-azabicyclo[3.1.1]hexane-6-carboxylate

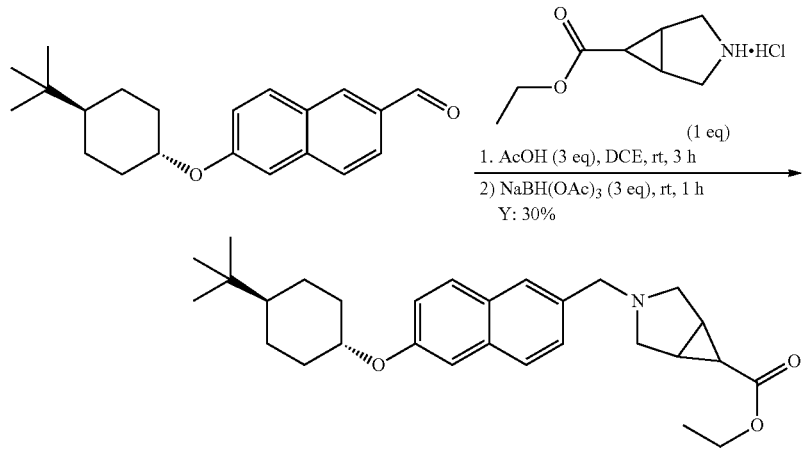

The preparation of ethyl 3-((6-((trans-4-(tert-butyl)cyclohexyl)oxy)naphthalen-2-yl)methyl)-3-azabicyclo[3.1.0]hexane-6-carboxylate was the same as that of methyl 4-(((6-((trans-4-(tert-butyl)cyclohexyl)oxy)quinolin-2-yl)methyl)amino)bicyclo[2.2.2]octane-1-carboxylate, 86 mg, as a yellow solid, Y: 30%. ESI-MS (M+H)$^+$: 450.3. $^1$H NMR (400 MHz, CDCl$_3$) δ: 7.75 (s, 1H), 7.72 (d, J=8.8 Hz, 2H), 7.40 (d, J=8.0 Hz, 1H), 7.18-7.13 (m, 2H), 4.31-4.24 (m, 3H), 4.12 (q, J=7.2 Hz, 2H), 3.79-3.72 (m, 2H), 3.28-3.25 (m, 2H), 2.41-2.39 (m, 1H), 2.24-2.19 (m, 4H), 1.91-1.88 (m, 2H), 1.48-1.37 (m, 2H), 1.26 (t, J=7.2 Hz, 3H), 1.17-1.02 (m, 3H), 0.90 (s, 9H).

Step 2: 3-((6-((trans-4-(tert-butyl)cyclohexyl)oxy)naphthalen-2-yl)methyl)-3-azabicyclo[3.1.0]hexane-6-carboxylic acid

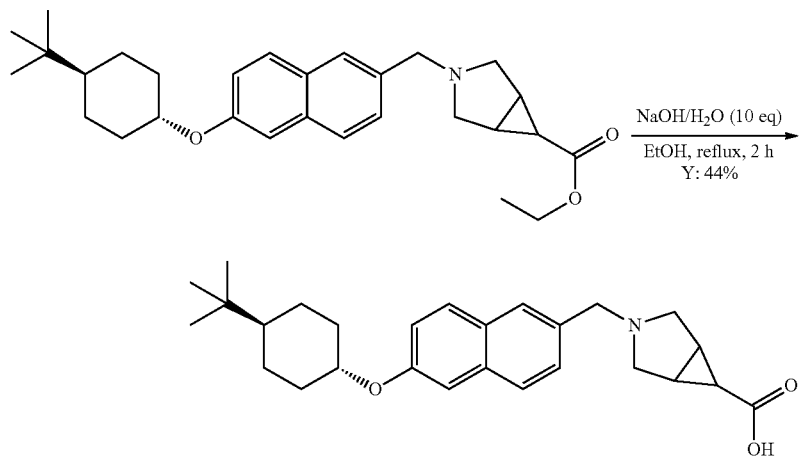

The preparation of 3-((6-((trans-4-(tert-butyl)cyclohexyl)oxy)naphthalen-2-yl)methyl)-3-azabicyclo[3.1.0]hexane-6-carboxylic acid was the same as that of 4-(((6-((trans-4-(tert-butyl)cyclohexyl)oxy)quinolin-2-yl)methyl)amino)bicyclo[2.2.2]octane-1-carboxylic acid. 35 mg, as a yellow solid, Y: 44%. ESI-MS (M+H)$^+$: 422.3, HPLC: 97.51%. $^1$H NMR (400 MHz, CD$_3$OD) δ: 7.82 (s, 1H), 7.79-7.75 (m, 2H), 7.44 (dd, J=8.4, 1.2 Hz, 1H), 7.24 (d, J=2.4 Hz, 1H), 7.14 (dd, J=8.8, 2.0 Hz, 1H), 4.35-4.32 (m, 1H), 4.28 (s, 2H), 3.44-3.36 (m, 4H), 2.26-2.23 (m, 2H), 2.17-2.15 (m, 2H), 1.94-1.87 (m, 3H), 1.43-1.35 (m, 2H), 1.28-1.22 (m, 2H), 1.12-1.06 (m, 1H), 0.90 (s, 9H).

Example 69

4-(((6-((trans-4-(tert-butyl)cyclohexyl)oxy)quinolin-2-yl)methyl)amino)bicyclo[2.2.2]octane-1-carboxylic acid

Step 1: methyl 4-(((6-((trans-4-(tert-butyl)cyclohexyl)oxy)quinolin-2-yl)methyl)amino)bicyclo[2.2.2]octane-1-carboxylate

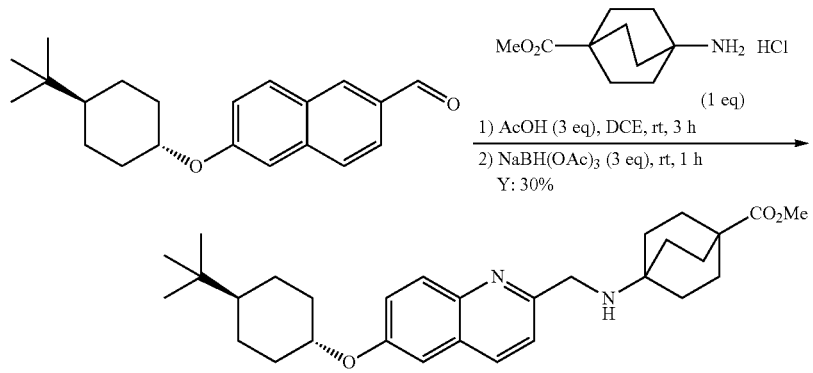

The solution of 6-((trans-4-(tert-butyl)cyclohexyl)oxy)quinoline-2-carbaldehyde (200 mg, 0.6 mmol) and methyl 4-aminobicyclo[2.2.2]octane-1-carboxylate (142 mg, 0.644 mmol) in Ethanol (2 mL, 30 mmol) was heated to reflux for 2 h. The yellow solution was cooled to room temperature and sodium cyanoborohydride (48.6 mg, 0.773 mmol) was added and was heated to reflux for 1 h. After cooled down to room temperature, citric acid was added and concentrated down. The solid was suspended in water and filtrate, and the collected solid was washed thoroughly with water. HPLC purification of the solid give the product (62.7 mg, 20%). LCMS Rt=1.67 min, m/z=479.30 [M+1]. Lithium hydroxide (15.7 mg, 0.655 mmol) was added to a solution of 4-{[6-(trans-4-tert-Butyl-cyclohexyloxy)-quinolin-2-ylmethyl]-amino}-bicyclo[2.2.2]octane-1-carboxylic acid methyl ester (62.7 mg, 0.131 mmol) in tetrahydrofuran (0.8 mL, 10 mmol) and methanol (0.8 mL, 20 mmol). The mixture was stirred at 50° C. overnight. the solvent was concentrated. The residue was taken up in DMSO and conc. HCl (200 uL) was added to solubilize. Purification by preparative HPLC gave the product as a white solid (63 mg, 20%). LCMS (100%, RT=1.57 min, m/z=465.30. $^1$H NMR (400 MHz, METHANOL-d4) δ ppm 0.94 (s, 9H) 1.06-1.60 (m, 5H), 1.86-1.99 (m, 2H), 2.00-2.10 (m, 12H), 2.24-2.37 (m, 2H) 4.32-4.46 (m, 1H) 4.49 (s, 2H) 7.34 (d, J=2.51 Hz, 1H) 7.42 (dd, J=9.29, 2.76 Hz, 1H), 7.47 (d, J=8.53 Hz, 1H) 8.01 (d, J=9.29 Hz, 1H) 8.28 (d, J=8.28 Hz, 1H).

Step 2: 4-(((6-((trans-4-(tert-butyl)cyclohexyl)oxy)quinolin-2-yl)methyl)amino)bicyclo[2.2.2]octane-1-carboxylic acid

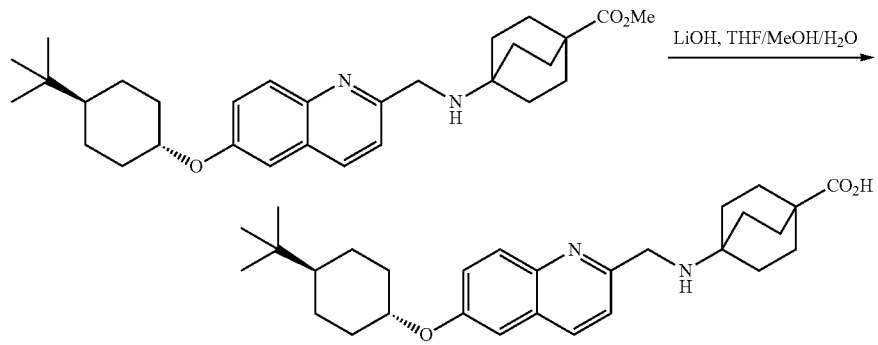

Lithium hydroxide (15.7 mg, 0.655 mmol) was added to a solution of 4-{[6-(trans-4-tert-butyl-cyclohexyloxy)-quinolin-2-ylmethyl]-amino}-bicyclo[2.2.2]octane-1-carboxylic acid methyl ester (62.7 mg, 0.131 mmol) in tetrahydrofuran (0.8 mL, 10 mmol) and methanol (0.8 mL, 20 mmol). The mixture was stirred at 50° C. overnight. the solvent was concentrated. The residue was taken up in DMSO and conc. HCl (200 uL) was added to solubilize. Purification by preparative HPLC gave the product as a white solid (2.3 mg, 4%). LCMS (100%, RT=1.57 min, m/z=465.30. 1H NMR (400 MHz, METHANOL-d4) δ ppm 0.94 (s, 9H) 1.06-1.60 (m, 5H), 1.86-1.99 (m, 2H), 2.00-2.10 (m, 12H), 2.24-2.37 (m, 2H) 4.32-4.46 (m, 1H) 4.49 (s, 2H) 7.34 (d, J=2.51 Hz, 1H) 7.42 (dd, J=9.29, 2.76 Hz, 1H), 7.47 (d, J=8.53 Hz, 1H) 8.01 (d, J=9.29 Hz, 1H) 8.28 (d, J=8.28 Hz, 1H).

Example 70

4-(((6-((trans-4-(tert-butyl)cyclohexyl)oxy)naphthalen-2-yl)methyl)(methyl)amino)bicyclo[2.2.2]octane-1-carboxylic acid

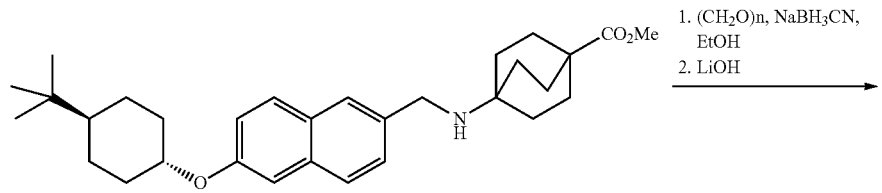

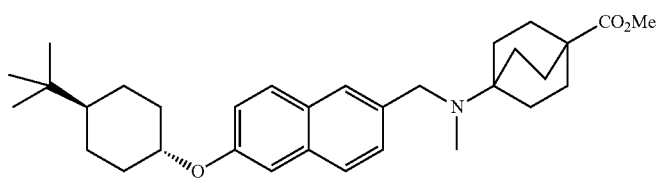

4-{[6-(trans-4-tert-Butyl-cyclohexyloxy)-naphthalen-2-ylmethyl]-amino}-bicyclo[2.2.2]octane-1-carboxylic acid methyl ester (223 mg, 0.467 mmol) and paraformaldehyde (80 mg, 3 mmol) in ethanol (2 mL, 30 mmol) was heated to 80° C. for 1 h, then sodium cyanoborohydride (80 mg, 1 mmol) was added and was heated to 80° C. for 1 h. After concentration, the residue was participated in EtOAc and Aq NaHCO$_3$. The collected organic layer was washed with brine and dried over Na$_2$SO$_4$. The residue was purified by chromatography with Si gel under MeOH/DCM gave product (173.2 mg, 75%). LCMS Rt=1.75 min, m/z=492.20.

2 M of lithium hydroxide, monohydrate in water (0.788 mL, 1.58 mmol) was added to a solution of 4-{[6-(trans-4-tert-butyl-cyclohexyloxy)-naphthalen-2-ylmethyl]-methyl-amino}-bicyclo[2.2.2]octane-1-carboxylic acid methyl ester (0.075 g, 0.15 mmol) in tetrahydrofuran (0.788 mL, 9.71 mmol) and methanol (0.788 mL, 19.4 mmol). The mixture was stirred at 50° C. overnight. The solvent was concentrated. The residue was taken up in MeOH and conc. HCl (200 uL) was added. The precipitate was washed thoroughly with water and dry over vacuum to give 4-(((6-((trans-4-(tert-butyl)cyclohexyl)oxy)naphthalen-2-yl)methyl)(methyl)amino)bicyclo[2.2.2]octane-1-carboxylic acid (100 mg, 100%). LCMS (100%, RT=1.68 min, m/z=478.20). $^1$H NMR (400 MHz, METHANOL-d4) δ 7.93 (s, 1H), 7.89 (d, J=8.60 Hz, 1H), 7.84 (d, J=9.04 Hz, 1H), 7.49 (dd, J=1.85, 8.50 Hz, 1H), 7.32 (d, J=2.38 Hz, 1H), 7.21 (dd, J=2.51, 8.97 Hz, 1H), 4.40 (tt, J=4.27, 10.75 Hz, 1H), 3.75 (m, 2H), 2.70 (s, 3H), 2.30 (d, J=11.92 Hz, 2H), 2.10 (br. s., 12H), 1.94 (d, J=13.43 Hz, 2H), 1.05-1.54 (m, 5H), 0.94 (s, 9H).

Example 71

8-((6-((trans-4-(tert-butyl)cyclohexyl)oxy)naphthalen-2-yl)methyl)-8-azabicyclo[3.2.1]octane-3-carboxylic acid

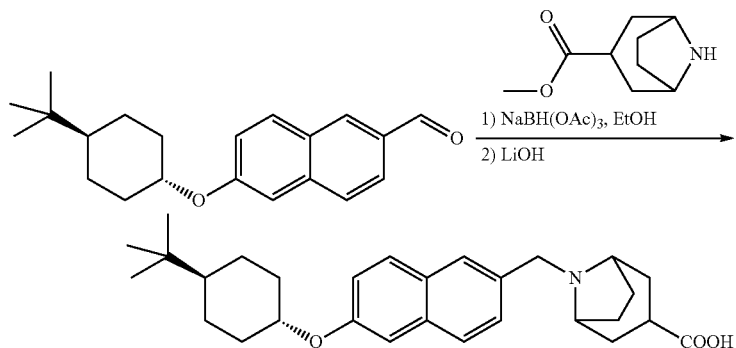

The preparation of 8-((6-((trans-4-(tert-butyl)cyclohexyl)oxy)naphthalen-2-yl)methyl)-8-azabicyclo[3.2.1]octane-3-carboxylic acid was the same as that of 3-((6-((trans-4-(tert-butyl)cyclohexyl)oxy)naphthalen-2-yl)methyl)-3-azabicyclo[3.1.0]hexane-6-carboxylic acid, 6.7 mg, as a yellow solid, Y: 34%. LCMS (100%, RT=1.65 min, m/z=450.20). $^1$H NMR (400 MHz, METHANOL-d$_4$) δ 7.92 (s, 1H), 7.88 (d, J=8.60 Hz, 1H), 7.82 (d, J=9.04 Hz, 1H), 7.51 (d, J=8.53 Hz, 1H), 7.31 (s, 1H), 7.19 (dd, J=2.48, 8.94 Hz, 1H), 4.37-4.48 (m, 1H), 4.28-4.36 (m, 2H), 3.43 (s, 2H), 1.06-2.64 (m, 18H), 0.94 (s, 9H).

Example 72

9-((6-((trans-4-(tert-butyl)cyclohexyl)oxy)naphthalen-2-yl)methyl)-9-azabicyclo[3.3.1]nonane-3-carboxylic acid

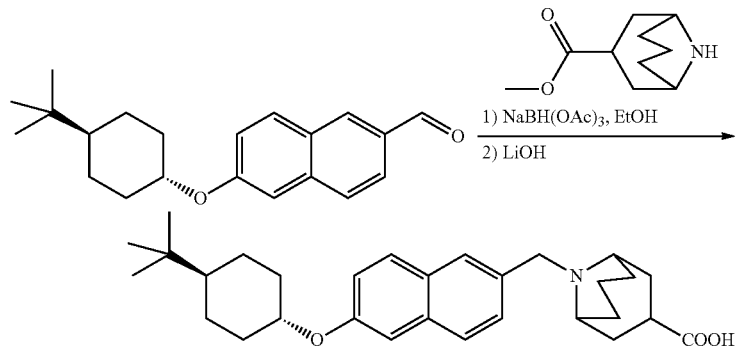

The preparation of 9-((6-((trans-4-(tert-butyl)cyclohexyl)oxy)naphthalen-2-yl)methyl)-9-azabicyclo[3.3.1]nonane-3-carboxylic acid was the same as that of 3-((6-((trans-4-(tert-butyl)cyclohexyl)oxy)naphthalen-2-yl)methyl)-3-azabicyclo[3.1.0]hexane-6-carboxylic acid, 237 mg, as a yellow solid, Y: 68%. LCMS (100%, RT=1.66 min, m/z=464.20). $^1$H NMR (400 MHz, METHANOL-$d_4$) δ 8.01 (d, J=4.20 Hz, 1H), 7.89 (d, J=8.41 Hz, 1H), 7.84 (d, J=9.16 Hz, 1H), 7.59 (d, J=8.41 Hz, 1H), 7.31 (s, 1H), 7.15-7.25 (m, 1H), 4.61-4.79 (m, 2H), 4.30-4.49 (m, 1H), 3.37-3.78 (m, 2H), 1.06-2.77 (m, 20H), 0.94 (s, 9H).

Example 73

3-((6-((trans-4-(tert-butyl)cyclohexyl)oxy)naphthalen-2-yl)methyl)-3-azabicyclo[3.3.1]nonane-9-carboxylic acid

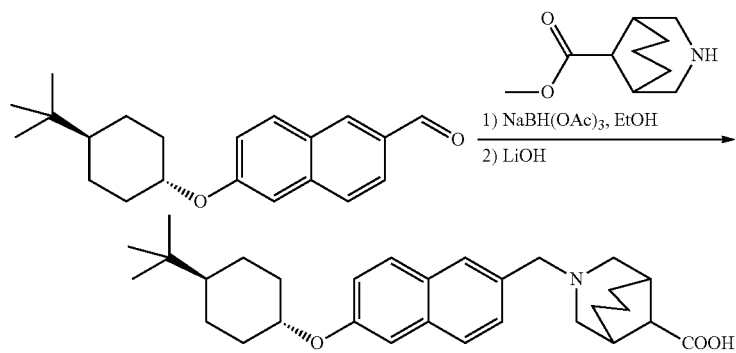

The preparation of 9-((6-((trans-4-(tert-butyl)cyclohexyl)oxy)naphthalen-2-yl)methyl)-9-azabicyclo[3.3.1]nonane-3-carboxylic acid was the same as that of 3-((6-((trans-4-(tert-butyl)cyclohexyl)oxy)naphthalen-2-yl)methyl)-3-azabicyclo[3.1.0]hexane-6-carboxylic acid, 150 mg, as a yellow solid, Y: 29%. LCMS Rt=1.69 min, m/z=464.20 [M+1]. $^1$H NMR (400 MHz, METHANOL-$d_4$) δ 7.94-8.03 (m, 1H), 7.90 (d, J=7.97 Hz, 1H), 7.85 (d, J=9.04 Hz, 1H), 7.47-7.62 (m, 1H), 7.33 (br. s., 1H), 7.22 (d, J=8.97 Hz, 1H), 4.46 (d, J=14.31 Hz, 2H), 4.28-4.41 (m, OH), 3.39-3.67 (m, 2H), 1.04-3.04 (m, 20H), 0.94 (s, 9H).

Example 74

3-((6-((trans-4-(tert-butyl)cyclohexyl)oxy)naphthalen-2-yl)methyl)-3-azabicyclo[3.1.1]heptane-6-carboxylic acid

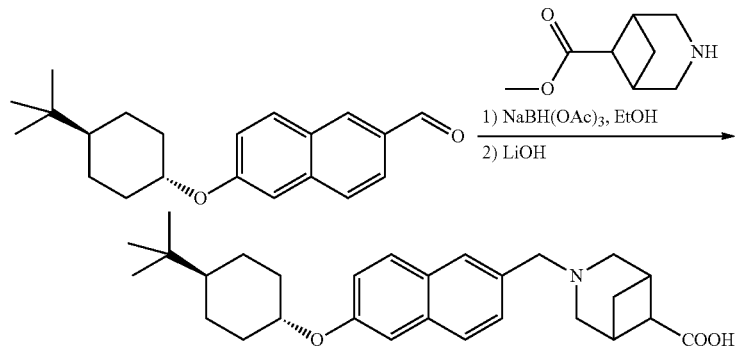

The preparation of 3-((6-((trans-4-(tert-butyl)cyclohexyl)oxy)naphthalen-2-yl)methyl)-3-azabicyclo[3.1.1]heptane-6-carboxylic acid was the same as that of 3-((6-((trans-4-(tert-butyl)cyclohexyl)oxy)naphthalen-2-yl)methyl)-3-azabicyclo[3.1.0]hexane-6-carboxylic acid, 150 mg, as a yellow solid, Y: 29%. LCMS Rt=1.69 min, m/z=436.3 [M+1]. $^1$H NMR (400 MHz, METHANOL-$d_4$) δ 7.94-8.03 (m, 1H), 7.90 (d, J=7.97 Hz, 1H), 7.85 (d, J=9.04 Hz, 1H), 7.47-7.62 (m, 1H), 7.33 (br. s., 1H), 7.22 (d, J=8.97 Hz, 1H), 4.46 (d, J=14.31 Hz, 2H), 4.28-4.41 (m, OH), 3.39-3.67 (m, 2H), 1.04-3.04 (m, 20H), 0.94 (s, 9H).

Example 75

4-(((6-((trans-4-(tert-butyl)cyclohexyl)oxy)naphthalen-2-yl)methyl)amino)bicyclo[2.2.1]heptane-1-carboxylic acid

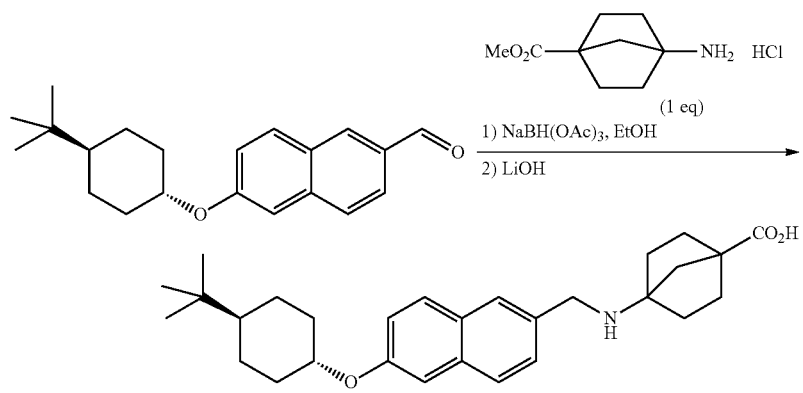

The preparation of 4-(((6-((trans-4-(tert-butyl)cyclohexyl)oxy)naphthalen-2-yl)methyl)amino)bicyclo[2.2.1]heptane-1-carboxylic acid was the same as that of 3-((6-((trans-4-(tert-butyl)cyclohexyl)oxy)naphthalen-2-yl)methyl)-3-azabicyclo[3.1.0]hexane-6-carboxylic acid, 64 mg, as a yellow solid, Y: 37%. LCMS (100%, RT=1.63 min, m/z=450.30). $^1$H NMR (400 MHz, METHANOL-d4) δ 7.92 (s, 1H), 7.88 (d, J=8.41 Hz, 1H), 7.82 (d, J=9.16 Hz, 1H), 7.51 (dd, J=1.85, 8.50 Hz, 1H), 7.31 (d, J=2.26 Hz, 1H), 7.20 (dd, J=2.48, 9.00 Hz, 1H), 4.38-4.46 (m, 1H), 4.37 (s, 2H), 1.82-2.36 (m, 14H), 1.03-1.55 (m, 5H), 0.94 (s, 9H).

Example 76

4-(((6-((trans-4-(tert-butyl)cyclohexyl)oxy)-5-(trifluoromethyl)naphthalen-2-yl)methyl)amino)bicyclo[2.2.1]heptane-1-carboxylic acid

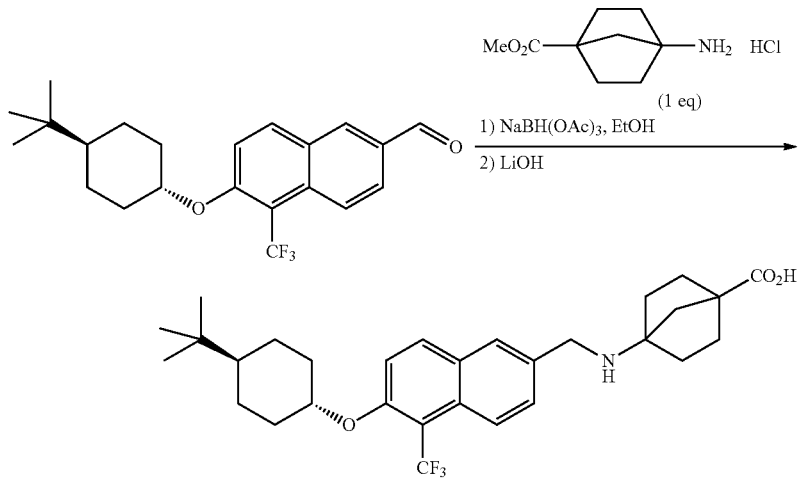

The preparation of 4-(((6-((trans-4-(tert-butyl)cyclohexyl)oxy)-5-(trifluoromethyl)naphthalen-2-yl)methyl)amino)bicyclo[2.2.1]heptane-1-carboxylic acid was the same as that of 3-((6-((trans-4-(tert-butyl)cyclohexyl)oxy)naphthalen-2-yl)methyl)-3-azabicyclo[3.1.0]hexane-6-carboxylic acid, 32 mg, as a yellow solid, Y: 19%. LCMS (100%, RT=1.73 min, m/z=519.30). $^1$H NMR (400 MHz, METHANOL-d4) δ 8.26 (dd, J=1.63, 9.04 Hz, 1H), 8.13 (d, J=9.29 Hz, 1H), 8.05 (d, J=1.82 Hz, 1H), 7.67 (dd, J=2.07, 9.10 Hz, 1H), 7.61 (d, J=9.29 Hz, 1H), 4.46-4.57 (m, 1H), 4.41 (s, 2H), 2.23 (dd, J=3.20, 9.91 Hz, 4H), 1.98-2.16 (m, 6H), 1.93 (d, J=10.67 Hz, 4H), 1.44-1.62 (m, 2H), 1.04-1.34 (m, 3H), 0.93 (s, 9H).

Example 77

4-((6-(trans-4-(Trimethylsilyl)cyclohexyloxy)naphthalen-2-yl)methylamino)bicyclo[2.2.2]octane-1-carboxylic acid

Step 1: (4-methoxyphenyl)trimethylsilane

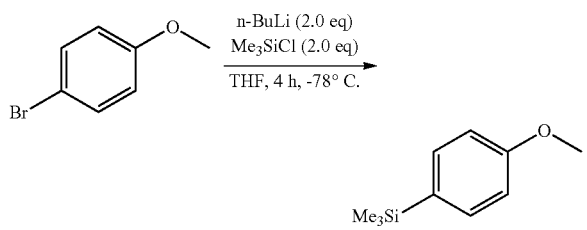

4-Bromoanisole (9.35 g, 50.0 mmol, 1.0 eq) was dissolved in anhydrous THF (200 mL). Me$_3$SiCl (12.7 mL, 100.0 mmol, 2.0 eq) was added at 0° C. followed by n-BuLi (2.5 M in hexanes, 40 mL, 100.0 mmol, 2.0 eq). The reaction mixture was stirred at room temperature for 1 h. Water (150 mL) was then added, the organic layer was separated and the aqueous layer was extracted with Et$_2$O (150 mL×2). The combined organic extracts were dried over anhydrous Na$_2$SO$_4$, filtered and concentrated in vacuo to give (4-methoxyphenyl)trimethylsilane as a light yellow oil (8.1 g, 90% yield). $^1$H NMR (300 MHz, CDCl$_3$) δ: 7.48 (d, J=11.2 Hz, 2H), 6.95 (d, J=11.2 Hz, 2H), 3.84 (s, 3H), 0.27 (s, 9H).

Step 2: 4-(Trimethylsilyl)cyclohexanone

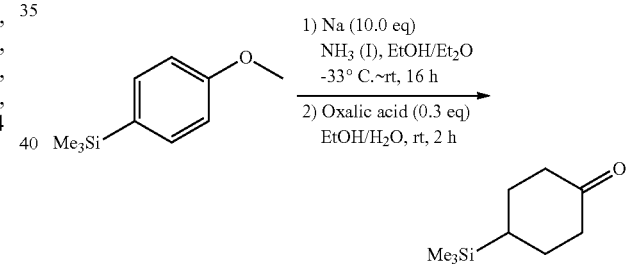

Ammonia (100 mL) was condensed at −78° C. (4-methoxyphenyl)trimethylsilane (18.0 g, 0.1 mol, 1.0 eq) in anhydrous Et$_2$O (110 mL) was added followed by EtOH (80 mL) and sodium (23.0 g, 1.0 mol, 10.0 eq) portionwise at −33° C. Additional EtOH ((50 mL) was added and ammonia was allowed to evaporated over 16 h. The water (250 mL) was added to the residue and the mixture was extracted with Et$_2$O (250 mL×3). The combined organic extracts were dried over anhydrous Na$_2$SO$_4$, filtered and concentrated in vacuo. The crude product was dissolved in EtOH (20 mL) and H$_2$O (20 mL) and oxalic acid (2.71 g, 0.03 mol, 0.3 eq) was then added. The resulting colorless solution was stirred at room temperature for 2 h. Water (100 mL) was then added and the mixture was extracted with Et$_2$O (100 mL×3). The combined organic extracts were washed with brine, dried over anhydrous Na$_2$SO$_4$, filtered and concentrated in vacuo. The residue was purified by column chromatography on silica gel (petroleum ether/EtOAc=10:1) to furnish 4-(trimethylsilyl)cyclohexanone as a light yellow oil (14.0 g, 72% yield). $^1$H NMR (300 MHz, CDCl₃) δ: 2.44-2.39 (m, 2H), 2.33-2.22 (m, 2H), 2.11-2.05 (m, 2H), 1.53-1.47 (m, 2H), 0.96-0.87 (m, 1H), 0.00 (s, 9H).

Step 3: cis-4-(Trimethylsilyl)cyclohexanol

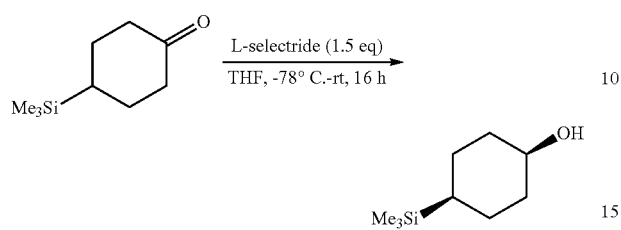

To a solution of L-selectride (165 mL, 0.165 mol, 1.5 eq) in anhydrous THF (200 mL) at −78° C. was added dropwise a solution of 4-(trimethylsilyl)cyclohexanone (20 g, 0.11 mol, 1.0 eq) in anhydrous THF (100 mL). The temperature was maintained for 3 h, and then the reaction mixture was stirred at room temperature for 16 h. Then the mixture was cooled to 0° C. before being quenched with water. The resulting mixture was warmed up to room temperature, and then sodium hydroxide aqueous solution (80 mL, 3 M) was added, followed by hydrogen peroxide (80 mL, 30%). After being stirred for 3 h, the mixture was extracted with EtOAc (300 mL×3), and the combined organic layers were washed with H₂O and brine, dried over Na₂SO₄, concentrated to give a residue which was purified by column chromatography on silica gel (petroleum ether/EtOAc=10:1) to obtain the product cis-4-(trimethylsilyl)cyclohexanol as a white solid (10.0 g, 51% yield). ¹H NMR (300 MHz, CDCl₃) δ: 4.05 (s, 1H), 1.75 (bs, 2H), 1.58-1.43 (m, 7H), 0.55 (bs, 1H), 0.00 (s, 9H).

Step 4: cis-4-(Trimethylsilyl)cyclohexyl methanesulfonate

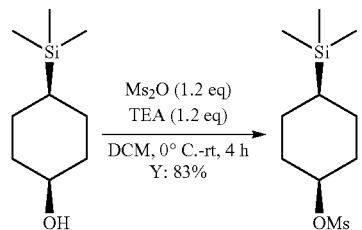

To a solution of cis-4-(trimethylsilyl)cyclohexanol (344 mg, 2.0 mmol, 1.0 eq) and Et₃N (242 mg, 2.4 mmol, 1.2 eq) in DCM (10 mL) was added Ms₂O (418 mg, 2.4 mmol, 1.2 eq) at 0° C. The resulting solution was allowed to warm up to rt and stirred for 4 h. The mixture was then diluted with DCM (30 mL), washed with brine (10 mL×2), dried over anhydrous sodium sulfate and filtered. The filtrate was concentrated under reduced pressure to give the crude product cis-4-(trimethylsilyl)cyclohexyl methanesulfonate as a yellow oil (415 mg, 83% yield), which was used in next step without further purification. LCMS: m/z 251.3 [M+H]⁺

Step 5: Methyl 4-((6-hydroxynaphthalen-2-yl)methylamino) bicyclo[2.2.2]octane-1-carboxylate

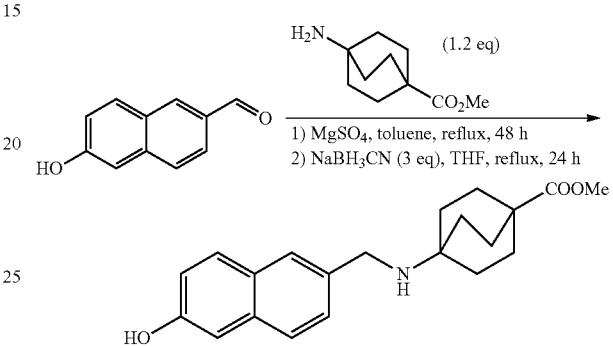

6-Hydroxy-2-naphthaldehyde (520 mg, 3.02 mmol, 1.0 eq) and methyl 4-aminobicyclo[2.2.2]octane-1-carboxylate (663 mg, 3.62 mmol, 1.2 eq) were dissolved in toluene (100 mL). MgSO₄ (72 mg, 0.60 mmol, 0.2 eq) was added to the solution and refluxed for 48 h. The solvent was removed in vacuo. The residue was dissolved in THF (150 mL) and NaBH₃CN (571 mg, 9.06 mmol, 3.0 eq) was added thereto. The mixture was refluxed for 24 h. The solvent was then removed in vacuo, and the residue was diluted with water (50 mL), extracted with EtOAc (150 mL×2). The combined organic layers were washed with brine (70 mL) and dried over Na₂SO₄. The organic phase was concentrated in vacuo to give methyl 4-((6-hydroxynaphthalen-2-yl)methylamino) bicyclo[2.2.2]octane-1-carboxylate as yellow solid (819 mg, 80% yield). ¹H NMR (400 MHz, CDCl₃) δ: 9.98 (s, 1H), 7.89 (s, 1H), 7.77 (d, J=9.2 Hz, 1H), 7.75 (d, J=8.4 Hz, 1H), 7.47 (dd, J=8.4, 1.6 Hz, 1H), 7.14 (d, J=8.0 Hz, 1H), 4.17 (s, 2H), 3.60 (s, 3H), 1.91-1.87 (m, 12H); ESI-MS (M+H)⁺: 340.2.

Step 6: Methyl 4-((6-(trans-4-(trimethylsilyl)cyclohexyloxy)naphthalen-2-yl)methylamino)bicyclo[2.2.2]octane-1-carboxylate

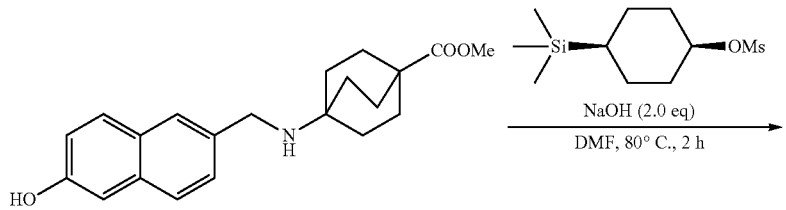

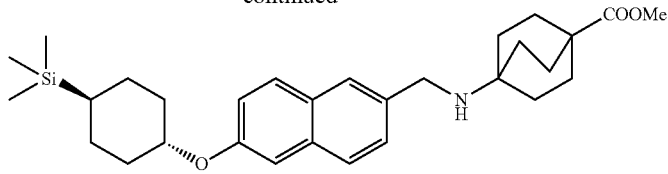

A mixture of methyl 4-((6-hydroxynaphthalen-2-yl)methylamino)bicyclo[2.2.2]octane-1-carboxylate (339 mg, 1.0 mmol, 1.0 eq), cis-4-(trimethylsilyl)cyclohexyl methanesulfonate (500 mg, 2.0 mmol, 2.0 eq) and NaOH (80 mg, 2.0 mmol, 2.0 eq) in DMF (2 mL) was heated to 80° C. and stirred for 2 h. The reaction mixture was then diluted with H₂O (5 mL) and adjusted to pH=6 with dilute HCl. The resulting mixture was purified by prep-HPLC (MeOH/H₂O with 0.05% TFA as mobile phase; from 20% to 95%) to furnish methyl 4-((6-(trans-4-(trimethylsilyl)cyclohexyloxy)naphthalen-2-yl)methylamino)bicyclo[2.2.2]octane-1-carboxylate 169 mg (34% yield) as a light yellow oil. LCMS: m/z 494.3 [M+H]+.

Step 7: 4-((6-(trans-4-(Trimethylsilyl)cyclohexyloxy)naphthalen-2-yl)methylamino)bicyclo[2.2.2]octane-1-carboxylic acid

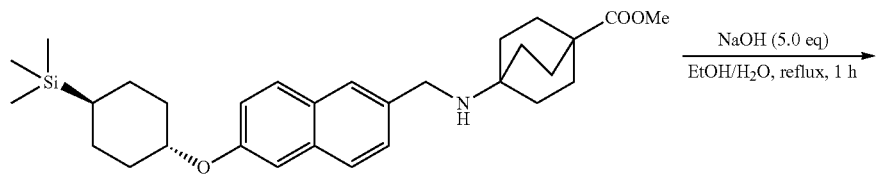

To a solution of methyl 4-((6-(trans-4-(trimethylsilyl)cyclohexyloxy)naphthalen-2-yl)methylamino)bicyclo[2.2.2]octane-1-carboxylate (169 mg, 0.34 mmol, 1.0 eq) in a mixed solvents (EtOH/H₂O=5:1, 6 mL) was added NaOH (68 mg, 1.7 mmol, 5.0 eq). The resulting solution was heated to reflux for 1 h. After cooling down to rt, the mixture was adjusted to pH=6.0 and purified with prep-HPLC (MeOH/H₂O with 10 mM NH₄HCO₃ as mobile phase; from 20% to 95%) to afford the title compound as a white solid (105 mg, 67% yield).

¹H NMR (400 MHz, DMSO-d₆) δ: 7.76-7.70 (m, 3H), 7.42 (d, J=10.0 Hz, 1H), 7.32 (s, 1H), 7.10 (dd, J=2.4, 8.8 Hz, 1H), 4.39-4.37 (m, 1H), 3.75 (s, 2H), 2.25-2.19 (m, 2H), 1.85-1.74 (m, 8H), 1.63-1.56 (m, 6H), 1.34-1.25 (m, 4H), 0.56-0.52 (m, 1H), 0.01 (s, 9); LCMS m/z 480.3 [M+H]+.

Example 78

4-(((6-((cis-4-(Trimethylsilyl)cyclohexyl)oxy)naphthalen-2-yl)methyl)amino)bicyclo[2.2.2]octane-1-carboxylic acid Step 1: trans-4-(trimethylsilyl)cyclohexanol

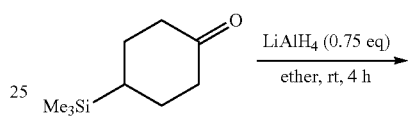

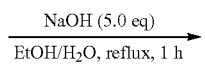

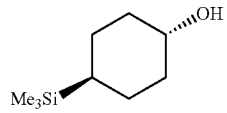

A 500-ml round-bottomed flask was placed with LiAlH₄ (1.8 g, 50 mmol, 0.75 eq) and anhydrous ether (150 mL). To this mixture was added dropwise a solution of 4-(trimethylsilyl)cyclohexanone (11.3 g, 66 mmol, 1.0 eq) in ether (75 mL). After the addition, the mixture was stirred at room temperature for 4 h; then the reaction was quenched carefully with dilute hydrochloric acid (2 M). The aqueous layer was extracted with ether (3×250 mL), the combined ether solutions were dried over magnesium sulfate, and the ether was removed under reduced pressure to give the residue, which was purified by column chromatogram (Petroleum ether/EtOAc=10:1) to obtain the title compound as a white solid (9.2 g, 45% yield). ¹H NMR (300 MHz, CDCl₃) δ:

3.58-3.52 (m, 1H), 2.09-2.06 (m, 2H), 1.83-1.79 (m, 2H), 1.29-1.13 (m, 5H), 0.50-0.42 (m, 1H), 0.00 (s, 9H).

Step 2: trans-4-(Trimethylsilyl)cyclohexyl methanesulfonate

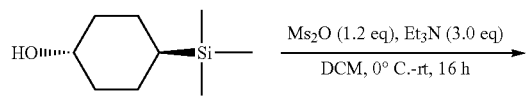

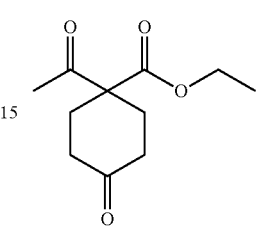

Following the same condition as in Step 4 of Example 77 (cis analog), the title compound was obtained as a yellow oil (350 mg, 20% yield). LCMS: m/z 251.1 [M+H]$^+$.

Step 3: 4-(((6-((cis-4-(Trimethylsilyl)cyclohexyl)oxy)naphthalen-2-yl)methyl)amino)bicyclo[2.2.2]octane-1-carboxylic acid

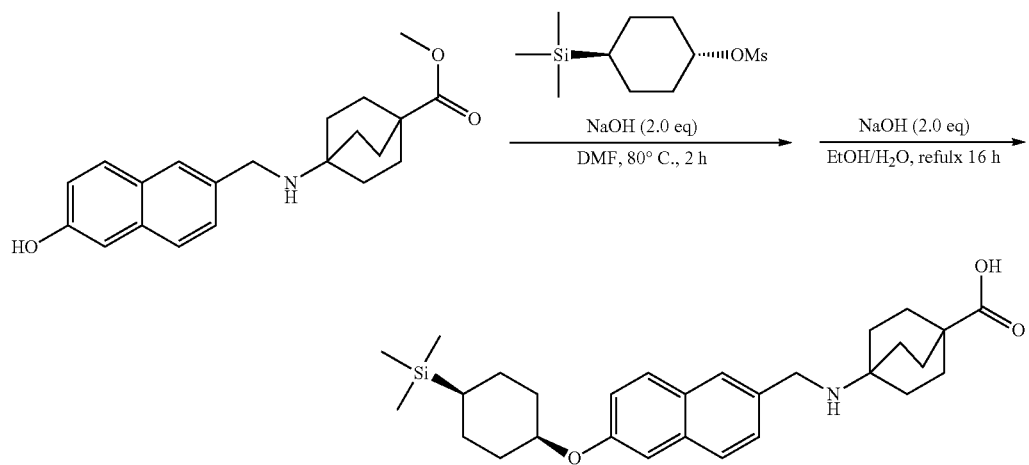

Using trans-4-(trimethylsilyl)cyclohexyl methanesulfonate, and following the same displacement and hydrolysis conditions as in Steps 6-7 of Example 77 (trans analog), the title compound was obtained as a white solid (10 mg, 53% yield). LCMS m/z 480.2 [M+H]$^+$; H NMR (400 MHz, DMSO-d$_6$, CD$_3$OD) δ: 7.86-7.80 (m, 3H), 7.47 (d, J=8.0 Hz, 1H), 7.26 (d, J=2.0 Hz, 1H), 7.21 (dd, J=2.0, 8.4 Hz, 1H), 4.55 (bs, 1H), 4.15 (bs, 2H), 2.16-2.12 (m, 2H), 1.96-1.89 (m, 12H), 1.66-1.61 (m, 6H), 0.75-0.70 (m, 1H), 0.01 (s, 9).

Example 80

4-((6-(trans-4-tert-Butylcyclohexyloxy)naphthalen-2-yl)methylamino)-2-hydroxybicyclo[2.2.2]octane-1-carboxylic acid Step 1: Ethyl 4-(benzylamino)-2-oxobicyclo[2.2.2]octane-1-carboxylate

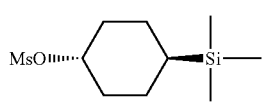

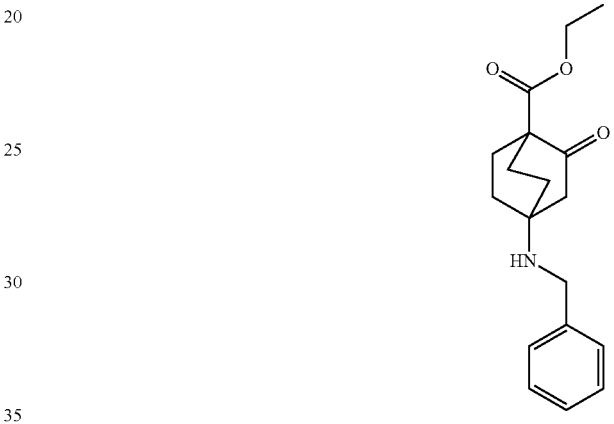

Ethyl 1-acetyl-4-oxocyclohexanecarboxylate (4.3 g, 20.0 mmol, 1.0 eq), PTSA (350 mg, 2.0 mmol, 0.1 eq) and benzylamine (2.4 g, 22.0 mmol, 1.1 eq) were dissolved in toluene (250 mL). The mixture was heated to reflux with dean stark trap for 24 h. The mixture was diluted with H$_2$O (500 mL) and extracted with EtOAc (500 mL×2). The combined organic layers were dried over anhydrous Na$_2$SO$_4$ and filtered, concentrated in vacuo to yield a crude product, which was purified by column chromatography on silica gel (DCM/MeOH=20:1), then followed by recrystallization from petroleum ether and ErtOAc to give the title compound as a yellow solid (1.3 g, Y: 20%). LCMS m/z 302.2 [M+1]+; 1H NMR (400 MHz, CDCl3) δ: 9.68 (bs, 1H), 7.35 (bs, 5H), 4.23 (q, J=7.2 Hz, 2H), 3.85 (s, 2H), 2.55 (s, 2H), 2.23-2.17 (m, 2H), 1.93-1.64 (m, 6H), 1.30 (t, J=7.2 Hz, 3H).

Step 2: Ethyl 4-amino-2-oxobicyclo[2.2.2]octane-1-carboxylate

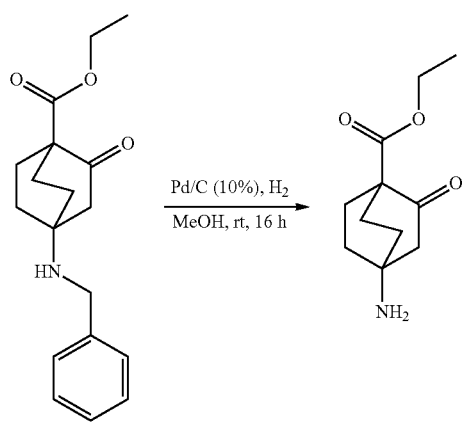 [SMILES: CCOC(=O)C12CCC(NCc3ccccc3)(CC1)CC2=O ; CCOC(=O)C12CCC(N)(CC1)CC2=O]

A solution of ethyl 4-(benzylamino)-2-oxobicyclo[2.2.2]octane-1-carboxylate (500 mg, 1.66 mmol, 1.0 eq) in MeOH (10 mL) was purged with N2 for 3 times. Pd/C (50 mg, 10% w/w) was added, and the mixture was purged with H2 for 2 times. The resulting mixture was stirred at rt under a H2 balloon for 16 h, and then filtered. The filtrate was concentrated in vacuo to get the title compound (280 mg 80%) as a white solid. LCMS m/z 212.1 [M+H]+; 1H NMR (400 MHz, DMSO-d6) δ: 8.42 (bs, 2H), 4.10 (q, J=7.2 Hz, 2H), 2.63 (bs, 2H), 2.15-1.89 (m, 8H), 1.17 (t, J=7.2 Hz, 3H).

Step 3: Ethyl 4-amino-2-hydroxybicyclo[2.2.2]octane-1-carboxylate

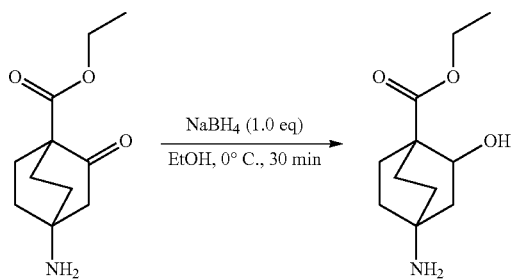

A mixture of ethyl 4-amino-2-oxobicyclo[2.2.2]octane-1-carboxylate (200 mg, 0.47 mmol, 1.0 eq) and NaBH4 (18 mg, 0.47 mmol, 1.0 eq) in EtOH (10 mL) was stirred at 0° C. for 30 min. Then the reaction was quenched with water (5 mL) and extracted with EtOAc (8 mL×3). The organic phase was concentrated in vacuo to give the title compound as a white solid (163 mg, 41% yield), which was used in next step without further purification. LCMS m/z 214.1 [M+H]+.

Step 4: Ethyl 4-((6-(trans-4-tert-butylcyclohexyloxy)naphthalen-2-yl)methylamino)-2-hydroxybicyclo[2.2.2]octane-1-carboxylate

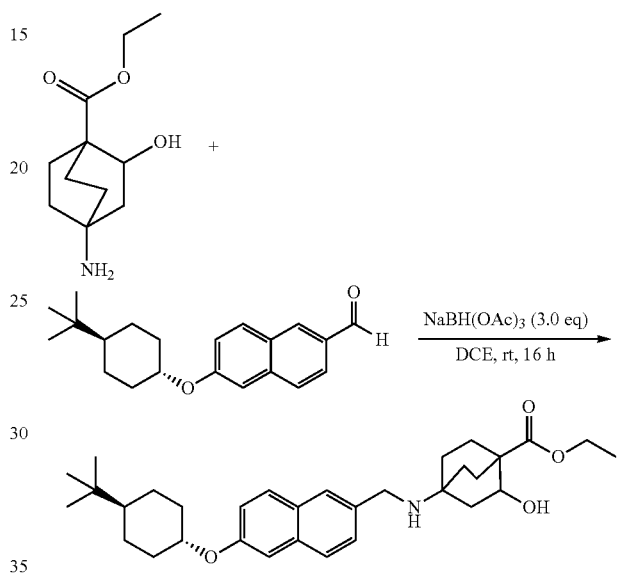

A mixture of ethyl 4-amino-2-hydroxybicyclo[2.2.2]octane-1-carboxylate (163 mg, 0.77 mol, 1.0 eq), 6-(trans-4-tert-butylcyclohexyloxy)-2-naphthaldehyde (239 mg, 0.77 mmol, 1.0 eq) and AcOH (139 mg, 2.31 mmol, 3.0 eq) in DCE (5 mL) was heated to reflux for 30 min. After cooling down to rt, NaBH(OAc)3 (490 mg, 2.31 mmol, 3.0 eq) was added and the mixture was stirred for additional 16 h at rt. The reaction was then quenched with water (5 mL) and extracted with DCM (5 mL×3). The combined organic phase was concentrated in vacuo, and the residue was purified by prep-HPLC (MeOH/H2O from 30% to 95%, containing 0.05% TFA) to give the title compound as a white solid (169 mg, 35% yield). LCMS m/z 508.3 [M+1]+;

Step 5: 4-((6-(trans-4-tert-Butylcyclohexyloxy)naphthalen-2-yl)methylamino)-2-hydroxybicyclo[2.2.2]octane-1-carboxylic acid

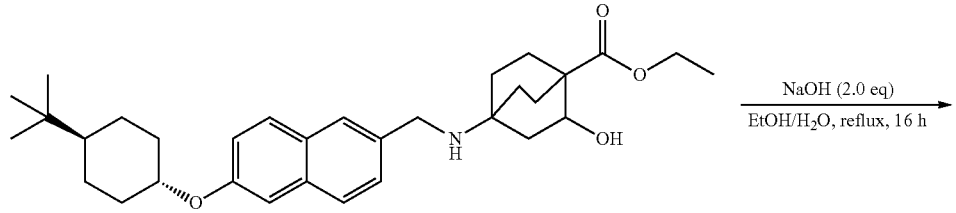

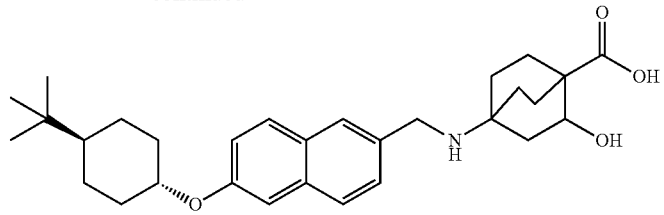

To a mixture of ethyl 4-((6-(trans-4-tert-butylcyclohexyloxy)naphthalen-2-yl)methylamino)-2-hydroxybicyclo[2.2.2]octane-1-carboxylate (169 mg, 0.33 mmol, 1.0 eq) in a mixed solvent (EtOH/H$_2$O=4:1, 5 mL) was added NaOH (26 mg, 0.66 mmol, 2.0 eq), the resulting mixture was heated to reflux for 16 h. After cooling down to rt, the reaction mixture was then adjusted to pH=6 with dilute aq. HCl (2 M). The resulting suspension was filtered, and the filtrate was purified by prep-HPLC (MeOH/H$_2$O from 30% to 95%, containing 0.05% TFA) to yield the title compound as a yellow solid (84 mg, 52% yield). LCMS m/z 480.3 [M+1]$^+$; $^1$H NMR (400 MHz, DMSO-d$_6$) δ: 7.82-7.76 (m, 3H), 7.48 (d, J=8.4 Hz, 1H), 7.35 (d, J=2.4 Hz, 1H), 7.13 (dd, J=8.8, 2.4 Hz, 1H), 4.37-4.36 (m, 1H), 4.10-4.08 (m, 1H), 3.96 (s, 2H), 2.21-2.11 (m, 4H), 1.83-1.55 (m, 10H), 1.36-1.07 (m, 5H), 0.88 (s, 9H).

Example 81

4-((6-(trans-4-tert-Butylcyclohexyloxy)naphthalen-2-yl)methylamino)-1-(hydroxymethyl)bicyclo[2.2.2]octan-2-ol Step 1:
4-Amino-1-(hydroxymethyl)bicyclo[2.2.2]octan-2-ol

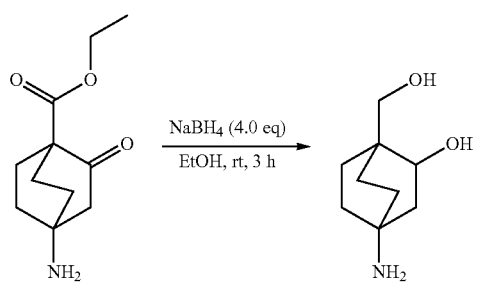

To a mixture of ethyl 4-amino-2-oxobicyclo[2.2.2]octane-1-carboxylate (200 mg, 0.47 mmol, 1.0 eq) in EtOH (10 mL) was added NaBH$_4$ (71 mg, 1.88 mmol, 4.0 eq) at 0° C., and the resulting mixture was stirred for 30 min. The reaction was then quenched with water (5 mL) and extracted with EtOAc (3×8 mL). The combined organic layers were concentrated in vacuo to give the title compound as a white solid (130 mg 56% yield), which was used for the next step without further purification. LCMS m/z 172.1 [M+H]+;

Step 2: 4-((6-(trans-4-tert-Butylcyclohexyloxy)naphthalen-2-yl)methylamino)-1-(hydroxymethyl)bicyclo[2.2.2]octan-2-ol

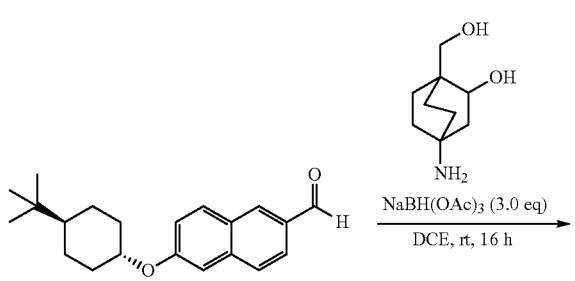

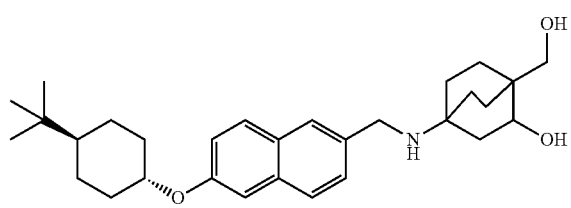

A mixture of 4-amino-1-(hydroxymethyl)bicyclo[2.2.2]octan-2-ol (130 mg, 0.76 mol, 1.0 eq), 6-(trans-4-tert-butylcyclohexyloxy)-2-naphthaldehyde (235 mg, 0.76 mmol, 1.0 eq) and HOAc (137 mg, 2.28 mmol, 3.0 eq) in DCM (5 mL) was heated to reflux for 30 min. After cooling down to rt, NaBH(OAc)$_3$ (483 mg, 2.28 mmol, 3.0 eq) was added and the mixture was stirred for additional 16 h at rt. Then the reaction was quenched with water (5 mL) and extracted by DCM (3×5 mL). The organic phase was concentrated in vacuo and purified by prep-HPLC (MeOH/H$_2$O from 30% to 95%, containing 0.05% TFA) to give the title compound as a white solid (39 mg, 14% yield). LCMS m/z 466.3 [M+1]$^+$; $^1$H NMR (400 MHz, DMSO-d$_6$) δ: 8.70 (bs, 2H), 7.92 (s, 1H), 7.87-7.82 (m, 2H), 7.52 (d, J=8.4 Hz, 1H), 7.41 (d, J=2.4 Hz, 1H), 7.19 (dd, J=8.8, 2.8 Hz, 1H), 4.84 (bs, 1H), 4.40-4.39 (m, 1H), 4.18 (bs, 2H), 3.81-3.79 (m, 1H), 3.28 (d, J=10.4 Hz, 1H), 3.12 (d, J=10.8 Hz, 1H), 2.21-2.19 (m, 3H), 1.84-1.08 (m, 16H), 0.88 (s, 9H).

Example 82

4-(((6-((trans-4-(tert-butyl)cyclohexyl)oxy)naphthalen-2-yl)methyl)amino)bicyclo[2.2.2]octane-1-carboxylic acid Step 1: 4-{[6-(trans-4-tert-Butyl-cyclohexyloxy)-naphthalen-2-ylmethyl]-amino}-bicyclo[2.2.2]octane-1-carboxylic acid methyl ester

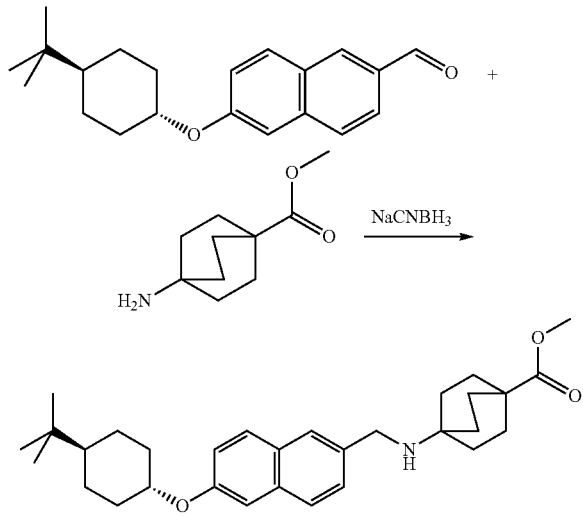

A solution of 6-(4-tert-Butyl-cyclohexyloxy)-naphthalene-2-carbaldehyde (238 mg, 0.767 mmol) (WO 2011/017561 A1) and methyl 4-aminobicyclo[2.2.2]octane-1-carboxylate (168 mg, 0.767 mmol) (Prime Organics) in Ethanol (2 mL, 30 mmol) was heated to reflux for 2 h. The yellow solution was cooled to room temperature and Sodium cyanoborohydride (57.8 mg, 0.920 mmol) was added and heated to reflux for 3d. The mixture was cooled and concentrated. The solid was suspended in aqueous NaHCO3 and EtOAc, The organic layer was washed with brine, dried and concentrated. Column chromatography in Silica gel with MeOH/DCM gives a solid as the product (217 mg, 59% yield). LCMS: Rt=1.69 min m/z 478.30 [M+1]. 1H NMR (400 MHz, CHLOROFORM-d) δ ppm 0.88-0.95 (m, 9H) 1.02-1.35 (m, 9H) 1.35-1.54 (m, 2H) 1.60-1.73 (m, 6H) 1.75-1.87 (m, 6H) 1.90 (d, J=12.99 Hz, 2H) 2.27 (d, J=11.67 Hz, 2H) 3.66 (s, 3H) 3.85 (s, 2H) 4.17-4.35 (m, 1H) 7.02-7.17 (m, 2H) 7.39 (d, J=8.41 Hz, 1H) 7.61-7.78 (m, 3H).

Step 2: 4-(((6-((trans-4-(tert-butyl)cyclohexyl)oxy)naphthalen-2-yl)methyl)amino)bicyclo[2.2.2]octane-1-carboxylic acid

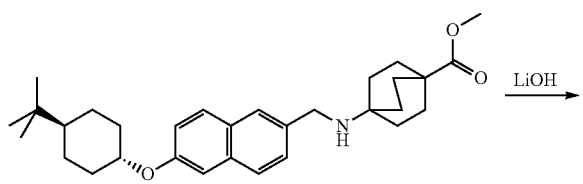

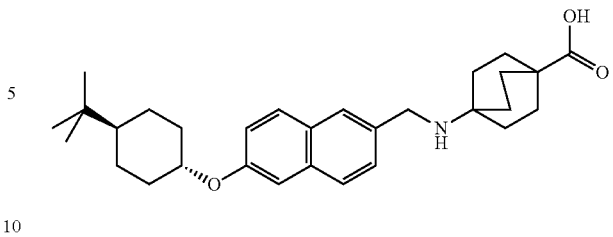

2 M Lithium hydroxide, monohydrate in Water (2 mL, 4 mmol) was added to a solution of 4-{[6-(trans-4-tert-Butyl-cyclohexyloxy)-naphthalen-2-ylmethyl]-amino}-bicyclo[2.2.2]octane-1-carboxylic acid methyl ester (217 mg, 0.454 mmol) in Tetrahydrofuran (2 mL, 20 mmol) and Methanol (1 mL, 20 mmol). The mixture was stirred at 70° C. overnight. The solvent was concentrated. The residue was taken up in DMSO and TFA (200 μL) was added to solubilize. Purification by preparative HPLC gave the product (135 mg, 64%). HPLC (100%, RT=1.483 min), LCMS (100%, RT=1.64 min, m/z=464.30). 1H NMR (400 MHz, METHANOL-d4) δ ppm 0.94 (s, 9H) 1.03-1.56 (m, 5H) 1.94 (d, J=14.56 Hz, 2H) 2.03 (d, J=7.03 Hz, 12H) 2.29 (d, J=11.23 Hz, 2H) 4.27 (s, 2H) 4.33-4.46 (m, 1H) 7.19 (d, J=11.36 Hz, 1H) 7.30 (s, 1H) 7.49 (d, J=8.41 Hz, 1H) 7.82 (d, J=8.97 Hz, 1H) 7.87 (d, J=8.60 Hz, 1H) 7.90 (s, 1H).

Example 83

9-((6-((cis-4-ethylcyclohexyl)oxy)naphthalen-2-yl)methyl)-9-azabicyclo[3.3.1]nonane-3-carboxylic acid

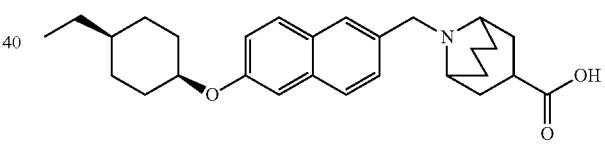

To a mixture of 9-aza-bicyclo[3.3.1]nonane-3-carboxylic acid methyl ester HCl salt (26 mg, 0.12 mmol) and 6-((cis-4-ethylcyclohexyl)oxy)-2-naphthaldehyde (28 mg, 0.10 mmol) in THF (0.6 mL) was added sodium triacetoxyborohydride (30 mg, 0.14 mmol). The reaction solution was heated with microwave irritation at 100° C. for 20 min. To the above mixture was added 3 M of NaOH in water (0.5 mL, 2 mmol) and MeOH (0.8 mL). It was heated with microwave irritation at 100° C. for 10 min. Neutralized with 1N HCl, filtered and purified by HPLC (TFA method) to collect the desired acid as a white powdered after lyophilization (30 mg, yield 54% for two steps). 1H NMR (400 MHz, METHANOL-d4) δ 8.00 (br. S., 1H), 7.78-7.90 (m, 2H), 7.57 (d, J=8.53 Hz, 1H), 7.29 (d, J=2.01 Hz, 1H), 7.23 (dd, J=2.38, 8.91 Hz, 1H), 4.52-4.78 (m, 3H), 3.58-3.70 (m, 2H), 3.35-3.47 (m, 1H), 2.47-2.69 (m, 2H), 1.82-2.35 (m, 9H), 1.24-1.79 (m, 10H), 0.93 (t, J=7.15 Hz, 3H); LCMS m/z 436.1 [M+H]+

Example 84

9-((5-(trifluoromethyl)-6-((cis-4-(trifluoromethyl)cyclohexyl)oxy)naphthalen-2-yl)methyl)-9-azabicyclo[3.3.1]nonane-3-carboxylic acid

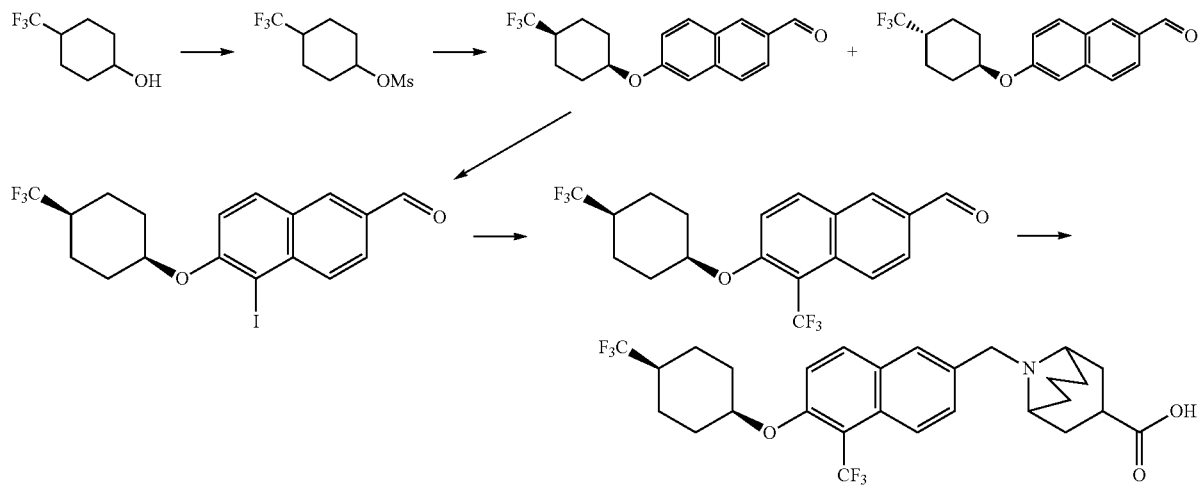

Step 1: 4-(trifluoromethyl)cyclohexyl methanesulfonate

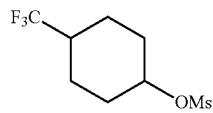

To a solution of 4-trifluoromethyl-cyclohexanol (20.0 g, 119 mmol, mixture of cis/trans, ~20/80, Youchemicals), and triethylamine (22 mL, 155 mmol) in methylene chloride (300.0 mL) was added methanesulfonyl chloride (12 mL, 155 mmol) dropwise at 0° C. A white precipitate formed. The reaction mixture was stirred from 0° C. to RT overnight. The mixture was diluted with dichloromethane and washed with citric acid (5% in water), sodium bicarbonate aqueous solution and water, dried over sulfate, filtered, concentrated and dried overnight on the lyophilizer and collected to give the titled compound as a white solid (23.9 g, 82%, a mixture of cis and trans, ratio is ~20/80 based on the NMR); 1H NMR (400 MHz, CHLOROFORM-d) δ 4.50-5.13 (m, 1H), 3.05 (s, 3H), 1.94-2.37 (m, 4H), 1.35-1.91 (m, 5H).

Step 2: 6-((cis-4-(trifluoromethyl)cyclohexyl)oxy)-2-naphthaldehyde and 6-((trans-4-(trifluoromethyl)cyclohexyl)oxy)-2-naphthaldehyde

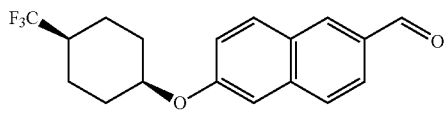

To a mixture of 6-hydroxy-naphthalene-2-carbaldehyde (4.0 g, 23 mmol) and cesium carbonate (15.14 g, 46 mmol) in N,N-dimethylformamide (100 mL) was added methanesulfonic acid 4-trifluoromethyl-cyclohexyl ester (11 g, 46 mmol) in two portions (the second portion was added after heating for 4 h). The resulting mixture was heated at 85° C. overnight. Diluted with ethyl acetate, washed with water, brine and dried over sodium sulfate. The crude mixture was then purified by ISCO column chromatography (ethyl acetate/heptane gradient 0% to 30%) to give two isomers (2.95 g, 39% of cis-isomer and 1.23 g, 16% of trans-isomer). For cis-isomer: LCMS: RT 2.01, MH+ 323.1, $^1$H NMR (400 MHz, CHLOROFORM-d) δ 10.10 (s, 1H), 8.26 (s, 1H), 7.93 (d, J=8.78 Hz, 2H), 7.78 (d, J=8.53 Hz, 1H), 7.25-7.30 (m, 1H), 7.20 (d, J=2.01 Hz, 1H), 4.76-4.86 (m, 1H), 2.28 (d, J=14.81 Hz, 2H), 2.07-2.22 (m, 1H), 1.75-1.92 (m, 4H), 1.61-1.72 (m, 2H); For trans-isomer: LCMS: RT 2.00 min; MH+ 323.1; $^1$H NMR (400 MHz, CHLOROFORM-d) δ 10.10 (s, 1H), 8.26 (s, 1H), 7.86-7.97 (m, 2H), 7.79 (d, J=8.53 Hz, 1H), 7.14-7.24 (m, 2H), 4.32-4.50 (m, 1H), 2.37 (d, J=5.77 Hz, 2H), 2.12 (d, J=6.02 Hz, 3H), 1.47-1.58 (m, 4H).

Step 3: 5-iodo-6-(cis-4-(trifluoromethyl)cyclohexyl)oxy)-2-naphthaldehyde

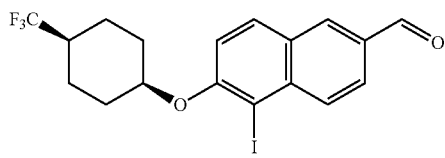 [SMILES: O=Cc1ccc2c(I)c(O[C@H]3CC[C@@H](C(F)(F)F)CC3)ccc2c1]

To a mixture of 6-((cis-4-(trifluoromethyl)cyclohexyl)oxy)-2-naphthaldehyde (3.0 g, 9.31 mmol) and zirconium chloride (0.30 g, 1.86 mmol) in methylene chloride (60 mL)

was added N-iodosuccinimide (2.51 g, 11.2 mmol). The reaction was then stirred at RT overnight. LC-MS showed complete conversion and the formation of the desired product. Worked up with aqueous sodium thiosulfate and ethyl acetate, the organic extracts were washed with sodium bicarbonate and dried over magnesium sulfate, and concentrated. The product was recrystallized from methanol to give the titled compound as a light yellow solid (4.06 g, 97%). LCMS: RT: 2.18 min., MH+ 449.0; $^1$H NMR (400 MHz, CHLOROFORM-d) δ 10.15 (s, 1H), 8.20-8.31 (m, 2H), 7.92-8.02 (m, 2H), 7.24 (d, J=9.04 Hz, 1H), 4.94 (br. S., 1H), 1.98-2.30 (m, 5H), 1.76-1.89 (m, 2H), 1.64 (t, J=14.06 Hz, 2H).

Step 4: 5-(trifluoromethyl)-6-((cis-4-(trifluoromethyl)cyclohexyl)oxy)-2-naphthaldehyde

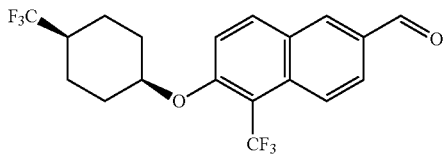 [SMILES: O=Cc1ccc2c(C(F)(F)F)c(O[C@H]3CC[C@@H](C(F)(F)F)CC3)ccc2c1]

According to the procedure reported in WO 2006/057869, by Aicher, Thomas. D. et al. (which is incorporated by reference in its entirety), a solution of 5-iodo-6-(cis-4-trifluoromethyl-cyclohexyloxy)-naphthalene-2-carbaldehyde (4.0 g, 8.9 mmol), hexamethylphosphoramide (7.8 mL, 44.6 mmol) in N,N-dimethylformamide (40 mL) was degassed with Ar. To this was added copper(I) iodide (3.06 g, 16.1 mmol) and methyl fluorosulphonyldifluoroacetate (5.8 mL, 44.6 mmol) and the reaction was stirred at 85° C. under an atmosphere of argon. After stirring for 5 hours, LCMS showed no starting material left and the formation of the desired product. The reaction mixture was diluted with ethyl acetate, and washed with water (5×). The organic layer was then dried over MgSO4, concentrated. The solid was then crystallized from methanol to give the product as a white powder (1.88 g, 54%). $^1$H NMR (400 MHz, DMSO-d6) δ 10.12 (s, 1H), 8.63 (d, J=1.51 Hz, 1H), 8.45 (d, J=9.29 Hz, 1H), 8.21 (d, J=8.28 Hz, 1H), 8.02 (dd, J=1.76, 9.04 Hz, 1H), 7.79 (d, J=9.29 Hz, 1H), 5.17 (br. S., 1H), 2.35-2.47 (m, 1H), 2.07 (d, J=13.55 Hz, 2H), 1.53-1.85 (m, 6H); ESI-MS (M+H)$^+$: 391.10

Step 5: 9-((5-(trifluoromethyl)-6-((cis-4-(trifluoromethyl)cyclohexyl)oxy)naphthalen-2-yl)methyl)-9-azabicyclo[3.3.1]nonane-3-carboxylic acid

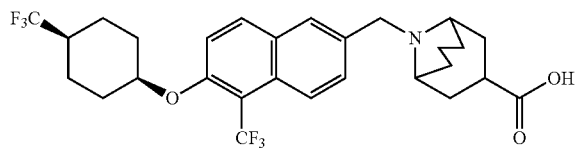 [SMILES: O=C(O)C1CC2CCCC(C1)N2Cc1ccc2c(C(F)(F)F)c(O[C@H]3CC[C@@H](C(F)(F)F)CC3)ccc2c1]

A mixture of 9-Aza-bicyclo[3.3.1]nonane-3-carboxylic acid methyl ester hydrochloride (Advanced Chemblocks, 63 mg, 0.29 mmol) and triethylamine (34 uL, 0.24 mmol) in 1,2-dichloroethane (2.00 mL) was stirred at rt for 20 min. 5-Trifluoromethyl-6-(cis-4-trifluoromethyl-cyclohexyloxy)-naphthalene-2-carbaldehyde (80.0 mg, 0.20 mmol) was then added. The reaction was then stirred at 50° C. for 1 h, cooled down, sodium triacetoxyborohydride (70 mg, 0.33 mmol) was added, and the reaction was stirred at rt overnight. LCMS showed the formation of methyl 9-((5-(trifluoromethyl)-6-((cis-4-(trifluoromethyl)cyclohexyl)oxy)naphthalen-2-yl)methy l)-9-azabicyclo[3.3.1]nonane-3-carboxylate (RT 1.56 min.; MH+ 558.3). Worked up with ethyl acetate and brine, dried over magnesium sulfate and concentrated. The crude was then dissolved in tetrahydrofuran (3.0 mL), 1.0 M of lithium hydroxide in water (2.0 mL, 2.0 mmol) was added. The mixture was stirred at rt for 3 h. Neutralized with conc. HCl, extracted with ethyl acetate. The organic layer was concentrated, and the crude was purified by HPLC to give the titled compound as a white powder (49 mg, TFA salt). LCMS: RT 1.47 min.; MH+ 544.2; 1H NMR (400 MHz, DMSO-d6) δ 9.36 (br. S., 1H), 8.09-8.30 (m, 3H), 7.83 (d, J=9.04 Hz, 1H), 7.71 (d, J=9.29 Hz, 1H), 5.12 (br. S., 1H), 4.56-4.79 (m, 2H), 3.53 (d, J=15.56 Hz, 2H), 3.13-3.32 (m, 1H), 2.32-2.47 (m, 3H), 1.85-2.28 (m, 8H), 1.50-1.82 (m, 8H).

Example 85

3-(((5-(trifluoromethyl)-6-((cis-4-(trifluoromethyl)cyclohexyl)oxy)naphthalene-2-yl)methyl)amino)spiro[3.5]nonane-1-carboxylic acid

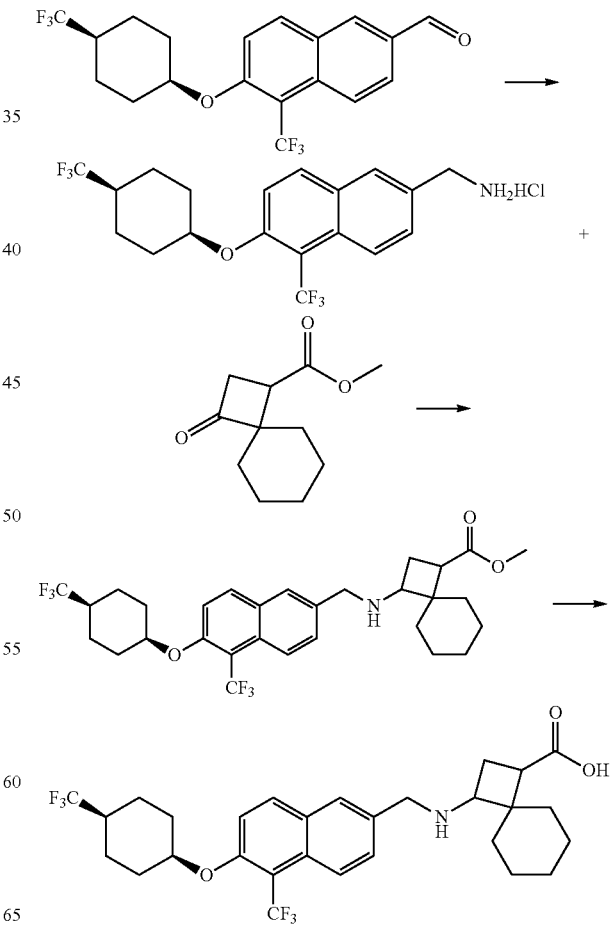

Step 1: (5-(trifluoromethyl)-6-((cis-4-(trifluoromethyl)cyclohexyl)oxy)naphthalen-2-yl)methanamine hydrochloride

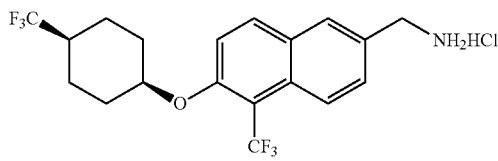

A mixture of 5-trifluoromethyl-6-(cis-4-trifluoromethyl-cyclohexyloxy)-naphthalene-2-carbaldehyde (5.6 g, 14.3 mmol) and hydroxylamine hydrochloride (1.5 g, 21.5 mmol) in 300 mL of ethanol was stirred at RT for 5 h. To the mixture was added conc. HCl (3 mL) and Pd/C (10%, wet, 1 g). The mixture was hydrogenated at RT under a pressure of 5 kgf/cm$^2$ for 8 h and filtered. The filtrate was concentrated to give a residue which was washed with 20 mL of water to afford the title compound as a light yellow solid (5.0 g, yield: 82%). $^1$H NMR (400 MHz, DMSO-d$_6$) δ 8.57 (br s, 3H), 8.16 (d, J=9.2 Hz, 1H), 8.07-8.06 (m, 2H), 7.75 (dd, J=1.6 Hz, 8.8 Hz, 1H), 7.66 (d, J=9.2 Hz, 1H), 5.08 (s, 1H), 4.15 (s, 2H), 2.49-2.41 (m, 1H), 2.05-2.02 (m, 2H), 1.74-1.60 (m, 6H); ESI-MS (M-NH$_2$): 375.1.

Step 2: 3-(((5-(trifluoromethyl)-6-((cis-4-(trifluoromethyl)cyclohexyl)oxy)naphthalen-2-yl)methyl)amino)spiro[3.5]nonane-1-carboxylic acid

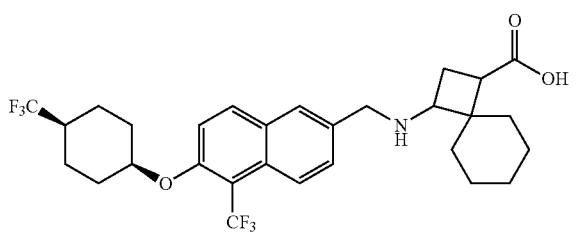 [SMILES: O=C(O)C1CC(NCc2ccc3c(C(F)(F)F)c(O[C@H]4CC[C@@H](C(F)(F)F)CC4)ccc3c2)C12CCCCC2]

To a mixture of (5-(trifluoromethyl)-6-((cis-4-(trifluoromethyl)cyclohexyl)oxy) naphthalen-2-yl)methanamine (80 mg, 0.20 mmol) and 3-oxo-spiro[3.5]nonane-1-carboxylic acid methyl ester (60 mg, 0.31 mmol) in tetrahydrofuran (2.0 mL) was added acetic acid (0.02 mL, 0.41 mmol), sodium triacetoxyborohydride (87 mg, 0.41 mmol) and titanium tetraisopropoxide (116 mg, 0.41 mmol), and the reaction was heated in microwave at 100° C. for 20 min. LCMS showed formation of desired ester, methyl 3-(((5-(trifluoromethyl)-6-((cis-4-(trifluoromethyl)cyclohexyl)oxy)naphthalene-2-yl)methyl)amino)spiro[3.5]nonane-1-carboxylate, (RT 1.66 min, MH+ 572.3). Worked up with ethyl acetate and brine, dried over magnesium sulfate and concentrated. The resulted crude was then dissolved in tetrahydrofuran (1.0 mL) and methanol (1.0 mL), treated with 3.0 M of sodium hydroxide in water (1.0 mL, 3.0 mmol), heated in microwave at 100° C. for 10 min., acidified with 2N HCl, the organic phase was dried and concentrated. The crude was purified by HPLC to give the title compound as a white powder (15 mg). LCMS: RT 1.57 min.; MH+ 558.3; 1H NMR (400 MHz, METHANOL-d4) δ 8.27 (d, J=8.53 Hz, 1H), 8.14 (d, J=9.29 Hz, 1H), 8.04 (d, J=1.26 Hz, 1H), 7.68 (dd, J=1.88, 9.16 Hz, 1H), 7.59 (d, J=9.29 Hz, 1H), 5.02 (br. S., 1H), 4.23-4.43 (m, 2H), 3.39 (t, J=8.41 Hz, 1H), 2.75 (t, J=8.53 Hz, 1H), 2.06-2.46 (m, 6H), 1.15-1.91 (m, 15H).

Example 86

3-(4-{[5-trifluoromethyl-6-(4-trifluoromethyl-cyclohexyloxy)-naphthalen-2-ylmethyl]-amino}-bicyclo[2.2.2]oct-1-yl)-propionic acid

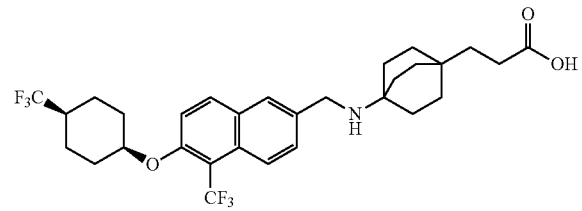

The title compound was prepared according to the procedure described for Example 84 from methyl 3-(4-aminobicyclo[2.2.2]octan-1-yl)propanoate and 5-trifluoromethyl-6-(cis-4-trifluoromethyl-cyclohexyloxy)-naphthalene-2-carbaldehyde. $^1$H NMR (400 MHz, DMSO-d6) δ 8.77 (br. S., 2H), 8.22 (d, J=9.54 Hz, 1H), 8.04-8.16 (m, 2H), 7.64-7.76 (m, 2H), 5.10 (br. S., 1H), 4.15-4.30 (m, 2H), 2.35-2.46 (m, 1H), 2.10-2.19 (m, 2H), 1.98-2.09 (m, 2H), 1.79-1.93 (m, 6H), 1.57-1.78 (m, 6H), 1.44-1.55 (m, 6H), 1.33-1.43 (m, 2H); ESI/MH+ 572.3

Example 87

3-(4-(methyl((5-(trifluoromethyl)-6-((cis-4-(trifluoromethyl)cyclohexyl)oxy)naphthalen-2-yl)methyl)amino)bicyclo[2.2.2]octan-1-yl)propanoic acid

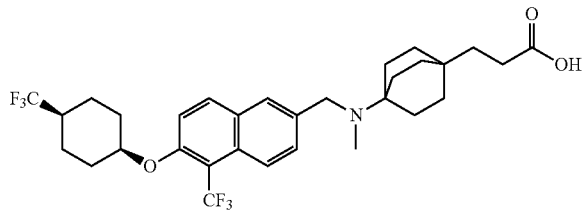 [SMILES: CN(Cc1ccc2c(C(F)(F)F)c(O[C@H]3CC[C@@H](C(F)(F)F)CC3)ccc2c1)C12CCC(CCC(=O)O)(CC1)CC2]

To a mixture of 3-(4-{[5-Trifluoromethyl-6-(4-trifluoromethyl-cyclohexyloxy)-naphthalen-2-ylmethyl]-amino}-bicyclo[2.2.2]oct-1-yl)-propionic acid (35.0 mg, 0.06 mmol) and acetic acid (0.1 mL, 2 mmol) in 37% formaldehyde in water (1.5 mL, 2.0E1 mmol) and methanol (0.5 mL, 10 mmol) was stirred at 50° C. for 1 h. Sodium triacetoxyborohydride (26 mg, 0.12 mmol) was then added. The reaction was then stirred at RT for 2 h. The reaction mixture was concentrated under reduced pressure. The crude was purified by HPLC to give the title compound as a white powder (24 mg). LCMS: RT 1.52 min.; MH+ 586.3; 1H NMR (400 MHz, METHANOL-d4) δ 8.24-8.32 (m, 1H), 8.12-8.19 (m, 1H), 8.05 (d, J=1.51 Hz, 1H), 7.54-7.69 (m, 2H), 5.03 (br. S., 1H), 4.89 (br. S., 1H), 3.99 (d, J=13.05 Hz, 1H), 2.67 (s, 3H), 1.95-2.38 (m, 11H), 1.62-1.91 (m, 12H), 1.49-1.59 (m, 2H)

Example 88

9-1-(5-(trifluoromethyl)-6-((cis-4-(trifluoromethyl)cyclohexyl)oxy)naphthalen-2-yl)ethyl)-9-azabicyclo[3.3.1]nonane-3-carboxylic acid Step 1: 1-(5-(trifluoromethyl)-6-((cis-4-(trifluoromethyl)cyclohexyl)oxy)-naphthalen-2-yl)ethano

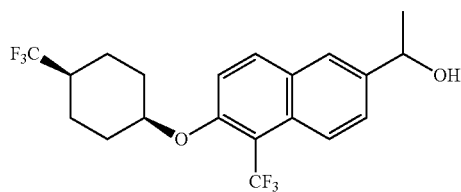 [SMILES: CC(O)c1ccc2c(C(F)(F)F)c(O[C@H]3CC[C@@H](C(F)(F)F)CC3)ccc2c1]

To a solution of 5-Trifluoromethyl-6-(4-trifluoromethyl-cyclohexyloxy)-naphthalene-2-carbaldehyde (3.0 g, 7.7 mmol) in dry tetrahydrofuran (50 mL) at −78° C. under argon was dropwise added 1.4 M of methylmagnesium bromide in toluene/THF (75/25 mixture) (8.2 mL, 12 mmol). After stirred at −78° C. for 1 h, allowed the reaction mixture to warm up a little before quenched with saturated aqueous ammonium chloride, extracted with ethyl acetate. The organic phase was dried, filtered and concentrated. The crude was purified by ISCO (EtOAc/heptane gradient from 0/100 to 60/40) to give the title product as a colorless oil (2.1 g). LC-MS: RT 1.97 min.; ESI: 389.0 (M−OH) and 429.0 (M+Na). $^{1}$H NMR (400 MHz, DMSO-d6) δ 8.17 (d, J=9.04 Hz, 1H), 7.98-8.05 (m, 1H), 7.89 (s, 1H), 7.57-7.65 (m, 2H), 5.31 (d, J=4.02 Hz, 1H), 5.06 (br. S., 1H), 4.77-4.96 (m, 1H), 2.42 (br. S., 1H), 2.00-2.10 (m, 2H), 1.57-1.80 (m, 6H), 1.39 (d, J=6.53 Hz, 3H).

Step 2: 6-(1-bromoethyl)-1-(trifluoromethyl)-2-((cis-4-(trifluoromethyl)cyclo-hexyl)oxy)naphthalene

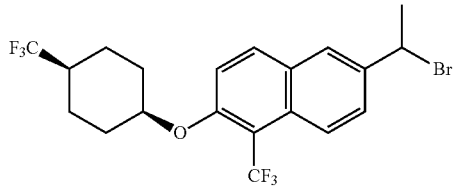 [SMILES: CC(Br)c1ccc2c(C(F)(F)F)c(O[C@H]3CC[C@@H](C(F)(F)F)CC3)ccc2c1]

To a solution of 1-[5-Trifluoromethyl-6-(4-trifluoromethyl-cyclohexyloxy)-naphthalen-2-yl]-ethanol (1.9 g, 4.7 mmol) in tetrahydrofuran (20 mL) was added 1.0 M of phosphorus tribromide in methylene chloride (4.7 mL, 4.7 mmol). The mixture was stirred at RT for 10 min. The reaction was diluted with EtOAc, washed with water. The organic layer was then dried and concentrated to give the title product as a colorless oil (2.1 g, with ~30% SM based on LCMS) which was used in the next step without further purifications. LCMS: RT 2.37 min.; ESI: 389.0 (M-Br).

Step 3: methyl 9-(1-(5-(trifluoromethyl)-6-((cis-4-(trifluoromethyl)cyclohexyl)-oxy)naphthalene-2-yl)ethyl)-9-azabicyclo[3.3.1]nonane-3-carboxylate

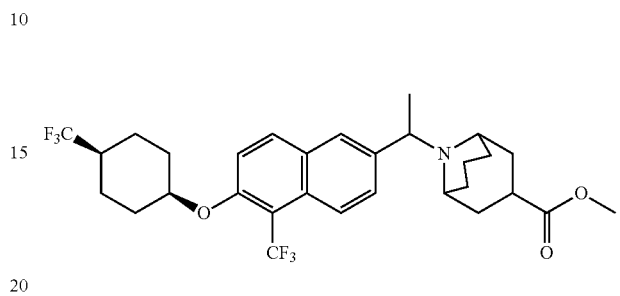

To a mixture of potassium carbonate (294 mg, 2.13 mmol) and 9-Aza-bicyclo[3.3.1]-nonane-3-carboxylic acid methyl ester hydrochloride (609 mg, 2.77 mmol) in N,N-dimethyl-formamide (15 mL) was added a solution of 6-(1-Bromo-ethyl)-1-trifluoro-methyl-2-(4-trifluoromethyl-cyclohexyloxy)-naphthalene (1.0 g, 2.1 mmol) in DMF (5 ml). The reaction mixture was stirred at RT overnight. The mixture partitioned between ethyl acetate and saturated aqueous sodium bicarbonate. The organic phase was then washed with brine, dried, filtered and concentrated. The crude was purified by ISCO (EtOAc/heptane, gradient 0/100 to 50/50) to give the title product as a white powder (555 mg). LC-MS: RT 1.61 min., MH+ 572.1.

Step 4: 9-(1-(5-(trifluoromethyl)-6-((cis-4-(trifluoromethyl)cyclohexyl)-oxy)-naphthalen-2-yl)ethyl)-9-azabicyclo[3.3.1]nonane-3-carboxylic acid

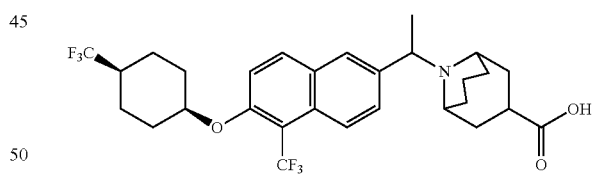

Methyl 9-(1-(5-(trifluoromethyl)-6-((cis-4-(trifluoromethyl)cyclohexyl)-oxy)naphthalene-2-yl)ethyl)-9-azabicyclo[3.3.1]nonane-3-carboxylate. was dissolved in tetrahydrofuran (2.0 mL) and methanol (1.0 mL). 3.0 M of aqueous sodium hydroxide (2.0 mL, 6.0 mmol) was then added. The reaction was heated in microwave at 100° C. for 10 min. The reaction mixture was then neutralized with 2N HCl. The organic phase was separated, dried and concentrated. The crude was purified by HPLC to give 9-(1-(5-(trifluoromethyl)-6-((cis-4-(trifluoromethyl)cyclohexyl)-oxy)-naphthalen-2-yl)ethyl)-9-azabicyclo[3.3.1]nonane-3-carboxylic acid as a white powder.

Example 89

9-((R)-1-(5-(trifluoromethyl)-6-((cis-4-(trifluoromethyl)cyclohexyl)oxy)naphthalen-2-yl)ethyl)-9-azabicyclo[3.3.1]nonane-3-carboxylic acid Step 1: 9-((R)-1-(5-trifluoromethyl-6-(cis-4-(trifluoromethyl)cyclohexyloxy)-naphthalen-2-yl)-ethyl)-9-aza-bicyclo[3.3.1]nonane-3-carboxylic acid methyl ester

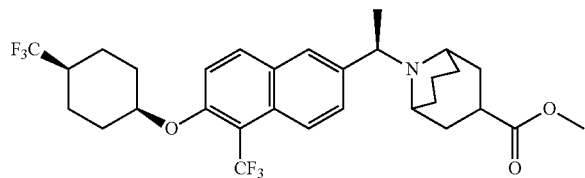 [SMILES: COC(=O)C1CC2CCCC(C1)N2[C@H](C)c1ccc2c(C(F)(F)F)c(O[C@H]3CC[C@@H](C(F)(F)F)CC3)ccc2c1]

Racemic 9-{1-[5-Trifluoromethyl-6-(4-trifluoromethyl-cyclohexyloxy)-naphthalen-2-yl]-ethyl}-9-aza-bicyclo [3.3.1]nonane-3-carboxylic acid methyl ester (493 mg, 0.86 mmol) was sent for chiral separation (by Lotus Separations). The methods: IC (2×15 cm), 25% methanol (0.1% DEA)/ $CO_2$, 100 bar; 60 ml/min., 220 nM.; ini vol: 1 mL, 20 mg/mL methanol. Two isomers were obtained after the chiral separation. Since the absolute stereo chemistry is unknown, Peak#1 (161 mg, purity>99% based on HPLC, ee>99%) was randomly assigned as the R-isomer, and Peak#2 (333 mg, purity >99% based on HPLC, ee>99%) was randomly assigned as the S-isomer (solvent residue presented this fraction was later confirmed by the recovery yield from next step).

Step 2: 9-((R)-1-(5-trifluoromethyl-6-(cis-4-(trifluoromethyl)cyclohexyloxy)-naphthalen-2-yl)-ethyl)-9-aza-bicyclo[3.3.1]nonane-3-carboxylic acid

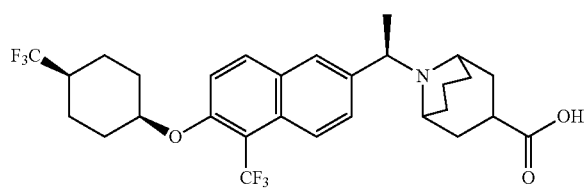 [SMILES: C[C@H](c1ccc2c(C(F)(F)F)c(O[C@H]3CC[C@@H](C(F)(F)F)CC3)ccc2c1)N1C2CCCC1CC(C(=O)O)C2]

9-((R)-1-(5-trifluoromethyl-6-(cis-4-(trifluoromethyl)cyclohexyloxy)-naphthalen-2-yl)-ethyl)-9-aza-bicyclo[3.3.1] nonane-3-carboxylic acid methyl ester (161 mg, 0.282 mmol, the chiral center was randomly assigned as R-isomer) was dissolved in tetrahydrofuran (2.0 mL, 25 mmol) and methanol (0.5 mL, 10 mmol). 3.0 M of aqueous sodium hydroxide (1.0 mL, 3.0 mmol) was then added. The reaction was heated in microwave at 100° C. for 10 min. The reaction mixture was then neutralized with 2N HCl. The organic phase was separated, dried and concentrated. The crude was purified by HPLC to give title product as a white powder (130 mg, TFA salt). LCMS: RT 1.51 min.; MH+ 558.0; 1H NMR (400 MHz, METHANOL-d4) δ 8.32 (d, J=9.04 Hz, 1H), 8.07-8.21 (m, 2H), 7.79 (d, J=9.29 Hz, 1H), 7.61 (d, J=9.29 Hz, 1H), 4.97-5.27 (m, 2H), 4.20 (d, J=12.05 Hz, 1H), 3.35-3.46 (m, 1H), 3.09-3.22 (m, 1H), 1.58-2.63 (m, 22H).

Example 90

9-((S)-1-(5-(trifluoromethyl)-6-((cis-4-(trifluoromethyl)cyclohexyl)oxy)naphthalen-2-yl)ethyl)-9-azabicyclo[3.3.1]nonane-3-carboxylic acid Step 1: 9-((S)-1-(5-(trifluoromethyl)-6-(cis-4-(trifluoromethyl)cyclohexyloxy)-naphthalen-2-yl)ethyl)-9-azabicyclo[3.3.1]nonane-3-carboxylic acid methyl ester

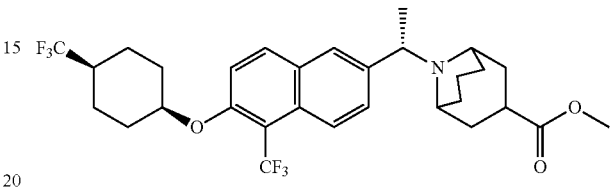

Racemic 9-{1-[5-Trifluoromethyl-6-(4-trifluoromethyl-cyclohexyloxy)-naphthalen-2-yl]-ethyl}-9-aza-bicyclo [3.3.1]nonane-3-carboxylic acid methyl ester (493 mg, 0.86 mmol) was sent for chiral separation (by Lotus Separations). The methods: IC (2×15 cm), 25% methanol (0.1% DEA)/ $CO_2$, 100 bar; 60 ml/min., 220 nM.; ini vol: 1 mL, 20 mg/mL methanol. Two isomers were obtained after the chiral separation. Since the absolute stereo chemistry is unknown, Peak#1 (161 mg, purity>99% based on HPLC, ee>99%) was randomly assigned as the R-isomer, and Peak#2 (333 mg, purity >99% based on HPLC, ee>99%) was randomly assigned as the S-isomer (solvent residue presented this fraction was later confirmed by the recovery yield from next step).

Step 2: 9-((S)-1-(5-(trifluoromethyl)-6-((cis-4-(trifluoromethyl)cyclohexyl)-oxy)-naphthalen-2-yl)ethyl)-9-azabicyclo[3.3.1]nonane-3-carboxylic acid

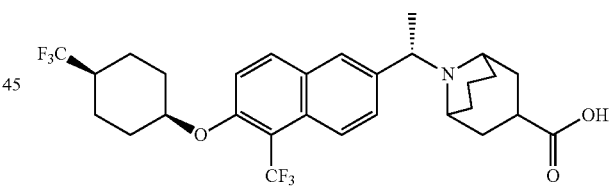

9-{(S)-1-[5-Trifluoromethyl-6-(cis-4-trifluoromethyl-cyclohexyloxy)-naphthalen-2-yl]ethyl}-9-aza-bicyclo[3.3.1] nonane-3-carboxylic acid methyl ester (333 mg, 0.582 mmol) chiral center was randomly assigned as S-isomer, may have residual solvent) was dissolved in tetrahydrofuran (2.0 mL) and methanol (1.0 mL). 3.0 M of aqueous sodium hydroxide (2.0 mL, 6.0 mmol) was then added. The reaction was heated in microwave at 100° C. for 10 min. The reaction mixture was then neutralized with 2N HCl. The organic phase was separated, dried and concentrated. The crude was purified by HPLC to give desired product as a white powder (152 mg, TFA salt). LCMS: RT 1.51 min.; MH+ 558.0; 1H NMR (400 MHz, METHANOL-d4) δ 8.32 (d, J=9.29 Hz, 1H), 8.08-8.20 (m, 2H), 7.79 (d, J=9.29 Hz, 1H), 7.61 (d, J=9.29 Hz, 1H), 4.97-5.28 (m, 2H), 4.20 (d, J=11.80 Hz, 1H), 3.33-3.46 (m, 1H), 3.11-3.23 (m, 1H), 1.58-2.63 (m, 22H).

Example 91

9-(1-(6-((cis-4-ethylcyclohexyl)oxy)-5-(trifluoromethyl)naphthalen-2-yl)ethyl)-9-azabicyclo[3.3.1]-nonane-3-carboxylic acid

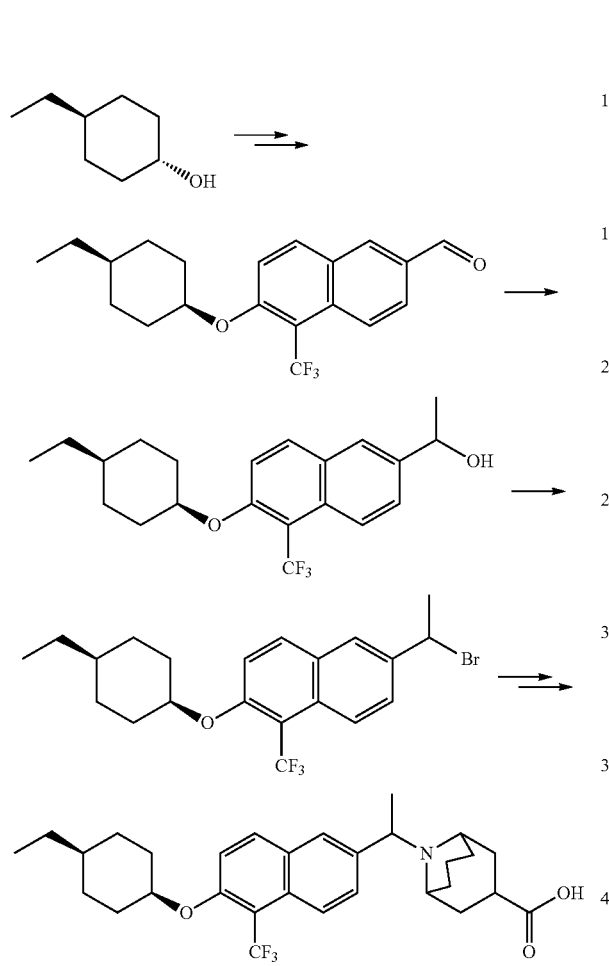

Step 1: 6-((cis-4-ethylcyclohexyl)oxy)-5-(trifluoromethyl)-2-naphthaldehyde

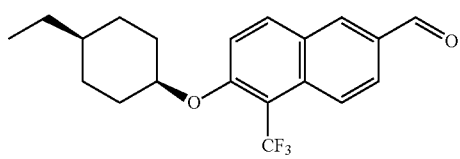 [SMILES: CC[C@H]1CC[C@@H](Oc2ccc3cc(C=O)ccc3c2C(F)(F)F)CC1]

The title compound was prepared according to the procedure described for 5-(trifluoromethyl)-6-((cis-4-(trifluoromethyl)cyclohexyl)oxy)-2-naphthaldehyde from trans-4-ethylcyclohexanol. $^1$H NMR (400 MHz, CHLOROFORM-d) δ 10.13 (s, 1H), 8.23-8.39 (m, 2H), 8.09 (d, J=9.04 Hz, 1H), 8.00 (dd, J=1.63, 9.16 Hz, 1H), 7.39 (d, J=9.29 Hz, 1H), 4.86 (br. S., 1H), 2.02-2.18 (m, 2H), 1.54-1.71 (m, 4H), 1.39-1.53 (m, 2H), 1.22-1.38 (m, 3H), 0.92 (t, J=7.15 Hz, 3H). ESI-MS (M+H)$^+$: 351.0

Step 2: 1-(6-((cis-4-ethylcyclohexyl)oxy)-5-(trifluoromethyl)naphthalen-2-yl)ethanol

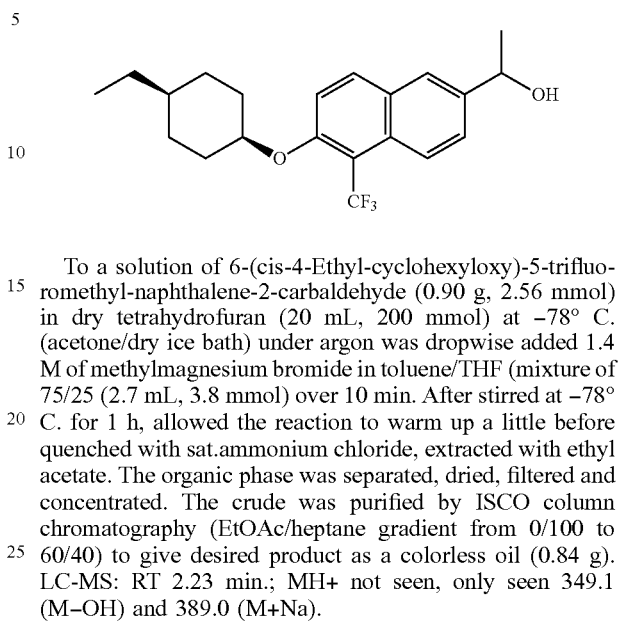

To a solution of 6-(cis-4-Ethyl-cyclohexyloxy)-5-trifluoromethyl-naphthalene-2-carbaldehyde (0.90 g, 2.56 mmol) in dry tetrahydrofuran (20 mL, 200 mmol) at −78° C. (acetone/dry ice bath) under argon was dropwise added 1.4 M of methylmagnesium bromide in toluene/THF (mixture of 75/25 (2.7 mL, 3.8 mmol) over 10 min. After stirred at −78° C. for 1 h, allowed the reaction to warm up a little before quenched with sat.ammonium chloride, extracted with ethyl acetate. The organic phase was separated, dried, filtered and concentrated. The crude was purified by ISCO column chromatography (EtOAc/heptane gradient from 0/100 to 60/40) to give desired product as a colorless oil (0.84 g). LC-MS: RT 2.23 min.; MH+ not seen, only seen 349.1 (M−OH) and 389.0 (M+Na).

Step 3: 6-(1-bromoethyl)-2-((cis-4-ethylcyclohexyl)oxy)-1-(trifluoromethyl) naphthalene

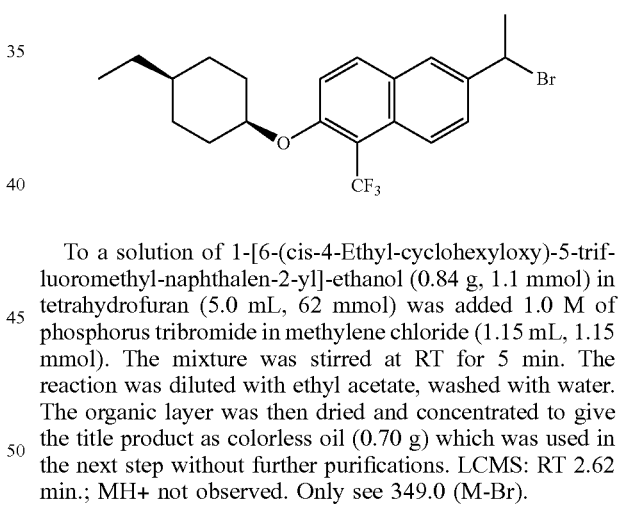

To a solution of 1-[6-(cis-4-Ethyl-cyclohexyloxy)-5-trifluoromethyl-naphthalen-2-yl]-ethanol (0.84 g, 1.1 mmol) in tetrahydrofuran (5.0 mL, 62 mmol) was added 1.0 M of phosphorus tribromide in methylene chloride (1.15 mL, 1.15 mmol). The mixture was stirred at RT for 5 min. The reaction was diluted with ethyl acetate, washed with water. The organic layer was then dried and concentrated to give the title product as colorless oil (0.70 g) which was used in the next step without further purifications. LCMS: RT 2.62 min.; MH+ not observed. Only see 349.0 (M-Br).

Step 4: 9-(1-(6-((cis-4-ethylcyclohexyl)oxy)-5-(trifluoromethyl)naphthalen-2-yl)ethyl)-9-azabicyclo[3.3.1]-nonane-3-carboxylic acid

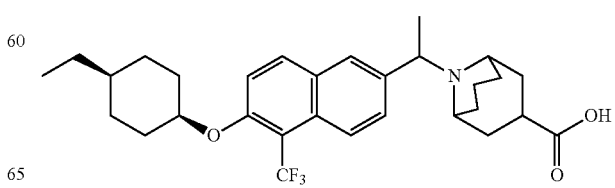

To a mixture of potassium carbonate (53.1 mg, 0.384 mmol) and 9-Aza-bicyclo[3.3.1]-nonane-3-carboxylic acid methyl ester (99.8 mg, 0.454 mmol) in N,N-dimethylformamide (3.0 mL, 39 mmol) was added a solution of 6-(1-Bromo-ethyl)-2-(4-ethyl-cyclohexyloxy)-1-trifluoromethyl-naphthalene (0.15 g, 0.35 mmol) in DMF (5 ml). The reaction mixture was stirred at RT overnight. The mixture partitioned between ethyl acetate and saturated sodium chloride. The organic phase was washed with brine, dried, filtered and concentrated. The crude was purified by HPLC to give methyl 9-(1-(6-(((cis-4-ethylcyclohexyl)oxy)-5-(trifluoromethyl)naphthalen-2-yl)ethyl)-9-azabicyclo[3.3.1]nonane-3-carboxylate as a white powder (LC-MS: RT 1.78 min., MH+ 532.1) which was then dissolved in tetrahydrofuran (2.0 mL, 25 mmol) and methanol (1.0 mL, 25 mmol). 3.0 M of aqueous sodium hydroxide (1.0 mL, 3.0 mmol) was added, and the reaction mixture was heated in microwave at 100° C. for 10 min. Ethyl acetate was added, the mixture was neutralized with 2N HCl (aq). The organic layer was separated, dried and concentrated. The crude was then purified by HPLC to give the titled product as a white powder (52 mg, TFA salt). LC-MS: RT 1.67 min., MH+ 518.1; 1H NMR (400 MHz, METHANOL-d4) δ 8.30 (d, J=9.04 Hz, 1H), 8.04-8.19 (m, 2H), 7.77 (d, J=9.29 Hz, 1H), 7.58 (d, J=9.29 Hz, 1H), 5.00-5.28 (m, 1H), 4.95 (br. S., 1H), 4.20 (d, J=12.05 Hz, 1H), 3.38 (dd, J=6.02, 11.80 Hz, 1H), 3.17 (d, J=14.31 Hz, 1H), 2.29-2.62 (m, 3H), 1.52-2.28 (m, 16H), 1.23-1.51 (m, 5H), 0.93 (t, J=7.15 Hz, 3H).

Example 92

9-(1-(6-(((cis-4-ethylcyclohexyl)oxy)-5-(trifluoromethyl)naphthalene-2-yl)propyl)-9-azabicyclo[3.3.1]nonane-3-carboxylic acid

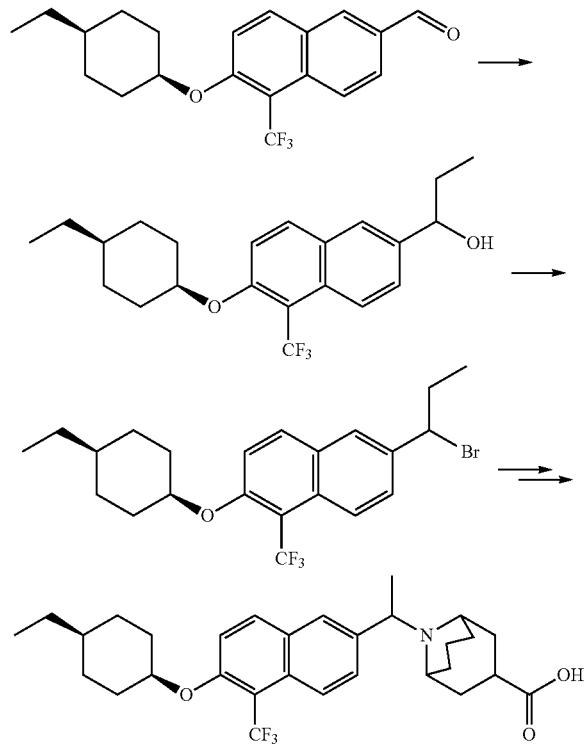

Step 1: 1-(6-(((cis-4-ethylcyclohexyl)oxy)-5-(trifluoromethyl)naphthalene-2-yl)-propan-1-ol

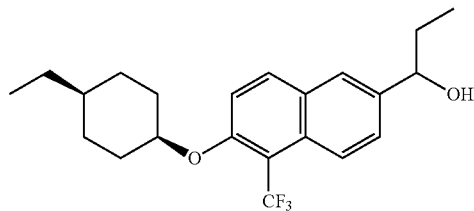 [SMILES: CCC(O)c1ccc2c(C(F)(F)F)c(O[C@H]3CC[C@@H](CC)CC3)ccc2c1]

To a solution of 6-(4-ethyl-cyclohexyloxy)-5-trifluoromethyl-naphthalene-2-carbaldehyde (1.0 g, 2.8 mmol) in dry tetrahydrofuran (20 mL, 200 mmol) at −78° C. (acetone/dry ice bath) under argon was dropwise added 3.0 M of ethyl-magnesium bromide in ether (1.05 mL, 3.14 mmol). After stirred at −78° C. for 2 h, the reaction was allowed to warm up a little before quenched with sat.ammonium chloride, the product was extracted with ethyl acetate. The organic phase was separated, dried, filtered and concentrated. The crude was purified by ISCO column chromatography (ethyl acetate/heptane gradient from 0/100 to 60/40) to give desired product as a colorless oil (0.60 g). LC-MS: RT 2.37 min.; MH+ not observed, only seen 363.0 (M-OH) and 403 (M+Na).

Step 2: 6-(1-bromopropyl)-2-((cis-4-ethylcyclohexyl)oxy)-1-(trifluoromethyl)-naphthalene

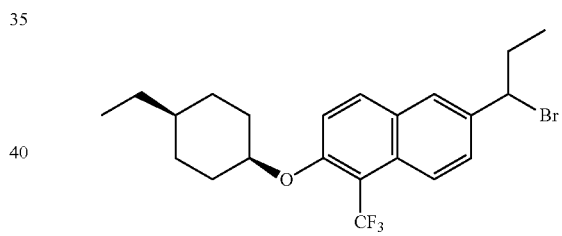

The title compound was prepared according to the procedure described for compound 6-(1-bromoethyl)-2-((cis-4-ethylcyclohexyl)oxy)-1-(trifluoromethyl) naphthalene. The compound was used in the next steps without further purifications. Step 3: 9-(1-(6-(((cis-4-ethylcyclohexyl)oxy)-5-(trifluoromethyl)naphthalene-2-yl)propyl)-9-azabicyclo[3.3.1]nonane-3-carboxylic acid

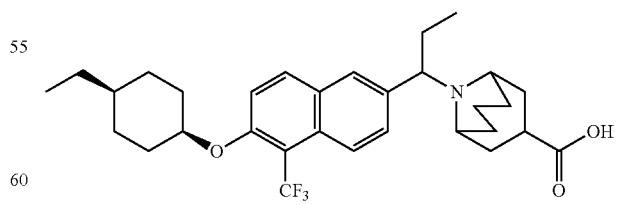

To a mixture of potassium carbonate (71.7 mg, 0.52 mmol) and 9-Aza-bicyclo[3.3.1]-nonane-3-carboxylic acid methyl ester hydrochloride (59.5 mg, 0.27 mmol) in N,N-dimethylformamide (2.0 mL, 26 mmol) was added a solution of 6-(1-Bromo-propyl)-2-(4-ethyl-cyclohexyloxy)-1- trifluoromethyl-naphthalene (0.10 g, 0.22 mmol) in DMF (5 ml). The reaction mixture was stirred at RT overnight. LCMS showed formation of the desired ester, methyl 9-(1-(6-((cis-4-ethylcyclohexyl)oxy)-5-(trifluoromethyl)naphthalene-2-yl)propyl)-9-azabicyclo[3.3.1]nonane-3-carboxylate (RT 1.84 min., MH+ 546.1). The mixture partitioned between ethyl acetate and water. The organic phase was washed with brine, dried, filtered and concentrated. The crude was purified by HPLC to give desired intermediate as a colorless oil which was then dissolved in tetrahydrofuran (1.0 mL, 12 mmol) and methanol (0.5 mL, 10 mmol), treated with 3.0 M of aqueous sodium hydroxide (1.0 mL, 3.0 mmol). The reaction was heated in microwave at 100° C. for 10 min. Cooled down, the reaction was neutralized with 2N HCl. The organic phase was then separated, dried and concentrated. The crude was purified by HPLC to give the title product as a white powder (6 mg, TFA salt). LC-MS: RT 1.74 min., MH+ 532.1; 1H NMR (400 MHz, METHANOL-d4) δ 8.32 (d, J=7.53 Hz, 1H), 8.12 (d, J=9.29 Hz, 2H), 7.74 (d, J=8.28 Hz, 1H), 7.59 (d, J=9.29 Hz, 1H), 4.89-5.01 (m, 2H), 4.24 (br. S., 1H), 3.35-3.45 (m, 1H), 3.05-3.23 (m, 1H), 1.82-2.61 (m, 13H), 1.52-1.80 (m, 5H), 1.23-1.52 (m, 5H), 0.93 (t, J=7.15 Hz, 3H), 0.76 (t, J=7.28 Hz, 3H).

Example 93

9-(1-(6-((cis-4-Methylcyclohexyl)oxy)-5-(trifluoromethyl)naphthalen-2-yl)ethyl)-9-azabicyclo[3.3.1]nonane-3-carboxylic acid

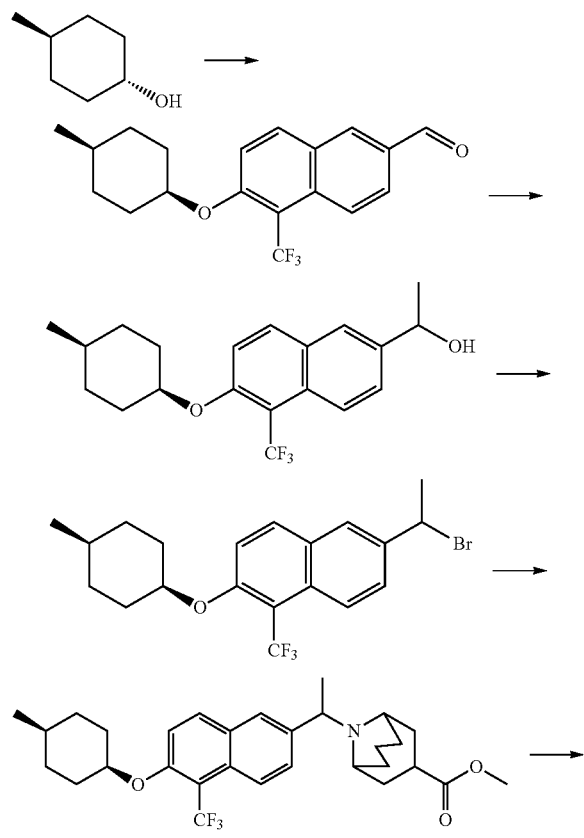

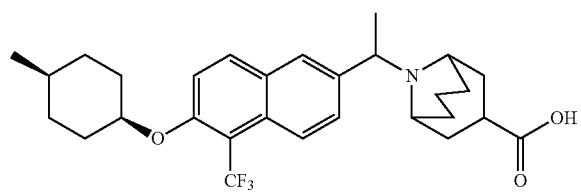

Step 1: 6-((cis-4-methylcyclohexyl)oxy)-5-(trifluoromethyl)-2-naphthaldehyde

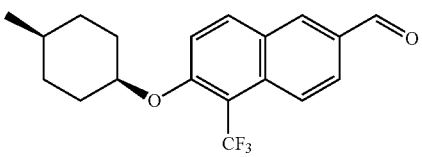 [SMILES: C[C@H]1CC[C@@H](Oc2ccc3cc(C=O)ccc3c2C(F)(F)F)CC1]

The titled compound was prepared according to the procedure described for 5-(trifluoromethyl)-6-((cis-4-(trifluoromethyl)cyclohexyl)oxy)-2-naphthaldehyde from trans-4-methylcyclohexan-1-ol. $^1$H NMR (400 MHz, CDCl$_3$) δ 10.11 (s, 1H), 8.31 (d, J=8.8 Hz, 1H), 8.26 (d, J=1.2 Hz, 1H), 8.07 (d, J=9.2 Hz, 1H), 7.98 (dd, J=1.6 Hz, 9.2 Hz, 1H), 7.37 (d, J=9.2 Hz, 1H), 4.84 (s, 1H), 2.09-2.06 (m, 2H), 1.68-1.62 (m, 2H), 1.54-1.43 (m, 5H), 0.96 (d, J=5.2 Hz, 3H); ESI-MS (M+H)$^+$: 336.9

Step 2: 1-(6-((cis-4-Methylcyclohexyl)oxy)-5-(trifluoromethyl)naphthalene-2-yl)ethanol

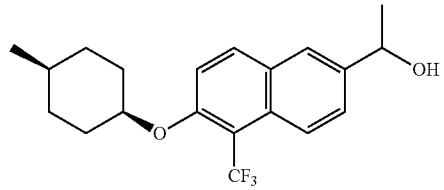 [SMILES: CC(O)c1ccc2c(C(F)(F)F)c(O[C@H]3CC[C@@H](C)CC3)ccc2c1]

To a solution of 6-((cis-4-methylcyclohexyl)oxy)-5-(trifluoromethyl)-2-naphthaldehyde (673 mg, 2.00 mmol) in dry THF (10 mL) at −78° C. (acetone/dry ice bath) under N$_2$ was added a solution of 1.4M MeMgBr in toluene/THF (2.14 mL, 3.00 mmol). After stirred at −78° C. for 40 min, it was switched to an ice-cold bath, and stirred at 0° C. for 30 min. The reaction was quenched with satd.NH$_4$Cl, extracted with EtOAc. The organic phase was dried, filtered and concentrated. The residue was purified by flash chromatography on silica gel column to provide the alcohol as a colorless oil (580 mg, yield 82%). $^1$H NMR (300 MHz, DMSO-d$_6$) δ 8.14 (d, J=9.06 Hz, 1H), 8.01 (d, J=7.18 Hz, 1H), 7.88 (s, 1H), 7.62 (dd, J=1.89, 9.06 Hz, 1H), 7.56 (d, J=9.44 Hz, 1H), 5.30 (d, J=4.15 Hz, 1H), 4.95 (br. S., 1H), 4.80-4.91 (m, 1H), 1.85-1.96 (m, 2H), 1.62 (t, J=13.22 Hz, 2H), 1.37 (d, J=12.46 Hz, 3H), 1.22-1.53 (m, 5H), 0.90 (d, J=6.04 Hz, 3H); LCMS m/z 335.2 [M+H−H$_2$O]$^+$ Step 3: 6-(1-Bromoethyl)-2-((cis-4-methylcyclo-hexyl)oxy)-1-(trifluoromethyl)naphthalene

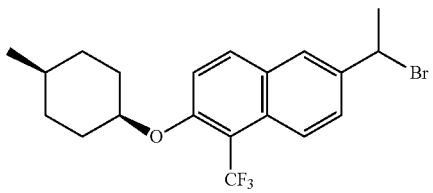 [SMILES: CC(Br)c1ccc2c(C(F)(F)F)c(O[C@H]3CC[C@@H](C)CC3)ccc2c1]

To a solution of 1-(6-((cis-4-methylcyclohexyl)oxy)-5-(trifluoromethyl)naphthalene-2-yl)ethanol (528 mg, 1.50 mmol) in THF under $N_2$ was added 1 M of $PBr_3$ in methylene chloride at room temperature. The reaction mixture was stirred at rt for 5 minutes, and then partitioned between EtOAc and water. The organic phase was dried, filtered and concentrated to get the bromide intermediate as a colorless oil. The oil product was dissolved in DMF (15 mL) to make a 0.1M solution, and used as such for next step directly.

Step 4: methyl 9-(1-(6-((cis-4-methylcyclohexyl)oxy)-5-(trifluoromethyl)naphthalene-2-yl)ethyl)-9-azabicyclo[3.3.1]nonane-3-carboxylate

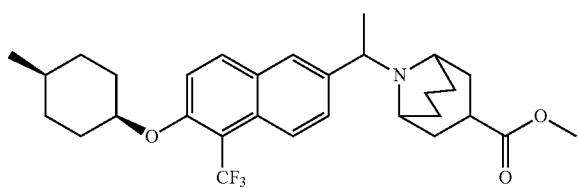

To a solution of 0.1M 6-(1-bromoethyl)-2-((cis-4-methylcyclohexyl)oxy)-1-(trifluoromethyl)naphthalene in DMF (8 mL, 0.8 mmol) was added 9-aza-bicyclo[3.3.1]nonane-3-carboxylic acid methyl ester; HCl salt (228 mg, 1.04 mmol) and $K_2CO_3$ (166 mg, 1.20 mmol). The reaction mixture was stirred at rt overnight. It was partitioned between EtOAc and brine. The organic phase was dried over $MgSO_4$, filtered and concentrated. The residue was purified by flash chromatography on silica gel column to get the desired ester as a colorless oil (235 mg, yield 57%). LCMS m/z 518.3 $[M+H]^+$ Step 5: 9-(1-(6-((cis-4-Methylcyclohexyl)oxy)-5-(trifluoromethyl)naphthalen-2-yl)ethyl)-9-azabicyclo[3.3.1]nonane-3-carboxylic acid

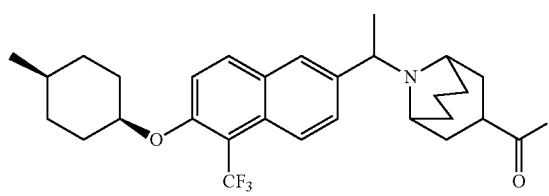

To a solution of above ester (235 mg, 0.454 mmol) in THF (1 mL) and MeOH (1 mL) was added 3 M of NaOH in water (0.3 mL, 0.9 mmol). The reaction mixture was heated with microwave irritation at 100° C. for 10 min. Neutralized with 1N HCl and purified by HPLC (TFA method) to collect the desired acid as a white powder after lyophilization (223 mg, yield 80%). $^1$H NMR (400 MHz, DMSO-$d_6$) δ 8.13 (d, J=9.29 Hz, 1H), 8.02 (d, J=7.53 Hz, 1H), 7.87 (s, 1H), 7.65 (d, J=9.04 Hz, 1H), 7.56 (d, J=9.29 Hz, 1H), 4.96 (br. S., 1H), 4.18 (q, J=6.19 Hz, 1H), 2.87-3.14 (m, 3H), 1.14-2.13 (m, 22H), 0.90 (d, J=6.27 Hz, 3H); LCMS m/z 504.3 $[M+H]^+$ Example 94

9-(1-(6-((cis-4-Methylcyclohexyl)oxy)-5-(trifluoromethyl)naphthalen-2-yl)ethyl)-9-azabicyclo[3.3.1]nonane-3-carboxylic acid, enantiomer 1

Racemic 9-(1-(6-((cis-4-Methylcyclohexyl)oxy)-5-(trifluoromethyl)naphthalen-2-yl)ethyl)-9-azabicyclo[3.3.1]nonane-3-carboxylic acid was subjected to preparative SFC by the following method: AS-H (2×15 cm); 15% ethanol (0.1% DEA)/$CO_2$, 100 bar; 70 mL/min, 220 nm; Inj vol.: 0.5 mL, 20 mg/mL ethanol. Enantiomer 1: $^1$H NMR (400 MHz, METHANOL-$d_4$) δ 8.30 (d, J=8.78 Hz, 1H), 8.11 (br. S., 2H), 7.77 (d, J=8.28 Hz, 1H), 7.58 (d, J=9.29 Hz, 1H), 5.00-5.28 (m, 1H), 4.94 (br. S., 1H), 4.18 (br. S., 1H), 3.36-3.46 (m, 1H), 3.06-3.23 (m, 1H), 1.82-2.64 (m, 11H), 1.78 (d, J=6.78 Hz, 3H), 1.69 (t, J=13.30 Hz, 3H), 1.33-1.58 (m, 5H), 0.95 (d, J=5.77 Hz, 3H); LCMS m/z 504.3 $[M+H]^+$ Example 95

9-(1-(6-((cis-4-Methylcyclohexyl)oxy)-5-(trifluoromethyl)naphthalen-2-yl)ethyl)-9-azabicyclo[3.3.1]nonane-3-carboxylic acid, enantiomer 2

Racemic 9-(1-(6-((cis-4-Methylcyclohexyl)oxy)-5-(trifluoromethyl)naphthalen-2-yl)ethyl)-9-azabicyclo[3.3.1]nonane-3-carboxylic acid was subjected to preparative SFC by the following method: AS-H (2×15 cm); 15% ethanol (0.1% DEA)/$CO_2$, 100 bar; 70 mL/min, 220 nm; Inj vol.: 0.5 mL, 20 mg/mL ethanol. Enantiomer 2: $^1$H NMR (400 MHz, METHANOL-$d_4$) δ 8.30 (d, J=8.78 Hz, 1H), 8.11 (br. S., 2H), 7.77 (d, J=9.04 Hz, 1H), 7.58 (d, J=9.29 Hz, 1H), 5.00-5.27 (m, 1H), 4.94 (br. S., 1H), 4.18 (br. S., 1H), 3.36-3.46 (m, 1H), 3.06-3.22 (m, 1H), 1.82-2.65 (m, 11H), 1.78 (d, J=6.53 Hz, 3H), 1.62-1.74 (m, 3H), 1.32-1.59 (m, 5H), 0.95 (d, J=5.77 Hz, 3H); LCMS m/z 504.3 $[M+H]^+$ Example 96

8-((6-((cis-4-Methylcyclohexyl)oxy)-5-(trifluoromethyl)naphthalen-2-yl)methyl)-8-azabicyclo[3.2.1]octane-3-carboxylic acid

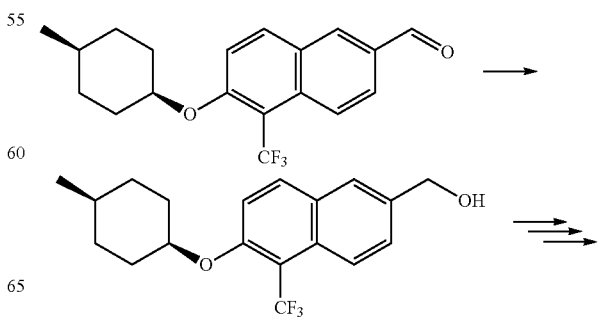

193
-continued

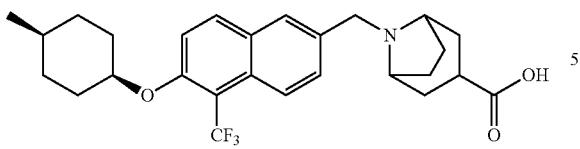

Step 1: (6-((cis-4-Methylcyclohexyl)oxy)-5-(trifluoromethyl)naphthalen-2-yl)methanol

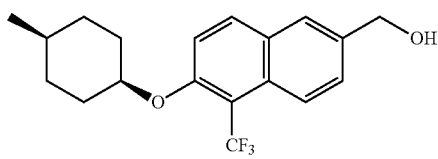 [SMILES: C[C@H]1CC[C@@H](Oc2ccc3cc(CO)ccc3c2C(F)(F)F)CC1]

To a mixture of 6-((cis-4-methylcyclohexyl)oxy)-5-(trifluoromethyl)-2-naphthaldehyde (1.34 g, 4.00 mmol) in methanol (20 mL) was added $NaBH_4$ (152 mg, 4.02 mmol), and stirred at rt for 30 min, LCMS shows the reaction was completed. Concentrated to remove most of the solvent, added water and extracted with ethyl acetate. The organic phase was dried, filtered and concentrated. The residue was purified by flash chromatography on silica gel column to give desired product as a white solid. (1.34 g, yield 99%). $^1$H NMR (300 MHz, METHANOL-$d_4$) δ 8.14 (dd, J=1.51, 9.06 Hz, 1H), 8.04 (d, J=9.44 Hz, 1H), 7.83 (s, 1H), 7.56 (dd, J=1.89, 9.06 Hz, 1H), 7.46 (d, J=9.06 Hz, 1H), 4.88 (br. S., 1H), 4.76 (s, 2H), 1.99-2.13 (m, 2H), 1.61-1.78 (m, 2H), 1.43-1.58 (m, 5H), 0.97 (d, J=5.67 Hz, 3H); LCMS m/z 321.1 $[M+H-H_2O]^+$

Step 2: 8-((6-((cis-4-Methylcyclohexyl)oxy)-5-(trifluoromethyl)naphthalen-2-yl)methyl)-8-azabicyclo[3.2.1]octane-3-carboxylic acid

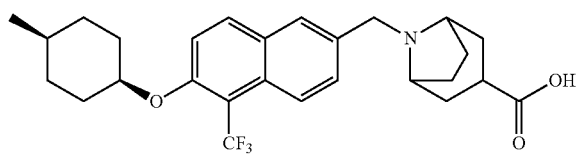 [SMILES: C[C@H]1CC[C@@H](Oc2ccc3cc(CN4C5CCC4CC(C(=O)O)C5)ccc3c2C(F)(F)F)CC1]

The title compound was synthesized according to the procedure described in Example 93, Steps 3-5 from (6-((cis-4-Methylcyclohexyl)oxy)-5-(trifluoromethyl)naphthalen-2-yl)methanol and methyl 8-azabicyclo[3.2.1]octane-3-carboxylate (total yield 61% for three steps). $^1$H NMR (300 MHz, METHANOL-$d_4$) δ 8.29 (d, J=7.93 Hz, 1H), 8.15 (d, J=9.44 Hz, 1H), 8.08 (s, 1H), 7.72 (dd, J=1.89, 9.06 Hz, 1H), 7.60 (d, J=9.06 Hz, 1H), 4.96 (br. S., 1H), 4.38 (br. S., 2H), 4.04 (br. S., 2H), 2.99 (quin, J=8.97 Hz, 1H), 2.51 (br. S., 2H), 2.04-2.23 (m, 8H), 1.72 (t, J=13.03 Hz, 2H), 1.39-1.59 (m, 5H), 0.97 (d, J=5.29 Hz, 3H); LCMS m/z 476.2 $[M+H]^+$

194

Example 97

9-((6-((cis-4-Methylcyclohexyl)oxy)-5-(trifluoromethyl)naphthalen-2-yl)methyl)-9-azabicyclo[3.3.1]nonane-3-carboxylic acid

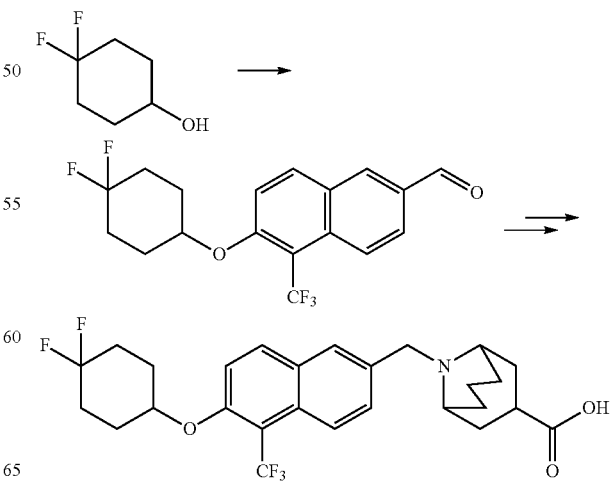

To a mixture of 6-((cis-4-methylcyclohexyl)oxy)-5-(trifluoromethyl)-2-naphthaldehyde (17 mg, 0.050 mmol), 9-aza-bicyclo[3.3.1]nonane-3-carboxylic acid methyl ester; HCl salt (15 mg, 0.068 mmol) and sodium triacetoxyborohydride (17 mg, 0.080 mmol) in THF (0.6 mL) was added acetic acid (5.7 uL, 0.10 mmol). The reaction mixture was heated with microwave irritation at 100° C. for 20 min. To the above mixture was added MeOH (0.4 mL) and 3 M of NaOH (0.20 mL, 0.60 mmol), and heated with microwave irritation at 100° C. for 10 min. LC-MS shows the hydrolysis was completed. Neutralized with 1N HCl, and purified by HPLC (TFA method) to provide the desired product as a white powder after lyophilization (13 mg, 43%). $^1$H NMR (400 MHz, DMSO-$d_6$) δ 8.09-8.28 (m, 3H), 7.82 (d, J=9.29 Hz, 1H), 7.68 (d, J=9.54 Hz, 1H), 5.02 (br. S., 1H), 4.44-4.75 (m, 2H), 3.42-3.64 (m, 2H), 3.23 (td, J=6.27, 12.55 Hz, 1H), 1.13-2.46 (m, 19H), 0.90 (d, J=6.02 Hz, 3H); LCMS m/z 490.3 $[M+H]^+$.

Example 98

9-((6-((4,4-difluorocyclohexyl)oxy)-5-(trifluoromethyl)naphthalene-2-yl)methyl)-9-azabicyclo[3.3.1]nonane-3-carboxylic acid

Step 1: 6-((4,4-difluorocyclohexyl)oxy)-5-(trifluoromethyl)-2-naphthaldehyde

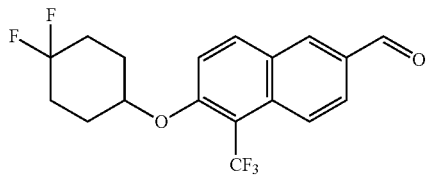 [SMILES: O=Cc1ccc2c(C(F)(F)F)c(OC3CCC(F)(F)CC3)ccc2c1]

A solution of 6-(4,4-Difluoro-cyclohexyloxy)-5-iodo-naphthalene-2-carbaldehyde (3.0 g, 7.2 mmol), hexamethylphosphoramide (6.02 mL, 34.3 mmol) in N,N-dimethylformamide (30 mL, 400 mmol) was degassed with argon. To this was added copper(I) iodide (2.34 g, 12.3 mmol) and methyl fluorosulphonyldifluoroacetate (4.49 mL, 34.3 mmol) and the reaction was stirred at 85° C. under an atmosphere of argon. After stirring for 3 hours, LCMS showed no starting material left and confirms the identity of the product (RT=2.01 min, MH+ 359.10). The reaction was diluted with EtOAc, filtered off the solid, and the filtrate was washed with brine, and water. The organic layer was then separated, dried, concentrated. The crude was recrystallized from methanol to give the title product as a white powder (1.95 g). LCMS: RT 2.01 min; MH+ 359.1; 1H NMR (400 MHz, CHLOROFORM-d) δ 10.15 (s, 1H), 8.28-8.40 (m, 2H), 8.14 (d, J=9.29 Hz, 1H), 8.03 (dd, J=1.63, 9.16 Hz, 1H), 7.40 (d, J=9.04 Hz, 1H), 4.86 (br. S., 1H), 2.11-2.37 (m, 4H), 1.93-2.08 (m, 4H).

Step 2: 9-((6-((4,4-difluorocyclohexyl)oxy)-5-(trifluoromethyl)naphthalene-2-yl)methyl)-9-azabicyclo[3.3.1]nonane-3-carboxylic acid

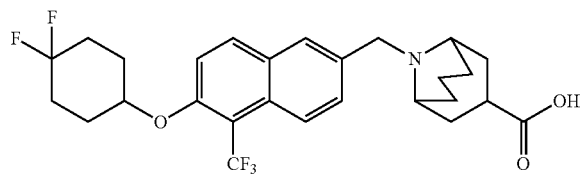 [SMILES: O=C(O)C1CC2CCCC(C1)N2Cc1ccc2c(C(F)(F)F)c(OC3CCC(F)(F)CC3)ccc2c1]

A mixture of 9-Aza-bicyclo[3.3.1]nonane-3-carboxylic acid methyl ester hydrochloride (74 mg, 0.33 mmol) and triethylamine (0.04 mL, 0.27 mmol) in 1,2-dichloroethane (2 mL) was stirred at RT for 20 min. 6-(4,4-difluoro-cyclohexyloxy)-5-trifluoromethyl-naphthalene-2-carbaldehyde (80.0 mg, 0.22 mmol) was then added. The reaction was then stirred at 50° C. for 1 h, cooled down, sodium triacetoxyborohydride (76 mg, 0.36 mmol) was added, and the reaction was stirred at rt for overnight. LCMS showed desired ester intermediate (RT 1.46 min.; MH+ 526.2). Worked up with ethyl acetate and brine, dried over magnesium sulfate, filtered and concentrated. The crude was then dissolved in tetrahydrofuran (1 mL), 1.0 M of aqueous lithium hydroxide (2 mL) was added. The mixture was stirred at RT for 3 h. Neutralized with conc. HCl, the product was extracted with ethyl acetate. The organic layer was concentrated. The crude was purified by HPLC to give the desired product as a white powder (49 mg, TFA salt). LCMS: RT 1.37 min.; MH+ 512.2; 1H NMR (400 MHz, METHANOL-d4) δ 8.28 (d, J=9.04 Hz, 1H), 8.11-8.21 (m, 2H), 7.76 (dd, J=1.25, 9.04 Hz, 1H), 7.64 (d, J=9.29 Hz, 1H), 4.97 (br. S., 1H), 4.62-4.79 (m, 2H), 3.65 (d, J=12.55 Hz, 2H), 3.35-3.53 (m, 1H), 2.44-2.69 (m, 2H), 1.64-2.38 (m, 16H).

Example 99

8-(1-(5-(difluoromethyl)-6-((cis-4-methylcyclohexyl)oxy)naphthalen-2-yl)propyl)-8-azabicyclo[3.2.1]octane-3-carboxylic acid

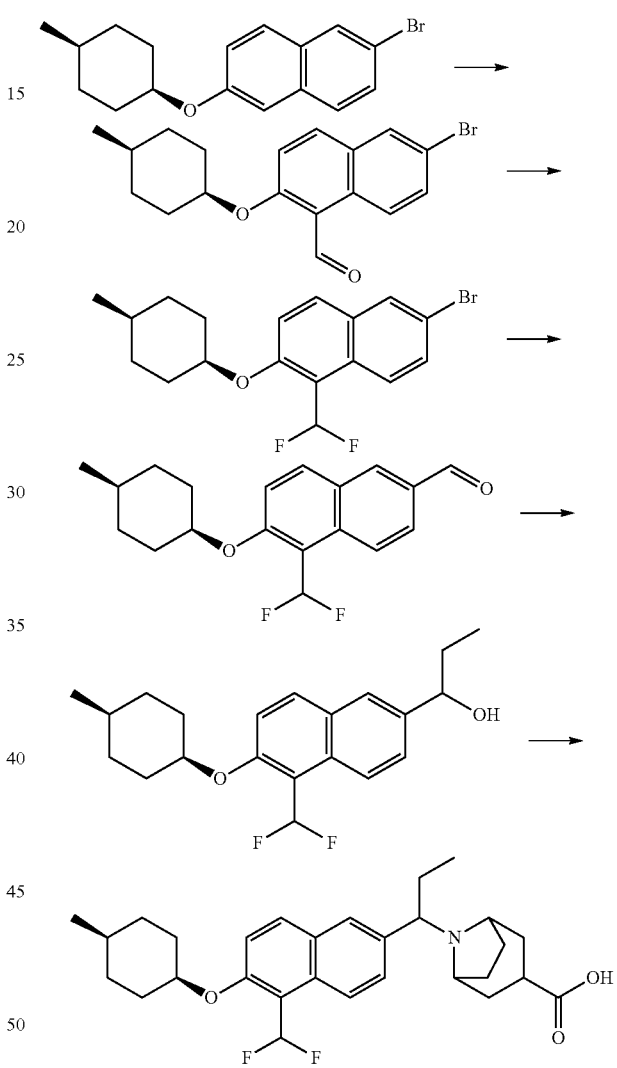

Step 1:
2-bromo-6-((cis-4-methylcyclohexyl)oxy)naphthalene

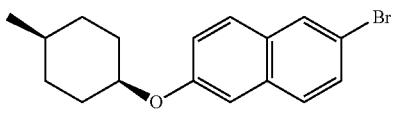 [SMILES: C[C@H]1CC[C@@H](Oc2ccc3cc(Br)ccc3c2)CC1]

To a mixture of trans-4-methylcyclohexan-1-ol (20.5 g, 179.6 mmol, 1.2 eq) and 6-bromonaphthalen-2-ol (33.1 g, 149.8 mmol) in THF (300 mL) was added PPh₃ (62.8 g, 239.5 mmol, 1.6 eq), followed by DIAD (48.4 g, 239.5 mmol, 1.6 eq) dropwise. The mixture was stirred at rt for 24 h and concentrated. The residue was diluted with EtOAc (300 mL), washed with water (100 mL) and brine (100 mL). The organic layer was dried over anhydrous $Na_2SO_4$ and evaporated. The residue was purified by column chromatography on silica gel (Petroleum ether/EtOAc=20/1) to give 2-bromo-6-((cis-4-methylcyclohexyl)oxy)naphthalene as a white solid (35.5 g, yield: 75%).

Step 2: 6-bromo-2-((cis-4-methylcyclohexyl)oxy)-1-naphthaldehyde

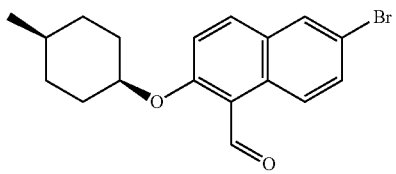 [SMILES: C[C@H]1CC[C@@H](Oc2ccc3cc(Br)ccc3c2C=O)CC1]

To a solution of 2-bromo-6-((cis-4-methylcyclohexyl)oxy)naphthalene (35.5 g, 111.6 mmol) in $CH_2Cl_2$ (350 mL) was added a solution of $TiCl_4$ (31.5 g, 167.5 mmol, 1.5 eq) and dichloro(methoxy)methane (14.0 g, 122.8 mmol, 1.1 eq) in $CH_2Cl_2$ (700 mL) at 0° C. After addition, the mixture was stirred at rt for 12 h. 1N HCl (200 mL) was added and the mixture was extracted with $CH_2Cl_2$ (500 mL×2). The organic layers were dried over $Na_2SO_4$, filtered and concentrated to give 6-bromo-2-((cis-4-methylcyclohexyl)oxy)-1-naphthaldehyde as a light yellow solid (38.0 g, yield: 98%), which was used to the next step without further purification.

Step 3: 6-bromo-1-(difluoromethyl)-2-((cis-4-methylcyclohexyl)oxy)naphthalene

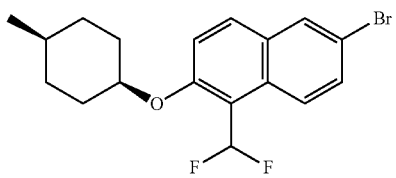 [SMILES: C[C@H]1CC[C@@H](Oc2ccc3cc(Br)ccc3c2C(F)F)CC1]

To a solution of 6-bromo-2-((cis-4-methylcyclohexyl)oxy)-1-naphthaldehyde (38.0 g, 109.83 mmol) in DCE (200 mL) was added DAST (106.1 g, 658.98 mmol, 6.0 eq) at rt. The mixture was stirred at 80° C. for 24 h and cooled down. Water (300 mL) was added and the mixture was extracted with $CH_2Cl_2$ (200 mL×2). The combined organic layers were washed with sat. aq. $NaHCO_3$ (200 mL), dried over $Na_2SO_4$, filtered and concentrated. The residue was washed with heptane to give 6-bromo-1-(difluoromethyl)-2-((cis-4-methylcyclohexyl)oxy)naphthalene as a white solid (38.0 g, yield: 95%). $^1$H NMR (400 MHz, $CDCl_3$) δ 8.24 (d, J=9.2 Hz, 1H), 7.93 (d, J=2.0 Hz, 1H), 7.77 (d, J=9.2 Hz, 1H), 7.58 (dd, J=2.0 Hz, 9.2 Hz, 1H), 7.56 (t, J=54.8 Hz, 1H), 7.24 (d, J=9.2 Hz, 1H), 4.72-4.70 (m, 1H), 2.04-2.00 (m, 2H), 1.63-1.54 (m, 5H), 1.35 (m, 2H), 0.96 (d, J=6.4 Hz, 3H).

Step 4: 5-(difluoromethyl)-6-((cis-4-methylcyclohexyl)oxy)-2-naphthaldehyde

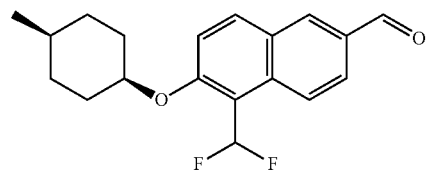 [SMILES: C[C@H]1CC[C@@H](Oc2ccc3cc(C=O)ccc3c2C(F)F)CC1]

To a solution of 6-bromo-1-(difluoromethyl)-2-((cis-4-methylcyclohexyl)oxy)naphthalene (17 g, 46.19 mmol) in THF (130 mL) was added "BuLi (33 mL, 1.6 M, 55.43 mmol, 1.2 eq) dropwise at −78° C. After addition, the mixture was stirred at −78° C. for 30 min. DMF (6.74 g, 92.38 mmol, 2.0 eq) was added to the mixture and stirring continued for 2 hours −78° C. and the reaction was quenched with water (200 mL) and extracted with $CH_2Cl_2$ (200 mL×2). The combined organic layers were washed with water (200 mL×2), brine (200 mL×2) and concentrated. The residue was washed with heptane to give 5-(difluoromethyl)-6-((cis-4-methylcyclohexyl)oxy)-2-naphthaldehyde as a white solid (12.5 g, yield: 85%). $^1$H NMR (400 MHz, $CDCl_3$) δ 10.12 (s, 1H), 8.46 (d, J=8.8 Hz, 1H), 8.27 (d, J=1.6 Hz, 1H), 8.03 (d, J=9.2 Hz, 1H), 7.99 (dd, J=2.0 Hz, 8.8 Hz, 1H), 7.59 (t, J=54.8 Hz, 1H), 7.32 (d, J=8.8 Hz, 1H), 4.80-4.78 (m, 1H), 2.07-2.03 (m, 2H), 1.67-1.55 (m, 5H) 1.37-1.33 (m, 2H) 0.97 (d, J=6.4 Hz, 3H). ESI-MS (M+H)$^+$: 319.1.

Step 5: Methyl 8-(1-(5-(difluoromethyl)-6-((cis-4-methylcyclohexyl)oxy)naphthalene-2-yl)propyl)-8-azabicyclo[3.2.1]octane-3-carboxylate

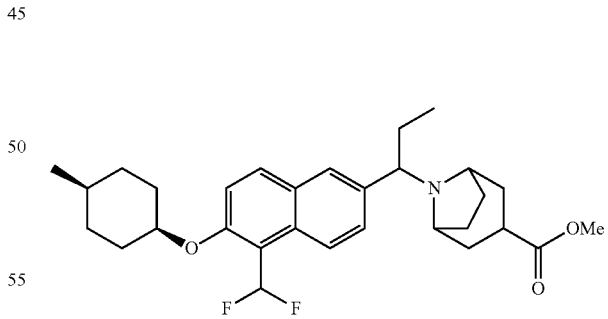

To a mixture of potassium carbonate (62 mg, 0.45 mmol) and 8-aza-bicyclo[3.2.1]octane-3-carboxylic acid methyl ester HCl salt (80 mg, 0.39 mmol) was added a solution of 6-(1-bromopropyl)-1-(difluoromethyl)-2-((cis-4-methylcyclohexyl)oxy)naphthalene in DMF (3 mL, 0.3 mmol). The reaction mixture was stirred at room temperature overnight. The mixture was filtered, and purified by HPLC (TFA method) to collect the desired ester as a white powder after lyophilization (81 mg, yield 44%). LCMS m/z 500.1 [M+H]

Step 6: 8-(1-(5-(Difluoromethyl)-6-((cis-4-4-methyl-cyclohexyl)oxy)naphthalen-2-yl)propyl)-8-azabicyclo[3.2.1]octane-3-carboxylic acid

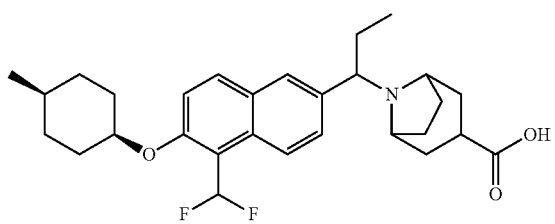 [SMILES: CCC(c1ccc2c(C(F)F)c(O[C@H]3CC[C@@H](C)CC3)ccc2c1)N1C2CCC1CC(C(=O)O)C2]

To the above ester in THF (0.6 mL) and MeOH (0.6 mL) was added 3 M of NaOH in water (0.200 mL, 0.600 mmol). The reaction mixture was heated at 55° C. (hot plate) for 1 h. Neutralized with 2N HCl, diluted with MeOH, and purified by HPLC (TFA method) to collect TFA salt of the the desired acid as a white powder after lyophilization (67 mg, yield 84%). $^1$H NMR (400 MHz, METHANOL-$d_4$) δ 8.45 (d, J=8.78 Hz, 1H), 8.05 (d, J=9.29 Hz, 1H), 7.99 (s, 1H), 7.40-7.78 (m, 3H), 4.89 (br. S., 1H), 4.51-4.65 (m, 1H), 4.07 (dd, J=3.26, 11.55 Hz, 1H), 3.37-3.50 (m, 1H), 2.86-3.05 (m, 1H), 2.49-2.64 (m, 1H), 2.35-2.48 (m, 1H), 1.86-2.33 (m, 10H), 1.65-1.80 (m, 2H), 1.46-1.63 (m, 3H), 1.27-1.42 (m, 2H), 0.98 (d, J=6.27 Hz, 3H), 0.79 (t, J=7.28 Hz, 3H); LCMS m/z 486.1 [M+H]$^+$ Example 100

9-((5-(difluoromethyl)-6-((cis-4-(trifluoromethyl)cyclohexyl)oxy)naphthalene-2-yl)methyl)-9-azabicyclo[3.3.1]nonane-3-carboxylic acid

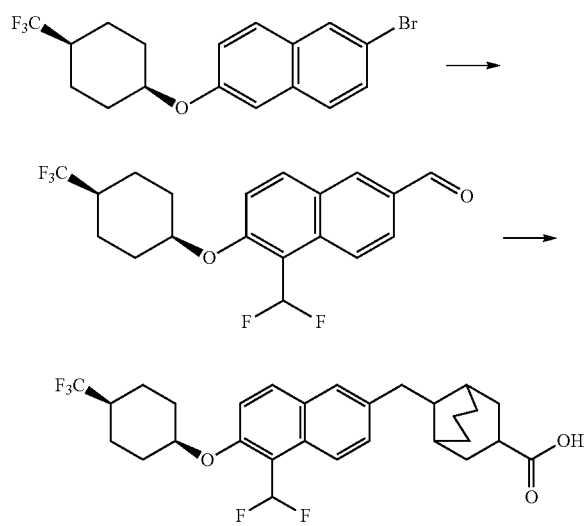

Step 1: 5-(difluoromethyl)-6-((cis-4-trifluoromethyl-cyclohexyl)oxy)-2-naphthaldehyde

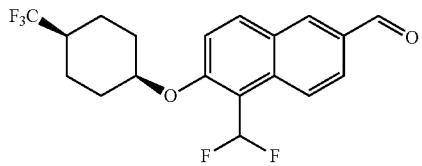 [SMILES: O=Cc1ccc2c(C(F)F)c(O[C@H]3CC[C@@H](C(F)(F)F)CC3)ccc2c1]

The title compound was prepared using the method described for compound 5-(difluoromethyl)-6-((cis-4-methylcyclohexyl)oxy)-2-naphthaldehyde from 6-bromonaphthalen-2-ol and trans-4-trifluoromethylcyclohexane-1-mesylate. ESI-MS (M+H)$^+$: 373.2

Step 2: 9-((5-(difluoromethyl)-6-((cis-4-(trifluoromethyl)cyclohexyl)oxy)naphthalene-2-yl)methyl)-9-azabicyclo[3.3.1]nonane-3-carboxylic acid

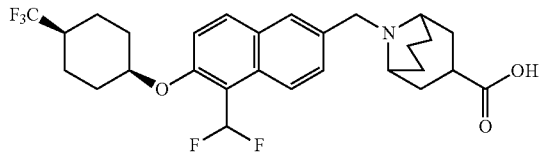 [SMILES: O=C(O)C1CC2CCCC(C1)N2Cc1ccc2c(C(F)F)c(O[C@H]3CC[C@@H](C(F)(F)F)CC3)ccc2c1]

A mixture of 5-(difluoromethyl)-6-((cis-4-trifluoromethylcyclohexyl)oxy)-2-naphthaldehyde (60 mg, 0.161 mmol, 1.0 eq), methyl 9-azabicyclo[3.3.1]nonane-3-carboxylate, HCl salt (32 mg, 0.177 mmol, 1.1 eq) and Titanium (IV) isopropoxide (92 mg, 0.323 mmol, 2.0 eq) in THF (3 mL) was stirred at 100° C. for 1 h and cooled to rt. NaBH(Oac)$_3$ (68 mg, 0.323 mmol, 2.0 eq) was added and the mixture was stirred at 100° C. for 1 h. Water (30 mL) was added and the mixture was extracted with CH$_2$Cl$_2$ (30 mL×2). The combined organic layers were washed with water (60 mL×2) and concentrated. The residue was purified by column chromatography on silica gel (PE/EA=6:1) to give the desired ester, methyl 9-((5-(difluoromethyl)-6-((cis-4-(trifluoromethyl)cyclohexyl)oxy)naphthalene-2-yl)methyl)-9-azabicyclo[3.3.1]nonane-3-carboxylate as a colorless solid (30 mg, yield: 34%). ESI-MS (M+H)$^+$: 540.1. The above ester was then converted to the title compound with the yield: 60%. $^1$H NMR (400 MHz, DMSO-$d_6$) δ: 12.54 (br s, 1H), 8.27 (d, J=8.8 Hz, 1H), 8.18 (s, 1H), 8.15 (d, J=9.2 Hz, 1H), 7.81 (d, J=8.8 Hz, 1H), 7.64 (d, J=9.2 Hz, 1H), 7.63 (t, J=54.4 Hz, 1H), 5.04 (s, 1H), 4.69-4.61 (m, 2H), 3.55-3.51 (m, 2H), 3.27-3.21 (m, 1H), 2.47-2.40 (m, 3H), 2.21-1.93 (m, 8H), 1.76-1.56 (m, 8H). ESI-MS (M+H)$^+$: 526.3.

Example 101

9-((5-(trifluoromethyl)-6-((cis-4-(trifluoromethyl)cyclohexyl)oxy)quinolin-2-yl)methyl)-9-azabicyclo[3.3.1]nonane-3-carboxylic acid

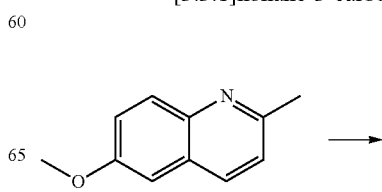

201
-continued

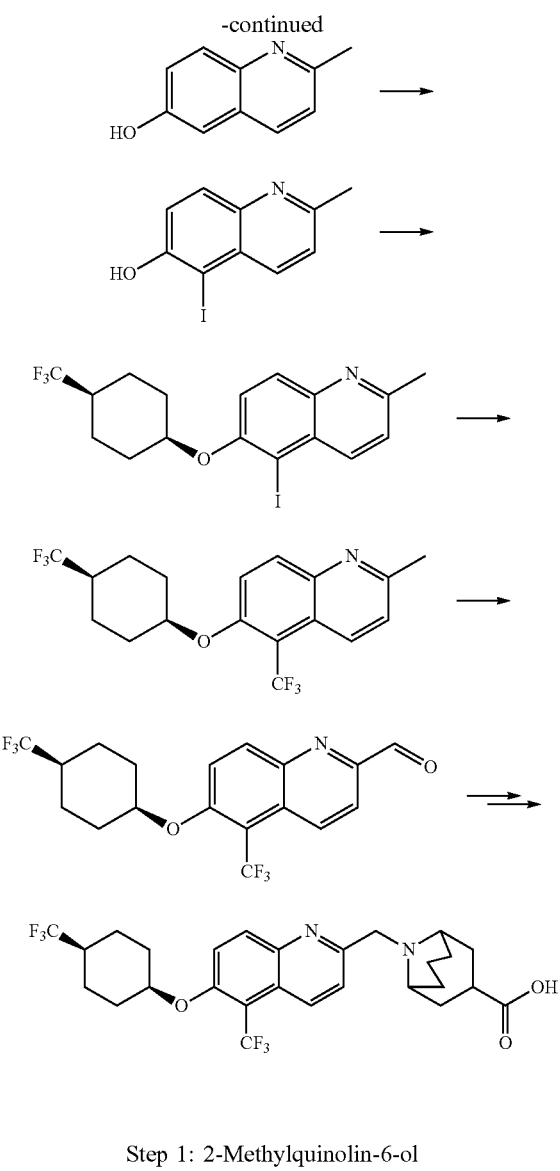

Step 1: 2-Methylquinolin-6-ol

To a solution of 6-methoxy-2-methylquinoline (prepared according to the procedure described in reference: Kitamura et al, *J. Syn. Org. Chem.* 2003 (15), 2415, which is incorporated by reference in its entirety) (10 g, 57.5 mmol) in 150 mL of dichloromethane was dropwise added a solution of BBr$_3$ (43.1 g, 172.5 mmol) in dichloromethane (100 mL) at −78° C. The mixture was allowed to warm to RT and stirred at RT for 16 h. The reaction was carefully quenched with methanol at 0° C. and the mixture was diluted with saturated aqueous sodium bicarbonate. The aqueous mixture was extracted with ethyl acetate (3×). The combined organics were dried, filtered, and concentrated to give the title compound as a yellow solid (7.2 g). $^1$H NMR (CDCl$_3$, 300 MHz) δ: 7.87-7.81 (m, 2H), 7.20-7.08 (m, 3H), 2.65 (s, 3H).

202

Step 2: 5-Iodo-2-methylquinolin-6-ol

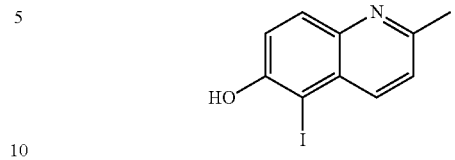

To a solution of 2-methylquinolin-6-ol (4.1 g, 27.3 mmol) in dichloromethane (200 mL) was added N-iodosuccinamide (9.2 g, 40.9 mmol) and trifluroacetic acid (1.9 g, 8.2 mmol). The mixture was stirred at room temperature for 16 h. The mixture was basified with ammonia to pH=7.5, and washed with 100 mL of water. The organic layer was dried and concentrated. The crude was purified by column chromatography on silica gel (petroleum ether/ethyl acetate 8/1) to give the title compound as a yellow solid (4.5 g). $^1$H NMR (DMSO-d6, 300 MHz) δ 10.76 (s, 1H), 8.16 (d, J=8.7 Hz, 1H), 7.80 (d, J=9.0 Hz, 1H), 7.41 (d, J=9.0 Hz, 1H), 7.40 (d, J=8.7 Hz, 1H), 2.62 (s, 3H).

Step 3: 5-Iodo-2-methyl-6-((cis-4-(trifluoromethyl) cyclohexyl)oxy)quinoline

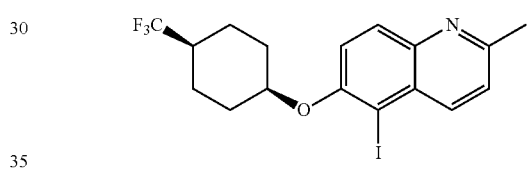

The mixture of 5-iodo-2-methylquinolin-6-ol (8.0 g, 28 mmol), trans-4-(tert-butyl)cyclohexyl methanesulfonate (6.9 g, 28 mmol, 1.0 eq) and cesium carbonate (9.2 g, 28 mmol) in tert-butanol (100 mL) was heated at 90° C. for 6 h. The mixture was cooled down and filtered. The filtrate was concentrated and the residue was purified by column chromatography on silica gel (petroleum ether/ethyl acetate 20/1) to give the title compound as a white solid (4.9 g). $^1$H NMR (400 MHz, CDCl$_3$) δ 8.32 (d, J=8.8 Hz, 1H), 7.98 (d, J=8.8 Hz, 1H), 7.36 (d, J=9.2 Hz, 1H), 7.31 (d, J=8.4 Hz, 1H), 4.86 (s, 1H), 2.74 (s, 3H), 2.23-2.19 (m, 2H), 2.17-2.01 (m, 3H), 1.81-1.78 (m, 2H), 1.63-1.57 (m, 2H); ESI-MS (M+H)$^+$: 436.1.

Step 4: 2-Methyl-5-(trifluoromethyl)-6-((cis-4-(trifluoromethyl)cyclohexyl)oxy)quinoline

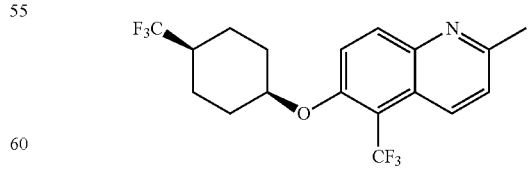

The title compound was synthesized using the same procedure described for compound 5-(trifluoromethyl)-6-((cis-4-(trifluoromethyl)cyclohexyl)oxy)-2-naphthaldehyde from 5-iodo-2-methyl-6-((cis-4-(trifluoromethyl)cyclohexyl)oxy)quinoline to give the title compound as a white solid (40% yield). ¹H NMR (400 MHz, CDCl₃) δ 8.45 (d, J=8.4 Hz, 1H), 8.17 (d, J=9.2 Hz, 1H), 7.48 (d, J=9.2 Hz, 1H), 7.37 (d, J=8.4 Hz, 1H), 4.86 (s, 1H), 2.73 (s, 3H), 2.25-2.21 (m, 2H), 2.14-2.11 (m, 1H), 1.89-1.78 (m, 4H), 1.68-1.58 (m, 2H); ESI-MS (M+H)⁺: 378.1.

Step 5: 5-(Trifluoromethyl)-6-((cis-4-(trifluoromethyl)cyclohexyl)oxy)quinoline-2-carbaldehyde

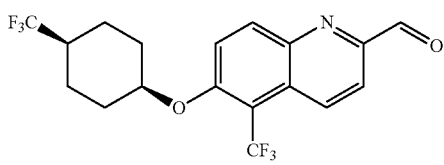 [SMILES: O=Cc1ccc2c(C(F)(F)F)c(O[C@H]3CC[C@@H](C(F)(F)F)CC3)ccc2n1]

To a solution of 2-methyl-5-(trifluoromethyl)-6-((cis-4-(trifluoromethyl)cyclohexyl)oxy)quinoline (1 eq.) in dioxane was added SeO₂ (2.5 eq.). The mixture was stirred at 100° C. for 1.5 h and concentrated. The residue was purified by column chromatography on silica gel with heptane and ethyl acetate to give the titled compound as a yellow solid (yield: 36%). 1H NMR (400 MHz, CDCl₃) δ 10.18 (s, 1H), 8.73 (d, J=8.8 Hz, 1H), 8.39 (d, J=9.6 Hz, 1H), 8.08 (d, J=9.6 Hz, 1H), 7.62 (d, J=9.6 Hz, 1H), 4.96 (s, 1H), 2.28-2.24 (m, 2H), 2.19-2.10 (m, 1H), 1.93-1.81 (m, 4H), 1.73-1.65 (m, 2H); ESI-MS (M+H)⁺: 392.0.

Step 6: 9-((5-(trifluoromethyl)-6-((cis-4-(trifluoromethyl)cyclohexyl)oxy) quinolin-2-yl)methyl)-9-azabicyclo[3.3.1]nonane-3-carboxylic acid

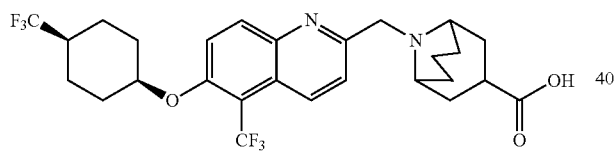

A mixture of 9-Aza-bicyclo[3.3.1]nonane-3-carboxylic acid methyl ester; HCl salt (67 mg, 0.31 mmol) and triethylamine (0.05 mL, 0.33 mmol) in 1,2-dichloroethane (2.0 mL) was stirred at RT for 20 min. 5-(trifluoromethyl)-6-((cis-4-(trifluoromethyl)-cyclohexyl)oxy)quinoline-2-carbaldehyde (80.0 mg, 0.20 mmol) was then added. The reaction was then stirred at 50° C. for 1 h, cooled down, sodium triacetoxy-borohydride (86.7 mg, 0.41 mmol) was added, and the reaction was stirred at RT overnight. LCMS showed desired intermediate (RT 1.50 min.; MH+ 559.3). Worked up with ethyl acetate and brine, dried over magnesium sulfate and concentrated. The crude was then dissolved in tetrahydrofuran (2.0 mL). 2.0 mL of 1.0 M Lithium hydroxide in Water was added. The mixture was stirred at RT for 3 h, then neutralized with conc. HCl, extracted with ethyl acetate. The organic layer was concentrated, and purified by HPLC to give the desired product as a white powder (35 mg). LCMS: RT 1.43 min.; MH+ 545.2; ¹H NMR (400 MHz, METHANOL-d4) δ 8.59 (d, J=9.04 Hz, 1H), 8.23 (d, J=9.54 Hz, 1H), 7.75 (d, J=9.54 Hz, 1H), 7.54 (d, J=9.04 Hz, 1H), 4.97 (br. S., 1H), 4.80-4.87 (m, 2H), 3.78 (br. S., 2H), 3.26-3.41 (m, 1H), 1.56-2.49 (m, 19H).

Example 102

8-(1-(5-(trifluoromethyl)-6-((cis-4-(trifluoromethyl)cyclohexyl)oxy)quinolin-2-yl)ethyl)-8-azabicyclo[3.2.1]octane-3-carboxylic acid

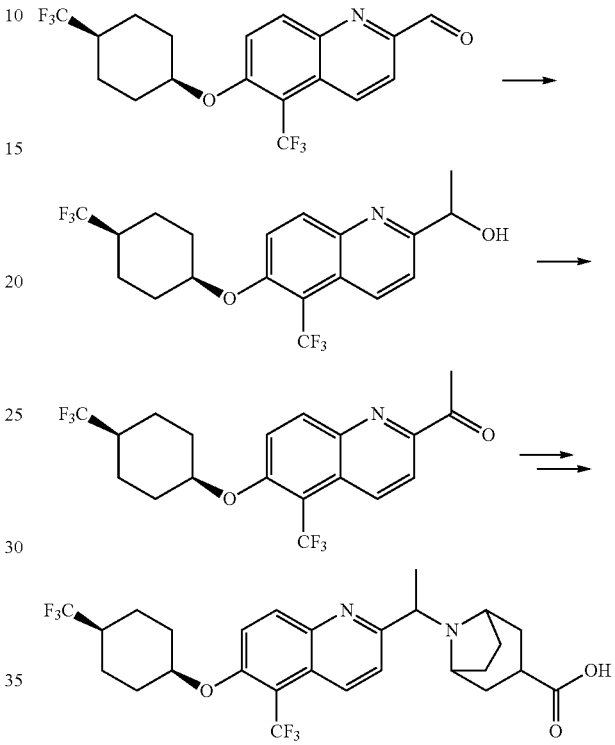

Step 1: 1-(5-(trifluoromethyl)-6-(cis-4-(trifluoromethyl)cyclohexyl)oxy)-quinolin-2-yl)ethanol

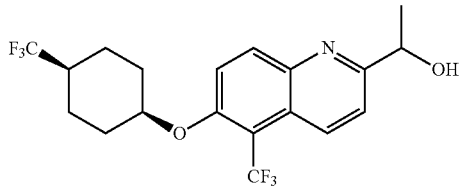 [SMILES: CC(O)c1ccc2c(C(F)(F)F)c(O[C@H]3CC[C@@H](C(F)(F)F)CC3)ccc2n1]

To a solution of 5-trifluoromethyl-6-(cis-4-trifluoromethyl-cyclohexyloxy)-quinoline-2-carbaldehyde (200.0 mg, 0.51 mmol) in dry tetrahydrofuran (4.0 mL, 49 mmol) at −78° C. under argon was dropwise added 1.4 M of methyl bromide in toluene/THF (solvent mixture, 75/25) (0.5476 mL, 0.7667 mmol). After stirred at −78° C. for 2 h, allowed the reaction to warm up a little before quenched with saturated ammonium chloride, extracted with ethyl acetate. The organic phase was dried, filtered and concentrated. The crude was purified by ISCO EtOAc/heptane gradient from 0/100 to 100/0) to give the title product as a colorless oil (133 mg). LC-MS: RT 1.53 min.; MH+ 408.0.

Step 2: 1-(5-(trifluoromethyl)-6-(cis-4-(trifluoromethyl)cyclohexyl)-oxy)quinolin-2-yl)ethanone

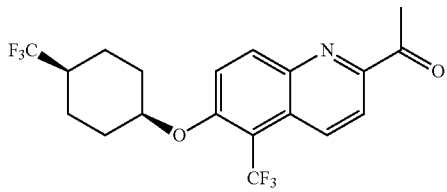 [SMILES: CC(=O)c1ccc2c(C(F)(F)F)c(O[C@H]3CC[C@@H](C(F)(F)F)CC3)ccc2n1]

To a solution of 1-[5-Trifluoromethyl-6-(4-trifluoromethyl-cyclohexyloxy)-quinolin-2-yl]-ethanol (0.13 g, 0.32 mmol) in acetonitrile (2.00 mL, 38.3 mmol) was added Dess-Martin periodinane (0.271 g, 0.638 mmol). After stirred at RT overnight, the reaction was diluted with ethyl acetate, washed with aqueous Na2S2O3/NaHCO3 (1:1), followed by water, and brine. The organic phase was dried, filtered and concentrated to give the desired product as a white powder (127 mg) which was used in the next step without further purifications. LC-MS: RT 2.16 min.; MH+ 405.9;

Step 3: 8-(1-(5-(trifluoromethyl)-6-((cis-4-(trifluoromethyl)cyclohexyl)oxy)quinolin-2-yl)ethyl)-8-azabicyclo[3.2.1]octane-3-carboxylic acid

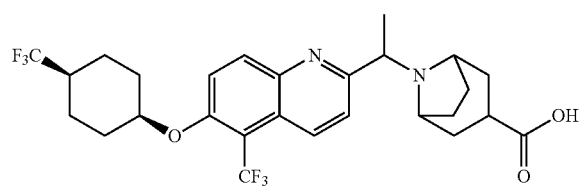 [SMILES: CC(c1ccc2c(C(F)(F)F)c(O[C@H]3CC[C@@H](C(F)(F)F)CC3)ccc2n1)N1C2CCC1CC(C(=O)O)C2]

To a mixture of 1-[5-Trifluoromethyl-6-(cis-4-trifluoromethyl-cyclohexyloxy)-quinolin-2-yl]-ethanone (40.0 mg, 0.0987 mmol) and 8-Aza-bicyclo[3.2.1]octane-3-carboxylic acid methyl ester; HCl salt (30.45 mg, 0.1480 mmol) in Tetrahydrofuran (2.0 mL, 24 mmol) was added Acetic acid (11.22 uL, 0.1974 mmol), Titanium tetraisopropoxide (33.66 mg, 0.1184 mmol) and Sodium triacetoxyborohydride (41.83 mg, 0.1974 mmol), and the reaction was heated in microwave at 100° C. for 10 min. LCMS showed desired ester (RT 1.53 min, MH+ 559.0) with 40% conversion, added one more eq of B and Na(OAc)3BH, heated in microwave at 100° C. for another 10 min. conversion improved to 50%, repeated one more time, conversion ~60%. Worked up with EtOAc and water. The organic layer was dried over MgSO4 and concentrated. The crude was re-dissolved in tetrahydrofuran (1.0 mL, 12 mmol) and methanol (1.0 mL, 25 mmol), treated with 3.0 M of sodium hydroxide in water (1.0 mL, 3.0 mmol), heated in microwave at 100° C. for 10 min., acidified with 2N HCl, the organic phase was dried and concentrated. The crude was purified by HPLC to give the desired product as a white powder (7 mg, bis-TFA salt). LCMS: RT 1.46 min.; MH+ 545.0; 1H NMR (400 MHz, METHANOL-d4) δ 8.72 (d, J=9.04 Hz, 1H), 8.37 (d, J=9.54 Hz, 1H), 7.88 (d, J=9.54 Hz, 1H), 7.68 (d, J=9.04 Hz, 1H), 5.10 (br. S., 1H), 4.71 (q, J=6.53 Hz, 1H), 4.52 (d, J=6.02 Hz, 1H), 3.74 (d, J=2.76 Hz, 1H), 2.93-3.10 (m, 1H), 1.93-2.62 (m, 11H), 1.68-1.91 (m, 9H);

Example 103

9-((6-(((trans,trans)-3,5-dimethylcyclohexyl)oxy)-5-(trifluoromethyl) naphthalene-2-yl)methyl)-9-azabicyclo[3.3.1]nonane-3-carboxylic acid

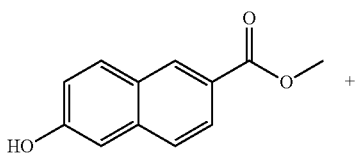

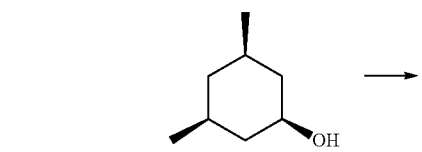

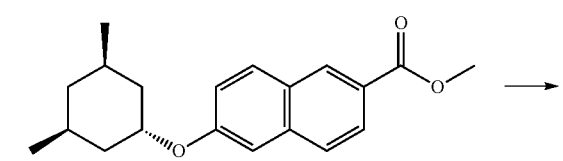

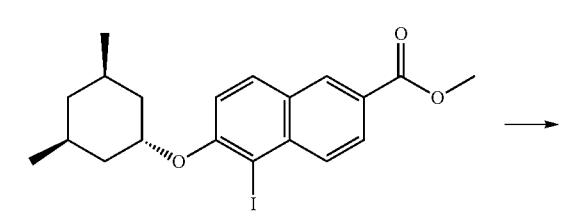

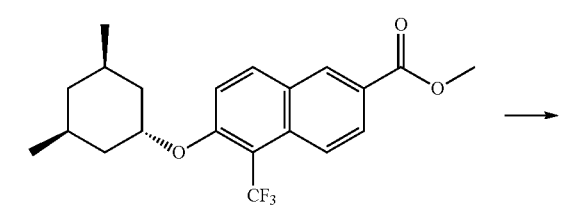

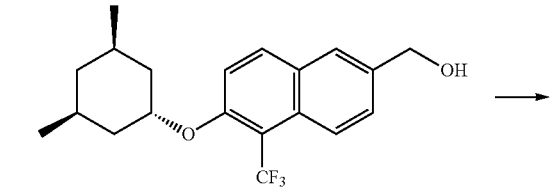

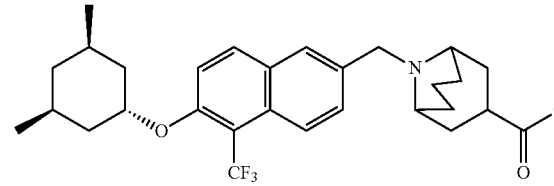

Step 1: methyl 6-((trans,trans)-3,5-dimethylcyclo-
hexyl)oxy)-2-naphthoate

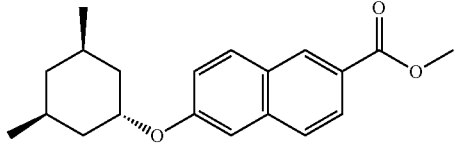

To a mixture of 6-hydroxy-naphthalene-2-carboxylic acid methyl ester (1.00 g, 4.94 mmol), (cis,cis,cis)-3,5-dimethyl-cyclohexanol (0.6341 g, 4.945 mmol) and triphenylphosphine (2.354 g, 8.977 mmol) in toluene (20 mL, 200 mmol) was stirred for 20 min, then, diisopropyl azodicarboxylate (1.1 mL, 5.4 mmol) was added drop wise at 0° C. The mixture became clear. The solution was stirred at reflux overnight. After concentration, the residue was purified with silica gel eluted with EtOAc in hexanes from 0 to 20% to give methyl 6-(((trans,trans)-3,5-dimethylcyclohexyl)oxy)-2-naphthoate as a white precipitate (247 mg, 16%). LCMS showed Rt=2.39 min, a M+H peak at m/z=313.20.

Step 2: methyl 6-((trans,trans)-3,5-dimethylcyclo-
hexyl)oxy)-5-iodo-2-naphthoate

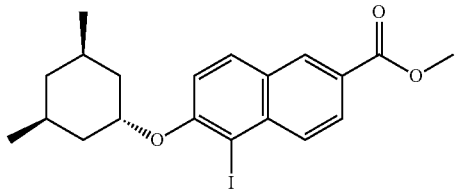

A mixture of methyl 6-(((trans,trans)-3,5-dimethylcyclo-hexyl)oxy)-2-naphthoate (247 mg, 0.000791 mol), N-iodo-succinimide (199 mg, 0.000886 mol) and zirconium tetra-chloride (28 mg, 0.00012 mol) in methylene chloride (5.07 mL, 0.0791 mol) was heated to reflux under Ar in a vial for 2 h. The precipitate was filtered off and the residue was purified with silica gel column eluted with EtOAc in hex from 0 to 40% to give methyl 6-(((trans,trans)-3,5-dimeth-ylcyclohexyl)oxy)-5-iodo-2-naphthoate as a solid (130 mg, 38%). LCMS: Rt=2.59 min, m/z=439.10 [M+1]. ¹H NMR (400 MHz, CHLOROFORM-d) δ 8.49 (s, 1H), 8.12-8.21 (m, 1H), 8.02-8.10 (m, 1H), 7.87 (d, J=8.91 Hz, 1H), 7.22 (d, J=9.10 Hz, 1H), 4.31-4.51 (m, 1H), 3.98 (s, 3H), 2.16 (d, J=12.49 Hz, 2H), 1.13-1.76 (m, 8H), 0.91-1.03 (m, 6H), 0.57-0.75 (m, 1H).

Step 3: methyl 6-(((trans, trans)-3,5-dimethylcyclo-
hexyl)oxy)-5-(trifluoromethyl)-2-naphthoate

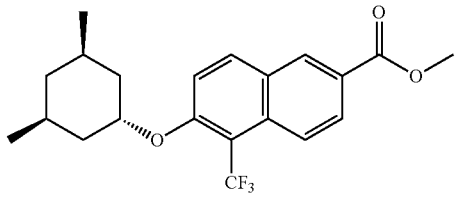

To a solution of methyl 6-((trans,trans)-3,5-dimethylcy-clohexyl)oxy)-5-iodo-2-naphthoate (130 mg, 0.30 mmol), hexamethylphosphoramide (0.26 mL, 1.5 mmol) and copper (I) iodide (85 mg, 0.44 mmol) in N,N-dimethylformamide (2 mL, 20 mmol) was added methyl fluorosulphonyldifluoro-acetate (0.19 mL, 1.5 mmol). The mixture was heated at 80° C. overnight. LCMS showed desired product peak, Rt=2.49 min, m/z=381.10 ([M+1], 100%). The solvent was evapo-rated and C/C with EA/HE gave the product methyl 6-(((trans,trans)-3,5-dimethylcyclohexyl)oxy)-5-(trifluo-romethyl)-2-naphthoate (106 mg, 94%). ¹H NMR (400 MHz, CHLOROFORM-d) δ 8.54 (s, 1H), 8.25 (d, J=9.22 Hz, 1H), 8.11 (d, J=11.11 Hz, 1H), 8.03 (d, J=9.22 Hz, 1H), 7.37 (d, J=9.16 Hz, 1H), 4.39-4.54 (m, 1H), 3.92-4.04 (m, 2H), 2.13 (d, J=12.49 Hz, 1H), 1.06-1.75 (m, 7H), 0.96 (br. S., 6H), 0.54-0.75 (m, 1H).

Step 4: (6-(((trans, trans)-3,5-dimethylcyclohexyl)
oxy)-5-(trifluoromethyl)naphthalene-2-yl)methanol

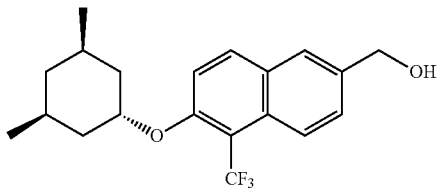 [SMILES: C[C@@H]1C[C@H](C)C[C@@H](Oc2ccc3cc(CO)ccc3c2C(F)(F)F)C1]

To a mixture of methyl 6-(((trans, trans)-3,5-dimethylcy-clohexyl)oxy)-5-(trifluoromethyl)-2-naphthoate (103 mg, 0.271 mmol) in tetrahydrofuran (4.2 mL, 52 mmol) was added 1.00 M of lithium tetrahydroaluminate in tetrahydro-furan (0.6769 mL, 0.6769 mmol). Gas evolution observed. The reaction was then stirred at rt for 30 min, LCMS showed complete conversion. EtOAc was added and Rocheles's salt was added and stirred for 30 min. The organic layer was washed with brine, dried and evaporated, and dried under high vacuum to give desired product, (6-(((trans,trans)-3,5-dimethylcyclohexyl)oxy)-5-(trifluoromethyl)naphthalene-2-yl)methanol (84 mg, 88%). LCMS: RT=2.17 min; m/z=335.10, M–H2O; ¹H NMR (400 MHz, CHLORO-FORM-d) δ 8.20 (d, J=7.78 Hz, 1H), 7.91 (d, J=9.10 Hz, 1H), 7.78 (s, 1H), 7.54 (d, J=8.97 Hz, 1H), 7.31 (d, J=9.16 Hz, 1H), 4.85 (s, 2H), 4.30-4.49 (m, 1H), 2.11 (d, J=12.30 Hz, 2H), 1.47-1.78 (m, 4H), 1.06-1.24 (m, 2H), 0.98 (s, 6H), 0.77-0.92 (m, 1H), 0.54-0.74 (m, 1H).

Step 5: 9-((6-(((trans, trans)-3,5-dimethylcyclohex-
loyl)oxy)-5-(trifluoromethyl)naphthalene-2-yl)
methyl)-9-azabicyclo[3.3.1]nonane-3-carboxylic
acid

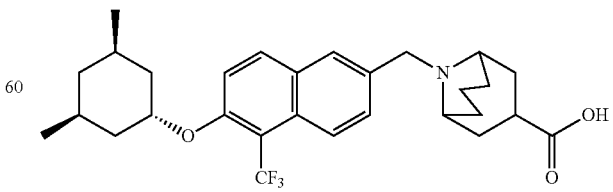

To a solution of [6-((trans, trans)-3,5-dimethyl-cyclo-hexyloxy)-5-trifluoromethyl-naphthalen-2-yl]-methanol (84 mg, 0.24 mmol) and N,N-diisopropylethylamine (0.12456 mL, 0.71512 mmol) in methylene chloride (1.1 mL, 17 mmol) was added methanesulfonyl chloride (0.036900 mL, 0.47674 mmol) drop wise. A white precipitate formed. The solution was stirred at rt for 1 h. LCMS showed no starting material left, and complete conversion to RT=2.52 min. The mixture was diluted with DCM and washed with sodium bicarbonate aq solution and water, dried over MgSO4, filtered, concentrated. The crude was then dissolved in N,N-dimethylformamide (2.8 mL, 36 mmol), 9-aza-bicyclo[3.3.1]nonane-3-carboxylic acid methyl ester; HCl salt (104.74 mg, 0.47674 mmol) was added, followed by cesium carbonate (233.00 mg, 0.71512 mmol). The reaction was then heated at 80° C. for 1 h. LCMS showed no starting material left, and the completion of the reaction (RT=1.73 min.; m/z=518.3, MH+). Cooled down, the reaction mixture was diluted with EtOAc, washed with water (2×). The organic phase was then separated, dried and concentrated. The crude was purified by HPLC, removed the solvent, the ester was then dissolved in tetrahydrofuran (1.1 mL, 14 mmol), treated with 1.0 M of lithium hydroxide in water (1.6 mL, 1.6 mmol) at rt overnight. Acidified with conc.HCl, the organic layer was dried and concentrated. The crude was then purified by HLPC to give the titled compound as a white powder (32 mg, 27%). LCMS: RT=1.65 min.; m/z=504.3, MH+; $^1$H NMR (400 MHz, METHANOL-d4) δ 8.28 (d, J=8.91 Hz, 1H), 8.09-8.21 (m, 2H), 7.75 (d, J=10.98 Hz, 1H), 7.62 (d, J=9.29 Hz, 1H), 4.65-4.81 (m, 2H), 4.45-4.65 (m, 1H), 3.67 (d, J=16.38 Hz, 2H), 3.46 (s, 2H), 2.48-2.72 (m, 2H), 2.01-2.38 (m, 8H), 1.92 (d, J=10.29 Hz, 2H), 1.48-1.82 (m, 4H), 1.04-1.21 (m, 2H), 0.99 (s, 6H), 0.56-0.77 (m, 1H).

Example 104

8-(6-((cis-4-Methylcyclohexyl)oxy)-5-(trifluoromethyl)-2-naphthoyl)-8-azabicyclo[3.2.1]octane-3-carboxylic acid

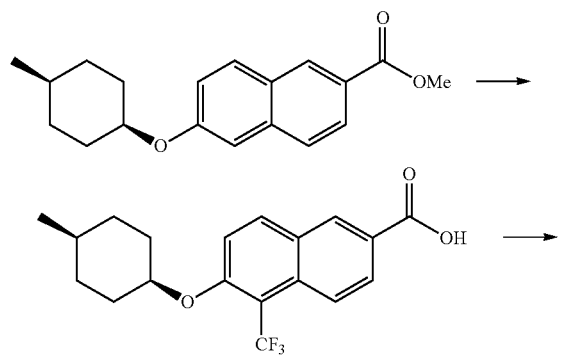

Step 1: Methyl 6-((cis-4-methylcyclohexyl)oxy)-2-naphthoate

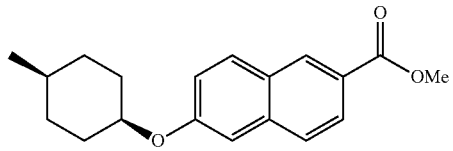 [SMILES: COC(=O)c1ccc2cc(O[C@H]3CC[C@@H](C)CC3)ccc2c1]

To a suspension of methyl 6-hydroxy-2-naphthoate (TCI, 809 mg, 4.00 mmol), trans-4-methyl-cyclohexanol (913 mg, 8.00 mmol) and triphenylphosphine (2.10 g, 8.00 mmol) in toluene (16 mL) at room temperature was added diisopropyl azodicarboxylate (1.68 mL, 8.00 mmol). During the addition, the suspension turned to a clear solution. After min, LCMS shows the reaction was completed. The reaction mixture was concentrated and purified by flash chromatography on silica gel column to provide the desired product as a white solid (995 mg, yield 83%). $^1$H NMR (300 MHz, METHANOL-d$_4$) δ 8.51 (s, 1H), 7.97 (dd, J=1.51, 8.69 Hz, 1H), 7.91 (d, J=8.69 Hz, 1H), 7.80 (d, J=8.69 Hz, 1H), 7.30 (d, J=2.27 Hz, 1H), 7.24 (dd, J=2.46, 8.88 Hz, 1H), 4.78 (t, J=3.21 Hz, 1H), 3.96 (s, 3H), 2.09 (dd, J=3.59, 13.03 Hz, 2H), 1.63-1.80 (m, 2H), 1.34-1.61 (m, 5H), 0.98 (d, J=5.67 Hz, 3H); LCMS m/z 299.2 [M+H]$^+$ Step 2: Methyl 5-iodo-6-((cis-4-methylcyclohexyl)oxy)-2-naphthoate

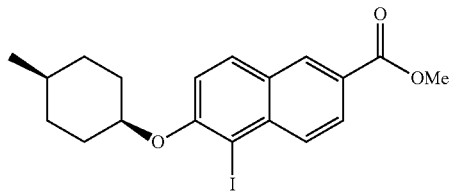 [SMILES: COC(=O)c1ccc2c(I)c(O[C@H]3CC[C@@H](C)CC3)ccc2c1]

To a mixture of methyl 6-((cis-4-methylcyclohexyl)oxy)-2-naphthoate (285 mg, 0.955 mmol) and zirconium (IV) chloride (23 mg, 0.1 mmol) in methylene chloride (5 mL) was added N-iodosuccinimide (258 mg, 1.15 mmol). The reaction mixture was stirred at rt for 3 h. It was then quenched with satd. NaS$_2$O$_3$ and extracted with EtOAc. The organic phase was washed with satd. NaHCO$_3$, dried, filtered and concentrated. The residue was purified by flash chromatography on silica gel column to provide desired product as an off-white solid (341 mg, yield 84%). LCMS m/z 425.1 [M+H]$^+$ Step 3: 6-((cis-4-Methylcyclohexyl)oxy)-5-(trifluoromethyl)-2-naphthoic acid

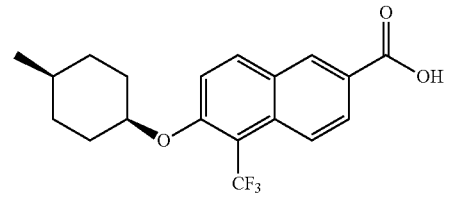 [SMILES: C[C@H]1CC[C@@H](Oc2ccc3cc(C(=O)O)ccc3c2C(F)(F)F)CC1]

To a mixture of methyl 5-iodo-6-((cis-4-methylcyclohexyl)oxy)-2-naphthoate (212 mg, 0.500 mmol) and copper (I) iodide (171 mg, 0.899 mmol), flushed with N₂, was added DMF (2 mL), followed by hexamethylphosphoramide (439 L, 2.50 mmol). To this was added methyl fluorosulphonyldifluoroacetate (328 uL, 2.50 mmol), and the suspension was heated at 85° C. under N₂ atmosphere for 1.5 h. The reaction mixture was diluted with EtOAc, filtered off the solid. The organic phase was washed with brine (×3), dried over MgSO₄, concentrated to provide the crude methyl ester as an oil. LCMS m/z 367.1 [M+H]⁺

The above ester was dissolved in MeOH (2 mL) and THF (2 mL), and added 3 M of NaOH (0.5 mL, 1.50 mmol). The mixture was heated with microwave irritation at 100° C. for 10 min, acidified with 1N HCl, and diluted with EtOAc. The organic phase was washed with brine, dried, filtered and concentrated to get a solid, which was triturated with MeCN to get the desired acid as an off-white solid (172 mg, 98%). ¹H NMR (300 MHz, METHANOL-d₄) δ 8.60 (d, J=1.51 Hz, 1H), 8.17-8.29 (m, 2H), 8.06-8.14 (m, 1H), 7.57 (d, J=9.44 Hz, 1H), 4.97 (br. S., 1H), 1.95-2.14 (m, 2H), 1.64-1.81 (m, 2H), 1.38-1.61 (m, 5H), 0.98 (d, J=5.29 Hz, 3H); LCMS m/z 353.1 [M+H]⁺

Step 4: 8-(6-((cis-4-Methylcyclohexyl)oxy)-5-(trifluoromethyl)-2-naphthoyl)-8-azabicyclo[3.2.1]octane-3-carboxylic acid

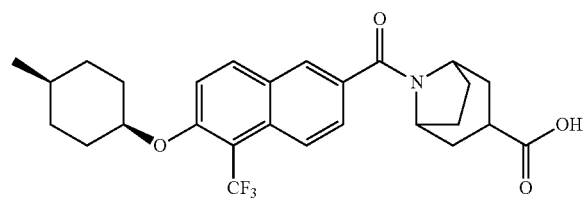 [SMILES: C[C@H]1CC[C@@H](Oc2ccc3cc(C(=O)N4C5CCC4CC(C(=O)O)C5)ccc3c2C(F)(F)F)CC1]

To a mixture of 6-((cis-4-methylcyclohexyl)oxy)-5-(trifluoromethyl)-2-naphthoic acid (18 mg, 0.051 mmol) and methyl 8-azabicyclo[3.2.1]octane-3-carboxylate; HCl salt (13 mg, 0.063 mmol) in DMF (0.5 mL) was added HATU (23 mg, 0.060 mmol), followed by N,N-diisopropylethylamine (45 uL). The mixture was stirred at room temperature for 10 min. To the above mixture was added AcOH (5.8 uL, 0.10 mmol), and stirred at rt for 10 min to quench the reaction. 3 M NaOH (0.2 mL, 0.6 mmol) was then added and heated with microwave irritation at 100° C. for 5 min. It was acidified with 1N HCl, and purified by HPLC (TFA method) to get the desired acid as a white solid (18 mg, yield 72%). ¹H NMR (400 MHz, METHANOL-d₄) δ 8.26 (d, J=9.04 Hz, 1H), 8.18 (d, J=9.29 Hz, 1H), 8.06 (d, J=1.51 Hz, 1H), 7.67 (dd, J=1.76, 9.04 Hz, 1H), 7.58 (d, J=9.29 Hz, 1H), 4.96 (br. S., 1H), 4.87 (br. S., 1H), 4.24 (br. S., 1H), 2.93-3.09 (m, 1H), 1.80-2.26 (m, 10H), 1.65-1.77 (m, 2H), 1.41-1.61 (m, 5H), 0.98 (d, J=5.52 Hz, 3H); LCMS m/z 490.2 [M+H]+

Example 105

9-(5-(trifluoromethyl)-6-((cis-4-(trifluoromethyl)cyclohexyl)oxy)-2-naphthoyl)-9-azabicyclo[3.3.1]nonane-3-carboxylic acid

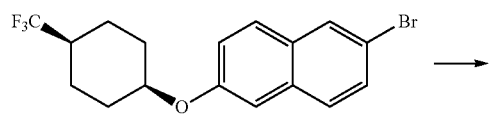

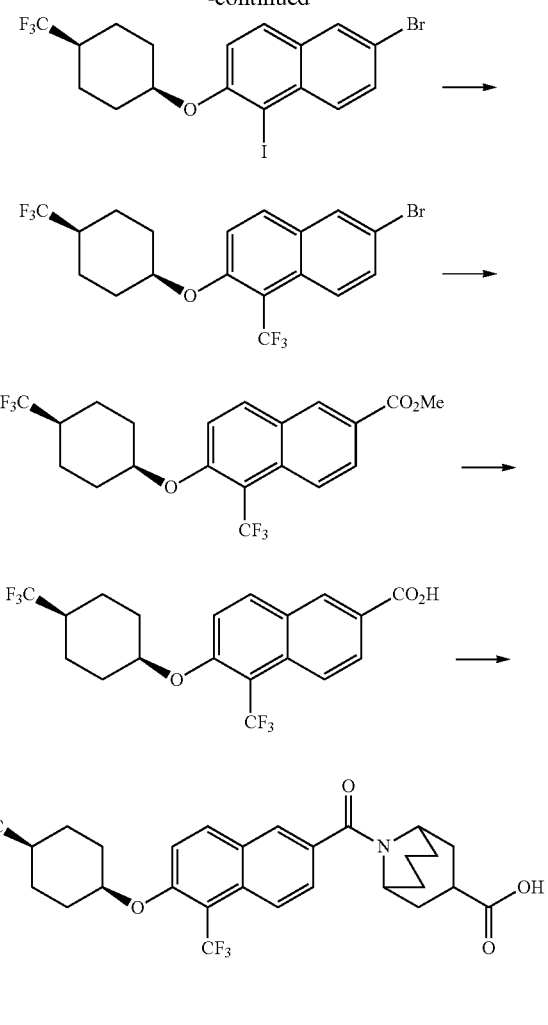

Step 1: 6-bromo-1-iodo-2-((cis-4-(trifluoromethyl)cyclohexyl)oxy)naphthalene

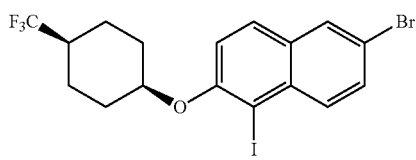 [SMILES: FC(F)(F)[C@H]1CC[C@@H](Oc2ccc3cc(Br)ccc3c2I)CC1]

Into a solution of 2-bromo-6-((cis-4-(trifluoromethyl)cyclohexyl)oxy)naphthalene (3.00 g, 8.04 mmol, 1.0 eq) and NIS (1.99 g, 8.85 mmol, 1.1 eq) in CH₃CN (50 mL) was added TFA (90 mg, 0.80 mmol, 0.1 eq). The mixture was stirred at rt overnight. The solvent was removed by reduced pressure and the residue dissolved in EtOAc (100 mL). The solvent was washed with water (100 mL), dried over Na₂SO₄ and concentrated. The residue was purified by column chromatography on silica gel (Petroleum ether/EtOAc=9/1) to give the titled compound as a yellow solid (3.6 g, yield: 90%). ¹H NMR (400 MHz, CDCl₃) δ 8.03 (d, J=9.2 Hz, 1H), 7.88 (s, 1H), 7.68 (d, J=8.8 Hz, 1H), 7.56 (dd, J=2.0 Hz, 9.2 Hz, 1H), 7.13 (d, J=9.2 Hz, 1H), 4.84 (s, 1H), 2.21-2.00 (m, 5H), 1.80-1.77 (m, 2H), 1.62-1.55 (m, 2H).

Step 2: 6-bromo-1-(trifluoromethyl)-2-((cis-4-(trifluoromethyl)cyclohexyl)oxy)naphthalene

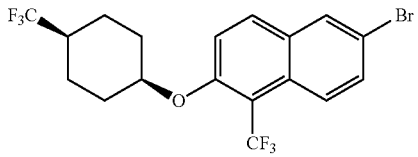 [SMILES: FC(F)(F)c1c(O[C@H]2CC[C@@H](C(F)(F)F)CC2)ccc2cc(Br)ccc12]

To a mixture of 6-bromo-1-iodo-2-((cis-4-(trifluoromethyl)cyclohexyl)oxy)naphthalene (3.00 g, 6.04 mmol), CuI (2.87 g, 15.10 mmol, 2.5 eq) and DIPEA (7.79 g, 60.40 mmol, 10.0 eq) in DMF (50 mL) was added $FSO_2CF_2CO_2CH_3$ (11.59 g, 60.40 mmol, 10.0 eq). The mixture stirred at 85° C. for 16 h and cooled down. The mixture was diluted with water (200 mL) and extracted with EtOAc (100 mL×2). The combined organic layers were washed with water (200 mL) and brine (200 mL). The solvent was removed and the residue was purified by column chromatography on silica gel (Petroleum ether/EtOAc=9/1) to give the titled compound as a yellow solid (2.4 g, yield 91%).

Step 3: methyl 5-(trifluoromethyl)-6-((cis-4-(trifluoromethyl)cyclohexyl)oxy)-2-naphthoate

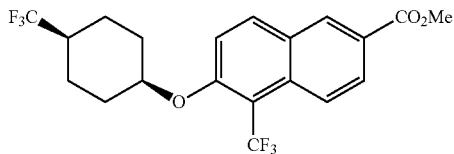 [SMILES: COC(=O)c1ccc2c(C(F)(F)F)c(O[C@H]3CC[C@@H](C(F)(F)F)CC3)ccc2c1]

Into an autoclave was added a solution of 6-bromo-1-(trifluoromethyl)-2-((cis-4-(trifluoromethyl)cyclohexyl)oxy)naphthalene (1.32 g, 3.0 mmol) in MeOH (50 mL), followed by $PdCl_2(dppf)$ (245 mg, 0.3 mmol, 0.1 eq) and TEA (1.26 mL, 9.0 mmol, 3.0 eq). The mixture was stirred at 100° C. for 4 h under CO (15 atm). The mixture was cooled down and concentrated. The crude product was purified by column chromatography on silica gel (Petroleum ether/EtOAc=4/1) to give the titled compound as a yellow solid (750 mg, yield 62%). $^1$H NMR (400 MHz, $CDCl_3$) δ 8.53 (d, J=1.6 Hz, 1H), 8.26 (d, J=9.6 Hz, 1H), 8.10 (dd, J=2.0 Hz, J=9.2 Hz, 1H), 8.05 (d, J=9.6 Hz, 1H), 7.32 (d, J=9.2 Hz, 1H), 4.88 (s, 1H), 3.98 (s, 3H), 2.24-2.20 (m, 2H), 2.14-2.10 (m, 1H), 1.90-1.77 (m, 4H), 1.68-1.56 (m, 2H); ESI-MS (M+H)$^+$: 421.1.

Step 4: 5-(trifluoromethyl)-6-((cis-4-(trifluoromethyl)cyclohexyl)oxy)-2-naphthoic acid

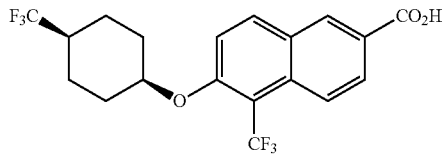 [SMILES: O=C(O)c1ccc2c(C(F)(F)F)c(O[C@H]3CC[C@@H](C(F)(F)F)CC3)ccc2c1]

To a mixture of methyl 5-(trifluoromethyl)-6-((cis-4-(trifluoromethyl)cyclohexyl)oxy)-2-naphthoate (750 mg, 1.78 mmol) in MeOH (10 mL) was added NaOH (214 mg, 5.36 mmol, 3.0 eq). The mixture was stirred at 70° C. for 2 h. Then the mixture was cooled to rt and concentrated. The residue was suspended in 3 mL of water and acidified to pH=6 with 1N HCl. The white solid was collected by filtration and dried to give the titled compound (660 mg, yield 90%). $^1$H NMR (400 MHz, $CD_3OD$) δ 8.57 (d, J=1.6 Hz, 1H), 8.20-8.18 (m, 2H), 8.10 (dd, J=1.6 Hz, J=9.2 Hz, 1H), 7.55 (d, J=9.2 Hz, 1H), 5.02 (s, 1H), 2.30-2.21 (m, 1H), 2.19-2.15 (m, 2H), 1.81-1.70 (m, 6H); ESI-MS (M+H)$^+$: 407.1.

Step 5: 9-(5-(trifluoromethyl)-6-((cis-4-(trifluoromethyl)cyclohexyl)oxy)-2-naphthoyl)-9-azabicyclo[3.3.1]nonane-3-carboxylic acid

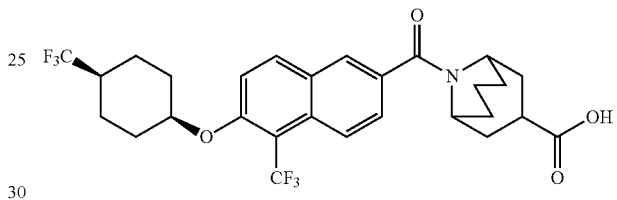

To a solution of 5-(trifluoromethyl)-6-((cis-4-(trifluoromethyl)cyclohexyl)oxy)-2-naphthoic acid (120 mg, 0.30 mmol) in 3 mL of DMF were added methyl 9-azabicyclo[3.3.1]nonane-3-carboxylate, HCl salt (60 mg, 0.33 mmol, 1.1 eq), HOBT (60 mg, 0.45 mmol, 1.5 eq), TEA (91 mg, 0.9 mmol, 3.0 eq) and EDCI (85 mg, 0.45 mmol, 1.5 eq). The reaction mixture was stirred at room temperature for 2 h. The solution was diluted with water (10 mL) and extracted with ethyl acetate (10 mL×3). The combined organic layers were dried over $Na_2SO_4$ and concentrated. The residue was purified by column chromatography on silica gel (DCM/MeOH=50/1) to give the desired ester as a colorless oil (80 mg, yield 63%). $^1$H NMR (400 MHz, $CDCl_3$) δ 8.24 (d, J=8.8 Hz, 1H), 7.97 (d, J=8.8 Hz, 1H), 7.89 (d, J=2.0 Hz, 1H), 7.55 (dd, J=2.0 Hz, 9.2 Hz, 1H), 7.31 (d, J=9.2 Hz, 1H), 4.98 (s, 1H), 4.88-4.86 (m, 1H), 4.01-3.99 (m, 1H), 3.70 (s, 3H), 3.39-3.30 (m, 1H), 2.22-2.18 (m, 2H), 2.13-1.95 (m, 6H), 1.91-1.82 (m, 8H), 1.75-1.59 (m, 3H); ESI-MS (M+H)$^+$: 572.2.

To a solution of the above ester (80 mg, 0.14 mmol) in MeOH/$H_2O$ (5 mL, 1:1) was added LiOH (10 mg, 0.42 mmol, 3.0 eq). The mixture was stirred at rt for 16 h. The solvent was removed by reduced pressure and the residue was suspended in water (1 mL). The mixture was acidified with 1N HCl to pH=6. The solid was collected by filtration and purified by HPLC (MeCN/$H_2O$-0.05% TFA) to give the title compound as a white solid (26 mg, yield 33%). $^1$H NMR (400 MHz, $CD_3OD$) δ 8.25 (d, J=8.8 Hz, 1H), 8.17 (d, J=9.6 Hz, 1H), 7.98 (d, J=1.6 Hz, 1H), 7.62-7.56 (m, 2H), 5.02 (s, 1H), 3.98-3.96 (m, 1H), 3.40-3.32 (m, 1H), 2.28-2.21 (m, 1H), 2.19-2.07 (m, 6H), 1.99-1.71 (m, 13H); ESI-MS (M+H)$^+$: 558.2.

Example 106

9-(2-(5-(trifluoromethyl)-6-((cis-4-(trifluoromethyl)cyclohexyl)oxy)naphthalene-2-yl) acetyl)-9-azabicyclo[3.3.1]nonane-3-carboxylic acid

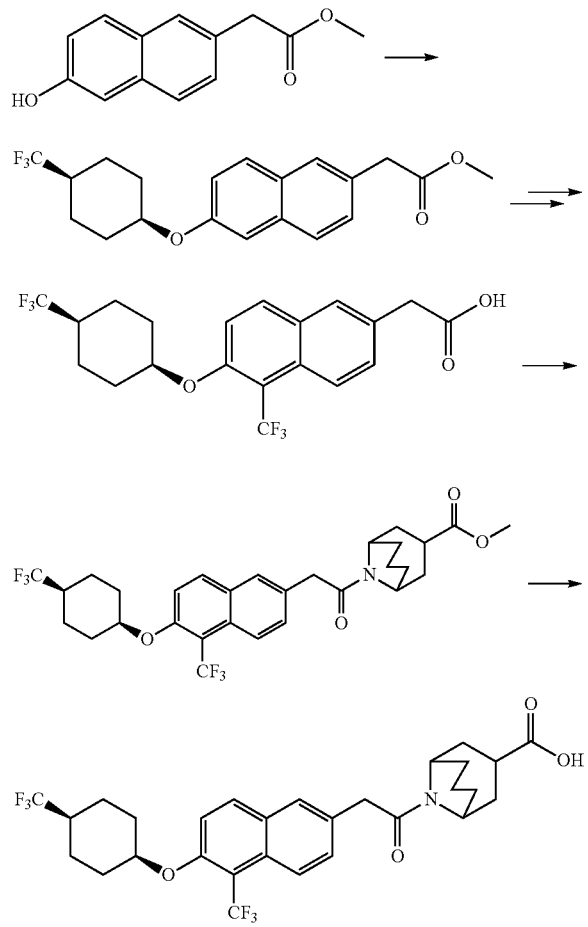

Step 1: methyl 2-(6-hydroxynaphthalen-2-yl)acetate

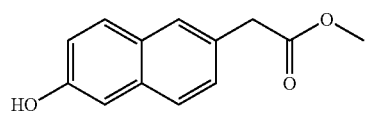 [SMILES: COC(=O)Cc1ccc2cc(O)ccc2c1]

To a solution of 2-(6-hydroxynaphthalen-2-yl)acetic acid (830 mg, 4.1 mmol) in 20 mL of MeOH was added 4 drops of conc. $H_2SO_4$. The reaction mixture was heated at reflux for 16 h and concentrated. The residue was purified by column chromatography on silica gel (petroleum ether/EtOAc=4/1) to give the title compound as a white solid (710 mg, yield 80%). $^1$H NMR (400 MHz, DMSO-$d_6$) δ 9.70 (s, 1H), 7.70 (d, J=8.8 Hz, 1H), 7.64-7.62 (m, 2H), 7.28 (dd, J=2.0 Hz, 8.8 Hz, 1H), 7.09-7.05 (m, 2H), 3.77 (s, 2H), 3.62 (s, 3H); ESI-MS (M+H)$^+$: 216.9.

Step 2: methyl 2-(6-((cis-4-(trifluoromethyl)cyclohexyl)oxy)naphthalene-2-yl)acetate

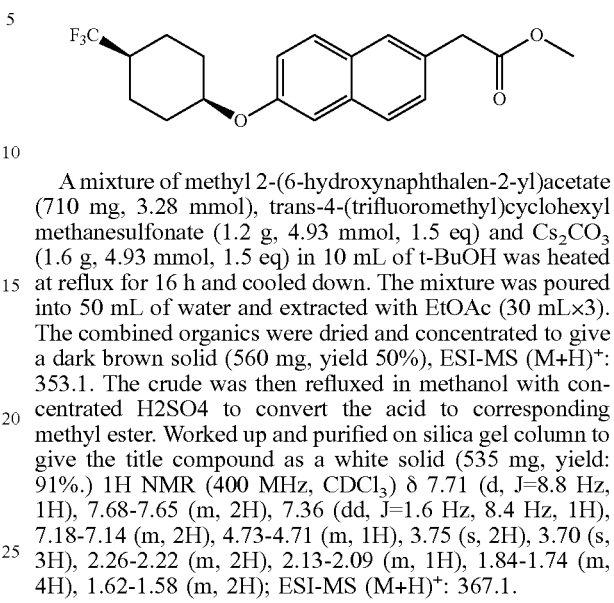

A mixture of methyl 2-(6-hydroxynaphthalen-2-yl)acetate (710 mg, 3.28 mmol), trans-4-(trifluoromethyl)cyclohexyl methanesulfonate (1.2 g, 4.93 mmol, 1.5 eq) and $Cs_2CO_3$ (1.6 g, 4.93 mmol, 1.5 eq) in 10 mL of t-BuOH was heated at reflux for 16 h and cooled down. The mixture was poured into 50 mL of water and extracted with EtOAc (30 mL×3). The combined organics were dried and concentrated to give a dark brown solid (560 mg, yield 50%), ESI-MS (M+H)$^+$: 353.1. The crude was then refluxed in methanol with concentrated H2SO4 to convert the acid to corresponding methyl ester. Worked up and purified on silica gel column to give the title compound as a white solid (535 mg, yield: 91%.) 1H NMR (400 MHz, CDCl$_3$) δ 7.71 (d, J=8.8 Hz, 1H), 7.68-7.65 (m, 2H), 7.36 (dd, J=1.6 Hz, 8.4 Hz, 1H), 7.18-7.14 (m, 2H), 4.73-4.71 (m, 1H), 3.75 (s, 2H), 3.70 (s, 3H), 2.26-2.22 (m, 2H), 2.13-2.09 (m, 1H), 1.84-1.74 (m, 4H), 1.62-1.58 (m, 2H); ESI-MS (M+H)$^+$: 367.1.

Step 3: methyl 2-(5-iodo-6-((cis-4-(trifluoromethyl)cyclohexyl)oxy)naphthalen-2-yl)acetate

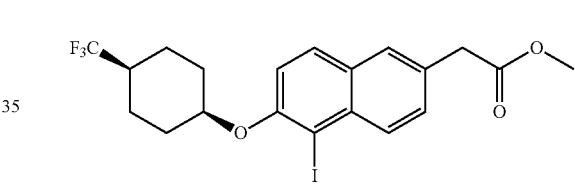

To a solution of methyl 2-(6-((cis-4-(trifluoromethyl)cyclohexyl)oxy)naphthalene-2-yl)acetate (535 mg, 1.46 mmol) in MeCN (5 mL) was added NIS (361 mg, 1.60 mmol, 1.1 eq), followed by TFA (50 mg, 0.44 mmol, 0.3 eq). The mixture was stirred at rt for 16 h. The reaction mixture was diluted with water (50 mL) and extracted with EtOAc (50 mL×3). The combined organic layers were dried and concentrated. The crude product was purified by column chromatography on silica gel (petroleum ether/EtOAc=20/1) to give the title compound as a white solid (500 g, yield: 70%). $^1$H NMR (400 MHz, CDCl$_3$) δ 8.10 (d, J=8.4 Hz, 1H), 7.74 (d, J=8.8 Hz, 1H), 7.63 (s, 1H), 7.45 (dd, J=1.6 Hz, 8.8 Hz, 1H), 7.14 (d, J=8.8 Hz, 1H), 4.85 (s, 1H), 3.98 (s, 2H), 3.78 (s, 3H), 2.22-2.05 (m, 5H), 1.79-1.76 (m, 2H), 1.61-1.55 (m, 2H).

Step 4: 2-(5-(trifluoromethyl)-6-((cis-4-(trifluoromethyl)cyclohexyl)oxy)naphthalen-2-yl)acetic acid

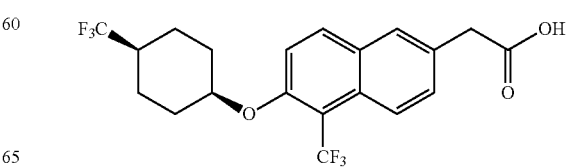

The title compound was prepared according to the procedure for 6-((cis-4-Methylcyclohexyl)oxy)-5-(trifluoromethyl)-2-naphthoic acid from methyl 2-(5-iodo-6-((cis-4-(trifluoromethyl)cyclohexyl)oxy)naphthalen-2-yl)acetate. ¹H NMR (400 MHz, CD₃OD) δ 8.12 (d, J=8.8 Hz, 1H), 8.03 (d, J=9.2 Hz, 1H), 7.77 (s, 1H), 7.53-7.43 (m, 2H), 4.92 (s, 1H), 3.76 (s, 2H), 2.26-2.24 (m, 1H), 2.18-1.24 (m, 2H), 1.88-1.73 (m, 6H); ESI-MS (M+H)⁺: 421.1.

Step 5: methyl 9-(2-(5-(trifluoromethyl)-6-((cis-4-(trifluoromethyl)cyclohexyl)oxy)naphthalen-2-yl)acetyl)-9-azabicyclo[3.3.1]nonane-3-carboxylate

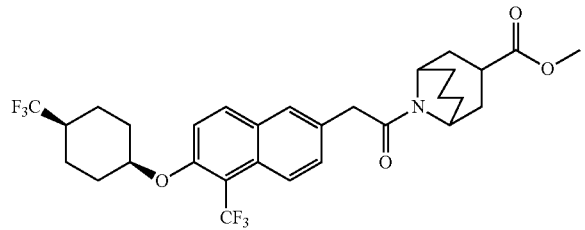 [SMILES: COC(=O)C1CC2CCCC(C1)N2C(=O)Cc1ccc2c(C(F)(F)F)c(O[C@H]3CC[C@@H](C(F)(F)F)CC3)ccc2c1]

To a solution of 2-(5-(trifluoromethyl)-6-((cis-4-(trifluoromethyl)cyclohexyl)oxy)naphthalen-2-yl)acetic acid (200 mg, 0.476 mmol, 1.0 eq) and methyl 9-azabicyclo[3.3.1]nonane-3-carboxylate, HCl salt (96 mg, 0.524 mmol, 1.1 eq) in CH₂Cl₂ (10 mL) was added HATU (362 mg, 0.952 mmol, 2.0 eq), followed by TEA (96 mg, 0.952 mmol, 2.0 eq). The mixture was stirred at rt for 5 h and diluted with 20 mL of water. The mixture was extracted with DCM (20 mL×3) and the combined organics were dried and concentrated. The residue was purified by column chromatography on silica gel (petroleum ether/EtOAc=4:1) to give the title compound as a colorless oil (220 mg, yield: 80%). ¹H NMR (400 MHz, CDCl₃) δ 8.11 (d, J=8.4 Hz, 1H), 7.82 (d, J=9.2 Hz, 1H), 7.61 (s, 1H), 7.38 (dd, J=1.6 Hz, 8.8 Hz, 1H), 7.19-7.17 (m, 1H), 4.87 (s, 1H), 4.75-4.73 (m, 1H), 4.08-4.06 (m, 1H), 3.76 (s, 2H), 3.57 (s, 3H), 3.19-3.15 (m, 1H), 2.16-2.00 (m, 3H), 1.90-1.50 (m, 16H); ESI-MS (M+H)⁺: 586.2.

Step 6: 9-(2-(5-(trifluoromethyl)-6-((cis-4-(trifluoromethyl)cyclohexyl)oxy)naphthalen-2-yl)acetyl)-9-azabicyclo[3.3.1]nonane-3-carboxylic acid

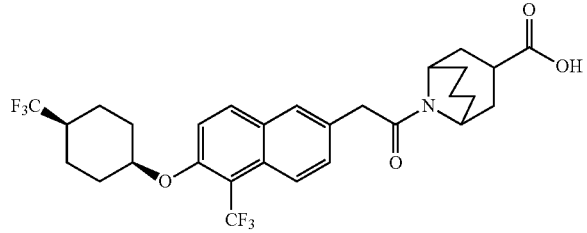 [SMILES: O=C(O)C1CC2CCCC(C1)N2C(=O)Cc1ccc2c(C(F)(F)F)c(O[C@H]3CC[C@@H](C(F)(F)F)CC3)ccc2c1]

The title compound was prepared according to the procedure for Example 104 as a white solid (15 mg, yield: 23%). ¹H NMR (400 MHz, CD₃OD) δ: 8.14 (d, J=8.4 Hz, 1H), 8.03 (d, J=9.2 Hz, 1H), 7.78 (s, 1H), 7.53-7.48 (m, 2H), 4.98 (s, 1H), 4.85-4.82 (m, 1H), 4.35-4.32 (m, 1H), 3.95-3.92 (m, 2H), 3.30-3.25 (m, 1H), 2.29-2.16 (m, 3H), 2.04-1.54 (m, 16H); ESI-MS (M+H)⁺: 572.3.

Example 107

9-(2-(5-(trifluoromethyl)-6-((cis-4-(trifluoromethyl)cyclohexyl)oxy)naphthalene-2-yl)ethyl)-9-azabicyclo[3.3.1]nonane-3-carboxylic acid

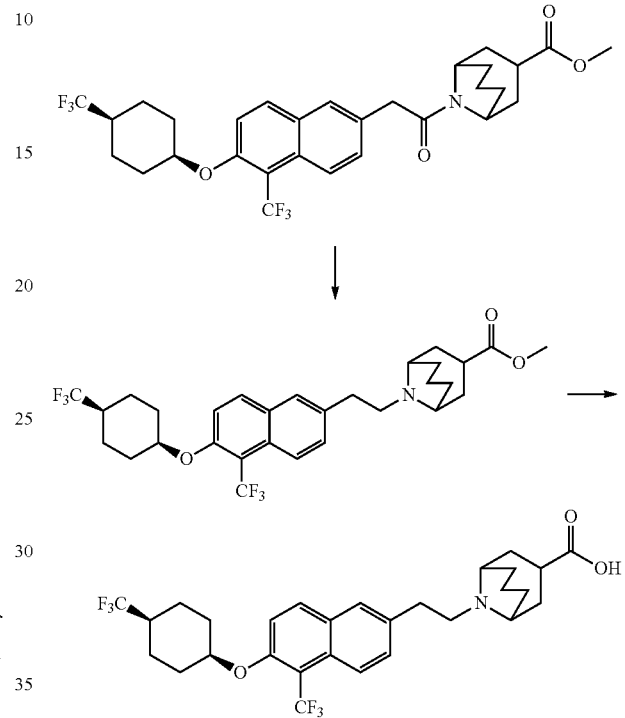

Step 1: methyl 9-(2-(5-(trifluoromethyl)-6-((cis-4-(trifluoromethyl)cyclohexyl)oxy)naphthalene-2-yl)ethyl)-9-azabicyclo[3.3.1]nonane-3-carboxylate

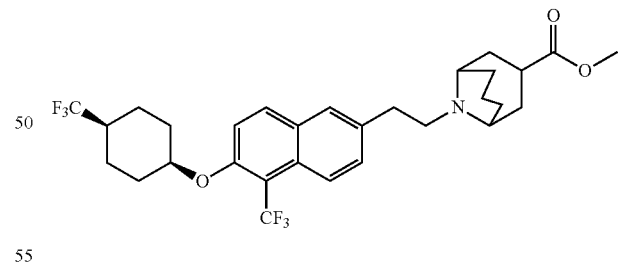

A mixture of methyl 9-(2-(5-(trifluoromethyl)-6-((cis-4-(trifluoromethyl)cyclohexyl)oxy)naphthalene-2-yl)acetyl)-9-azabicyclo[3.3.1]nonane-3-carboxylate (200 mg, 0.342 mmol, 1.0 eq) and BH₃/THF (3.4 mL, 1M, 3.42 mmol, 10.0 eq) in THF (5 mL) was stirred at 60° C. for 6 h and diluted with 30 mL of water. The mixture was extracted with DCM (30 mL×3) and the combined organics were dried and concentrated. The residue was purified by column chromatography on silica gel (petroleum ether/EtOAc=4:1) to give the title compound as a white solid (60 mg, yield: 31%). ESI-MS (M+H)⁺: 572.1.

Step 2: 9-(2-(5-(trifluoromethyl)-6-((cis-4-(trifluoromethyl)cyclohexyl)oxy)naphthalene-2-yl)ethyl)-9-azabicyclo[3.3.1]nonane-3-carboxylic acid

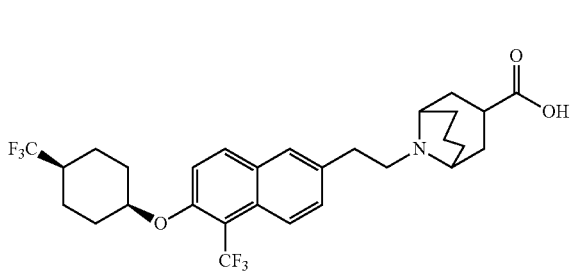 [SMILES: O=C(O)C1CC2CCCC(C1)N2CCc1ccc2c(C(F)(F)F)c(O[C@H]3CC[C@@H](C(F)(F)F)CC3)ccc2c1]

The title compound was prepared according to the procedure for Example 104 as a white solid (40 mg, yield: 69%). ¹H NMR (400 MHz, CD₃OD) δ 8.19 (d, J=8.8 Hz, 1H), 8.08 (d, J=9.2 Hz, 1H), 7.85 (s, 1H), 7.57 (d, J=8.8 Hz, 1H), 7.53 (d, J=9.2 Hz, 1H), 4.98 (s, 1H), 3.81-3.78 (m, 2H), 3.70-3.60 (m, 2H), 3.46-3.36 (m, 1H), 3.28-3.19 (m, 2H), 2.38-2.24 (m, 6H), 2.22-2.01 (m, 5H), 1.90-1.70 (m, 8H). ESI-MS (M+H)⁺: 558.1.

Example 108

9-((6-((cis-4-methylcyclohexyl)amino)-5-(trifluoromethyl)naphthalen-2-yl)methyl)-9-azabicyclo[3.3.1]nonane-3-carboxylic acid

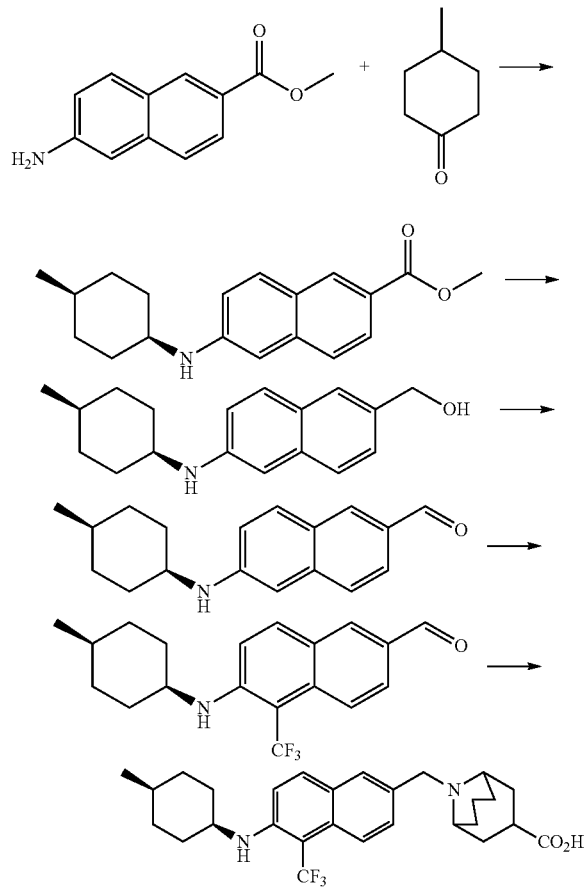

Step 1: Methyl 6-((cis-4-(methyl)cyclohexyl)amino)-2-naphthoate

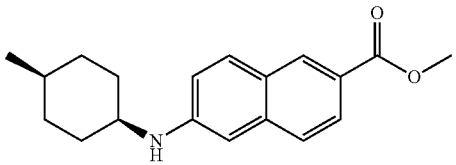

To a solution of methyl 6-amino-2-naphthoate (1.2 g, 6.0 mmol, 1.0 eq) and 4-methylcyclohexanone (900 mg, 8.0 mmol, 1.3 eq) in DCE (20 mL) were added NaBH(Oac)₃ (2.6 g, 12.0 mmol, 2.0 eq) and HOAc (720 mg, 12.0 mol, 2.0 eq). The mixture was stirred at 80° C. for 16 h and cooled down. The mixture was partitioned between DCM (30 mL) and sat. aq. NaHCO₃ (30 mL). The organic layer was dried over Na₂SO₄ and concentrated to yield a crude product, which was washed with MeOH (5 mL×3) to give the title compound as a yellow solid (712 mg, yield: 40%). ¹H NMR (400 MHz, CDCl₃) δ 8.39 (s, 1H), 7.91 (dd, J=1.6 Hz, 8.8 Hz, 1H), 7.69 (d, J=8.8 Hz, 1H), 7.56 (d, J=8.8 Hz, 1H), 6.90 (d, J=8.8 Hz, 1H), 6.79 (s, 1H), 3.94 (s, 3H), 3.72-3.69 (m, 1H), 1.87-1.81 (m, 2H), 1.77-1.67 (m, 2H), 1.62-1.59 (m, 3H), 1.31-1.21 (m, 2H), 0.95 (d, J=6.4 Hz, 3H); ESI-MS (M+H)⁺: 298.2.

Step 2: (6-((cis-4-(methyl)cyclohexyl)amino)naphthalen-2-yl)methanol

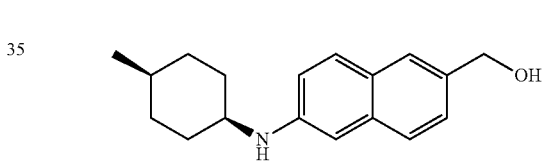

To a solution of methyl 6-((cis-4-(methyl)cyclohexyl)amino)-2-naphthoate (179 mg, 0.6 mmol, 1.0 eq) in dry THF (2 mL) was added LiAlH₄ (31 mg, 0.8 mmol, 1.5 eq) at 0° C. The mixture was stirred at 0° C. for 2 h and quenched with Na₂SO₄·10H₂O. The mixture was diluted with water (15 mL) and extracted with EtOAc (15 mL×2). The combined organic layers were dried and concentrated to give the title compound as a yellow oil, which was used for the next step without further purification (130 mg, yield: 80%). ESI-MS (M+H)⁺: 270.2.

Step 3: 6-((cis-4-(methyl)cyclohexyl)amino)-2-naphthaldehyde

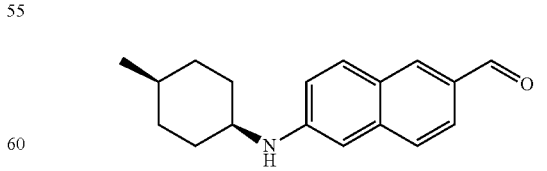

A mixture of (6-((cis-4-(methyl)cyclohexyl)amino)naphthalen-2-yl)methanol (134 mg, 0.5 mmol, 1.0 eq) and MnO₂ (440 mg, 5.0 mmol, 10.0 eq) in DCM (5 mL) was stirred at rt for 16 h. The mixture was filtered and the filtrate was concentrated to give the title compound as a yellow oil, which was used for the next step without further purification (81 mg, yield: 60%). ESI-MS (M+H)⁺: 268.2.

Step 4: 6-((cis-4-methylcyclohexyl)amino)-5-(trifluoromethyl)-2-naphthaldehyde

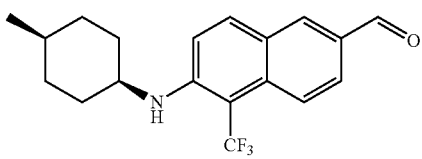 [SMILES: C[C@H]1CC[C@@H](Nc2ccc3cc(C=O)ccc3c2C(F)(F)F)CC1]

A mixture of 6-((cis-4-(methyl)cyclohexyl)amino)-2-naphthaldehyde (400 mg, 1.5 mmol, 1.0 eq) and 1-trifluoromethyl-1,3-dihydro-3,3-dimethyl-1,2-benziodoxole (reference see M. S. Wiehn et al. *J. Fluorine Chem.* 131 (2010) P-951, which is incorporated by reference in its entirety) (741 mg, 2.25 mmol, 1.5 eq) in CAN (4 mL) was heated at 80° C. for 16 h in a sealed tube. The mixture was cooled to rt, and partitioned between DCM (30 mL) and H₂O (30 mL). The organic layer was dried over Na₂SO₄ and concentrated. The residue was purified by column chromatography on silica gel (petroleum ether/EtOAc=6/1) to give the title compound as a yellow solid (200 mg, yield: 60%). ¹H NMR (400 MHz, CDCl₃) δ 10.04 (s, 1H), 8.14 (d, J=1.6 Hz, 1H), 8.03 (dd, J=1.6 Hz, 8.8 Hz, 1H), 7.92-7.87 (m, 2H), 7.14 (d, J=9.6 Hz, 1H), 3.86-3.84 (m, 1H), 1.87-1.83 (m, 2H), 1.76-1.68 (m, 2H), 1.65-1.55 (m, 3H), 1.27-1.21 (m, 2H), 0.97 (d, J=6.4 Hz, 3H); ESI-MS (M+H)⁺: 336.2.

Step 5: 9-((6-((cis-4-methylcyclohexyl)amino)-5-(trifluoromethyl)naphthalen-2-yl)methyl)-9-azabicyclo[3.3.1]nonane-3-carboxylic acid

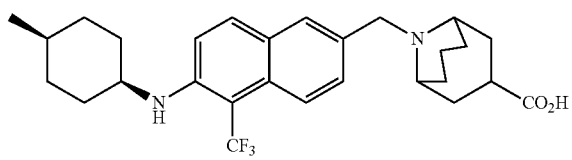 [SMILES: C[C@H]1CC[C@@H](Nc2ccc3cc(CN4C5CCCC4CC(C(=O)O)C5)ccc3c2C(F)(F)F)CC1]

To a mixture of 9-aza-bicyclo[3.3.1]nonane-3-carboxylic acid methyl ester HCl salt (26 mg, 0.12 mmol) in THF (0.7 mL) was added triethylamine (17 μL, 0.12 mmol), and stirred at rt for 15 min. To this mixture was added 6-((cis-4-methylcyclohexyl)amino)-5-(trifluoromethyl)-2-naphthaldehyde (34 mg, 0.10 mmol), followed by sodium triacetoxyborohydride (28 mg, 0.13 mmol) and acetic acid (6.8 μL, 0.12 mmol). The reaction mixture was heated with microwave irritation at 100° C. for 20 min. To the above mixture was added 3 M of NaOH in water (0.5 mL, 2 mmol) and MeOH (0.8 mL). The reaction mixture was heated with microwave irritation at 100° C. for 10 min, It was neutralized with 1N HCl, filtered and purified by HPLC (TFA method) to collect the desired acid as a white powder after lyophilization (35 mg, yield 58%). ¹H NMR (300 MHz, METHANOL-d₄) δ 7.83-8.11 (m, 3H), 7.60 (d, J=9.06 Hz, 1H), 7.30 (d, J=9.44 Hz, 1H), 4.50-4.73 (m, 2H), 3.92 (br. S., 1H), 3.62 (br. S., 2H), 3.34-3.47 (m, 1H), 2.47-2.65 (m, 2H), 1.99-2.38 (m, 6H), 1.45-1.96 (m, 9H), 1.12-1.36 (m, 2H), 0.97 (d, J=6.42 Hz, 3H); LCMS m/z 489.1 [M+H]⁺

Example 109

2-(9-Azabicyclo[3.3.1]nonan-9-yl)-2-(6-((cis-4-methylcyclohexyl)oxy)-5-(trifluoromethyl)naphthalen-2-yl)acetic acid

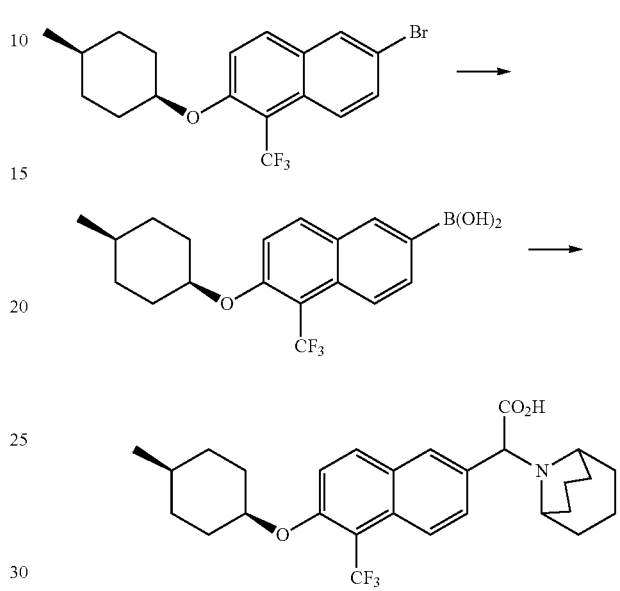

Step 1: (6-((cis-4-Methylcyclohexyl)oxy)-5-(trifluoromethyl)naphthalene-2-yl)boronic acid

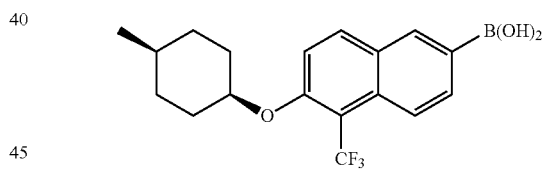

To a solution of 6-bromo-2-((cis-4-methylcyclohexyl)oxy)-1-(trifluoromethyl) naphthalene, prepared according to the procedure for 6-bromo-1-(trifluoromethyl)-2-((cis-4-(trifluoromethyl)cyclohexyl)oxy)naphthalene from trans-4-methylcyclohexanol (774 mg, 2.00 mmol) in THF (4 mL) at −78° C. was added 2.5 M of n-butyllithium in hexane (0.96 mL, 2.4 mmol) dropwise under N₂. The reaction mixture was stirred at −78° C. for 30 min. Triisopropyl borate (0.69 mL, 3.0 mmol) was added, and stirred at −78° C. for 1 h. The reaction was quenched with 1N HCl, and extracted with EtOAc. The organic phase was washed with brine, dried over MgSO₄, filtered and concentrated. The residue was purified by flash chromatography on silica gel column, eluted with EtOAc/MeOH/AcOH (100:10:1) to get the desired boronic acid as a white solid (234 mg, yield 33%). ¹H NMR (300 MHz, METHANOL-d₄) δ 8.00-8.19 (m, 3H), 7.76 (dd, J=1.13, 8.69 Hz, 1H), 7.45 (d, J=9.06 Hz, 1H), 4.89 (br, s, 1H), 1.91-2.15 (m, 2H), 1.59-1.79 (m, 2H), 1.38-1.57 (m, 5H), 0.96 (d, J=5.29 Hz, 3H); LCMS m/z 353.1 [M+H]⁺

Step 2: 2-(9-Azabicyclo[3.3.1]nonan-9-yl)-2-(6-((cis-4-methylcyclohexyl)oxy)-5-(trifluoromethyl)naphthalen-2-yl)acetic acid

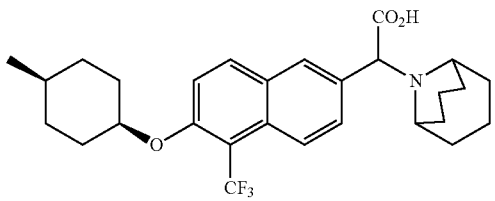 [SMILES: C[C@H]1CC[C@@H](Oc2ccc3cc(C(C(=O)O)N4C5CCCC4CCC5)ccc3c2C(F)(F)F)CC1]

To a mixture of glyoxalic acid hydrate (21 mg, 0.23 mmol) and (6-((cis-4-methylcyclohexyl)oxy)-5-(trifluoromethyl)naphthalene-2-yl)boronic acid (67 mg, 0.19 mmol) in 1,1,1,3,3,3-hexafluoropropan-2-ol (2 mL) was added 9-azabicyclo[3.3.1]nonane HCl salt (46 mg, 0.28 mmol). To the above suspension was added N,N-diisopropylethylamine (50 μL, 0.28 mmol), and stirred at rt for 2 days. The mixture was purified by HPLC (TFA method) to collect the desired product as a white powder after lyophilization (3 mg, yield 3%). $^1$H NMR (300 MHz, METHANOL-$d_4$) δ 8.22-8.28 (m, 2H), 8.10 (d, J=9.06 Hz, 1H), 7.87 (d, J=9.44 Hz, 1H), 7.57 (d, J=9.06 Hz, 1H), 5.50 (s, 1H), 4.93 (br. S., 1H), 3.38-4.03 (m, 2H), 1.23-2.35 (m, 21H), 0.95 (d, J=5.29 Hz, 3H); LCMS m/z 490.1.1 [M+H]$^+$

Example 110

9-((5-Chloro-6-((cis-4-ethylcyclohexyl)oxy)naphthalen-2-yl)methyl)-9-azabicyclo[3.3.1]nonane-3-carboxylic acid

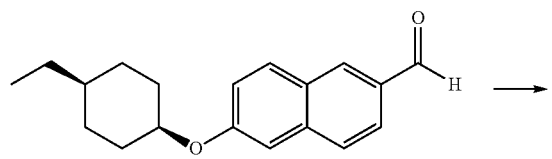

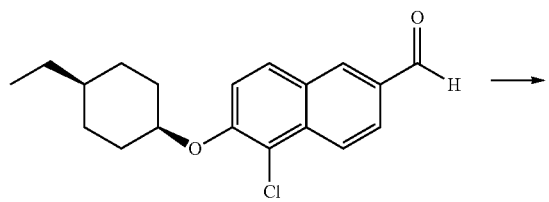

Step 1: 5-Chloro-6-((cis-4-ethylcyclohexyl)oxy)-2-naphthaldehyde

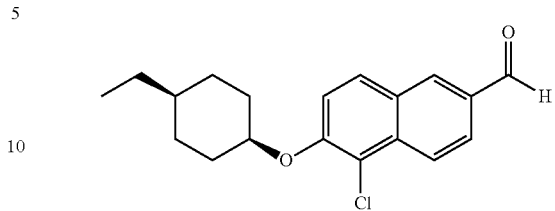

The solution of 6-((cis-4-ethylcyclohexyl)oxy)-2-naphthaldehyde (1.41 g, 5.00 mmol), N-chlorosuccinimide (801 mg, 6.00 mmol) in acetonitrile (10 mL) was heated with microwave irritation at 100° C. for 20 min. The mixture was partitioned between EtOAc and brine. The organic phase was washed with brine, dried over MgSO$_4$, filtered and concentrated to get the desired aldehyde as a pale yellow solid (1.84 g, yield 100%). LCMS m/z 317.0 [M+H]$^+$

Step 2: 9-((5-Chloro-6-((cis-4-ethylcyclohexyl)oxy)naphthalen-2-yl)methyl)-9-azabicyclo[3.3.1]nonane-3-carboxylic acid

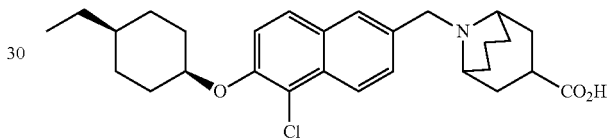

To a mixture of 9-aza-bicyclo[3.3.1]nonane-3-carboxylic acid methyl ester HCl salt (46 mg, 0.21 mmol) and 5-chloro-6-((cis-4-ethylcyclohexyl)oxy)-2-naphthaldehyde (56 mg, 0.15 mmol) in THF (1 mL) was added sodium triacetoxyborohydride (46 mg, 0.22 mmol). The reaction solution was heated with microwave irritation at 100° C. for 20 min.

To the above mixture was added 3 M of NaOH in water (0.8 mL, 2 mmol) and MeOH (0.8 mL), and heated with microwave irritation at 100° C. for 10 min. It was neutralized with 1N HCl. Filtered and purified by HPLC (TFA method) to collect the TFA salt of the desired product as a white powder after lyophilization (47 mg, yield 53%). $^1$H NMR (300 MHz, METHANOL-$d_4$) δ 8.29 (d, J=8.69 Hz, 1H), 8.09 (s, 1H), 7.90 (d, J=9.44 Hz, 1H), 7.74 (dd, J=1.89, 8.69 Hz, 1H), 7.52 (d, J=9.06 Hz, 1H), 4.88 (br. S., 1H), 4.61-4.75 (m, 2H), 3.64 (br. S., 2H), 3.41 (t, J=9.25 Hz, 1H), 2.56 (br. S., 2H), 1.42-2.39 (m, 16H), 1.17-1.40 (m, 3H), 0.93 (t, J=6.99 Hz, 3H); LCMS m/z 470.0 [M+H]$^+$

Example 111

9-((5-Chloro-6-((cis-4-(trifluoromethyl)cyclohexyl)oxy)naphthalen-2-yl)methyl)-9-azabicyclo[3.3.1]nonane-3-carboxylic acid

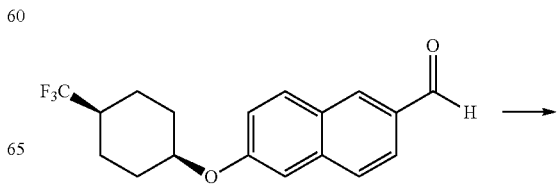

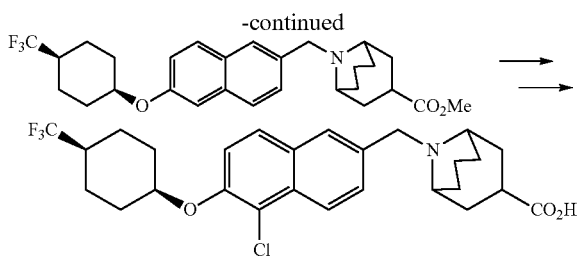

Step 1: Methyl 9-((6-((cis-4-(trifluoromethyl)cyclo-hexyl)oxy)naphthalene-2-yl)methyl)-9-azabicyclo[3.3.1]nonane-3-carboxylate

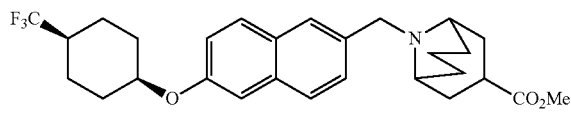 [SMILES: COC(=O)C1CC2CCCC(C1)N2Cc1ccc2cc(O[C@H]3CC[C@@H](C(F)(F)F)CC3)ccc2c1]

To a mixture of 6-((cis-4-(trifluoromethyl)cyclohexyl)oxy)-2-naphthaldehyde (161 mg, 0.500 mmol) and 9-azabicyclo[3.3.1]nonane-3-carboxylic acid methyl ester HCl salt (132 mg, 0.600 mmol) in THF (2 mL) was added acetic acid (43 μL, 0.76 mmol) and sodium triacetoxyborohydride (159 mg, 0.750 mmol). The reaction mixture was then heated with microwave irritation at 100° C. for 20 min. It was partitioned between EtOAc and brine. The organic phase was washed with brine, dried, filtered and concentrated. The residue was purified by flash chromatography on silica gel column to get the desired ester as a colorless oil (215 mg, yield 88%). LCMS m/z 490.1 [M+H]+

Step 2: 9-((5-Chloro-6-((cis-4-(trifluoromethyl)cyclohexyl)oxy)naphthalen-2-yl)methyl)-9-azabicyclo[3.3.1]nonane-3-carboxylic acid

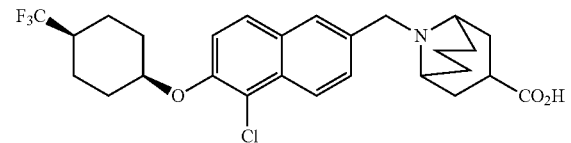 [SMILES: O=C(O)C1CC2CCCC(C1)N2Cc1ccc2c(Cl)c(O[C@H]3CC[C@@H](C(F)(F)F)CC3)ccc2c1]

The solution of methyl 9-((6-((cis-4-(trifluoromethyl)cyclohexyl)oxy)naphthalene-2-yl)methyl)-9-azabicyclo[3.3.1]nonane-3-carboxylate (98 mg, 0.20 mmol), N-chlorosuccinimide (41 mg, 0.31 mmol) in acetonitrile (1 mL) was heated with microwave irritation at 80° C. for 20 min. The mixture was purified by HPLC (TFA method) to get the ester intermediate (53 mg, yield 42%). LCMS m/z 524.0 [M+H]+.

The above ester was dissolved in THF (0.6 mL) and MeOH (0.6 mL), added 3 M of NaOH in water (0.2 mL, 0.6 mmol), and heated at 50° C. (hot plate) for 1 h. It was neutralized with 1N HCl, and purified by HPLC (TFA method) to get the desired product as a white powder after lyophilization (34 mg, yield 64%). $^1$H NMR (400 MHz, METHANOL-$d_4$) δ 8.32 (d, J=8.78 Hz, 1H), 8.11 (br. S., 1H), 7.93 (d, J=9.04 Hz, 1H), 7.75 (d, J=8.78 Hz, 1H), 7.55 (d, J=9.04 Hz, 1H), 4.95 (br. S., 1H), 4.61-4.78 (m, 2H), 3.65 (d, J=15.56 Hz, 2H), 3.36-3.46 (m, 1H), 2.58 (d, J=9.29 Hz, 2H), 2.02-2.38 (m, 9H), 1.64-2.01 (m, 8H); LCMS m/z 510.0 [M+H]+.

Example 112

4-(((5-(trifluoromethyl)-6-((cis-4-(trifluoromethyl)cyclohexyl)oxy)naphthalen-2-yl)methyl)carbamoyl)bicyclo[2.2.2]octane-1-carboxylic acid

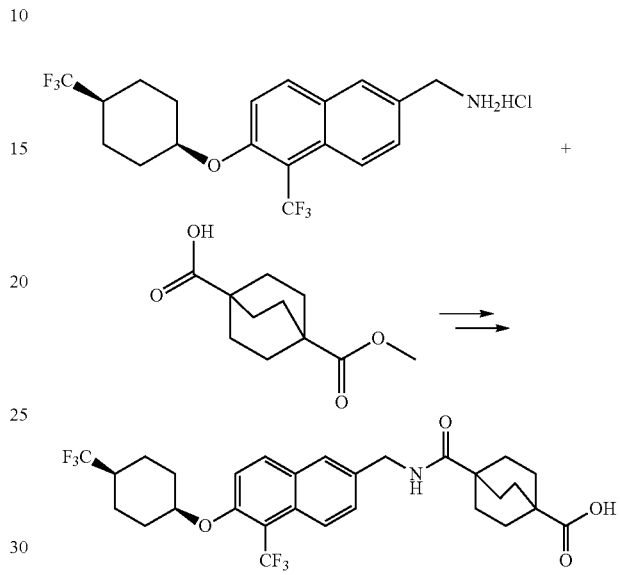

To a solution of (5-(trifluoromethyl)-6-((cis-4-(trifluoromethyl)cyclohexyl)oxy)naphthalen-2-yl)methanamine hydrochloride salt (100 mg, 0.25 mmol) in 2 mL of DMF were added 4-(methoxycarbonyl)bicyclo[2.2.2]octane-1-carboxylic acid (60 mg, 0.28 mmol, 1.1 eq), HOBT (51 mg, 0.38 mmol, 1.5 eq), TEA (76 mg, 0.75 mmol, 3.0 eq) and EDCI (73 mg, 0.38 mmol, 1.5 eq). The reaction mixture was stirred at room temperature for 16 h. The solution was diluted with water (10 mL) and extracted with ethyl acetate (10 mL×3). The combined organic layers were dried over $Na_2SO_4$ and concentrated. The residue was purified by column chromatography on silica gel (DCM/MeOH=50/1) to give the corresponding methyl ester as a colorless oil (56 mg, yield: 37%). ESI-MS (M+H)+: 586.2.

To a solution of the above ester (56 mg, 0.096 mmol) in MeOH/H2O (5 mL, 1:1) was added NaOH (12 mg, 0.287 mmol, 3.0 eq). The mixture was stirred at 65° C. overnight. The solvent was removed by reduced pressure and the residue was suspended in water (1 mL). The mixture was acidified with 1N HCl to pH=6. The resulting mixture was purified by reversed HPLC (MeCN/H2O-0.05% TFA) to give the title compound as a white solid (30 mg, yield: 55%). $^1$H NMR (400 MHz, CD3OD) δ 8.01 (d, J=8.4 Hz, 1H), 7.91 (d, J=9.6 Hz, 1H), 7.60 (s, 1H), 7.38-7.35 (m, 2H), 4.85 (s, 1H), 4.39 (m, 2H), 2.20-2.05 (m, 3H), 1.75-1.56 (m, 18H); ESI-MS (M+H) +: 572.1.

Example 113

N-(6-((cis-4-trifluoromethylcyclohexyl)oxy)-5-(trifluoromethyl)naphthalene-2-ylcarbonyl)-1-aminoindane-6-carboxylic acid The title compound was prepared according to the method of Example 105. $^1$H NMR (400 MHz, CD$_3$OD) δ: 8.43 (d, J=1.6 Hz, 1H), 8.22 (d, J=8.4 Hz, 1H), 8.17 (d, J=9.2 Hz, 1H), 8.03 (dd, J=2.4 Hz, 9.6 Hz, 1H), 7.98 (s, 1H), 7.92 (d, J=7.6 Hz, 1H), 7.55 (d, J=9.6 Hz, 1H), 7.37 (d, J=8.0 Hz, 1H), 5.74-5.71 (m, 1H), 5.01 (s, 1H), 3.17-3.10 (m, 1H), 3.03-2.97 (m, 1H), 2.69-2.65 (m, 1H), 2.27-2.24 (m, 1H), 2.18-2.09 (m, 3H), 1.83-1.72 (m, 6H); ESI-MS (M+H)+: 566.2.

Example 114

N-(6-((cis-4-trifluoromethylcyclohexyl)oxy)-5-(trifluoromethyl)naphthalene-2-ylcarbonyl)-6-aminoindole-3-carboxylic acid The title compound was prepared according to the method of Example 105. $^1$H NMR (400 MHz, CD$_3$OD) δ: 8.44 (s, 1H), 8.19 (d, J=8.0 Hz, 1H), 8.14 (d, J=9.2 Hz, 1H), 8.05 (d, J=1.2 Hz, 1H), 8.02 (dd, J=2.0 Hz, 9.2 Hz, 1H), 7.95 (d, J=9.2 Hz, 1H), 7.86 (s, 1H), 7.50 (d, J=9.6 Hz, 1H), 7.28 (dd, J=2.0 Hz, 8.8 Hz, 1H), 4.94 (s, 1H), 2.20-2.17 (m, 1H), 2.11-2.08 (m, 2H), 1.76-1.62 (m, 6H); ESI-MS (M+H)$^+$: 565.1.

Example 115

N-(6-((cis-4-trifluoromethylcyclohexyl)oxy)-5-(trifluoromethyl)naphthalene-2-ylcarbonyl)-2-azabicyclo[1.2.3]octane-7-carboxylic acid The title compound was prepared according to the method of Example 105. $^1$H NMR (400 MHz, CD$_3$OD) δ: 8.14 (d, J=7.2 Hz, 1H), 8.08 (d, J=9.2 Hz, 1H), 7.98 (d, J=1.6 Hz, 1H), 7.58 (dd, J=2.0 Hz, 9.6 Hz, 1H), 7.47 (d, J=9.6 Hz, 1H), 4.92 (s, 1H), 4.74-4.72 (m, 1H), 4.05-4.02 (m, 1H), 2.73-2.64 (m, 1H), 2.21-2.06 (m, 3H), 1.97-1.60 (m, 14H); ESI-MS (M+H)$^+$: 544.1.

Example 116

N-(6-((cis-4-trifluoromethylcyclohexyl)oxy)-5-(trifluoromethyl)naphthalene-2-ylcarbonyl)-decahydroisoquinoline-5-carboxylic acid The title compound was prepared according to the method of Example 105. $^1$H NMR (400 MHz, CD$_3$OD) δ: 8.22 (d, J=8.8 Hz, 1H), 8.14 (d, J=8.8 Hz, 1H), 7.94 (s, 1H), 7.58-7.54 (m, 2H), 5.01 (s, 1H), 4.53-4.42 (m, 1H), 3.91-3.88 (m, 1H), 3.58-3.50 (m, 1H), 3.38-3.32 (m, 1H), 2.48-2.38 (m, 1H), 2.27-2.20 (m, 1H), 2.18-2.15 (m, 2H), 2.02-1.48 (m, 13H), 1.45-1.30 (m, 3H); ESI-MS (M+H)$^+$: 572.2.

Example 117

2-(2-(5-(trifluoromethyl)-6-((cis-4-(trifluoromethyl)cyclohexyl)oxy)naphthalene-2-yl) acetyl)-2-azabicyclo[1.2.3]octane-7-carboxylic acid The title compound was prepared according to the method of Example 106. $^1$H NMR (400 MHz, CD$_3$OD) δ: 8.13 (d, J=7.2 Hz, 1H), 8.03 (d, J=9.2 Hz, 1H), 7.78 (s, 1H), 7.52 (dd, J=1.6 Hz, 9.2 Hz, 1H), 7.48 (d, J=9.2 Hz, 1H), 4.97 (s, 1H), 4.70-4.69 (m, 1H), 4.51-4.49 (m, 1H), 3.90 (AB, 2H), 2.95-2.89 (m, 1H), 2.29-2.16 (m, 3H), 2.00-1.61 (m, 14H). ESI-MS (M+H)$^+$: 558.1

Example 118

2-(2-(5-(difluoromethyl)-6-((cis-4-(trifluoromethyl)cyclohexyl)oxy)naphthalene-2-yl) acetyl)-2-azabicyclo[1.2.3]octane-7-carboxylic acid The title compound was prepared according to the method of Example 106. $^1$H NMR (400 MHz, DMSO-d$_6$) δ: 12.53 (br s, 1H), 8.28 (d, J=8.8 Hz, 1H), 8.16 (d, J=9.2 Hz, 2H), 7.78-7.51 (m, 3H), 5.05 (s, 1H), 4.30 (s, 2H), 3.91 (s, 2H), 2.89-2.83 (m, 1H), 2.46-2.37 (m, 2H), 2.13-1.56 (m, 15H); ESI-MS (M+H)$^+$: 512.3

Example 119

4-(((5-(trifluoromethyl)-6-((cis-4-(trifluoromethyl)cyclohexyl)oxy)naphthalen-2-yl)methyl)aminomethyl)bicyclo[2.2.2]octane-1-carboxylic acid The title compound was prepared according to the method of Example 85. $^1$H NMR (400 MHz, CD$_3$OD) δ: 8.16 (d, J=8.4 Hz, 1H), 8.03 (d, J=9.2 Hz, 1H), 7.94 (d, J=1.2 Hz, 1H), 7.57 (dd, J=2.0 Hz, 9.2 Hz, 1H), 7.49 (d, J=9.2 Hz, 1H), 4.92 (s, 1H), 4.28 (s, 2H), 2.72 (s, 2H), 2.19-2.06 (m, 3H), 1.74-1.65 (m, 12H), 1.45-1.41 (m, 6H). ESI-MS (M+H)$^+$: 558.2

Example 120

4-(((5-(trifluoromethyl)-6-((cis-4-(trifluoromethyl)cyclohexyl)oxy)naphthalen-2-yl)methyl)amino)-2-hydroxybicyclo[2.2.2]octane-1-carboxylic acid The title compound was prepared according to the method of Example 85. $^1$H NMR (400 MHz, CD$_3$OD) d: 8.15 (d, J=8.0 Hz, 1H), 8.04 (d, J=9.2 Hz, 1H), 7.94 (d, J=2.0 Hz, 1H), 7.56 (dd, J=1.6 Hz, 9.2 Hz, 1H), 7.48 (d, J=9.6 Hz, 1H), 4.92 (s, 1H), 4.30-4.28 (m, 2H), 4.20 (s, 1H), 2.35-2.09 (m, 5H), 1.92-1.81 (m, 8H), 1.79-1.61 (m, 6H); ESI-MS (M+H)$^+$: 559.9

Example 121

7-(((5-(trifluoromethyl)-6-((cis-4-(trifluoromethyl)cyclohexyl)oxy)naphthalen-2-yl)methyl)amino)-tricyclo[3.1.1.0]heptane-5-carboxylic acid

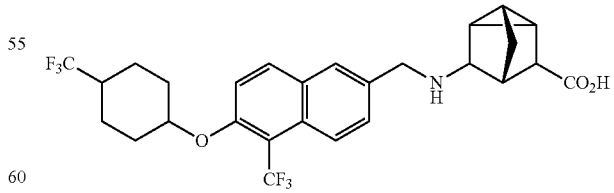

The title compound was prepared according to the method of Example 85. $^1$H NMR (400 MHz, CD$_3$OD) δ: 8.16 (d, J=8.8 Hz, 1H), 8.04 (d, J=9.2 Hz, 1H), 7.96 (s, 1H), 7.59 (dd, J=2.0 Hz, 8.8 Hz, 1H), 7.49 (d, J=9.2 Hz, 1H), 4.92 (s, 1H), 4.34-4.31 (m, 2H), 3.31-3.29 (m, 1H), 2.91 (s, 0.5H), 2.60

(s, 0.5H), 2.55 (s, 0.5H), 2.49 (s, 0.5H), 2.21-2.02 (m, 3H), 1.78-1.45 (m, 11H). ESI-MS (M+H)$^+$: 528.1

Example 122

8-(1-(5-(trifluoromethyl)-6-((cis-4-(trifluoromethyl) cyclohexyl)oxy)-naphthalene-2-yl)ethyl)-8-azabicyclo[3.2.1]octane-3-carboxylic acid The title compound was prepared according to the method of Example 88. $^1$H NMR (400 MHz, CD$_3$OD) δ: 8.22 (d, J=8.4 Hz, 1H), 8.05 (d, J=9.2 Hz, 1H), 7.94 (s, 1H), 7.63 (d, J=9.2 Hz, 1H), 7.51 (d, J=8.8 Hz, 1H), 4.93 (s, 1H), 4.46-4.45 (m, 1H), 4.33-4.28 (m, 1H), 3.38-3.36 (m, 1H), 2.90-2.83 (m, 1H), 2.48-2.40 (m, 1H), 2.22-2.02 (m, 7H), 1.92-1.81 (m, 3H), 1.73-1.61 (m, 9H). ESI-MS (M+H)$^+$: 543.9

Example 123

3-(((5-(trifluoromethyl)-6-((cis-4-(trifluoromethyl) cyclohexyl)oxy)naphthalen-2-yl)methyl)amino)-7,7-dimethylbicyclo[2.2.1]heptane-4-carboxylic acid The title compound was prepared according to the method of Example 85. $^1$H NMR (400 MHz, CD$_3$OD) δ: 8.30 (d, J=8.4 Hz, 1H), 8.04 (d, J=8.8 Hz, 1H), 7.93 (s, 1H), 7.59 (d, J=9.2 Hz, 1H), 7.47 (d, J=9.2 Hz, 1H), 4.91 (s, 1H), 4.21-4.11 (m, 2H), 2.33-2.30 (m, 1H), 2.19-2.06 (m, 3H), 1.84-1.60 (m, 8H), 1.33-1.06 (m, 5H), 0.97 (s, 6H). ESI-MS (M+H)$^+$: 557.9

Example 124

8-(1-(6-((cis-4-Methylcyclohexyl)oxy)-5-(trifluoromethyl)naphthalen-2-yl)ethyl)-8-azabicyclo[3.2.1]octane-3-carboxylic acid The title compound was prepared according to the method of Example 93. $^1$H NMR (300 MHz, METHANOL-d$_4$) δ 8.32 (d, J=8.31 Hz, 1H), 8.13 (d, J=9.06 Hz, 1H), 8.03 (d, J=1.89 Hz, 1H), 7.72 (dd, J=1.89, 9.06 Hz, 1H), 7.60 (d, J=9.44 Hz, 1H), 4.96 (br. s., 1H), 4.57 (d, J=6.42 Hz, 1H), 4.41 (q, J=6.67 Hz, 1H), 3.49 (d, J=6.04 Hz, 1H), 2.88-3.06 (m, 1H), 2.48-2.61 (m, 1H), 1.90-2.40 (m, 9H), 1.84 (d, J=6.42 Hz, 3H), 1.72 (t, J=12.84 Hz, 2H), 1.37-1.61 (m, 5H), 0.97 (d, J=5.29 Hz, 3H); LCMS m/z 490.3 [M+H]+

Example 125

9-(6-((cis-4-Methylcyclohexyl)oxy)-5-(trifluoromethyl)-2-naphthoyl)-9-azabicyclo[3.3.1]nonane-3-carboxylic acid The title compound was prepared according to the method of Example 104. $^1$H NMR (400 MHz, METHANOL-d$_4$) δ 8.26 (d, J=8.53 Hz, 1H), 8.16 (d, J=9.29 Hz, 1H), 7.98 (d, J=1.51 Hz, 1H), 7.61 (dd, J=1.76, 9.04 Hz, 1H), 7.57 (d, J=9.29 Hz, 1H), 4.90-4.98 (m, 2H), 4.01 (br. s., 1H), 3.31-3.45 (m, 1H), 1.85-2.25 (m, 10H), 1.63-1.82 (m, 4H), 1.40-1.60 (m, 5H), 0.98 (d, J=5.52 Hz, 3H); LCMS m/z 504.3 [M+H]+

Example 126

9-((6-(((cis-4-Methylcyclohexyl)oxy)-5-(trifluoromethyl)naphthalen-2-yl)methyl)-9-aza-7-oxa-bicyclo [3.3.1]nonane-3-carboxylic acid The title compound was prepared according to the method of Example 97. $^1$H NMR (400 MHz, METHANOL-d$_4$) δ 8.28 (d, J=8.28 Hz, 1H), 8.08-8.19 (m, 2H), 7.72 (dd, J=1.76, 9.04 Hz, 1H), 7.58 (d, J=9.29 Hz, 1H), 4.94 (br. s., 1H), 4.80 (br. s., 2H), 3.75-4.08 (m, 1H), 3.70-3.85 (m, 1H), 3.50-3.59 (m, 2H), 3.18-3.26 (m, 2H), 2.33-2.38 (m, 2H), 1.96-2.13 (m, 2H), 1.70 (t, J=13.18 Hz, 2H), 1.37-1.60 (m, 5H), 0.96 (d, J=5.77 Hz, 3H); LCMS m/z 492.2 [M+H]+

Example 127

8-(1-(6-((cis-4-Methylcyclohexyl)oxy)-5-(trifluoromethyl)naphthalen-2-yl)propyl)-8-azabicyclo [3.2.1]octane-3-carboxylic acid The title compound was prepared according to the method of Example 93. $^1$H NMR (400 MHz, METHANOL-d$_4$) δ 8.32 (d, J=8.78 Hz, 1H), 8.12 (d, J=9.29 Hz, 1H), 8.01 (s, 1H), 7.67 (d, J=9.29 Hz, 1H), 7.59 (d, J=9.29 Hz, 1H), 4.95 (br. s., 1H), 4.58 (d, J=6.27 Hz, 1H), 4.09 (dd, J=3.01, 11.55 Hz, 1H), 3.41 (d, J=2.01 Hz, 1H), 2.84-3.03 (m, 1H), 2.35-2.65 (m, 2H), 2.01-2.32 (m, 8H), 1.87-1.99 (m, 2H), 1.70 (t, J=13.05 Hz, 2H), 1.35-1.59 (m, 5H), 0.96 (d, J=5.77 Hz, 3H), 0.78 (t, J=7.28 Hz, 3H); LCMS m/z 504.3 [M+H]+

Example 128

9-(1-(6-((cis-4-Methylcyclohexyl)oxy)-5-(trifluoromethyl)naphthalen-2-yl)propyl)-9-azabicyclo [3.3.1]nonane-3-carboxylic acid The title compound was prepared according to the method of Example 93. $^1$H NMR (400 MHz, METHANOL-d$_4$) δ 8.33 (br. s., 1H), 8.06-8.22 (m, 2H), 7.76 (d, J=7.78 Hz, 1H), 7.61 (d, J=9.29 Hz, 1H), 4.97 (br. s., 1H), 4.72-4.95 (m, 1H), 4.18-4.32 (m, 1H), 3.30-3.49 (m, 1H), 3.09-3.23 (m, 1H), 1.37-2.63 (m, 21H), 0.98 (d, J=5.77 Hz, 3H), 0.77 (t, J=7.28 Hz, 3H); LCMS m/z 518.3 [M+H]+

Example 129

9-((6-(((cis-4-Methylcyclohexyl)oxy)-5-(trifluoromethyl)naphthalen-2-yl)methyl)-7-hydroxy-9-azabicyclo[3.3.1]nonane-3-carboxylic acid The title compound was prepared according to the method of Example 97. $^1$H NMR (400 MHz, METHANOL-d$_4$) δ 8.28 (d, J=8.53 Hz, 1H), 8.07-8.18 (m, 2H), 7.72 (d, J=7.78 Hz, 1H), 7.59 (d, J=9.29 Hz, 1H), 4.95 (br. s., 1H), 4.55-4.72 (m, 2H), 4.48-4.53 (m, 1H), 4.02-4.30 (m, 1H), 3.62-3.81 (m, 2H), 2.22-2.88 (m, 4H), 1.80-2.28 (m, 7H), 1.70 (t, J=13.05 Hz, 2H), 1.36-1.59 (m, 5H), 0.96 (d, J=5.77 Hz, 3H); LCMS m/z 506.3 [M+H]+

Example 130

8-(1-(6-((cis-4-Methylcyclohexyl)oxy)-5-(trifluoromethyl)naphthalen-2-yl)ethyl)-8-azabicyclo[3.2.1] octane-3-carboxylic acid, enantiomer 1

The title compound was prepared according to the method of Example 94. $^1$H NMR (400 MHz, METHANOL-d$_4$) δ

8.33 (d, J=8.78 Hz, 1H), 8.14 (d, J=9.29 Hz, 1H), 8.04 (d, J=1.51 Hz, 1H), 7.73 (dd, J=1.63, 9.16 Hz, 1H), 7.60 (d, J=9.29 Hz, 1H), 4.96 (br. s., 1H), 4.51-4.63 (m, 1H), 4.41 (q, J=6.53 Hz, 1H), 3.46-3.55 (m, 1H), 2.89-3.04 (m, 1H), 2.48-2.66 (m, 1H), 2.12-2.41 (m, 4H), 1.91-2.10 (m, 5H), 1.84 (d, J=6.78 Hz, 3H), 1.72 (t, J=13.05 Hz, 2H), 1.39-1.60 (m, 5H), 0.98 (d, J=5.77 Hz, 3H); LCMS m/z 490.2 [M+H]+

Example 131

8-(1-(6-((cis-4-Methylcyclohexyl)oxy)-5-(trifluoromethyl)naphthalen-2-yl)ethyl)-8-azabicyclo[3.2.1]octane-3-carboxylic acid, enantiomer 2

The title compound was prepared according to the method of Example 95. $^1$H NMR (400 MHz, METHANOL-$d_4$) δ 8.31 (d, J=8.78 Hz, 1H), 8.12 (d, J=9.29 Hz, 1H), 8.02 (s, 1H), 7.71 (dd, J=1.76, 9.04 Hz, 1H), 7.58 (d, J=9.29 Hz, 1H), 4.94 (br. s., 1H), 4.47-4.61 (m, 1H), 4.39 (q, J=6.53 Hz, 1H), 3.43-3.52 (m, 1H), 2.95 (tt, J=6.09, 11.73 Hz, 1H), 2.47-2.63 (m, 1H), 2.10-2.38 (m, 4H), 1.89-2.09 (m, 5H), 1.83 (d, J=6.53 Hz, 3H), 1.70 (t, J=13.18 Hz, 2H), 1.36-1.58 (m, 5H), 0.96 (d, J=5.77 Hz, 3H); LCMS m/z 490.3 [M+H]+

Example 132

9-(1-(5-(difluoromethyl)-6-((cis-4-methylcyclohexyl)oxy)naphthalen-2-yl)ethyl)-9-azabicyclo[3.3.1]nonane-3-carboxylic acid The title compound was prepared according to the method of Example 99. $^1$H NMR (400 MHz, METHANOL-$d_4$) δ 8.43 (d, J=8.78 Hz, 1H), 8.07 (dd, J=9.41, 15.69 Hz, 2H), 7.40-7.79 (m, 3H), 4.99-5.26 (m, 1H), 4.88 (br. s., 1H), 4.11-4.27 (m, 1H), 3.34-3.46 (m, 1H), 3.08-3.24 (m, 1H), 1.82-2.63 (m, 11H), 1.78 (d, J=6.53 Hz, 3H), 1.71 (t, J=13.43 Hz, 3H), 1.49-1.63 (m, 3H), 1.25-1.32 (m, 2H), 0.98 (d, J=6.02 Hz, 3H); LCMS m/z 486.1 [M+H]+

Example 133

8-(1-(5-(difluoromethyl)-6-((cis-4-methylcyclohexyl)oxy)naphthalen-2-yl)ethyl)-8-aza bicyclo[3.2.1]octane-3-carboxylic acid The title compound was prepared according to the method of Example 99. $^1$H NMR (400 MHz, METHANOL-$d_4$) δ 8.44 (d, J=8.78 Hz, 1H), 8.05 (d, J=9.04 Hz, 1H), 8.00 (s, 1H), 7.41-7.76 (m, 3H), 4.89 (br. s., 1H), 4.51-4.61 (m, 1H), 4.38 (q, J=6.53 Hz, 1H), 3.44-3.53 (m, 1H), 2.95 (tt, J=6.12, 11.70 Hz, 1H), 2.47-2.63 (m, 1H), 2.10-2.36 (m, 4H), 1.89-2.09 (m, 5H), 1.83 (d, J=6.78 Hz, 3H), 1.65-1.76 (m, 2H), 1.49-1.63 (m, 3H), 1.25-1.42 (m, 2H), 0.98 (d, J=6.27 Hz, 3H); LCMS m/z 472.1 [M+H]+

Example 134

8-(1-(5-(difluoromethyl)-6-((cis-4-methylcyclohexyl)oxy)naphthalen-2-yl)methyl)-8-azabicyclo[3.2.1]octane-3-carboxylic acid The title compound was prepared according to the method of Example 99. $^1$H NMR (400 MHz, METHANOL-$d_4$) δ 8.41 (d, J=8.78 Hz, 1H), 7.98-8.13 (m, 2H), 7.42-7.77 (m, 3H), 4.87-4.92 (m, 1H), 4.34 (s, 2H), 4.02 (br. s., 2H), 2.89-3.08 (m, 1H), 2.42-2.63 (m, 2H), 1.96-2.23 (m, 8H), 1.71 (t, J=13.43 Hz, 2H), 1.49-1.63 (m, 3H), 1.23-1.42 (m, 2H), 0.98 (d, J=6.02 Hz, 3H); LCMS m/z 458.1 [M+H]+

Example 135

9-(1-(5-(difluoromethyl)-6-((cis-4-methylcyclohexyl)oxy)naphthalen-2-yl)propyl)-9-azabicyclo[3.3.1]nonane-3-carboxylic acid $^1$H NMR (400 MHz, METHANOL-$d_4$) δ 8.45 (d, J=6.27 Hz, 1H), 8.00-8.14 (m, 2H), 7.41-7.78 (m, 3H), 4.87-4.94 (m, 1H), 4.69-4.79 (m, 1H), 4.20-4.31 (m, 1H), 3.34-3.47 (m, 1H), 3.07-3.21 (m, 1H), 1.80-2.63 (m, 13H), 1.48-1.78 (m, 6H), 1.24-1.43 (m, 2H), 0.98 (d, J=6.02 Hz, 3H), 0.76 (t, J=7.28 Hz, 3H); LCMS m/z 500.1 [M+H]+

Example 136

8-(1-(5-(difluoromethyl)-6-((cis-4-methylcyclohexyl)oxy)naphthalen-2-yl)ethyl)-8-azabicyclo[3.2.1]octane-3-carboxylic acid, enantiomer 1

The title compound was prepared according to the method of Example 133 and purified by chiral chromatography. $^1$H NMR (400 MHz, METHANOL-$d_4$) δ 8.44 (d, J=8.78 Hz, 1H), 8.05 (d, J=9.04 Hz, 1H), 8.00 (s, 1H), 7.41-7.76 (m, 3H), 4.89 (br. s., 1H), 4.51-4.61 (m, 1H), 4.38 (q, J=6.53 Hz, 1H), 3.44-3.53 (m, 1H), 2.95 (tt, J=6.12, 11.70 Hz, 1H), 2.47-2.63 (m, 1H), 2.10-2.36 (m, 4H), 1.89-2.09 (m, 5H), 1.83 (d, J=6.78 Hz, 3H), 1.65-1.76 (m, 2H), 1.49-1.63 (m, 3H), 1.25-1.42 (m, 2H), 0.98 (d, J=6.27 Hz, 3H); LCMS m/z 472.1 [M+H]+

Example 137

8-(1-(5-(difluoromethyl)-6-((cis-4-methylcyclohexyl)oxy)naphthalen-2-yl)ethyl)-8-azabicyclo[3.2.1]octane-3-carboxylic acid, enantiomer 1

The title compound was prepared according to the method of Example 133 and purified by chiral chromatography. $^1$H NMR (400 MHz, METHANOL-$d_4$) δ 8.44 (d, J=8.78 Hz, 1H), 8.05 (d, J=9.04 Hz, 1H), 8.00 (s, 1H), 7.41-7.76 (m, 3H), 4.89 (br. s., 1H), 4.51-4.61 (m, 1H), 4.38 (q, J=6.53 Hz, 1H), 3.44-3.53 (m, 1H), 2.95 (tt, J=6.12, 11.70 Hz, 1H), 2.47-2.63 (m, 1H), 2.10-2.36 (m, 4H), 1.89-2.09 (m, 5H), 1.83 (d, J=6.78 Hz, 3H), 1.65-1.76 (m, 2H), 1.49-1.63 (m, 3H), 1.25-1.42 (m, 2H), 0.98 (d, J=6.27 Hz, 3H); LCMS m/z 472.1 [M+H]+

Example 138

9-(1-(5-(difluoromethyl)-6-((cis-4-methylcyclohexyl)oxy)naphthalen-2-yl)ethyl)-9-azabicyclo[3.3.1]nonane-3-carboxylic acid, enantiomer 1

The title compound was prepared according to the method of Example 132, and purified by chiral chromatography. $^1$H NMR (400 MHz, METHANOL-$d_4$) δ 8.43 (d, J=8.78 Hz, 1H), 8.07 (dd, J=9.41, 15.69 Hz, 2H), 7.40-7.79 (m, 3H), 4.99-5.26 (m, 1H), 4.88 (br. s., 1H), 4.11-4.27 (m, 1H), 3.34-3.46 (m, 1H), 3.08-3.24 (m, 1H), 1.82-2.63 (m, 11H), 1.78 (d, J=6.53 Hz, 3H), 1.71 (t, J=13.43 Hz, 3H), 1.49-1.63 (m, 3H), 1.25-1.32 (m, 2H), 0.98 (d, J=6.02 Hz, 3H); LCMS m/z 486.1 [M+H]+

Example 139

9-(1-(5-(difluoromethyl)-6-((cis-4-methylcyclohexyl)oxy)naphthalen-2-yl)ethyl)-9-aza bicyclo[3.3.1]nonane-3-carboxylic acid, enantiomer 2

The title compound was prepared according to the method of Example 132, and purified by chiral chromatography. $^1$H NMR (400 MHz, METHANOL-d$_4$) δ 8.43 (d, J=8.78 Hz, 1H), 8.07 (dd, J=9.41, 15.69 Hz, 2H), 7.40-7.79 (m, 3H), 4.99-5.26 (m, 1H), 4.88 (br. s., 1H), 4.11-4.27 (m, 1H), 3.34-3.46 (m, 1H), 3.08-3.24 (m, 1H), 1.82-2.63 (m, 11H), 1.78 (d, J=6.53 Hz, 3H), 1.71 (t, J=13.43 Hz, 3H), 1.49-1.63 (m, 3H), 1.25-1.32 (m, 2H), 0.98 (d, J=6.02 Hz, 3H); LCMS m/z 486.1 [M+H]+

Example 140

8-(1-(5-(difluoromethyl)-6-((cis-4-methylcyclohexyl)oxy)naphthalen-2-yl)propyl)-8-azabicyclo[3.2.1]octane-3-carboxylic acid, enantiomer 1

The title compound was prepared according to the method of Example 99, and purified by chiral chromatography. $^1$H NMR (400 MHz, METHANOL-d$_4$) δ 8.45 (d, J=8.78 Hz, 1H), 8.05 (d, J=9.29 Hz, 1H), 7.99 (s, 1H), 7.40-7.78 (m, 3H), 4.89 (br. s., 1H), 4.51-4.65 (m, 1H), 4.07 (dd, J=3.26, 11.55 Hz, 1H), 3.37-3.50 (m, 1H), 2.86-3.05 (m, 1H), 2.49-2.64 (m, 1H), 2.35-2.48 (m, 1H), 1.86-2.33 (m, 10H), 1.65-1.80 (m, 2H), 1.46-1.63 (m, 3H), 1.27-1.42 (m, 2H), 0.98 (d, J=6.27 Hz, 3H), 0.79 (t, J=7.28 Hz, 3H); LCMS m/z 486.1 [M+H]+

Example 141

8-(1-(5-(difluoromethyl)-6-((cis-4-methylcyclohexyl)oxy)naphthalen-2-yl)propyl)-8-azabicyclo[3.2.1]octane-3-carboxylic acid, enantiomer 2

The title compound was prepared according to the method of Example 99, and purified by chiral chromatography. $^1$H NMR (400 MHz, METHANOL-d$_4$) δ 8.45 (d, J=8.78 Hz, 1H), 8.05 (d, J=9.29 Hz, 1H), 7.99 (s, 1H), 7.40-7.78 (m, 3H), 4.89 (br. s., 1H), 4.51-4.65 (m, 1H), 4.07 (dd, J=3.26, 11.55 Hz, 1H), 3.37-3.50 (m, 1H), 2.86-3.05 (m, 1H), 2.49-2.64 (m, 1H), 2.35-2.48 (m, 1H), 1.86-2.33 (m, 10H), 1.65-1.80 (m, 2H), 1.46-1.63 (m, 3H), 1.27-1.42 (m, 2H), 0.98 (d, J=6.27 Hz, 3H), 0.79 (t, J=7.28 Hz, 3H); LCMS m/z 486.1 [M+H]+

Example 142

9-((6-((cis-4-trifluoromethylcyclohexyl)oxy)naphthalen-2-yl)methyl)-9-azabicyclo[3.3.1]nonane-3-carboxylic acid The title compound was prepared according to the method of Example 83. $^1$H NMR (400 MHz, METHANOL-d$_4$) δ 7.97-8.07 (m, 1H), 7.80-7.93 (m, 2H), 7.53-7.66 (m, 1H), 7.31-7.38 (m, 1H), 7.20-7.30 (m, 1H), 4.88-4.94 (m, 1H), 4.59-4.74 (m, 2H), 3.55-3.74 (m, 2H), 3.36-3.46 (m, 1H), 2.47-2.71 (m, 2H), 1.99-2.37 (m, 9H), 1.56-1.95 (m, 8H); LCMS m/z 476.1 [M+H]+

Example 143 methyl 2-((5-(trifluoromethyl)-6-((cis-4-(trifluoromethyl)cyclohexyl)oxy)naphthalen-2-yl)methyl)-(7R,9aR)-octahydro-1H-pyrido[1,2-a]pyrazine-7-carboxylic acid The title compound was prepared according to the method of Example 84. $^1$H NMR (400 MHz, CHLOROFORM-d) δ 8.27 (d, J=8.53 Hz, 1H), 7.89-8.02 (m, 2H), 7.52 (dd, J=1.76, 9.04 Hz, 1H), 7.35 (d, J=9.29 Hz, 1H), 4.88 (br. s., 1H), 4.16-4.39 (m, 2H), 3.75 (s, 3H), 3.65 (d, J=11.80 Hz, 1H), 3.36-3.55 (m, 2H), 3.07-3.32 (m, 5H), 2.68-2.84 (m, 2H), 2.35 (d, J=12.30 Hz, 1H), 2.05-2.28 (m, 3H), 1.52-1.97 (m, 9H); LCMS m/z 573.3 [M+H]+

Example 144

3-(4-{[5-trifluoromethyl-6-(4-trifluoromethyl-cyclohexyloxy)-naphthalen-2-ylmethyl]-amino}-bicyclo[2.2.2]oct-1-yl)-carboxylic acid The title compound was prepared according to the method of Example 86. $^1$H NMR (400 MHz, DMSO-d$_6$) δ 12.29 (br. s., 1H), 8.84 (br. s., 1H), 8.22 (d, J=9.29 Hz, 1H), 8.06-8.16 (m, 2H), 7.65-7.76 (m, 2H), 5.10 (br. s., 1H), 4.23 (br. s., 2H), 2.39-2.47 (m, 1H), 2.04 (d, J=12.80 Hz, 2H), 1.88 (s, 12H), 1.53-1.78 (m, 7H); LCMS m/z 544.2 [M+H]+

Example 145

2-((5-(trifluoromethyl)-6-((cis-4-(trifluoromethyl)cyclohexyl)oxy)naphthalen-2-yl)methyl)-(7R,9aR)-octahydro-1H-pyrido[1,2-a]pyrazine-7-carboxylic acid The title compound was prepared according to the method of Example 84. $^1$H NMR (400 MHz, CHLOROFORM-d) δ 8.28 (d, J=8.53 Hz, 1H), 7.89-8.02 (m, 2H), 7.52 (d, J=8.78 Hz, 1H), 7.35 (d, J=9.29 Hz, 1H), 4.89 (br. s., 1H), 4.18-4.41 (m, 2H), 3.22-3.74 (m, 6H), 2.87 (br. s., 1H), 2.67 (s, 1H), 2.03-2.37 (m, 5H), 1.55-1.96 (m, 10H); LCMS m/z 559.3 [M+H]+

Example 146

2-((5-(trifluoromethyl)-6-((cis-4-(trifluoromethyl)cyclohexyl)oxy)naphthalen-2-yl)methyl)-2-azaspiro[3.3]heptane-6-carboxylic acid The title compound was prepared according to the method of Example 84. $^1$H NMR (400 MHz, DMSO-d$_6$) δ 8.23 (dd, J=2.89, 9.41 Hz, 1H), 8.02-8.18 (m, 2H), 7.61-7.79 (m, 2H), 5.11 (br. s., 1H), 4.45 (d, J=5.52 Hz, 1H), 4.27-4.39 (m, 2H), 3.89-4.24 (m, 2H), 3.13 (br. s., 1H), 2.74-3.00 (m, 1H), 2.27-2.46 (m, 4H), 1.97-2.11 (m, 2H), 1.81-1.91 (m, 1H), 1.54-1.80 (m, 6H); LCMS m/z 516.2 [M+H]+

Example 147

N-((5-(trifluoromethyl)-6-((cis-4-(trifluoromethyl)cyclohexyl)oxy)naphthalen-2-yl)methyl)-3-aminoindane-5-carboxylic acid The title compound was prepared according to the method of Example 84. $^1$H NMR (400 MHz, DMSO-d$_6$) δ 9.38 (br. s., 2H), 8.30 (s, 1H), 8.22 (d, J=9.29 Hz, 1H), 8.08-8.16 (m, 2H), 7.96 (dd, J=1.13, 7.91 Hz, 1H), 7.77 (dd, J=1.76, 9.04 Hz, 1H), 7.69 (d, J=9.54 Hz, 1H), 7.49 (d, J=8.03 Hz, 1H), 5.11 (br. s., 1H), 4.94 (br. s., 1H), 4.30-4.55 (m, 2H), 3.13-3.29 (m, 1H), 2.90-3.08 (m, 1H), 2.55-2.70 (m, 1H), 2.30-2.45 (m, 2H), 2.04 (d, J=12.80 Hz, 2H), 1.54-1.81 (m, 6H); LCMS m/z 552.2 [M+H]$^{30}$ Example 148

3-((5-(trifluoromethyl)-6-((cis-4-(trifluoromethyl) cyclohexyl)oxy)naphthalen-2-yl)methyl)-3-azabicyclo[3.1.0]hexane-6-carboxylic acid The title compound was prepared according to the method of Example 84. $^1$H NMR (400 MHz, DMSO-d$_6$) δ 9.75-9.97 (m, 1H), 8.22 (d, J=9.29 Hz, 1H), 8.10 (d, J=12.55 Hz, 2H), 7.71 (d, J=9.29 Hz, 2H), 5.12 (br. s., 1H), 4.52 (br. s., 2H), 3.58 (br. s., 4H), 2.36-2.46 (m, 1H), 2.21 (br. s., 2H), 1.89-2.11 (m, 3H), 1.52-1.81 (m, 6H); LCMS m/z 502.2 [M+H]$^+$ Example 149

2-((5-(trifluoromethyl)-6-((cis-4-(trifluoromethyl) cyclohexyl)oxy)naphthalen-2-yl)methyl)-2-azaspiro[3.2]hexane-5-carboxylic acid The title compound was prepared according to the method of Example 84. $^1$H NMR (400 MHz, METHANOL-d$_4$) δ 8.27 (d, J=8.53 Hz, 1H), 8.15 (d, J=9.29 Hz, 1H), 8.03 (s, 1H), 7.54-7.67 (m, 2H), 5.02 (br. s., 1H), 4.62 (br. s., 2H), 4.04-4.52 (m, 4H), 2.08-2.37 (m, 3H), 1.99 (dd, J=5.77, 9.04 Hz, 1H), 1.65-1.90 (m, 6H), 1.41 (dd, J=5.52, 9.04 Hz, 1H), 1.23-1.35 (m, 1H); LCMS m/z 502.2 [M+H]$^+$ Example 150

N-((5-(trifluoromethyl)-6-((cis-4-(trifluoromethyl) cyclohexyl)oxy)naphthalen-2-yl)methyl)-decahydroisoquinoline-8-carboxylic acid The title compound was prepared according to the method of Example 84. $^1$H NMR (400 MHz, METHANOL-d$_4$) δ 8.27 (d, J=8.53 Hz, 1H), 8.15 (d, J=9.29 Hz, 1H), 8.04 (s, 1H), 7.57-7.71 (m, 2H), 5.03 (br. s., 1H), 4.40-4.59 (m, 2H), 3.36 (br. s., 1H), 3.09-3.28 (m, 2H), 2.52-2.74 (m, 2H), 2.28 (d, J=8.03 Hz, 1H), 2.17 (d, J=12.05 Hz, 2H), 1.89-2.10 (m, 3H), 1.69-1.88 (m, 10H), 1.35-1.55 (m, 3H); LCMS m/z 558.2 [M+H]$^+$ Example 151

3-((6-((cis-4-trifluoromethylcyclohexyl)oxy)naphthalen-2-yl)methyl)-3-azabicyclo[3.3.1]nonane-9-carboxylic acid The title compound was prepared according to the method of Example 84. $^1$H NMR (400 MHz, METHANOL-d$_4$) δ 8.28 (d, J=7.53 Hz, 1H), 8.17 (d, J=9.29 Hz, 1H), 8.05-8.12 (m, 1H), 7.71 (ddd, J=1.63, 9.10, 13.62 Hz, 1H), 7.60 (d, J=9.29 Hz, 1H), 5.03 (br. s., 1H), 4.48 (d, J=14.31 Hz, 2H), 3.37-3.69 (m, 4H), 2.50-2.80 (m, 3H), 2.11-2.38 (m, 3H), 1.61-2.05 (m, 12H); LCMS m/z 544.2 [M+H]$^+$ Example 152

N-(5-trifluoromethyl-6-(4-trifluoromethyl-cyclohexyloxy)-naphthalen-2-ylmethyl)-4-aminobicyclo[2.2.1]heptane-1-carboxylic acid The title compound was prepared according to the method of Example 84. $^1$H NMR (400 MHz, METHANOL-d$_4$) δ 8.27 (d, J=8.53 Hz, 1H), 8.14 (d, J=9.29 Hz, 1H), 8.04 (d, J=1.25 Hz, 1H), 7.67 (dd, J=2.01, 9.04 Hz, 1H), 7.59 (d, J=9.29 Hz, 1H), 5.02 (br. s., 1H), 4.40 (s, 2H), 2.14-2.36 (m, 5H), 1.96-2.13 (m, 6H), 1.86-1.95 (m, 2H), 1.68-1.86 (m, 6H); LCMS m/z 530.2 [M+H]$^+$ Example 153

N-(5-trifluoromethyl-6-(4-trifluoromethyl-cyclohexyloxy)-naphthalen-2-ylmethyl)-1-aminoadamantane-3-carboxylic acid The title compound was prepared according to the method of Example 84. $^1$H NMR (400 MHz, METHANOL-d$_4$) δ 8.22-8.31 (m, 1H), 8.10-8.18 (m, 1H), 8.03 (d, J=1.51 Hz, 1H), 7.63-7.70 (m, 1H), 7.54-7.62 (m, 1H), 5.01 (br. s., 1H), 4.37 (s, 2H), 2.39 (br. s., 2H), 2.27 (td, J=7.69, 11.23 Hz, 1H), 2.12-2.21 (m, 4H), 1.96-2.11 (m, 6H), 1.65-1.94 (m, 10H); LCMS m/z 570.3 [M+H]$^+$ Example 154

3-(5-trifluoromethyl-6-(4-trifluoromethyl-cyclohexyloxy)-naphthalen-2-ylmethyl)-3-azabicyclo[3.3.0]octane-7-carboxylic acid The title compound was prepared according to the method of Example 84. $^1$H NMR (400 MHz, METHANOL-d$_4$) δ 8.27 (d, J=9.04 Hz, 1H), 8.15 (d, J=9.29 Hz, 1H), 8.04 (br. s., 1H), 7.53-7.72 (m, 2H), 5.02 (br. s., 1H), 4.51 (d, J=2.76 Hz, 2H), 3.72 (br. s., 1H), 3.37-3.59 (m, 1H), 2.73-3.25 (m, 5H), 2.08-2.38 (m, 4H), 1.55-2.05 (m, 9H); LCMS m/z 530.2 [M+H]$^+$ Example 155

2-((5-(trifluoromethyl)-6-((cis-4-(trifluoromethyl) cyclohexyl)oxy)naphthalen-2-yl)methyl)-((9S,9aR)-octahydro-1H-pyrido[1,2-a]pyrazin-9-yl)methanol The title compound was prepared according to the method of Example 84. $^1$H NMR (400 MHz, METHANOL-d$_4$) δ 8.17 (d, J=7.53 Hz, 1H), 8.06 (d, J=9.29 Hz, 1H), 7.86 (br. s., 1H), 7.58-7.69 (m, 1H), 7.51 (d, J=9.29 Hz, 1H), 4.98 (br. s., 1H), 3.65-4.03 (m, 3H), 3.37-3.64 (m, 3H), 3.06-3.22 (m, 3H), 2.91-3.05 (m, 1H), 2.52-2.89 (m, 1H), 2.07-2.45 (m, 4H), 1.64-2.04 (m, 11H); LCMS m/z 545.3 [M+H]$^+$ Example 156

8-((6-((4,4-difluorocyclohexyl)oxy)-5-(trifluoromethyl)naphthalene-2-yl)methyl)-8-azabicyclo[3.2.1]octane-3-carboxylic acid The title compound was prepared according to the method of Example 98. $^1$H NMR (400 MHz, METHANOL-d$_4$) δ 8.25-8.33 (m, 1H), 8.18 (d, J=9.29 Hz, 1H), 8.09 (d, J=1.26 Hz, 1H), 7.69-7.76 (m, 1H), 7.61-7.68 (m, 1H), 4.98 (br. s., 1H), 4.36 (s, 2H), 4.03 (br. s., 2H), 2.89-3.06 (m, 1H), 2.43-2.60 (m, 2H), 1.87-2.29 (m, 14H); LCMS m/z 545.3 [M+H]$^+$ Example 157

2-(5-trifluoromethyl-6-(4-trifluoromethyl-cyclohexyloxy)-naphthalen-2-ylmethyl)-2-aza-6-oxaspiro[3.4]octane-7-carboxylic acid The title compound was prepared according to the method of Example 84. $^1$H NMR (400 MHz, METHANOL-d$_4$) δ 8.26 (d, J=8.53 Hz, 1H), 8.15 (d, J=9.04 Hz, 1H), 8.02 (d, J=1.51 Hz, 1H), 7.55-7.66 (m, 2H), 5.02 (br. s., 1H), 4.46-4.62 (m, 3H), 3.98-4.44 (m, 6H), 2.58-2.70 (m, 1H), 2.45 (dd, J=5.15, 13.43 Hz, 1H), 2.07-2.36 (m, 3H), 1.65-1.90 (m, 6H); LCMS m/z 532.2 [M+H]$^+$ Example 158

(1R,5S,7r)-3-((2-(4-(trifluoromethyl)cyclohexyloxy)-1-(trifluoromethyl)naphthalen-6-yl)methyl)-3-aza-bicyclo[3.3.1]nonane-7-carboxylic acid The title compound was prepared according to the method of Example 84. $^1$H NMR (400 MHz, METHANOL-d$_4$) δ 8.28 (d, J=8.78 Hz, 1H), 8.16 (d, J=9.29 Hz, 1H), 8.04-8.10 (m, 1H), 7.66-7.75 (m, 1H), 7.60 (d, J=9.29 Hz, 1H), 5.03 (br. s., 1H), 4.46 (s, 2H), 3.35-3.74 (m, 3H), 2.87-3.26 (m, 2H), 2.03-2.53 (m, 7H), 1.68-1.96 (m, 10H); LCMS m/z 544.2 [M+H]$^+$ Example 159

N-(5-trifluoromethyl-6-(cis-4-trifluoromethyl-cyclohexyloxy)-naphthalen-2-ylmethyl)-3-(azetidine-3-yl)-cyclohexane-1-carboxylic acid The title compound was prepared according to the method of Example 84. $^1$H NMR (400 MHz, METHANOL-d$_4$) δ 8.26 (d, J=8.78 Hz, 1H), 8.15 (d, J=9.29 Hz, 1H), 8.02 (s, 1H), 7.55-7.65 (m, 2H), 5.02 (br. s., 1H), 4.39-4.63 (m, 2H), 3.93-4.30 (m, 4H), 2.52-2.79 (m, 1H), 2.08-2.37 (m, 4H), 1.52-2.06 (m, 11H), 1.13-1.50 (m, 2H), 0.98 (q, J=12.30 Hz, 1H), 0.75-0.90 (m, 1H); LCMS m/z 558.3 [M+H]$^+$ Example 160

8-((5-(trifluoromethyl)-6-((cis-4-(trifluoromethyl)cyclohexyl)oxy)quinolin-2-yl)methyl)-8-azabicyclo[3.2.1]octane-3-carboxylic acid The title compound was prepared according to the method of Example 101. $^1$H NMR (400 MHz, METHANOL-d$_4$) δ 8.67 (d, J=9.04 Hz, 1H), 8.34 (d, J=9.54 Hz, 1H), 7.85 (d, J=9.54 Hz, 1H), 7.60 (d, J=9.04 Hz, 1H), 5.07 (br. s., 1H), 4.60 (s, 2H), 4.25 (br. s., 2H), 3.05 (tt, J=5.80, 12.14 Hz, 1H), 2.08-2.55 (m, 11H), 1.68-1.89 (m, 6H); LCMS m/z 531.2 [M+H]$^+$ Example 161

2-(5-trifluoromethyl-6-(cis-4-trifluoromethyl-cyclohexyloxy)-naphthalen-2-ylmethyl)-2-aza-5-oxaspiro[5.4]decane-8-carboxylic acid The title compound was prepared according to the method of Example 84. $^1$H NMR (400 MHz, METHANOL-d$_4$) δ 1.63-2.39 (m, 14H) 2.87-3.08 (m, 1H) 3.21 (br. s., 2H) 3.34-3.47 (m, 1H) 3.80-3.98 (m, 2H) 4.51 (s, 2H) 5.03 (br. s., 1H) 7.61 (d, J=9.29 Hz, 1H) 7.68 (dd, J=9.04, 1.76 Hz, 1H) 8.07 (s, 1H) 8.16 (d, J=9.29 Hz, 1H) 8.29 (d, J=8.53 Hz, 1H); LCMS m/z 560.2 [M+H]$^+$ Example 162

N-(5-trifluoromethyl-6-(cis-4-trifluoromethyl-cyclohexyloxy)-naphthalen-2-ylmethyl)-8-aminobicyclo[3.2.1]octane-3-carboxylic acid, enantiomer 1

The title compound was prepared according to the method of Example 84. $^1$H NMR (400 MHz, METHANOL-d$_4$) δ 8.28 (d, J=8.28 Hz, 1H), 8.15 (d, J=9.29 Hz, 1H), 8.08 (d, J=1.51 Hz, 1H), 7.71 (dd, J=1.76, 9.04 Hz, 1H), 7.59 (d, J=9.29 Hz, 1H), 5.02 (br. s., 1H), 4.47 (s, 2H), 2.81 (tt, J=6.24, 11.95 Hz, 1H), 2.49 (br. s., 2H), 2.10-2.35 (m, 3H), 1.63-1.97 (m, 15H); LCMS m/z 544.2 [M+H]$^+$ Example 163

N-(5-trifluoromethyl-6-(cis-4-trifluoromethyl-cyclohexyloxy)-naphthalen-2-ylmethyl)-8-aminobicyclo[3.2.1]octane-3-carboxylic acid, enantiomer 2

The title compound was prepared according to the method of Example 84. $^1$H NMR (400 MHz, METHANOL-d$_4$) δ 8.27 (d, J=8.53 Hz, 1H), 8.14 (d, J=9.29 Hz, 1H), 8.06 (d, J=1.51 Hz, 1H), 7.69 (dd, J=1.76, 9.04 Hz, 1H), 7.59 (d, J=9.54 Hz, 1H), 5.02 (br. s., 1H), 4.43 (s, 2H), 2.54-2.76 (m, 3H), 2.10-2.37 (m, 3H), 1.59-2.06 (m, 15H); LCMS m/z 544.2 [M+H]$^+$ Example 164

N-(5-trifluoromethyl-6-(cis-4-trifluoromethyl-cyclohexyloxy)-naphthalen-2-ylmethyl)-1-amino-3,5-dimethyladamantane The title compound was prepared according to the method of Example 84. $^1$H NMR (400 MHz, METHANOL-d$_4$) δ 8.27 (d, J=8.28 Hz, 1H), 8.14 (d, J=9.29 Hz, 1H), 8.02 (d, J=1.51 Hz, 1H), 7.65 (dd, J=1.88, 9.16 Hz, 1H), 7.59 (d, J=9.29 Hz, 1H), 5.02 (br. s., 1H), 4.34 (s, 2H), 2.32-2.42 (m, 1H), 2.13-2.22 (m, 2H), 1.62-1.95 (m, 13H), 1.39-1.55 (m, 4H), 1.23-1.36 (m, 2H), 0.95-1.04 (m, 6H); LCMS m/z 554.3 [M+H]$^+$ Example 165

7-(5-trifluoromethyl-6-(cis-4-trifluoromethyl-cyclohexyloxy)-naphthalen-2-ylmethyl)-7-azabicyclo[2.2.1]heptane-2-carboxylic acid The title compound was prepared according to the method of Example 84. $^1$H NMR (400 MHz, METHANOL-d$_4$) δ 8.30 (d, J=8.78 Hz, 1H), 8.17 (d, J=9.29 Hz, 1H), 8.09 (d, J=2.76 Hz, 1H), 7.71 (dd, J=2.01, 9.04 Hz, 1H), 7.61 (d, J=9.29 Hz, 1H), 5.03 (br. s., 1H), 4.39-4.60 (m, 2H), 4.28-4.37 (m, 1H), 4.14 (br. s., 1H), 3.34-3.91 (m, 1H), 2.56-2.71 (m, 1H), 2.45 (br. s., 1H), 2.12-2.37 (m, 4H), 1.99-2.11 (m, 1H), 1.91-1.98 (m, 1H), 1.68-1.89 (m, 7H); LCMS m/z 516.2 [M+H]$^+$

Example 166

N-(5-trifluoromethyl-6-(cis-4-trifluoromethyl-cyclohexyloxy)-naphthalen-2-ylmethyl)-9-aminobicyclo[3.3.1]nonane-3-carboxylic acid The title compound was prepared according to the method of Example 84. $^1$H NMR (400 MHz, METHANOL-d$_4$) δ 8.28 (d, J=8.53 Hz, 1H), 8.15 (d, J=9.29 Hz, 1H), 8.08 (d, J=1.26 Hz, 1H), 7.71 (dd, J=2.01, 9.04 Hz, 1H), 7.60 (d, J=9.29 Hz, 1H), 5.02 (br. s., 1H), 4.45 (s, 2H), 3.18-3.25 (m, 1H), 2.59-2.71 (m, 1H), 2.04-2.38 (m, 9H), 1.59-1.90 (m, 10H), 1.36-1.56 (m, 2H); LCMS m/z 558.3 [M+H]$^+$

Example 167

9-(5-trifluoromethyl-6-(cis-4-trifluoromethyl-cyclohexyloxy)-naphthalen-2-ylmethyl)-9-aza-7-oxabicyclo[3.3.1]nonane-3-carboxylic acid The title compound was prepared according to the method of Example 84. $^1$H NMR (400 MHz, METHANOL-d$_4$) δ 8.29 (d, J=8.78 Hz, 1H), 8.10-8.21 (m, 2H), 7.74 (dd, J=1.76, 9.04 Hz, 1H), 7.61 (d, J=9.29 Hz, 1H), 5.03 (br. s., 1H), 4.82 (br. s., 2H), 4.10 (br. s., 2H), 3.70-3.86 (m, 1H), 3.55 (br. s., 2H), 2.04-2.88 (m, 8H), 1.58-1.90 (m, 7H); LCMS m/z 558.3 [M+H]$^+$

Example 168

9-(5-trifluoromethyl-6-(cis-4-trifluoromethyl-cyclohexyloxy)-naphthalen-2-ylmethyl)-9-azabicyclo[3.3.1]nonane The title compound was prepared according to the method of Example 84. $^1$H NMR (400 MHz, METHANOL-d$_4$) δ 8.28 (d, J=8.53 Hz, 1H), 8.10-8.19 (m, 2H), 7.75 (dd, J=2.01, 9.04 Hz, 1H), 7.60 (d, J=9.29 Hz, 1H), 5.03 (br. s., 1H), 4.71 (s, 2H), 3.53 (br. s., 2H), 2.47-2.63 (m, 2H), 1.96-2.37 (m, 9H), 1.62-1.95 (m, 10H); LCMS m/z 500.2 [M+H]$^+$

Example 169

9-(5-trifluoromethyl-6-(cis-4-trifluoromethyl-cyclohexyloxy)-naphthalen-2-ylmethyl)-7-hydroxy-9-azabicyclo[3.3.1]nonane-3-carboxylic acid The title compound was prepared according to the method of Example 84. $^1$H NMR (400 MHz, METHANOL-d$_4$) δ 8.29 (d, J=8.53 Hz, 1H), 8.08-8.21 (m, 2H), 7.74 (dd, J=1.51, 9.04 Hz, 1H), 7.60 (d, J=9.29 Hz, 1H), 5.03 (br. s., 1H), 4.41-4.73 (m, 3H), 3.98-4.34 (m, 1H), 3.69 (br. s., 2H), 2.79 (d, J=15.81 Hz, 1H), 2.50 (br. s., 1H), 1.65-2.37 (m, 15H); LCMS m/z 560.2 [M+H]$^+$

Example 170

9-(5-trifluoromethyl-6-(cis-4-trifluoromethyl-cyclohexyloxy)-naphthalen-2-ylmethyl)-7-oxo-9-azabicyclo[3.3.1]nonane-3-carboxylic acid The title compound was prepared according to the method of Example 84. $^1$H NMR (400 MHz, METHANOL-d$_4$) δ 8.31 (d, J=7.53 Hz, 1H), 8.13-8.21 (m, 2H), 7.79 (dd, J=2.01, 9.04 Hz, 1H), 7.61 (d, J=9.29 Hz, 1H), 5.03 (br. s., 1H), 4.11 (br. s., 2H), 3.36 (d, J=3.26 Hz, 1H), 2.60-2.77 (m, 3H), 2.08-2.46 (m, 7H), 1.65-1.91 (m, 6H); LCMS m/z 558.0 [M+H]$^+$

Example 171

9-((6-((cis-4-ethylcyclohexyl)oxy)-5-(trifluoromethyl)naphthalen-2-yl)methyl)-9-azabicyclo[3.3.1]nonane-3-carboxylic acid The title compound was prepared according to the method of Example 97. $^1$H NMR (400 MHz, METHANOL-d$_4$) δ 8.26 (d, J=8.53 Hz, 1H), 8.08-8.16 (m, 2H), 7.73 (d, J=9.04 Hz, 1H), 7.57 (d, J=9.54 Hz, 1H), 4.95 (br. s., 1H), 4.58-4.77 (m, 2H), 3.65 (d, J=12.55 Hz, 2H), 3.35-3.51 (m, 1H), 2.57 (d, J=8.53 Hz, 2H), 1.98-2.40 (m, 8H), 1.90 (dd, J=5.65, 14.43 Hz, 1H), 1.52-1.79 (m, 5H), 1.22-1.51 (m, 5H), 0.85-0.99 (m, 3H); LCMS m/z 504.1 [M+H]$^+$

Example 172

8-((6-((cis-4-ethylcyclohexyl)oxy)-5-(trifluoromethyl)naphthalen-2-yl)methyl)-8-azabicyclo[3.2.1]octane-3-carboxylic acid The title compound was prepared according to the method of Example 97. $^1$H NMR (400 MHz, METHANOL-d$_4$) δ 8.27 (d, J=8.28 Hz, 1H), 8.02-8.18 (m, 2H), 7.69 (dd, J=1.76, 9.04 Hz, 1H), 7.58 (d, J=9.29 Hz, 1H), 4.95 (br. s., 1H), 4.35 (s, 2H), 4.02 (br. s., 2H), 2.88-3.06 (m, 1H), 2.42-2.60 (m, 2H), 1.96-2.25 (m, 8H), 1.20-1.77 (m, 9H), 0.93 (t, J=7.15 Hz, 3H); LCMS m/z 490.1 [M+H]$^{30}$

Example 173

8-(1-(5-(trifluoromethyl)-6-((cis-4-(trifluoromethyl)cyclohexyl)oxy)naphthalen-2-yl)ethyl)-8-azabicyclo[3.2.1]octane-3-carboxylic acid, enantiomer 1

The title compound was prepared according to the method of Example 88. $^1$H NMR (400 MHz, METHANOL-d$_4$) δ 8.32 (d, J=8.78 Hz, 1H), 8.15 (d, J=9.29 Hz, 1H), 8.04 (s, 1H), 7.73 (dd, J=1.38, 9.16 Hz, 1H), 7.61 (d, J=9.29 Hz, 1H), 5.03 (br. s., 1H), 4.50-4.61 (m, 1H), 4.40 (q, J=6.53 Hz, 1H), 3.47 (d, J=6.27 Hz, 1H), 2.88-3.05 (m, 1H), 2.47-2.62 (m, 1H), 2.08-2.41 (m, 7H), 1.65-2.06 (m, 12H); LCMS m/z 544.0 [M+H]$^+$

Example 174

8-(1-(5-(trifluoromethyl)-6-((cis-4-(trifluoromethyl)cyclohexyl)oxy)naphthalen-2-yl)ethyl)-8-azabicyclo[3.2.1]octane-3-carboxylic acid, enantiomer 2

The title compound was prepared according to the method of Example 88. $^1$H NMR (400 MHz, METHANOL-d$_4$) δ 8.32 (d, J=8.78 Hz, 1H), 8.01-8.20 (m, 2H), 7.73 (dd, J=1.76, 9.04 Hz, 1H), 7.61 (d, J=9.29 Hz, 1H), 5.03 (br. s., 1H), 4.50-4.61 (m, 1H), 4.40 (q, J=6.53 Hz, 1H), 3.47 (d, J=6.27 Hz, 1H), 2.95 (tt, J=6.09, 11.73 Hz, 1H), 2.47-2.62 (m, 1H), 2.07-2.44 (m, 7H), 1.64-2.05 (m, 12H); LCMS m/z 544.0 [M+H]$^+$

Example 175

9-(1-(6-((cis-4-ethylcyclohexyl)oxy)-5-(trifluoromethyl)naphthalen-2-yl)ethyl)-9-azabicyclo[3.3.1]nonane-3-carboxylic acid The title compound was prepared according to the method of Example 93. $^1$H NMR (400 MHz, METHANOL-$d_4$) δ 8.30 (d, J=9.04 Hz, 1H), 8.04-8.19 (m, 2H), 7.77 (d, J=9.29 Hz, 1H), 7.58 (d, J=9.29 Hz, 1H), 5.00-5.28 (m, 1H), 4.95 (br. s., 1H), 4.20 (d, J=12.05 Hz, 1H), 3.38 (dd, J=6.02, 11.80 Hz, 1H), 3.17 (d, J=14.31 Hz, 1H), 2.29-2.62 (m, 3H), 1.52-2.28 (m, 16H), 1.23-1.51 (m, 5H), 0.93 (t, J=7.15 Hz, 3H); LCMS m/z 518.1 [M+H]$^+$

Example 176

8-(1-(6-((cis-4-ethylcyclohexyl)oxy)-5-(trifluoromethyl)naphthalen-2-yl)ethyl)-8-azabicyclo[3.2.1]octane-3-carboxylic acid The title compound was prepared according to the method of Example 93. $^1$H NMR (400 MHz, METHANOL-$d_4$) δ 8.20 (d, J=8.53 Hz, 1H), 8.02 (d, J=9.29 Hz, 1H), 7.92 (d, J=1.25 Hz, 1H), 7.61 (dd, J=1.76, 9.04 Hz, 1H), 7.49 (d, J=9.29 Hz, 1H), 4.85 (br. s., 1H), 4.40-4.51 (m, 1H), 4.29 (q, J=6.53 Hz, 1H), 3.29-3.43 (m, 1H), 2.76-2.94 (m, 1H), 2.36-2.52 (m, 1H), 1.77-2.31 (m, 9H), 1.66-1.75 (m, 3H), 1.43-1.65 (m, 4H), 1.13-1.42 (m, 5H), 0.83 (t, J=7.15 Hz, 3H); LCMS m/z 504.1 [M+H]$^+$

Example 177

9-(1-(6-((cis-4-trifluoromethylcyclohexyl)oxy)-5-(trifluoromethyl)naphthalen-2-yl)propyl)-9-azabicyclo[3.3.1]nonane-3-carboxylic acid The title compound was prepared according to the method of Example 88. $^1$H NMR (400 MHz, METHANOL-$d_4$) δ 8.34 (d, J=7.53 Hz, 1H), 8.04-8.22 (m, 2H), 7.76 (d, J=8.53 Hz, 1H), 7.62 (d, J=9.29 Hz, 1H), 5.03 (br. s., 1H), 4.93 (dd, J=3.39, 11.42 Hz, 1H), 4.26 (d, J=12.05 Hz, 1H), 3.35-3.46 (m, 1H), 3.06-3.20 (m, 1H), 1.54-2.63 (m, 21H), 0.75 (t, J=7.15 Hz, 3H); LCMS m/z 572.1 [M+H]$^+$

Example 178

8-(1-(6-((cis-4-trifluoromethylcyclohexyl)oxy)-5-(trifluoromethyl)naphthalen-2-yl)propyl)-8-azabicyclo[3.2.1]octane-3-carboxylic acid The title compound was prepared according to the method of Example 88. $^1$H NMR (400 MHz, METHANOL-$d_4$) δ 8.34 (d, J=8.78 Hz, 1H), 8.15 (d, J=9.29 Hz, 1H), 8.03 (s, 1H), 7.69 (d, J=9.04 Hz, 1H), 7.62 (d, J=9.29 Hz, 1H), 5.03 (br. s., 1H), 4.58 (d, J=6.02 Hz, 1H), 4.09 (dd, J=2.89, 11.42 Hz, 1H), 3.41 (d, J=2.76 Hz, 1H), 2.86-3.03 (m, 1H), 1.65-2.62 (m, 19H), 0.78 (t, J=7.28 Hz, 3H); LCMS m/z 558.0 [M+H]$^+$

Example 179

9-(1-(6-((cis-4-ethylcyclohexyl)oxy)-5-(trifluoromethyl)naphthalen-2-yl)propyl)-9-azabicyclo[3.3.1]nonane-3-carboxylic acid The title compound was prepared according to the method of Example 92. $^1$H NMR (400 MHz, METHANOL-$d_4$) δ 8.32 (d, J=7.53 Hz, 1H), 8.12 (d, J=9.29 Hz, 2H), 7.74 (d, J=8.28 Hz, 1H), 7.59 (d, J=9.29 Hz, 1H), 4.89-5.01 (m, 2H), 4.24 (br. s., 1H), 3.35-3.45 (m, 1H), 3.05-3.23 (m, 1H), 1.82-2.61 (m, 13H), 1.52-1.80 (m, 5H), 1.23-1.52 (m, 5H), 0.93 (t, J=7.15 Hz, 3H), 0.76 (t, J=7.28 Hz, 3H); LCMS m/z 532.1 [M+H]$^+$

Example 180

8-(1-(6-((cis-4-ethylcyclohexyl)oxy)-5-(trifluoromethyl)naphthalen-2-yl)propyl)-8-azabicyclo[3.2.1]octane-3-carboxylic acid The title compound was prepared according to the method of Example 92. $^1$H NMR (400 MHz, METHANOL-$d_4$) δ 8.32 (d, J=8.53 Hz, 1H), 8.12 (d, J=9.29 Hz, 1H), 7.98-8.09 (m, 1H), 7.67 (dd, J=1.63, 9.16 Hz, 1H), 7.60 (d, J=9.29 Hz, 1H), 4.96 (br. s., 1H), 4.58 (d, J=6.27 Hz, 1H), 4.09 (dd, J=3.26, 11.55 Hz, 1H), 3.37-3.46 (m, 1H), 2.85-3.05 (m, 1H), 1.86-2.63 (m, 12H), 1.54-1.76 (m, 4H), 1.38-1.52 (m, 2H), 1.25-1.37 (m, 3H), 0.93 (t, J=7.15 Hz, 3H), 0.78 (t, J=7.28 Hz, 3H); LCMS m/z 518.1 [M+H]$^+$

Example 181

8-((5-(trifluoromethyl)-6-((cis-4-(trifluoromethyl)cyclohexyl)oxy)naphthalen-2-yl)methyl)-8-azabicyclo[3.2.1]octane-3-carboxylic acid The title compound was prepared according to the method of Example 84. $^1$H NMR (400 MHz, METHANOL-$d_4$) δ 8.26-8.32 (m, 1H), 8.12-8.21 (m, 2H), 7.76 (dd, J=2.01, 9.04 Hz, 1H), 7.60 (d, J=9.04 Hz, 1H), 5.03 (br. s., 1H), 4.71 (br. s., 2H), 3.65 (br. s., 2H), 3.35-3.45 (m, 1H), 1.62-2.75 (m, 19H); LCMS m/z 544.2 [M+H]$^+$

Example 182

9-(1-(6-((cis-4-ethylcyclohexyl)oxy)-5-chloronaphthalen-2-yl)ethyl)-9-azabicyclo[3.3.1]nonane-3-carboxylic acid The title compound was prepared according to the method of Example 94. $^1$H NMR (400 MHz, METHANOL-$d_4$) δ 8.33 (d, J=9.06 Hz, 1H), 8.08 (d, J=4.91 Hz, 1H), 7.88 (d, J=9.06 Hz, 1H), 7.78 (d, J=8.69 Hz, 1H), 7.52 (d, J=9.06 Hz, 1H), 5.00-5.31 (m, 1H), 4.88 (br. s., 1H), 4.18 (br. s., 1H), 3.35-3.48 (m, 1H), 3.08-3.21 (m, 1H), 1.43-2.67 (m, 21H), 1.20-1.42 (m, 3H), 0.93 (t, J=7.18 Hz, 3H); LCMS m/z 484.1 [M+H]$^+$

Example 183

9-((5-Chloro-6-((cis-4-methylcyclohexyl)oxy)naphthalen-2-yl)methyl)-9-azabicyclo[3.3.1]nonane-3-carboxylic acid The title compound was prepared according to the method of Example 110. $^1$H NMR (400 MHz, METHANOL-$d_4$) δ 8.30 (d, J=9.06 Hz, 1H), 8.09 (s, 1H), 7.90 (d, J=9.06 Hz, 1H), 7.73 (d, J=9.06 Hz, 1H), 7.52 (d, J=9.06 Hz, 1H), 4.87-4.91 (m, 1H), 4.59-4.77 (m, 2H), 3.61-3.70 (m, 2H), 3.35-3.46 (m, 1H), 2.48-2.75 (m, 2H), 1.80-2.36 (m, 9H), 1.42-1.78 (m, 8H), 0.97 (d, J=4.91 Hz, 3H); LCMS m/z 456.0 [M+H]$^+$

Example 184

8-(1-(5-Chloro-6-((cis-4-ethylcyclohexyl)oxy)naphthalen-2-yl)ethyl)-8-azabicyclo[3.2.1]octane-3-carboxylic acid The title compound was prepared according to the method of Example 110. $^1$H NMR (400 MHz, METHANOL-$d_4$) δ 8.33 (d, J=9.04 Hz, 1H), 7.99 (s, 1H), 7.88 (d, J=9.04 Hz, 1H), 7.71 (dd, J=1.51, 9.04 Hz, 1H), 7.53 (d, J=9.04 Hz, 1H), 4.88 (br. s., 1H), 4.54 (d, J=6.27 Hz, 1H), 4.40 (q, J=6.53 Hz, 1H), 3.38-3.53 (m, 1H), 2.95 (tt, J=5.93, 11.76 Hz, 1H), 2.46-2.63 (m, 1H), 1.75-2.37 (m, 12H), 1.45-1.73 (m, 6H), 1.23-1.39 (m, 3H), 0.93 (t, J=7.15 Hz, 3H); LCMS m/z 470.0 [M+H]

Example 185

8-((5-Chloro-6-((cis-4-ethylcyclohexyl)oxy)naphthalen-2-yl)methyl)-8-azabicyclo[3.2.1]octane-3-carboxylic acid The title compound was prepared according to the method of Example 110. $^1$H NMR (400 MHz, METHANOL-$d_4$) δ 8.30 (d, J=8.78 Hz, 1H), 8.04 (s, 1H), 7.90 (d, J=9.04 Hz, 1H), 7.70 (dd, J=1.51, 8.78 Hz, 1H), 7.52 (d, J=9.04 Hz, 1H), 4.88 (br. s., 1H), 4.36 (s, 2H), 4.02 (br. s., 2H), 2.97 (t, J=6.02 Hz, 1H), 2.42-2.63 (m, 2H), 1.97-2.24 (m, 8H), 1.43-1.73 (m, 6H), 1.20-1.39 (m, 3H), 0.93 (t, J=7.28 Hz, 3H); LCMS m/z 456.1 [M+H]$^+$

Example 186

8-(5-chloro-6-((cis-4-(trifluoromethyl)cyclohexyl)oxy)-2-naphthoyl)-8-azabicyclo[3.2.1]octane-3-carboxylic acid

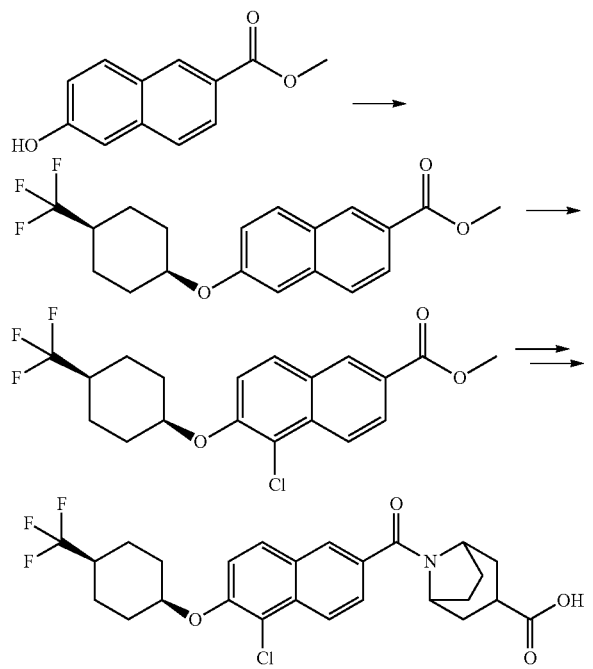

Step 1: methyl 6-((cis-4-(trifluoromethyl)cyclohexyl)oxy)-2-naphthoate

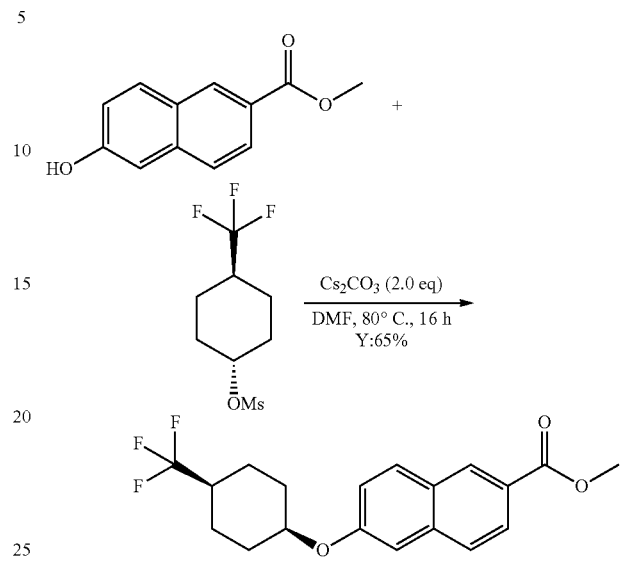

A mixture of methyl 6-hydroxy-2-naphthoate (14.0 g, 70.0 mmol, 1.0 eq), cis-4-(trifluoromethyl)cyclohexyl methanesulfonate (21.0 g, 84.0 mmol, 1.2 eq) and Cs$_2$CO$_3$ (45.0 g, 140.0 mmol, 2.0 eq) in DMF (150 mL) was heated at 80° C. for 16 h and cooled down. The mixture was diluted with EtOAc (300 mL) and washed with H$_2$O (300 mL×3). The organic layer was dried over Na$_2$SO$_4$ and concentrated to yield a crude product, which was purified by column chromatography on silica gel (petroleum ether as eluent) to give methyl 6-((cis-4-(trifluoromethyl)cyclohexyl)oxy)-2-naphthoate as yellow solid (13.0 g, yield: 65%). $^1$H NMR (400 MHz, CDCl$_3$) δ: 8.52 (s, 1H), 8.01 (d, J=8.8 Hz, 1H), 7.85 (d, J=8.8 Hz, 1H), 7.71 (d, J=8.8 Hz, 1H), 7.22 (dd, J=2.4 Hz, 8.8 Hz, 1H), 7.16 (s, 1H), 4.76 (s, 1H), 3.96 (s, 3H), 2.27-2.11 (m, 3H), 1.85-1.78 (m, 4H), 1.65-1.59 (m, 2H). LCMS m/z 353.1 [M+H]$^+$ Step 2: methyl 5-chloro-6-((cis-4-(trifluoromethyl)cyclohexyl)oxy)-2-naphthoate

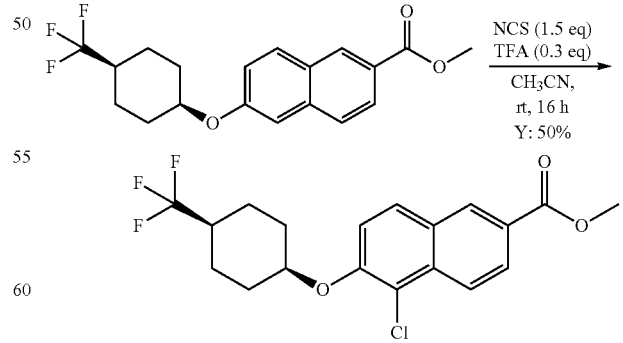

To a mixture of methyl 6-((cis-4-(trifluoromethyl)cyclohexyl)oxy)-2-naphthoate (1.75 g, 5.0 mmol, 1.0 eq) and NCS (1.05 g, 7.5 mmol, 1.5 eq) in MeCN (10 mL) was added TFA (170 mg, 1.5 mmol, 0.3 eq). The mixture was stirred at rt for 16 h and quenched with aq. Na₂SO₃ (50 mL). The mixture was extracted with EtOAc (50 mL×2). The organic layers were dried over Na₂SO₄ and concentrated to yield a crude product, which was purified by column chromatography on silica gel (petroleum ether/EtOAc=50:1) to give methyl 5-chloro-6-((cis-4-(trifluoromethyl)cyclohexyl)oxy)-2-naphthoate as a yellow solid (900 mg, yield: 50%). LCMS m/z 387.1 [M+H]⁺

Step 3: 8-(5-chloro-6-((cis-4-(trifluoromethyl)cyclohexyl)oxy)-2-naphthoyl)-8-azabicyclo[3.2.1]octane-3-carboxylic acid

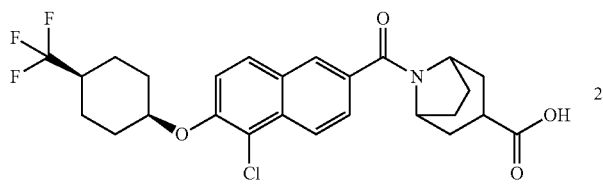

The title compound was prepared according to the method of Example 105. ¹H NMR (400 MHz, METHANOL-d₄) δ: 8.15 (d, J=8.8 Hz, 1H), 7.92 (s, 1H), 7.82 (d, J=9.6 Hz, 1H), 7.56 (d, J=8.8 Hz, 1H), 7.38 (d, J=9.6 Hz, 1H), 4.80 (s, 1H), 4.76-4.72 (m, 1H), 4.11-4.08 (m, 1H), 2.95-2.84 (m, 1H), 2.18-1.96 (m, 6H), 1.88-1.55 (m, 11H). LCMS m/z 510.1 [M+H]⁺

Example 187

8-(1-(5-cyano-6-((cis-4-methylcyclohexyl)oxy)naphthalen-2-yl)ethyl)-8-azabicyclo[3.2.1]octane-3-carboxylic acid

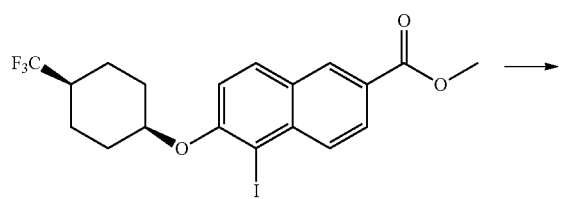

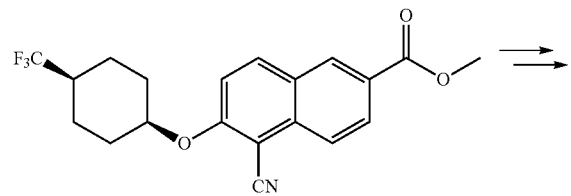

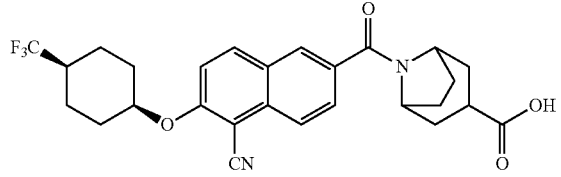 [SMILES: N#Cc1c(O[C@H]2CC[C@@H](C(F)(F)F)CC2)ccc2cc(C(=O)N3C4CCC3CC(C(=O)O)C4)ccc12]

Step 1: methyl 5-cyano-6-((cis-4-(trifluoromethyl)cyclohexyl)oxy)-2-naphthoate

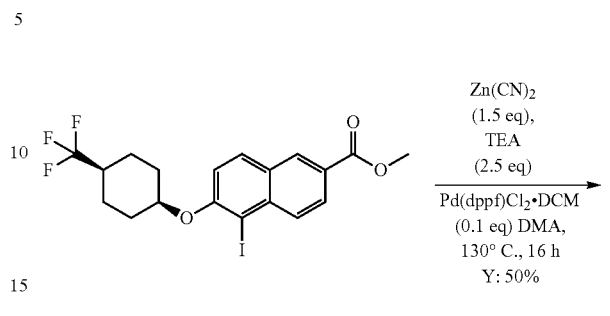

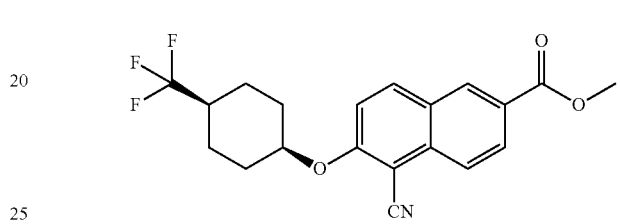

A mixture of methyl 5-iodo-6-((cis-4-(trifluoromethyl)cyclohexyl)oxy)-2-naphthoate (2.4 g, 5.0 mmol, 1.0 eq), Zn(CN)₂ (870 mg, 7.5 mmol, 1.5 eq) and TEA (1.3 g, 12.5 mmol, 2.5 eq) in DMA (15 mL) was purged with N₂ for 3 times, then Pd(dppf)Cl₂·DCM (410 mg, 0.5 mmol, 0.1 eq) was added. The mixture was stirred at 130° C. for 16 h and cooled down. The mixture was diluted with EtOAc (150 mL) and washed with H₂O (100 mL×3). The organic layer was dried over Na₂SO₄ and concentrated to yield a crude product, which was purified by column chromatography on silica gel (petroleum ether/EtOAc=10:1) to give methyl 5-cyano-6-((cis-4-(trifluoromethyl)cyclohexyl)oxy)-2-naphthoate as a yellow solid (900 mg, yield: 50%). LCMS m/z 378.1 [M+H]⁺

Step 2: 8-(1-(5-cyano-6-((cis-4-methylcyclohexyl)oxy) naphthalen-2-yl)ethyl)-8-azabicyclo[3.2.1]octane-3-carboxylic acid

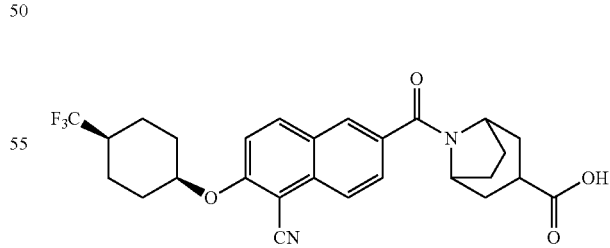

The title compound was prepared according to the method of Example 105. ¹H NMR (400 MHz, CD₃OD) δ: 8.28 (d, J=9.2 Hz, 1H), 8.11-8.09 (m, 2H), 7.78 (d, J=10.0 Hz, 1H), 7.60 (d, J=9.2 Hz, 1H), 5.09 (s, 1H), 4.22-4.18 (m, 1H), 3.05-2.96 (m, 1H), 2.32-1.83 (m, 18H). LCMS m/z 501.2 [M+H]⁺

Example 188

8-((5-cyano-6-((cis-4-methylcyclohexyl)oxy)naphthalen-2-yl)methyl)-8-azabicyclo[3.2.1]octane-3-carboxylic acid

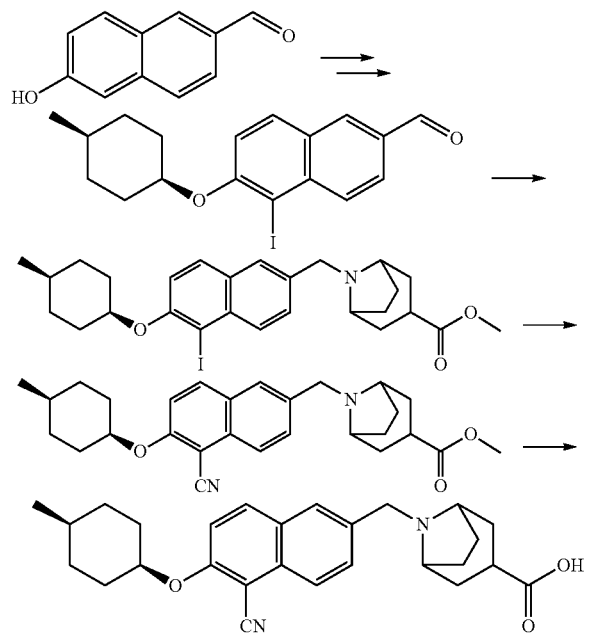

Step 1: 5-iodo-6-((cis-4-methylcyclohexyl)oxy)-2-naphthaldehyde

The title compound was prepared according to the method of Example 84. LCMS m/z 395.1 [M+H]+

Step 2: methyl 8-((5-iodo-6-((cis-4-methylcyclohexyl)oxy)naphthalen-2-yl)methyl)-8-azabicyclo[3.2.1]octane-3-carboxylate

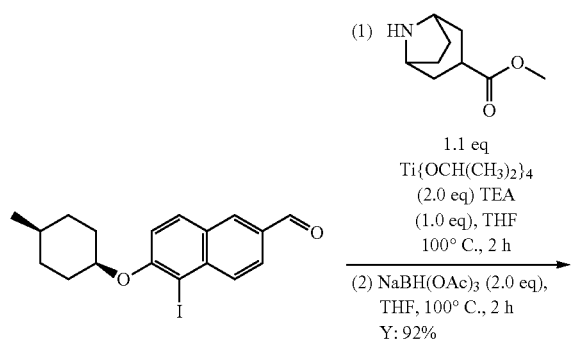

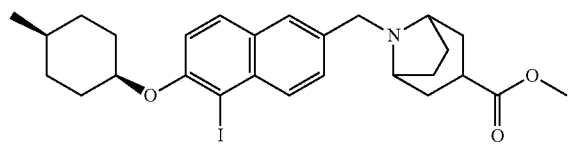

Into a mixture of 5-iodo-6-((cis-4-methylcyclohexyl)oxy)-2-naphthaldehyde (130 mg, 0.33 mmol, 1.0 eq), TEA (50 mg, 0.50 mmol, 1.5 eq) and methyl 8-azabicyclo[3.2.1]octane-3-carboxylate (62 mg, 0.36 mmol, 1.1 eq) in THF (2 mL) was added Ti(OiPr)4 (188 mg, 0.66 mmol, 2.0 eq). The mixture was stirred at 100° C. for 2 h and cooled down. NaBH(OAc)3 (140 mg, 0.66 mmol, 2.0 eq) was added, and the mixture was stirred at 100° C. for additional 2 h. The mixture was diluted with water (10 mL) and extracted with EtOAc (10 mL×2). The combined organic layers were washed with water (10 mL), brine (10 mL), dried over Na2SO4 and concentrated. The residue was purified by reversed phase HPLC (MeCN/H2O-0.05% TFA) to give methyl 8-((5-iodo-6-((cis-4-methylcyclohexyl)oxy)naphthalen-2-yl)methyl)-8-azabicyclo[3.2.1]octane-3-carboxylate as a yellow solid (130 mg, yield: 92%). LCMS m/z 548.2 [M+H]+

Step 3: methyl 8-((5-cyano-6-((cis-4-methylcyclohexyl)oxy)naphthalen-2-yl)methyl)-8-azabicyclo[3.2.1]octane-3-carboxylate

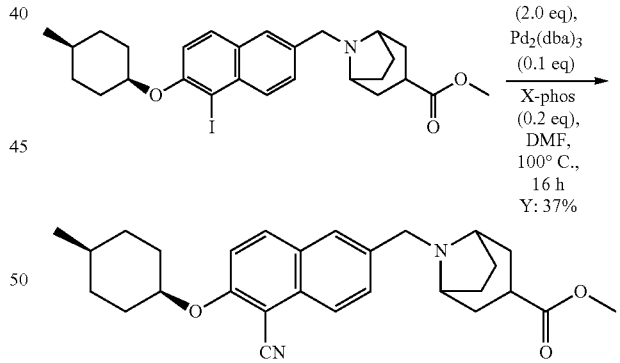

Into a mixture of methyl 8-((5-iodo-6-((cis-4-methylcyclohexyl)oxy)naphthalen-2-yl)methyl)-8-azabicyclo[3.2.1]octane-3-carboxylate (130 mg, 0.24 mmol, 1.0 eq), Zn(CN)2 (55 mg, 0.48 mmol, 2.0 eq) and X-phos (23 mg, 0.048 mmol, 0.2 eq) in DMF (3 mL) was added Pd2(dba)3 (22 mg, 0.024 mmol, 0.1 eq). The mixture was stirred at 100° C. for 16 h under N2 atmosphere. After cooling to rt, the mixture was filtrated and the filtrate was purified by reversed phase HPLC (MeCN/H2O-0.05% TFA) to give methyl 8-((5-cyano-6-((cis-4-methylcyclohexyl)oxy)naphthalen-2-yl)methyl)-8-azabicyclo[3.2.1]octane-3-carboxylate as a yellow solid (40 mg, yield: 37%). LCMS m/z 447.3 [M+H]+

Step 4: 8-((5-cyano-6-((cis-4-methylcyclohexyl)oxy)naphthalen-2-yl)methyl)-8-azabicyclo[3.2.1]octane-3-carboxylic acid

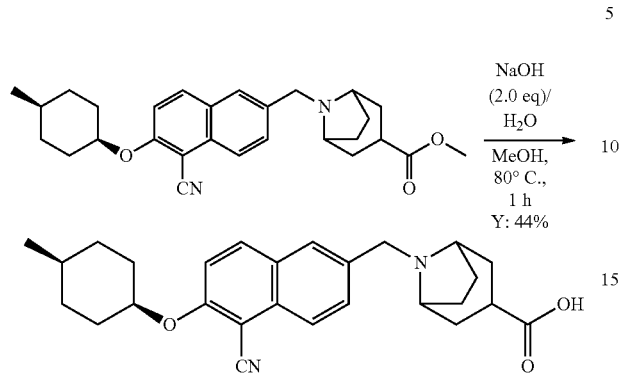

Into a solution of methyl 8-((5-cyano-6-((cis-4-methylcyclohexyl)oxy)naphthalen-2-yl)methyl)-8-azabicyclo[3.2.1]octane-3-carboxylate (40 mg, 0.09 mmol, 1.0 eq) in MeOH (3 mL) was added NaOH (7 mg, 0.18 mmol, 2.0 eq) and H₂O (0.5 mL). The reaction mixture was stirred at 80° C. for 1 h. Then the reaction was cooled to rt, and acidified with 1N HCl to pH=6. The mixture was directly purified by reversed phase HPLC (MeCN/H2O-0.05% TFA) to give 8-((5-cyano-6-((cis-4-methylcyclohexyl)oxy)naphthalen-2-yl)methyl)-8-azabicyclo[3.2.1]octane-3-carboxylic acid as a white solid (17 mg, yield: 44%). $^1$H NMR (400 MHz, CD3OD) δ: 8.21 (d, J=9.2 Hz, 1H), 8.11-8.09 (m, 2H), 7.82 (d, J=8.8 Hz, 1H), 7.57 (d, J=9.2 Hz, 1H), 5.02 (s, 1H), 4.27 (s, 2H), 3.85-3.81 (m, 2H), 2.70-2.64 (m, 1H), 2.40-2.38 (m, 2H), 2.09-2.02 (m, 6H), 1.96-1.92 (m, 2H), 1.77-1.72 (m, 2H), 1.59-1.56 (m, 5H), 1.01 (d, J=7.2 Hz, 3H). LCMS m/z 433.3 [M+H]$^+$ Example 189

8-(1-(5-cyano-6-((cis-4-methylcyclohexyl)oxy)naphthalen-2-yl)ethyl)-8-azabicyclo[3.2.1]octane-3-carboxylic acid

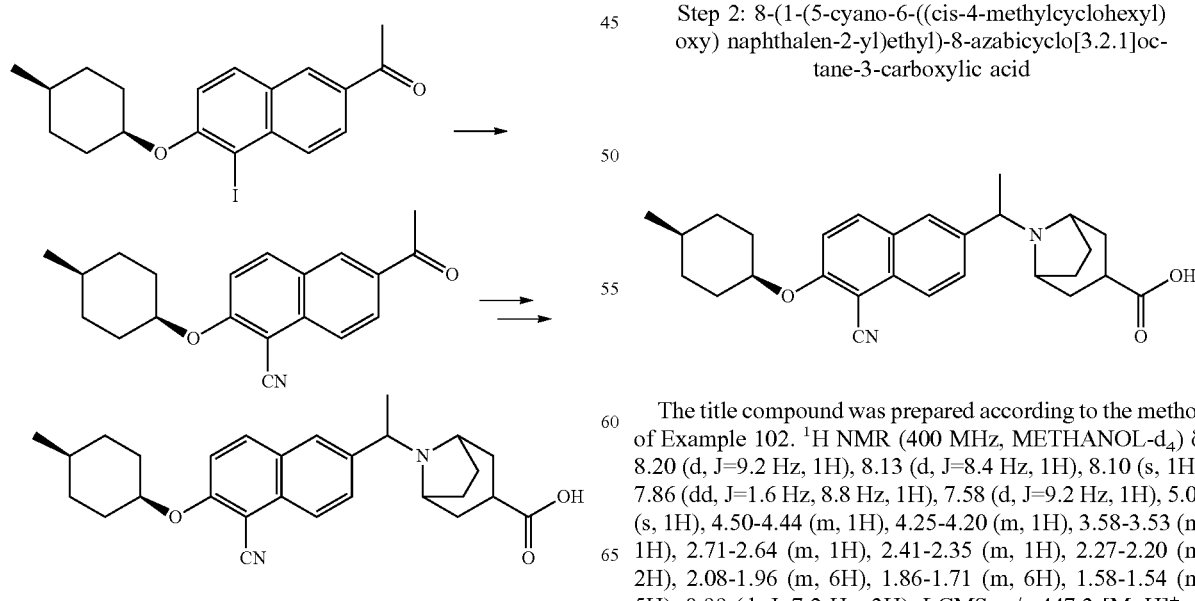

Step 1: 6-Acetyl-2-((cis-4-methylcyclohexyl)oxy)-1-naphthonitrile

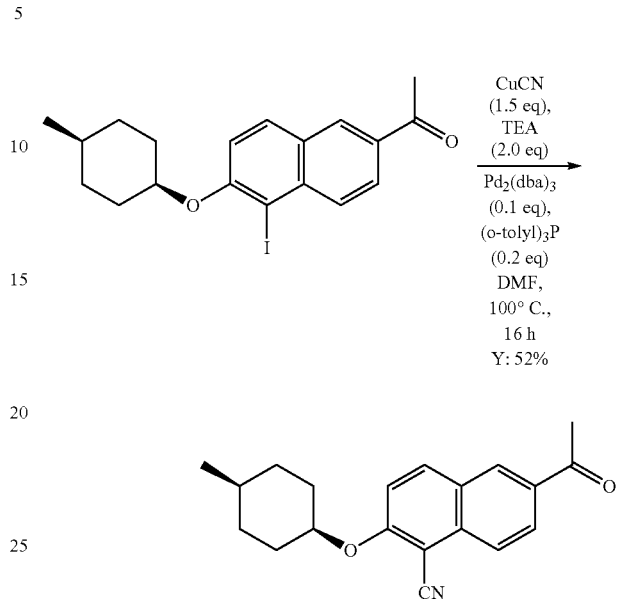

To a mixture of 1-(5-iodo-6-((cis-4-methylcyclohexyl)oxy)naphthalen-2-yl)ethanone (690 mg, 1.69 mmol, 1.0 eq), CuCN (226 mg, 2.54 mmol, 1.5 eq), TEA (342 mg, 3.38 mmol, 2.0 eq) and (o-tolyl)₃P (103 mg, 0.34 mmol, 0.2 eq) in DMF (4 mL) was added Pd₂(dba)₃ (155 mg, 0.17 mmol, 0.1 eq). The mixture was stirred at 100° C. for 16 h under N₂ atmosphere. After cooling to rt, the mixture was diluted with EtOAc (30 mL) and washed with H₂O (15 mL×3). The organic phase was dried and concentrated. The residue was purified by column chromatography on silica gel (petroleum ether/EtOAc=10:1) to give 6-Acetyl-2-((cis-4-methylcyclohexyl)oxy)-1-naphthonitrile as a yellow solid (270 mg, yield: 52%). LCMS m/z 308.2 [M+H]$^+$ Step 2: 8-(1-(5-cyano-6-((cis-4-methylcyclohexyl)oxy)naphthalen-2-yl)ethyl)-8-azabicyclo[3.2.1]octane-3-carboxylic acid The title compound was prepared according to the method of Example 102. $^1$H NMR (400 MHz, METHANOL-d₄) δ: 8.20 (d, J=9.2 Hz, 1H), 8.13 (d, J=8.4 Hz, 1H), 8.10 (s, 1H), 7.86 (dd, J=1.6 Hz, 8.8 Hz, 1H), 7.58 (d, J=9.2 Hz, 1H), 5.01 (s, 1H), 4.50-4.44 (m, 1H), 4.25-4.20 (m, 1H), 3.58-3.53 (m, 1H), 2.71-2.64 (m, 1H), 2.41-2.35 (m, 1H), 2.27-2.20 (m, 2H), 2.08-1.96 (m, 6H), 1.86-1.71 (m, 6H), 1.58-1.54 (m, 5H), 0.99 (d, J=7.2 Hz, 3H). LCMS m/z 447.3 [M+H]$^+$

Example 190

8-(5-(trifluoromethyl)-6-((cis-4-(trifluoromethyl)cyclohexyl)amino)-2-naphthoyl)-8-azabicyclo[3.2.1]octane-3-carboxylic acid

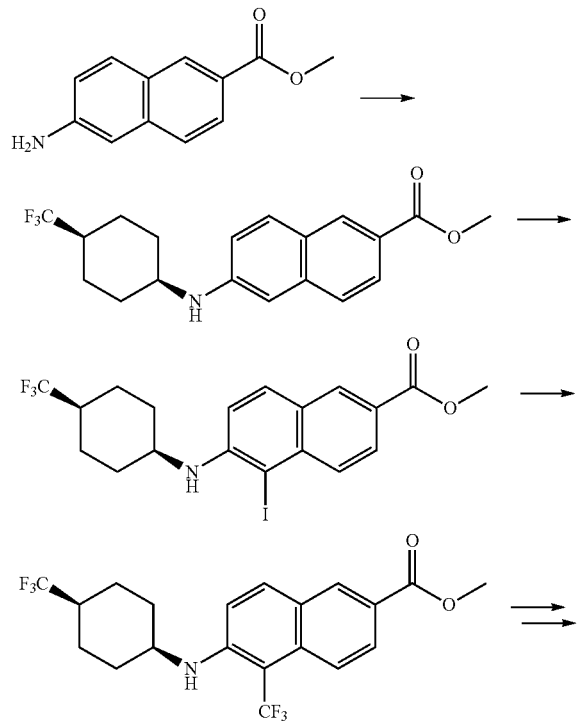

Step 1: methyl 5-cyano-6-((cis-4-(trifluoromethyl)cyclohexyl)oxy)-2-naphthoate

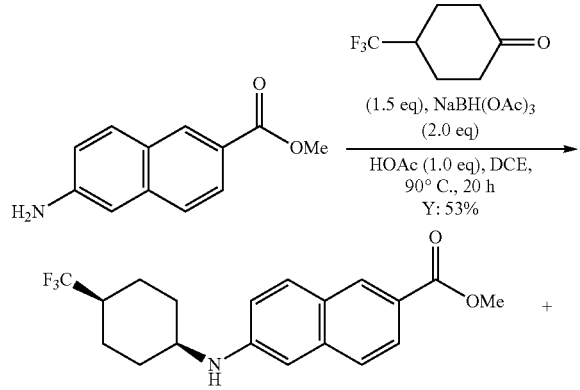

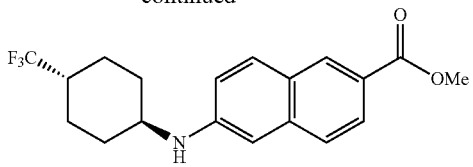

To a solution of methyl 6-amino-2-naphthoate (2.5 g, 12.4 mmol, 1.0 eq), 4-(trifluoromethyl)cyclohexanone (3.1 g, 18.6 mmol, 1.5 eq) and HOAc (744 mg, 12.4 mmol, 1.0 eq) in DCE (50 mL) was added NaBH(OAc)$_3$ (5.2 g, 25.0 mmol, 2.0 eq) portionwise. The mixture was stirred at 90° C. for 20 h. Water (100 mL) was added and the mixture was extracted with DCM (50 mL×3). The organic phase was dried and concentrated. The residue was purified by column chromatography on silica (petroleum ether/EtOAc=5:1) to afford methyl 6-((cis-4-(trifluoromethyl)cyclohexyl)amino)-2-naphthoate (1.1 g, yield 26%) and methyl 6-(((trans)-4-(trifluoromethyl)cyclohexyl)amino)-2-naphthoate (1.2 g, yield 27%) as yellow solid.

cis isomer: $^1$H NMR (400 MHz, CDCl$_3$) δ: 8.04 (s, 1H), 7.93 (dd, J=2.0 Hz, 8.8 Hz, 1H), 7.72 (d, J=8.8 Hz, 1H), 7.58 (d, J=8.8 Hz, 1H), 6.94 (dd, J=2.4 Hz, 8.8 Hz, 1H), 6.80 (s, 1H), 3.94 (s, 3H), 3.82 (s, 1H), 2.35-2.05 (m, 3H), 1.83-1.65 (m, 6H). LCMS m/z 352.1 [M+H]$^+$.

trans isomer: $^1$H NMR (400 MHz, CDCl$_3$) δ: 8.40 (d, J=0.8 Hz, 1H), 7.93 (dd, J=2.0 Hz, 8.0 Hz, 1H), 7.71 (d, J=8.8 Hz, 1H), 7.58 (d, J=8.8 Hz, 1H), 6.86 (dd, J=2.4 Hz, 8.8 Hz, 1H), 6.79 (s, 1H), 3.94 (s, 3H), 3.44-3.39 (m, 1H), 2.35-2.32 (m, 2H), 2.09-2.06 (m, 3H), 1.58-1.48 (m, 2H), 2.28-1.18 (m, 2H). LCMS m/z 352.1 [M+H]$^+$.

Step 2: methyl 5-iodo-6-((cis-4-(trifluoromethyl)cyclohexyl)amino)-2-naphthoate

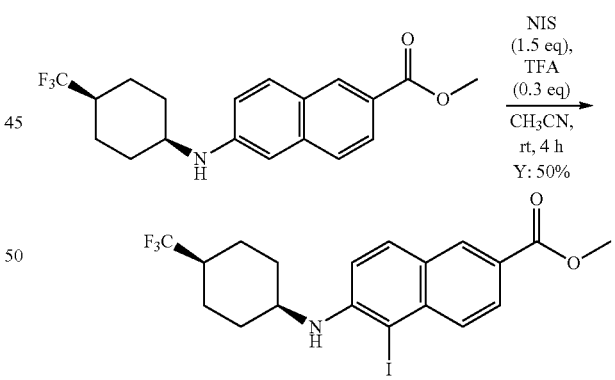

A mixture of methyl 6-((cis-4-(trifluoromethyl)cyclohexyl)amino)-2-naphthoate (1.0 g, 2.8 mmol, 1.0 eq), TFA (97 mg, 0.8 mmol, 0.3 eq), NIS (0.95 g, 4.2 mmol, 1.5 eq) in CH$_3$CN (20 mL) was stirred at rt for 4 h. The mixture was concentrated to give a residue which was purified by column chromatography on silica (petroleum ether/EtOAc=5:1) to afford methyl 5-iodo-6-((cis-4-(trifluoromethyl)cyclohexyl)amino)-2-naphthoate (679 mg, yield 50%) as a yellow solid.
$^1$H NMR (400 MHz, CDCl$_3$) δ: 8.38 (d, J=1.6 Hz, 1H), 8.00 (dd, J=1.6 Hz, 8.4 Hz, 1H), 7.91 (d, J=9.2 Hz, 1H), 7.77 (d, J=8.8 Hz, 1H), 7.01 (d, J=8.8 Hz, 1H), 5.13 (br s, 1H), 4.02-3.95 (m, 1H), 3.95 (s, 3H), 2.18-2.14 (m, 1H), 2.08-2.00 (m, 2H), 1.89-1.82 (m, 2H), 1.77-1.67 (m, 4H). LCMS m/z 478.0 [M+H]+

Step 3: methyl 5-(trifluoromethyl)-6-((cis-4-(trifluoromethyl)cyclohexyl)amino)-2-naphthoate

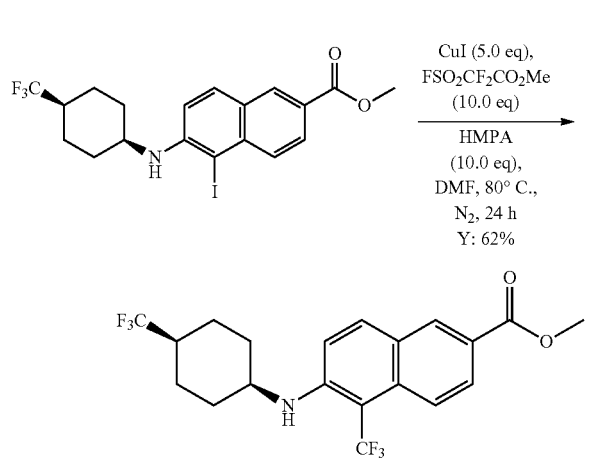

A mixture of methyl 5-iodo-6-((cis-4-(trifluoromethyl)cyclohexyl)amino)-2-naphthoate (679 mg, 1.4 mmol, 1.0 eq), FSO₂CF₂CO₂Me (2.7 g, 14.0 mmol, 10.0 eq), CuI (1.3 g, 7.0 mmol, 5.0 eq) and HMPA (2.5 g, 14.0 mmol, 10.0 eq) in DMF (10 mL) was stirred at 80° C. for 24 h under N₂. The mixture was diluted with EtOAc (150 mL) and washed with water (100 mL×2). The organic layer was dried and concentrated to give a residue which was purified by column chromatography on silica gel (petroleum ether/EtOAc=5:1) to afford methyl 5-(trifluoromethyl)-6-((cis-4-(trifluoromethyl)cyclohexyl)amino)-2-naphthoate as a yellow solid (369 mg, yield 62%). ¹H NMR (400 MHz, CDCl₃) δ: 8.40 (d, J=1.6 Hz, 1H), 8.04-7.97 (m, 2H), 7.87 (d, J=9.2 Hz, 1H), 7.09 (d, J=9.2 Hz, 1H), 5.52 (br s, 1H), 3.99 (s, 3H), 3.98 (s, 1H), 2.19-2.11 (m, 1H), 2.04-2.01 (m, 2H), 1.88-1.84 (m, 2H), 1.77-1.59 (m, 4H). LCMS m/z 420.1 [M+H]+

Step 4: 8-(5-(trifluoromethyl)-6-((cis-4-(trifluoromethyl)cyclohexyl)amino)-2-naphthoyl)-8-azabicyclo[3.2.1]octane-3-carboxylic acid

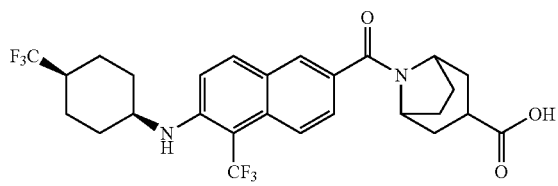 [SMILES: O=C(O)C1CC2CCC(C1)N2C(=O)c1ccc2c(C(F)(F)F)c(N[C@H]3CC[C@@H](C(F)(F)F)CC3)ccc2c1]

The title compound was prepared according to the method of Example 105. ¹H NMR (400 MHz, METHANOL-d₄) δ: 7.71-8.03 (m, 3H), 7.46 (dd, J=1.76, 9.04 Hz, 1H), 7.21 (d, J=9.29 Hz, 1H), 4.65-4.72 (m, 1H), 4.16 (br. s., 1H), 3.95 (br. s., 1H), 2.79-2.97 (m, 1H), 2.11-2.30 (m, 1H), 1.62-2.08 (m, 14H), 1.36-1.58 (m, 2H). LCMS m/z 543.2 [M+H]+

Example 191

9-(2-((trans-4-(tert-butyl)cyclohexyl)amino) quinazoline-6-carbonyl)-9-azabicyclo[3.3.1]nonane-3-carboxylic acid

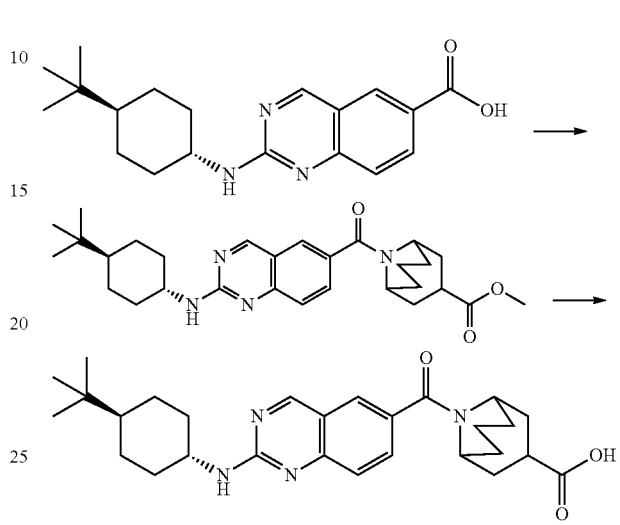

Step 1: methyl 9-(2-((trans-4-(tert-butyl)cyclohexyl)amino)quinazoline-6-carbonyl)-9-azabicyclo[3.3.1]nonane-3-carboxylate

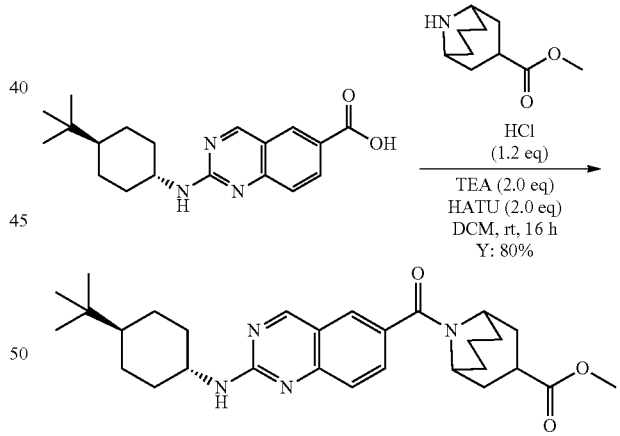

Into a mixture of 2-((trans-4-(tert-butyl)cyclohexyl)amino)quinazoline-6-carboxylic acid (70 mg, 0.21 mmol, 1.0 eq), methyl 9-aza-bicyclo[3.3.1]nonane-3-carboxylate HCl (56 mg, 0.25 mmol, 1.2 eq) and HATU (162 mg, 0.42 mmol, 2.0 eq) in DCM (20 mL) was added TEA (43 mg, 0.42 mmol, 2.0 eq). The reaction was stirred at rt for 16 h. The mixture was washed with H₂O (2×20 mL) and concentrated. The residue was purified by TLC on silica gel to give methyl 9-(2-((trans-4-(tert-butyl)cyclohexyl)amino)quinazoline-6-carbonyl)-9-azabicyclo[3.3.1]nonane-3-carboxylate (80 mg, yield 80%) as a light yellow solid. LCMS m/z 493.3 [M+H]+

Step 2: 9-(2-((trans-4-(tert-butyl)cyclohexyl)amino)quinazoline-6-carbonyl)-9-azabicyclo[3.3.1]nonane-3-carboxylic acid

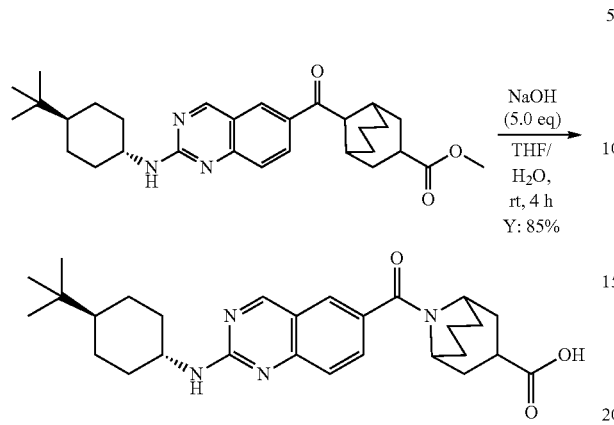

To a solution of methyl 9-(2-((trans-4-(tert-butyl)cyclohexyl)amino)quinazoline-6-carbonyl)-9-azabicyclo[3.3.1]nonane-3-carboxylate (80 mg, 0.16 mmol, 1.0 eq) in THF/H₂O (5 mL, 4:1) was added NaOH (33 mg, 0.81 mmol, 5.0 eq). The mixture was stirred at rt for 4 h. THF was removed and the residue was acidified to pH=6 with 1N HCl. The mixture was directly purified by reversed phase HPLC (MeCN/water=5%~95%) to give 9-(2-((trans-4-(tert-butyl)cyclohexyl)amino) quinazoline-6-carbonyl)-9-azabicyclo[3.3.1]nonane-3-carboxylic acid as a white solid (65 mg, yield 85%). ¹H NMR (400 MHz, CD₃OD) δ: 9.12 (s, 1H), 7.88 (d, J=1.6 Hz, 1H), 7.76 (dd, J=2.0 Hz, 8.8 Hz, 1H), 7.61 (d, J=8.8 Hz, 1H), 4.90-4.85 (m, 1H), 4.30-4.25 (m, 1H), 4.05-4.00 (m, 1H), 3.38-3.30 (m, 1H), 2.15-1.88 (m, 10H), 1.77-1.60 (m, 5H), 1.42-1.10 (m, 4H), 0.92 (s, 9H); LCMS m/z 479.2 [M+H]⁺

Example 192

9-((3-((cis-4-methylcyclohexyl)amino)isoquinolin-7-yl)methyl)-9-azabicyclo[3.3.1]nonane-3-carboxylic acid

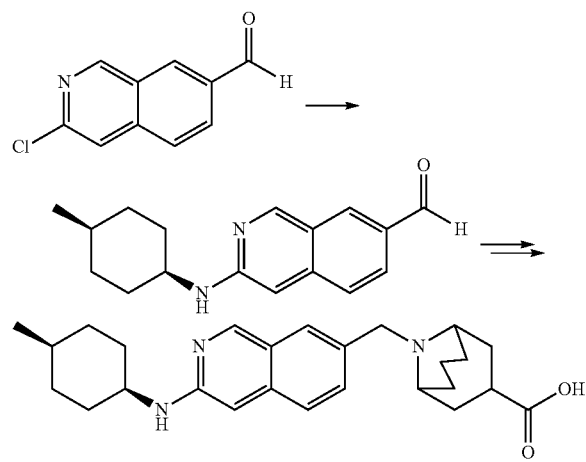

Step 1: 3-((cis-4-methylcyclohexyl)amino)isoquinoline-7-carbaldehyde

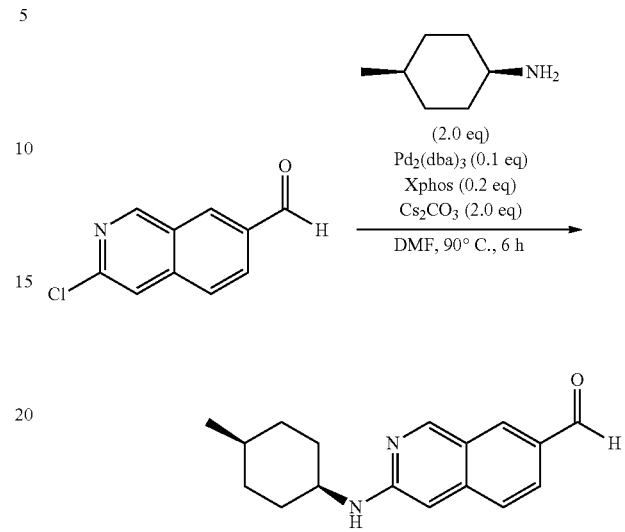

A mixture of 3-chloroisoquinoline-7-carbaldehyde (1.0 g, 5.23 mmol, 1.0 eq), cis-4-methylcyclohexanamine (1.2 g, 10.46 mmol, 2.0 eq), Pd₂(dba)₃ (480 mg, 0.52 mmol, 0.1 eq), Xphos (430 mg, 1.04 mmol, 0.2 eq) and Cs₂CO₃ (3.4 g, 10.46 mmol, 2.0 eq) in DMF (10 mL) was stirred at 90° C. for 6 h under N₂ atmosphere. The mixture was diluted with water (50 mL) and extracted with DCM (50 mL×2). The combined organic layers were washed with water (100 mL×2), dried over Na₂SO₄, filtrate and concentrated. The crude product was purified by column chromatography on silica gel (DCM/methanol=20:1) to give 3-((cis-4-methylcyclohexyl)amino)isoquinoline-7-carbaldehyde as a yellow solid (715 mg, yield: 51%). ESI-MS m/z 352.1 [M+H]⁺.

Step 2: 9-((3-((cis-4-methylcyclohexyl)amino)isoquinolin-7-yl)methyl)-9-azabicyclo[3.3.1]nonane-3-carboxylic acid

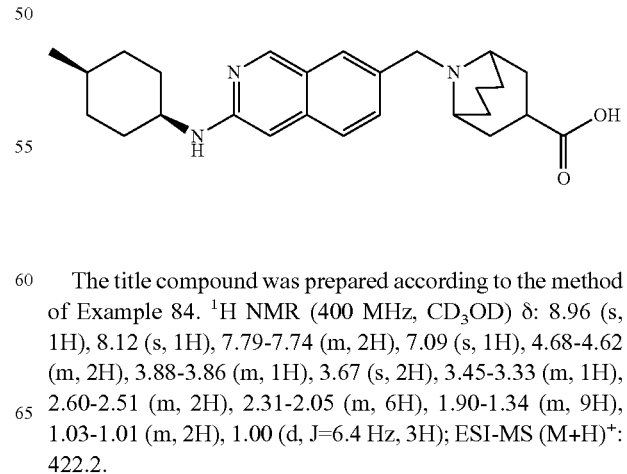

The title compound was prepared according to the method of Example 84. ¹H NMR (400 MHz, CD₃OD) δ: 8.96 (s, 1H), 8.12 (s, 1H), 7.79-7.74 (m, 2H), 7.09 (s, 1H), 4.68-4.62 (m, 2H), 3.88-3.86 (m, 1H), 3.67 (s, 2H), 3.45-3.33 (m, 1H), 2.60-2.51 (m, 2H), 2.31-2.05 (m, 6H), 1.90-1.34 (m, 9H), 1.03-1.01 (m, 2H), 1.00 (d, J=6.4 Hz, 3H); ESI-MS (M+H)⁺: 422.2.

Example 193

8-((4-chloro-3-((cis-4-methylcyclohexyl)amino)iso-quinolin-7-yl)methyl)-8-azabicyclo[3.2.1]octane-3-carboxylic acid

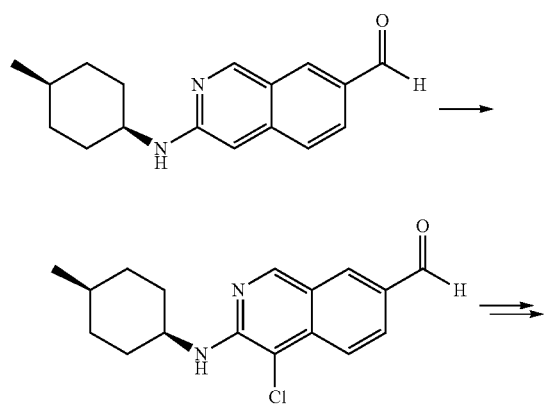

Step 1: 4-chloro-3-((cis-4-methylcyclohexyl)amino)isoquinoline-7-carbaldehyde

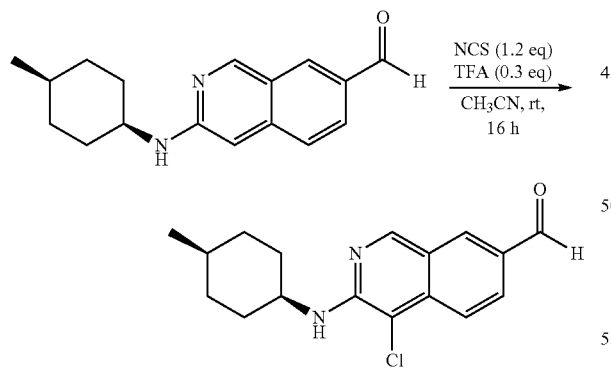

To a mixture of 3-((cis-4-methylcyclohexyl)amino)isoquinoline-7-carbaldehyde (400 mg, 1.49 mmol, 1.0 eq) and NCS (238 mg, 1.79 mmol, 1.2 eq) in CH$_3$CN (10 mL) was added TFA (58 mg, 0.45 mmol, 0.3 eq). The mixture was stirred at rt for 16 h and concentrated. The residue was purified by column chromatography on silica gel (petroleum ether/EtOAc=20:1) to give 4-chloro-3-((cis-4-methylcyclohexyl)amino)isoquinoline-7-carbaldehyde as a yellow solid (324 mg, yield 72%). ESI-MS (M+H)$^+$: 303.3.

Step 2: 8-((4-chloro-3-((cis-4-methylcyclohexyl)amino)isoquinolin-7-yl)methyl)-8-azabicyclo[3.2.1]octane-3-carboxylic acid

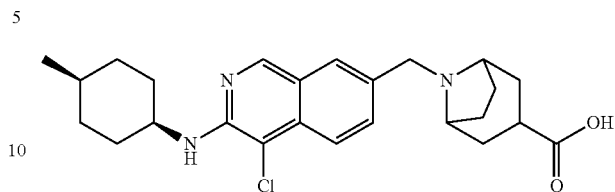

The title compound was prepared according to the method of Example 84. $^1$H NMR (400 MHz, CD$_3$OD) δ: 8.91 (s, 1H), 8.05 (s, 1H), 7.99 (d, J=8.8 Hz, 1H), 7.76 (d, J=8.8 Hz, 1H), 4.32 (s, 2H), 4.34-4.30 (m, 1H), 4.06-4.03 (m, 2H), 3.01-2.96 (m, 1H), 2.54-2.51 (m, 2H), 2.17-2.03 (m, 6H), 1.87-1.66 (m, 7H), 1.40-1.32 (m, 2H), 1.02 (d, J=6.0 Hz, 3H); ESI-MS (M+H)$^+$: 442.2.

Example 194

8-(3-((trans-4-(tert-butyl)cyclohexyl)amino)isoquinoline-7-carbonyl)-8-azabicyclo[3.2.1]octane-3-carboxylic acid

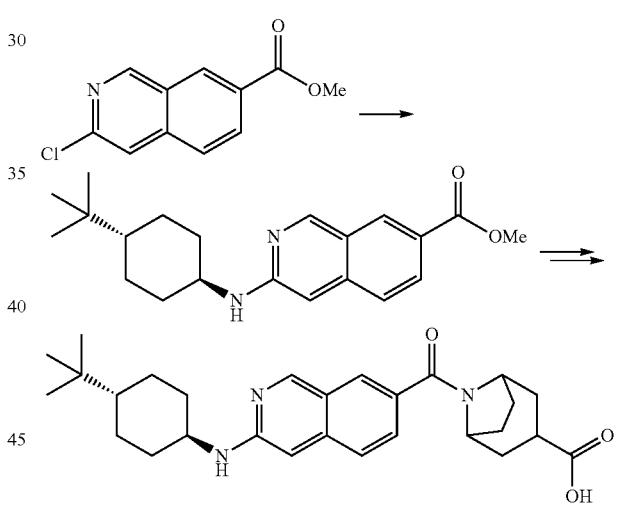

Step 1: methyl 3-((trans-4-(tert-butyl)cyclohexyl)amino)isoquinoline-7-carboxylate

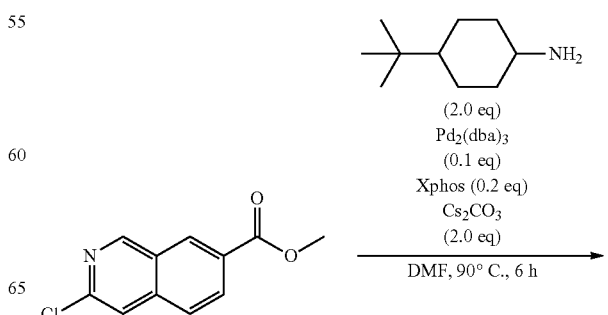

-continued

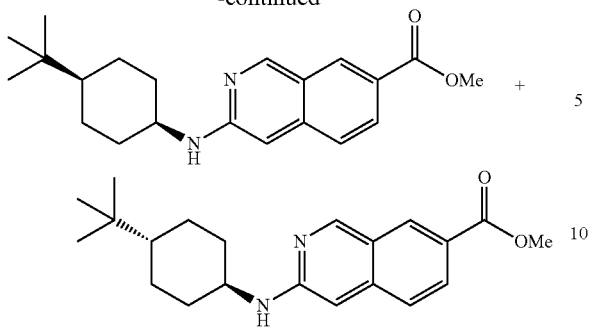

The preparation of the tile compound was the same as Example 193; step 1: trans isomer was obtained as a yellow solid (350 mg, yield: 35%), along with cis isomer (300 mg, yield 33%). ESI-MS (M+H)+: 341.2.

Step 2: 8-(3-((trans-4-(tert-butyl)cyclohexyl)amino) isoquinoline-7-carbonyl)-8-azabicyclo[3.2.1]octane-3-carboxylic acid

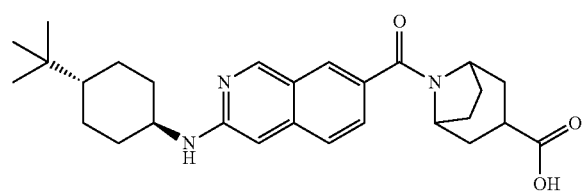 [SMILES: CC(C)(C)[C@H]1CC[C@H](Nc2cc3ccc(C(=O)N4C5CCC4CC(C(=O)O)C5)cc3cn2)CC1]

The title compound was prepared according to the method of Example 105. $^1$H NMR (400 MHz, CD$_3$OD) δ: 9.03 (s, 1H), 8.11 (s, 1H), 7.80 (d, J=9.2 Hz, 1H), 7.75 (d, J=9.2 Hz, 1H), 7.25 (s, 1H), 4.82 (s, 1H), 4.27-4.24 (m, 1H), 3.58-3.53 (m, 1H), 3.03-2.99 (m, 1H), 2.22-1.88 (m, 12H), 1.43-1.25 (m, 4H), 1.17-1.11 (m, 1H), 0.93 (s, 9H); ESI-MS (M+H)+: 464.3.

Example 195

9-((8-chloro-7-((cis-4-ethylcyclohexyl)oxy) isoquinolin-3-yl)methyl)-9-azabicyclo[3.3.1]nonane-3-carboxylic acid

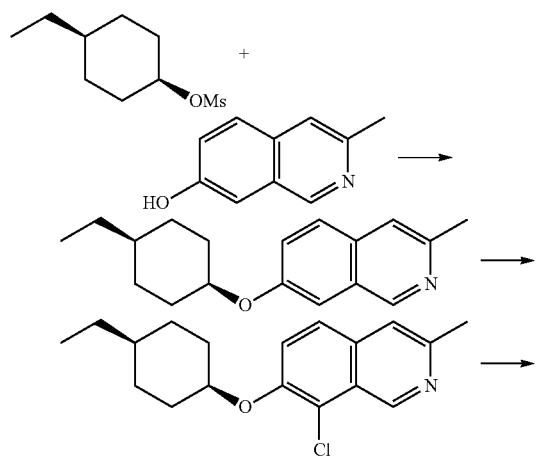

-continued

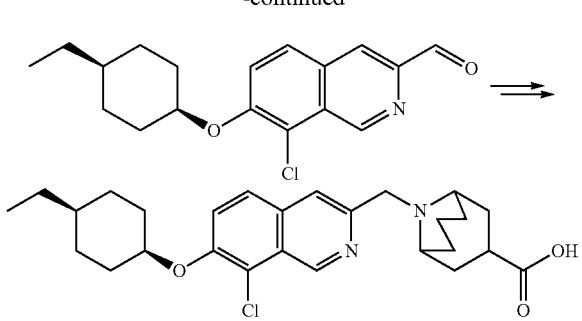

Step 1: 7-((cis-4-ethylcyclohexyl)oxy)-3-methylisoquinoline

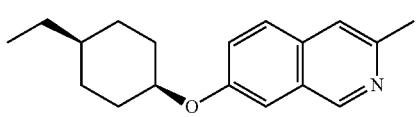 [SMILES: CC[C@H]1CC[C@@H](Oc2ccc3cc(C)ncc3c2)CC1]

A mixture of 3-methylisoquinolin-7-ol (5.0 g, 31.4 mmol), (1r,4r)-4-ethylcyclohexyl methanesulfonate (7.1 g, 31.4 mmol) and Cs$_2$CO$_3$ (10.3 g, 31.4 mmol) in t-BuOH (200 mL) was stirred at 90° C. for 6 h. The reaction was then cooled down. The mixture was filtered and the filtrate was concentrated. The residue was purified by column chromatography on silica gel (petroleum ether/EtOAc=20/1) to give the title compound as a white solid (5.7 g, yield: 40%). ESI-MS (M+H)+: 270.2.

Step 2: 8-chloro-7-((cis-4-ethylcyclohexyl)oxy)-3-methylisoquinoline

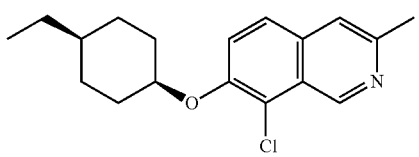 [SMILES: CC[C@H]1CC[C@@H](Oc2ccc3cc(C)ncc3c2Cl)CC1]

To a solution of 7-((cis-4-ethylcyclohexyl)oxy)-3-methylisoquinoline (800 mg, 2.97 mmol) in acetonitrile (10 mL) was added NCS (475 mg, 3.57 mmol), followed by TFA (101 mg, 0.89 mmol). The reaction was stirred at RT for 16 h. The mixture was then diluted with water (50 mL), and extracted with EtOAc (3×50 mL). The combined organic layers were dried and concentrated. The crude product was purified by column chromatography on silica gel (petroleum ether/EtOAc=20/1) to give the title compound as a white solid (800 mg, yield: 89%). ESI-MS (M+H)+: 304.1

Step 3: 8-chloro-7-((cis-4-ethylcyclohexyl)oxy)isoquinoline-3-carbaldehyde

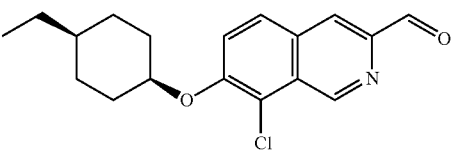 [SMILES: CC[C@H]1CC[C@@H](Oc2ccc3cc(C=O)ncc3c2Cl)CC1]

A mixture of 8-chloro-7-((cis-4-ethylcyclohexyl)oxy)-3-methylisoquinoline (800 mg, 2.64 mmol) and SeO$_2$ (586 mg, 5.28 mmol) in diphenyl oxide (5 mL) was stirred at 180° C. for 6 h and cooled down. The mixture was filtered and the filtrate was concentrated. The residue was purified by column chromatography on silica gel (petroleum ether/EtOAc=100%-95%) to give the title compound as a yellow solid (418 g, yield: 50%). ESI-MS (M+H)$^+$: 318.2.

Step 4: Isopropyl 9-((8-chloro-7-((cis-4-ethylcyclohexyl)oxy)isoquinolin-3-yl)methy)-9-azabicyclo[3.3.1]nonane-3-carboxylate

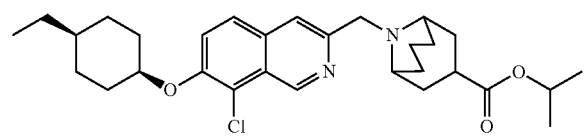 [SMILES: CC[C@H]1CC[C@@H](Oc2ccc3cc(CN4C5CCCC4CC(C(=O)OC(C)C)C5)ncc3c2Cl)CC1]

A mixture of 8-chloro-7-((cis-4-ethylcyclohexyl)oxy)isoquinoline-3-carbaldehyde (100 mg, 0.315 mmol), methyl 9-azabicyclo[3.3.1]nonane-3-carboxylate hydrochloride (83 mg, 0.378 mmol) and titanium(IV) isopropoxide (179 mg, 0.63 mmol) in THF (3 mL) was stirred at 80° C. for 2 h in a sealed tube. The mixture was cooled to RT and NaBH(OAc)$_3$ (134 mg, 0.630 mmol) was added. The reaction was stirred at 80° C. for 1 h. Water (30 mL) was added and the mixture was extracted with CH$_2$Cl$_2$ (2×30 mL). The combined organic layer was washed with water (2×60 mL), separated, and then dried over Na$_2$SO$_4$, and concentrated. The residue was purified by column chromatography on silica gel (petroleum ether/EtOAc=5:1) to give the title compound as colorless oil (93 mg, yield: 58%). ESI-MS (M+H)$^+$: 513.3.

Step 5: 9-((8-chloro-7-((cis-4-ethylcyclohexyl)oxy)isoquinolin-3-yl)methyl)-9-azabicyclo[3.3.1]nonane-3-carboxylic acid

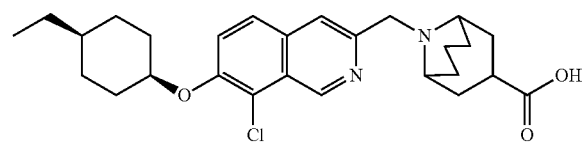 [SMILES: CC[C@H]1CC[C@@H](Oc2ccc3cc(CN4C5CCCC4CC(C(=O)O)C5)ncc3c2Cl)CC1]

To a solution of isopropyl 9-((8-chloro-7-((cis-4-ethylcyclohexyl)oxy)isoquinolin-3-yl)methyl)-9-azabicyclo[3.3.1]nonane-3-carboxylate (100 mg, 0.195 mmol) in 10 mL of MeOH was added a solution of NaOH (23 mg, 0.58 mmol) in H$_2$O (5 mL). The reaction mixture was stirred at 65° C. for 2 h. The solvent was removed and water (10 mL) was added. The mixture was acidified to pH=6 with 1N HCl. The solid was collected by filtration and purified by HPLC (MeCN/H$_2$O-0.05% TFA) to give the title compound as a white solid (64 mg, yield: 70%). $^1$H NMR (400 MHz, CD$_3$OD) δ: 9.62 (s, 1H), 8.00 (s, 1H), 7.95 (d, J=9.2 Hz, 1H), 7.79 (d, J=9.2 Hz, 1H), 4.93 (s, 1H), 4.72 (s, 2H), 3.58-3.54 (m, 2H), 3.15-3.08 (m, 1H), 2.46-2.31 (m, 4H), 2.19-2.04 (m, 5H), 1.93-1.90 (m, 2H), 1.81-1.49 (m, 7H), 1.38-1.33 (m, 3H), 0.94 (t, J=6.8 Hz, 3H). ESI-MS (M+H)$^+$: 471.2.

Example 196

9-((8-bromo-7-((cis-4-ethylcyclohexyl)oxy) isoquinolin-3-yl)methyl)-9-azabicyclo[3.3.1]nonane-3-carboxylic acid

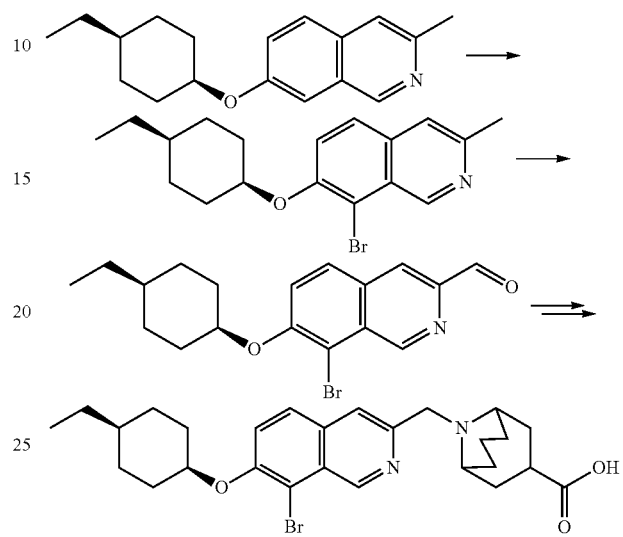

Step 1: 8-bromo-7-((cis-4-ethylcyclohexyl)oxy)-3-methylisoquinoline

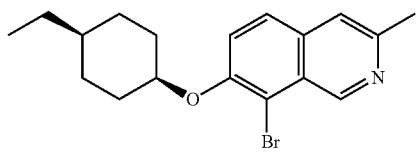 [SMILES: CC[C@H]1CC[C@@H](Oc2ccc3cc(C)ncc3c2Br)CC1]

Bromine (1.2 g, 7.44 mmol, 2.0 eq) was added to a solution of 7-((cis-4-ethylcyclohexyl)oxy)-3-methylisoquinoline (1.0 g, 3.72 mmol) in AcOH (20 mL) at rt. The mixture was stirred at RT for 3 h. After the reaction completed, the mixture was diluted with water (50 mL) and extracted with EtOAc (2×50 mL). The combined organic layer was washed with water (2×100 mL), aq. NaHCO$_3$ (100 mL), dried over Na$_2$SO$_4$ and concentrated. The residue was purified by column chromatography on silica gel (petroleum ether/EtOAc=20/1) to give the title compound as a white solid (1.1 g, yield: 85%). ESI-MS (M+H)$^+$: 348.1.

Step 1: 8-bromo-7-((cis-4-ethylcyclohexyl)oxy)isoquinoline-3-carbaldehyde

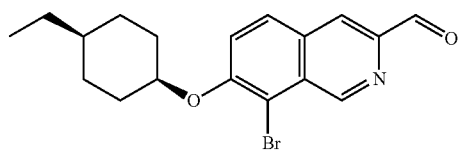 [SMILES: CC[C@H]1CC[C@@H](Oc2ccc3cc(C=O)ncc3c2Br)CC1]

The title compound was prepared according to the method of Example 196 to give a yellow solid (400 mg, yield: 67%). ESI-MS (M+H)+: 362.2.

Step 2: Isopropyl 9-((8-bromo-7-((cis-4-ethylcyclohexyl)oxy)isoquinolin-3-yl)methyl)-9-azabicyclo[3.3.1]nonane-3-carboxylate

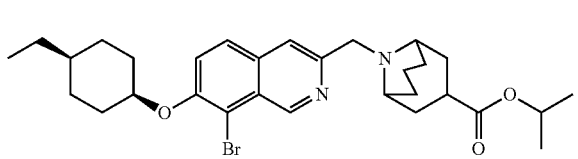 [SMILES: CC[C@H]1CC[C@@H](Oc2ccc3cc(CN4C5CCCC4CC(C(=O)OC(C)C)C5)ncc3c2Br)CC1]

The title compound was prepared according to the method of Example 196 to give a yellow solid (109 mg, yield: 60%). ESI-MS (M+H)+: 557.2.

Step 3: 9-((8-bromo-7-((cis-4-ethylcyclohexyl)oxy)isoquinolin-3-yl)methyl)-9-azabicyclo[3.3.1]nonane-3-carboxylic acid

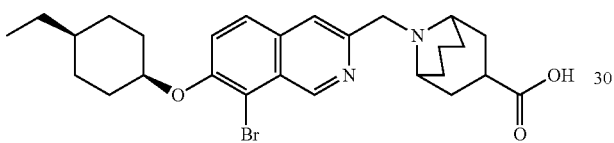

The title compound was prepared according to the method of Example 196 to give a yellow solid (80 mg, yield: 70%). 
$^1$H NMR (400 MHz, CD$_3$OD) δ: 9.50 (s, 1H), 7.88 (d, J=8.8 Hz, 1H), 7.87 (s, 1H), 7.65 (d, J=8.8 Hz, 1H), 4.85 (s, 1H), 4.65 (s, 2H), 3.50-3.48 (m, 2H), 3.09-3.00 (m, 1H), 2.36-2.22 (m, 4H), 2.06-1.93 (m, 5H), 1.83-1.81 (m, 2H), 1.71-1.43 (m, 7H), 1.26-1.18 (m, 3H), 0.84 (t, J=6.8 Hz, 3H). ESI-MS (M+H)+: 515.2.

Example 197

9-((8-(trifluoromethyl)-7-((cis-4-(trifluoromethyl)cyclohexyl)oxy)isoquinolin-3-yl)methyl)-9-azabicyclo[3.3.1]nonane-3-carboxylic acid

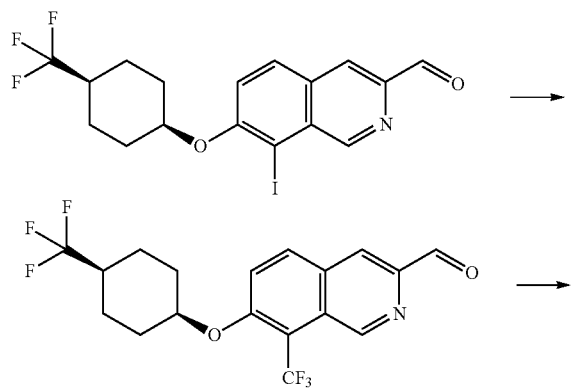

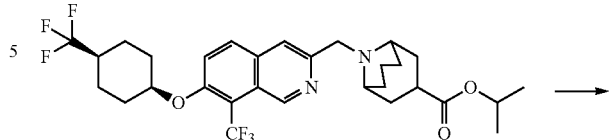

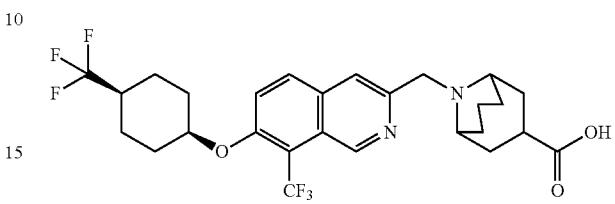

Step 1: 8-(trifluoromethyl)-7-((cis-4-(trifluoromethyl)cyclohexyl)oxy) isoquinoline-3-carbaldehyde

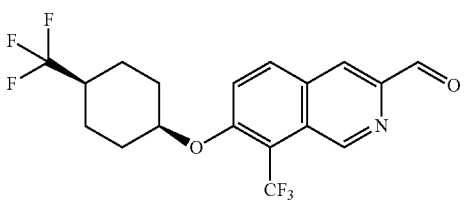 [SMILES: O=Cc1cc2ccc(O[C@H]3CC[C@@H](C(F)(F)F)CC3)c(C(F)(F)F)c2cn1]

A mixture of 8-iodo-7-((cis-4-(trifluoromethyl)cyclohexyl)oxy)isoquinoline-3-carbaldehyde (500 mg, 1.11 mmol), HMPA (1.99 g, 11.13 mmol), CuI (527 mg, 2.27 mmol) and FSO$_2$CF$_2$CO$_2$CH$_3$ (2.11 g, 11.13 mmol) in DMF (5 mL) was stirred in a sealed tube at 90° C. for 16 h. The reaction mixture was concentrated and the residue was purified by column chromatography on silica gel (petroleum ether/EtOAc=20:1) to yield the title compound as a yellow solid (130 mg, yield: 30%). ESI-MS (M+H)+: 392.1.

Step 2: Isopropyl 9-((8-(trifluoromethyl)-7-((cis-4-(trifluoromethyl)cyclohexyl)oxy)isoquinolin-3-yl)methyl)-9-azabicyclo[3.3.1]nonane-3-carboxylate

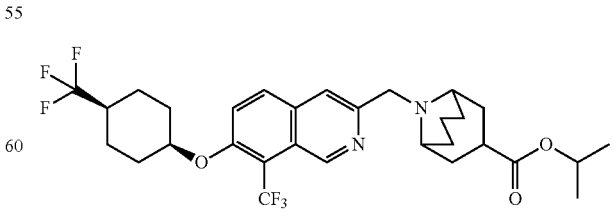

The title compound was prepared according to the method of Example 196 to give the title compound as a yellow solid (80 mg, yield: 60%). ESI-MS (M+H)+: 587.3.

Step 3: 9-((8-(trifluoromethyl)-7-((cis-4-(trifluoromethyl)cyclohexyl)oxy)isoquinolin-3-yl)methyl)-9-azabicyclo[3.3.1]nonane-3-carboxylic acid

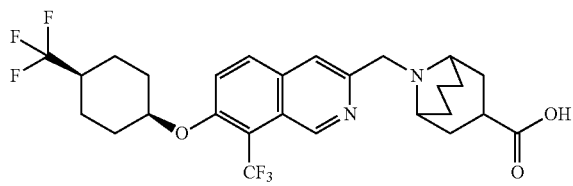 [SMILES: O=C(O)C1CC2CCCC(C1)N2Cc1cc2ccc(O[C@H]3CC[C@@H](C(F)(F)F)CC3)c(C(F)(F)F)c2cn1]

The title compound was prepared according to the method of Example 196 to give the title compound as a yellow solid (58 mg, yield: 70%). $^1$H NMR (400 MHz, CD$_3$OD) δ: 9.65 (s, 1H), 8.23 (d, J=9.6 Hz, 1H), 8.05 (s, 1H), 7.88 (d, J=9.6 Hz, 1H), 5.09 (s, 1H), 4.80 (s, 2H), 3.76-3.72 (m, 2H), 3.45-3.40 (m, 1H), 2.52-1.90 (m, 12H), 1.87-1.75 (m, 7H). ESI-MS (M+H)$^+$: 545.1.

Example 198

9-((6-((cis-4-ethylcyclohexyl)oxy)-5-(trifluoromethyl)quinolin-2-yl)amino)bicyclo[3.3.1]nonane-3-carboxylic acid

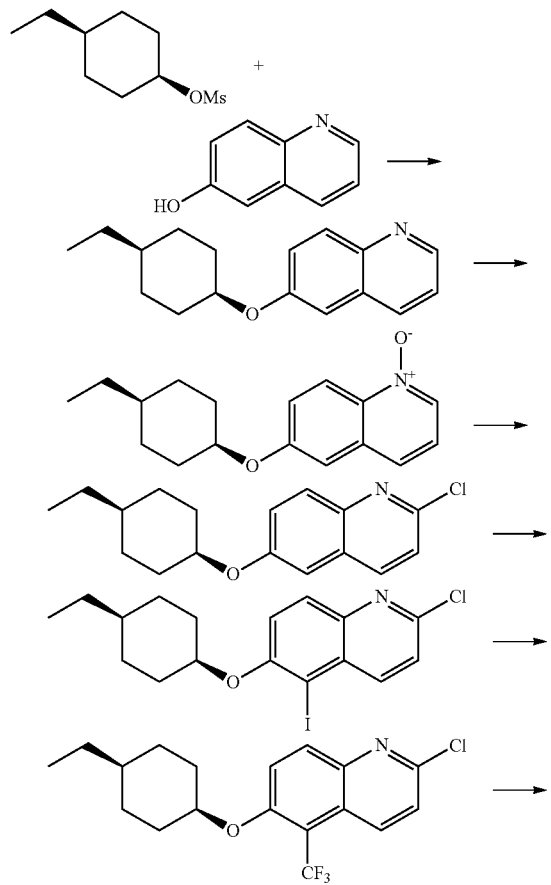

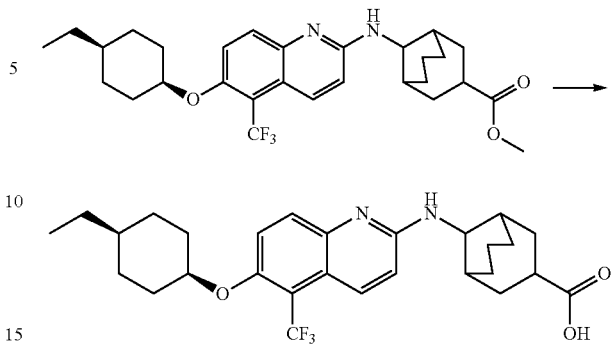

Step 1: 6-((cis-4-ethylcyclohexyl)oxy)quinoline

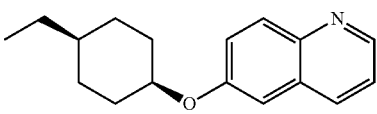 [SMILES: CC[C@H]1CC[C@@H](Oc2ccc3ncccc3c2)CC1]

To a solution of quinolin-6-ol (9.5 g, 65.5 mmol) and cis-4-ethylcyclohexyl methanesulfonate (14.8 g, 72.0 mmol) in t-BuOH (150 mL) was added Cs$_2$CO$_3$ (21.3 g, 65.5 mmol). The mixture was stirred at 90° C. for 10 h. The mixture was cooled down, diluted with water (200 mL) and extracted with EtOAc (300 mL×2). The combined organic layers were dried over Na$_2$SO$_4$ and concentrated. The residue was purified by column chromatography on silica gel (petroleum ether/EtOAc=15/1) to give the title compound as a white solid (12.0 g, yield: 72%). ESI-MS (M+H)$^+$: 256.2.

Step 2: 6-((cis-4-Ethylcyclohexyl)oxy)quinoline 1-oxide

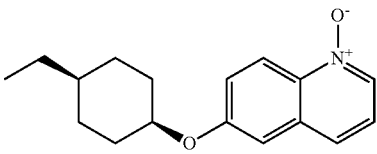 [SMILES: CC[C@H]1CC[C@@H](Oc2ccc3c(ccc[n+]3[O-])c2)CC1]

To a solution of 6-((cis-4-ethylcyclohexyl)oxy)quinoline (2.0 g, 7.84 mmol) in CH$_2$Cl$_2$ (30 mL) was portionwise added m-CPBA (2.7 g, 15.68 mmol). The mixture was stirred at RT for 16 h. Aqueous Na$_2$SO$_3$ (50 mL) was added and the mixture was stirred at RT for 30 min. The mixture was separated and the aqueous was extracted with CH$_2$Cl$_2$ (50 mL). The combined organics were washed with water (100 mL), dried over Na$_2$SO$_4$, filtered and concentrated. The crude product was purified by column chromatography on silica gel (DCM/methanol=20/1) to give the title compound as a yellow solid (1.8 g, yield: 83%). ESI-MS (M+H)$^+$: 272.1.

Step 3: 2-Chloro-6-((cis-4-ethylcyclohexyl)oxy)quinoline

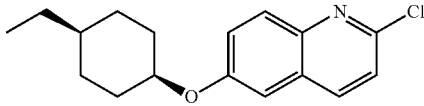 [SMILES: CC[C@H]1CC[C@@H](Oc2ccc3nc(Cl)ccc3c2)CC1]

A mixture of 6-((cis-4-ethylcyclohexyl)oxy)quinoline 1-oxide (9.0 g, 33 mmol) in POCl₃ (50 mL) was heated at 100° C. for 16 h and cooled down. The mixture was carefully poured onto ice water (200 mL). The aqueous was neutralized with NaOH and extracted with DCM (100 mL×3). The combined organics were dried over Na₂SO₄, and concentrated. The residue was purified by column chromatography on silica gel (petroleum ether/EtOAc=100:1) to give the title compound as a yellow solid (6.0 g, yield: 63%). ESI-MS (M+H)⁺: 290.1. An isomer 4-chloro-6-((cis-4-ethylcyclohexyl)oxy)quinoline was also isolated (2.9 g, yield: 30%) as a yellow solid.

Step 4: 2-chloro-6-((cis-4-ethylcyclohexyl)oxy)-5-iodoquinoline

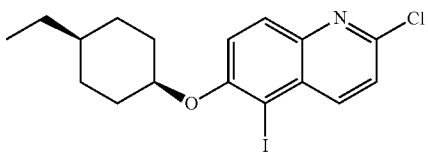 [SMILES: CC[C@H]1CC[C@@H](Oc2ccc3nc(Cl)ccc3c2I)CC1]

To a solution of 2-chloro-6-((cis-4-ethylcyclohexyl)oxy)quinoline (100 mg, 0.35 mmol) in acetonitrile (2 mL) was added NIS (93 mg, 0.42 mmol), followed by TFA (8 mg, 0.07 mmol). The mixture was stirred at RT for 16 h. The solvent was removed under vacuo. The residue was purified by column chromatography on silica gel (petroleum ether/EtOAc=10/1) to give the title compound as a yellow solid (130 mg, yield: 92%). ¹H NMR (400 MHz, CDCl₃) δ: 8.38 (d, J=8.8 Hz, 1H), 7.96 (d, J=9.2 Hz, 1H), 7.40-7.35 (m, 2H), 4.82 (s, 1H), 2.07-2.06 (m, 2H), 1.69-1.58 (m, 6H), 1.36-1.28 (m, 3H), 0.92 (t, J=7.2 Hz, 3H). ESI-MS (M+H)⁺: 416.1.

Step 5: 2-chloro-6-((cis-4-ethylcyclohexyl)oxy)-5-(trifluoromethyl)quinoline

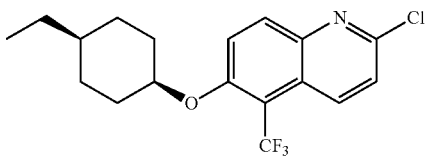 [SMILES: CC[C@H]1CC[C@@H](Oc2ccc3nc(Cl)ccc3c2C(F)(F)F)CC1]

The title compound was prepared according to the method of Example 198 to give the title compound as a yellow solid (70 mg, yield: 63%). ESI-MS (M+H)⁺: 358.1.

Step 6: Methyl 9-((6-((cis-4-ethylcyclohexyl)oxy)-5-(trifluoromethyl)quinolin-2-yl)amino)bicyclo[3.3.1]nonane-3-carboxylate

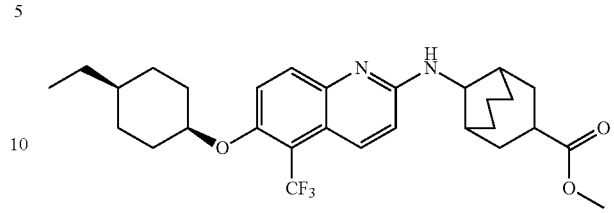

A mixture of 2-chloro-6-((cis-4-ethylcyclohexyl)oxy)-5-(trifluoromethyl) quinoline (70 mg, 0.2 mmol), methyl 9-aminobicyclo[3.3.1]nonane-3-carboxylate (58 mg, 0.3 mmol), Cs₂CO₃ (130 mg, 0.4 mmol), S-phos (16 mg, 0.04 mmol) and Pd₂(dba)₃ (18 mg, 0.02 mmol) in DMF (2 mL) was stirred at 100° C. for 16 h under N₂ atmosphere. Water (20 mL) was added and the mixture was extracted with EtOAc (20 mL×3). The organic phase was dried and concentrated. The residue was purified by reversed phase HPLC (MeOH/H₂O-0.05% TFA) to give the title compound as a yellow solid (30 mg, yield 30%). ESI-MS (M+H)⁺: 519.2.

Step 7: 9-((6-((cis-4-Ethylcyclohexyl)oxy)-5-(trifluoromethyl)quinolin-2-yl)amino)bicyclo[3.3.1]nonane-3-carboxylic acid

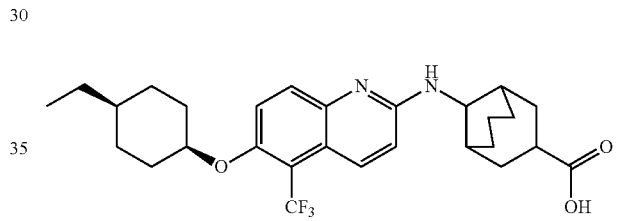

To a solution of methyl 9-((6-((cis-4-ethylcyclohexyl)oxy)-5-(trifluoromethyl) quinolin-2-yl)amino)bicyclo[3.3.1]nonane-3-carboxylate (30 mg, 0.06 mmol) in MeOH (1 mL) was added NaOH (7 mg, 0.17 mmol) and H₂O (0.5 mL). The reaction mixture was stirred at 65° C. for 16 h. Then the reaction was cooled to RT, acidified with 1N HCl to pH =6. The mixture was directly purified by reversed phase HPLC (MeOH/H₂O) to give the title compound as a white solid (15 mg, yield: 52%). ¹H NMR (400 MHz, CD₃OD, a mixture of cis and trans isomers) δ: 8.05-8.02 (m, 1H), 7.69-7.65 (m, 1H), 7.35-7.31 (m, 1H), 6.90-6.80 (m, 1H), 4.66 (s, 1H), 4.21-4.17 (m, 0.5H), 3.70-3.69 (m, 0.5H), 2.88-2.74 (m, 1H), 2.29-1.91 (m, 6H), 1.78-1.19 (m, 17H), 0.82 (t, J=6.8 Hz, 3H). ESI-MS (M+H)⁺: 505.2.

Example 199

9-((5-cyano-6-((cis-4-ethylcyclohexyl)oxy)naphthalen-2-yl)methyl)-9-azabicyclo[3.3.1]nonane-3-carboxylic acid

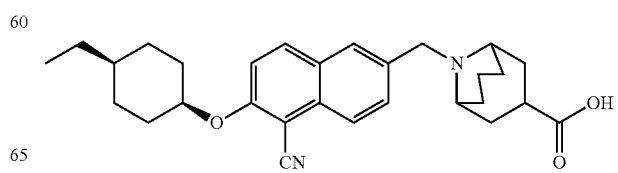

The title compound was prepared according to the method of Example 188. ¹H NMR (400 MHz, CD₃OD) δ: 8.17 (d, J=9.6 Hz, 1H), 8.08 (s, 1H), 8.04 (d, J=8.4 Hz, 1H), 7.83 (d, J=8.4 Hz, 1H), 7.53 (d, J=9.2 Hz, 1H), 5.00 (s, 1H), 4.45 (s, 2H), 3.33-3.30 (m, 2H), 3.07-3.05 (m, 1H), 2.39-2.21 (m, 4H), 2.09-2.07 (m, 3H), 1.95-1.91 (m, 2H), 1.74-1.52 (m, 9H), 1.37-1.30 (m, 3H), 0.95 (t, J=6.8 Hz, 3H). LCMS m/z 461.2 [M+H]⁺

Example 200

8-((5-cyano-6-((cis-4-ethylcyclohexyl)oxy)naphthalen-2-yl)methyl)-8-azabicyclo[3.2.1]octane-3-carboxylic acid

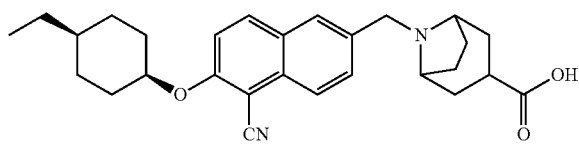 [SMILES: CC[C@H]1CC[C@@H](Oc2ccc3cc(CN4C5CCC4CC(C(=O)O)C5)ccc3c2C#N)CC1]

The title compound was prepared according to the method of Example 188. ¹H NMR (400 MHz, CD₃OD) δ: 8.21 (d, J=9.6 Hz, 1H), 8.12 (s, 1H), 8.09 (d, J=8.8 Hz, 1H), 7.82 (dd, J=1.6 Hz, 8.4 Hz, 1H), 7.57 (d, J=9.2 Hz, 1H), 5.03 (s, 1H), 4.33 (s, 2H), 3.90-3.88 (m, 2H), 2.72-2.65 (m, 1H), 2.44-2.41 (m, 2H), 2.09-1.95 (m, 8H), 1.72-1.33 (m, 6H), 1.37-1.33 (m, 3H), 0.95 (t, J=6.8 Hz, 3H). LCMS m/z 447.2 [M+H]⁺

Example 201

9-(5-chloro-6-((cis-4-(trifluoromethyl)cyclohexyl) oxy)-2-naphthoyl)-9-azabicyclo[3.3.1]nonane-3-carboxylic acid

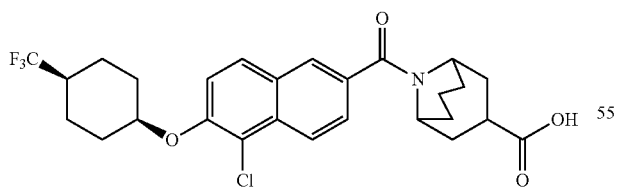

The title compound was prepared according to the method of Example 186. ¹H NMR (400 MHz, CD₃OD) δ: 8.16 (d, J=8.4 Hz, 1H), 7.86-7.81 (m, 2H), 7.52 (d, J=9.2 Hz, 1H), 7.41 (d, J=8.8 Hz, 1H), 4.83 (s, 1H), 3.85-3.82 (m, 1H), 3.20-3.12 (m, 1H), 2.20-1.77 (m, 14H), 1.67-1.58 (m, 6H). LCMS m/z 524.2 [M+H]⁺

Example 202

8-(1-(5-chloro-6-((cis-4-(trifluoromethyl)cyclohexyl) oxy)naphthalen-2-yl)propyl)-8-azabicyclo[3.2.1] octane-3-carboxylic acid

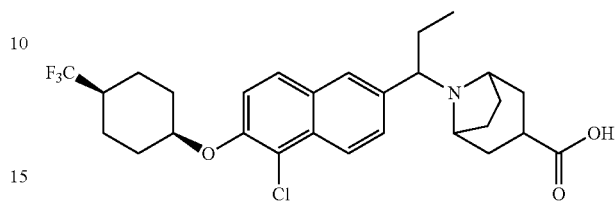

The title compound was prepared according to the method of Example 92. ¹H NMR (400 MHz, CD₃OD) δ: 8.33 (d, J=8.4 Hz, 1H), 8.02 (s, 1H), 7.90 (d, J=8.8 Hz, 1H), 7.73 (d, J=8.4 Hz, 1H), 7.54 (d, J=9.2 Hz, 1H), 4.95 (s, 1H), 4.23-4.19 (m, 2H), 3.52-3.49 (m, 1H), 2.69-2.62 (m, 1H), 2.39-1.68 (m, 19H), 0.77 (t, J=7.2 Hz, 3H). LCMS m/z 524.2 [M+H]⁺

Example 203

8-(5-chloro-6-((cis-4-methylcyclohexyl)oxy)-2-naphthoyl)-8-azabicyclo[3.2.1]octane-3-carboxylic acid

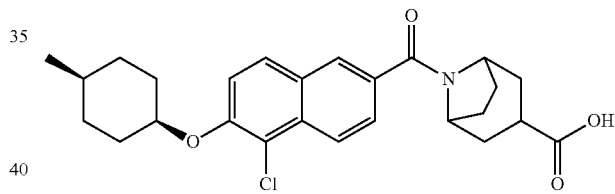

The title compound was prepared according to the method of Example 186. ¹H NMR (400 MHz, CD₃OD) δ: 8.17 (d, J=8.8 Hz, 1H), 7.92 (s, 1H), 7.83 (d, J=8.8 Hz, 1H), 7.56 (dd, J=1.2 Hz, 8.8 Hz, 1H), 7.41 (d, J=8.8 Hz, 1H), 4.78 (s, 1H), 4.14-4.09 (m, 1H), 2.92-2.88 (m, 1H), 2.04-1.74 (m, 11H), 1.60-1.44 (m, 7H), 0.89 (d, J=6.0 Hz, 3H). LCMS m/z 456.1.1 [M+H]⁺

Example 204

8-(1-(6-((cis-4-(1,1-difluoroethyl)cyclohexyl)oxy)-5-(trifluoromethyl)naphthalen-2-yl) propyl)-8-azabicyclo[3.2.1]octane-3-carboxylic acid

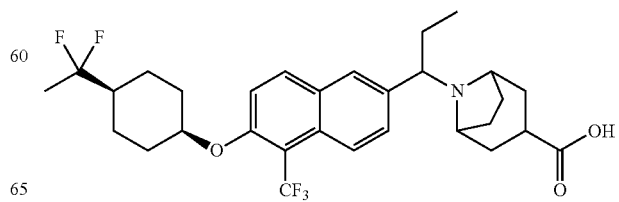

The title compound was prepared according to the method of Example 92. $^1$H NMR (400 MHz, CD$_3$OD) δ: 8.32 (d, J=8.8 Hz, 1H), 8.15 (d, J=9.6 Hz, 1H), 8.06 (s, 1H), 7.73 (d, J=8.8 Hz, 1H), 7.61 (d, J=9.6 Hz, 1H), 5.02 (s, 1H), 4.40-3.99 (m, 2H), 3.69-3.45 (m, 1H), 2.78-2.75 (m, 1H), 2.46-2.39 (m, 2H), 2.32-1.91 (m, 11H), 1.74-1.67 (m, 6H), 1.56 (t, J=18.8 Hz, 3H), 0.78 (t, J=7.2 Hz, 3H). LCMS m/z 554.3 [M+H]$^+$ Example 205

8-(1-(5-chloro-6-((cis-4-methylcyclohexyl)oxy) naphthalen-2-yl)ethyl)-8-azabicyclo[3.2.1]octane-3-carboxylic acid

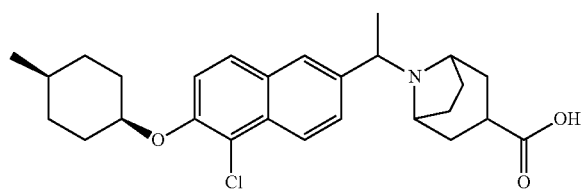 [SMILES: CC(c1ccc2c(Cl)c(O[C@H]3CC[C@@H](C)CC3)ccc2c1)N1C2CCC1CC(C(=O)O)C2]

The title compound was prepared according to the method of Example 93. $^1$H NMR (400 MHz, CD$_3$OD) δ: 8.32 (d, J=9.2 Hz, 1H), 8.02 (s, 1H), 7.88 (d, J=8.8 Hz, 1H), 7.74 (dd, J=1.6 Hz, 8.8 Hz, 1H), 7.52 (d, J=9.2 Hz, 1H), 4.87 (s, 1H), 4.46-4.42 (m, 1H), 4.34-4.30 (m, 1H), 3.53-3.49 (m, 1H), 2.71-2.63 (m, 1H), 2.41-2.37 (m, 1H), 2.27-1.79 (m, 12H), 1.69-1.53 (m, 7H), 0.97 (d, J=4.8 Hz, 3H). LCMS m/z 456.2 [M+H]$^+$ Example 206

9-(5-cyano-6-((cis-4-(trifluoromethyl)cyclohexyl) oxy)-2-naphthoyl)-9-azabicyclo[3.3.1]nonane-3-carboxylic acid

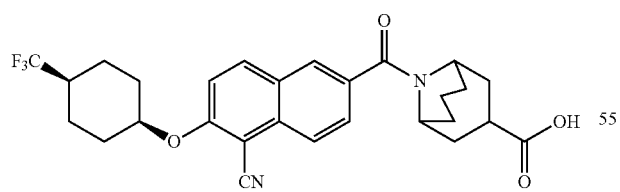

The title compound was prepared according to the method of Example 187. $^1$H NMR (400 MHz, DMSO-d$_6$) δ: 8.38 (d, J=9.2 Hz, 1H), 8.11 (s, 1H), 7.98 (d, J=8.4 Hz, 1H), 7.75-7.71 (m, 2H), 5.15 (s, 1H), 4.76-4.72 (m, 1H), 3.85-3.81 (m, 1H), 3.20-3.15 (m, 1H), 2.46-2.42 (m, 1H), 2.09-1.96 (m, 4H), 1.92-1.59 (m, 14H). LCMS m/z 515.2 [M+H]$^+$ Example 207

9-((5-cyano-6-((cis-4-methylcyclohexyl)oxy)naphthalen-2-yl)methyl)-9-azabicyclo[3.3.1]nonane-3-carboxylic acid

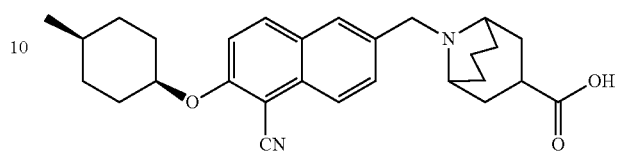

The title compound was prepared according to the method of Example 188. $^1$H NMR (400 MHz, CD$_3$OD) δ: 8.21 (d, J=9.2 Hz, 1H), 8.15 (s, 1H), 8.08 (d, J=8.4 Hz, 1H), 7.85 (dd, J=1.6 Hz, 8.4 Hz, 1H), 7.57 (d, J=9.2 Hz, 1H), 5.01 (s, 1H), 4.62 (s, 2H), 3.53-3.50 (m, 2H), 3.09-3.05 (m, 1H), 2.44-2.38 (m, 4H), 2.14-2.04 (m, 5H), 1.84-1.71 (m, 5H), 1.59-1.56 (m, 5H), 0.98 (d, J=7.6 Hz, 3H). LCMS m/z 447.2 [M+H]$^+$ Example 208

9-(5-chloro-6-((cis-4-methylcyclohexyl)oxy)-2-naphthoyl)-9-azabicyclo[3.3.1]nonane-3-carboxylic acid

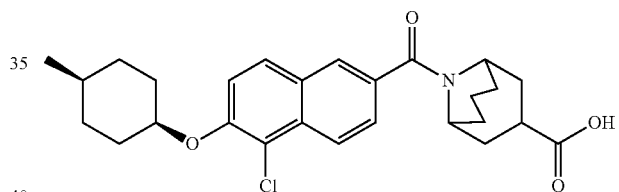

The title compound was prepared according to the method of Example 186. $^1$H NMR (400 MHz, DMSO-d$_6$) δ: 8.12 (d, J=8.8 Hz, 1H), 8.02 (d, J=9.2 Hz, 1H), 7.96 (s, 1H), 7.69-7.57 (m, 2H), 4.92 (s, 1H), 4.68-4.63 (m, 1H), 3.76-3.70 (m, 1H), 2.71-2.68 (m, 1H), 2.06-1.40 (m, 19H), 0.92 (d, J=6.0 Hz, 3H). LCMS m/z 470.2 [M+H]$^+$ Example 209

9-((6-((cis-4-(1,1-difluoroethyl)cyclohexyl)oxy)-5-(trifluoro-methyl)naphthalen-2-yl)methyl)-9-azabicyclo[3.3.1]nonane-3-carboxylic acid

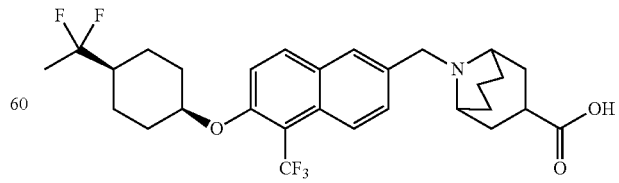

The title compound was prepared according to the method of Example 84. $^1$H NMR (400 MHz, CD$_3$OD) δ: 8.15 (d, J=8.4 Hz, 1H), 8.05-8.01 (m, 2H), 7.64 (dd, J=2.0 Hz, 8.8

Hz, 1H), 7.47 (d, J=9.6 Hz, 1H), 4.90 (s, 1H), 4.54 (s, 2H), 3.46-3.44 (m, 2H), 3.03-2.99 (m, 1H), 2.35-1.98 (m, 10H), 1.90-1.56 (m, 9H), 1.45 (t, J=18.8 Hz, 3H); LCMS m/z 540.2 [M+H]$^+$

Example 210

8-(1-(5-chloro-6-((cis-4-methylcyclohexyl)oxy) naphthalen-2-yl)propyl)-8-azabicyclo[3.2.1]octane-3-carboxylic acid

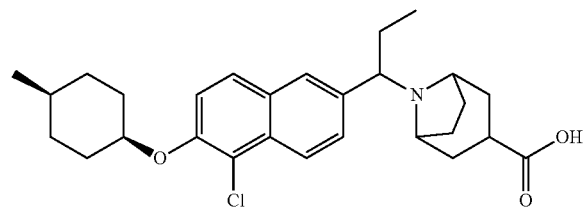 [SMILES: CCC(c1ccc2c(Cl)c(O[C@H]3CC[C@@H](C)CC3)ccc2c1)N1C2CCC1CC(C(=O)O)C2]

The title compound was prepared according to the method of Example 92. $^1$H NMR (400 MHz, CD$_3$OD) δ: 8.34 (d, J=8.4 Hz, 1H), 8.00 (s, 1H), 7.89 (d, J=9.2 Hz, 1H), 7.71 (dd, J=1.2 Hz, 8.8 Hz, 1H), 7.53 (d, J=9.6 Hz, 1H), 4.89-4.86 (m, 1H), 4.44-4.38 (m, 1H), 4.13-4.08 (m, 1H), 2.71-2.63 (m, 1H), 2.44-2.36 (m, 2H), 2.44-1.81 (m, 11H), 1.70-1.54 (m, 7H), 0.99-0.96 (m, 3H), 0.78 (t, J=7.2 Hz, 3H). LCMS m/z 470.2 [M+H]$^+$ Example 211

9-(1-(5-chloro-6-((cis-4-methylcyclohexyl)oxy) naphthalen-2-yl)propyl)-9-azabicyclo[3.3.1]nonane-3-carboxylic acid

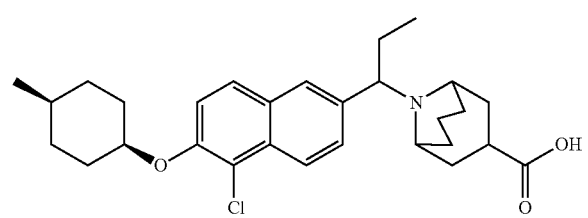 [SMILES: CCC(c1ccc2c(Cl)c(O[C@H]3CC[C@@H](C)CC3)ccc2c1)N1C2CCCC1CC(C(=O)O)C2]

The title compound was prepared according to the method of Example 92. $^1$H NMR (400 MHz, CD$_3$OD) δ: 8.32 (d, J=8.8 Hz, 1H), 8.08 (s, 1H), 7.89 (d, J=8.8 Hz, 1H), 7.76 (d, J=8.4 Hz, 1H), 7.52 (d, J=8.8 Hz, 1H), 4.89 (s, 1H), 4.84-4.79 (m, 1H), 3.23-3.30 (m, 2H), 3.06-3.00 (m, 1H), 2.43-1.53 (m, 21H), 0.98 (d, J=5.2 Hz, 3H), 0.75 (t, J=7.2 Hz, 3H). LCMS m/z 484.3 [M+H]+

Example 212

8-(1-(5-cyano-6-((cis-4-ethylcyclohexyl)oxy)naphthalen-2-yl)ethyl)-8-azabicyclo[3.2.1]octane-3-carboxylic acid

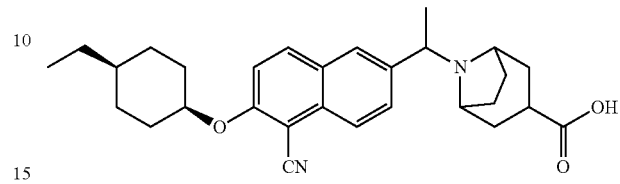

The title compound was prepared according to the method of Example 189. $^1$H NMR (400 MHz, CD$_3$OD) δ: 8.20 (d, J=8.8 Hz, 1H), 8.15-8.10 (m, 2H), 7.85 (dd, J=2.0 Hz, 9.2 Hz, 1H), 7.59 (d, J=9.6 Hz, 1H), 5.03 (s, 1H), 4.48-4.45 (m, 1H), 4.28-4.24 (m, 1H), 3.56-3.51 (m, 1H), 2.71-2.65 (m, 1H), 2.44-2.38 (m, 1H), 2.27-2.20 (m, 2H), 2.10-1.49 (m, 16H), 1.37-1.33 (m, 3H), 0.95 (t, J=7.6 Hz, 3H). LCMS m/z 461.3 [M+H]$^+$ Example 213

9-(1-(5-cyano-6-((cis-4-ethylcyclohexyl)oxy)naphthalen-2-yl)ethyl)-9-azabicyclo[3.3.1]nonane-3-carboxylic acid

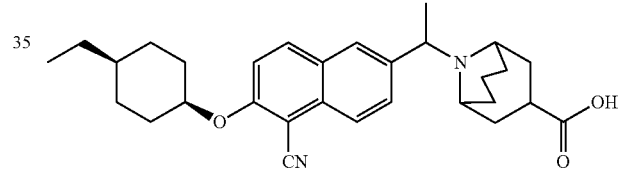

The title compound was prepared according to the method of Example 189. $^1$H NMR (400 MHz, CD$_3$OD) δ: 8.20 (d, J=9.2 Hz, 1H), 8.16 (s, 1H), 8.12 (d, J=9.2 Hz, 1H), 7.89 (d, J=9.2 Hz, 1H), 7.57 (d, J=9.2 Hz, 1H), 5.03-5.00 (m, 2H), 3.72-3.70 (m, 2H), 3.05-3.03 (m, 1H), 2.48-2.00 (m, 8H), 1.77-1.51 (m, 12H), 1.37-1.30 (m, 4H), 0.95 (t, J=7.6 Hz, 3H). LCMS m/z 475.3 [M+H]$^+$ Example 214

9-(1-(5-chloro-6-((cis-4-methylcyclohexyl)oxy) naphthalen-2-yl)ethyl)-9-azabicyclo[3.3.1]nonane-3-carboxylic acid

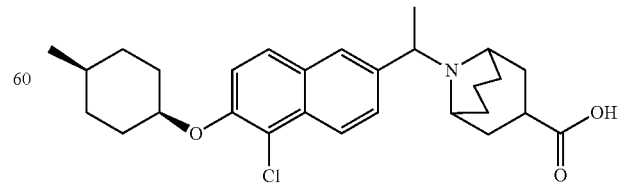 [SMILES: CC[C@H]1CC[C@@H](Oc2ccc3cc(C(C)N4C5CCCC4CC(C(=O)O)C5)ccc3c2C#N)CC1]

The title compound was prepared according to the method of Example 93. $^1$H NMR (400 MHz, CD$_3$OD) δ: 8.21 (d, J=8.8 Hz, 1H), 8.02 (s, 1H), 7.79 (d, J=9.2 Hz, 1H), 7.73 (d, J=8.8 Hz, 1H), 7.42 (d, J=9.2 Hz, 1H), 5.02-4.96 (m, 1H), 4.81-4.77 (m, 2H), 3.55-3.50 (m, 1H), 3.01-2.96 (m, 1H), 2.43-2.35 (m, 1H), 2.24-1.92 (m, 8H), 1.74-1.44 (m, 13H), 0.88 (d, J=5.6 Hz, 3H). LCMS m/z 470.2 [M+H]$^+$ Example 215

8-(5-chloro-6-((cis-4-ethylcyclohexyl)oxy)-2-naphthoyl)-8-azabicyclo[3.2.1]octane-3-carboxylic acid

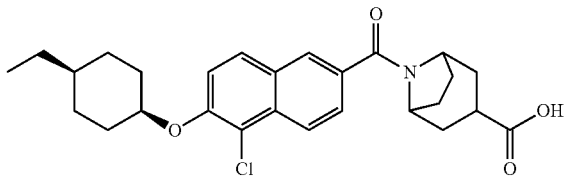

The title compound was prepared according to the method of Example 186. $^1$H NMR (400 MHz, CD$_3$OD) δ: 8.24 (d, J=9.2 Hz, 1H), 8.00 (s, 1H), 7.91 (d, J=8.8 Hz, 1H), 7.64 (d, J=8.8 Hz, 1H), 7.47 (d, J=9.2 Hz, 1H), 4.86-4.82 (m, 2H), 4.21-4.15 (m, 1H), 3.02-2.93 (m, 1H), 2.16-1.82 (m, 10H), 1.65-1.25 (m, 9H), 0.92 (t, J=7.2 Hz, 3H). LCMS m/z 470.2 [M+H]$^+$ Example 216

8-(1-(6-((cis-4-(1,1-difluoroethyl)cyclohexyl)oxy)-5-(trifluoromethyl)naphthalen-2-yl)ethyl)-8-azabicyclo[3.2.1]octane-3-carboxylic acid

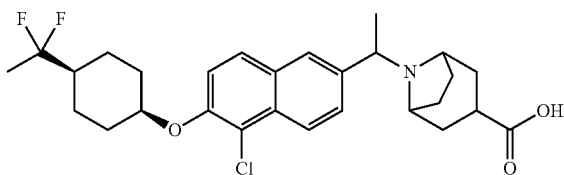 [SMILES: CC(c1ccc2c(Cl)c(O[C@H]3CC[C@@H](C(C)(F)F)CC3)ccc2c1)N1C2CCC1CC(C(=O)O)C2]

The title compound was prepared according to the method of Example 88. $^1$H NMR (400 MHz, CD$_3$OD) δ: 8.33 (d, J=9.2 Hz, 1H), 8.16 (d, J=9.2 Hz, 1H), 8.05 (s, 1H), 7.75 (d, J=9.2 Hz, 1H), 7.63 (d, J=9.2 Hz, 1H), 5.02 (s, 1H), 4.57-4.55 (m, 1H), 4.47-4.38 (m, 1H), 3.48-3.46 (m, 1H), 3.00-2.92 (m, 1H), 2.58-2.50 (m, 1H), 2.33-2.12 (m, 6H), 2.06-1.89 (m, 4H), 1.84 (d, J=6.8 Hz, 3H), 1.76-1.67 (m, 6H), 1.56 (t, J=19.2 Hz, 3H). LCMS m/z 540.3 [M+H]$^+$ Example 217

9-(1-(6-((cis-4-(1,1-difluoroethyl)cyclohexyl)oxy)-5-(trifluoromethyl)naphthalen-2-yl)ethyl)-9-azabicyclo[3.3.1]nonane-3-carboxylic acid

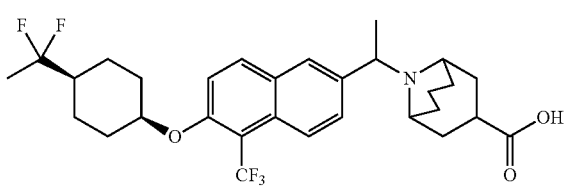 [SMILES: CC(c1ccc2c(C(F)(F)F)c(O[C@H]3CC[C@@H](C(C)(F)F)CC3)ccc2c1)N1C2CCCC1CC(C(=O)O)C2]

The title compound was prepared according to the method of Example 88. $^1$H NMR (400 MHz, CD$_3$OD) δ: 8.33 (d, J=8.8 Hz, 1H), 8.16-8.13 (m, 2H), 7.81 (d, J=9.2 Hz, 1H), 7.62 (d, J=9.6 Hz, 1H), 5.22-5.20 (m, 1H), 5.02 (s, 1H), 4.22-4.20 (m, 1H), 3.40-3.32 (m, 1H), 3.19-3.16 (m, 1H), 2.53-1.92 (m, 12H), 1.80-1.70 (m, 10H), 1.61 (t, J=18.8 Hz, 3H). LCMS m/z 554.3 [M+H]$^+$ Example 218

9-(5-cyano-6-((cis-4-methylcyclohexyl)oxy)-2-naphthoyl)-9-azabicyclo[3.3.1]nonane-3-carboxylic acid

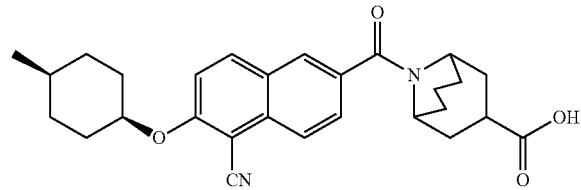 [SMILES: C[C@H]1CC[C@@H](Oc2ccc3cc(C(=O)N4C5CCCC4CC(C(=O)O)C5)ccc3c2C#N)CC1]

The title compound was prepared according to the method of Example 187. $^1$H NMR (400 MHz, DMSO-d$_6$) δ: 8.36 (d, J=9.2 Hz, 1H), 810 (s, 1H), 7.97 (d, J=8.4 Hz, 1H), 7.72-7.69 (m, 2H), 5.07 (s, 1H), 4.75-4.72 (m, 1H), 3.84-3.80 (m, 1H), 3.26-3.18 (m, 1H), 2.02-1.38 (m, 19H), 0.93 (d, J=6.4 Hz, 3H). LCMS m/z 461.2 [M+H]$^+$ Example 219

8-(5-cyano-6-((cis-4-methylcyclohexyl)oxy)-2-naphthoyl)-8-azabicyclo[3.2.1]octane-3-carboxylic acid

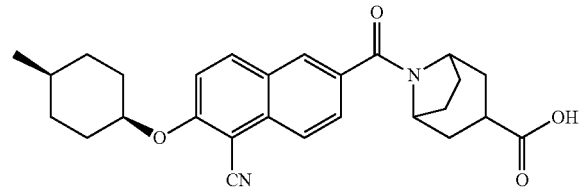

BIO-34182

The title compound was prepared according to the method of Example 187. $^1$H NMR (400 MHz, CD$_3$OD) δ: 8.26 (d, J=9.2 Hz, 1H), 8.10-8.08 (m, 2H), 7.77 (dd, J=1.6 Hz, 8.8 Hz, 1H), 7.58 (d, J=9.2 Hz, 1H), 5.03-5.02 (m, 1H), 4.86-4.83 (m, 1H), 4.22-4.18 (m, 1H), 3.01-2.98 (m, 1H), 2.12-1.71 (m, 12H), 1.60-1.55 (m, 5H), 0.99 (d, J=4.4 Hz, 3H). LCMS m/z 447.2 [M+H]$^+$

Example 220

8-(1-(5-cyano-6-((cis-4-ethylcyclohexyl)oxy)naphthalen-2-yl)propyl)-8-azabicyclo[3.2.1]octane-3-carboxylic acid

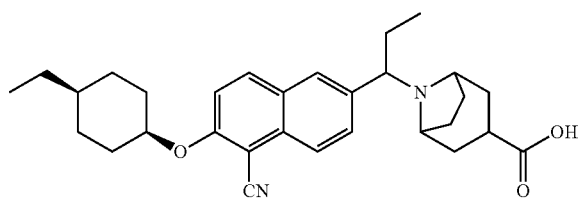 [SMILES: CCC(c1ccc2c(C#N)c(O[C@H]3CC[C@@H](CC)CC3)ccc2c1)N1C2CCC1CC(C(=O)O)C2]

The title compound was prepared according to the method of Example 189. ¹H NMR (400 MHz, CD₃OD) δ: 8.12 (d, J=9.2 Hz, 1H), 7.98-7.93 (m, 2H), 7.81 (d, J=8.0 Hz, 1H), 7.47 (d, J=9.6 Hz, 1H), 4.99 (s, 1H), 3.91-3.87 (m, 1H), 3.38-3.34 (m, 1H), 3.20-3.15 (m, 1H), 2.60-2.55 (m, 1H), 2.10-1.99 (m, 7H), 1.74-1.31 (m, 14H), 0.95 (t, J=7.2 Hz, 3H), 0.66 (t, J=7.2 Hz, 3H). LCMS m/z 475.2 [M+H]⁺

Example 221

9-(5-cyano-6-((cis-4-ethylcyclohexyl)oxy)-2-naphthoyl)-9-azabicyclo[3.3.1]nonane-3-carboxylic acid

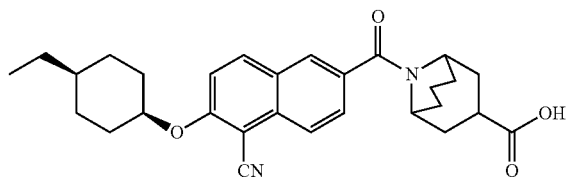 [SMILES: CC[C@H]1CC[C@@H](Oc2ccc3cc(C(=O)N4C5CCCC4CC(C(=O)O)C5)ccc3c2C#N)CC1]

The title compound was prepared according to the method of Example 187. ¹H NMR (400 MHz, CD₃OD) δ: 8.24 (d, J=8.8 Hz, 1H), 8.09 (d, J=8.4 Hz, 1H), 8.03 (d, J=1.2 Hz, 1H), 7.71 (dd, J=1.6 Hz, 8.4 Hz, 1H), 7.57 (d, J=9.2 Hz, 1H), 5.03 (s, 1H), 4.93-4.89 (m, 1H), 4.00-3.95 (m, 1H), 3.42-3.35 (m, 1H), 2.12-1.92 (m, 10H), 1.72-1.52 (m, 8H), 1.37-1.33 (m, 3H), 0.95 (t, J=6.8 Hz, 3H). LCMS m/z 475.2 [M+H]⁺

Example 222

8-(6-((cis-4-ethylcyclohexyl)oxy)-5-(trifluoromethyl)-2-naphthoyl)-8-azabicyclo[3.2.1]octane-3-carboxylic acid

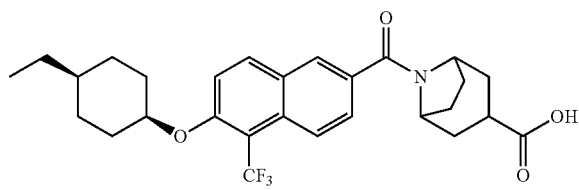 [SMILES: CC[C@H]1CC[C@@H](Oc2ccc3cc(C(=O)N4C5CCC4CC(C(=O)O)C5)ccc3c2C(F)(F)F)CC1]

The title compound was prepared according to the method of Example 104. ¹H NMR (400 MHz, DMSO-d₆) δ: 8.32 (d, J=9.6 Hz, 1H), 8.13-8.09 (m, 2H), 7.68 (d, J=8.8 Hz, 2H), 5.04 (s, 1H), 4.71-4.68 (m, 1H), 4.14-4.10 (m, 1H), 2.85-2.67 (m, 1H), 1.97-1.51 (m, 14H), 1.33-1.23 (m, 5H), 0.87 (t, J=7.2 Hz, 3H). LCMS m/z 504.2 [M+H]⁺

Example 223

8-(5-cyano-6-((cis-4-ethylcyclohexyl)oxy)-2-naphthoyl)-8-azabicyclo[3.2.1]octane-3-carboxylic acid

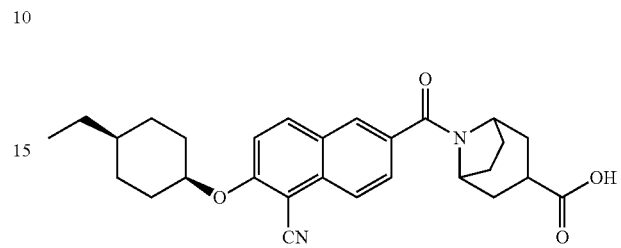

The title compound was prepared according to the method of Example 187. ¹H NMR (400 MHz, CD₃OD) δ: 8.26 (d, J=9.6 Hz, 1H), 8.11-8.07 (m, 2H), 7.78 (dd, J=1.6 Hz, 8.8 Hz, 1H), 7.58 (d, J=9.6 Hz, 1H), 5.03 (s, 1H), 4.89-4.80 (m, 1H), 4.19-4.15 (m, 1H), 2.95-2.88 (m, 1H), 2.11-1.52 (m, 16H), 1.37-1.29 (m, 3H), 0.95 (t, J=7.2 Hz, 3H). LCMS m/z 461.2 [M+H]⁺

Example 224

9-(6-((cis-4-ethylcyclohexyl)oxy)-5-(trifluoromethyl)-2-naphthoyl)-9-azabicyclo[3.3.1]nonane-3-carboxylic acid

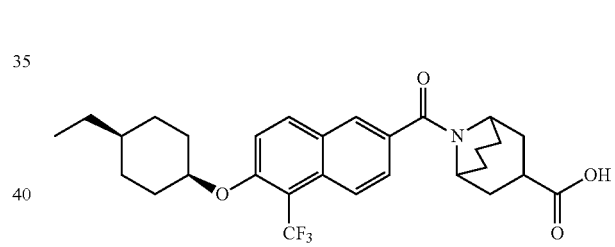

The title compound was prepared according to the method of Example 104. ¹H NMR (400 MHz, CD₃OD) δ: 8.09 (d, J=7.2 Hz, 1H), 8.00 (d, J=9.2 Hz, 1H), 7.84 (s, 1H), 7.47 (dd, J=2.0 Hz, 9.2 Hz, 1H), 7.41 (d, J=9.2 Hz, 1H), 4.80 (s, 1H), 3.82-3.78 (m, 1H), 3.13-3.06 (m, 1H), 2.06-1.73 (m, 10H), 1.59-1.15 (m, 12H), 0.79 (t, J=7.2 Hz, 3H). LCMS m/z 518.2 [M+H]⁺

Example 225

9-(1-(5-cyano-6-((cis-4-methylcyclohexyl)oxy)naphthalen-2-yl)ethyl)-9-azabicyclo[3.3.1]nonane-3-carboxylic acid

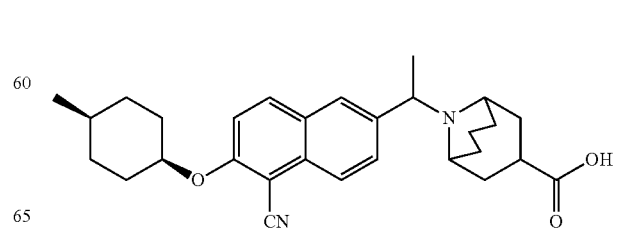

The title compound was prepared according to the method of Example 189. $^1$H NMR (400 MHz, CD$_3$OD) δ: 8.20 (d, J=9.6 Hz, 1H), 8.16 (s, 1H), 8.12 (d, J=8.8 Hz, 1H), 7.89 (dd, J=1.6 Hz, 8.8 Hz, 1H), 7.57 (d, J=9.6 Hz, 1H), 5.04-5.01 (m, 2H), 3.75-3.68 (m, 2H), 3.07-3.02 (m, 1H), 2.48-1.95 (m, 9H), 1.56-1.72 (m, 8H), 1.58-1.54 (m, 5H), 0.99 (d, J=4.8 Hz, 3H). LCMS m/z 461.2 [M+H]$^{30}$ Example 226

8-(1-(5-cyano-6-((cis-4-methylcyclohexyl)oxy)naphthalen-2-yl)propyl)-8-azabicyclo[3.2.1]octane-3-carboxylic acid

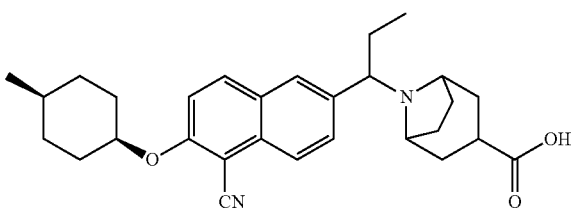 [SMILES: CCC(c1ccc2c(C#N)c(O[C@H]3CC[C@@H](C)CC3)ccc2c1)N1C2CCC1CC(C(=O)O)C2]

The title compound was prepared according to the method of Example 92. $^1$H NMR (400 MHz, CD$_3$OD) δ: 8.21 (d, J=9.2 Hz, 1H), 8.18 (d, J=8.8 Hz, 1H), 8.17 (s, 1H), 7.80 (d, J=8.8 Hz, 1H), 7.61 (d, J=9.2 Hz, 1H), 5.03 (s, 1H), 4.63-4.47 (m, 1H), 4.23-4.11 (m, 1H), 3.51-3.39 (m, 1H), 2.99-2.91 (m, 1H), 2.53-2.40 (m, 2H), 2.31-1.90 (m, 10H), 1.77-1.68 (m, 2H), 1.57-1.48 (m, 5H), 0.98 (d, J=5.6 Hz, 3H), 0.80 (t, J=7.6 Hz, 3H). LCMS m/z 461.2 [M+H]$^+$ Example 227

9-(5-chloro-6-((cis-4-ethylcyclohexyl)oxy)-2-naphthoyl)-9-azabicyclo[3.3.1]nonane-3-carboxylic acid

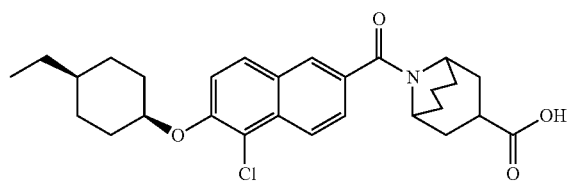

The title compound was prepared according to the method of Example 186. $^1$H NMR (400 MHz, CD$_3$OD) δ: 8.26 (d, J=8.8 Hz, 1H), 7.97 (s, 1H), 7.91 (d, J=9.2 Hz, 1H), 7.62 (dd, J=1.2 Hz, 8.8 Hz, 1H), 7.50 (d, J=9.2 Hz, 1H), 4.90-4386 (m, 2H), 3.95-3.92 (m, 1H), 3.29-3.19 (m, 1H), 2.20-1.85 (m, 10H), 1.74-1.54 (m, 8H), 1.37-1.29 (m, 3H), 0.94 (t, J=7.2 Hz, 3H). LCMS m/z 484.2 [M+H]$^+$ Example 228

9-(1-(5-cyano-6-(((1s,4s)-4-(trifluoromethyl)cyclohexyl)oxy)naphthalen-2-yl)ethyl)-9-azabicyclo[3.3.1]nonane-3-carboxylic acid

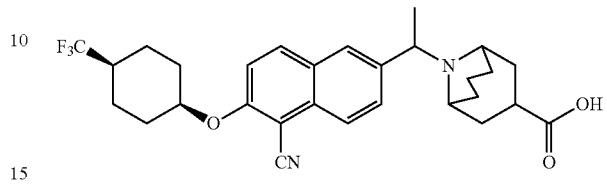

The title compound was prepared according to the method of Example 189. $^1$H NMR (400 MHz, CD$_3$OD) δ: 8.25-8.17 (m, 3H), 7.91 (d, J=8.8 Hz, 1H), 7.62 (d, J=9.2 Hz, 1H), 5.26-5.22 (m, 1H), 5.09 (s, 1H), 4.23-4.19 (m, 1H), 3.43-3.36 (m, 1H), 3.18-3.14 (m, 1H), 2.56-2.15 (m, 10H), 2.07-1.65 (m, 12H). LCMS m/z 515.2 [M+H]$^+$ Example 229

9-((5-cyano-6-((cis-4-(trifluoromethyl)cyclohexyl)oxy)naphthalen-2-yl)methyl)-9-azabicyclo[3.3.1]nonane-3-carboxylic acid

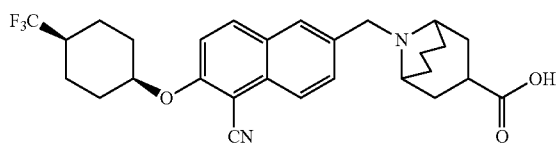 [SMILES: N#Cc1c(O[C@H]2CC[C@@H](C(F)(F)F)CC2)ccc2cc(CN3C4CCCC3CC(C(=O)O)C4)ccc12]

The title compound was prepared according to the method of Example 188. $^1$H NMR (300 MHz, METHANOL-d$_4$) δ 8.03-8.30 (m, 3H), 7.86 (dd, J=1.89, 8.69 Hz, 1H), 7.61 (d, J=9.06 Hz, 1H), 5.08 (br. s, 1H), 4.67-4.78 (m, 2H), 3.65 (br. s., 2H), 3.37-3.51 (m, 1H), 1.64-2.75 (m, 19H). LCMS m/z 501.1 [M+H]$^+$ Example 230

9-((5-(trifluoromethyl)-6-((cis-4-(trifluoromethyl)cyclohexyl)amino)naphthalen-2-yl)methyl)-9-azabicyclo[3.3.1]nonane-3-carboxylic acid

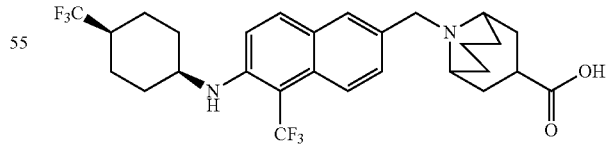

The title compound was prepared according to the method of Example 108. $^1$H NMR (400 MHz, METHANOL-d$_4$) δ 7.70-8.01 (m, 3H), 7.53 (d, J=9.04 Hz, 1H), 7.23 (d, J=9.54 Hz, 1H), 4.42-4.64 (m, 2H), 3.95 (br. s, 1H), 3.48-3.64 (m, 2H), 3.26-3.36 (m, 1H), 2.36-2.61 (m, 2H), 1.86-2.31 (m, 9H), 1.56-1.85 (m, 6H), 1.38-1.55 (m, 2H). LCMS m/z 543.3 [M+H]$^+$

Example 231 methyl 8-(5-(trifluoromethyl)-6-((cis-4-(trifluoromethyl)cyclohexyl)amino)-2-naphthoyl)-8-azabicyclo[3.2.1]octane-3-carboxylate

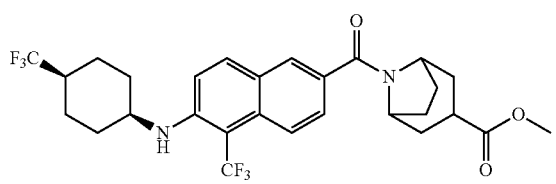 [SMILES: COC(=O)C1CC2CCC(C1)N2C(=O)c1ccc2c(C(F)(F)F)c(N[C@H]3CC[C@@H](C(F)(F)F)CC3)ccc2c1]

The title compound was prepared according to the method of Example 190. ¹H NMR (400 MHz, METHANOL-d₄) δ 7.87-8.11 (m, 3H), 7.58 (d, J=9.04 Hz, 1H), 7.33 (d, J=9.29 Hz, 1H), 4.65-4.75 (m, 1H), 4.28 (br. s., 1H), 4.07 (br. s., 1H), 3.70 (s, 3H), 2.94-3.12 (m, 1H), 2.28-2.39 (m, 1H), 1.73-2.20 (m, 14H), 1.49-1.71 (m, 2H). LCMS m/z 557.0 [M+H]⁺

Example 232

8-((r)-1-(6-((cis-4-methylcyclohexyl)oxy)-5-(trifluoromethyl) naphthalen-2-yl)propyl)-8-azabicyclo[3.2.1]octane-3-carboxylic acid and

Example 233

8-((s)-1-(6-((cis-4-methylcyclohexyl)oxy)-5-(trifluoromethyl) naphthalen-2-yl)propyl)-8-azabicyclo[3.2.1]octane-3-carboxylic acid

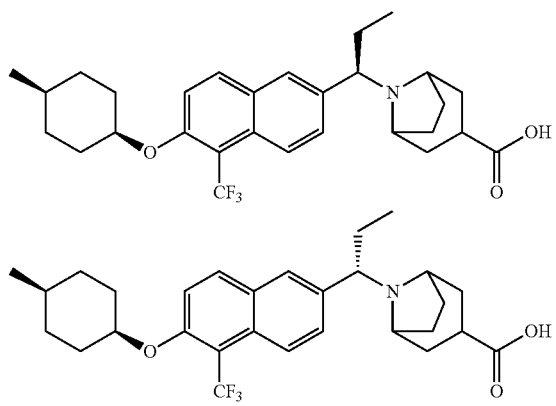

8-(1-(6-((cis-4-methylcyclohexyl)oxy)-5-(trifluoromethyl)naphthalen-2-yl)propyl)-8-azabicyclo[3.2.1]octane-3-carboxylic acid (350 mg) was put under the following SFC separation yielded 141 mg of peak-1(chemical purity >99%, ee >99%) and 141 mg of peak-2(chemical purity >99%, ee >99%). IC (2×15 cm); 30% methanol (0.1% NPA)/CO₂, 100 bar; 70 mL/min, 220 nm; inj vol.: 0.5 mL, 18 mg/mL methanol Peak-1 was assigned as Example 233: ¹H NMR (400 MHz, METHANOL-d₄) δ 8.32 (d, J=8.53 Hz, 1H), 8.12 (d, J=9.29 Hz, 1H), 8.01 (s, 1H), 7.68 (d, J=1.25 Hz, 1H), 7.59 (d, J=9.29 Hz, 1H), 4.94 (br. s., 1H), 4.51-4.65 (m, 1H), 4.08 (dd, J=3.01, 11.55 Hz, 1H), 3.37-3.45 (m, 1H), 2.85-3.05 (m, 1H), 1.87-2.68 (m, 12H), 1.70 (t, J=13.18 Hz, 2H), 1.33-1.58 (m, 5H), 0.96 (d, J=5.52 Hz, 3H), 0.78 (t, J=7.28 Hz, 3H). LCMS m/z 504.1 [M+H]⁺

Peak-2 was assigned as Example 234: ¹H NMR (400 MHz, METHANOL-d₄) δ 8.32 (d, J=8.53 Hz, 1H), 8.12 (d, J=9.29 Hz, 1H), 8.01 (s, 1H), 7.68 (d, J=1.25 Hz, 1H), 7.59 (d, J=9.29 Hz, 1H), 4.94 (br. s., 1H), 4.51-4.65 (m, 1H), 4.08 (dd, J=3.01, 11.55 Hz, 1H), 3.37-3.45 (m, 1H), 2.85-3.05 (m, 1H), 1.87-2.68 (m, 12H), 1.70 (t, J=13.18 Hz, 2H), 1.33-1.58 (m, 5H), 0.96 (d, J=5.52 Hz, 3H), 0.78 (t, J=7.28 Hz, 3H). LCMS m/z 504.1 [M+H]⁺

Example 234

8-(1-(5-chloro-6-((cis-4-(trifluoromethyl)cyclohexyl)oxy) naphthalen-2-yl)ethyl)-8-azabicyclo[3.2.1]octane-3-carboxylic acid

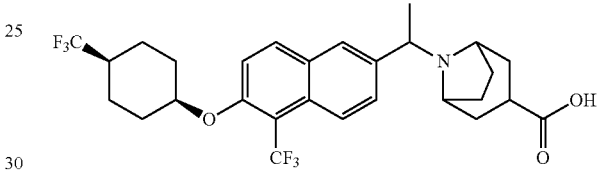

The title compound was prepared according to the method of Example 88. ¹H NMR (400 MHz, METHANOL-d₄) d 8.34 (d, J=8.78 Hz, 1H), 8.02 (s, 1H), 7.91 (d, J=9.04 Hz, 1H), 7.74 (d, J=8.78 Hz, 1H), 7.55 (d, J=9.29 Hz, 1H), 4.94 (br. s., 1H), 4.55 (br. s., 1H), 4.40 (d, J=6.53 Hz, 1H), 3.40-3.52 (m, 1H), 2.85-3.04 (m, 1H), 2.48-2.53 (m, 1H), 2.08-2.36 (m, 7H), 1.65-2.05 (m, 12H). LCMS m/z 510.0 [M+H]⁺

Example 235

9-(1-(5-chloro-6-((cis-4-(trifluoromethyl)cyclohexyl)oxy)naphthalen-2-yl)ethyl)-9-azabicyclo[3.3.1]nonane-3-carboxylic acid

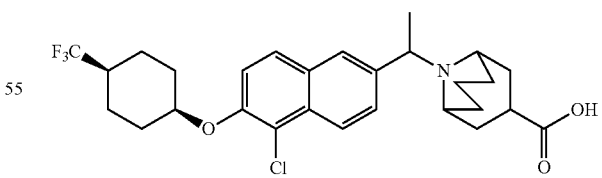

The title compound was prepared according to the method of Example 88. ¹H NMR (400 MHz, METHANOL-d₄) d 8.34 (d, J=8.78 Hz, 1H), 8.10 (d, J=8.03 Hz, 1H), 7.85-7.97 (m, 1H), 7.74-7.83 (m, 1H), 7.55 (d, J=9.29 Hz, 1H), 5.02-5.29 (m, 1H), 4.94 (br. s, 1H), 4.09-4.31 (m, 1H), 3.33-3.45 (m, 1H), 3.03-3.20 (m, 1H), 1.57-2.65 (m, 22H). LCMS m/z 524.0 [M+H]+

Example 236

8-(1-(5-chloro-6-((cis-4-ethylcyclohexyl)oxy)naph-thalen-2-yl)propyl)-8-azabicyclo[3.2.1]octane-3-carboxylic acid

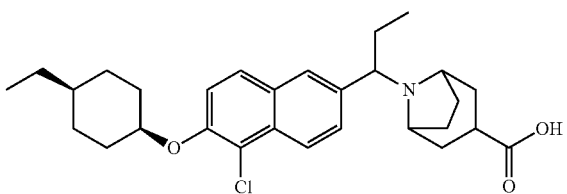 [SMILES: CCC(c1ccc2c(Cl)c(O[C@H]3CC[C@@H](CC)CC3)ccc2c1)N1C2CCC1CC(C(=O)O)C2]

The title compound was prepared according to the method of Example 92. ¹H NMR (400 MHz, METHANOL-d₄) δ 8.35 (d, J=8.78 Hz, 1H), 7.98 (s, 1H), 7.88 (d, J=9.04 Hz, 1H), 7.67 (dd, J=1.38, 8.91 Hz, 1H), 7.54 (d, J=9.04 Hz, 1H), 4.88 (br. s., 1H), 4.57 (d, J=6.53 Hz, 1H), 4.09 (dd, J=3.26, 11.55 Hz, 1H), 3.35-3.44 (m, 1H), 2.83-3.03 (m, 1H), 1.85-2.66 (m, 12H), 1.43-1.78 (m, 6H), 1.13-1.40 (m, 3H), 0.93 (t, J=7.15 Hz, 3H), 0.78 (t, J=7.28 Hz, 3H). LCMS m/z 484.1 [M+H]⁺

Example 237

9-(1-(5-chloro-6-((cis-4-ethylcyclohexyl)oxy)naph-thalen-2-yl)propyl)-9-azabicyclo[3.3.1]nonane-3-carboxylic acid

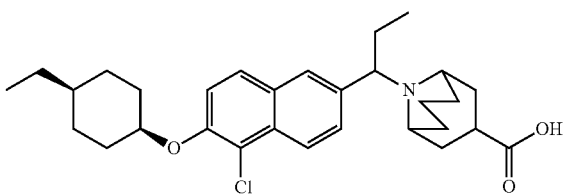 [SMILES: CCC(c1ccc2c(Cl)c(O[C@H]3CC[C@@H](CC)CC3)ccc2c1)N1C2CCCC1CC(C(=O)O)C2]

The title compound was prepared according to the method of Example 92. ¹H NMR (400 MHz, METHANOL-d₄) δ 8.35 (d, J=7.78 Hz, 1H), 8.07 (br. s., 1H), 7.84-7.95 (m, 1H), 7.74 (br. s., 1H), 7.53 (d, J=9.04 Hz, 1H), 4.83-4.93 (m, 1H), 4.70-4.80 (m, 1H), 4.21-4.30 (m, 1H), 3.37-3.45 (m, 1H), 3.01-3.18 (m, 1H), 1.80-2.64 (m, 13H), 1.41-1.79 (m, 7H), 1.21-1.41 (m, 3H), 0.93 (t, J=7.15 Hz, 3H), 0.75 (t, J=7.28 Hz, 3H). LCMS m/z 498.0 [M+H]⁺

Example 238

9-((R)-1-(5-chloro-6-((cis-4-ethylcyclohexyl)oxy)naphthalen-2-yl)ethyl)-9-azabicyclo[3.3.1]nonane-3-carboxylic acid and

Example 239

9-((S)-1-(5-chloro-6-((cis-4-ethylcyclohexyl)oxy)naphthalen-2-yl)ethyl)-9-azabicyclo[3.3.1]nonane-3-carboxylic acid

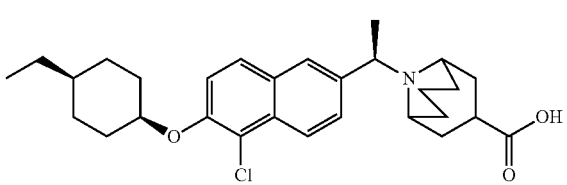

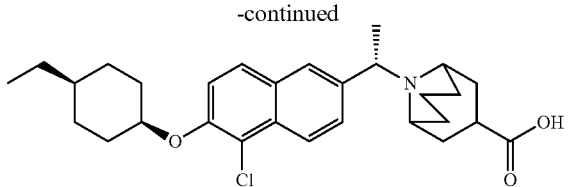

9-(1-(5-chloro-6-((cis-4-ethylcyclohexyl)oxy)naphtha-len-2-yl)ethyl)-9-azabicyclo[3.3.1]nonane-3-carboxylic acid (217 mg) was put under the following SFC separation yielded 42 mg of peak-1(chemical purity >99%, ee >99%) and 46 mg of peak-2(chemical purity >99%, ee >99%). Whelk0-1 from Regis Technologies (3×25 cm); acetonitrile:methanol (3:1) (1% isopropylamine)/CO₂, 100 bar; 80 mL/min, 220 nm; inj vol.: 0.5 mL, 18 mg/mL methanol Peak-1 was assigned as Example 239: ¹H NMR (400 MHz, METHANOL-d4) δ 8.33 (d, J=9.04 Hz, 1H), 8.08 (d, J=8.03 Hz, 1H), 7.83-7.93 (m, 1H), 7.78 (d, J=8.78 Hz, 1H), 7.53 (d, J=9.04 Hz, 1H), 5.00-5.29 (m, 1H), 4.88 (br. s., 1H), 4.11-4.28 (m, 1H), 3.28-3.42 (m, 1H), 3.07-3.20 (m, 1H), 1.40-2.65 (m, 21H), 1.21-1.41 (m, 3H), 0.93 (t, J=7.15 Hz, 3H). LCMS m/z 484.1 [M+H]⁺

Peak-2 was assigned as Example 240: ¹H NMR (400 MHz, METHANOL-d4) δ 8.33 (d, J=9.04 Hz, 1H), 8.08 (d, J=8.03 Hz, 1H), 7.83-7.93 (m, 1H), 7.78 (d, J=8.78 Hz, 1H), 7.53 (d, J=9.04 Hz, 1H), 5.00-5.29 (m, 1H), 4.88 (br. s., 1H), 4.11-4.28 (m, 1H), 3.28-3.42 (m, 1H), 3.07-3.20 (m, 1H), 1.40-2.65 (m, 21H), 1.21-1.41 (m, 3H), 0.93 (t, J=7.15 Hz, 3H). LCMS m/z 484.1 [M+H]⁺

Example 240

9-((R)-1-(5-chloro-6-((cis-4-(trifluoromethyl)cyclo-hexyl)oxy)naphthalen-2-yl)ethyl)-9-azabicyclo[3.3.1]nonane-3-carboxylic acid and

Example 241

9-((S)-1-(5-chloro-6-((cis-4-(trifluoromethyl)cyclo-hexyl)oxy)naphthalen-2-yl)ethyl)-9-azabicyclo[3.3.1]nonane-3-carboxylic acid

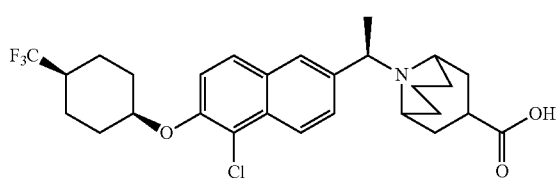

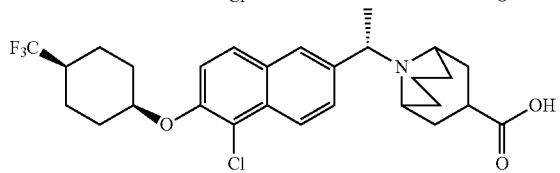

9-(1-(5-chloro-6-((cis-4-(trifluoromethyl)cyclohexyl)oxy)naphthalen-2-yl)ethyl)-9-azabicyclo[3.3.1]nonane-3-carboxylic acid (285 mg) was put under the following SFC separation yielded 115 mg of peak-1(chemical purity >99%, ee >99%) and 122 mg of peak-2(chemical purity >99%, ee >99%). Whelk0-1 from Regis Technologies (3×25 cm); isopropanol:methanol (1:1) (1% isopropylamine)/CO₂, 100 bar; 80 mL/min, 220 nm; inj vol.: 0.5 mL, 18 mg/mL methanol:dichloromethane (8:2)

Peak-1 was assigned as Example 241: $^1$H NMR (400 MHz, METHANOL-d4) δ 8.34 (d, J=8.78 Hz, 1H), 8.10 (d, J=8.03 Hz, 1H), 7.85-7.97 (m, 1H), 7.74-7.83 (m, 1H), 7.55 (d, J=9.29 Hz, 1H), 5.02-5.29 (m, 1H), 4.94 (br. s., 1H), 4.09-4.31 (m, 1H), 3.33-3.45 (m, 1H), 3.03-3.20 (m, 1H), 1.57-2.65 (m, 22H). LCMS m/z 524.0 [M+H]$^+$ Peak-2 was assigned as Example 242: $^1$H NMR (400 MHz, METHANOL-d4) δ 8.34 (d, J=8.78 Hz, 1H), 8.10 (d, J=8.03 Hz, 1H), 7.85-7.97 (m, 1H), 7.74-7.83 (m, 1H), 7.55 (d, J=9.29 Hz, 1H), 5.02-5.29 (m, 1H), 4.94 (br. s., 1H), 4.09-4.31 (m, 1H), 3.33-3.45 (m, 1H), 3.03-3.20 (m, 1H), 1.57-2.65 (m, 22H). LCMS m/z 524.0 [M+H]$^+$ Example 242

8-((R)-1-(5-chloro-6-((cis-4-(trifluoromethyl)cyclohexyl)oxy)naphthalen-2-yl)ethyl)-8-azabicyclo[3.2.1]octane-3-carboxylic acid and Example 243

8-((S)-1-(5-chloro-6-((cis-4-(trifluoromethyl)cyclohexyl)oxy)naphthalen-2-yl)ethyl)-8-azabicyclo[3.2.1]octane-3-carboxylic acid

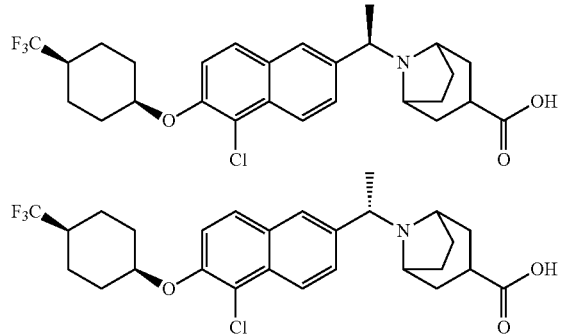

8-(1-(5-chloro-6-((cis-4-(trifluoromethyl)cyclohexyl)oxy)naphthalen-2-yl)ethyl)-8-azabicyclo[3.2.1]octane-3-carboxylic acid (300 mg) was put under the following SFC separation yielded 118 mg of peak-1(chemical purity >99%, ee >99%) and 118 mg of peak-2(chemical purity >99%, ee >99%). IC (2.1×25 cm); methanol (1% isopropylamine)/CO$_2$, 100 bar; 80 mL/min, 220 nm; inj vol.: 0.5 mL, 18 mg/mL methanol Peak-1 was assigned as Example 243: $^1$H NMR (400 MHz, METHANOL-d$_4$) δ 8.34 (d, J=8.78 Hz, 1H), 8.02 (s, 1H), 7.91 (d, J=9.04 Hz, 1H), 7.74 (d, J=8.78 Hz, 1H), 7.55 (d, J=9.29 Hz, 1H), 4.94 (br. s., 1H), 4.55 (br. s., 1H), 4.40 (d, J=6.53 Hz, 1H), 3.40-3.52 (m, 1H), 2.85-3.04 (m, 1H), 2.48-2.53 (m, 1H), 2.08-2.36 (m, 7H), 1.65-2.05 (m, 12H) LCMS m/z 510.0 [M+H]$^+$ Peak-2 was assigned as Example 244: $^1$H NMR (400 MHz, METHANOL-d$_4$) δ 8.34 (d, J=8.78 Hz, 1H), 8.02 (s, 1H), 7.91 (d, J=9.04 Hz, 1H), 7.74 (d, J=8.78 Hz, 1H), 7.55 (d, J=9.29 Hz, 1H), 4.94 (br. s., 1H), 4.55 (br. s., 1H), 4.40 (d, J=6.53 Hz, 1H), 3.40-3.52 (m, 1H), 2.85-3.04 (m, 1H), 2.48-2.53 (m, 1H), 2.08-2.36 (m, 7H), 1.65-2.05 (m, 12H) LCMS m/z 510.0 [M+H]$^+$ Example 244 methyl 9-(5-(trifluoromethyl)-6-((cis-4-(trifluoromethyl)cyclohexyl)amino)-2-naphthoyl)-9-azabicyclo[3.3.1]nonane-3-carboxylate

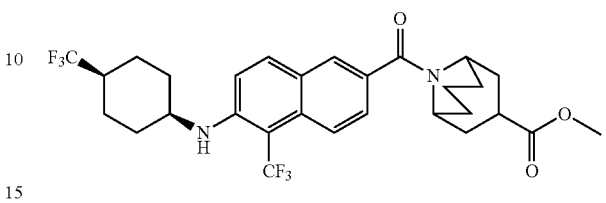

The title compound was prepared according to the method of Example 190. $^1$H NMR (400 MHz, METHANOL-d$_4$) δ 7.88-8.04 (m, 2H), 7.83 (d, J=1.76 Hz, 1H), 7.49 (dd, J=1.76, 9.04 Hz, 1H), 7.30 (d, J=9.29 Hz, 1H), 4.88 (s, 1H), 4.04 (br. s, 2H), 3.68 (s, 3H), 3.36-3.51 (m, 1H), 2.20-2.41 (m, 1H), 1.42-2.17 (m, 18H). LCMS m/z 571.0 [M+H]$^+$ Example 245

9-(5-(trifluoromethyl)-6-((cis-4-(trifluoromethyl)cyclohexyl)amino)-2-naphthoyl)-9-azabicyclo[3.3.1]nonane-3-carboxylic acid

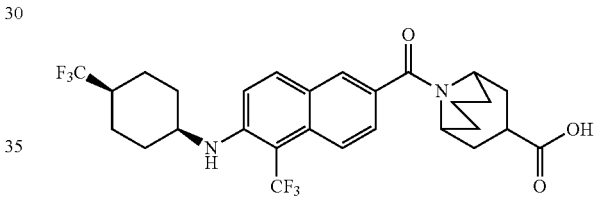

The title compound was prepared according to the method of Example 190. $^1$H NMR 1H NMR (400 MHz, METHANOL-d$_4$) δ 7.90-8.06 (m, 2H), 7.83 (s, 1H), 7.50 (dd, J=1.51, 9.04 Hz, 1H), 7.30 (d, J=9.29 Hz, 1H), 4.91 (s, 1H), 4.04 (br. s, 2H), 3.36-3.45 (m, 1H), 2.22-2.45 (m, 1H), 1.45-2.17 (m, 18H). LCMS m/z 557.0 [M+H]$^+$ Example 246

8-((R)-1-(5-chloro-6-((cis-4-ethylcyclohexyl)oxy)naphthalen-2-yl)propyl)-8-azabicyclo[3.2.1]octane-3-carboxylic acid and Example 247

8-((S)-1-(5-chloro-6-((cis-4-ethylcyclohexyl)oxy)naphthalen-2-yl)propyl)-8-azabicyclo[3.2.1]octane-3-carboxylic acid

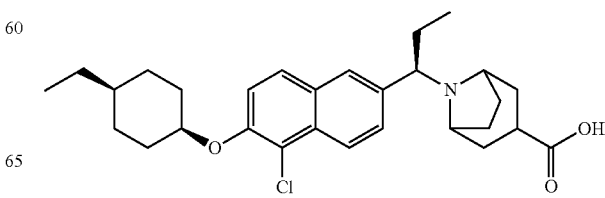

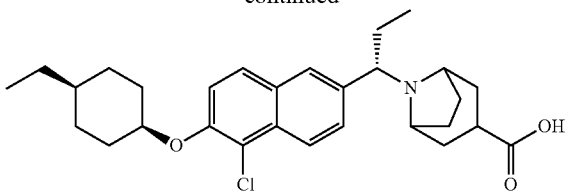

8-(1-(5-chloro-6-((cis-4-ethylcyclohexyl)oxy)naphthalen-2-yl)propyl)-8-azabicyclo[3.2.1]octane-3-carboxylic acid (312 mg) was put under the following SFC separation yielded 118 mg of peak-1(chemical purity >99%, ee >99%) and 120 mg of peak-2(chemical purity >99%, ee >98%). IC (2×25 cm); 50% methanol (0.1% DEA)/$CO_2$, 100 bar; 70 mL/min, 220 nm; inj vol.: 0.8 mL, 15.6 mg/mL methanol Peak-1 was assigned as Example 247: 1H NMR (400 MHz, METHANOL-$d_4$) δ 8.35 (d, J=8.78 Hz, 1H), 7.98 (s, 1H), 7.88 (d, J=9.04 Hz, 1H), 7.67 (dd, J=1.38, 8.91 Hz, 1H), 7.54 (d, J=9.04 Hz, 1H), 4.88 (br. s., 1H), 4.57 (d, J=6.53 Hz, 1H), 4.09 (dd, J=3.26, 11.55 Hz, 1H), 3.35-3.44 (m, 1H), 2.83-3.03 (m, 1H), 1.85-2.66 (m, 12H), 1.43-1.78 (m, 6H), 1.13-1.40 (m, 3H), 0.93 (t, J=7.15 Hz, 3H), 0.78 (t, J=7.28 Hz, 3H). LCMS m/z 484.1 $[M+H]^+$ Peak-2 was assigned as Example 248: $^1$H NMR (400 MHz, METHANOL-$d_4$) δ 8.35 (d, J=8.78 Hz, 1H), 7.98 (s, 1H), 7.88 (d, J=9.04 Hz, 1H), 7.67 (dd, J=1.38, 8.91 Hz, 1H), 7.54 (d, J=9.04 Hz, 1H), 4.88 (br. s., 1H), 4.57 (d, J=6.53 Hz, 1H), 4.09 (dd, J=3.26, 11.55 Hz, 1H), 3.35-3.44 (m, 1H), 2.83-3.03 (m, 1H), 1.85-2.66 (m, 12H), 1.43-1.78 (m, 6H), 1.13-1.40 (m, 3H), 0.93 (t, J=7.15 Hz, 3H), 0.78 (t, J=7.28 Hz, 3H). LCMS m/z 484.1 $[M+H]^+$ Example 248

9-((R)-1-(5-chloro-6-((cis-4-ethylcyclohexyl)oxy)naphthalen-2-yl)propyl)-9-azabicyclo[3.3.1]nonane-3-carboxylic acid and Example 249

9-((S)-1-(5-chloro-6-((cis-4-ethylcyclohexyl)oxy)naphthalen-2-yl)propyl)-9-azabicyclo[3.3.1]nonane-3-carboxylic acid

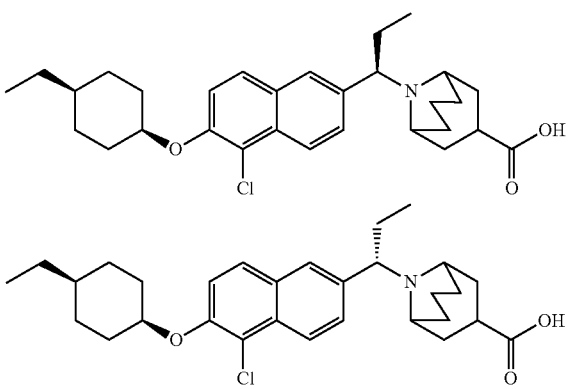

9-(1-(5-chloro-6-((cis-4-ethylcyclohexyl)oxy)naphthalen-2-yl)propyl)-9-azabicyclo[3.3.1]nonane-3-carboxylic acid (99 mg) was put under the following SFC separation yielded 37 mg of peak-1(chemical purity >99%, ee >99%) and 39 mg of peak-2(chemical purity >99%, ee >98%). AS-H (2×25 cm); 30% ethanol (0.1% DEA)/$CO_2$, 100 bar; 70 mL/min, 220 nm; inj vol.: 0.5 mL, 9.9 mg/mL methanol Peak-1 was assigned as Example 249: 1H NMR (400 MHz, METHANOL-$d_4$) δ 8.35 (d, J=7.78 Hz, 1H), 8.07 (br. s., 1H), 7.84-7.95 (m, 1H), 7.74 (br. s., 1H), 7.53 (d, J=9.04 Hz, 1H), 4.83-4.93 (m, 1H), 4.70-4.80 (m, 1H), 4.21-4.30 (m, 1H), 3.37-3.45 (m, 1H), 3.01-3.18 (m, 1H), 1.80-2.64 (m, 13H), 1.41-1.79 (m, 7H), 1.21-1.41 (m, 3H), 0.93 (t, J=7.15 Hz, 3H), 0.75 (t, J=7.28 Hz, 3H). LCMS m/z 498.1$[M+H]^+$ Peak-2 was assigned as Example 250: $^1$H NMR (400 MHz, METHANOL-$d_4$) δ 8.35 (d, J=7.78 Hz, 1H), 8.07 (br. s., 1H), 7.84-7.95 (m, 1H), 7.74 (br. s., 1H), 7.53 (d, J=9.04 Hz, 1H), 4.83-4.93 (m, 1H), 4.70-4.80 (m, 1H), 4.21-4.30 (m, 1H), 3.37-3.45 (m, 1H), 3.01-3.18 (m, 1H), 1.80-2.64 (m, 13H), 1.41-1.79 (m, 7H), 1.21-1.41 (m, 3H), 0.93 (t, J=7.15 Hz, 3H), 0.75 (t, J=7.28 Hz, 3H). LCMS m/z 498.1$[M+H]^+$ Example 250

8-((R)-1-(5-chloro-6-((cis-4-ethylcyclohexyl)oxy)naphthalen-2-yl)ethyl)-8-azabicyclo[3.2.1]octane-3-carboxylic acid and Example 251

8-((S)-1-(5-chloro-6-((cis-4-ethylcyclohexyl)oxy)naphthalen-2-yl)ethyl)-8-azabicyclo[3.2.1]octane-3-carboxylic acid

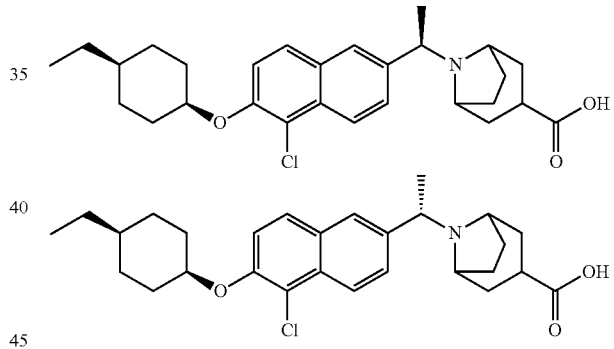

8-(1-(5-chloro-6-((cis-4-ethylcyclohexyl)oxy)naphthalen-2-yl)ethyl)-8-azabicyclo[3.2.1]octane-3-carboxylic acid (268 mg) was put under the following SFC separation yielded 89 mg of peak-1(chemical purity >99%, ee >99%) and 92 mg of peak-2(chemical purity >99%, ee >98%). AY-H (2×25 cm); 25% isopropanol (0.1% DEA)/$CO_2$, 100 bar; 85 mL/min, 220 nm; inj vol.: 0.75 mL, 3 mg/mL methanol Peak-1 was assigned as Example 251: $^1$H NMR (400 MHz, METHANOL-$d_4$) δ 8.33 (d, J=9.04 Hz, 1H), 7.99 (s, 1H), 7.88 (d, J=9.04 Hz, 1H), 7.71 (dd, J=1.51, 9.04 Hz, 1H), 7.53 (d, J=9.04 Hz, 1H), 4.88 (br. s., 1H), 4.54 (d, J=6.27 Hz, 1H), 4.40 (q, J=6.53 Hz, 1H), 3.38-3.53 (m, 1H), 2.95 (tt, J=5.93, 11.76 Hz, 1H), 2.46-2.63 (m, 1H), 1.75-2.37 (m, 12H), 1.45-1.73 (m, 6H), 1.23-1.39 (m, 3H), 0.93 (t, J=7.15 Hz, 3H). LCMS m/z 470.1 $[M+H]^+$ Peak-2 was assigned as Example 252: $^1$H NMR (400 MHz, METHANOL-$d_4$) δ 8.33 (d, J=9.04 Hz, 1H), 7.99 (s, 1H), 7.88 (d, J=9.04 Hz, 1H), 7.71 (dd, J=1.51, 9.04 Hz, 1H), 7.53 (d, J=9.04 Hz, 1H), 4.88 (br. s., 1H), 4.54 (d, J=6.27 Hz, 1H), 4.40 (q, J=6.53 Hz, 1H), 3.38-3.53 (m, 1H), 2.95 (tt, J=5.93, 11.76 Hz, 1H), 2.46-2.63 (m, 1H), 1.75-2.37 (m, 12H), 1.45-1.73 (m, 6H), 1.23-1.39 (m, 3H), 0.93 (t, J=7.15 Hz, 3H). LCMS m/z 470.1 [M+H]+

Example 252 methyl 8-(5-(trifluoromethyl)-6-((cis-4-(trifluoromethyl)cyclohexyl)amino)-2-naphthoyl)-8-azabicyclo[3.2.1]octane-3-carboxylate

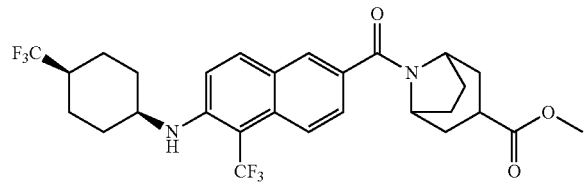 [SMILES: COC(=O)C1CC2CCC(C1)N2C(=O)c1ccc2c(C(F)(F)F)c(N[C@H]3CC[C@@H](C(F)(F)F)CC3)ccc2c1]

The title compound was prepared according to the method of Example 190. ¹H NMR (400 MHz, METHANOL-d₄) d 8.05 (d, J=8.78 Hz, 1H), 7.90 (d, J=1.25 Hz, 1H), 7.82 (d, J=9.04 Hz, 1H), 7.58 (dd, J=1.63, 8.66 Hz, 1H), 7.27 (d, J=9.04 Hz, 1H), 4.81 (br. s., 1H), 4.24 (br. s., 1H), 3.99 (t, J=3.26 Hz, 1H), 3.67 (s, 3H), 3.03 (tt, J=5.87, 11.70 Hz, 1H), 2.21-2.38 (m, 1H), 1.59-2.16 (m, 16H). LCMS m/z 523.0 [M+H]+

Example 253

8-(5-(trifluoromethyl)-6-((cis-4-(trifluoromethyl)cyclohexyl)amino)-2-naphthoyl)-8-azabicyclo[3.2.1]octane-3-carboxylic acid

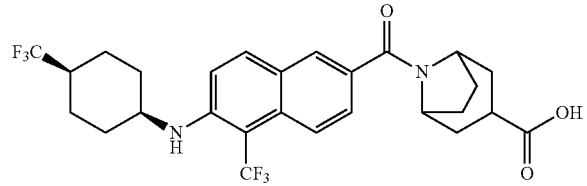

The title compound was prepared according to the method of Example 190. ¹H NMR (400 MHz, METHANOL-d₄) d 8.06 (d, J=8.78 Hz, 1H), 7.91 (d, J=1.00 Hz, 1H), 7.82 (d, J=9.04 Hz, 1H), 7.58 (dd, J=1.76, 8.78 Hz, 1H), 7.28 (d, J=9.04 Hz, 1H), 4.81 (br. s., 1H), 4.25 (br. s., 1H), 4.00 (t, J=3.26 Hz, 1H), 2.98 (tt, J=5.99, 11.58 Hz, 1H), 2.22-2.43 (m, 1H), 1.54-2.18 (m, 16H). LCMS m/z 509.0 [M+H]+

Example 254

9-(2-((cis-4-(tert-butyl)cyclohexyl)amino) quinazoline-6-carbonyl)-9-azabicyclo[3.3.1]nonane-3-carboxylic acid

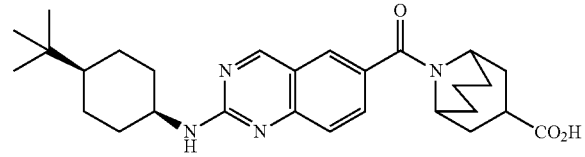 [SMILES: CC(C)(C)[C@H]1CC[C@@H](Nc2ncc3cc(C(=O)N4C5CCCC4CC(C(=O)O)C5)ccc3n2)CC1]

The title compound was prepared according to the method of Example 192. ¹H NMR (400 MHz, CD₃OD) δ: 9.08 (s, 1H), 7.86 (d, J=1.2 Hz, 1H), 7.75 (dd, J=2.0 Hz, 8.8 Hz, 1H), 7.60 (d, J=8.0 Hz, 1H), 4.63-4.57 (m, 1H), 4.05-4.00 (m, 1H), 3.90-3.85 (m, 1H), 3.37-3.33 (m, 1H), 2.18-1.73 (m, 14H), 1.38-1.07 (m, 5H), 0.92 (s, 9H); LCMS m/z 479.3 [M+H]+

Example 255

8-((3-((trans-4-methylcyclohexyl)amino) isoquinolin-7-yl)methyl)-8-azabicyclo[3.2.1]octane-3-carboxylic acid

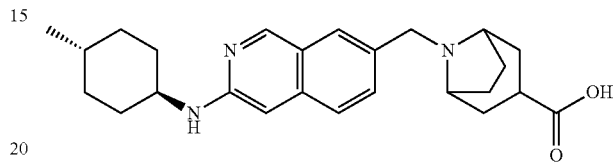

The title compound was prepared according to the method of Example 193. ¹H NMR (400 MHz, CD₃OD) δ: 8.77 (s, 1H), 7.84 (s, 1H), 7.59 (s, 2H), 6.65 (s, 1H), 3.98 (s, 2H), 3.62-3.58 (m, 2H), 3.53-3.50 (m, 1H), 2.62-2.59 (m, 1H), 2.28-2.25 (m, 2H), 2.13-2.11 (m, 2H), 2.15-1.98 (m, 2H), 1.90-1.88 (m, 2H), 1.82-1.78 (m, 4H), 1.45-1.43 (m, 1H), 1.31-1.24 (m, 2H), 1.21-1.14 (m, 2H), 0.97 (d, J=6.4 Hz, 3H); ESI-MS (M+H)+: 408.1.

Example 256

8-(2-((cis-4-(tert-butyl)cyclohexyl)amino) quinazoline-6-carbonyl)-8-azabicyclo[3.2.1]octane-3-carboxylic acid

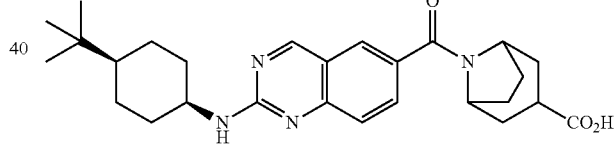

The title compound was prepared according to the method of Example 192. ¹H NMR (400 MHz, DMSO-d₆) δ: 9.30 (s, 1H), 8.04 (s, 1H), 7.82 (d, J=8.8 Hz, 1H), 7.56 (d, J=8.8 Hz, 1H), 4.68-4.63 (m, 1H), 4.26-4.16 (m, 2H), 2.89-2.85 (m, 1H), 1.96-1.75 (m, 10H), 1.59-1.36 (m, 6H), 1.06-1.00 (m, 1H), 0.86 (s, 9H). LCMS m/z 465.3 [M+H]+

Example 257

8-(2-((trans-4-methylcyclohexyl)amino) quinazoline-6-carbonyl)-8-azabicyclo[3.2.1]octane-3-carboxylic acid

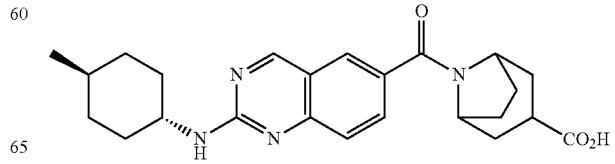

The title compound was prepared according to the method of Example 192. ¹H NMR (400 MHz, DMSO-d₆) δ: 9.27 (s, 1H), 8.20 (br s, 1H), 8.03 (s, 1H), 7.82 (d, J=8.8 Hz, 1H), 7.56 (d, J=8.8 Hz, 1H), 4.68-4.63 (m, 1H), 4.18-4.10 (m, 2H), 2.88-2.84 (m, 1H), 1.94-1.71 (m, 12H), 1.40-1.31 (m, 3H), 1.10-1.04 (m, 2H), 0.90 (d, J=6.4 Hz, 3H). LCMS m/z 423.2 [M+H]³⁰

Example 258

9-((3-(((trans-4-methylcyclohexyl)amino)isoquinolin-7-yl)methyl)-9-azabicyclo[3.3.1]nonane-3-carboxylic acid

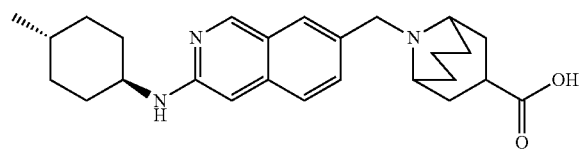 [SMILES: C[C@H]1CC[C@H](Nc2cc3ccc(CN4C5CCCC4CC(C(=O)O)C5)cc3cn2)CC1]

The title compound was prepared according to the method of Example 193. ¹H NMR (400 MHz, CD₃OD) δ: 8.93 (s, 1H), 8.13 (s, 1H), 7.77 (s, 2H), 7.10 (s, 1H), 4.65 (s, 2H), 3.69-3.66 (m, 2H), 3.59-3.53 (m, 1H), 3.43-3.40 (m, 1H), 2.52-1.82 (m, 14H), 1.48-1.35 (m, 3H), 1.28-1.14 (m, 2H), 0.98 (d, J=6.4 Hz, 3H). ESI-MS (M+H)⁺: 422.1.

Example 259

8-((4-chloro-3-((trans-4-methylcyclohexyl)amino)isoquinolin-7-yl)methyl)-8-azabicyclo[3.2.1]octane-3-carboxylic acid

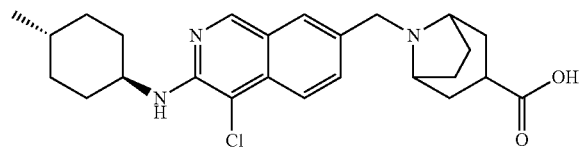 [SMILES: C[C@H]1CC[C@H](Nc2ncc3cc(CN4C5CCC4CC(C(=O)O)C5)ccc3c2Cl)CC1]

The title compound was prepared according to the method of Example 194. ¹H NMR (400 MHz, CD₃OD) δ: 8.88 (s, 1H), 8.03 (s, 1H), 7.97 (d, J=8.8 Hz, 1H), 7.74 (dd, J=1.6 Hz, 9.2 Hz, 1H), 4.31 (s, 2H), 4.07-4.01 (m, 3H), 3.00-2.95 (m, 1H), 2.53-2.51 (m, 2H), 2.17-2.03 (m, 8H), 1.82-1.79 (m, 2H), 1.48-1.35 (m, 3H), 1.20-1.11 (m, 2H), 0.97 (d, J=6.4 Hz, 3H); ESI-MS (M+H)⁺: 442.2.

Example 260

9-(3-(((1s,4s)-4-methylcyclohexyl)amino) isoquinoline-7-carbonyl)-9-azabicyclo[3.3.1]nonane-3-carboxylic acid

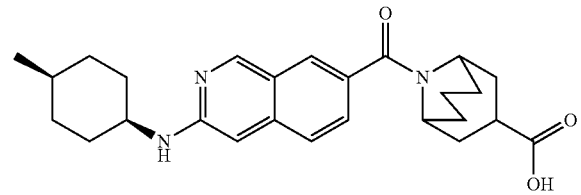 [SMILES: C[C@H]1CC[C@@H](Nc2cc3ccc(C(=O)N4C5CCCC4CC(C(=O)O)C5)cc3cn2)CC1]

The title compound was prepared according to the method of Example 195. ¹H NMR (400 MHz, CD₃OD) δ: 8.78 (s, 1H), 7.81 (s, 1H), 7.55 (d, J=8.4 Hz, 1H), 7.43 (dd, J=1.6 Hz, 8.4 Hz, 1H), 6.60 (s, 1H), 4.79 (s, 1H), 4.00-3.97 (m, 1H), 3.77-3.75 (m, 1H), 3.31-3.27 (m, 1H), 2.08-1.74 (m, 10H), 1.68-1.61 (m, 4H), 1.56-1.53 (m, 3H), 1.34-1.25 (m, 2H), 0.92 (d, J=6.8 Hz, 3H); ESI-MS (M+H)⁺: 436.2.

Example 261

8-(3-((cis-4-methylcyclohexyl)amino) isoquinoline-7-carbonyl)-8-azabicyclo[3.2.1]octane-3-carboxylic acid

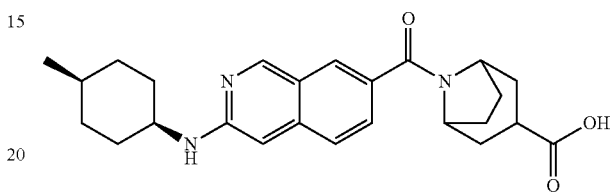

The title compound was prepared according to the method of Example 195. ¹H NMR (400 MHz, CD₃OD) δ: 8.88 (s, 1H), 7.97 (s, 1H), 7.63 (d, J=8.4 Hz, 1H), 7.56 (dd, J=1.6 Hz, 8.8 Hz, 1H), 6.68 (s, 1H), 4.81 (s, 1H), 4.30-4.26 (m, 1H), 3.85-3.83 (m, 1H), 3.00-2.97 (m, 1H), 2.11-1.85 (m, 10H), 1.77-1.69 (m, 2H), 1.65-1.61 (m, 3H), 1.42-1.34 (m, 2H), 1.00 (d, J=6.0 Hz, 3H); ESI-MS (M+H)⁺: 422.2.

Example 262

8-(2-((trans-4-(tert-butyl)cyclohexyl)amino) quinazoline-6-carbonyl)-8-azabicyclo[3.2.1]octane-3-carboxylic acid

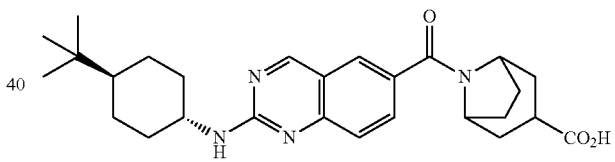

The title compound was prepared according to the method of Example 192. ¹H NMR (400 MHz, DMSO-d₆) δ: 9.25 (s, 1H), 8.02 (s, 1H), 7.81 (d, J=8.0 Hz, 1H), 7.55 (d, J=8.0 Hz, 1H), 4.68-4.63 (m, 1H), 4.15-4.10 (m, 1H), 3.84-3.78 (m, 1H), 2.88-2.83 (m, 1H), 2.02-1.95 (m, 4H), 1.81-1.75 (m, 8H), 1.32-1.29 (m, 2H), 1.14-1.00 (m, 3H), 0.87 (s, 9H). LCMS m/z 465.3 [M+H]⁺

Example 263

9-(3-((trans-4-methylcyclohexyl)amino)isoquinoline-7-carbonyl)-9-azabicyclo[3.3.1]nonane-3-carboxylic acid

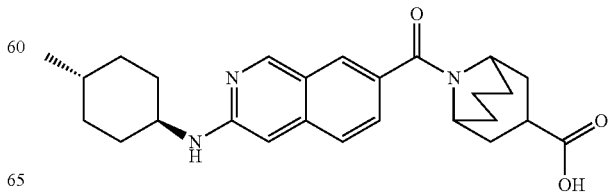

The title compound was prepared according to the method of Example 195. ¹H NMR (400 MHz, CD₃OD) δ: 8.84 (s, 1H), 7.88 (s, 1H), 7.62 (d, J=8.8 Hz, 1H), 7.50 (dd, J=1.2 Hz, 8.8 Hz, 1H), 6.66 (s, 1H), 4.87 (s, 1H), 4.09-4.05 (m, 1H), 3.56-3.50 (m, 1H), 3.39-3.34 (m, 1H), 2.14-2.08 (m, 5H), 2.04-1.91 (m, 5H), 1.88-1.72 (m, 4H), 1.49-1.40 (m, 1H), 1.36-1.26 (m, 2H), 1.21-1.11 (m, 2H), 0.97 (d, J=6.4 Hz, 3H); ESI-MS (M+H)⁺: 436.2.

Example 264

8-(3-((trans-4-methylcyclohexyl)amino) isoquinoline-7-carbonyl)-8-azabicyclo[3.2.1]octane-3-carboxylic acid

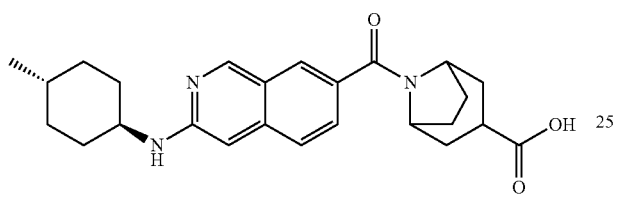

The title compound was prepared according to the method of Example 195. ¹H NMR (400 MHz, CD₃OD) δ: 8.86 (s, 1H), 7.96 (s, 1H), 7.62 (d, J=8.4 Hz, 1H), 7.56 (dd, J=1.6 Hz, 8.8 Hz, 1H), 6.65 (s, 1H), 4.81 (s, 1H), 4.30-4.28 (m, 1H), 3.57-3.54 (m, 1H), 3.01-2.97 (m, 1H), 2.14-1.79 (m, 12H), 1.48-1.44 (m, 1H), 1.35-1.22 (m, 2H), 1.18-1.12 (m, 2H), 0.97 (d, J=6.4 Hz, 3H); ESI-MS (M+H)⁺: 422.2.

Example 265

9-(2-((trans-4-methylcyclohexyl)amino) quinazoline-6-carbonyl)-9-azabicyclo[3.3.1]nonane-3-carboxylic acid

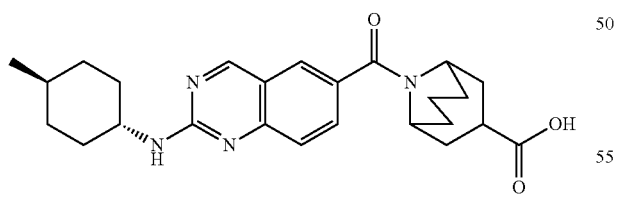

The title compound was prepared according to the method of Example 192. ¹H NMR (400 MHz, DMSO-d₆) δ: 9.16 (br s, 1H), 7.85 (d, J=1.2 Hz, 1H), 7.66 (d, J=8.8 Hz, 1H), 7.54-7.47 (m, 2H), 4.69 (s, 1H), 3.92-3.90 (m, 1H), 3.85-3.76 (m, 1H), 3.24-3.22 (m, 1H), 1.99-1.61 (m, 14H), 1.36-1.29 (m, 3H), 1.07-1.03 (m, 2H), 0.90 (d, J=6.4 Hz, 3H). ESI-MS (M+H)⁺: 437.3.

Example 266

9-(2-((cis-4-methylcyclohexyl)amino) quinazoline-6-carbonyl)-9-azabicyclo[3.3.1]nonane-3-carboxylic acid

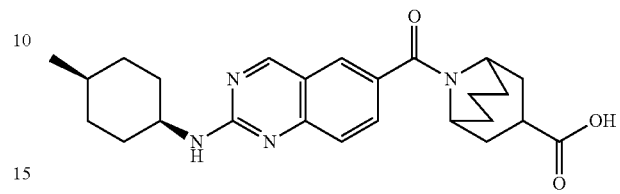

The title compound was prepared according to the method of Example 192. ¹H NMR (400 MHz, DMSO-d₆) δ: 9.18 (s, 1H), 7.85 (s, 1H), 7.63 (d, J=8.4 Hz, 1H), 7.47-7.43 (m, 2H), 4.70-4.65 (m, 1H), 4.08-4.02 (m, 1H), 3.93-3.87 (m, 1H), 3.15-3.08 (m, 1H), 1.96-1.41 (m, 19H), 0.93 (d, J=6.8 Hz, 3H). LCMS m/z 437.3 [M+H]³⁰

Example 267

9-((4-chloro-3-((trans-4-methylcyclohexyl)amino)isoquinolin-7-yl)methyl)-9-azabicyclo[3.3.1]nonane-3-carboxylic acid

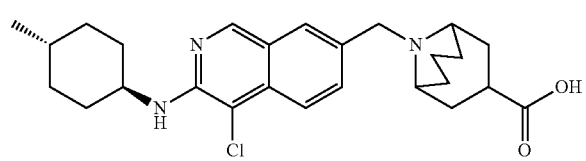 [SMILES: C[C@H]1CC[C@H](Nc2ncc3cc(CN4C5CCCC4CC(C(=O)O)C5)ccc3c2Cl)CC1]

The title compound was prepared according to the method of Example 194. ¹H NMR (400 MHz, CD₃OD) δ: 8.84 (s, 1H), 8.03 (s, 1H), 7.90 (d, J=8.8 Hz, 1H), 7.71 (d, J=8.8 Hz, 1H), 4.65-4.58 (m, 2H), 4.03-3.95 (m, 1H), 3.63-3.59 (m, 2H), 3.39-3.34 (m, 1H), 2.53-2.50 (m, 2H), 2.24-1.68 (m, 12H), 1.41-1.25 (m, 3H), 1.18-1.05 (m, 2H), 0.91 (d, J=6.8 Hz, 3H). ESI-MS (M+H)⁺: 456.2.

Example 268

8-(3-((cis-4-(tert-butyl)cyclohexyl)amino)isoquinoline-7-carbonyl)-8-azabicyclo[3.2.1]octane-3-carboxylic acid

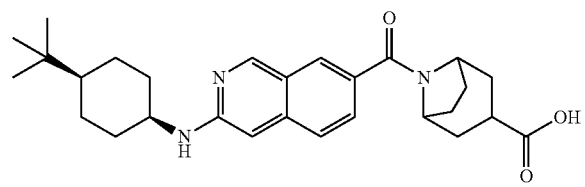 [SMILES: CC(C)(C)[C@H]1CC[C@@H](Nc2cc3ccc(C(=O)N4C5CCC4CC(C(=O)O)C5)cc3cn2)CC1]

The title compound was prepared according to the method of Example 195. ¹H NMR (400 MHz, CD₃OD) δ: 9.08 (s, 1H), 8.12 (s, 1H), 7.82 (d, J=9.2 Hz, 1H), 7.77 (d, J=9.2 Hz, 1H), 7.28 (s, 1H), 4.83 (s, 1H), 4.27-4.24 (m, 1H), 4.00-3.97

(m, 1H), 3.03-2.97 (m, 1H), 2.12-1.73 (m, 14H), 1.42-1.33 (m, 2H), 1.20-1.14 (m, 1H), 0.93 (s, 9H); ESI-MS (M+H)+: 464.3.

Example 269

8-(2-((cis-4-methylcyclohexyl)amino)quinazoline-6-carbonyl)-8-azabicyclo[3.2.1]octane-3-carboxylic acid

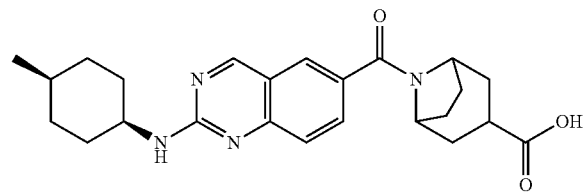 [SMILES: C[C@H]1CC[C@@H](Nc2ncc3cc(C(=O)N4C5CCC4CC(C(=O)O)C5)ccc3n2)CC1]

The title compound was prepared according to the method of Example 192. $^1$H NMR (400 MHz, DMSO-d$_6$) δ: 9.19 (s, 1H), 8.42 (s, 1H), 7.94 (s, 1H), 7.72 (d, J=8.0 Hz, 1H), 7.46-7.44 (m, 2H), 4.65-4.60 (m, 1H), 4.18-4.13 (m, 1H), 4.10-4.02 (m, 1H), 2.78-2.70 (m, 1H), 1.74-1.41 (m, 17H), 0.92 (d, J=6.8 Hz, 3H). LCMS m/z 423.2 [M+H]$^{30}$

Example 270

8-((3-((cis-4-methylcyclohexyl)amino)isoquinolin-7-yl)methyl)-8-azabicyclo[3.2.1]octane-3-carboxylic acid

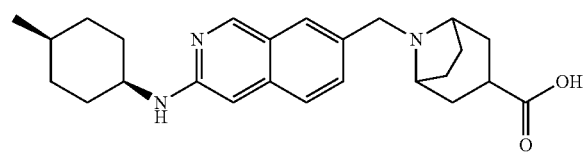 [SMILES: C[C@H]1CC[C@@H](Nc2cc3ccc(CN4C5CCC4CC(C(=O)O)C5)cc3cn2)CC1]

The title compound was prepared according to the method of Example 193. $^1$H NMR (400 MHz, CD$_3$OD) δ: 8.77 (s, 1H), 7.84 (s, 1H), 7.59 (s, 2H), 6.65 (s, 1H), 3.98 (s, 2H), 3.62-3.58 (m, 2H), 3.53-3.50 (m, 1H), 2.62-2.59 (m, 1H), 2.28-2.25 (m, 2H), 2.13-2.11 (m, 2H), 2.15-1.98 (m, 2H), 1.90-1.88 (m, 2H), 1.82-1.78 (m, 4H), 1.45-1.43 (m, 1H), 1.31-1.24 (m, 2H), 1.21-1.14 (m, 2H), 0.97 (d, J=6.4 Hz, 3H); ESI-MS (M+H)+: 408.1.

Example 271

9-((4-chloro-3-((cis-4-methylcyclohexyl)amino)isoquinolin-7-yl)methyl)-9-azabicyclo[3.3.1]nonane-3-carboxylic acid

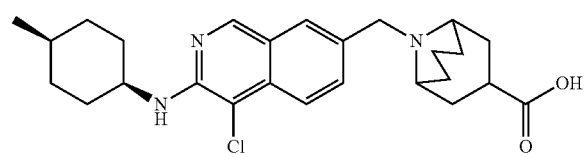 [SMILES: C[C@H]1CC[C@@H](Nc2ncc3cc(CN4C5CCCC4CC(C(=O)O)C5)ccc3c2Cl)CC1]

The title compound was prepared according to the method of Example 194. $^1$H NMR (400 MHz, CD$_3$OD) δ: 8.90 (s, 1H), 8.10 (s, 1H), 7.99 (d, J=8.0 Hz, 1H), 7.80 (d, J=8.4 Hz, 1H), 4.71-4.64 (m, 2H), 4.31-4.30 (m, 1H), 3.68-3.65 (m, 2H), 3.45-3.40 (m, 1H), 2.58-2.56 (m, 2H), 2.31-2.06 (m, 6H), 1.94-1.66 (m, 9H), 1.40-1.33 (m, 2H), 1.02 (d, J=6.4 Hz, 3H); ESI-MS (M+H)+: 456.2

Example 272

8-(3-((cis-4-(tert-butyl)cyclohexyl)amino)-4-chloroisoquinoline-7-carbonyl)-8-azabicyclo[3.2.1]octane-3-carboxylic acid

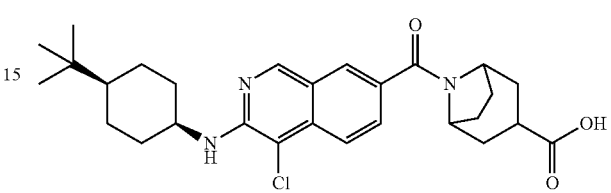

The title compound was prepared according to the method of Example 195. $^1$H NMR (400 MHz, CD$_3$OD) δ: 8.95 (s, 1H), 8.07 (s, 1H), 7.96 (d, J=8.8 Hz, 1H), 7.75 (dd, J=1.6 Hz, 9.2 Hz, 1H), 4.88 (s, 1H), 4.44-4.40 (m, 1H), 4.28-4.24 (m, 1H), 3.03-2.97 (m, 1H), 2.12-1.86 (m, 10H), 1.73-1.63 (m, 4H), 1.37-1.27 (m, 2H), 1.19-1.13 (m, 1H), 0.93 (s, 9H); ESI-MS (M+H)+: 498.1

Example 273

8-(3-((trans-4-(tert-butyl)cyclohexyl)amino)-4-chloroisoquinoline-7-carbonyl)-8-azabicyclo[3.2.1]octane-3-carboxylic acid

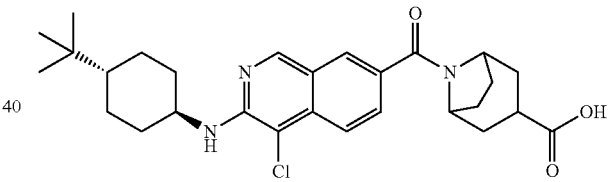

The title compound was prepared according to the method of Example 195. $^1$H NMR (400 MHz, CD$_3$OD) δ: 8.94 (s, 1H), 8.05 (s, 1H), 7.94 (d, J=8.8 Hz, 1H), 7.74 (dd, J=1.6 Hz, 9.2 Hz, 1H), 4.83 (s, 1H), 4.28-4.25 (m, 1H), 4.04-3.99 (m, 1H), 3.04-2.96 (m, 1H), 2.17-1.86 (m, 12H), 1.42-1.08 (m, 5H), 0.93 (s, 9H); ESI-MS (M+H)+: 498.1.

Example 274

9-((8-bromo-7-((cis-4-(trifluoromethyl)cyclohexyl)oxy)isoquinolin-3-yl)methyl)-9-azabicyclo[3.3.1]nonane-3-carboxylic acid

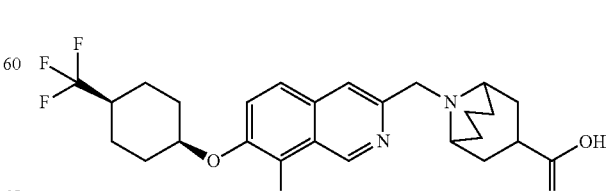

The title compound was prepared according to the method of Example 197. 1H NMR (400 MHz, CD₃OD) δ: 9.54 (s, 1H), 7.92 (d, J=8.8 Hz, 1H), 7.87 (s, 1H), 7.69 (d, J=9.2 Hz, 1H), 4.93 (s, 1H), 4.70 (s, 2H), 3.63-3.60 (m, 2H), 3.34-3.30 (m, 1H), 2.36-2.00 (m, 11H), 1.91-1.80 (m, 3H), 1.69-1.61 (m, 5H); ESI-MS (M+H)⁺: 555.1.

Example 275

8-((8-bromo-7-((cis-4-(trifluoromethyl)cyclohexyl)oxy)isoquinolin-3-yl)methyl)-8-azabicyclo[3.2.1]octane-3-carboxylic acid

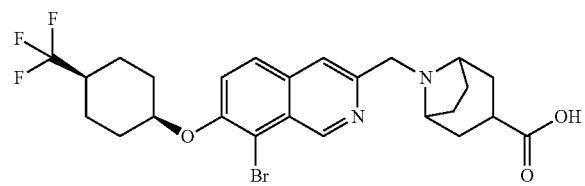 [SMILES: O=C(O)C1CC2CCC(C1)N2Cc1cc2ccc(O[C@H]3CC[C@@H](C(F)(F)F)CC3)c(Br)c2cn1]

The title compound was prepared according to the method of Example 197. ¹H NMR (400 MHz, CD₃OD) δ: 9.54 (s, 1H), 7.91 (d, J=8.8 Hz, 1H), 7.82 (s, 1H), 7.69 (d, J=8.8 Hz, 1H), 4.93 (s, 1H), 4.37 (s, 2H), 4.04-4.00 (m, 2H), 2.92-2.87 (m, 1H), 2.40-2.38 (m, 2H), 2.24-2.36 (m, 9H), 1.90-1.80 (m, 2H), 1.69-1.61 (m, 4H); ESI-MS (M+H)⁺: 541.1.

Example 276

8-((8-bromo-7-((cis-4-ethylcyclohexyl)oxy)isoquinolin-3-yl)methyl)-8-azabicyclo[3.2.1]octane-3-carboxylic acid

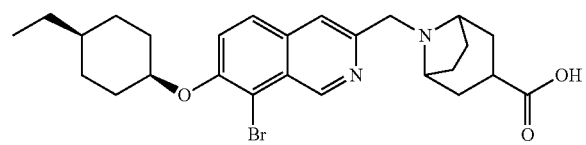

The title compound was prepared according to the method of Example 197. ¹H NMR (400 MHz, CD₃OD) δ: 9.60 (s, 1H), 7.97 (d, J=8.8 Hz, 1H), 7.93 (s, 1H), 7.74 (d, J=9.2 Hz, 1H), 4.96 (s, 1H), 4.47 (s, 2H), 4.05-4.03 (m, 2H), 2.78-2.71 (m, 1H), 2.44-2.41 (m, 2H), 2.19-2.00 (m, 8H), 1.73-1.51 (m, 6H), 1.38-1.29 (m, 3H), 0.94 (t, J=6.4 Hz, 3H); ESI-MS (M+H)⁺: 501.2.

Example 277

8-((8-chloro-7-((cis-4-ethylcyclohexyl)oxy)isoquinolin-3-yl)methyl)-8-azabicyclo[3.2.1]octane-3-carboxylic acid

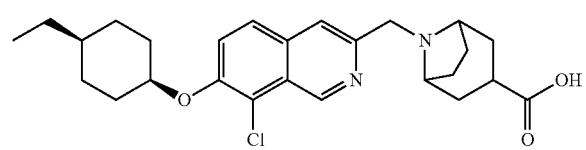 [SMILES: CC[C@H]1CC[C@@H](Oc2ccc3cc(CN4C5CCC4CC(C(=O)O)C5)ncc3c2Cl)CC1]

The title compound was prepared according to the method of Example 196. ¹H NMR (400 MHz, CD₃OD) δ: 9.54 (s, 1H), 7.97 (s, 1H), 7.93 (d, J=9.2 Hz, 1H), 7.75 (d, J=9.2 Hz, 1H), 4.91 (s, 1H), 4.21 (s, 2H), 3.73-3.70 (m, 2H), 2.64-2.61 (m, 1H), 2.30-2.28 (m, 2H), 2.12-2.03 (m, 4H), 1.94-1.84 (m, 4H), 1.71-1.52 (m, 6H), 1.39-1.32 (m, 3H), 0.94 (t, J=6.4 Hz, 3H); ESI-MS (M+H)⁺: 457.0.

Example 278

8-((6-((cis 4-ethylcyclohexyl)oxy)quinolin-2-yl)amino)bicyclo[3.2.1]octane-3-carboxylic acid

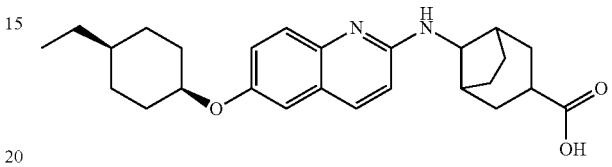

The title compound was prepared according to the method of Example 199 to give the title compound as a white solid (5 mg, yield: 33%). ¹H NMR (400 MHz, CD₃OD) δ: 7.77 (d, J=9.2 Hz, 1H), 7.48 (d, J=8.8 Hz, 1H), 7.13 (dd, J=2.4 Hz, 8.8 Hz, 1H), 7.03 (d, J=2.4 Hz, 1H), 6.86 (d, J=8.8 Hz, 1H), 4.52 (s, 1H), 3.94-3.90 (m, 1H), 2.57-2.51 (m, 1H), 2.27 (m, 2H), 1.94-1.77 (m, 6H), 1.57-1.47 (m, 6H), 1.37-1.19 (m, 7H), 0.83 (t, J=7.2 Hz, 3H). ESI-MS (M+H)⁺: 423.3.

Example 279

9-((8-bromo-7-((cis-4-methylcyclohexyl)oxy) isoquinolin-3-yl)methyl)-9-azabicyclo[3.3.1]nonane-3-carboxylic acid

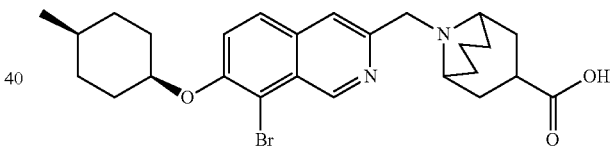

The title compound was prepared according to the method of Example 197. ¹H NMR (400 MHz, CD3OD) δ: 9.63 (s, 1H), 8.00 (d, J=9.2 Hz, 1H), 7.97 (s, 1H), 7.77 (d, J=9.6 Hz, 1H), 4.95 (s, 1H), 4.79 (s, 2H), 3.72-3.70 (m, 2H), 3.41-3.35 (m, 1H), 2.49-2.42 (m, 4H), 2.25-1.97 (m, 7H), 1.85-1.70 (m, 3H), 1.60-1.50 (m, 5H), 1.00 (d, J=6.0 Hz, 3H); ESI-MS (M+H)⁺: 501.1.

Example 280

8-((6-((cis-4-ethylcyclohexyl)oxy)-5-(trifluoromethyl)quinolin-2-yl)amino)bicyclo[3.2.1]octane-3-carboxylic acid

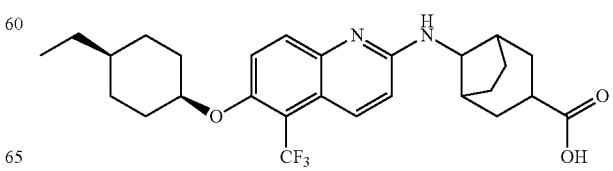

The title compound was prepared according to the method of Example 198 to give the title compound as a white solid (10 mg, yield: 42%). ¹H NMR (400 MHz, CD₃OD, a mixture of cis and trans isomers) δ: 8.14 (d, J=8.8 Hz, 1H), 7.79-7.75 (m, 1H), 7.46-7.42 (m, 1H), 7.01 (d, J=9.6 Hz, 0.3H), 6.90 (d, J=9.6 Hz, 0.7H), 4.78 (s, 1H), 4.30-4.27 (m, 0.3H), 3.92-3.89 (m, 0.7H), 2.64-2.45 (m, 1H), 2.36 (m, 1.4H), 2.25 (m, 0.6H), 2.06-1.85 (m, 7H), 1.67-1.30 (m, 12H), 0.93 (t, J=6.8 Hz, 3H). ESI-MS (M+H)⁺: 491.3.

Example 281

9-((5-chloro-6-((cis-4-ethylcyclohexyl)oxy)quinolin-2-yl)amino)bicyclo[3.3.1]nonane-3-carboxylic acid

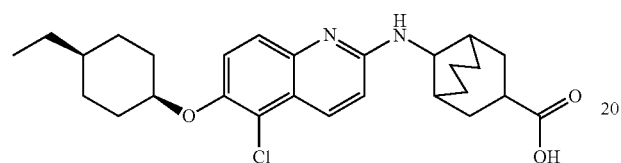

The title compound was prepared according to the method of Example 199 and Example 196 to give the title compound as a yellow solid (15 mg, yield: 38%). ¹H NMR (400 MHz, CD₃OD, a mixture of cis and trans isomers) δ: 8.08-8.04 (m, 1H), 7.46-7.41 (m, 1H), 7.29-7.25 (m, 1H), 6.92-6.82 (m, 1H), 4.57 (s, 1H), 4.16 (s, 0.4H), 3.97 (s, 0.2H), 3.70 (s, 0.4H), 3.03-2.80 (m, 1H), 2.27-1.76 (m, 23H), 0.83 (t, J=7.2 Hz, 3H). ESI-MS (M+H)⁺: 471.3.

Example 282

(1R,3S,5S)-9-((5-(trifluoromethyl)-6-((cis-4-(trifluoromethyl)cyclohexyl)oxy)naphthalen-2-yl)methyl)-9-azabicyclo[3.3.1]nonane-3,7-dicarboxylic acid

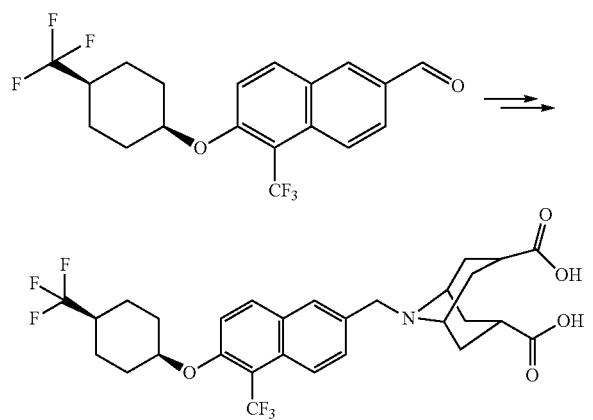

To a mixture of 5-trifluoromethyl-6-(4-trifluoromethyl-cyclohexyloxy)-naphthalene-2-carbaldehyde (80 mg, 0.21 mmol, prepared according to the method Example 84) and 9-Aza-bicyclo[3.3.1]nonane-3,7-dicarboxylic acid diethyl ester hydrochloride (94 mg, 0.31 mmol) in THF (2.0 mL) was added triethylamine (0.043 mL, 0.31 mmol), sonicated for 5 min. followed by the addition of acetic acid (0.02 mL, 0.31 mmol) and sodium triacetoxyborohydride (87 mg, 0.41 mmol), the reaction was then heated in microwave at 100° C. for 10 min. LCMS showed desired intermediate formation (RT 1.64 min, MH+644.0). The reaction mixture was diluted with EtOAc and washed with brine. The organic phase was dried over MgSO₄ and concentrated. The crude was then dissolved in THF (1.0 mL) and methanol (1.0 mL), treated with aqueous 3N NaOH (1.0 mL), the mixture was then heated in microwave at 100° C. for 10 min. The reaction mixture was then neutralized with 2N HCl. The organic phase was dried, concentrated. The crude was purified by HPLC to give the title compound as a white powder (75.6 mg; yield 62.8%). ¹H NMR (400 MHz, METHANOL-d4) δ 8.29 (d, J=8.53 Hz, 1H), 8.08-8.22 (m, 2H), 7.74 (dd, J=1.88, 9.16 Hz, 1H), 7.60 (d, J=9.54 Hz, 1H), 5.03 (br. s., 1H), 4.69 (s, 2H), 3.78 (br. s., 2H), 3.38 (br. s., 1H), 1.98-2.82 (m, 12H), 1.65-1.90 (m, 6H); 19F NMR (376 MHz, METHANOL-d4) d ppm −77.06 (br. s., 3 F, TFA) −75.57 (br. s., 3 F) −53.67 (s, 3 F); ESI-MS (M+H)⁺: 588.0.

Example 283

9-(1R,3S,5S,7S)-2-((5-(trifluoromethyl)-6-((cis-4-(trifluoromethyl)cyclohexyl)oxy)naphthalen-2-yl)methyl)-2-azaadamantane-5-carboxylic acid

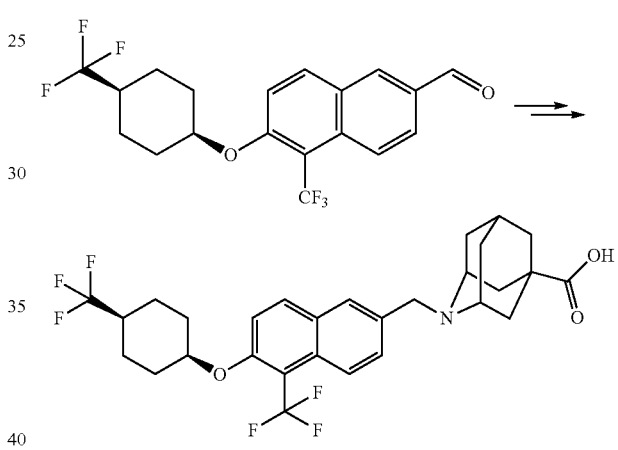

The title compound was prepared according to the method of Example 84. ¹H NMR (400 MHz, METHANOL-d4) δ 8.28 (d, J=8.53 Hz, 1H), 8.07-8.20 (m, 2H), 7.72 (dd, J=1.63, 9.16 Hz, 1H), 7.60 (d, J=9.29 Hz, 1H), 5.03 (br. s., 1H), 4.72 (d, J=19.33 Hz, 2H), 3.72 (d, J=6.02 Hz, 2H), 2.52-2.77 (m, 2H), 1.97-2.41 (m, 11H), 1.64-1.96 (m, 7H); ESI-MS (M+H)⁺: 556.0.

Example 284

9-(1R,3R,5S)-7-amino-9-((5-(trifluoromethyl)-6-((cis-4-(trifluoromethyl)cyclohexyl)oxy)naphthalen-2-yl)methyl)-9-azabicyclo[3.3.1]nonane-3-carboxylic acid

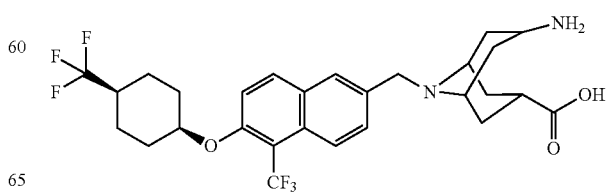

The title compound was prepared according to the method of Example 84. ¹H NMR (400 MHz, METHANOL-d4) δ 8.28 (d, J=8.28 Hz, 1H), 8.08-8.20 (m, 2H), 7.75 (dd, J=1.76, 9.04 Hz, 1H), 7.60 (d, J=9.29 Hz, 1H), 5.03 (br. s., 1H), 4.69 (s, 2H), 4.06-4.23 (m, 1H), 3.83 (br. s., 2H), 3.10 (tt, J=6.21, 12.74 Hz, 1H), 2.07-2.56 (m, 11H), 1.65-1.90 (m, 6H); ESI-MS (M+H)⁺: 559.0.

Example 285

9-((6-(bicyclo[3.1.0]hexan-3-yloxy)-5-(trifluoromethyl) naphthalen-2-yl)methyl)-9-azabicyclo[3.3.1]nonane-3-carboxylic acid

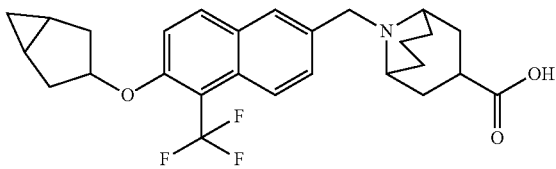 [SMILES: O=C(O)C1CC2CCCC(C1)N2Cc1ccc2c(C(F)(F)F)c(OC3CC4CC4C3)ccc2c1]

The title compound was prepared according to the method of Example 84. ¹H NMR (400 MHz, METHANOL-d4) δ 8.25 (d, J=8.78 Hz, 1H), 8.06-8.18 (m, 2H), 7.73 (d, J=8.78 Hz, 1H), 7.54 (d, J=9.29 Hz, 1H), 4.59-4.83 (m, 3H), 3.65 (d, J=13.30 Hz, 2H), 3.36-3.52 (m, 2H), 2.57 (d, J=8.03 Hz, 2H), 2.40 (dd, J=7.03, 12.80 Hz, 2H), 1.82-2.35 (m, 9H), 1.36-1.49 (m, 2H), 0.42-0.55 (m, 1H), 0.18 (q, J=4.18 Hz, 1H); ESI-MS (M+H)⁺: 474.0.

Example 286

8-((6-(bicyclo[3.1.0]hexan-3-yloxy)-5-(trifluoromethyl) naphthalen-2-yl)methyl)-8-azabicyclo[3.2.1]octane-3-carboxylic acid

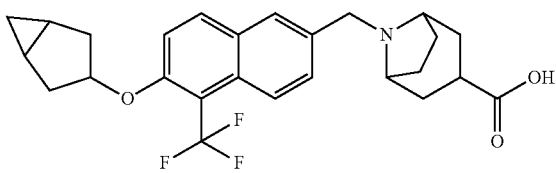 [SMILES: O=C(O)C1CC2CCC(C1)N2Cc1ccc2c(C(F)(F)F)c(OC3CC4CC4C3)ccc2c1]

The title compound was prepared according to the method of Example 84. ¹H NMR (400 MHz, METHANOL-d4) δ 8.21-8.30 (m, 1H), 8.11-8.18 (m, 1H), 8.03-8.10 (m, 1H), 7.65-7.74 (m, 1H), 7.51-7.59 (m, 1H), 4.69-4.83 (m, 2H), 4.35 (s, 2H), 4.02 (br. s., 2H), 2.97 (tt, J=6.12, 11.70 Hz, 1H), 2.33-2.62 (m, 4H), 1.90-2.27 (m, 9H), 1.36-1.51 (m, 1H), 0.44-0.54 (m, 1H), 0.18 (q, J=4.02 Hz, 1H); ESI-MS (M+H)⁺: 460.0.

Example 287

8-((R)-1-(5-(trifluoromethyl)-6-((cis-4-(trifluoromethyl)cyclohexyl)oxy)naphthalen-2-yl)propyl)-8-azabicyclo[3.2.1]octane-3-carboxylic acid and Example 288

8-((S)-1-(5-(trifluoromethyl)-6-((cis-4-(trifluoromethyl)cyclohexyl)oxy)naphthalen-2-yl)propyl)-8-azabicyclo[3.2.1]octane-3-carboxylic acid

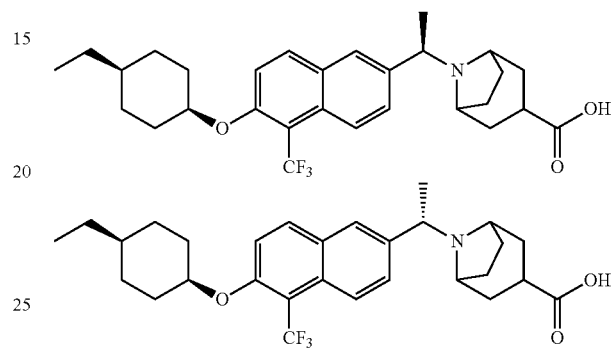

The chiral separation of 8-{1-[5-trifluoromethyl-6-(4-trifluoromethyl-cyclohexyloxy)-naphthalen-2-yl]-propyl}-8-aza-bicyclo[3.2.1]octane-3-carboxylic acid (prepared according to the method of Example 92) gave the two title compounds. The chiral method is as follow: Column: 2.1× 25.0 cm ChiralPak IC from Chiral Technologies (West Chester, Pa.); CO₂ co-solvent (Solvent B): Acetonitrile: Methanol (3:1) with 1% isopropylamine; Isocratic Method: 50% Co-solvent at 80 mL/min; System Pressure: 100bar; Column Temperature: 25° C.; Sample Diluent: Methanol: Dichloromethane (9:1). Two isomers were obtained after the chiral separation. Since the absolute stereo chemistry is unknown, Peak#1 (chiral HPLC: RT 2.3 min.; 100% ee was randomly assigned as the R-isomer); 1H NMR (400 MHz, METHANOL-d4) δ 8.34 (d, J=8.78 Hz, 1H), 8.15 (d, J=9.29 Hz, 1H), 8.03 (s, 1H), 7.71 (d, J=1.25 Hz, 1H), 7.62 (d, J=9.29 Hz, 1H), 5.03 (br. s., 1H), 4.53-4.67 (m, 1H), 4.09 (dd, J=3.01, 11.55 Hz, 1H), 3.41 (d, J=6.02 Hz, 1H), 2.87-3.03 (m, 1H), 1.64-2.62 (m, 19H), 0.78 (t, J=7.15 Hz, 3H); ESI-MS (M+H)⁺: 558.1; Peak#2 (chiral HPLC: RT 3.5 min.; 99.2% ee, was randomly assigned as the S-isomer); LCMS: RT 1.57 min.; MH+ 558.0. 1H NMR (400 MHz, METHANOL-d4) δ 8.34 (d, J=8.78 Hz, 1H), 8.15 (d, J=9.29 Hz, 1H), 8.03 (s, 1H), 7.66-7.74 (m, 1H), 7.62 (d, J=9.29 Hz, 1H), 5.03 (br. s., 1H), 4.58 (d, J=6.02 Hz, 1H), 4.09 (dd, J=2.89, 11.42 Hz, 1H), 3.40 (br. s., 1H), 2.84-3.04 (m, 1H), 1.61-2.62 (m, 19H), 0.78 (t, J=7.28 Hz, 3H); ESI-MS (M+H)⁺: 558.0

Example 289

8-((R)-1-(6-((cis-4-ethylcyclohexyl)oxy)-5-(trifluoromethyl)naphthalen-2-yl)ethyl)-8-azabicyclo[3.2.1]octane-3-carboxylic acid and Example 290

8-((S)-1-(6-((cis-4-ethylcyclohexyl)oxy)-5-(trifluoromethyl)naphthalen-2-yl)ethyl)-8-azabicyclo[3.2.1]octane-3-carboxylic acid

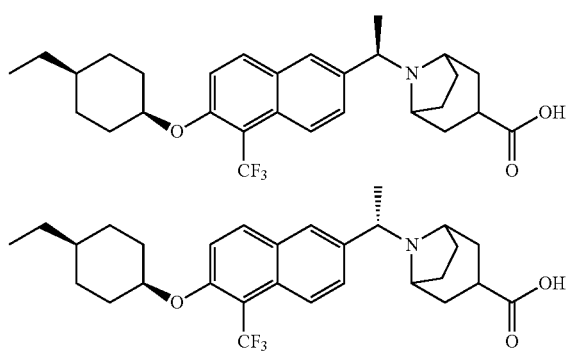

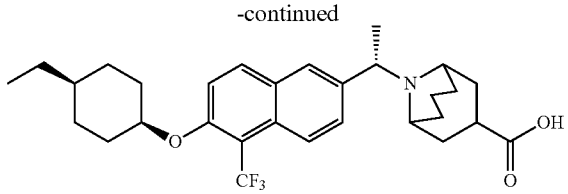

The chiral separation of 8-{1-[6-(4-Ethyl-cyclohexyloxy)-5-trifluoromethyl-naphthalen-2-yl]-ethyl}-8-aza-bicyclo[3.2.1]octane-3-carboxylic acid (prepared according to the method of Example 88) gave the two title compounds. The chiral method is as follow: Column: 2.1×25.0 cm ChiralPak IC from Chiral Technologies (West Chester, Pa.); $CO_2$ co-solvent (Solvent B): Methanol with 1% isopropylamine; Isocratic Method: 45% Co-solvent at 80 mL/min; System Pressure: 100bar; Column Temperature: 25° C.; Sample Diluent: Methanol: Dichloromethane (9:1). Two isomers were obtained after the chiral separation. Since the absolute stereo chemistry is unknown, Peak#1 (chiral HPLC: RT 1.7 min.; 100% ee was randomly assigned as the R-isomer). $^1$H NMR (400 MHz, METHANOL-d4) δ 8.30 (d, J=8.53 Hz, 1H), 8.12 (d, J=9.29 Hz, 1H), 8.03 (s, 1H), 7.72 (dd, J=1.38, 9.16 Hz, 1H), 7.58 (d, J=9.29 Hz, 1H), 4.95 (br. s., 1H), 4.48-4.61 (m, 1H), 4.39 (q, J=6.53 Hz, 1H), 3.38-3.52 (m, 1H), 2.87-3.08 (m, 1H), 1.18-2.61 (m, 22H), 0.93 (t, J=7.15 Hz, 3H); ESI-MS (M+H)$^+$: 504.1; Peak#2 (chiral HPLC: RT 3.0 min.; 99.3% ee, was randomly assigned as the S-isomer). $^1$H NMR (400 MHz, METHANOL-d4) δ 8.30 (d, J=8.53 Hz, 1H), 8.12 (d, J=9.29 Hz, 1H), 8.04 (s, 1H), 7.72 (dd, J=1.25, 9.04 Hz, 1H), 7.57 (d, J=9.29 Hz, 1H), 4.94 (br. s., 1H), 4.50-4.60 (m, 1H), 4.39 (q, J=6.53 Hz, 1H), 3.39-3.52 (m, 1H), 2.87-3.10 (m, 1H), 2.46-2.63 (m, 1H), 1.88-2.43 (m, 9H), 1.83 (d, J=6.53 Hz, 3H), 1.52-1.74 (m, 4H), 1.22-1.51 (m, 5H), 0.92 (t, J=7.15 Hz, 3H); ESI-MS (M+H)$^+$: 504.1

Example 291

9-((R)-1-(6-((cis-4-ethylcyclohexyl)oxy)-5-(trifluoromethyl)naphthalen-2-yl)ethyl)-9-azabicyclo[3.3.1]nonane-3-carboxylic acid and Example 292

9-((S)-1-(6-((cis-4-ethylcyclohexyl)oxy)-5-(trifluoromethyl)naphthalen-2-yl)ethyl)-9-azabicyclo[3.3.1]nonane-3-carboxylic acid The chiral separation of 9-{1-[6-(4-Ethyl-cyclohexyloxy)-5-trifluoromethyl-naphthalen-2-yl]-ethyl}-9-aza-bicyclo[3.3.1]nonane-3-carboxylic acid (prepared according to the method of Example 88) gave the two title compounds. The chiral method is as follow: Column: 3.0×25.0 cm (S,S) Whelk0-1 from Regis Technologies (Morton Grove, Ill.) $CO_2$ co-solvent (Solvent B): Acetonitrile: Methanol (3:1) with 1% isopropylamine; Isocratic Method: 35% Co-solvent at 80 mL/min; System Pressure: 100bar; Column Temperature: 25° C.; Sample Diluent: Methanol:Dichloromethane (9:1). Two isomers were obtained after the chiral separation. Since the absolute stereo chemistry is unknown, Peak#1 (chiral HPLC: RT 1.4 min.; 99.7% ee was randomly assigned as the R-isomer). $^1$H NMR (400 MHz, METHANOL-d4) δ 8.29 (d, J=8.78 Hz, 1H), 8.05-8.18 (m, 2H), 7.79 (dd, J=1.88, 9.16 Hz, 1H), 7.57 (d, J=9.29 Hz, 1H), 5.00-5.27 (m, 1H), 4.94 (br. s., 1H), 4.18 (br. s., 1H), 3.38 (td, J=6.18, 12.49 Hz, 1H), 3.17 (d, J=13.30 Hz, 1H), 2.30-2.63 (m, 3H), 1.52-2.28 (m, 16H), 1.21-1.51 (m, 5H), 0.92 (t, J=7.15 Hz, 3H); ESI-MS (M+H)$^+$: 518.1; For Peak#2 (chiral HPLC: RT 2.0 min.; 99.3% ee, was randomly assigned as the S-isomer). $^1$H NMR (400 MHz, METHANOL-d4) δ 8.29 (d, J=8.78 Hz, 1H), 8.12 (d, J=8.28 Hz, 2H), 7.78 (dd, J=1.76, 9.04 Hz, 1H), 7.57 (d, J=9.29 Hz, 1H), 5.00-5.27 (m, 1H), 4.94 (br. s., 1H), 4.18 (br. s., 1H), 3.38 (td, J=6.15, 12.30 Hz, 1H), 3.17 (d, J=12.80 Hz, 1H), 2.30-2.63 (m, 3H), 1.52-2.29 (m, 16H), 1.21-1.50 (m, 5H), 0.92 (t, J=7.15 Hz, 3H); ESI-MS (M+H)$^+$: 518.1

Example 293

8-((R)-1-(6-((cis-4-ethylcyclohexyl)oxy)-5-(trifluoromethyl) naphthalen-2-yl)propyl)-8-azabicyclo[3.2.1]octane-3-carboxylic acid and Example 294

8-((S)-1-(6-((cis-4-ethylcyclohexyl)oxy)-5-(trifluoromethyl) naphthalen-2-yl)propyl)-8-azabicyclo[3.2.1]octane-3-carboxylic acid

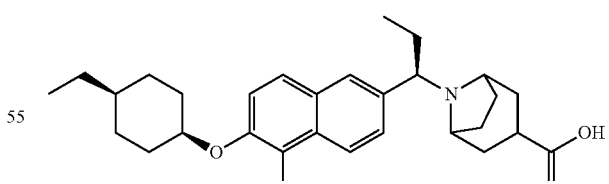

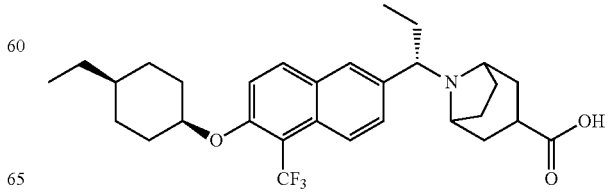

The chiral separation of 8-{1-[6-(4-Ethyl-cyclohexyloxy)-5-trifluoromethyl-naphthalen-2-yl]-propyl}-8-aza-bicyclo[3.2.1]octane-3-carboxylic acid (prepared according to the method of Example 92). Two isomers were obtained after the chiral separation. Since the absolute stereo chemistry is unknown, Peak#1 (chiral HPLC: RT 2.7 min.; 100% ee was randomly assigned as the R-isomer); 1H NMR (400 MHz, METHANOL-d4) δ 8.32 (d, J=8.53 Hz, 1H), 8.12 (d, J=9.29 Hz, 1H), 8.01 (s, 1H), 7.67 (dd, J=1.51, 9.04 Hz, 1H), 7.59 (d, J=9.29 Hz, 1H), 4.96 (br. s., 1H), 4.39-4.65 (m, 1H), 4.09 (dd, J=3.01, 11.55 Hz, 1H), 3.41 (d, J=6.27 Hz, 1H), 2.86-3.04 (m, 1H), 1.86-2.62 (m, 12H), 1.53-1.81 (m, 4H), 1.24-1.51 (m, 5H), 0.93 (t, J=7.03 Hz, 3H), 0.78 (t, J=7.28 Hz, 3H); ESI-MS (M+H)+: 518.1; Peak#2 (chiral HPLC: RT 3.9 min.; 99.6% ee, was randomly assigned as the S-isomer, 1H NMR (400 MHz, METHANOL-d4) δ 8.32 (d, J=8.53 Hz, 1H), 8.07-8.17 (m, 1H), 8.01 (s, 1H), 7.68 (dd, J=1.51, 9.04 Hz, 1H), 7.59 (d, J=9.29 Hz, 1H), 4.96 (br. s., 1H), 4.36-4.65 (m, 1H), 4.08 (dd, J=3.26, 11.55 Hz, 1H), 3.41 (d, J=6.02 Hz, 1H), 2.86-3.03 (m, 1H), 2.48-2.62 (m, 1H), 1.86-2.48 (m, 11H), 1.53-1.75 (m, 4H), 1.22-1.52 (m, 5H), 0.93 (t, J=7.15 Hz, 3H), 0.78 (t, J=7.28 Hz, 3H); ESI-MS (M+H)+: 518.1.

Example 295

9-((R)-1-(5-(trifluoromethyl)-6-((cis-4-(trifluoromethyl)cyclohexyl)oxy)naphthalen-2-yl)propyl)-9-azabicyclo[3.3.1]nonane-3-carboxylic acid and Example 296

9-((S)-1-(5-(trifluoromethyl)-6-((cis-4-(trifluoromethyl)cyclohexyl)oxy)naphthalen-2-yl)propyl)-9-azabicyclo[3.3.1]nonane-3-carboxylic acid

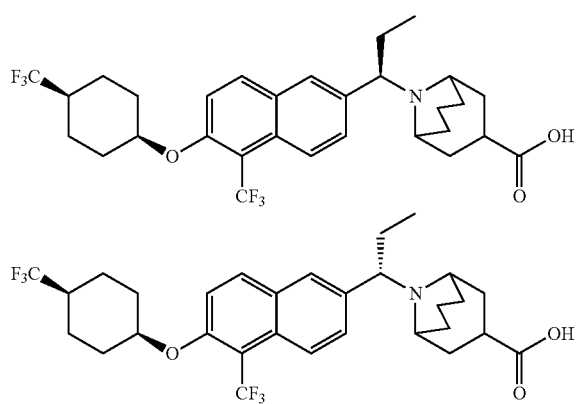

The chiral separation of 9-{1-[5-Trifluoromethyl-6-(4-trifluoromethyl-cyclohexyloxy)-naphthalen-2-yl]-propyl}-9-aza-bicyclo[3.3.1]nonane-3-carboxylic acid (prepared according to the method of Example 92). Two isomers were obtained after the chiral separation. Since the absolute stereo chemistry is unknown, Peak#1 (chiral HPLC: RT 1.2 min.; 99.9% ee, was randomly assigned as the R-isomer). 1H NMR (400 MHz, METHANOL-d4) δ 8.34 (d, J=7.28 Hz, 1H), 8.04-8.21 (m, 2H), 7.76 (d, J=8.28 Hz, 1H), 7.62 (d, J=9.29 Hz, 1H), 5.03 (br. s., 1H), 4.93 (dd, J=3.51, 11.55 Hz, 1H), 4.26 (d, J=11.80 Hz, 1H), 3.35-3.46 (m, 1H), 3.07-3.21 (m, 1H), 1.52-2.60 (m, 21H), 0.75 (t, J=7.15 Hz, 3H); ESI-MS (M+H)+: 572.1; Peak#2 (chiral HPLC: RT 1.8 min.; 98.6% ee, was randomly assigned as the S-isomer. 1H NMR (400 MHz, METHANOL-d4) δ 8.34 (d, J=7.28 Hz, 1H), 8.05-8.21 (m, 2H), 7.76 (d, J=8.53 Hz, 1H), 7.62 (d, J=9.29 Hz, 1H), 5.04 (br. s., 1H), 4.93 (dd, J=3.76, 11.80 Hz, 1H), 4.26 (d, J=12.30 Hz, 1H), 3.39 (dd, J=5.65, 12.17 Hz, 1H), 3.08-3.21 (m, 1H), 1.54-2.60 (m, 21H), 0.75 (t, J=7.15 Hz, 3H);); ESI-MS (M+H)+: 572.1.

Example 297

9-((R)-1-(6-(((1s,4S)-4-ethylcyclohexyl)oxy)-5-(trifluoromethyl) naphthalen-2-yl)propyl)-9-azabicyclo[3.3.1]nonane-3-carboxylic acid and Example 298

9-((S)-1-(6-(((1S,4R)-4-ethylcyclohexyl)oxy)-5-(trifluoromethyl) naphthalen-2-yl)propyl)-9-azabicyclo[3.3.1]nonane-3-carboxylic acid

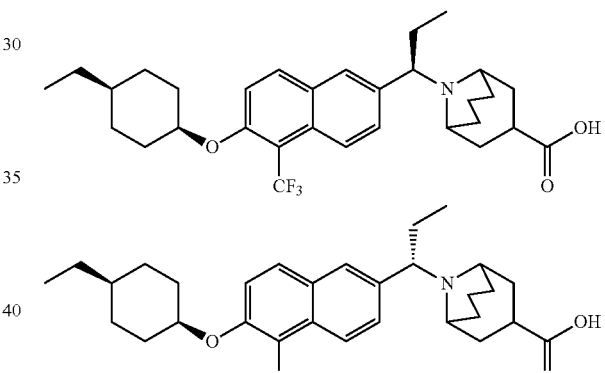

The chiral separation of 9-{1-[6-(4-Ethyl-cyclohexyloxy)-5-trifluoromethyl-naphthalen-2-yl]-propyl}-9-aza-bicyclo[3.3.1]nonane-3-carboxylic acid (prepared according to the method of Example 92). Two isomers were obtained after the chiral separation. Since the absolute stereo chemistry is unknown, Peak#1 (chiral HPLC: RT 1.7 min.; 100% ee) was randomly assigned as the R-isomer; 1H NMR (400 MHz, METHANOL-d4) δ 8.23-8.39 (m, 1H), 8.11 (br. s., 2H), 7.67-7.82 (m, 1H), 7.59 (d, J=9.29 Hz, 1H), 4.96 (br. s., 2H), 4.17-4.33 (m, 1H), 3.35-3.46 (m, 1H), 3.05-3.23 (m, 1H), 2.06 (d, J=11.29 Hz, 13H), 1.19-1.78 (m, 10H), 0.93 (t, J=7.15 Hz, 3H), 0.75 (t, J=7.15 Hz, 3H); ESI-MS (M+H)+: 532.1; Peak#2 (chiral HPLC: RT 2.8 min.; 99.4% ee), was randomly assigned as the S-isomer; 1H NMR (400 MHz, METHANOL-d4) δ 8.32 (d, J=7.28 Hz, 1H), 8.01-8.18 (m, 2H), 7.75 (d, J=8.03 Hz, 1H), 7.59 (d, J=9.29 Hz, 1H), 4.90-5.00 (m, 2H), 4.26 (d, J=11.80 Hz, 1H), 3.35-3.46 (m, 1H), 3.14 (d, J=14.56 Hz, 1H), 1.79-2.61 (m, 13H), 1.53-1.79 (m, 5H), 1.23-1.51 (m, 5H), 0.93 (t, J=7.15 Hz, 3H), 0.75 (t, J=7.28 Hz, 3H); ESI-MS (M+H)+: 532.1.

Example 299

4-(2-(1-(5-(trifluoromethyl)-6-((cis-4-(trifluoromethyl)cyclohexyl)oxy)naphthalen-2-yl)propyl)-2H-tetrazol-5-yl)piperidine

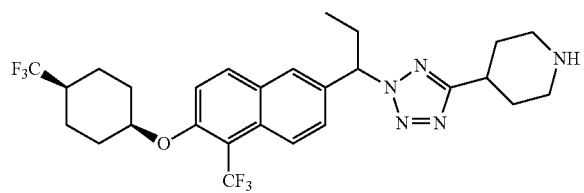 [SMILES: CCC(c1ccc2c(C(F)(F)F)c(O[C@H]3CC[C@@H](C(F)(F)F)CC3)ccc2c1)n1nnc(C2CCNCC2)n1]

Step 1: 1-(5-(trifluoromethyl)-6-((cis-4-(trifluoromethyl)cyclohexyl)oxy)naphthalen-2-yl)propyl methanesulfonate

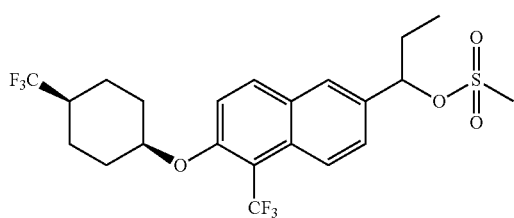 [SMILES: CCC(OS(C)(=O)=O)c1ccc2c(C(F)(F)F)c(O[C@H]3CC[C@@H](C(F)(F)F)CC3)ccc2c1]

To a solution of 1-[5-trifluoromethyl-6-(4-trifluoromethyl-cyclohexyloxy)-naphthalen-2-yl]-propan-1-ol (220 mg, 0.52 mmol) and N,N-diisopropylethylamine (0.27 mL, 1.57 mmol) in methylene chloride (2 mL) was added methanesulfonyl chloride (0.081 mL, 1.05 mmol) dropwise. A white precipitate formed. The solution was stirred at rt for 5h. LCMS showed no starting material left, and complete conversion to RT 2.36 min. The mixture was diluted with DCM and washed with sodium bicarbonate solution and water, dried over MgSO$_4$, filtered, concentrated. The residue was used as in the next step.

Step 2: 4-(2-(1-(5-(trifluoromethyl)-6-((cis-4-(trifluoromethyl)cyclohexyl)oxy)naphthalen-2-yl)propyl)-2H-tetrazol-5-yl)piperidine

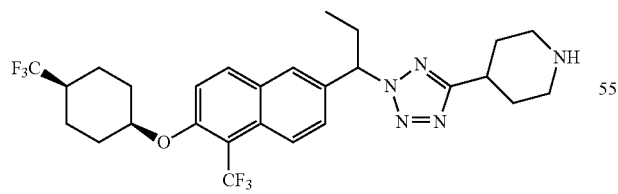

To a solution of methanesulfonic acid 1-[5-trifluoromethyl-6-(4-trifluoromethyl-cyclohexyloxy)-naphthalen-2-yl]-propyl ester (0.26 g, 0.52 mmol) in N,N-dimethylformamide (2 mL), 4-(1H-Tetrazol-5-yl)-piperidine (0.15980 g, 1.0432 mmol) was added, followed by Cesium Carbonate (0.51 g, 1.56 mmol). The reaction was then heated at 60° C. for 2h and 80° C. overnight. Cooled down, the reaction mixture was diluted with EtOAc, washed with water (×3). The organic phase was then separated, dried and concentrated. The crude was purified by silica gel column with Heptane/ethyl acetate to give a jell (39 mg, yield 13%). $^1$H NMR (400 MHz, METHANOL-d4) δ 8.17 (d, J=7.40 Hz, 1H), 8.10 (d, J=9.35 Hz, 1H), 7.84-8.01 (m, 1H), 7.58-7.70 (m, 1H), 7.49-7.58 (m, 1H), 6.08 (dd, J=6.84, 8.72 Hz, 0.75H), 5.80 (t, J=7.65 Hz, 0.12H), 5.00 (br. s., 1H), 3.36-3.54 (m, 2H), 3.09-3.28 (m, 2H), 1.66-2.77 (m, 14H), 0.95 (t, J=7.31 Hz, 3H). LCMS m/z 556.0 [M+H]$^+$

Example 300

9-(1-(5-(trifluoromethyl)-6-((cis-4-(trifluoromethyl)cyclohexyl)oxy)naphthalen-2-yl)ethyl)-9-azabicyclo[3.3.1]nonane-3-carbonitrile

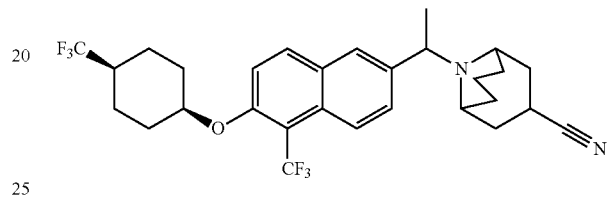

Step 1: 1-(5-(trifluoromethyl)-6-(cis-4-(trifluoromethyl)cyclohexyl)oxy)naphthalen-2-yl)ethyl methanesulfonate

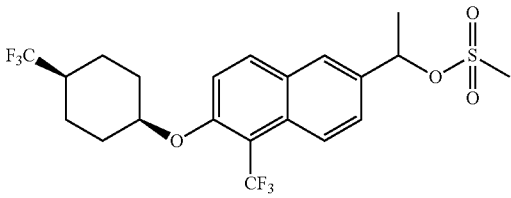 [SMILES: CC(OS(C)(=O)=O)c1ccc2c(C(F)(F)F)c(O[C@H]3CC[C@@H](C(F)(F)F)CC3)ccc2c1]

To a solution of 1-[5]-trifluoromethyl-6-(4-trifluoromethyl-cyclohexyloxy)-naphthalen-2-yl]-ethanol (1.03 g, 2.53 mmol) and N,N-diisopropylethylamine (1.32 mL, 7.60 mmol) in methylene chloride (9.75 mL) was added methanesulfonyl chloride (0.39 mL, 5.07 mmol) dropwise. A white precipitate formed. The solution was stirred at rt for 5h. LCMS showed no starting material left, and complete conversion to RT 2.36 min. The mixture was diluted with DCM and washed with sodium bicarbonate solution and water, dried over MgSO$_4$, filtered, concentrated. The residue was used as in the next step.

Step 2: 9-(1-(5-(trifluoromethyl)-6-((cis-4-(trifluoromethyl)cyclohexyl)oxy)naphthalen-2-yl)ethyl)-9-azabicyclo[3.3.1]nonane-3-carbonitrile

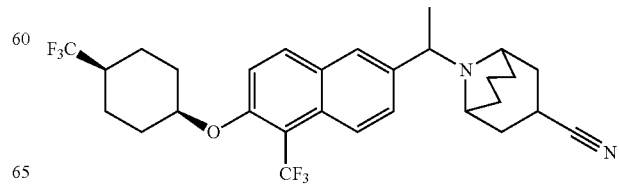

To a solution of methanesulfonic acid 1-[5-trifluoromethyl-6-(4-trifluoromethyl-cyclohexyloxy)-naphthalen-2-yl]-ethyl ester (0.62 g, 1.3 mmol) in N,N-dimethylformamide (5 mL), 9-aza-bicyclo[3.3.1]nonane-3-carbonitrile (0.478 g, 2.56 mmol) was added, followed by Cesium Carbonate (1.25 g, 3.84 mmol). The reaction was then heated at 60° C. for 2h and 80° C. overnight. Cooled down, the reaction mixture was diluted with EtOAc, washed with water (×3). The organic phase was then separated, dried and concentrated. The crude was purified by silica gel column with HE/EA to give a jell (0.26 g, yield 37%). $^1$H NMR (400 MHz, METHANOL-d4) δ 8.35 (d, J=9.10 Hz, 1H), 8.18 (br. s., 2H), 7.80 (d, J=11.80 Hz, 1H), 7.63 (d, J=9.29 Hz, 1H), 5.24 (br. s., 1H), 5.05 (br. s., 1H), 4.24 (br. s., 1H), 3.80 (s, 1H), 3.19 (br. s., 1H), 1.52-2.88 (m, 23H). LCMS m/z 539.0 [M+H]$^+$ Example 301

8-(1-(5-(trifluoromethyl)-6-((cis-4-(trifluoromethyl)cyclohexyl)oxy)naphthalen-2-yl)ethyl)-8-azabicyclo[3.2.1]octane-3-carbonitrile

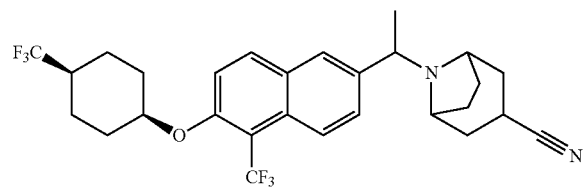 [SMILES: CC(c1ccc2c(C(F)(F)F)c(O[C@H]3CC[C@@H](C(F)(F)F)CC3)ccc2c1)N1C2CCC1CC(C#N)C2]

To a solution of methanesulfonic acid 1-[5-trifluoromethyl-6-(4-trifluoromethyl-cyclohexyloxy)-naphthalen-2-yl]-ethyl ester (0.62 g, 1.3 mmol) in N,N-dimethylformamide (5 mL), 8-azabicyclo[3.2.1]octane-3-carbonitrile (0.442 g, 2.56 mmol) was added, followed by Cesium Carbonate (1.25 g, 3.84 mmol). The reaction was then heated at 60° C. for 2h and 80° C. overnight. Cooled down, the reaction mixture was diluted with EtOAc, washed with water (×3). The organic phase was then separated, dried and concentrated. The crude was purified by silica gel column with HE/EA to give a jell (0.414 g, yield 62%). $^1$H NMR (400 MHz, METHANOL-d4) δ 8.32 (d, J=9.10 Hz, 1H), 8.16 (s, 1H), 8.08 (br. s., 1H), 7.74 (d, J=8.97 Hz, 1H), 7.61 (d, J=9.29 Hz, 1H), 5.03 (br. s., 1H), 4.57 (br. s., 1H), 4.39 (br. s., 1H), 3.48 (br. s., 1H), 1.89-2.70 (m, 11H), 1.60-1.88 (m, 10H). LCMS m/z 526.0 [M+H]$^+$ Example 302

S1P Receptor Activity Assays

Compounds that are not specific for a particular S1P receptor can cause undesirable side effects. Accordingly, compounds are tested to identify those that are specific. Accordingly, the test compounds are tested in a calcium mobilization assay/S1P receptor activity assay. The procedure is essentially as described in Davis et al. (2005) *Journal of Biological Chemistry*, vol. 280, pp. 9833-9841, which is incorporated by reference in its entirety with the following modifications. Calcium mobilization assays are performed in recombinant CHEM cells expressing human $S1P_1$, $S1P_2$, $S1P_3$, $S1P_4$, or $S1P_5$ purchased from Millipore (Billerica, Mass.). To detect free intracellular calcium, $S1P_1$, $S1P_2$, $S1P_3$, $S1P_4$, or $S1P_5$ cells are loaded with FLIPR Calcium 4 dye from Molecular Devices (Sunnyvale, Calif.). Cells are imaged for calcium mobilization using a FLIPR$^{TETRA}$ equipped with a 96-well dispense head.

Agonist percentage activation determinations were obtained by assaying sample compounds and referencing the $E_{max}$ control for each receptor profiled. Antagonist percentage inhibition determinations were obtained by assaying sample compounds and referencing the control $EC_{80}$ wells for each receptor profiled.

Calcium Flux Assay: Agonist Assay Format

Sample compounds were plated in an eight-point, four-fold dilution series in duplicate with a top concentration of 10 μM. The concentrations described here reflect the final concentration of the compounds during the antagonist assay. During the agonist assay the compound concentrations were 1.25 fold higher to allow for the final desired concentration to be achieved with further dilution by $EC_{80}$ of reference agonists during the antagonist assay.

Reference agonists were handled as mentioned above serving as assay control. The reference agonists were handled as described above for $E_{max}$.

Assay was read for 180 seconds using the FLIPR$^{TETRA}$ (This assay run added sample compounds and reference agonist to respective wells). At the completion of the first "Single Addition" assay run, assay plate was removed from the FLIPR$^{TETRA}$ and placed at 25° C. for seven (7) minutes.

Calcium Flux Assay: Antagonist Assay Format

Using the $EC_{80}$ values determined during the agonist assay, stimulated all pre-incubated sample compound and reference antagonist (if applicable) wells with $EC_{80}$ of reference agonist. Read for 180 seconds using the FLIPR$^{TETRA}$ (This assay added reference agonist to respective wells-then fluorescence measurements were collected to calculate percentage inhibition values).

With regard to S1P4 antagonist activity, the compounds of examples 58 and 74 had $IC_{50}$ values of no greater than 100 nM. The compounds of examples 4, 11, and 80 had $IC_{50}$ values of no greater than 250 nM. The compounds of examples 44, 46, and 67 had $IC_{50}$ values of no greater than 500 nM.

With regard to S1P4 agonist activity, the compound of example 62 had an $IC_{50}$ value of no greater than 500 nM.

Example 303

ATX Activity Measurements

ATX (Autotaxin) is a 125 KDa glycoprotein with lysophospholipase D (LPLD) activity that generates the bioactive lipid lysophosphatidic acid (LPA) from lysophosphatidylcholine (LPC). The ATX biochemical assay utilizes a FRET (fluorescence resonance energy transfer) technology platform. The fluorescence signal of FRET substrate FS-3 is quenched due to intra-molecular FRET of a fluorophore to a non-fluorescing quencher (Ferguson, C. G., et al., Org Lett. 2006 May 11; 8(10): 2023-2026, which is incorporated by reference in its entirety). ATX catalyzes the hydrolysis of the substrate which separates the dabsyl quencher from the fluorescein reporter, which becomes fluorescent. The reaction is monitored by a SpectraMax M5 (Molecular Devices, Sunnyvale, Calif.) with at excitation wavelength 485 nm and emission wavelength 535 nm.

Reagents

Fatty acid free-BSA (Sigma A8806): 10 mg/mL in $H_2O$, stored at 4° C. 2×ATX assay buffer: 100 mM Tris, 280 mM NaCl, 10 mM KCl, 2 mM $CaCl_2$, 2 mM $MgCl_2$, pH 7.4.

Human ATX protein: expressed and purified in house. Stored at −80° C.

Substrate FS-3 (Echelon, L-2000): 100 μg in 77.74 μL H$_2$O (1 mM stock), stored at −20° C.

384-well flat bottom plates—Corning #3575.

Assay

Compound dilution—All compounds were provided at 10 mM in 100% DMSO. In the first well, 2 μL of 10 mM compound was added to 78 μL of DMSO (1:40 dilution). In subsequent wells 3-fold dilution (total 10 dilutions) were performed.

1×ATX assay buffer was made up with a final concentration of 1 mg/mL fatty acid free-BSA using 2×ATX assay buffer, 10 mg/ml fatty acid free-BSA and ddH$_2$O.

ATX protein was diluted with 1×ATX assay buffer to a concentration of 1.32 μg/mL (1.32×). 38 μL was added per well to the assay plate. The final concentration of ATX in the reaction as 1.0 μg/mL. 2 μL per well of compounds was transferred to provide the desired concentration. The plate was centrifuged, then incubated at room temperature for 30 minutes on the shaker.

FS-3 was diluted with 1×ATX assay buffer to a concentration of FS-3 of 10 μM (5×). Then, 10 μL was added per well to the assay plate. The final concentration of FS-3 in the reaction was 2 μM. The plate was centrifuged. The plate was kept shaking at room temperature for 2 hours. Because FS-3 substrate is light sensitive, plates were kept covered and protected from light.

Fluorescence was measured using SpectraMax M5 (excitation at 485 nm/emission at 538 nm, top read).

The compounds of examples 84, 88, 89, 90, 93, 94, 95, 97, 99, 100, 101, 102, 104, 105, 110, 115, 118, 122, 124, 127, 128, 131, 132, 133, 134, 135, 136, 137, 138, 139, 140, 141, 171, 173, 174, 175, 176, 177, 178, 179, 180, 181, 182, 184, 185, 187, 190, 191, 194, 198, 199, 202, 204, 206, 207, 209, 210, 211, 212, 213, 214, 216, 217, 218, 219, 220, 221, 222, 223, 224, 225, 226, 227, 228, 229, 230, 233, 234, 235, 236, 238, 239, 240, 241, 242, 244, 245, 246, 249, 250, 251, 253, 262, 280, 281, 282, 283, 287, 289, 290, 291, 292, 294, 296 and 298 had an IC$_{50}$ of no greater than 100 nM.

The compounds of examples 109, 111, 125, 126, 130, 146, 149, 150, 154, 162, 165, 167, 172, 183, 186, 189, 201, 203, 205, 208, 231, 237, 252, 272, 274, 284, 288, 295 and 297 had an IC$_{50}$ of no greater than 250 nM.

The compounds of examples 83, 85, 96, 106, 117, 123, 129, 144, 159, 169, 170, 188, 197, 200, 215, 232, 244, 247, 248, 263, 264, 271, 279 and 293 had an IC$_{50}$ of no greater than 500 nM.

OPC Differentiation Assay

Enriched populations of oligodendrocytes were grown from post-natal day 2 (P2) female Sprague Dawley rats. The forebrain was dissected out and placed in Hank's buffered saline solution (HBSS; Invitrogen, Grand Island, N.Y.). The tissue was cut into 1 mm fragments and incubated at 37° C. for 15 minutes in 0.01% trypsin and 10 μg/mL DNase. Dissociated cells were plated on poly-L-lysine-coated T75 tissue culture flasks and grown at 37° C. for 10 days in Dulbecco's modified Eagle's medium (DMEM) with 20% fetal calf serum (Invitrogen). A2B$^{5+}$ OPCs were collected by shaking the flask overnight at 200 rpm and 37° C., resulting in a 95% pure population.

For the differentiation assay, 2 μM and 20 μM antagonist or the same concentrations of vehicle (DMSO) were applied to OPCs cultured in CNTF/T3 containing media. After a 3-day incubation, cells were lysed in 80 μL lysis buffer (50 mM HEPES [4-(2-hydroxyethyl)-1-piperazineethanesulfonic acid], pH 7.5, 150 mM NaCl, 1.5 mM MgCl$_2$, 1 mM ethylene glycol tetraacetic acid [EGTA], 1% Triton X-100 and 10% glycerol) for 30 minutes at 4° C. After centrifugation at 14,000 g for 15 minutes, the supernatants were boiled in Laemmli sample buffer, subjected to 4-20% SDS-PAGE, and analyzed by Western blotting with anti-MBP, anti-myelin-associated glycoprotein (MAG), or anti-beta actin antibodies. The secondary antibodies used were anti-mouse IgG-HRP (horseradish peroxidase) and anti-rabbit IgG-HRP respectively.

DRG-OPC Myelination Assay

Embryonic neocortical neurons are dissected from embryonic day 18 (E18) Sprague Dawley rats, and then plated on poly-D-lysine (100 μg/mL)-coated cover slips and grown in neurobasal medium supplemented with B27 (Invitrogen) for one week. A2B$^{5+}$ OPCs are prepared as described above and then added into the cultured neocortical neurons. One day later, different concentrations of an S1P4 receptor antagonist or ATX inhibitor and control reagents are applied into the co-cultures. Fresh media containing the different concentrations of an S1P4 receptor antagonist or ATX inhibitor or control compounds are supplied every three days. After ten days, co-cultures are subjected to sodium dodecyl sulfate polyacrylamide gel electrophoresis (SDS-PAGE)/Western blot analyses to quantify MAG, MBP, and MOG.

Remyelination Assay in Brain Slice Culture

Approximately three to four consecutive 300 μm slices are taken from the junction of the corpus callosum to the hippocampus in post-natal, day 17 Sprague Dawley rats (Charles River, Willmington, Mass.). Slices are cultured in basal DMEM supplemented with 25% horse serum for three days, before being treated with 6 mg/mL LPC (Sigma L-4129) for a further three days. The medium is then changed, and slices incubated with medium containing an S1P4 receptor antagonist or ATX inhibitor or vehicle control for a final period of three days, after which myelination is visualized by black gold staining (Millipore, Bedford, Mass.) following the manufacture's protocol. Images are acquired using a Leica M420 microscope (Bannockburn, Ill.) and the staining intensity of corpus callosum is analyzed using Metamorph software (Molecular Devices, Downingtown, Pa.). Three or four brain slices are used for each treatment group.

Lysolecithin Demyelination Model

Adult Sprague Dawley rats (220-260 g) are anesthetized by intraperitoneal injection of a cocktail, consisting of Ketamine (35 mg/kg), Xylazine (6 mg/kg) and Acepromazine (1 mg/kg). The back of the animal is shaved from the lower thoracic to the lumbar region, subsequently sanitized with 70% isopropanol, Betadine Scrub solution, and 70% isopropanol again. The animal is then placed onto stereotaxic frame.

After ensuring an adequate anesthetic level, the skin is incised along the midline over the thoracic region. The dorsal fascia is incised and the paraspinal muscles separated from the spinous processes of the thoracic vertebrae T-9 through T-11. The T-10 vertebra is demolished, and the lamina removed with micro-rongeurs. Once the dorsal spinal cord region is exposed, a microcapillary glass needle is inserted into the dorsal column to a depth of 0.6 mm. The demyelinating reagent, 1.5 μL of 1% Lysolecithin (LPC, Sigma#L1381) in saline is injected with the infusion rate of 2 nL/sec controlled by a micro-pump (World Precision Instrument #micro4). Once the injection is completed, the needle is placed for additional 1 min before removal. The paraspinal muscles and the lumbar fascia are closed with suture (#5, silk). The skin incision is closed with wound clips. Animals are allowed to recover from the anesthesia and are observed in the humidified incubator.

Buprenorphine (0.05 mg/kg) is administered subcutaneously (s.c.) twice a day for additional two days following operation.

Three days following the primary surgery, treatments with an S1P4 receptor antagonist or ATX inhibitor (30 pmol), LPA (30 pmol) or control (0.1% DMSO in saline) are injected at the primary injection region in a volume of 1.5 μL with the same infusion speed as indicated above. Nine days following the primary surgery, the animals are anesthetized and perfused trans-cardially with heparin (10 iu/mL) in saline followed by 4% PFA in PBS. The spinal cords are removed and post fixed in PFA overnight. Then the cords are cut into 100 μM thickness longitudinally and then 1% loxuol fast blue is stained and histological evaluation for remyelination and repair is assessed under microscope.

For systemic treatment, the animals are administered once daily intraperitoneally with either an S1P4 receptor antagonist or ATX inhibitor (10 mg/kg) or control (15% HPCD (hydroxypropyl-β-cyclodextrin)) 2 days following the primary surgery. Nine days after the primary surgery, animals are sacrificed and the spinal cords were processed as indicated above.

In Vivo Screening Assays

Measurement of circulating lymphocytes: Compounds are dissolved in 30% HPCD. Mice (C57bl/6 male, 6-10 week-old) are administered 0.5 and 5 mg/kg of a compound via oral gavage 30% HPCD is included as a negative control.

Blood is collected from the retro-orbital sinus 5 and 24 hours after drug administration under short isoflurane anesthesia. Whole blood samples are subjected to hematology analysis. Peripheral lymphocyte counts are determined using an automated analyzer (HEMAVE™ 3700). Subpopulations of peripheral blood lymphocytes are stained by fluorochrome-conjugated specific antibodies and analyzed using a fluorescent activating cell sorter (FACSCALIBUR™). Three mice are used to assess the lymphocyte depletion activity of each compound screened.

Compounds of the invention can induce full lymphopenia at times as short as 4 hours or less to as long as 48 hours or more; for example, 4 to 36 hours, or 5 to 24 hours. In some cases, a compound of formula can induce full lymphopenia at 5 hours and partial lymphopenia at 24 hours. The dosage required to induce lymphopenia can be in the range of, e.g., 0.001 mg/kg to 100 mg/kg; or 0.01 mg/kg to 10 mg/kg. The dosage can be 10 mg/kg or less, such as 5 mg/kg or less, 1 mg/kg or less, or 0.1 mg/kg or less.

CFA Inflammatory Pain Model

In the CFA (complete Freund's adjuvant) model, adult male SD (250-300 g) rats are anesthetized with isoflurane inhalation (4.5% induction/2.0% maintenance). Heat-killed M. Tuberculosis H37 RA (non-viable) suspended at a concentration of 1.0 mg/ml in incomplete Freund's adjuvant is used (Chondrex Inc., catalog#7008). At day 0, intradermal injection (i.d.) of 100 μl of CFA (1:1 oil/saline) is slowly perfused into the right footpad of the rats. At day 1, baseline tactile allodynia test are conducted: rats that develop sensitive painful response are enrolled to the study. At day 2, rats are orally dosed once with either vehicle or ATX inhibitor, then at 2 hrs, 4 hrs, 6 hrs and 24 hrs after dosage, all rats are tested for mechanical allodynia response.

Tactile allodynia is tested as follows. A rat is placed in an elevated Plexiglas observation chamber (approximately 4"×6"×10") having a wire grid (1 cm² spacing) mesh floor under polycarbonate cages. The rat is left to acclimate to the experimental conditions for 20 minutes before testing begins. After the rat is calm, tactile allodynia is assessed using a series of von Frey filaments ranging from 2.04-28.84 g (Stoelting, Wood Dale, Ill.). Graded pressure is presented to a localized area on the plantar surface of the paw via the use of Von Frey hairs (monofilaments which are calibrated to bend at a known pressure). A response to the VonFrey hair is recorded as the rat withdrawing the tested paw and is usually followed by lifting and licking. A series of filaments are used to determine the threshold response using the established "Up-Down" method. Each paw is tested 4-6 times repeatedly with 1-2 seconds (modified from Seltzer et al., 1991) in between each probe to accurately assess the behavior. A sharp lifting of the paw is scored as a positive response.

Rat Model of Neuropathic Pain

Chronic Constriction Injury (CCI) Surgery: In the CCI model (Bennett and Xie, *Pain,* 1989, which is incorporated by reference in its entirety), adult male SD (250-275 g) rats are anesthetized with isoflurane inhalation (4.5% induction/2.0% maintenance). The surgery is performed under aseptic conditions and involves exposing the sciatic nerve at the mid-thigh level. Ocular lubricant is used as needed to prevent corneal drying. After shaving and disinfecting the skin (betadine followed by 70% ethanol), a small incision is made just caudal to the biceps femoris. Care is taken to not disturb the sciatic nerve. The nerve is slightly elevated, and 4 loose ligatures of 4-0 chromic gut suture are inserted under the nerve, and then are loosely tied around it. The sutures constrict the nerve but do not strangle it. Prior to inserting the chromic gut, it is rinsed twice in sterile saline. The incision is closed with wound clips, and rats are allowed to recover from anesthesia on a circulating water heating pad before being returned to their home cages. In the sham controls the skin is opened, and the sciatic nerve is identified and elevated, but no sutures are tied around the nerve. All rats are screened for pain response around post-surgery day 7 and only rats with sensitive pain response are enrolled to the study.

Animals are orally dosed twice/day for 3 times/week with either vehicle or ATX inhibitor post-surgery at days 10, 12, 14, 17, 19 and 21, and animals are also tested at the same schedule for three types of neuropathic pain: thermal hyperalgesia, tactile allodynia and incapacitance.

(1) Plantar thermal hyperalgesia: Rats are tested for hyperalgesia using a plantar device (Ugo Basile Inc., Cat.#37370). After acclimation to the testing room, rats are placed on an elevated glass floor beneath inverted clear plastic cages, and a radiant heat source beneath the glass is aimed at the mid-plantar surface of the hindpaw after they have ceased all exploratory behavior. The onset of light activates a timer, which is terminated by a hindpaw withdrawal response. A cutoff time of 30 seconds is used to avoid tissue damage in the absence of a response. The average withdrawal latency value of three trials from the ipsilateral hindpaw is measured with at least 5-10 minutes between each trial to avoid any tissue damage.

(2) Tactile allodynia is tested as described above.

(3) Incapacitance: The incapacitance test measures the weight the rat places on each of its hindpaws. The rat is placed in a small, clear Plexiglas box (6"long x 3"wide x 4"tall). The box is tilted up and opens in the front. The rat is placed in the box so that its hindpaws are at the back (lower) portion of the box, and the forepaws are at the front (raised) part of the box. The rat's head is at the opening in the front of the box. The box is placed on a divided scale such that each of the rat's hindpaws is on one of the two weighing pans of the scale. The weight that the rat placed on each hindpaw is then measured. The procedure is rapid (about 10 sec) and does not cause the animal any pain.

Other embodiments are within the scope of the following claims.

What is claimed is:
1. A compound represented by formula (I):

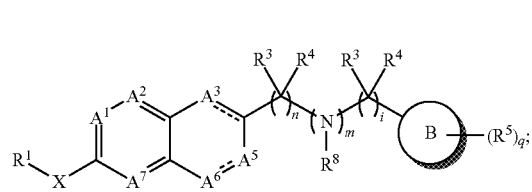

(I)

or a pharmaceutically acceptable salt thereof, wherein:
X is O, or $NR^{12}$;
$A^1$, $A^2$, $A^3$, $A^5$, $A^6$ and $A^7$ are each independently $CR^2$;
"------" indicates a double bond;
$R^1$ is a $C_{6-20}$alkyl, a $C_{3-14}$carbocyclyl, a 3- to 15-membered heterocyclyl, a $C_{6-10}$aryl, or a five- to 14-membered heteroaryl, wherein $R^1$ may be optionally substituted with from one to six independently selected $R^6$;
$R^2$, for each occurrence, is independently selected from the group consisting of hydrogen, halo, hydroxyl, nitro, cyano, carboxy, $C_{1-6}$alkyl, $C_{1-6}$haloalkyl, $C_{3-8}$cycloalkyl, $C_{3-8}$halocycloalkyl, $C_{1-6}$alkoxy, $C_{1-6}$haloalkoxy, $C_{3-8}$cycloalkoxy, $C_{3-8}$halocycloalkoxy, $C_{1-6}$alkanoyl, amino, N—($C_{1-6}$alkyl)amino, N,N-di-($C_{1-6}$alkyl)amino, $C_{1-6}$alkoxycarbonyl, $C_{1-6}$alkanoyloxy, carbamoyl, N—($C_{1-6}$alkyl)carbamoyl, N,N-di-($C_{1-6}$alkyl)carbamoyl, $C_{1-6}$alkylamido, mercapto, $C_{1-6}$alkylthio, $C_{1-6}$alkylsulfonyl, sulfamoyl, N—($C_{1-6}$alkyl)sulfamoyl, N,N-di-($C_{1-6}$alkyl)sulfamoyl, and $C_{1-6}$alkylsulfonamido;
each $R^3$ and each $R^4$ are each independently hydrogen, a carboxy, $C_{1-6}$alkyl, or a $C_{2-6}$alkenyl; or $R^3$ and $R^4$ together with the carbon to which they are attached are —C(=O)—, a $C_{3-8}$spirocycloalkyl, or a 3- to 8-membered spiroheterocycloalkyl;
$R^6$, for each occurrence, is independently selected from the group consisting of halo, $C_{1-6}$alkyl, $C_{1-6}$alkoxy, $C_{1-6}$haloalkyl, $C_{3-8}$cycloalkyl, $C_{6-10}$aryl, $C_{1-6}$alkoxy-$C_{1-6}$alkyl, and tri-($C_{1-6}$alkyl)silyl; or two $R^6$ that are attached to the same carbon atom may form $C_{3-8}$spirocycloalkyl or 3- to 8-membered spiroheterocycloalkyl;
$R^8$, and $R^{12}$ are each independently hydrogen or a $C_{1-6}$alkyl;
i is an integer from 0 to 6;
n is an integer from 1 to 6; and
(i) m is 1;
B is a ring system represented by the following formula:

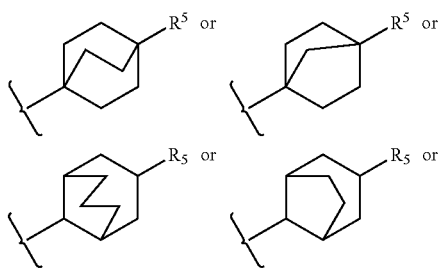

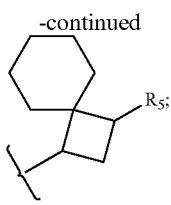

and
$R^5$ is $CO_2H$; or
(ii) m is 0;

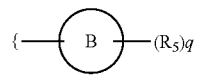

is a ring system represented by the following formula:

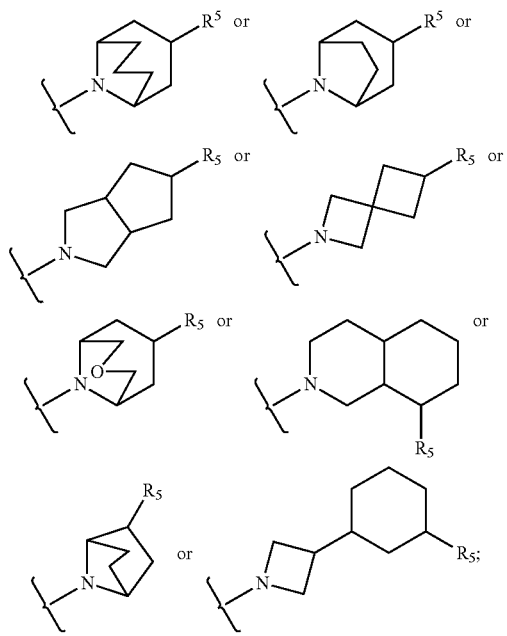

wherein B is optionally further substituted by oxo, hydroxy, —$NH_2$, —$CONH_2$, or —$CO_2H$; and
$R^5$ is $CO_2H$.
2. The compound according to claim 1, or a pharmaceutically acceptable salt thereof, wherein:
m is 1;

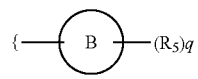

is a ring system represented by the following formula:

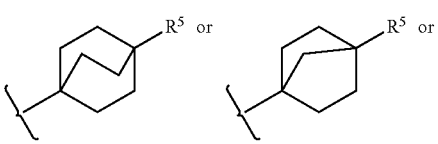

-continued

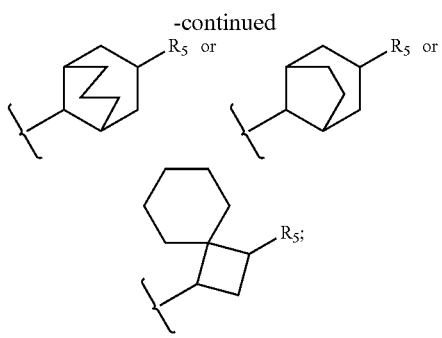

and
R⁵ is CO₂H.

3. The compound according to claim 2, or a pharmaceutically acceptable salt thereof, wherein:

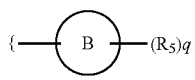

is a bridged ring system represented by the following formula:

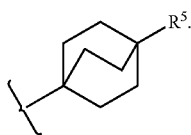

4. The compound according to claim 1, or a pharmaceutically acceptable salt thereof, wherein:
m is 0;

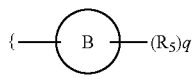

is a ring system represented by the following formula:

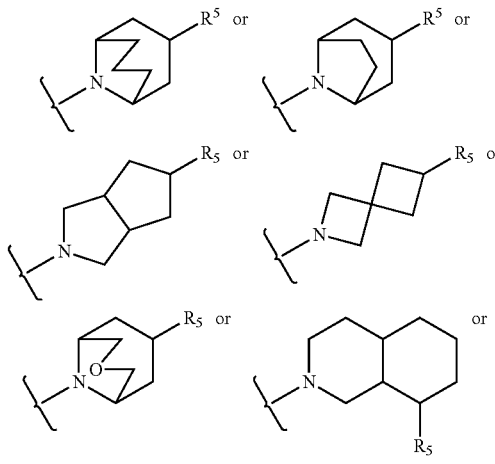

-continued

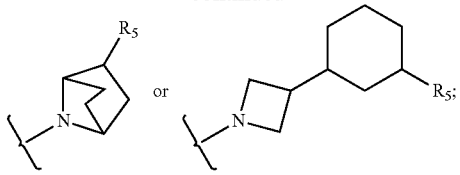

wherein B is optionally further substituted by oxo, hydroxy, —NH₂, —CONH₂, or —CO₂H; and
R⁵ is CO₂H.

5. The compound according to claim 1, wherein the compound is represented by formula (II):

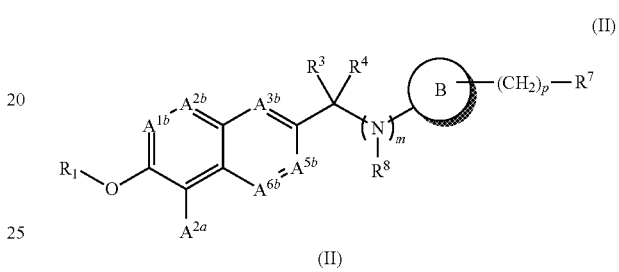

(II)

or a pharmaceutically acceptable salt thereof, wherein:
$A^{1b}$, $A^{2b}$, $A^{3b}$, $A^{5b}$, and $A^{6b}$ are $CR^{2b}$;
$R^{2a}$ is a halo, $C_{1-6}$haloalkyl or cyano;
$R^{2b}$, for each occurrence, is independently selected from the group consisting of hydrogen, halo, hydroxyl, nitro, cyano, carboxy, $C_{1-6}$alkyl, $C_{1-6}$haloalkyl, $C_{3-8}$cycloalkyl, $C_{3-8}$halocycloalkyl, $C_{1-6}$alkoxy, $C_{1-6}$haloalkoxy, $C_{3-8}$cycloalkoxy, $C_{3-8}$halocycloalkoxy, $C_{-6}$alkanoyl, amino, N—($C_{1-6}$alkyl)amino, N,N-di-($C_{1-6}$alkyl)amino, $C_{1-6}$alkoxycarbonyl, carbamoyl, N—($C_{1-6}$ alkyl)carbamoyl, N,N-di-($C_{1-6}$alkyl)carbamoyl, $C_{1-6}$alkylamido, mercapto, $C_{1-6}$alkylthio, $C_{1-6}$alkylsulfonyl, sulfamoyl, N—($C_{1-6}$alkyl)sulfamoyl, N,N-di-($C_{1-6}$alkyl)sulfamoyl, and $C_{1-6}$alkylsulfonamido; and
—(CH₂)$_p$—R⁷ is R⁵.

6. The compound according to claim 5, or a pharmaceutically acceptable salt thereof, wherein $R^{2b}$, for each occurrence, is independently hydrogen or a halo.

7. The compound according to claim 6, wherein the compound is represented by formula (IIa):

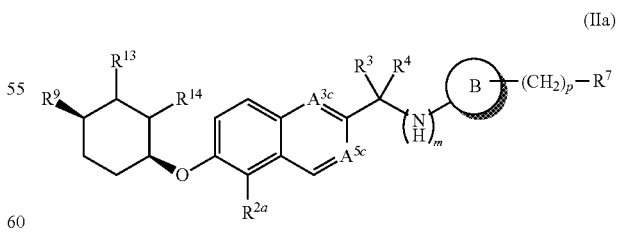

(IIa)

or a pharmaceutically acceptable salt thereof, wherein:
$A^{3c}$ and $A^{5c}$ are CH;
$R^9$ is a halo, an $C_{1-6}$alkyl, or a $C_{1-6}$haloalkyl; and
$R^{13}$ and $R^{14}$ are each independently hydrogen or a $C_{1-6}$alkyl; and
—(CH₂)$_p$—R⁷ is R⁵.

8. The compound according to claim 7, wherein the compound is represented by formula (IIb):

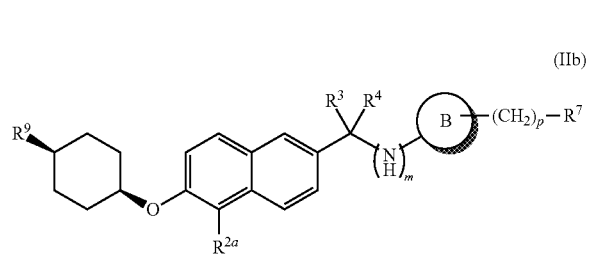

(IIb)

or a pharmaceutically acceptable salt thereof.

9. The compound according to claim 8, or a pharmaceutically acceptable salt thereof, wherein:
m is 0;

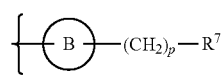

is a ring system represented by the following formula:

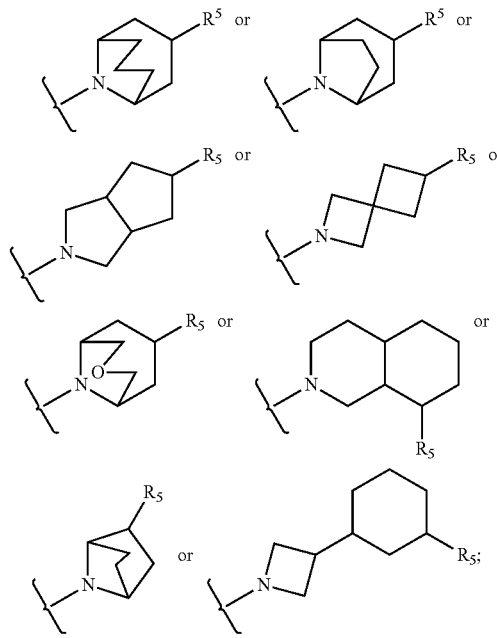

wherein B is optionally further substituted by oxo, hydroxy, —NH$_2$, —CONH$_2$, or —CO$_2$H; and
R$^5$ is CO$_2$H.

10. The compound according to claim 9, or a pharmaceutically acceptable salt thereof, wherein R$^{2a}$ is —Cl, —CF$_3$ or —CHF$_2$.

11. The compound according to claim 10, or a pharmaceutically acceptable salt thereof, wherein R$^9$ is methyl, ethyl, —CF$_3$ or tert-butyl.

12. The compound according to claim 1, wherein the compound is represented by formula (III):

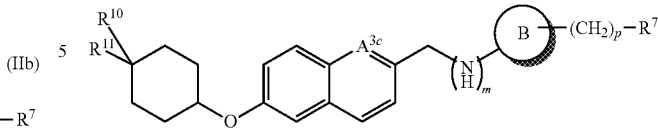

(III)

or a pharmaceutically acceptable salt thereof, wherein:
A$^{3c}$ is CH;
R$^{10}$ and R$^{11}$ are each independently hydrogen, C$_{1-6}$alkyl, C$_{1-6}$haloalkyl, tri-C$_{1-6}$alkylsilyl, or phenyl, wherein at least one of R$^{10}$ or R$^{11}$ is not hydrogen; or R$^{10}$ and R$^{11}$ together with the carbon to which they are attached form a C$_{3-8}$spirocycloalkyl or 3- to 8-membered spiroheterocycloalkyl; and
—(CH$_2$)$_p$—R$^7$ is R$^5$.

13. The compound according to claim 12, or a pharmaceutically acceptable salt thereof, wherein:
m is 1;

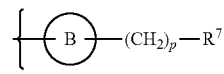

is a bridged ring system represented by the following formula:

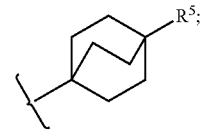

and
R$^5$ is CO$_2$H.

14. The compound of claim 1, or a pharmaceutically acceptable salt thereof, wherein R$^6$ is trifluoromethyl, difluoromethyl or monofluoromethyl.

15. The compound of claim 1, or a pharmaceutically acceptable salt thereof, wherein R$^6$ is methyl, ethyl or isopropyl.

16. The compound according to claim 1, or a pharmaceutically acceptable salt thereof, wherein: X is NH.

17. The compound of claim 1, wherein the compound is selected from the group consisting of:
   4-(((6-(cyclohexyloxy)naphthalen-2-yl)methyl)amino)bicyclo[2.2.2]octane-1-carboxylic acid;
   4-(((6-((trans-4-methylcyclohexyl)oxy)naphthalen-2-yl)methyl) amino)bicyclo [2.2.2]octane-1-carboxylic acid;
   4-(((6-((trans-4-ethylcyclohexyl)oxy)naphthalen-2-yl)methyl)amino)bicyclo [2.2.2] octane-1-carboxylic acid;
   4-(((6-((trans-4-isopropylcyclohexyl)oxy)naphthalen-2-yl)methyl)amino)bicyclo[2.2.2]octane-1-carboxylic acid;
   4-(((6-((trans-4-(tert-pentyl)cyclohexyl)oxy)naphthalen-2-yl)methyl)amino)bicyclo[2.2.2]octane-1-carboxylic acid;
   4-(((6-((trans-4-phenylcyclohexyl)oxy)naphthalen-2-yl)methyl)amino)bicyclo[2.2.2]octane-1-carboxylic acid;

4-(((6-((4,4-dimethylcyclohexyl)oxy)naphthalen-2-yl)methyl)amino)bicyclo [2.2.2]octane-1-carboxylic acid;

4-(((6-(spiro [2.5]octan-6-yloxy)naphthalen-2-yl)methyl)amino)bicyclo [2.2.2]octane-1-carboxylic acid;

4-(((6-(spiro[3.5]nonan-7-yloxy)naphthalen-2-yl)methyl)amino)bicyclo[2.2.2]octane-1-carboxylic acid;

4-(((6-(spiro [4.5]decan-8-yloxy)naphthalen-2-yl)methyl)amino)bicyclo [2.2.2]octane-1-carboxylic acid;

4-(((6-(spiro[5.5]undecan-3-yloxy)naphthalen-2-yl)methyl)amino)bicyclo[2.2.2]octane-1-carboxylic acid;

4-(((6-(heptyloxy)naphthalen-2-yl)methyl)amino)bicyclo [2.2.2]octane-1-carboxylic acid;

4-(((6-((cis-4-methylcyclohexyl)oxy)naphthalen-2-yl)methyl)amino)bicyclo [2.2.2] octane-1-carboxylic acid;

4-(((6-((cis-4-ethylcyclohexyl)oxy)naphthalen-2-yl)methyl)amino)bicyclo[2.2.2]octane-1-carboxylic acid;

4-(((6-((cis-4-isopropylcyclohexyl)oxy)naphthalen-2-yl)methyl) amino)bicyclo [2.2.2]octane-1-carboxylic acid;

4-(((6-((cis-4-(trifluoromethyl)cyclohexyl)oxy)naphthalen-2-yl)methyl)amino)bicyclo[2.2.2]octane-1-carboxylic acid;

4-(((6-((cis-4-phenylcyclohexyl)oxy)naphthalen-2-yl)methyl)amino)bicyclo[2.2.2]octane-1-carboxylic acid;

4-(((6-((trans-4-(trifluoromethyl)cyclohexyl)oxy)naphthalen-2-yl)methyl)amino)bicyclo[2.2.2]octane-1-carboxylic acid;

4-(((6-((cis-4-(tert-butyl)cyclohexyl)oxy)naphthalen-2-yl)methyl)amino)bicyclo[2.2.2]octane-1-carboxylic acid;

4-(((6-(heptyloxy)naphthalen-2-yl)methyl)amino)bicyclo[2.2.2]octane-1-carboxylate;

4-(((6-((trans-4-(tert-butyl)cyclohexyl)oxy)-5-(trifluoromethyl)naphthalen-2-yl)methyl)amino)bicyclo [2.2.2]octane-1-carboxylic acid;

3-(1-((6-((cis-4-isopropylcyclohexyl)oxy)naphthalen-2-yl)methyl)azetidin-3-yl)cyclohexanecarboxylic acid;

3-(1-((6-((trans-4-(tert-butyl)cyclohexyl)oxy)naphthalen-2-yl)methyl)azetidin-3-yl)cyclohexanecarboxylic acid;

3-(1-((6-((4,4-dimethylcyclohexyl)oxy)quinolin-2-yl)methyl)azetidin-3-yl)cyclohexanecarboxylic acid;

3-(1-((6-(heptyloxy)naphthalen-2-yl)methyl)azetidin-3-yl)cyclohexanecarboxylic acid;

3-(1-((6-((cis-4-ethylcyclohexyl)oxy)naphthalen-2-yl)methyl)azetidin-3-yl)cyclohexanecarboxylic acid;

3-(1-((6-((4,4-dimethylcyclohexyl)oxy)naphthalen-2-yl)methyl)azetidin-3-yl)cyclohexanecarboxylic acid;

3-((1(6-(spiro[4.5]decan-8-yloxy)naphthalen-2-yl)methyl)azetidin-3-yl)cyclohexanecarboxylic acid;

4-(((6-((trans-4-(tert-butyl)cyclohexyl)oxy)naphthalen-2yl)methyl)(methyl)amino)bicyclo[2.2.2]octane-1-carboxylic acid;

8-((6-(((trans-4-(tert-butyl)cyclohexyl)oxy)naphthalen-2-yl)methyl)-8-azabicyclo[3.2.1]octane-3-carboxylic acid;

9-((6-(((trans-4-(tert-butyl)cyclohexyl)oxy)naphthalen-2-yl)methyl)-9-azabicyclo[3.3.1]nonane-3-carboxylic acid;

3-(6-(((trans-4-(tert-butyl)cyclohexyl)oxy)naphthalen-2-yl)methyl)-3-azabicyclo[3.3.1]nonane-9-carboxylic acid;

4-(((6-(((trans-4-(tert-butyl)cyclohexyl)oxy)naphthalen-2-yl)methyl)amino)bicyclo[2.2.1]heptane-1-carboxylic acid;

4-(((6-((trans-4-(tert-butyl)cyclohexyl)oxy)-5-(trifluoromethyl)naphthalen-2-yl)methyl)amino)bicyclo [2.2.1]heptane-1-carboxylic acid;

4-((6-(trans-4-(Trimethylsilyl)cyclohexyloxy)naphthalen-2-yl)methylamino)bicyclo[2.2.2]octane-1-carboxylic acid;

4-(((6-((cis-4-(Trimethylsilyl)cyclohexyl)oxy)naphthalen-2-yl)methyl)amino)bicyclo[2.2.2]octane-1-carboxylic acid;

4-(((6-((trans-4-(tert-butyl)cyclohexyl)oxy)naphthalen-2-yl)methyl)amino)bicyclo[2.2.2]octane-1-carboxylic acid;

or a pharmaceutically acceptable salt thereof.

18. The compound of claim 1, wherein the compound is selected from the group consisting of:

9-((6-((cis-4-ethylcyclohexyl)oxy)naphthalen-2-yl)methyl)-9-azabicyclo[3.3.1]nonane-3-carboxylic acid;

9-((5-(trifluoromethyl)-6-((cis-4-(trifluoromethyl)cyclohexyl)oxy)naphthalen-2-yl)methyl)-9-azabicyclo[3.3.1]nonane-3-carboxylic acid;

3-(((5-(trifluoromethyl)-6-((cis-4-(trifluoromethyl)cyclohexyl)oxy)naphthalene-2-yl)methyl)amino)spiro[3.5]nonane-1-carboxylic acid;

9-1-(5-(trifluoromethyl)-6-((cis-4-(trifluoromethyl)cyclohexyl)oxy)naphthalen-2-yl)ethyl)-9-azabicyclo[3.3.1]nonane-3-carboxylic acid;

9-((R)-1-(5-(trifluoromethyl)-6-((cis-4-(trifluoromethyl)cyclohexyl)oxy)naphthalen-2-yl)ethyl)-9-azabicyclo [3.3.1]nonane-3-carboxylic acid;

9-((S)-1-(5-(trifluoromethyl)-6-((cis-4-(trifluoromethyl)cyclohexyl)oxy)naphthalen-2-yl)ethyl)-9-azabicyclo [3.3.1]nonane-3-carboxylic acid;

9-(1-(6-((cis-4-ethylcyclohexyl)oxy)-5-(trifluoromethyl)naphthalene-2-yl)ethyl)-9-azabicyclo[3.3.1]-nonane-3-carboxylic acid;

9-(1-(6-((cis-4-ethylcyclohexyl)oxy)-5-(trifluoromethyl)naphthalene-2-yl)propyl)-9-azabicyclo[3.3.1]nonane-3-carboxylic acid;

9-(1-(6-((cis-4-Methylcyclohexyl)oxy)-5-(trifluoromethyl)naphthalen-2-yl)ethyl)-9-azabicyclo[3.3.1]nonane-3-carboxylic acid;

9-(1-(6-((cis-4-Methylcyclohexyl)oxy)-5-(trifluoromethyl)naphthalen-2-yl)ethyl)-9-azabicyclo[3.3.1]nonane-3-carboxylic acid, enantiomer 1;

9-(1-(6-((cis-4-Methylcyclohexyl)oxy)-5-(trifluoromethyl)naphthalen-2-yl)ethyl)-9-azabicyclo[3.3.1]nonane-3-carboxylic acid, enantiomer 2;

8-((6-((cis-4-Methylcyclohexyl)oxy)-5-(trifluoromethyl)naphthalen-2-yl)methyl)-8-azabicyclo[3.2.1]octane-3-carboxylic acid;

9-((6-((cis-4-Methylcyclohexyl)oxy)-5-(trifluoromethyl)naphthalen-2-yl)methyl)-9-azabicyclo[3.3.1]nonane-3-carboxylic acid;

9-((6-((4,4-difluorocyclohexyl)oxy)-5-(trifluoromethyl)naphthalene-2-yl)methyl)-9-azabicyclo[3.3.1]nonane-3-carboxylic acid;

8-(1-(5-(difluoromethyl)-6-((cis-4-methylcyclohexyl)oxy)naphthalen-2-yl)propyl)-8-azabicyclo[3.2.1]octane-3-carboxylic acid;

9-((5-(difluoromethyl)-6-((cis-4-(trifluoromethyl)cyclohexyl)oxy)naphthalene-2-yl)methyl)-9-azabicyclo [3.3.1]nonane-3-carboxylic acid;

9-((6-(((trans,trans)-3,5-dimethylcyclohexyl)oxy)-5-(trifluoromethyl) naphthalene-2-yl)methyl)-9-azabicyclo [3.3.1]nonane-3-carboxylic acid;

8-(6-((cis-4-Methylcyclohexyl)oxy)-5-(trifluoromethyl)-2-naphthoyl)-8-azabicyclo[3.2.1]octane-3-carboxylic acid;
9-(5-(trifluoromethyl)-6-((cis-4-(trifluoromethyl)cyclohexyl)oxy)-2-naphthoyl)-9-azabicyclo[3.3.1]nonane-3-carboxylic acid;
9-(2-(5-(trifluoromethyl)-6-((cis-4-(trifluoromethyl)cyclohexyl)oxy)naphthalene-2-yl)acetyl)-9-azabicyclo[.3.1]nonane-3-carboxylic acid;
9-(2-(5-(trifluoromethyl)-6-((cis-4-(trifluoromethyl)cyclohexyl)oxy)naphthalene-2-yl)ethyl)-9-azabicyclo[3.3.1]nonane-3-carboxylic acid;
9-((6-((cis-4-methylcyclohexyl)amino)-5-(trifluoromethyl)naphthalen-2-yl)methyl)-9-azabicyclo[3.3.1]nonane-3-carboxylic acid;
9-((5-Chloro-6-((cis-4-ethylcyclohexyl)oxy)naphthalen-2-yl)methyl)-9-azabicyclo[3.3.1]nonane-3-carboxylic acid;
9-((5-Chloro-6-((cis-4-(trifluoromethyl)cyclohexyl)oxy)naphthalen-2-yl)methyl)-9-azabicyclo[3.3.1]nonane-3-carboxylic acid;
4-(((5-(trifluoromethyl)-6-((cis-4-(trifluoromethyl)cyclohexyl)oxy)naphthalen-2-yl)methyl)carbamoyl)bicyclo[2.2.2]octane-1-carboxylic acid;
N-(6-((cis-4-trifluoromethylcyclohexyl)oxy)-5-(trifluoromethyl)naphthalene-2-ylcarbonyl) -2-azabicyclo[1.2.3]octane-7-carboxylic acid;
N-(6-((cis-4-trifluoromethylcyclohexyl)oxy)-5-(trifluoromethyl)naphthalene-2-ylcarbonyl) -decahydroisoquinoline-5-carboxylic acid;
2-(2-(5-(trifluoromethyl)-6-((cis-4-(trifluoromethyl)cyclohexyl)oxy)naphthalene-2-yl)acetyl)-2-azabicyclo[1.2.3]octane-7-carboxylic acid;
2-(2-(5-(difluoromethyl)-6-((cis-4-(trifluoromethyl)cyclohexyl)oxy)naphthalene-2-yl)acetyl)-2-azabicyclo[1.2.3]octane-7-carboxylic acid;
4-(((5-(trifluoromethyl)-6-((cis-4-(trifluoromethyl)cyclohexyl)oxy)naphthalen-2-yl)methyl)aminomethyl)bicyclo[2.2.2]octane-1-carboxylic acid;
8-(1-(5-(trifluoromethyl)-6-((cis-4-(trifluoromethyl)cyclohexyl)oxy)-naphthalene-2-yl)ethyl)-8-azabicyclo[.2.1]octane-3-carboxylic acid;
8-(1-(6-((cis-4-Methylcyclohexyl)oxy)-5-(trifluoromethyl)naphthalen-2-yl)ethyl)-8-azabicyclo[3.2.1]octane-3-carboxylic acid;
9-(6-((cis-4-Methylcyclohexyl)oxy)-5-(trifluoromethyl)-2-naphthoyl)-9-azabicyclo[3.3.1]nonane-3-carboxylic acid;
9-((6-((cis-4-Methylcyclohexyl)oxy)-5-(trifluoromethyl)naphthalen-2-yl)methyl)-9-aza-7-oxa-bicyclo[3.3.1]nonane-3-carboxylic acid;
8-(1-(6-((cis-4-Methylcyclohexyl)oxy)-5-(trifluoromethyl)naphthalen-2-yl)propyl)-8-azabicyclo[3.2.1]octane-3-carboxylic acid;
9-(1-(6-((cis-4-Methylcyclohexyl)oxy)-5-(trifluoromethyl)naphthalen-2-yl)propyl)-9-azabicyclo[3.3.1]nonane-3-carboxylic acid;
9-((6-((cis-4-Methylcyclohexyl)oxy)-5-(trifluoromethyl)naphthalen-2-yl)methyl)-7-hydroxy-9-aza-bicyclo[3.3.1]nonane-3-carboxylic acid;
8-(1-(6-((cis-4-Methylcyclohexyl)oxy)-5-(trifluoromethyl)naphthalen-2-yl)ethyl)-8-azabicyclo[3.2.1]octane-3-carboxylic acid, enantiomer 1;
8-(1-(6-((cis-4-Methylcyclohexyl)oxy)-5-(trifluoromethyl)naphthalen-2-yl)ethyl)-8-azabicyclo[3.2.1]octane-3-carboxylic acid, enantiomer 2;
9-(1-(5-(difluoromethyl)-6-((cis-4-methylcyclohexyl)oxy)naphthalen-2-yl)ethyl)-9-azabicyclo[3.3.1]nonane-3-carboxylic acid;
8-(1-(5-(difluoromethyl)-6-((cis-4-methylcyclohexyl)oxy)naphthalen-2-yl)ethyl)-8-azabicyclo[3.2.1]octane-3-carboxylic acid;
8-(1-(5-(difluoromethyl)-6-((cis-4-methylcyclohexyl)oxy)naphthalen-2-yl)methyl)-8-azabicyclo[3.2.1]octane-3-carboxylic acid;
9-(1-(5-(difluoromethyl)-6-((cis-4-methylcyclohexyl)oxy)naphthalen-2-yl)propyl)-9-azabicyclo[3.3.1]nonane-3-carboxylic acid;
8-(1-(5-(difluoromethyl)-6-((cis-4-methylcyclohexyl)oxy)naphthalen-2-yl) ethyl)-8-azabicyclo[3.2.1]octane-3-carboxylic acid, enantiomer 1;
8-(1-(5-(difluoromethyl)-6-((cis-4-methylcyclohexyl)oxy)naphthalen-2-yl) ethyl)-8-azabicyclo[3.2.1]octane-3-carboxylic acid, enantiomer 1;
9-(1-(5-(difluoromethyl)-6-((cis-4-methylcyclohexyl)oxy)naphthalen-2-yl)ethyl)-9-azabicyclo[3.3.1]nonane-3-carboxylic acid, enantiomer 1;
9-(1-(5-(difluoromethyl)-6-((cis-4-methylcyclohexyl)oxy)naphthalen-2-yl)ethyl)-9-azabicyclo[3.3.1]nonane-3-carboxylic acid, enantiomer 2;
8-(1-(5-(difluoromethyl)-6-((cis-4-methylcyclohexyl)oxy)naphthalen-2-yl)propyl)-8-azabicyclo[3.2.1]octane-3-carboxylic acid, enantiomer 1;
8-(1-(5-(difluoromethyl)-6-((cis-4-methylcyclohexyl)oxy)naphthalen-2-yl)propyl)-8-azabicyclo[3.2.1]octane-3-carboxylic acid, enantiomer 2;
9-((6-((cis-4-trifluoromethylcyclohexyl)oxy)naphthalen-2-yl)methyl)-9-azabicyclo[3.3.1]nonane-3-carboxylic acid;
3-(4-{[5-trifluoromethyl-6-(4-trifluoromethyl-cyclohexyloxy)-naphthalen-2-ylmethyl]-amino}-bicyclo[2.2.2]oct-1-yl)-carboxylic acid;
2-((5-(trifluoromethyl)-6-((cis-4-(trifluoromethyl)cyclohexyl)oxy)naphthalen-2-yl)methyl)-2-azaspiro[3.3]heptane-6-carboxylic acid;
N-((5-(trifluoromethyl)-6-((cis-4-(trifluoromethyl)cyclohexyl)oxy)naphthalen-2-yl)methyl) -decahydroisoquinoline-8-carboxylic acid;
3-((6-((cis-4-trifluoromethylcyclohexyl)oxy)naphthalen-2-yl)methyl)-3-azabicyclo[3.3.1]nonane-9-carboxylic acid;
N-(5-trifluoromethyl-6-(4-trifluoromethyl-cyclohexyloxy)-naphthalen-2-ylmethyl)-4-aminobicyclo[2.2.1]heptane-1-carboxylic acid;
3-(5-trifluoromethyl-6-(4-trifluoromethyl-cyclohexyloxy)-naphthalen-2-ylmethyl)-3-azabicyclo[3.3.0]octane-7-carboxylic acid;
8-((6-((4,4-difluorocyclohexyl)oxy)-5-(trifluoromethyl)naphthalene-2-yl)methyl)-8-azabicyclo[3.2.1]octane-3-carboxylic acid;
N-(5-trifluoromethyl-6-(cis-4-trifluoromethyl-cyclohexyloxy)-naphthalen-2-ylmethyl)-3-(azetidine-3-yl)-cyclohexane-1-carboxylic acid;
N-(5-trifluoromethyl-6-(cis-4-trifluoromethyl-cyclohexyloxy)-naphthalen-2-ylmethyl)-8-aminobicyclo[3.2.1]octane-3-carboxylic acid, enantiomer 1;
N-(5-trifluoromethyl-6-(cis-4-trifluoromethyl-cyclohexyloxy)-naphthalen-2-ylmethyl)-8-aminobicyclo[3.2.1]octane-3-carboxylic acid, enantiomer 2;
7-(5-trifluoromethyl-6-(cis-4-trifluoromethyl-cyclohexyloxy)-naphthalen-2-ylmethyl)-7-azabicyclo[2.2.1]heptane-2-carboxylic acid;

N-(5-trifluoromethyl-6-(cis-4-trifluoromethyl-cyclohexyloxy)-naphthalen-2-ylmethyl)-9-aminobicyclo[3.3.1]nonane-3-carboxylic acid;
9-(5-trifluoromethyl-6-(cis-4-trifluoromethyl-cyclohexyloxy)-naphthalen-2-ylmethyl)-9-aza-7-oxabicyclo [3.3.1]nonane-3-carboxylic acid;
9-(5-trifluoromethyl-6-(cis-4-trifluoromethyl-cyclohexyloxy)-naphthalen-2-ylmethyl)-7-hydroxy-9-azabicyclo[3.3.1]nonane-3-carboxylic acid;
9-(5-trifluoromethyl-6-(cis-4-trifluoromethyl-cyclohexyloxy)-naphthalen-2-ylmethyl)-7-oxo-9-azabicyclo [3.3.1]nonane-3-carboxylic acid;
9-((6-((cis-4-ethylcyclohexyl)oxy)-5-(trifluoromethyl) naphthalen-2-yl)methyl)-9-azabicyclo[3.3.1]nonane-3-carboxylic acid;
8-((6-((cis-4-ethylcyclohexyl)oxy)-5-(trifluoromethyl) naphthalen-2-yl)methyl)-8-azabicyclo[3.2.1]octane-3-carboxylic acid;
8-(1-(5-(trifluoromethyl)-6-((cis-4-(trifluoromethyl)cyclohexyl)oxy)naphthalen-2-yl)ethyl)-8-azabicyclo [3.2.1]octane-3-carboxylic acid, enantiomer 1;
8-(1-(5-(trifluoromethyl)-6-((cis-4-(trifluoromethyl)cyclohexyl)oxy)naphthalen-2-yl)ethyl)-8-azabicyclo [3.2.1]octane-3-carboxylic acid, enantiomer 2;
9-(1-(6-((cis-4-ethylcyclohexyl)oxy)-5-(trifluoromethyl) naphthalen-2-yl)ethyl)-9-azabicyclo[3.3.1]nonane-3-carboxylic acid;
8-(1-(6-((cis-4-ethylcyclohexyl)oxy)-5-(trifluoromethyl) naphthalen-2-yl)ethyl)-8-azabicyclo[3.2.1]octane-3-carboxylic acid;
9-(1-(6-((cis-4-trifluoromethylcyclohexyl)oxy)-5-(trifluoromethyl)naphthalen-2-yl) propyl)-9-azabicyclo [3.3.1]nonane-3-carboxylic acid;
8-(1-(6-((cis-4-trifluoromethylcyclohexyl)oxy)-5-(trifluoromethyl)naphthalen-2-yl) propyl)-8-azabicyclo [3.2.1]octane-3-carboxylic acid;
9-(1-(6-((cis-4-ethylcyclohexyl)oxy)-5-(trifluoromethyl) naphthalen-2-yl)propyl)-9-azabicyclo[3.3.1]nonane-3-carboxylic acid;
8-(1-(6-((cis-4-ethylcyclohexyl)oxy)-5-(trifluoromethyl) naphthalen-2-yl)propyl)-8-azabicyclo[3.2.1]octane-3-carboxylic acid;
8-((5-(trifluoromethyl)-6-((cis-4-(trifluoromethyl)cyclohexyl)oxy)naphthalen-2-yl)methyl)-8-azabicyclo [3.2.1]octane-3-carboxylic acid;
9-(1-(6-((cis-4-ethylcyclohexyl)oxy)-5-chloronaphthalen-2-yl)ethyl)-9-azabicyclo[3.3.1]nonane-3-carboxylic acid;
9-((5-Chloro-6-((cis-4-methylcyclohexyl)oxy)naphthalen-2-yl)methyl)-9-azabicyclo[3.3.1]nonane-3-carboxylic acid;
8-(1-(5-Chloro-6-((cis-4-ethylcyclohexyl)oxy)naphthalen-2-yl)ethyl)-8-azabicyclo[3.2.1]octane-3-carboxylic acid; and
8-((5-Chloro-6-((cis-4-ethylcyclohexyl)oxy)naphthalen-2-yl)methyl)-8-azabicyclo[3.2.1]octane-3-carboxylic acid;
or a pharmaceutically acceptable salt thereof.

19. The compound of claim 1, wherein the compound is selected from the group consisting of:
8-(5-chloro-6-((cis-4-(trifluoromethyl)cyclohexyl)oxy)-2-naphthoyl)-8-azabicyclo[3.2.1]octane-3-carboxylic acid;
8-(1-(5-cyano-6-((cis-4-methylcyclohexyl)oxy) naphthalen-2-yl)ethyl)-8-azabicyclo[3.2.1]octane-3-carboxylic acid;
8-((5-cyano-6-((cis-4-methylcyclohexyl)oxy)naphthalen-2-yl)methyl)-8-azabicyclo[3.2.1]octane-3-carboxylic acid;
8-(1-(5-cyano-6-((cis-4-methylcyclohexyl)oxy) naphthalen-2-yl)ethyl)-8-azabicyclo[3.2.1]octane-3-carboxylic acid;
8-(5-(trifluoromethyl)-6-((cis-4-(trifluoromethyl)cyclohexyl)amino)-2-naphthoyl)-8-azabicyclo[13.2.1]octane-3-carboxylic acid;
9-((5-cyano-6-((cis-4-ethylcyclohexyl)oxy)naphthalen-2-yl)methyl)-9-azabicyclo[3.3.1]nonane-3-carboxylic acid;
8-((5-cyano-6-((cis-4-ethylcyclohexyl)oxy)naphthalen-2-yl)methyl)-8-azabicyclo[3.2.1]octane-3-carboxylic acid;
9-(5-chloro-6-((cis-4-(trifluoromethyl)cyclohexyl)oxy)-2-naphthoyl)-9-azabicyclo[3.3.1]nonane-3-carboxylic acid;
8-(1-(5-chloro-6-((cis-4-(trifluoromethyl)cyclohexyl) oxy)naphthalen-2-yl)propyl)-8-azabicyclo[3.2.1]octane-3-carboxylic acid;
8-(5-chloro-6-((cis-4-methylcyclohexyl)oxy)-2-naphthoyl)-8-azabicyclo[3.2.1]octane-3-carboxylic acid;
8-(1-(6-((cis-4-(1,1-difluoroethyl)cyclohexyl)oxy)-5-(trifluoromethyl)naphthalen-2-yl)propyl)-8-azabicyclo [3.2.1]octane-3-carboxylic acid;
8-(1-(5-chloro-6-((cis-4-methylcyclohexyl)oxy)naphthalen-2-yl)ethyl)-8-azabicyclo[3.2.1]octane-3-carboxylic acid;
9-(5-cyano-6-((cis-4-(trifluoromethyl)cyclohexyl)oxy)-2-naphthoyl)-9-azabicyclo[3.3.1]nonane-3-carboxylic acid;
9-((5-cyano-6-((cis-4-methylcyclohexyl)oxy)naphthalen-2-yl)methyl)-9-azabicyclo[3.3.1]nonane-3-carboxylic acid;
9-(5-chloro-6-((cis-4-methylcyclohexyl)oxy)-2-naphthoyl)-9-azabicyclo[3.3.1]nonane-3-carboxylic acid;
9-((6-((cis-4-(1,1-difluoroethyl)cyclohexyl)oxy)-5-(trifluoro-methyl)naphthalen-2-yl)methyl)-9-azabicyclo [3.3.1]nonane-3-carboxylic acid;
8-(1-(5-chloro-6-((cis-4-methylcyclohexyl)oxy)naphthalen-2-yl)propyl)-8-azabicyclo[3.2.1]octane-3-carboxylic acid;
9-(1-(5-chloro-6-((cis-4-methylcyclohexyl)oxy)naphthalen-2-yl)propyl)-9-azabicyclo[3.3.1]nonane-3-carboxylic acid;
8-(1-(5-cyano-6-((cis-4-ethylcyclohexyl)oxy)naphthalen-2-yl)ethyl)-8-azabicyclo[3.2.1]octane-3-carboxylic acid;
9-(1-(5-cyano-6-((cis-4-ethylcyclohexyl)oxy)naphthalen-2-yl)ethyl)-9-azabicyclo[3.3.1]nonane-3-carboxylic acid;
9-(1-(5-chloro-6-((cis-4-methylcyclohexyl)oxy)naphthalen-2-yl)ethyl)-9-azabicyclo[3.3.1]nonane-3-carboxylic acid;
8-(5-chloro-6-((cis-4-ethylcyclohexyl)oxy)-2-naphthoyl)-8-azabicyclo[3.2.1]octane-3-carboxylic acid;
8-(1-(6-((cis-4-(1,1-difluoroethyl)cyclohexyl)oxy)-5-(trifluoromethyl)naphthalen-2-yl)ethyl)-8-azabicyclo [3.2.1]octane-3-carboxylic acid;
9-(1-(6-((cis-4-(1,1-difluoroethyl)cyclohexyl)oxy)-5-(trifluoromethyl)naphthalen-2-yl)ethyl)-9-azabicyclo [3.3.1]nonane-3-carboxylic acid;
9-(5-cyano-6-((cis-4-methylcyclohexyl)oxy)-2-naphthoyl)-9-azabicyclo[3.3.1]nonane-3-carboxylic acid;
8-(5-cyano-6-((cis-4-methylcyclohexyl)oxy)-2-naphthoyl)-8-azabicyclo[3.2.1]octane-3-carboxylic acid;

8-(1-(5-cyano-6-((cis-4-ethylcyclohexyl)oxy)naphthalen-2-yl)propyl)-8-azabicyclo[3.2.1]octane-3-carboxylic acid;

9-(5-cyano-6-((cis-4-ethylcyclohexyl)oxy)-2-naphthoyl)-9-azabicyclo[3.3.1]nonane-3-carboxylic acid;

8-(6-((cis-4-ethylcyclohexyl)oxy)-5-(trifluoromethyl)-2-naphthoyl)-8-azabicyclo[3.2.1]octane-3-carboxylic acid;

8-(5-cyano-6-((cis-4-ethylcyclohexyl)oxy)-2-naphthoyl)-8-azabicyclo[3.2.1]octane-3-carboxylic acid;

9-(6-((cis-4-ethylcyclohexyl)oxy)-5-(trifluoromethyl)-2-naphthoyl)-9-azabicyclo[3.3.1]nonane-3-carboxylic acid;

9-(1-(5-cyano-6-((cis-4-methylcyclohexyl)oxy)naphthalen-2-yl)ethyl)-9-azabicyclo[3.3.1]nonane-3-carboxylic acid;

8-(1-(5-cyano-6-((cis-4-methylcyclohexyl)oxy)naphthalen-2-yl)propyl)-8-azabicyclo[3.2.1]octane-3-carboxylic acid;

9-(5-chloro-6-((cis-4-ethylcyclohexyl)oxy)-2-naphthoyl)-9-azabicyclo[3.3.1]nonane-3-carboxylic acid;

9-(1-(5-cyano-6-(((1s,4s)-4-(trifluoromethyl)cyclohexyl)oxy)naphthalen-2-yl)ethyl)-9-azabicyclo[3.3.1]nonane-3-carboxylic acid;

9-((5-cyano-6-((cis-4-(trifluoromethyl)cyclohexyl)oxy)naphthalen-2-yl)methyl)-9-azabicyclo[3.3.1]nonane-3-carboxylic acid;

9-((5-(trifluoromethyl)-6-((cis-4-(trifluoromethyl)cyclohexyl)amino)naphthalen-2-yl)methyl)-9-azabicyclo[3.3.1]nonane-3-carboxylic acid;

methyl 8-(5-(trifluoromethyl)-6-((cis-4-(trifluoromethyl)cyclohexyl) amino)-2-naphthoyl)-8-azabicyclo[3.2.1]octane-3-carboxylate;

8-((r)-1-(6-((cis-4-methylcyclohexyl)oxy)-5-(trifluoromethyl) naphthalen-2-yl)propyl)-8-azabicyclo[3.2.1]octane-3-carboxylic acid;

8-((s)-1-(6-((cis-4-methylcyclohexyl)oxy)-5-(trifluoromethyl) naphthalen-2-yl)propyl)-8-azabicyclo[3.2.1]octane-3-carboxylic acid;

8-(1-(5-chloro-6-((cis-4-(trifluoromethyl)cyclohexyl)oxy) naphthalen-2-yl)ethyl)-8-azabicyclo[3.2.1]octane-3-carboxylic acid;

9-(1-(5-chloro-6-((cis-4-(trifluoromethyl)cyclohexyl)oxy)naphthalen-2-yl)ethyl)-9-azabicyclo[3.3.1]nonane-3-carboxylic acid;

8-(1-(5-chloro-6-((cis-4-ethylcyclohexyl)oxy)naphthalen-2-yl)propyl)-8-azabicyclo[3.2.1]octane-3-carboxylic acid;

9-(1-(5-chloro-6-((cis-4-ethylcyclohexyl)oxy)naphthalen-2-yl)propyl)-9-azabicyclo[3.3.1]nonane-3-carboxylic acid;

9-((R)-1-(5-chloro-6-((cis-4-ethylcyclohexyl)oxy)naphthalen-2-yl)ethyl)-9-azabicyclo[3.3.1]nonane-3-carboxylic acid;

9-((S)-1-(5-chloro-6-((cis-4-ethylcyclohexyl)oxy)naphthalen-2-yl)ethyl)-9-azabicyclo[3.3.1]nonane-3-carboxylic acid;

9-((R)-1-(5-chloro-6-((cis-4-(trifluoromethyl)cyclohexyl)oxy)naphthalen-2-yl)ethyl)-9-azabicyclo[3.3.1]nonane-3-carboxylic acid;

9-((S)-1-(5-chloro-6-((cis-4-(trifluoromethyl)cyclohexyl)oxy)naphthalen-2-yl)ethyl)-9-azabicyclo[3.3.1]nonane-3-carboxylic acid;

8-((R)-1-(5-chloro-6-((cis-4-(trifluoromethyl)cyclohexyl)oxy)naphthalen-2-yl)ethyl)-8-azabicyclo[3.2.1]octane-3-carboxylic acid;

8-((S)-1-(5-chloro-6-((cis-4-(trifluoromethyl)cyclohexyl)oxy)naphthalen-2-yl)ethyl)-8-azabicyclo[3.2.1]octane-3-carboxylic acid;

methyl 9-(5-(trifluoromethyl)-6-((cis-4-(trifluoromethyl)cyclohexyl)amino)-2-naphthoyl)-9-azabicyclo[3.3.1]nonane-3-carboxylate;

methyl 9-(5-(trifluoromethyl)-6-((cis-4-(trifluoromethyl)cyclohexyl)amino)-2-naphthoyl)-9-azabicyclo[3.3.1]nonane-3-carboxylate;

8-((R)-1-(5-chloro-6-((cis-4-ethylcyclohexyl)oxy)naphthalen-2-yl)propyl)-8-azabicyclo[3.2.1]octane-3-carboxylic acid;

8-((S)-1-(5-chloro-6-((cis-4-ethylcyclohexyl)oxy)naphthalen-2-yl)propyl)-8-azabicyclo[3.2.1]octane-3-carboxylic acid;

9-((R)-1-(5-chloro-6-((cis-4-ethylcyclohexyl)oxy)naphthalen-2-yl)propyl)-9-azabicyclo[3.3.1]nonane-3-carboxylic acid;

9-((S)-1-(5-chloro-6-((cis-4-ethylcyclohexyl)oxy)naphthalen-2-yl)propyl)-9-azabicyclo[3.3.1]nonane-3-carboxylic acid;

8-((R)-1-(5-chloro-6-((cis-4-ethylcyclohexyl)oxy)naphthalen-2-yl)ethyl)-8-azabicyclo[3.2.1]octane-3-carboxylic acid;

8-((S)-1-(5-chloro-6-((cis-4-ethylcyclohexyl)oxy)naphthalen-2-yl)ethyl)-8-azabicyclo[3.2.1]octane-3-carboxylic acid;

methyl 8-(5-(trifluoromethyl)-6-((cis-4-(trifluoromethyl)cyclohexyl)amino)-2-naphthoyl)-8-azabicyclo[3.2.1]octane-3-carboxylate;

8-(5-(trifluoromethyl)-6-((cis-4-(trifluoromethyl)cyclohexyl) amino)-2-naphthoyl)-8-azabicyclo[3.2.1]octane-3-carboxylic acid;

9-((6-(bicyclo[3.1.0]hexan-3-yloxy)-5-(trifluoromethyl) naphthalen-2-yl)methyl)-9-azabicyclo[3.3.1]nonane-3-carboxylic acid;

8-((6-(bicyclo[3.1.0]hexan-3-yloxy)-5-(trifluoromethyl) naphthalen-2-yl)methyl)-8-azabicyclo[3.2.1]octane-3-carboxylic acid;

8-((R)-1-(5-(trifluoromethyl)-6-((cis-4-(trifluoromethyl)cyclohexyl)oxy)naphthalen-2-yl)propyl)-8-azabicyclo[3.2.1]octane-3-carboxylic acid;

8-((S)-1-(5-(trifluoromethyl)-6-((cis-4-(trifluoromethyl)cyclohexyl)oxy)naphthalen-2-yl)propyl)-8-azabicyclo[3.2.1]octane-3-carboxylic acid;

8-((R)-1-(6-((cis-4-ethylcyclohexyl)oxy)-5-(trifluoromethyl)naphthalen-2-yl)ethyl)-8-azabicyclo[3.2.1]octane-3-carboxylic acid;

8-((S)-1-(6-((cis-4-ethylcyclohexyl)oxy)-5-(trifluoromethyl)naphthalen-2-yl)ethyl)-8-azabicyclo[3.2.1]octane-3-carboxylic acid;

9-((R)-1-(6-((cis-4-ethylcyclohexyl)oxy)-5-(trifluoromethyl)naphthalen-2-yl)ethyl)-9-azabicyclo[3.3.1]nonane-3-carboxylic acid;

9-((S)-1-(6-((cis-4-ethylcyclohexyl)oxy)-5-(trifluoromethyl)naphthalen-2-yl)ethyl)-9-azabicyclo[3.3.1]nonane-3-carboxylic acid;

8-((R)-1-(6-((cis-4-ethylcyclohexyl)oxy)-5-(trifluoromethyl) naphthalen-2-yl)propyl)-8-azabicyclo[3.2.1]octane-3-carboxylic acid;

8-((S)-1-(6-((cis-4-ethylcyclohexyl)oxy)-5-(trifluoromethyl) naphthalen-2-yl)propyl)-8-azabicyclo[3.2.1]octane-3-carboxylic acid;

9-((R)-1-(5-(trifluoromethyl)-6-((cis-4-(trifluoromethyl)cyclohexyl)oxy)naphthalen-2-yl)propyl)-9-azabicyclo[3.3.1]nonane-3-carboxylic acid;

9-((S)-1-(5-(trifluoromethyl)-6-((cis-4-(trifluoromethyl) cyclohexyl)oxy)naphthalen-2-yl)propyl)-9-azabicyclo [3.3.1]nonane-3-carboxylic acid;

9-((R)-1-(6-(((1s,4S)-4-ethylcyclohexyl)oxy)-5-(trifluoromethyl) naphthalen-2-yl)propyl)-9-azabicyclo[3.3.1] nonane-3-carboxylic acid;

9-((S)-1-(6-(((1s,4R)-4-ethylcyclohexyl)oxy)-5-(trifluoromethyl) naphthalen-2-yl)propyl)-9-azabicyclo[3.3.1] nonane-3-carboxylic acid;

or a pharmaceutically acceptable salt thereof.

20. A pharmaceutical composition comprising a pharmaceutically acceptable carrier or excipient and a compound, or a pharmaceutically acceptable salt thereof, according to claim 1.

21. A method of treating or reducing symptoms of multiple sclerosis in a mammal comprising administering to said mammal an effective amount of a compound according to claim 1, or a pharmaceutically acceptable salt thereof.

22. The method of claim 21, further comprising administering to said mammal an effective amount of one or more drugs selected from the group consisting of: a corticosteroid, a bronchodilator, an antiasthmatic, an antiinflammatory, an antirheumatic, an immunosuppressant, an antimetabolite, an immunomodulating agent, an antipsoriatic, and an antidiabetic.

23. A method of treating or reducing chronic pain in a mammal comprising administering to said mammal an effective amount of a compound according to claim 1, or a pharmaceutically acceptable salt thereof.

24. The method of claim 23, wherein the chronic pain is inflammatory pain.

25. The method of claim 23, wherein the chronic pain is neuropathic pain.

* * * * *